US012685764B2

(12) United States Patent
Pardi et al.

(10) Patent No.: US 12,685,764 B2
(45) Date of Patent: Jul. 21, 2026

(54) UNIVERSAL INFLUENZA VACCINE USING NUCLEOSIDE-MODIFIED MRNA

(71) Applicants: The Trustees of the University of Pennsylvania, Philadelphia, PA (US); Icahn School of Medicine at Mount Sinai, New York, NY (US); Raffael Nachbagauer, New York, NY (US); Peter Palese, New York, NY (US); Florian Krammer, New York, NY (US); Adolfo Garcia-Sastre, New York, NY (US); Alec W. Freyn, New York, NY (US)

(72) Inventors: Norbert Pardi, Philadelphia, PA (US); Drew Weissman, Wynnewood, PA (US); Raffael Nachbagauer, New York, NY (US); Scott Hensley, Philadelphia, PA (US); Peter Palese, New York, NY (US); Florian Krammer, New York, NY (US); Adolfo Garcia-Sastre, New York, NY (US); Alec W. Freyn, New York, NY (US)

(73) Assignees: The Trustees of the University of Pennsylvania, Philadelphia, PA (US); Icahn School of Medicine at Mount Sinai, New York, NY (US)

(*) Notice: Subject to any disclaimer, the term of this patent is extended or adjusted under 35 U.S.C. 154(b) by 826 days.

(21) Appl. No.: 17/995,207

(22) PCT Filed: Mar. 31, 2021

(86) PCT No.: PCT/US2021/025174

§ 371 (c)(1),
(2) Date: Sep. 30, 2022

(87) PCT Pub. No.: WO2021/202734

PCT Pub. Date: Oct. 7, 2021

(65) Prior Publication Data

US 2023/0181715 A1 Jun. 15, 2023

Related U.S. Application Data

(60) Provisional application No. 63/002,682, filed on Mar. 31, 2020.

(51) Int. Cl.
*A61K 39/145* (2006.01)
*A61P 31/16* (2006.01)

(52) U.S. Cl.
CPC ............ *A61K 39/145* (2013.01); *A61P 31/16* (2018.01)

(58) Field of Classification Search
None
See application file for complete search history.

(56) References Cited

U.S. PATENT DOCUMENTS

| | | | | |
|---|---|---|---|---|
| 2,856,420 | A | 10/1958 | Crawford, Jr. | |
| 3,340,299 | A | 9/1967 | Weintraub | |
| 3,931,430 | A | 1/1976 | Tada | |
| 6,034,137 | A | 3/2000 | Belloni | |
| 6,333,433 | B1 | 12/2001 | Banerjee | |
| 6,458,381 | B1 | 10/2002 | Sourovoi | |
| 8,278,036 | B2 | 10/2012 | Kariko | |
| 8,420,102 | B2 * | 4/2013 | Song | A61P 37/04 424/192.1 |
| 8,748,089 | B2 | 6/2014 | Kariko | |
| 8,835,108 | B2 | 9/2014 | Kariko | |
| 9,352,042 | B2 | 5/2016 | Heyes | |
| 9,737,619 | B2 | 8/2017 | Ansell | |
| 9,738,593 | B2 | 8/2017 | Ansell | |
| 9,750,824 | B2 | 9/2017 | Kariko | |
| 9,795,566 | B2 | 10/2017 | Oya | |
| 10,106,490 | B2 | 10/2018 | Du | |
| 10,144,725 | B2 | 12/2018 | Brown | |
| 10,166,298 | B2 | 1/2019 | Ansell | |
| 10,221,127 | B2 | 3/2019 | Du | |
| 10,723,692 | B2 | 7/2020 | Ansell | |
| 11,648,324 | B2 | 5/2023 | Ansell | |
| 2003/0153081 | A1 | 8/2003 | Tagawa | |
| 2005/0032730 | A1 | 2/2005 | Von Der Mulbe et al. | |

(Continued)

FOREIGN PATENT DOCUMENTS

| | | | |
|---|---|---|---|
| EP | 1083232 | A1 | 3/2001 |
| EP | 2567951 | | 3/2013 |

(Continued)

OTHER PUBLICATIONS

Alabi C.A, et al., "Multiparametric approach for the evaluation of lipid nanoparticles for siRNA delivery," PNAS, vol. 110, No. 32, , ISSN 0027-8424, pp. 12881-12886, Aug. 6, 2013.
Alameh MG et al., "Lipid nanoparticles enhance the efficacy of mRNA and protein subunit vaccines by inducing robust T follicular helper cell and humoral responses," Immunity. Dec. 14, 2021;54(12):2877-2892.e7.
Anderson et al., 2010, "Incorporation of pseudouridine into mRNA enhances translation by diminishing PKR activation." Nucleic Acids Res 38:5884-5892.
Anderson et al., 2011. "Nucleoside modifications in RNA limit activation of 2'-5'-oligoadenylate synthetase and increase resistance to cleavage by RNase L. Nucleic Acids Research," 39:9329-9338.

(Continued)

*Primary Examiner* — Agnieszka Boesen
(74) *Attorney, Agent, or Firm* — Riverside Law LLP

(57) ABSTRACT

The present invention relates to compositions and methods for inducing an immune response against influenza virus in a subject. In some embodiments, the present invention provides a composition comprising a nucleoside-modified nucleic acid molecule encoding at least one influenza virus antigen, such as a hemagglutinin antigen or a fragment thereof, neuraminidase antigen or a fragment thereof, nucleoprotein antigen or a fragment thereof, matrix protein 1 antigen or a fragment thereof, or matrix-2 ion channel antigen or a fragment thereof.

18 Claims, 41 Drawing Sheets

Specification includes a Sequence Listing.

(56) References Cited

U.S. PATENT DOCUMENTS

| | | | | |
|---|---|---|---|---|
| 2005/0059624 | A1 | 3/2005 | Hoerr | |
| 2005/0250723 | A1 | 11/2005 | Hoerr | |
| 2006/0100177 | A1 | 5/2006 | Nishimura | |
| 2006/0188490 | A1 | 8/2006 | Hoerr | |
| 2008/0025944 | A1 | 1/2008 | Hoerr | |
| 2009/0324584 | A1 | 12/2009 | Hoerr | |
| 2010/0189729 | A1 | 7/2010 | Hoerr | |
| 2010/0203076 | A1 | 8/2010 | Fotin-Mleczek | |
| 2010/0291156 | A1 | 11/2010 | Barner | |
| 2010/0305196 | A1 | 12/2010 | Probst | |
| 2011/0150921 | A1 | 6/2011 | Roingeard | |
| 2011/0229518 | A1 | 9/2011 | Fomsgaard | |
| 2011/0250225 | A1 | 10/2011 | Fotin-Mleczek | |
| 2011/0256175 | A1 | 10/2011 | Hope | |
| 2011/0300205 | A1 | 12/2011 | Geall | |
| 2011/0305770 | A1 | 12/2011 | Zhao | |
| 2012/0021043 | A1 | 1/2012 | Kramps | |
| 2012/0276209 | A1 | 11/2012 | Cullis | |
| 2012/0288510 | A1 | 11/2012 | Ambrosino | |
| 2013/0129754 | A1 | 5/2013 | Thess | |
| 2013/0259879 | A1 | 10/2013 | Baumhof | |
| 2013/0261172 | A1 | 10/2013 | Kariko | |
| 2013/0266640 | A1 | 10/2013 | De Fougerolles | |
| 2013/0280283 | A1 | 10/2013 | Lorenz | |
| 2013/0280305 | A1 | 10/2013 | Kuboyama | |
| 2013/0295043 | A1 | 11/2013 | Kallen | |
| 2013/0336998 | A1 | 12/2013 | Kallen | |
| 2014/0134175 | A1 | 5/2014 | Ambrosino | |
| 2014/0323548 | A1 | 10/2014 | Budzik | |
| 2015/0037326 | A1 | 2/2015 | Butler-Ransohoff | |
| 2015/0050302 | A1 | 2/2015 | Thess | |
| 2015/0057340 | A1 | 2/2015 | Thess | |
| 2015/0093413 | A1 | 4/2015 | Thess | |
| 2015/0118183 | A1 | 4/2015 | Baumhof | |
| 2015/0118264 | A1 | 4/2015 | Baumhof | |
| 2015/0165006 | A1 | 6/2015 | Thess | |
| 2015/0184195 | A1 | 7/2015 | Thess | |
| 2015/0203446 | A1 | 7/2015 | Manoharan | |
| 2015/0218554 | A1 | 8/2015 | Thess | |
| 2015/0306249 | A1 | 10/2015 | Baumhof | |
| 2015/0376115 | A1 | 12/2015 | Ansell | |
| 2016/0130345 | A1 | 5/2016 | Fotin-Mleczek | |
| 2016/0166668 | A1 | 6/2016 | Kallen | |
| 2016/0166678 | A1* | 6/2016 | Kallen .................. | A61K 39/12 536/23.4 |
| 2016/0166710 | A1 | 6/2016 | Baumhof | |
| 2016/0168207 | A1 | 6/2016 | Kramps | |
| 2016/0168227 | A1 | 6/2016 | Kallen | |
| 2016/0235864 | A1 | 8/2016 | Schlake | |
| 2016/0304883 | A1 | 10/2016 | Grund | |
| 2016/0331828 | A1 | 11/2016 | Ciaramella | |
| 2016/0361411 | A1 | 12/2016 | Gindy | |
| 2016/0376224 | A1 | 12/2016 | Du | |
| 2017/0029847 | A1 | 2/2017 | Thess | |
| 2017/0119904 | A1 | 5/2017 | Ansell | |
| 2017/0157268 | A1 | 6/2017 | Ansell | |
| 2017/0252430 | A1 | 9/2017 | Fotin-Mleczek | |
| 2017/0283367 | A1 | 10/2017 | Ansell | |
| 2017/0326225 | A1 | 11/2017 | Rauch | |
| 2018/0044687 | A1 | 2/2018 | Thess | |
| 2018/0125952 | A1 | 5/2018 | Fotin-Mleczek | |
| 2018/0126003 | A1 | 5/2018 | Hoerr | |
| 2018/0148727 | A1 | 5/2018 | Grund | |
| 2018/0214537 | A1 | 8/2018 | Mutzke | |
| 2018/0237786 | A1 | 8/2018 | Schlake | |
| 2018/0296663 | A1 | 10/2018 | Hipp | |
| 2018/0312545 | A1 | 11/2018 | Baumhof | |
| 2019/0022247 | A1 | 1/2019 | Ansell | |
| 2019/0024096 | A1 | 1/2019 | Schmid | |
| 2019/0160164 | A1 | 5/2019 | Rauch | |
| 2019/0270697 | A1 | 9/2019 | Ansell | |
| 2019/0274968 | A1 | 9/2019 | Weissman | |
| 2019/0314524 | A1 | 10/2019 | Ansell | |
| 2019/0336595 | A1 | 11/2019 | Ciaramella | |
| 2019/0359556 | A1 | 11/2019 | Du | |
| 2020/0046838 | A1 | 2/2020 | Ansell | |
| 2020/0121809 | A1 | 4/2020 | Hope | |
| 2020/0163878 | A1 | 5/2020 | Baumhof | |
| 2020/0172472 | A1 | 6/2020 | Du | |
| 2020/0283372 | A1 | 9/2020 | Du | |
| 2021/0107861 | A1 | 4/2021 | Ansell | |

FOREIGN PATENT DOCUMENTS

| | | | |
|---|---|---|---|
| EP | 3289083 | | 3/2018 |
| JP | H103643 | | 1/1998 |
| JP | 2001338416 | | 12/2001 |
| JP | 5331118 | | 10/2013 |
| WO | 1987007183 | | 12/1987 |
| WO | 1997003939 | | 2/1997 |
| WO | 1999005094 | | 2/1999 |
| WO | 2000030444 | | 6/2000 |
| WO | 2003053409 | | 7/2003 |
| WO | 2005004910 | | 1/2005 |
| WO | 2005060934 | | 7/2005 |
| WO | 2006138380 | A2 | 12/2006 |
| WO | 2007024708 | | 3/2007 |
| WO | 2011143230 | | 11/2011 |
| WO | 2011153493 | | 12/2011 |
| WO | 2012016184 | | 2/2012 |
| WO | 2012068176 | | 5/2012 |
| WO | 2013016058 | | 1/2013 |
| WO | 2013086373 | | 6/2013 |
| WO | 2013143555 | | 10/2013 |
| WO | 2014028487 | | 2/2014 |
| WO | 2014160243 | | 10/2014 |
| WO | 2014160284 | | 10/2014 |
| WO | 2015164674 | A1 | 10/2015 |
| WO | 2015177752 | A1 | 11/2015 |
| WO | 2015199952 | | 12/2015 |
| WO | 2016176330 | | 11/2016 |
| WO | 2017006182 | | 1/2017 |
| WO | 2017021546 | | 2/2017 |
| WO | 2017048770 | | 3/2017 |
| WO | 2017049245 | | 3/2017 |
| WO | 2017075531 | A1 | 5/2017 |
| WO | 2017140905 | | 8/2017 |
| WO | 2017173054 | | 10/2017 |
| WO | 2017182634 | | 10/2017 |
| WO | 2018081638 | | 5/2018 |
| WO | 2018191657 | | 10/2018 |

OTHER PUBLICATIONS

Antrobus RD et al., "Clinical assessment of a novel recombinant simian adenovirus ChAdOx1 as a vectored vaccine expressing conserved Influenza A antigens," Mol Ther. Mar. 2014;22(3):668-674.

Awasthi S et al., "Nucleoside-modified mRNA encoding HSV-2 glycoproteins C, D, and E prevents clinical and subclinical genital herpes," 2019, Sci. Immunol., 4:eaaw7083.

Bahl K et al., "Preclinical and Clinical Demonstration of Immunogenicity by mRNA Vaccines against H10N8 and H7N9 Influenza Viruses," Mol Ther. Jun. 7, 2017;25(6):1316-1327.

Baiersdorfer M et al., "A Facile Method for the Removal of dsRNA Contaminant from In Vitro-Transcribed mRNA," Mol Ther Nucleic Acids. Apr. 15, 2019:15:26-35.

Bajic G et al., "Influenza Antigen Engineering Focuses Immune Responses to a Subdominant but Broadly Protective Viral Epitope," Cell Host Microbe. Jun. 12, 2019;25(6):827-835.e6.

Belliveau et al., 2012, "Microfluidic Synthesis of Highly Potent Limit-size Lipid Nanoparticles for In Vivo Delivery of siRNA." Mol Ther Nucleic Acids, 1: e37, 9 pages.

Bernstein DI et al., "Immunogenicity of chimeric haemagglutinin-based, universal influenza virus vaccine candidates: interim results of a randomised, placebo-controlled, phase 1 clinical trial," Lancet Infect Dis. Jan. 2020;20(1):80-91.

Berthoud TK et al., "Potent CD8+ T-cell immunogenicity in humans of a novel heterosubtypic influenza A vaccine, MVA-NP+M1," Clin Infect Dis. Jan. 1, 2011;52(1):1-7.

(56) References Cited

OTHER PUBLICATIONS

Bhattacharya et al., "Synthesis, Thermotropic Behavior, and Permeability Properties of Vesicular Membranes Composed of Cationic Mixed-Chain Surfactants," Langmuir 11:4748-4757, 1995.
Brito et al: 'Self-Amplifying mRNA Vaccines,' Adv Genet, 2015;89:179-233.
Chahal JS et al., "Dendrimer-RNA nanoparticles generate protective immunity against lethal Ebola, H1N1 influenza, and Toxoplasma gondii challenges with a single dose," Proc Natl Acad Sci U S A. Jul. 19, 2016;113(29):E4133-42.
Chen et al., "Influence of particle size on the in vivo potency of lipid nanoparticle formulations of siRNA," Journal of Controlled Release 235:236-244, 2016.
Chen YQ et al., "Influenza Infection in Humans Induces Broadly Cross-Reactive and Protective Neuraminidase-Reactive Antibodies," Cell. Apr. 5, 2018;173(2):417-429.e10.
Cheng ZJ et al., "Development of a robust reporter-based ADCC assay with frozen, thaw-and-use cells to measure Fc effector function of therapeutic antibodies," J Immunol Methods. Dec. 1, 2014:414:69-81.
Choi A et al., "Chimeric Hemagglutinin-Based Influenza Virus Vaccines Induce Protective Stalk-Specific Humoral Immunity and Cellular Responses in Mice," Immunohorizons. Apr. 1, 2019;3(4):133-148.
Coughlan L et al., "Heterologous Two-Dose Vaccination with Simian Adenovirus and Poxvirus Vectors Elicits Long-Lasting Cellular Immunity to Influenza Virus A in Healthy Adults," EBioMedicine. Mar. 2018:29:146-154.
Crooks GE et al., "WebLogo: a sequence logo generator," Genome Res. Jun. 2004;14(6):1188-90.
D.N. Nguyen et al: "Lipid-derived nanoparticles for immunostimulatory RNA adjuvant delivery", Proceedings of the National Academy of Sciences of the United States of America, vol. 109, No. 14, Apr. 3, 2012 (Apr. 3, 2012), pp. E797-E803.
De Filette M et al., "An influenza A vaccine based on tetrameric ectodomain of matrix protein 2," J Biol Chem. Apr. 25, 2008;283(17):11382-7.
Deng L et al., "M2e-Based Universal Influenza A Vaccines," Vaccines (Basel) Feb. 13, 2015;3(1):105-36.
Dhar N et al., "Hemagglutinin Stalk Antibody Responses Following Trivalent Inactivated Influenza Vaccine Immunization of Pregnant Women and Association With Protection From Influenza Virus Illness," 2019, Clin. Infect. Dis., ciz927.
DiLillo DJ et al., "Broadly neutralizing hemagglutinin stalk-specific antibodies require FcγR interactions for protection against influenza virus in vivo," Nat Med. Feb. 2014;20(2):143-51.
Durbin et al., "RNAs Containing Modified Nucleotides Fail to Trigger RIG-I Conformational Changes for Innate Immune Signaling," mBio 7(5):e00833-16, 2016 (11 pages).
Egan KP et al., "An HSV-2 nucleoside-modified mRNA genital herpes vaccine containing glycoproteins gC, gD, and gE protects mice against HSV-1 genital lesions and latent infection," PLoS Pathog. Jul. 27, 2020;16(7):e1008795.
Eggink D et al., "Guiding the immune response against influenza virus hemagglutinin toward the conserved stalk domain by hyperglycosylation of the globular head domain," J Virol. Jan. 2014;88(1):699-704.
Eichelberger MC et al., "Influenza neuraminidase as a vaccine antigen," Curr Top Microbiol Immunol. 2015:386:275-99.
Eichelberger MC et al., "Neuraminidase as an influenza vaccine antigen: a low hanging fruit, ready for picking to improve vaccine effectiveness," Curr Opin Immunol. Aug. 2018:53:38-44.
El Bakkouri K et al., "Universal vaccine based on ectodomain of matrix protein 2 of influenza A: Fc receptors and alveolar macrophages mediate protection," J Immunol. Jan. 15, 2011;186(2):1022-31.
Ernsting et al., "Factors controlling the pharmacokinetics, biodistribution and intratumoral penetration of nanoparticles," Journal of Controlled Release 172:782-794, 2013.
Falcone et al., "Both the 5' Untranslated Region and the Sequences Surrounding the Start Site Contribute to Efficient Initiation of Translation In Vitro," Molecular and Cellular Biology 11(5):2656-2664, 1991.
Feldman RA et al., "mRNA vaccines against H10N8 and H7N9 influenza viruses of pandemic potential are immunogenic and well tolerated in healthy adults in phase 1 randomized clinical trials," Vaccine. May 31, 2019;37(25):3326-3334.
Freyn AW et al., "A Multi-Targeting, Nucleoside-Modified mRNA Influenza Virus Vaccine Provides Broad Protection in Mice," Mol Ther. Jul. 8, 2020;28(7):1569-1584.
Fulton BO et al., 2018, "The Influenza B Virus Hemagglutinin Head Domain Is Less Tolerant to Transposon Mutagenesis than That of the Influenza A Virus," J Virol. Jul. 31, 2018;92(16):e00754-18.
Graham BS et al., "Structure-Based Vaccine Antigen Design," Annu Rev Med. Jan. 27, 2019:70:91-104.
Hekele et al., "Rapidly produced SAM® vaccine against H7N9 influenza is immunogenic in mice," Emerging Microbes and Infections 2:e52, 2013 (7 pages).
Houser K et al., "Influenza vaccines: challenges and solutions," Cell Host Microbe. Mar. 11, 2015;17(3):295-300.
Impagliazzo A et al., "A stable trimeric influenza hemagglutinin stem as a broadly protective immunogen" Science. Sep. 18, 2015;349(6254):1301-6.
Jacobsen H et al., "Influenza Virus Hemagglutinin Stalk-Specific Antibodies in Human Serum are a Surrogate Marker for In Vivo Protection in a Serum Transfer Mouse Challenge Model," mBio. Sep. 19, 2017;8(5):e01463-17.
John S et al., "Multi-antigenic human cytomegalovirus mRNA vaccines that elicit potent humoral and cell-mediated immunity," Vaccine. Mar. 14, 2018;36(12):1689-1699.
Karikó et al., "Incorporation of Pseudouridine Into mRNA Yields Superior Nonimmunogenic Vector With Increased Translational Capacity and Biological Stability," Mol Ther, vol. 16, Issue 11, Nov. 2008, pp. 1833-1840.
Karikó et al., "Suppression of RNA Recognition by Toll-like Receptors: The Impact of Nucleoside Modification and the Evolutionary Origin of RNA," Immunity, Aug. 2005, vol. 23, 165-175.
Kariko et al., 2011. "Generating the optimal mRNA for therapy: HPLC purification eliminates immune activation and improves translation of nucleosidemodified, protein-encoding mRNA." Nucleic Acids Research 39(21):e142, pp. 1-10.
Karikó et al., 2012, "Increased Erythropoiesis in Mice Injected with Submicrogram Quantities of Pseudouridine-containing mRNA Encoding Erythropoietin." Mol Ther 20:948-953.
Krammer F et al., "A carboxy-terminal trimerization domain stabilizes conformational epitopes on the stalk domain of soluble recombinant hemagglutinin substrates," PLoS One. 2012;7(8):e43603.
Krammer F et al., "Chimeric hemagglutinin influenza virus vaccine constructs elicit broadly protective stalk-specific antibodies," J Virol. Jun. 2013;87(12):6542-50.
Krammer F et al., "NAction! How Can Neuraminidase-Based Immunity Contribute to Better Influenza Virus Vaccines?," mBio. Apr. 3, 2018;9(2):e02332-17.
Lambe T et al., "Immunity against heterosubtypic influenza virus induced by adenovirus and MVA expressing nucleoprotein and matrix protein-1," Sci Rep. 2013:3:1443.
Lee PS et al., "Structural characterization of viral epitopes recognized by broadly cross-reactive antibodies," Curr Top Microbiol Immunol. 2015:386:323-41.
Lillie PJ et al., "Preliminary assessment of the efficacy of a T-cell-based influenza vaccine, MVA-NP+M1, in humans," Clin Infect Dis. Jul. 2012;55(1):19-25.
Lindgren G et al., "Induction of Robust B Cell Responses after Influenza mRNA Vaccination Is Accompanied by Circulating Hemagglutinin-Specific ICOS+ PD-1+ CXCR3+ T Follicular Helper Cells," Front Immunol. Nov. 13, 2017:8:1539.
Luis A Brito et al: "A Cationic Nanoemulsion for the Delivery of Next-generation RNA Vaccines", Molecular Therapy, vol. 22, No. 12, Jul. 16, 2014 (Jul. 16, 2014) pp. 2118-2129.

(56) References Cited

OTHER PUBLICATIONS

Maier et al., 2013, "Biodegradable lipids enabling rapidly eliminated lipid nanoparticles for systemic delivery of RNAi therapeutics." Mol Ther., 21(8): 1570-1578, XP055551712, ISSN: 1525-0016.
Margine I et al., "Expression of functional recombinant hemagglutinin and neuraminidase proteins from the novel H7N9 influenza virus using the baculovirus expression system," J Vis Exp. Nov. 6, 2013:(81):e51112.
Masuda et al., "Envelope-type lipid nanoparticles incorporating a short PEG-lipid conjugate for improved control of intracellular trafficking and transgene transcription," Biomaterials 30:4806-4814, 2009.
Meyer M et al., "Modified mRNA-Based Vaccines Elicit Robust Immune Responses and Protect Guinea Pigs From Ebola Virus Disease," J Infect Dis. Jan. 17, 2018;217(3):451-455.
Nachbagauer R et al., "Defining the antibody cross-reactome directed against the influenza virus surface glycoproteins, " Nat Immunol. Apr. 2017;18(4):464-473.
Ng S et al., "Novel correlates of protection against pandemic H1N1 influenza A virus infection," Nat Med. Jun. 2019;25(6):962-967.
Pardi et al., "Expression kinetics of nucleoside-modified mRNA delivered in lipid nanoparticles to mice by various routes," Journal of Controlled Release vol. 217, Nov. 10, 2015, pp. 345-351.
Pardi N et al., "Nucleoside-modified mRNA vaccines induce potent T follicular helper and germinal center B cell responses," J Exp Med. Jun. 4, 2018;215(6):1571-1588.
Pardi N et al., "Nucleoside-modified mRNA immunization elicits influenza virus hemagglutinin stalk-specific antibodies," Nat Commun. Aug. 22, 2018;9(1):3361.
Pardi N et al., "Zika virus protection by a single low-dose nucleoside-modified mRNA vaccination," Nature. Mar. 9, 2017;543(7644):248-251.
Petsch et al., "Protective efficacy of in vitro synthesized, specific mRNA vaccines against influenza A virus infection," Nature Biotechnology 30:1210-1216, 2012.
Rajesh et al., "Dramatic Influence of the Orientation of Linker between Hydrophilic and Hydrophobic Lipid Moiety in Liposomal Gene Delivery," Journal of the American Chemical Society 129(37):11408-11420, 2007.
Rekstin A et al., "Immunogenicity and Cross Protection in Mice Afforded by Pandemic H1N1 Live Attenuated Influenza Vaccine Containing Wild-Type Nucleoprotein," Biomed Res Int. 2017:2017:9359276.
Richner JM et al., "Modified mRNA Vaccines Protect against Zika Virus Infection," Cell. Mar. 9, 2017;168(6):1114-1125.
Schnee et al., "An mRNA Vaccine Encoding Rabies Virus Glycoprotein Induces Protection against Lethal Infection in Mice and Correlates of Protection in Adult and Newborn Pigs," PLoS Negl. Trop. Dis. 10(6):e0004746, 2016, 20 pages.
Schotsaert M et al., "Long-Lasting Cross-Protection Against Influenza A by Neuraminidase and M2e-based immunization strategies," Sci Rep. Apr. 13, 2016:6:24402.
Scorza FB et al., "New Kids on the Block: RNA-Based Influenza Virus Vaccines," 2018, Vaccines, 6:20.
Stadlbauer D et al., "Broadly protective human antibodies that target the active site of influenza virus neuraminidase," Science. Oct. 25, 2019;366(6464):499-504.
Steel J et al., "Influenza virus vaccine based on the conserved hemagglutinin stalk domain," 2010, mBio. May 18, 2010;1(1):e00018-10.
Thyagarajan B et al., "The inherent mutational tolerance and antigenic evolvability of influenza hemagglutinin," Elife. Jul. 8, 2014:3:e03300.
Topham DJ et al., "CD8+ T cells clear influenza virus by perforin or Fas-dependent processes," J Immunol. Dec. 1, 1997;159(11):5197-200.
Torrecilla, J et al., "Lipid Nanoparticles as Carriers for RNAi against Viral infections: Current Status and Future Perspectives.", BioMed Research International., (Aug. 12, 2014), vol. 2014, No. 2014, pp. 1-18, XP055326069.
Watanabe T et al., "Influenza A virus can undergo multiple cycles of replication without M2 ion channel activity," J Virol. Jun. 2001;75(12):5656-62.
Whitehead et al: "Synergistic Silencing: Combinations of Lipid-like Materials for Efficacious siRNA Delivery", Molecular Therapy, vol. 19, No. 9, Sep. 1, 2011 (Sep. 1, 2011), pp. 1688-1694.
Wohlbold TJ et al., "Vaccination with adjuvanted recombinant neuraminidase induces broad heterologous, but not heterosubtypic, cross-protection against influenza virus infection in mice," mBio. Mar. 10, 2015;6(2):e02556.
Xue et al., "Lipid-Based Nanocarriers for RNA Delivery," Current Pharmaceutical Design 21:3140-3147, 2015.
Yassine HM et al., "Hemagglutinin-stem nanoparticles generate heterosubtypic influenza protection," Nat Med. Sep. 2015;21(9):1065-70.
Zhu X et al., "Influenza virus neuraminidases with reduced enzymatic activity that avidly bind sialic Acid receptors," J Virol. Dec. 2012;86(24):13371-83.
Zhuang, Q et al., "Diversity and distribution of type A influenza viruses: an updated panorama analysis based on protein sequences," Virol J. Jun. 26, 2019;16(1):85.

* cited by examiner

NP (Mich15)
OD 490nm
Reciprocal Dilution

M2 (Mich15)
OD 490nm
Reciprocal Dilution
Combination
Mini HA
NA (Mich15)
M2 (Mich15)
NP (Mich15)
Luciferase Microneutralization:
H1N1pdm
Endpoint Titer
Mini HA
NA (Mich15)
M2 (Mich15)
NP (Mich15)
Combination
Luciferase ADCC:
H1N1pdm
Fold Change
Reciprocal Dilution Figure 7A
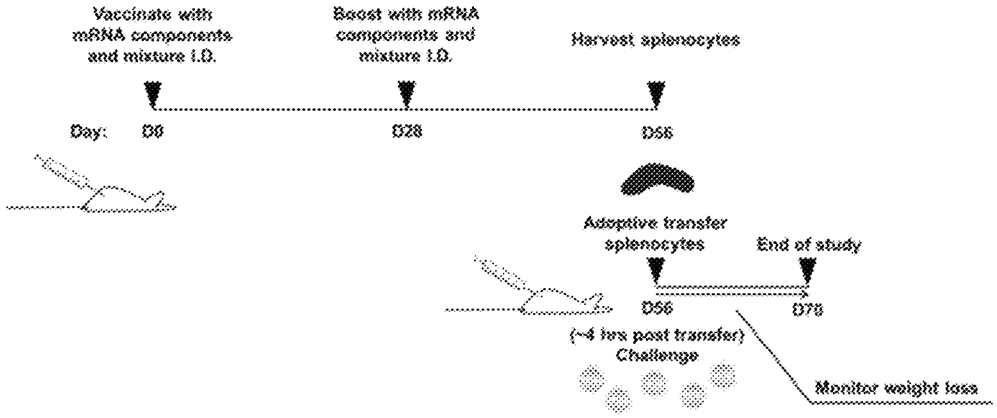
Figure 7B
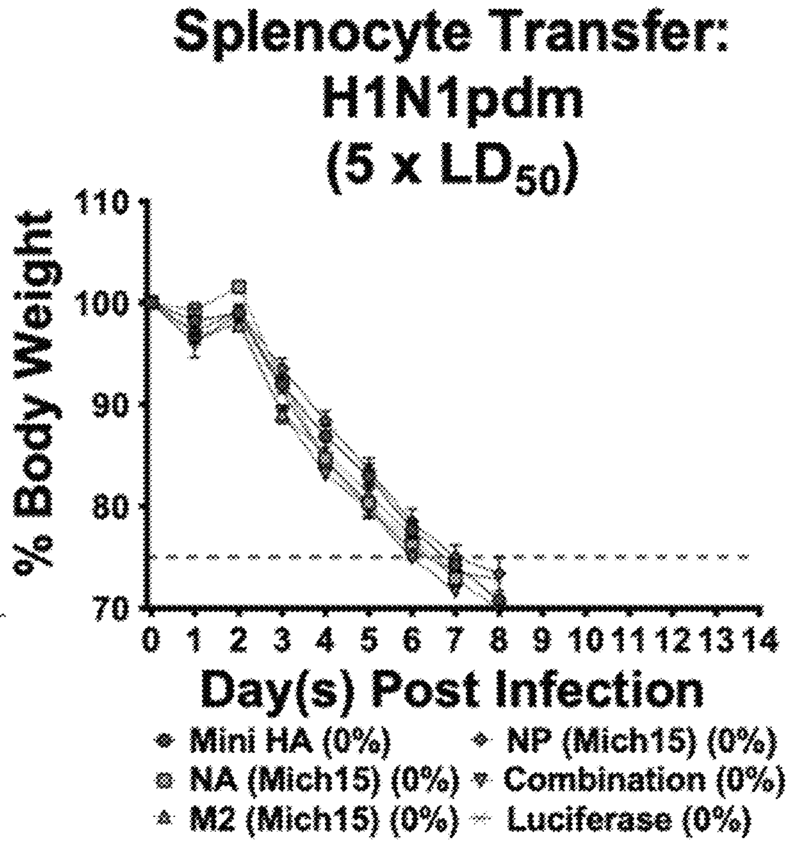
Figure 7

Vaccine antigen

Virus strain

| | HA | NA | M2 | NP |
|---|---|---|---|---|
| H1N1pdm | 77.8% | ~100% | 82.5% | 90.4% |
| NC99 | 87.0% | 81.7% | 81.4% | 89.6% |
| PR8 | 81.5% | 82.8% | 86.6% | 91.2% |
| H5N8 | 65.1% | 52.9% | 86.6% | 91.2% |
| cH6/1N5 | 77.4% | 52.6% | 86.6% | 91.2% |

Figure 12

Figure 28E
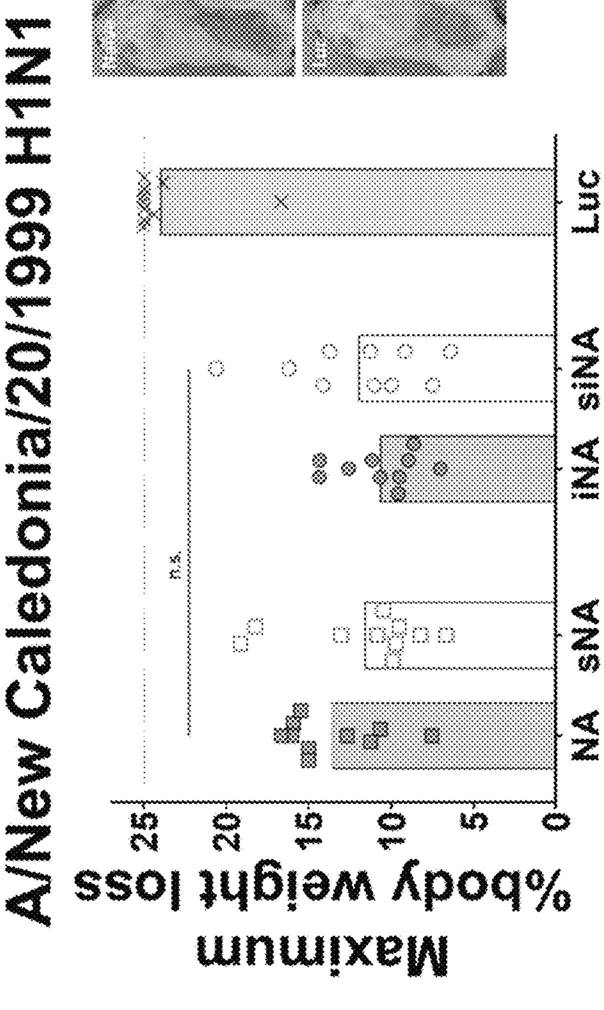
Figure 28F
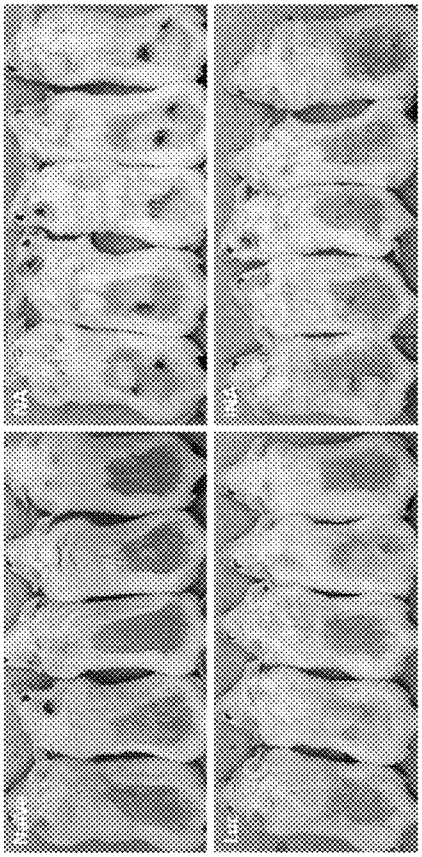
Figure 28 (cont.)

UNIVERSAL INFLUENZA VACCINE USING NUCLEOSIDE-MODIFIED MRNA

STATEMENT REGARDING FEDERALLY SPONSORED RESEARCH OR DEVELOPMENT

This invention was made with government support under AI146101 and AI153064 awarded by the National Institutes of Health. The government has certain rights in the invention.

CROSS-REFERENCE TO RELATED APPLICATIONS

This application claims priority to International Patent Application No. PCT/US21/25174, filed Mar. 31, 2021, claiming priority to U.S. Provisional Application Ser. No. 63/002,682, filed Mar. 31, 2020, each of which is hereby incorporated by reference herein in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "046483-6188-00US_SequenceListing.txt"; created on Sep. 19, 2022, and 362,373 bytes in size, is hereby incorporated by reference.

BACKGROUND OF THE INVENTION

Influenza viruses cause substantial morbidity and mortality in humans across the globe leading to the death of over half a million individuals annually (WHO, 2019, Influenza (Seasonal) Fact Sheet). Vaccination is the most common preventative measure utilized, but current influenza virus vaccines remain imperfect and do not provide broad and durable protective immunity. Quadrivalent inactivated influenza virus vaccines (QIVs) are most commonly administered to the public, but effectiveness of these vaccines lies in the range of 10-60% due to a variety of factors including poor immunogenicity and strain mismatches (CDC, 2019, Seasonal Influenza Vaccine Effectiveness, 2004-2019; Osterholm, M T et al., 2012, Lancet. Infect. Dis., 12:36-44). In addition, seasonal vaccines are formulated to aid in protection from influenza viruses circulating in the human population, but provide minimal protection from emerging influenza viruses with pandemic potential (DiMenna L J et al., 2009, Curr. Top. Microbiol. Immunol., 333:291-321). Therefore, development of a novel vaccine platform targeting multiple conserved epitopes of influenza viruses capable of providing broadly-reactive and long-lasting protection is highly desirable as a candidate for a universal influenza virus vaccine.

Previous work has focused on identifying conserved regions of influenza viruses, which can act as targets for the induction of broadly protective humoral and cellular responses. The stalk of the major surface glycoprotein, hemagglutinin (HA), has been the object of much attention due to its ability to elicit broadly-reactive neutralizing antibodies, which can protect from infection by influenza viruses displaying a wide variety of HA subtypes (Steel J et al., 2010, MBio., 1:e00018-10; Krammer F et al., 2013, J. Virol., 87:6542-6550; Bernstein D I et al., 2019, Lancet. Infect. Dis., 20:80-91; Impagliazzo A et al., 2015, Science, 349:1301-1306; Yassine H M et al., 2015, Nat. Med. 21:1065-1070). Importantly, antibodies against the HA stalk have been shown to correlate with protection in humans (Jacobsen H et al., 2017, MBio, 8:e01463-17; Ng S et al., 2019, Nat. Med., 25:962-967; Dhar N et al., 2019, Clin. Infect. Dis., ciz927). More recently, the influenza virus minor surface glycoprotein, neuraminidase (NA), has raised considerable interest after antibodies to this protein were found to provide protection within a single subtype and broadly reactive NA-specific antibodies were isolated from human donors (Chen Y Q et al., 2018, Cell, 173:417-429; Stadlbauer D et al., 2019, Science, 366:499-504; Wohlbold T J et al., 2015, MBio, 6:e02556-14; Eichelberger M C et al., 2015, Curr. Top. Microbiol. Immunol., 386:275-299; Eichelberger M C et al., 2018, Curr. Opin. Immunol., 53:38-44). The highly conserved matrix-2 (M2) ion channel protein and nucleoprotein (NP) of the influenza virus have also been found to elicit broad protective immune responses through antibody Fc-mediated mechanisms and cellular responses (Deng L et al., 2015, Vaccines, 3:105-136; Schotsaert M et al., 2016, Sci. Rep., 6:24402; Lambe T et al., 2013, Sci. Rep., 3:1443; Rekstin A et al., 2017, Biomed. Res. Int., 637:9359276).

Thus, there is a need in the art for improved universal influenza vaccines. The present invention addresses this need.

SUMMARY OF THE INVENTION

In one aspect, the present invention provides a composition for inducing an immune response against one or more influenza viruses in a subject, the composition comprising at least one isolated nucleoside-modified RNA encoding at least one influenza virus antigen or a fragment thereof.

In various embodiments, the at least one influenza virus antigen is a glycoprotein or a fragment thereof, nucleoprotein (NP) antigen or a fragment thereof, matrix-2 (M2) ion channel antigen or a fragment thereof, or any combination thereof. In some embodiments, the at least one influenza virus antigen is a hemagglutinin (HA) antigen or a fragment thereof, neuraminidase (NA) antigen or a fragment thereof, NP antigen or a fragment thereof, matrix protein 1 (M1) antigen or a fragment thereof, M2 ion channel antigen or a fragment thereof, or any combination thereof. In some embodiments, the at least one influenza virus antigen is a full length HA antigen or a fragment thereof, HA-stalk domain or a fragment thereof, HA-head domain or a fragment thereof, full length NA antigen or a fragment thereof, NA-stalk domain or a fragment thereof, NA-head domain or a fragment thereof, full length NP antigen or a fragment thereof, full length M1 antigen or a fragment thereof, full length M2 ion channel antigen or a fragment thereof, M2 ion channel-extracellular domain or a fragment thereof, M2 ion channel-intracellular domain or a fragment thereof, or any combination thereof.

In some embodiments, the HA antigen comprises an amino acid sequence as set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or any combination thereof.

In some embodiments, the NA antigen comprises an amino acid sequence as set forth in SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, or any combination thereof.

In some embodiments, the NP antigen comprises an amino acid sequence as set forth in SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, or any combination thereof.

In some embodiments, the M2 ion channel antigen comprises an amino acid sequence as set forth in SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, or any combination thereof.

In some embodiments, the M1 antigen comprises an amino acid sequence as set forth in SEQ ID NO: 107.

Thus, in some embodiments, the at least one influenza virus antigen comprises an amino acid sequence as set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, or any combination thereof.

In one embodiment, the at least one influenza virus antigen is a combination of a HA-stalk domain or a fragment thereof, full length NA antigen or a fragment thereof, full length NP antigen or a fragment thereof, and full length M2 ion channel antigen or a fragment thereof. In one embodiment, the at least one influenza virus antigen is a combination of a HA-stalk domain comprising an amino acid sequence as set forth in SEQ ID NO: 27, full length NA antigen comprising an amino acid sequence as set forth in SEQ ID NO: 41, full length NP antigen comprising an amino acid sequence as set forth in SEQ ID NO: 67, and full length M2 ion channel antigen comprising an amino acid sequence as set forth in SEQ ID NO: 93.

In various embodiments, the at least one isolated nucleoside-modified RNA encodes a glycoprotein or a fragment thereof, NP antigen or a fragment thereof, M2 ion channel antigen or a fragment thereof, or any combination thereof. In some embodiments, the at least one isolated nucleoside-modified RNA encodes a HA antigen or a fragment thereof, NA antigen or a fragment thereof, NP antigen or a fragment thereof, M2 ion channel antigen or a fragment thereof, or any combination thereof.

In some embodiments, the at least one nucleoside-modified RNA comprises a nucleic acid sequence that is encoded by a DNA sequence comprising at least one nucleotide sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, and SEQ ID NO: 28.

In some embodiments, the at least one nucleoside-modified RNA comprises a nucleic acid sequence that is encoded by a DNA sequence comprising at least one nucleotide sequence selected from the group consisting of: SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, and SEQ ID NO: 54.

In some embodiments, the at least one nucleoside-modified RNA comprises a nucleic acid sequence that is encoded by a DNA sequence comprising at least one nucleotide sequence selected from the group consisting of: SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, and SEQ ID NO: 80.

In some embodiments, the at least one nucleoside-modified RNA comprises a nucleic acid sequence that is encoded by a DNA sequence comprising at least one nucleotide sequence selected from the group consisting of: SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, and SEQ ID NO: 106.

In some embodiments, the at least one nucleoside-modified RNA comprises a nucleic acid sequence that is encoded by a DNA sequence comprising at least one nucleotide sequence as set forth in SEQ ID NO: 108.

Thus, in some embodiments, the at least one nucleoside-modified RNA comprises a nucleic acid sequence that is encoded by a DNA sequence comprising at least one nucleotide sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, and SEQ ID NO: 108.

In one embodiment, the at least one nucleoside-modified RNA comprises a nucleic acid sequence that is encoded by a DNA sequence comprising a combination of a nucleotide sequence as set forth in SEQ ID NO: 28, nucleotide sequence as set forth in SEQ ID NO: 42, nucleotide sequence as set forth in SEQ ID NO: 68, and nucleotide sequence as set forth in SEQ ID NO: 94.

In one embodiment, the composition of the present invention further comprises an adjuvant. For example, in one embodiment, the at least one nucleoside-modified RNA further encodes at least one adjuvant.

In one embodiment, the composition of the present invention further comprises a lipid nanoparticle (LNP). For example, in one embodiment, the at least one nucleoside-modified RNA is encapsulated within the LNP.

In one embodiment, the at least one isolated nucleoside-modified RNA comprises pseudouridine. For example, in one embodiment, the at least one isolated nucleoside-modified RNA comprises 1-methyl-pseudouridine.

In one embodiment, the at least one isolated nucleoside-modified RNA is a purified nucleoside-modified mRNA.

In one aspect of the invention, the composition of the present invention is a vaccine.

In one aspect, the present invention provides a method of inducing an immune response against influenza virus in a subject comprising administering to the subject an effective amount of a composition comprising at least one nucleoside-modified RNA encoding at least one influenza virus antigen.

In various embodiments, the composition is any composition of the present invention. Thus, in various embodiments, the at least one nucleoside-modified RNA is any nucleoside-modified RNA described herein or a fragment or variant thereof. In various embodiments, the at least one influenza virus antigen is any influenza virus antigen described herein or a fragment or variant thereof.

In various embodiments, the influenza virus is an influenza virus A, influenza virus B, influenza virus C, influenza virus D, or any combination thereof. In some embodiments, the influenza virus is an influenza HA group 1 virus, influenza NA group 1 virus, or any combination thereof. In some embodiments, the influenza HA group 1 virus is H1, H2, H5, H6, H8, H9, H11, H12, H13, H16, or any combination thereof. In some embodiments, the influenza NA group 1 virus is N1, N4, N5, N8, or any combination thereof. Thus, in some embodiments, the influenza virus is H1N1, H2N2, H3N2, H5N1, H7N7, H1N2, H9N2, H7N2, H7N3, H10N7, H7N9, H6N1, or any combination thereof.

In various embodiments, the method of the present invention treats or prevents an infection, disease, disorder, or any combination thereof associated with influenza virus in the subject.

In some embodiments, the composition of the present invention is administered by a delivery route selected from the group consisting of intradermal, subcutaneous, inhalation, intranasal, and intramuscular.

In one embodiment, the method comprises a single administration of the composition. In one embodiment, the method comprises multiple administrations of the composition.

In one embodiment, the method of the present invention further comprises administering to the subject an effective amount of an adjuvant. For example, in one embodiment, the at least one nucleoside-modified RNA further encodes an effective amount of at least one adjuvant.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 2A through FIG. 2C, depicts a representative characterization of neuraminidase (NA), matrix-2 (M2), and mini-HA encoding mRNAs by Western blot analyses. mRNAs were transfected into NIH/3T3 cells. FIG. 2A depicts a representative NA expression in cell lysates was probed by Western blot, using firefly luciferase (Luc)-encoding mRNA-transfected cells and untransfected (unt) cells as negative controls. FIG. 2B depicts a representative M2 expression in cell lysates was probed by Western blot, using firefly luciferase (Luc)-encoding mRNA-transfected cells and untransfected (unt) cells as negative controls. FIG. 2C depicts a representative mini-HA protein expression in cell lysates was probed by Western blot, using firefly luciferase (Luc)-encoding mRNA-transfected cells and untransfected (unt) cells as negative controls.

FIG. 4A depicts a schematic representation demonstrating that mice were vaccinated once intradermally with 20 μg of mRNA-LNPs per antigen. Sera were collected on day 28 post vaccination and binding of antibodies to corresponding antigen was measured by ELISA. FIG. 4B depicts mean optical density at 490 nm is plotted with SD for each dilution (n=19-20 individual sera per group) against Mini HA. FIG. 4C depicts mean optical density at 490 nm is plotted with SD for each dilution (n=19-20 individual sera per group) against NA (Mich15). FIG. 4D depicts mean optical density at 490 nm is plotted with SD for each dilution (n=19-20 individual sera per group) against NP (Mich15). FIG. 4E depicts cell-based ELISAs that were utilized to detect antibody binding to M2 (Mich15). Mean optical density at 490 nm is plotted with SD for each dilution displayed with SD (n=4 repeats of pooled sera). FIG. 4F depicts representative endpoint titers of a multi-cycle microneutralization assay to determine the neutralization potential of antibodies elicited by vaccination. Sera were pooled and run in duplicate against H1N1pdm virus. FIG. 4G depicts representative ADCC activity of sera that were measured using a reporter assay to determine engagement with the mouse FcγRIV. Luminescence was measured and data from pooled sera run in triplicate is represented as fold change over background (average of negative wells plus 3 times the standard deviation, indicated as a dashed line) with SD.

FIG. 5A through FIG. 5D, depicts representative results demonstrating that vaccination with a combination of nucleoside-modified mRNA-LNP encoded influenza virus antigens protects mice from a highly lethal dose of matched challenge virus. FIG. 5A depicts representative sera collected 28 days after mRNA-LNP vaccination was measured against H1N1pdm virus. Individual data are represented as AUC with lines indicating mean and SD of responses (n=19-20 per group). FIG. 5B depicts representative results for mice that were challenged with $5\times LD_{50}$ of H1N1pdm and weight loss was monitored for 14 days. Data are shown as mean and SEM (n=5 per group). Mortality is reported as the % of surviving mice for each group. FIG. 5C depicts representative results for mice that were challenged with $50\times LD_{50}$ of H1N1pdm and weight loss was monitored for 14 days. Data are shown as mean and SEM (n=5 per group). Mortality is reported as the % of surviving mice for each group. FIG. 5D depicts representative results for mice that were challenged with $500\times LD_{50}$ of H1N1pdm and weight loss was monitored for 14 days. Data are shown as mean and SEM (n=5 per group). Mortality is reported as the % of surviving mice for each group.

FIG. 6A through FIG. 6D, depicts representative results demonstrating that nucleoside-modified mRNA-LNP vaccine-induced protection from influenza virus challenge is mediated primarily by the humoral arm of the immune system. FIG. 6A depicts a schematic representation demonstrating that mice were vaccinated twice (4-week intervals) intradermally with 10 μg of mRNA-LNPs. Animals were euthanized on day 56 post initial vaccination and sera were collected and transferred into naïve mice. Two hours post transfer, recipient mice were infected with $5\times LD_{50}$ of H1N1pdm (IVR-180) and weight loss was monitored for 14 days. FIG. 5B representative ELISAs that were performed to measure the ELISA reactivity of sera from hyperimmune mice to H1N1pdm before transfer (n=9-10 per group). Lines indicate mean and SD. FIG. 5C depicts representative results for sera that were pooled, transferred into naïve mice, and reactivity to H1N1pdm was measured by ELISA from sera taken 2 hours after transfer (n=5 per group). Lines indicate mean and SD. FIG. 5D depicts weight loss curves of mice that received hyper-immune sera. Average weight loss with SEM is plotted (n=5 per group). Mortality is reported as the % of surviving mice for each group.

FIG. 7, comprising FIG. 7A and FIG. 7B, depicts representative results demonstrating that adoptive transfer of splenocytes did not provide protection from influenza virus challenge. FIG. 7A depicts a schematic representation demonstrating that mice were vaccinated intradermally with 10 μg of mRNA-LNPs in four-week intervals. Animals were euthanized on day 56 post initial vaccination and splenocytes were harvested, pooled, and transferred into naïve mice. FIG. 7B depicts that 2 hours post transfer, recipient mice were infected with $5\times LD_{50}$ of H1N1pdm and weight loss was monitored for 14 days. Weight loss curves of mice adoptively transferred 80 million splenocytes from hyper immune mice (n=5). Average weight loss with SEM is plotted. Mortality is reported as the % of surviving mice for each group.

FIG. 8A through FIG. 8I, depicts representative results demonstrating that nucleoside-modified NA and NP mRNA-LNP vaccines elicit robust antigen-specific T cell responses in mice. Values from NA and NP-immunized mice were compared to values from Luc-immunized animals for each cytokine combination (FIG. 8D, FIG. 8E, FIG. 8H, and FIG. 8I). Each symbol represents one animal and error is shown as SEM (n=10 mice per group). Data from 2 independent experiments are shown. Statistical analysis: Mann-Whitney test, * $P<0.05$;  $P<0.01$; * $P<0.001$. FIG. 8A depicts a schematic representation demonstrating that mice were vaccinated intradermally with a single dose of 20 μg of NA or NP mRNA-LNPs. Splenocytes were stimulated with NA or NP peptides 12 days after immunization, and cytokine production by CD4+ and CD8+ T cells was assessed by flow cytometry. FIG. 8B depicts percentages of NA-specific CD4+ T cells producing IFN-γ, TNF-α, and IL-2. FIG. 8C depicts percentages of NA-specific CD8+ T cells producing IFN-γ, TNF-α, and IL-2. FIG. 8D depicts percentages of NA-specific CD4+ T cells producing IFN-γ, TNF-α, and IL-2 and frequencies of combinations of cytokines produced by CD4+ cells. FIG. 8E depicts percentages of NA-specific CD8+ T cells producing IFN-γ, TNF-α, and IL-2 and frequencies of combinations of cytokines produced by CD8+ cells. FIG. 8F depicts percentages of NP-specific CD4+ T cells producing IFN-γ, TNF-α, and IL-2. FIG. 8G depicts percentages of NP-specific CD8+ T cells producing IFN-γ, TNF-α, and IL-2. FIG. 8H depicts frequencies of combinations of cytokines produced by NP-specific CD4+ T cells. FIG. 8I depicts frequencies of combinations of cytokines produced by NP-specific CD8+ T cells.

FIG. 10A through FIG. 10D, depicts representative results demonstrating that addition of influenza virus antigens enhances protection of NA-mediated immunity in the nanogram range. FIG. 10A depicts representative results for serum from mice vaccinated with a single intradermal dose of 5, 0.5, 0.05, or 0.005 g of nucleoside-modified mRNA-LNPs of NA alone were tested against H1N1pdm in ELISA assays. Luciferase mRNA-LNP was used as a negative control at a dose of 5 μg and quadrivalent inactivated influenza virus vaccine (QIV) was used as a standard of care control at a dose of 1.5 μg. Data are represented as AUC with the mean and SD plotted. FIG. 10B depicts representative results for serum from mice vaccinated with a single intradermal dose of 5, 0.5, 0.05, or 0.005 μg of nucleoside-modified mRNA-LNPs of NA supplemented with Mini HA, M2, and NP constructs additively (combination) were tested against H1N1pdm in ELISA assays. Luciferase mRNA-LNP was used as a negative control at a dose of 5 μg and quadrivalent inactivated influenza virus vaccine (QIV) was used as a standard of care control at a dose of 1.5 μg. Data are represented as AUC with the mean and SD plotted. FIG. 10C depicts representative results for mice that were infected with $5\times LD_{50}$ of H1N1pdm virus and body weight was monitored for 14 days. Weight loss curves after infection for mice vaccinated with NA alone. Luciferase and QIV groups are shown. Mean plus SEM is plotted for each group (n=5 per group). Mortality is reported as the % of surviving mice for each group. FIG. 10D depicts representative results for mice that were infected with $5\times LD_{50}$ of H1N1pdm virus and body weight was monitored for 14 days. Weight loss curves after infection for mice vaccinated with NA in combination of antigens. Luciferase and QIV groups are shown. Mean plus SEM is plotted for each group (n=5 per group). Mortality is reported as the % of surviving mice for each group.

FIG. 11A through FIG. 11D, depicts representative results demonstrating vaccine-induced responses to purified virus preparations corresponding to viral challenge strains. Twenty-eight days after intradermal vaccination with 20 μg of mRNA-LNPs, mice were bled to perform serological analysis. Mean of AUC for individual mouse sera responses plus SD are shown. FIG. 11A depicts representative results for ELISAs that were ran against purified virus (250 ng per well) for the A/New Caledonia/20/1999 H1N1 virus (n=5 per groups) strain. FIG. 11B depicts representative results for ELISAs that were ran against purified virus (250 ng per well) for the A/Puerto Rico/8/1934 H1N1 virus (n=4-5 per group) strain. FIG. 11C depicts representative results for ELISAs that were ran against purified virus (250 ng per well) for the H5N8 virus (n=5 per group) strain. FIG. 11D depicts representative results for ELISAs that were ran against purified virus (250 ng per well) for the cH6/1N5 virus (n=5 per group) strain.

FIG. 12 depicts representative results demonstrating amino acid identity between vaccine antigens and corresponding influenza virus proteins. Amino acid sequences from vaccine antigens were aligned to appropriate proteins from influenza virus challenge strains using the Clustal Omega multiple sequence alignment tool (Gamblin S J et al., 2004, Science, 303:1838-1842). Percent amino acid identity was determined using the computed Percent Identity Matrix and examined for each virus used.

FIG. 13A through FIG. 13E, depicts representative results demonstrating that a single immunization with a combination of nucleoside-modified mRNA-encoded influenza virus antigens protects mice from heterologous challenge. Twenty-eight days after a single intradermal vaccination with 20 μg of mRNA-LNPs mice were bled and challenged with $5\times LD_{50}$ of influenza virus. Mean and SEM is shown for weight loss curves. Mortality is reported as the % of surviving mice for each group. Summarized maximum weight loss of all challenges at $5\times LD_{50}$ of the respective viruses is represented. Mean plus SEM is plotted for each group. Statistical analysis: Two-way ANOVA with Dunnett's correction for multiple comparisons, * P<0.0332; 807  P<0.0021; * P<0.0002; ** P<0.0001. FIG. 13A depicts representative results for weight loss that was monitored for 14 days for A/New Caledonia/20/1999 H1N1 virus (n=5 per group). FIG. 13B depicts representative results for weight loss that was monitored for 14 days for A/Puerto Rico/8/1934 H1N1 virus (n=4-5 per group). FIG. 13C depicts representative results for weight loss that was monitored for 14 days for H5N8 virus (n=5 per group). FIG. 13D depicts representative results for weight loss that was monitored for 14 days for cH6/1N5 virus (n=5 per group). FIG. 13**E depicts representative results for maximum body weight loss for influenza A viruses (n=5 per group).

FIG. 14A through FIG. 14C, depicts representative results demonstrating that mRNA vaccine administered as a prime-boost regimen increases serum antibody responses with a modest increase in protection. To determine the effect of multiple vaccinations on immune responses, 10 μg of vaccine was delivered twice, four weeks apart. FIG. 14A depicts representative results for ELISAs that were ran against purified H1N1pdm virus using serum from animals four weeks after prime. FIG. 14B depicts representative results for ELISAs that were ran against purified H1N1pdm virus using serum from animals four weeks after boost. FIG. 14C depicts representative results for mice that were challenged with $5\times LD_{50}$ of H1N1pdm virus and weight loss was monitored for 14 days (n=5 per group). Average weight loss with SEM is plotted. Mortality is reported as the % of surviving mice for each group.

FIG. 26A through FIG. 23C, depicts schematic representations of the design of optimized influenza virus antigens for a combination nucleoside-modified mRNA-LNP vaccine. FIG. 23A depicts a schematic representation of studies designed to evaluate the effect of antigen modifications on nucleoside-modified mRNA-based influenza virus vaccines in mice. FIG. 23B depicts representative modeled images of the mutations introduced to each influenza virus vaccine target that are illustrated onto their respective protein. Functional sites were targeted to determine the resulting effect of mutations on conferred immunogenicity and reactogenicity for each antigen. Not drawn to scale. FIG. 23C depicts a representative diagram of the vaccination scheme used for comparison of antigen constructs for each individual antigen. Mice were given a single immunization of nucleoside-modified mRNA-LNP vaccine I.D. followed by sera collection four weeks later before challenge with a heterologous H1N1 influenza virus.

FIG. 24A through FIG. 24E, depicts representative results demonstrating that membrane-bound hemagglutinin constructs elicit more potent immune responses than soluble forms. Mice were vaccinated with 20 μg of HA-expressing mRNA-LNP vaccines and sera were collected four weeks post immunization before challenge with NC99 H1N1 virus. Two-way ANOVAs with Tukey's correction for multiple comparisons were performed to determine significance: ** p<0.0001. FIG. 24A depicts representative results for ELISAs that were ran against purified H1N1pdm virus using sera from individual mice. Data are reported as area under the curve for each sample with group average plus standard deviation (SD; n=5/group). FIG. 24B depicts representative results for Hemagglutination inhibition assays that were performed against H1N1pdm virus using pooled sera from each group. The assay was run in triplicate with individual values reported as endpoint titer. Bars represent the average of reported values with SD. FIG. 24C depicts representative results demonstrating microneutralization capability of pooled sera that were assessed against H1N1pdm influenza virus. Sera were run in triplicate and individual values were reported as endpoint titer as well as the average plus SD of reported values. FIG. 24D depicts representative results for antibody-dependent cell-mediated cytotoxicity reporter assays that were performed using H1N1pdm infected MDCK cells. Pooled sera from each group were run in triplicate and effector cells expressing murine FcγRIV and an NFAT-controlled luciferase reporter were incubated with the infected cells. Data are represented as area under the curve calculated from background-normalized fold change values with the average and SD plotted. FIG. 24**E depicts representative results demonstrating maximum percent body weight loss that was calculated after challenge with NC99 and is represented as the average plus individual values for each mouse.

FIG. 25A through FIG. 25D, depicts representative results demonstrating that raw ELISA curves showed antibody binding to purified virion. Values are represented as the average of absorbance values measured at 490 nm plus SD (FIG. 25A, FIG. 25C, and FIG. 25D: n=5/group) (FIG. 25B: n=10/group). FIG. 25A depicts representative results for sera from mice vaccinated with HA-based mRNA-LNPs were ran against purified H1N1pdm virus. FIG. 25B depicts representative results for sera from mice vaccinated with NA-based mRNA-LNPs were ran against purified H1N1pdm virus. FIG. 25C depicts representative results for sera from mice vaccinated with M2-based mRNA-LNPs were ran against purified H1N1pdm virus. FIG. 25D depicts representative results for sera from mice vaccinated with internal protein-based mRNA-LNPs were ran against purified H1N1pdm virus.

FIG. 26, comprising FIG. 26A through FIG. 26C, depicts representative results for raw luminescence curves for antibody-dependent cell-mediated cytotoxicity reporter assay. Relative light units are reported as a proxy for luciferase expression controlled by an NFAT promoter which is activated by Fc receptor engagement. Data are reported as the average value plus SD. Sera were pooled and run in triplicate. FIG. 26A depicts representative results for sera that were used from mice vaccinated with HA-based mRNA-LNP constructs. FIG. 26B depicts representative results for sera that were used from mice vaccinated with NA-based mRNA-LNP constructs. FIG. 26C depicts representative results for sera that were used from mice vaccinated with M2-based mRNA-LNP constructs.

FIG. 27A through FIG. 27E, depicts representative weight loss curves for heterologous infection of mRNA-LNP vaccinated mice. Data are reported as average plus standard error of the mean for each group (n=5-10). Survival is reported as a percentage of surviving mice for each group. FIG. 27A depicts representative weigh loss curves for mice vaccinated with membrane-bound HA mRNA-LNP constructs. After infection with the heterologous A/New Caledonia/20/1999 H1N1, weight loss was measured daily and is reported as percent of baseline for mice vaccinated with membrane-bound HA mRNA-LNP constructs. FIG. 27B depicts representative weigh loss curves for mice vaccinated with soluble HA mRNA-LNP constructs. After infection with the heterologous A/New Caledonia/20/1999 H1N1, weight loss was measured daily and is reported as percent of baseline for mice vaccinated with soluble HA mRNA-LNP constructs. FIG. 27C depicts representative weigh loss curves for mice vaccinated with NA mRNA-LNP constructs. After infection with the heterologous A/New Caledonia/20/1999 H1N1, weight loss was measured daily and is reported as percent of baseline for mice vaccinated with NA mRNA-LNP constructs. FIG. 27D depicts representative weigh loss curves for mice vaccinated with M2 mRNA-LNP constructs. After infection with the heterologous A/New Caledonia/20/1999 H1N1, weight loss was measured daily and is reported as percent of baseline for mice vaccinated with m2 mRNA-LNP constructs. FIG. 27E depicts representative weigh loss curves for mice vaccinated with internal protein mRNA-LNP constructs. After infection with the heterologous A/New Caledonia/20/1999 H1N1, weight loss was measured daily and is reported as percent of baseline for mice vaccinated with internal protein mRNA-LNP constructs.

FIG. 28A through FIG. 28F, depicts representative results demonstrating that diminished neuraminidase catalytic activity reduced reactogenicity while preserving immunogenicity. Mice were vaccinated and challenged as described in FIG. 24. One-way ANOVAs with Tukey's correction for multiple comparisons were performed to determine significance: * p<0.033,  p<0.002, * p <0.0002, ** p<0.0001. FIG. 28A depicts representative results for ELISAs of sera from individual mice that were ran against purified H1N1pdm influenza virus preparations to determine binding titers. Data are reported as area under the curve with the average and SD of values plotted (n=5/group). FIG. 28B depicts representative neutralizing potential of sera that was determined through a multi-cycle microneutralization assay against H1N1pdm virus. Pooled sera for each group were ran in triplicates and endpoint titers were reported for each replicate. FIG. 28C depicts representative results for a neuraminidase inhibition assay against H1N1pdm virus that was performed to examine the ability of sera to block NA catalytic activity. Pooled sera were ran in duplicate and the median effective concentration was reported for each replicate. FIG. 28D depicts representative results for an ADCC reporter assay that was performed on cells infected with H1N1pdm influenza virus. Pooled sera were run in triplicate and the area under the curve from background normalized fold change values is reported as the average plus SD for each group. FIG. 28E depicts representative maximum percent body weight loss after heterologous NC99 challenge for each individual mouse is reported (n=10/group). FIG. 28**F depicts representative images of mice that were vaccinated with 10 μg of mRNA-LNP I.D. in a prime/boost regimen with three weeks between administrations. One-week post boost, mice were photographed to visually examine lesions at the site of vaccination (n=5/group). Representative images from two independent experiments are shown.

FIG. 29A depicts representative results for ELISAs that were performed using sera from individual mice against purified H1N1pdm virus. Area under the curve was calculated after fitting regression curves to the data and is reported as individual values with average and SD (n=5/group). FIG. 29B depicts representative results for ADCC reporter assays that were performed to determine effector functionality of antibodies present in sera of immunized mice. Cells were infected with H1N1pdm virus and luminescence was measured as a readout of Fc-receptor engagement. Sera were pooled and run in triplicate for each group. FIG. 29C depicts representative maximum percent body weight loss from NC99 challenge data that is shown as average with each individual point for each animal (n=5/group).

FIG. 30A through FIG. 30E, depicts representative results demonstrating that alteration of nucleoprotein nuclear localization signals altered secretion in vitro, but had no effect on conferred protection in vivo. FIG. 30A depicts a schematic representation of design of NP constructs with mutations in NLS regions: Wt—A/Michigan/45/2015 H1N1pdm NP, NLS—K7A, R8A, R213A, R214A, and R216A mutations were introduced to ablate two putative NLS sequences, Cleave—E14A and G16A mutations were introduced to prevent cleavage of a putative site, Δ1-18—removal of first 18 amino acids were performed to mimic cleavage. Hexa-His tags were included at the C-terminus of each construct. Not drawn to scale. FIG. 30B depicts representative results for western blot against His tag that was performed to determine the abundance of NP in the cell lysate versus the supernatant (sup). FIG. 30C depicts representative results for quantification of protein abundance that was performed for both supernatant and cell lysate and % secreted NP was calculated by dividing the supernatant value by the cell lysate value, multiplying by 100, and dividing by the Wt value to normalize to Wt. FIG. 30D depicts representative results for ELISA assays that were performed on mice that were vaccinated with 50 μg of pCAGGS plasmid DNA expressing each NP construct or a GFP control in a prime-boost regimen spaced 3 weeks apart. Mice were bled following the boost and sera were ran against a purified H1N1pdm virus prep in ELISA. Data are reported as average of individual values plus SD (n=5/group). FIG. 30E depicts representative weight loss that was measured as a percent of baseline and reported as the average plus SEM (n=5/group) in mice that were challenged with a lethal dose of cH6/1N5 recombinant influenza virus. One-way ANOVA with Tukey's correction for multiple comparisons was performed to determine statistical significance: n.s. $p>0.05$.

(FIG. 31A and FIG. 31B) One-way ANOVA with Tukey's correction for multiple comparisons was performed to determine statistical significance: ** $p<0.0001$. (FIG. 31D through FIG. 31**G) Statistical analysis: paired t test, *$p<0.05$, $p<0.01$, *$p<0.001$, ** $p<0.0001$. FIG. 31A depicts representative results for ELISA binding titers that are displayed as the average area under the curve value for each individual mouse serum sample reactivity to H1N1pdm purified virus (n=5/group). FIG. 31B depicts representative maximum percent body weight loss after heterologous NC99 challenge that is reported as the average with each individual value plotted. FIG. 31C depicts a schematic representation of studies in which mice were vaccinated I.D. with a single dose of 20 μg of M1 mRNA-LNP. Splenocytes were stimulated with an M1 peptide pool 12 days after immunization, and cytokine production by CD4+ and CD8+ T cells was analyzed by flow cytometry. FIG. 31D depicts representative percentages of M1-specific CD4+ T cells producing IFNγ, TNF-α, and IL-2. FIG. 31E depicts representative percentages of M1-specific CD8+ T cells producing IFNγ, TNF-α, and IL-2. FIG. 31F depicts representative frequencies of combinations of cytokines produced by CD4+ T cells. FIG. 31**G depicts representative frequencies of combinations of cytokines produced by CD8+ T cells.

DETAILED DESCRIPTION

Figure 1:
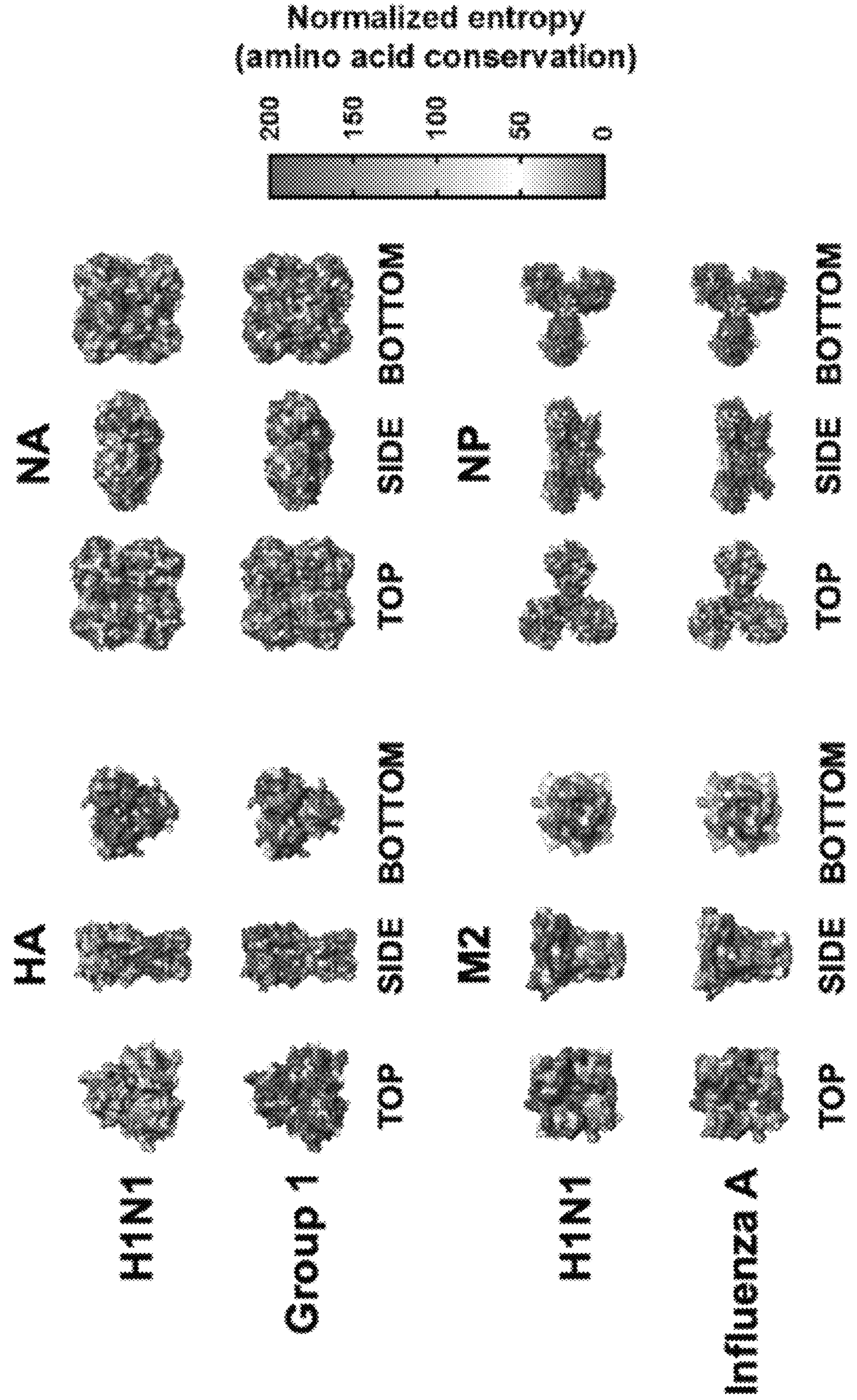
FIG. 1 depicts schematic representations demonstrating that influenza viruses display conserved epitopes, which can be targeted in the development of a universal influenza virus vaccine. Single amino acid polymorphism of proteins from a representative set of influenza virus strains was scored using a formula derived by Crooks et al (Crooks G E et al., 2004, Genome Res., 14:1188-1190). Scores were mapped to corresponding amino acid residues and represented as a heat map; blue residues show no variation and red residues show substantial variation. H1N1 strains were selected for each year available dating back to 1918 (n=49-52/group). Influenza virus strains were selected to evenly distribute between influenza A group one HAs, group one NAs, or influenza A human, avian, and swine strains for M2 and NP (n=50/group). Angles are shown for top, side, and bottom views for all antigens: A/Puerto Rico/8/1934 H1 trimer (PDB: 1RU7) (Gamblin S J et al., 2004, Science, 303:1838-1842), A/Brevig Mission/1/1918 N1 tetramer (PDB: 3B7E) (Xu X et al., 2008, J. Virol., 82:10493-10501), A/Udorn/307/1972 M2 tetramer (PDB: 2L0J) (Sharma M et al., 2010, Science, 330:509-512), and A/Wilson-Smith/1933 NP trimer (PDB: 2IQH) (Ye Q et al., 2006, Nature, 444:1078-1082). Proteins are not rendered to scale.

The present invention relates to compositions and methods for inducing an immune response against influenza virus in a subject. In some embodiments, the invention provides a composition comprising at least one nucleoside-modified RNA encoding at least one influenza virus antigen. For example, in one embodiment, the composition is a vaccine comprising at least one nucleoside-modified RNA encoding at least one influenza virus antigen, wherein the vaccine induces an immune response in the subject to various influenza viruses, and therefore the vaccine is a universal influenza vaccine. In some embodiments, the at least one nucleoside-modified RNA encodes hemagglutinin (HA) antigen or a fragment thereof, neuraminidase (NA) antigen or a fragment thereof, nucleoprotein (NP) antigen or a fragment thereof, matrix protein 1 (M1) antigen or a fragment thereof, matrix-2 (M2) ion channel antigen or a fragment thereof, or any combination thereof. In one embodiment, the nucleoside-modified RNA is a nucleoside-modified mRNA. In some embodiments, the at least one nucleoside-modified RNA is encapsulated in a lipid-nanoparticle (LNP).

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule, which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody, which is generated using recombinant DNA technology. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. The term should also be construed to mean an antibody, which has been generated by the synthesis of an RNA molecule encoding the antibody. The RNA molecule expresses an antibody protein, or an amino acid sequence specifying the antibody, wherein the RNA has been obtained by transcribing DNA (synthetic or cloned), synthesizing the RNA, or other technology, which is available and well known in the art.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more other species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "immunogen" as used herein, is intended to denote a substance of matter, which is capable of inducing an adaptive immune response in an individual, where said adaptive immune response is capable of inducing an immune response, which significantly engages pathogenic agents, which share immunological features with the immunogen. "Immunogen" refers to any substance introduced into the body in order to generate an immune response. That substance can a physical molecule, such as a protein, or can be encoded by a vector, such as DNA, mRNA, or a virus.

The term "antigen" or "Ag" as used herein is defined as a molecule that provokes an adaptive immune response. This immune response may involve either antibody production, or the activation of specific immunogenically-competent cells, or both. The skilled artisan will understand that any macromolecule, including virtually all proteins or peptides, can serve as an antigen. Furthermore, antigens can be derived from recombinant or genomic DNA or RNA. A skilled artisan will understand that any DNA or RNA, which comprises a nucleotide sequence or a partial nucleotide sequence encoding a protein that elicits an adaptive immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Immune response," as the term is used herein, means a process involving the activation and/or induction of an effector function in, by way of non-limiting examples, a T cell, B cell, natural killer (NK) cell, and/or an antigen-presenting cell (APC). Thus, an immune response, as would be understood by the skilled artisan, includes, but is not limited to, any detectable antigen-specific activation and/or induction of a helper T cell or cytotoxic T cell activity or response, production of antibodies, antigen presenting cell activity or infiltration, macrophage activity or infiltration, neutrophil activity or infiltration, and the like.

As used herein, an "immunogenic composition" may comprise an antigen (e.g., a peptide or polypeptide), a nucleic acid encoding an antigen, a cell expressing or presenting an antigen or cellular component, a virus expressing or presenting an antigen or cellular component, or a combination thereof. In particular embodiments, the composition comprises or encodes all or part of any peptide antigen described herein, or an immunogenically functional equivalent thereof. In other embodiments, the composition is in a mixture that comprises an additional immunostimulatory agent or nucleic acids encoding such an agent. Immunostimulatory agents include but are not limited to an additional antigen, an immunomodulator, an antigen presenting cell, lipid nanoparticle, or an adjuvant. In other embodiments, one or more of the additional agent(s) is covalently bonded to the antigen or an immunostimulatory agent, in any combination.

As used herein, the term "vaccine" refers to a composition that induces an immune response upon inoculation into a subject. In some embodiments, the induced immune response provides protective immunity.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) RNA, and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein, a nucleotide sequence is "substantially homologous" to any of the nucleotide sequences described herein when its nucleotide sequence has a degree of identity with respect to the original nucleotide sequence at least 60%, of at least 65%, of at least 70%, of at least 75%, of at least 80%, of at least 85%, of at least 90%, of at least 91%, of at least 92%, of at least 93%, of at least 94%, of at least 95%, of at least 96%, of at least 97%, of at least 98%, of at least 99%, or of at least 99.5%.

As used herein, an amino acid sequence is "substantially homologous" to any of the amino acid sequences described herein when its amino acid sequence has a degree of identity with respect to the original amino acid sequence of at least 60%, of at least 65%, of at least 70%, of at least 75%, of at least 80%, of at least 85%, of at least 90%, of at least 91%, of at least 92%, of at least 93%, of at least 94%, of at least 95%, of at least 96%, of at least 97%, of at least 98%, of at least 99%, or of at least 99.5%.The identity between two amino acid sequences can be determined by using the BLASTN algorithm (BLAST Manual, Altschul, S., et al., NCBI NLM NIH Bethesda, Md. 20894, Altschul, S., et al., J. Mol. Biol. 215: 403-410 (1990)).

The term "variant" as used herein with respect to a nucleic acid refers (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto. A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof.

The term "variant" as used with respect to a peptide or polypeptide refers to a peptide or polypeptide that differs in amino acid sequence by the insertion, deletion, or conservative substitution of amino acids, but retain at least one biological activity. Variant may also refer to a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., 1982, J. Mol. Biol. 157:105-132). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

As used herein, the terms "fragment" or "functional fragment" refer to a fragment of an influenza virus antigen or a nucleic acid sequence encoding an influenza virus antigen that, when administered to a subject, provides an increased immune response. Fragments are generally 10 or more amino acids or nucleic acids in length. "Fragment" may mean a polypeptide fragment of an antigen that is capable of eliciting an immune response in a subject. A fragment of an antigen may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antigen, excluding any heterologous signal peptide added. The fragment may comprise a fragment of a polypeptide that is 95% or more, 96% or more, 97% or more, 98% or more or 99% or more identical to the antigen and additionally comprise an N terminal methionine or heterologous signal peptide which is not included when calculating percent identity.

A fragment of a nucleic acid sequence that encodes an antigen may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antigen and additionally optionally comprise sequence encoding an N terminal methionine or heterologous signal peptide which is not included when calculating percent identity.

"Isolated" means altered or removed from the natural state. For example, a nucleic acid or a peptide naturally present in a living subject is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleosides (nucleobase bound to ribose or deoxyribose sugar via N-glycosidic linkage) are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. The phrase nucleotide sequence that encodes a protein or an RNA may also include introns to the extent that the nucleotide sequence encoding the protein may in some version contain an intron(s). In addition, the nucleotide sequence may contain modified nucleosides that are capable of being translated by translational machinery in a cell. Exemplary modified nucleosides are described elsewhere herein. For example, an mRNA where some or all of the uridines have been replaced with pseudouridine, 1-methyl psuedouridine, or another modified nucleoside, such as those described elsewhere herein. In some embodiments, the nucleotide sequence may contain a sequence where some or all cytodines are replaced with methylated cytidine, or another modified nucleoside, such as those described elsewhere herein.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA or RNA sequences are contiguous and, where necessary to join two protein coding regions, in the same reading frame.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

In some instances, the polynucleotide or nucleic acid of the invention is a "nucleoside-modified nucleic acid," which refers to a nucleic acid comprising at least one modified nucleoside. A "modified nucleoside" refers to a nucleoside with a modification. For example, over one hundred different nucleoside modifications have been identified in RNA (Rozenski, et al., 1999, The RNA Modification Database: 1999 update. Nucl Acids Res 27: 196-197).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence. By way of one non-limiting example, a promoter that is recognized by bacteriophage RNA polymerase and is used to generate the mRNA by in vitro transcription.

The term "adjuvant" as used herein is defined as any molecule to enhance an antigen-specific adaptive immune response.

In some embodiments, "pseudouridine" refers to $m^1acp^3\Psi$ (1-methyl-3-(3-amino-3-carboxypropyl) pseudouridine). In another embodiment, the term refers to $m^1\Psi$ (1-methylpseudouridine). In another embodiment, the term refers to $\Psi$m (2'-O-methylpseudouridine. In another embodiment, the term refers to $m^5D$ (5-methyldihydrouridine). In another embodiment, the term refers to $m^3\Psi$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

The term "lipid nanoparticle" refers to a particle having at least one dimension on the order of nanometers (e.g., 1-1,000 nm), which includes one or more lipids.

The term "lipid" refers to a group of organic compounds that are derivatives of fatty acids (e.g., esters) and are generally characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids. In some embodiments, the cationic lipid comprises a zwitterionic lipid that assumes a positive charge on pH decrease.

The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydro sphingomyelins, cephalins, and cerebrosides.

The term "anionic lipid" refers to any lipid that is negatively charged at physiological pH.

The term "polymer conjugated lipid" refers to a molecule comprising both a lipid portion and a polymer portion. An example of a polymer conjugated lipid is a pegylated lipid.

The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-s-DMG) and the like.

"Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

The terms "subject," "patient," "individual," and the like are used interchangeably herein, and refer to any animal, or cells thereof whether in vitro or in situ, amenable to the methods described herein. In some non-limiting embodiments, the patient, subject or individual is a mammal, bird, poultry, cattle, pig, horse, sheep, ferret, primate, dog, cat, guinea pig, rabbit, bat, or human.

A "disease" is a state of health of a subject wherein the subject cannot maintain homeostasis, and wherein if the disease is not ameliorated then the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, such as a human.

To "treat" a disease as the term is used herein, means to reduce the frequency or severity of at least one sign or symptom of a disease or disorder experienced by a subject.

An "effective amount" as used herein, means an amount which provides a therapeutic or prophylactic benefit.

The term "therapeutic" as used herein means a treatment and/or prophylaxis. A therapeutic effect is obtained by suppression, diminution, remission, prevention, or eradication of at least one sign or symptom of a disease or disorder.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, PA), which is incorporated herein by reference.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for inducing an immune response against influenza virus in a subject. In some embodiments, the invention provides a composition comprising at least one nucleoside-modified RNA encoding at least one influenza virus antigen. For example, in one embodiment, the composition is a vaccine comprising at least one nucleoside-modified RNA encoding at least one influenza virus antigen, wherein the vaccine induces an immune response in the subject to various influenza viruses, and therefore the vaccine is a universal influenza vaccine. In some embodiments, the at least one nucleoside-modified RNA encodes HA antigen or a fragment thereof, NA antigen or a fragment thereof, NP antigen or a fragment thereof, M1 antigen or a fragment thereof, M2 ion channel antigen or a fragment thereof, or any combination thereof. In one embodiment, the nucleoside-modified RNA is a nucleoside-modified mRNA. In some embodiments, the at least one nucleoside-modified RNA is encapsulated in an LNP.

Vaccine

In one embodiment, the present invention provides an immunogenic composition for inducing an immune response against influenza virus in a subject. For example, in one embodiment, the immunogenic composition is a vaccine. For a composition to be useful as a vaccine, the composition must induce an immune response against the influenza virus antigen in a cell, tissue or subject. In some embodiments, the composition induces an immune response against the influenza virus antigen in a cell, tissue or subject. In some instances, the vaccine induces a protective immune response in the subject.

A vaccine of the present invention may vary in its composition of nucleic acid and/or cellular components. In one embodiment, the vaccine comprises a nucleic acid encoding an influenza virus antigen. In a non-limiting example, a nucleic acid encoding an influenza virus antigen might also be formulated with an adjuvant. Of course, it will be understood that various compositions described herein may further comprise additional components. For example, one or more vaccine components may be comprised in a lipid, liposome, or lipid nanoparticle. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

In various embodiments, the induction of immunity by the expression of the influenza virus antigen can be detected by observing in vivo or in vitro the response of all or any part of the immune system in the host against the influenza virus antigen.

For example, a method for detecting the induction of cytotoxic T lymphocytes is well known. A foreign substance that enters the living body is presented to T cells and B cells by the action of antigen presenting cells (APCs). Some T cells that respond to the antigen presented by APC in an antigen specific manner differentiate into cytotoxic T cells (also referred to as cytotoxic T lymphocytes or CTLs) due to stimulation by the antigen. These antigen-stimulated cells then proliferate. This process is referred to herein as "activation" of T cells. Therefore, CTL induction by an epitope of a polypeptide or peptide or combinations thereof can be evaluated by presenting an epitope of a polypeptide or peptide or combinations thereof to a T cell by APC, and detecting the induction of CTL. Furthermore, APCs have the effect of activating B cells, CD4+ T cells, CD8+ T cells, macrophages, eosinophils and NK cells.

A method for evaluating the inducing action of CTL using dendritic cells (DCs) as APC is well known in the art. DC is a representative APC having a robust CTL inducing action among APCs. In the methods of the invention, the epitope of a polypeptide or peptide or combinations thereof is initially expressed by the DC and then this DC is contacted with T cells. Detection of T cells having cytotoxic effects against the cells of interest after the contact with DC shows that the epitope of a polypeptide or peptide or combinations thereof has an activity of inducing the cytotoxic T cells. Furthermore, the induced immune response can also be examined by measuring IFN-gamma produced and released by CTL in the presence of antigen-presenting cells that carry immobilized peptide or a combination of peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The antigens confirmed to possess CTL-inducing activity by these methods are antigens having DC activation effect and subsequent CTL-inducing activity. Furthermore, CTLs that have acquired cytotoxicity due to presentation of the antigen by APC can be also used as vaccines against antigen-associated disorders.

The induction of immunity by expression of the influenza virus antigen can be further confirmed by observing the induction of antibody production against the influenza virus antigen. For example, when antibodies against an antigen are induced in a laboratory subject immunized with the composition encoding the antigen, and when antigen-associated pathology is suppressed by those antibodies, the composition is determined to induce immunity.

The specificity of the antibody response induced in a subject can include binding to many regions of the delivered antigen, as well as, the induction of neutralization capable antibodies that that prevent infection or reduce disease severity.

The induction of immunity by expression of the influenza virus antigen can be further confirmed by observing the induction of T cells, such as CD4+ T cells, CD8+ T cells, or a combination thereof. For example, CD4+ T cells can also lyse target cells, but mainly supply help in the induction of other types of immune responses, including CTL and antibody generation. The type of CD4+ T cell help can be characterized, as Th1, Th2, Th9, Th17, Tregulatory (Treg), or T follicular helper (Tfh) cells. Each subtype of CD4+ T cell supplies help to certain types of immune responses. In one embodiment, the composition selectively induces T follicular helper cells, which drive potent antibody responses.

The therapeutic compounds or compositions of the invention may be administered prophylactically (i.e., to prevent a disease or disorder) or therapeutically (i.e., to treat a disease or disorder) to subjects suffering from, or at risk of (or susceptible to) developing a disease or disorder. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity, which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

Antigen

The present invention provides a composition that induces an immune response in a subject. In one embodiment, the composition comprises an influenza virus antigen. In one embodiment, the composition comprises a nucleic acid sequence, which encodes an influenza virus antigen, or a fragment or variant thereof. For example, in some embodiments, the composition comprises a nucleoside-modified RNA encoding an influenza virus antigen, or a fragment or variant thereof. In some embodiments, the composition comprises a purified, nucleoside-modified RNA encoding an influenza virus antigen, or a fragment or variant thereof. The antigen may include, but is not limited to a polypeptide, peptide, protein, virus, or cell that induces an immune response in a subject.

In various embodiments, the antigen comprises a polypeptide or peptide associated with influenza virus, such that the antigen induces an immune response against the antigen, and therefore influenza virus. In one embodiment, the antigen comprises a fragment of a polypeptide or peptide associated with influenza virus, such that the antigen induces an immune response against influenza virus.

In some embodiments, the influenza virus antigen comprises at least one glycoprotein, or a fragment or variant thereof, nucleoprotein (NP) antigen, or a fragment or variant thereof, matrix protein 1 (M1) antigen or a fragment thereof, matrix-2 (M2) ion channel antigen, or a fragment or variant thereof, or any combination thereof.

In one embodiment, the influenza virus antigen comprises at least one glycoprotein, or a fragment or variant thereof. In one embodiment, the glycoprotein antigen is a hemagglutinin (HA) antigen or a fragment thereof. In some embodiments, the HA antigen is a full length HA antigen, or a fragment or variant thereof, HA-stalk domain, or a fragment or variant thereof, HA-head domain, or a fragment or variant thereof, HA-headless domain, or a fragment or variant thereof, optimized full length HA antigen, or a fragment or variant thereof, optimized HA domain, or a fragment or variant thereof, mini HA domain, or a fragment or variant thereof, or any combination thereof.

For example, in one embodiment, the at least one influenza virus antigen is a combination of a HA-stalk domain or a fragment thereof, full length NA antigen or a fragment thereof, full length NP antigen or a fragment thereof, and full length M2 ion channel antigen or a fragment thereof.

In one embodiment, the HA antigen comprises an amino acid sequence set forth in: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or any combination thereof. Other amino acid sequences for HA antigens are known in the art, including but not limited to, amino acid sequences for HA-headless domains (see, e.g., U.S. Pat. No. 9,051,359 and U.S. Patent Application Publication No. 2019/0314490 A1) and amino acid sequences for mini HA domains (see e.g., International Publication No. WO 2014/191435 A1), each of which is incorporated herein in its entirety by reference.

In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 2 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 4 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 6 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 8 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 10 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 12 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 14 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 16 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 18 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 20 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 22 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 24 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 26 or a fragment or variant thereof, wherein the nucleic acid sequence comprises at least one modified nucleoside. In one embodiment, the composition comprises a nucleoside-modified RNA comprising a nucleic acid sequence encoding HA antigen or a fragment thereof, wherein the nucleic acid sequence is encoded by a DNA sequence comprising SEQ ID NO: 28 or a fragment or variant thereof, wherein the nucleic acid sequence comprises at least one modified nucleoside.

Other nucleic acid sequences encoding the nucleoside-modified RNA encoding HA antigens are known in the art, including but not limited to, nucleic acid sequences encoding the nucleoside-modified RNA encoding HA-headless domains (see, e.g., U.S. Pat. No. 9,051,359 and U.S. Patent Application Publication No. 2019/0314490 A1) and nucleic acid sequences encoding the nucleoside-modified RNA encoding mini HA domains (see e.g., International Publication No. WO 2014/191435 A1), each of which is incorporated herein in its entirety by reference.

In one embodiment, the glycoprotein antigen is a neuraminidase (NA) antigen, or a fragment or variant thereof. In some embodiments, the NA antigen is a full length NA antigen, or a fragment or variant thereof, NA-stalk domain, or a fragment or variant thereof, NA-head domain, or a fragment or variant thereof, NA-head domain with tetramerization domains, or a fragment or variant thereof, secreted NA domain, or a fragment or variant thereof, optimized full length NA antigen, or a fragment or variant thereof, optimized NA domain, or a fragment or variant thereof, or any combination thereof.

In one embodiment, the NA antigen comprises an amino acid sequence set forth in: SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, or any combination thereof.

In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 30 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 32 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 34 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 36 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 38 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 40 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 42 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 44 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 46 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 48 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 50 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 52 or a fragment or variant thereof, wherein the nucleic acid sequence comprises at least one modified nucleoside. In one embodiment, the composition comprises a nucleoside-modified RNA comprising a nucleic acid sequence encoding NA antigen or a fragment thereof, wherein the nucleic acid sequence is encoded by a DNA sequence comprising SEQ ID NO: 54 or a fragment or variant thereof, wherein the nucleic acid sequence comprises at least one modified nucleoside.

In some embodiments, the influenza virus antigen comprises at least one NP antigen, or a fragment or variant thereof. In some embodiments, the NP antigen is a full length NP antigen, or a fragment or variant thereof, optimized full length NP antigen, or a fragment or variant thereof, optimized NP domain, or a fragment or variant thereof, or any combination thereof.

In one embodiment, the NP antigen comprises an amino acid sequence set forth in SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, or any combination thereof.

In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 56 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 58 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 60 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 62 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 64 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 66 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 68 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 70 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 72 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 74 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 76 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 78 or a fragment or variant thereof, wherein the nucleic acid sequence comprises at least one modified nucleoside. In one embodiment, the composition comprises a nucleoside-modified RNA comprising a nucleic acid sequence encoding NP antigen or a fragment thereof, wherein the nucleic acid sequence is encoded by a DNA sequence comprising SEQ ID NO: 80 or a fragment or variant thereof, wherein the nucleic acid sequence comprises at least one modified nucleoside.

In some embodiments, the influenza virus antigen is at least one M2 ion channel protein antigen, or a fragment or variant thereof. In some embodiments, the M2 ion channel antigen is a full length M2 ion channel antigen, or a fragment or variant thereof, optimized full length M2 ion channel antigen, or a fragment or variant thereof, optimized M2 ion channel domain, or a fragment or variant thereof, full length M2 ion channel antigen or a fragment or variant thereof, M2 ion channel-extracellular domain or a fragment or variant thereof, M2 ion channel-intracellular domain or a fragment or variant thereof, or any combination thereof.

In one embodiment, the M2 ion channel antigen comprises an amino acid sequence set forth in SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, or any combination thereof.

In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 82 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 84 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 86 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 88 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 90 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 92 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 94 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 96 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 98 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 100 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 102 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 104 or a fragment or variant thereof, wherein the nucleic acid sequence comprises at least one modified nucleoside. In one embodiment, the composition comprises a nucleoside-modified RNA comprising a nucleic acid sequence encoding M2 ion channel antigen or a fragment thereof, wherein the nucleic acid sequence is encoded by a DNA sequence comprising SEQ ID NO: 106 or a fragment or variant thereof, wherein the nucleic acid sequence comprises at least one modified nucleoside.

In some embodiments, the influenza virus antigen comprises at least one M1 antigen, or a fragment or variant thereof. In some embodiments, the M1 antigen is a full length M1 antigen, or a fragment or variant thereof, optimized full length M1 antigen, or a fragment or variant thereof, optimized M1 domain, or a fragment or variant thereof, or any combination thereof.

In one embodiment, the M1 antigen comprises an amino acid sequence set forth in SEQ ID NO: 107 or a variant or fragment thereof.

In one embodiment, the composition comprises a nucleoside-modified RNA comprising a nucleic acid sequence encoding M1 antigen or a fragment thereof, wherein the nucleic acid sequence is encoded by a DNA sequence comprising SEQ ID NO: 108 or a fragment or variant thereof, wherein the nucleic acid sequence comprises at least one modified nucleoside.

In some embodiments, the influenza virus antigen is at least one glycoprotein antigen, or a fragment or variant thereof, NP antigen, or a fragment or variant thereof, M2 ion channel protein antigen, or a fragment or variant thereof. In some embodiments, the influenza virus antigen is at least one HA antigen, or a fragment or variant thereof, NA antigen, or a fragment or variant thereof, NP antigen, or a fragment or variant thereof, M1 antigen, or a fragment or variant thereof, or M2 ion channel protein antigen, or a fragment or variant thereof. In some embodiments, the influenza virus antigen comprises an amino acid sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, or any combination thereof.

Thus, in one embodiment, the composition comprises a nucleoside-modified RNA comprising a nucleic acid sequence encoding influenza virus antigen comprising an amino acid sequence comprising at least one of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, or a fragment or variant thereof, wherein the nucleic acid sequence comprises at least one modified nucleoside. Additional examples of such amino acid sequences are provided in amino acid sequences as set forth in SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, or a fragment or variant thereof, and/or in U.S. Pat. No. 10,328,144, the disclosure of which is hereby incorporated by reference herein in its entirety.

For example, in one embodiment, the at least one influenza virus antigen is a combination of a HA-stalk domain comprising an amino acid sequence as set forth in SEQ ID NO: 27, full length NA antigen comprising an amino acid sequence as set forth in SEQ ID NO: 41, full length NP antigen comprising an amino acid sequence as set forth in SEQ ID NO: 67, and full length M2 ion channel antigen comprising an amino acid sequence as set forth in SEQ ID NO: 93. In one embodiment, the at least one influenza virus antigen is a combination of a fragment of HA-stalk domain comprising an amino acid sequence as set forth in SEQ ID NO: 27, fragment of full length NA antigen comprising an amino acid sequence as set forth in SEQ ID NO: 41, fragment of full length NP antigen comprising an amino acid sequence as set forth in SEQ ID NO: 67, and fragment of full length M2 ion channel antigen comprising an amino acid sequence as set forth in SEQ ID NO: 93.

In some embodiments, the composition comprises a nucleoside-modified RNA comprising a nucleic acid sequence encoding an influenza virus antigen, wherein the nucleic acid sequence is encoded by a DNA sequence comprising at least one of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, or a fragment or variant thereof, wherein the nucleic acid sequence comprises at least one modified nucleoside. Additional examples of such nucleic acid sequences are provided in U.S. Pat. No. 10,328,144, the disclosure of which is hereby incorporated by reference herein in its entirety.

For example, in one embodiment, the composition comprises a nucleoside-modified RNA comprising a nucleic acid sequence encoding at least one HA antigen, or a fragment or variant thereof, NA antigen, or a fragment or variant thereof, NP antigen, or a fragment or variant thereof, M1 antigen, or a fragment or variant thereof, or M2 ion channel antigen, or a fragment or variant thereof, wherein the nucleic acid sequence is encoded by a DNA sequence comprising at least one of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, or a fragment or variant thereof, wherein the nucleic acid sequence comprises at least one modified nucleoside.

For example, in one embodiment, the at least one nucleoside-modified RNA comprises a nucleic acid sequence that is encoded by a DNA sequence comprising a combination of a nucleotide sequence as set forth in SEQ ID NO: 28, nucleotide sequence as set forth in SEQ ID NO: 42, nucleotide sequence as set forth in SEQ ID NO: 68, and nucleotide sequence as set forth in SEQ ID NO: 94.

In one embodiment, the antigen comprises a protein comprising a signal peptide (SP) from MHC class II. Other signal peptides that may be used include, but are not limited to, signal sequences derived from IL-2, tPA, mouse and human IgG, and synthetic optimized signal sequences.

The influenza virus antigen may be of any type or strain of influenza virus. For example, in one embodiment, the influenza virus antigen is a protein, or fragment thereof, of an influenza virus strain including, but not limited to, an influenza virus A strain, or a fragment or variant thereof, influenza virus B strain, or a fragment or variant thereof, influenza virus C strain, or a fragment or variant thereof, influenza virus D strain, or a fragment or variant thereof, or any combination thereof. In one embodiment, the influenza virus antigen is a protein, or fragment thereof, of an influenza virus strain including, but not limited to, H1N1 strain, or a fragment or variant thereof, H2N2 strain, or a fragment or variant thereof, H3N2 strain, or a fragment or variant thereof, H5N1 strain, or a fragment or variant thereof, H7N7 strain, or a fragment or variant thereof, H1N2 strain, or a fragment or variant thereof, H9N2 strain, or a fragment or variant thereof, H7N2 strain, or a fragment or variant thereof, H7N3 strain, or a fragment or variant thereof, H10N7 strain, or a fragment or variant thereof, H7N9 strain, or a fragment or variant thereof, H6N1 strain, or a fragment or variant thereof, and any combination thereof.

In one embodiment, the influenza virus antigen is a protein, or fragment thereof, of an influenza virus strain including, but not limited to, an influenza HA group 1 virus strain, or a fragment or variant thereof, influenza NA group 1 virus strain, or a fragment or variant thereof, and any combination thereof. In one embodiment, the influenza HA group 1 virus strain includes, but is not limited to, H1 strain, or a fragment or variant thereof, H2 strain, or a fragment or variant thereof, H3 strain, or a fragment or variant thereof, H4 strain, or a fragment or variant thereof, H5 strain, or a fragment or variant thereof, H6 strain, or a fragment or variant thereof, H7 strain, or a fragment or variant thereof, H8 strain, or a fragment or variant thereof, H9 strain, or a fragment or variant thereof, H10 strain, or a fragment or variant thereof, H11 strain, or a fragment or variant thereof, H12 strain, or a fragment or variant thereof, H13 strain, or a fragment or variant thereof, H15 strain, or a fragment or variant thereof, H15 strain, or a fragment or variant thereof, H16 strain, or a fragment or variant thereof, H17 strain, or a fragment or variant thereof, H18 strain, or a fragment or variant thereof, and any combination thereof. In one embodiment, the influenza NA group 1 virus strain includes, but is not limited to, N1 strain, or a fragment or variant thereof, N2 strain, or a fragment or variant thereof, N3 strain, or a fragment or variant thereof, N4 strain, or a fragment or variant thereof, N5 strain, or a fragment or variant thereof, N6 strain, or a fragment or variant thereof, N7 strain, or a fragment or variant thereof, N8 strain, or a fragment or variant thereof, N9 strain, or a fragment or variant thereof, N10 strain, or a fragment or variant thereof, N11 strain, or a fragment or variant thereof, and any combination thereof.

In some embodiments, the influenza virus antigen comprises an amino acid sequence that is substantially homologous to the amino acid sequence of an influenza virus antigen described herein and retains the immunogenic function of the original amino acid sequence. For example, in some embodiments, the amino acid sequence of the influenza virus antigen has a degree of identity with respect to the original amino acid sequence of at least 60%, of at least 65%, of at least 70%, of at least 75%, of at least 80%, of at least 85%, of at least 90%, of at least 91%, of at least 92%, of at least 93%, of at least 94%, of at least 95%, of at least 96%, of at least 97%, of at least 98%, of at least 99%, or of at least 99.5%.

In one embodiment, the influenza virus antigen is encoded by a nucleic acid sequence of a nucleic acid molecule. In some embodiments, the nucleic acid sequence comprises DNA, RNA, cDNA, viral DNA, a variant thereof, a fragment thereof, or a combination thereof. In one embodiment, the nucleic acid sequence comprises a modified nucleic acid sequence. For example, in one embodiment the influenza virus antigen-encoding nucleic acid sequence comprises nucleoside-modified RNA, as described in detail elsewhere herein. In some instances, the nucleic acid sequence comprises include additional sequences that encode linker or tag sequences that are linked to the antigen by a peptide bond.

Adjuvant

In one embodiment, the composition comprises an adjuvant. In one embodiment, the composition comprises a nucleic acid molecule encoding an adjuvant. In one embodiment, the adjuvant-encoding nucleic acid molecule is IVT RNA. In one embodiment, the adjuvant-encoding nucleic acid molecule is nucleoside-modified RNA. In one embodiment, the adjuvant-encoding nucleic acid molecule is nucleoside-modified mRNA.

Exemplary adjuvants include, but are not limited to, alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHIC, CD80, CD86. Other genes which may be useful adjuvants include those encoding: MCP-I, MIP-Ia, MIP-Ip, IL-8, RANTES, L-selectin, P-selectin, E-selectin, CD34, GlyCAM-1, MadCAM-1, LFA-I, VLA-I, Mac-1, p150.95, PECAM, ICAM-I, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-I, DR3, TRAMP, Apo-3, AIR, LARD, NGRF, DR4, DR5, KILLER, TRAIL-R2, TRICK2, DR6, Caspase ICE, Fos, c-jun, Sp-I, Ap-I, Ap-2, p38, p65Rel, MyD88, IRAK, TRAF6, IkB, Inactive NIK, SAP K, SAP-I, INK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP 1, TAP2, anti-CTLA4-sc, anti-LAG3-Ig, anti-TIM3-Ig, and functional fragments thereof.

In some embodiments, the composition comprises an LNP, where the LNP acts as an adjuvant.

Nucleic Acids

In one embodiment, the invention includes a nucleic acid molecule encoding an influenza virus antigen. In one embodiment, the invention includes a nucleoside-modified nucleic acid molecule. In one embodiment, the nucleoside-modified nucleic acid molecule encodes an influenza virus antigen. In one embodiment, the nucleoside-modified nucleic acid molecule encodes a plurality of antigens, including one or more influenza virus antigens. In some embodiments, the nucleoside-modified nucleic acid molecule encodes an influenza virus antigen that induces an adaptive immune response against the influenza virus antigen. In one embodiment, the invention includes a nucleoside-modified nucleic acid molecule encoding an adjuvant.

The nucleic acid molecule can be made using any methodology in the art, including, but not limited to, in vitro transcription, chemical synthesis, or the like.

The nucleotide sequences encoding an influenza virus antigen or adjuvant, as described herein, can alternatively comprise sequence variations with respect to the original nucleotide sequences, for example, substitutions, insertions and/or deletions of one or more nucleotides, with the condition that the resulting polynucleotide encodes a polypeptide according to the invention. Therefore, the scope of the present invention includes nucleotide sequences that are substantially homologous to the nucleotide sequences recited herein and encode an influenza virus antigen or adjuvant of interest.

A nucleotide sequence that is substantially homologous to a nucleotide sequence encoding an antigen can typically be isolated from a producer organism of the antigen based on the information contained in the nucleotide sequence by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art.

Further, the scope of the invention includes nucleotide sequences that encode amino acid sequences that are substantially homologous to the amino acid sequences recited herein and preserve the immunogenic function of the original amino acid sequence.

In one embodiment, the invention relates to a construct, comprising a nucleotide sequence encoding an influenza virus antigen. In one embodiment, the construct comprises a plurality of nucleotide sequences encoding a plurality of influenza virus antigens. For example, in some embodiments, the construct encodes 1 or more, 2 or more, 3 or more, or all influenza virus antigens. In one embodiment, the invention relates to a construct, comprising a nucleotide sequence encoding an adjuvant. In one embodiment, the construct comprises a first nucleotide sequence encoding an influenza virus antigen and a second nucleotide sequence encoding an adjuvant.

In one embodiment, the composition comprises a plurality of constructs, each construct encoding one or more influenza virus antigens. In some embodiments, the composition comprises 1 or more, 2 or more, 3 or more, 4 or more, 5 or more, 6 or more, 7 or more, 8 or more, 9 or more, 10 or more, 15 or more, or 20 or more constructs. In one embodiment, the composition comprises about 5 to 11 constructs. In one embodiment, the composition comprises a first construct, comprising a nucleotide sequence encoding an influenza virus antigen; and a second construct, comprising a nucleotide sequence encoding an adjuvant.

In another particular embodiment, the construct is operatively bound to a translational control element. The construct can incorporate an operatively bound regulatory sequence for the expression of the nucleotide sequence of the invention, thus forming an expression cassette.

Vectors

The nucleic acid sequences coding for the influenza virus antigen or adjuvant can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The nucleic acid can be cloned into a number of types of vectors. For example, the nucleic acid can be cloned into a vector including, but not limited to a plasmid, a phagemid, a phage derivative, an animal virus, a PCR-generated linear DNA sequence, and a cosmid. Vectors of particular interest include expression vectors, replication vectors, probe generation vectors, sequencing vectors and vectors optimized for in vitro transcription.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, carbohydrates, peptides, cationic polymers, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/RNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as it is more readily evaporated than methanol.

Regardless of the method used to introduce exogenous nucleic acids into a host cell or otherwise expose a cell to a composition of the present invention, in order to confirm the presence of the mRNA sequence in the host cell, a variety of assays may be performed. Such assays include, for example, "molecular biological" assays well known to those of skill in the art, such as Northern blotting and RT-PCR; "biochemical" assays, such as detecting the presence or absence of a particular peptide, e.g., by immunogenic means (ELISAs and Western blots) or by assays described herein to identify agents falling within the scope of the invention.

In Vitro Transcribed RNA

In one embodiment, the composition of the invention comprises in vitro transcribed (IVT) RNA encoding an influenza virus antigen. In one embodiment, the composition of the invention comprises IVT RNA encoding a plurality of influenza virus antigens. In one embodiment, the composition of the invention comprises IVT RNA encoding an adjuvant. In one embodiment, the composition of the invention comprises IVT RNA encoding one or more influenza virus antigens and one or more adjuvants.

In one embodiment, an IVT RNA can be introduced to a cell as a form of transient transfection. The RNA is produced by in vitro transcription using a plasmid DNA template generated synthetically. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. In one embodiment, the desired template for in vitro transcription is an influenza virus antigen capable of inducing an adaptive immune response. In one embodiment, the desired template for in vitro transcription is an adjuvant capable of enhancing an adaptive immune response.

In one embodiment, the DNA to be used for PCR contains an open reading frame. The DNA can be from a naturally occurring DNA sequence from the genome of an organism. In one embodiment, the DNA is a full-length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. In another embodiment, the DNA to be used for PCR is a gene from a pathogenic or commensal organism, including bacteria, viruses, parasites, and fungi. In another embodiment, the DNA to be used for PCR is from a pathogenic or commensal organism, including bacteria, viruses, parasites, and fungi, including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that induce or enhance an adaptive immune response in an organism. In some instances, the genes are useful for a short term treatment. In some instances, the genes have limited safety concerns regarding dosage of the expressed gene.

In various embodiments, a plasmid is used to generate a template for in vitro transcription of mRNA, which is used for transfection.

Chemical structures with the ability to promote stability and/or translation efficiency may also be used. In some embodiments, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 RNA polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability of mRNA in the cell. On a circular DNA template, for instance, plasmid DNA, RNA polymerase produces a long concatameric product, which is not suitable for expression in eukaryotic cells. The transcription of plasmid DNA linearized at the end of the 3' UTR results in normal sized mRNA, which is effective in eukaryotic transfection when it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003)).

The conventional method of integration of polyA/T stretches into a DNA template is molecular cloning. However, polyA/T sequence integrated into plasmid DNA can cause plasmid instability, which can be ameliorated through the use of recombination incompetent bacterial cells for plasmid propagation.

Poly(A) tails of RNAs can be further extended following in vitro transcription with the use of a poly(A) polymerase, such as *E. coli* polyA polymerase (E-PAP) or yeast polyA polymerase. In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to mRNA molecules. In one embodiment, RNAs produced by the methods to include a 5' cap1 structure. Such cap1 structure can be generated using Vaccinia capping enzyme and 2'-O-methyltransferase enzymes (CellScript, Madison, WI). Alternatively, 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001)). In some embodiments RNA of the invention is introduced to a cell with a method comprising the use of TransIT®-mRNA transfection Kit (Mirus, Madison WI), which, in some instances, provides high efficiency, low toxicity, transfection.

Nucleoside-Modified RNA

In one embodiment, the composition of the present invention comprises a nucleoside-modified nucleic acid encoding an influenza virus antigen as described herein. In one embodiment, the composition of the present invention comprises a nucleoside-modified nucleic acid encoding a plurality of antigens, including one or more influenza virus antigens. In one embodiment, the composition of the present invention comprises a nucleoside-modified nucleic acid encoding an adjuvant as described herein. In one embodiment, the composition of the present invention comprises a nucleoside-modified nucleic acid encoding one or more influenza virus antigens and one or more adjuvants.

In one embodiment, the composition of the present invention comprises a series of nucleoside-modified nucleic acid encoding one or more influenza virus antigens that change for each subsequent injection to follow the lineage scheme.

For example, in one embodiment, the composition comprises a nucleoside-modified RNA. In one embodiment, the composition comprises a nucleoside-modified mRNA. Nucleoside-modified mRNA have particular advantages over non-modified mRNA, including for example, increased stability, low or absent innate immunogenicity, and enhanced translation. Nucleoside-modified mRNA useful in the present invention is further described in U.S. Pat. Nos. 8,278,036, 8,691,966, and 8,835,108, each of which is incorporated by reference herein in its entirety.

In some embodiments, nucleoside-modified mRNA does not activate any pathophysiologic pathways, translates very efficiently and almost immediately following delivery, and serve as templates for continuous protein production in vivo lasting for several days to weeks (Karikó et al., 2008, Mol Ther 16:1833-1840; Karikó et al., 2012, Mol Ther 20:948-953). The amount of mRNA required to exert a physiological effect is small, making it applicable for human therapy.

For example, as described herein, nucleoside-modified mRNA encoding an influenza virus antigen has demonstrated the ability to induce antigen-specific antibody production. For example, in some instances, antigen encoded by nucleoside-modified mRNA induces greater production of antigen-specific antibody production as compared to antigen encoded by non-modified mRNA.

In some instances, expressing a protein by delivering the encoding mRNA has many benefits over methods that use protein, plasmid DNA or viral vectors. During mRNA transfection, the coding sequence of the desired protein is the only substance delivered to cells, thus avoiding all the side effects associated with plasmid backbones, viral genes, and viral proteins. More importantly, unlike DNA- and viral-based vectors, the mRNA does not carry the risk of being incorporated into the genome and protein production starts immediately after mRNA delivery. For example, high levels of circulating proteins have been measured within 15 to 30 minutes of in vivo injection of the encoding mRNA. In some embodiments, using mRNA rather than the protein also has many advantages. Half-lives of proteins in the circulation or in tissues are often short, thus protein treatment would need frequent dosing, while mRNA provides a template for continuous protein production for several days to weeks. Purification of proteins is problematic and they can contain aggregates and other impurities that cause adverse effects (Kromminga and Schellekens, 2005, Ann NY Acad Sci 1050:257-265).

In some embodiments, the nucleoside-modified RNA comprises the naturally occurring modified-nucleoside pseudouridine. In some embodiments, inclusion of pseudouridine makes the mRNA more stable, non-immunogenic, and highly translatable (Karikó et al., 2008, Mol Ther 16:1833-1840; Anderson et al., 2010, Nucleic Acids Res 38:5884-5892; Anderson et al., 2011, Nucleic Acids Research 39:9329-9338; Karikó et al., 2011, Nucleic Acids Research 39:e142; Karikó et al., 2012, Mol Ther 20:948-953; Karikó et al., 2005, Immunity 23:165-175).

It has been demonstrated that the presence of modified nucleosides, including pseudouridines in RNA suppress their innate immunogenicity (Karikó et al., 2005, Immunity 23:165-175). Further, protein-encoding, in vitro-transcribed RNA containing pseudouridine can be translated more efficiently than RNA containing no or other modified nucleosides (Karikó et al., 2008, Mol Ther 16:1833-1840). Subsequently, it is shown that the presence of pseudouridine improves the stability of RNA (Anderson et al., 2011, Nucleic Acids Research 39:9329-9338) and abates both activation of PKR and inhibition of translation (Anderson et al., 2010, Nucleic Acids Res 38:5884-5892).

Similar effects as described for pseudouridine have also been observed for RNA containing 1-methyl-pseudouridine.

In some embodiments, the nucleoside-modified nucleic acid molecule is a purified nucleoside-modified nucleic acid molecule. For example, in some embodiments, the composition is purified to remove double-stranded contaminants. In some instances, a preparative high-performance liquid chromatography (HPLC) purification procedure is used to obtain pseudouridine-containing RNA that has superior translational potential and no innate immunogenicity (Karikó et al., 2011, Nucleic Acids Research 39:e142). Administering HPLC-purified, pseudouridine-containing RNA coding for erythropoietin into mice and macaques resulted in a significant increase of serum EPO levels (Karikó et al., 2012, Mol Ther 20:948-953), thus confirming that pseudouridine-containing mRNA is suitable for in vivo protein therapy. In some embodiments, the nucleoside-modified nucleic acid molecule is purified using non-HPLC methods. In some instances, the nucleoside-modified nucleic acid molecule is purified using chromatography methods, including but not limited to HPLC and fast protein liquid chromatography (FPLC). An exemplary FPLC-based purification procedure is described in Weissman et al., 2013, Methods Mol Biol, 969: 43-54. Exemplary purification procedures are also described in U.S. Patent Application Publication No. US2016/0032316, which is hereby incorporated by reference in its entirety.

The present invention encompasses RNA, oligoribonucleotide, and polyribonucleotide molecules comprising pseudouridine or a modified nucleoside. In some embodiments, the composition comprises an isolated nucleic acid encoding an antigen, wherein the nucleic acid comprises a pseudouridine or a modified nucleoside. In some embodiments, the composition comprises a vector, comprising an isolated nucleic acid encoding an antigen, adjuvant, or combination thereof, wherein the nucleic acid comprises a pseudouridine or a modified nucleoside.

In one embodiment, the nucleoside-modified RNA of the invention is IVT RNA, as described elsewhere herein. For example, in some embodiments, the nucleoside-modified RNA is synthesized by T7 phage RNA polymerase. In another embodiment, the nucleoside-modified mRNA is synthesized by SP6 phage RNA polymerase. In another embodiment, the nucleoside-modified RNA is synthesized by T3 phage RNA polymerase.

In one embodiment, the modified nucleoside is $m^1acp^3\Psi$ (1-methyl-3-(3-amino-3-carboxypropyl) pseudouridine. In another embodiment, the modified nucleoside is $m^1\Psi$ (1-methylpseudouridine). In another embodiment, the modified nucleoside is $\Psi$m (2'-O-methylpseudouridine). In another embodiment, the modified nucleoside is $m^5D$ (5-methyldihydrouridine). In another embodiment, the modified nucleoside is $m^3\Psi$ (3-methylpseudouridine). In another embodiment, the modified nucleoside is a pseudouridine moiety that is not further modified. In another embodiment, the modified nucleoside is a monophosphate, diphosphate, or triphosphate of any of the above pseudouridines. In another embodiment, the modified nucleoside is any other pseudouridine-like nucleoside known in the art.

In another embodiment, the nucleoside that is modified in the nucleoside-modified RNA the present invention is uridine (U). In another embodiment, the modified nucleoside is cytidine (C). In another embodiment, the modified nucleoside is adenosine (A). In another embodiment, the modified nucleoside is guanosine (G).

In another embodiment, the modified nucleoside of the present invention is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is $\Psi$ (pseudouridine). In another embodiment, the modified nucleoside is Um (2'-O-methyluridine).

In other embodiments, the modified nucleoside is $m^1A$ (1-methyladenosine); $m^2A$ (2-methyladenosine); Am (2'-O-methyladenosine); $ms^2m6A$ (2-methylthio-$N^6$-methyladenosine); $i^6A$ ($N^6$-isopentenyladenosine); $ms^2i6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl) adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2{}_2G$ ($N^2$,$N^2$-dimethylguanosine); $m^2Gm$ ($N^2$,2'-O-dimethylguanosine); $m^2{}_2Gm$ ($N^2$,$N^2$,2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $nCm^5U$ (5-carbamoylmethyluridine); $nCm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6{}_2A$ ($N^6$, $N^6$-dimethyladenosine); Im (2'-O-methylinosine); $m^4C$ ($N^4$-methylcytidine); $m^4Cm$ ($N^4$,2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6{}_2Am$ ($N^6$,$N^6$,O-2'-trimethyladenosine); $m^{2,7}G$ ($N^2$,7-dimethylguanosine); $m^{2,2,7}G$ ($N^2$,$N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); or $ac^6A$ ($N^6$-acetyladenosine).

In another embodiment, a nucleoside-modified RNA of the present invention comprises a combination of 2 or more of the above modifications. In another embodiment, the nucleoside-modified RNA comprises a combination of 3 or more of the above modifications. In another embodiment, the nucleoside-modified RNA comprises a combination of more than 3 of the above modifications.

In various embodiments, between 0.1% and 100% of the residues in the nucleoside-modified RNA of the present invention are modified (e.g., either by the presence of pseudouridine, 1-methyl-pseudouridine, or another modified nucleoside base). In one embodiment, the fraction of modified residues is 0.1%. In another embodiment, the fraction of modified residues is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.7%. In another embodiment, the fraction is 0.8%. In another embodiment, the fraction is 0.9%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 7%. In another embodiment, the fraction is 8%. In another embodiment, the fraction is 9%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 55%. In another embodiment, the fraction is 60%. In another embodiment, the fraction is 65%. In another embodiment, the fraction is 70%. In another embodiment, the fraction is 75%. In another embodiment, the fraction is 80%. In another embodiment, the fraction is 85%. In another embodiment, the fraction is 90%. In another embodiment, the fraction is 91%. In another embodiment, the fraction is 92%. In another embodiment, the fraction is 93%. In another embodiment, the fraction is 94%. In another embodiment, the fraction is 95%. In another embodiment, the fraction is 96%. In another embodiment, the fraction is 97%. In another embodiment, the fraction is 98%. In another embodiment, the fraction is 99%. In another embodiment, the fraction is 100%.

In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 8%. In another embodiment, the fraction is less than 10%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, 0.1% of the residues of a given nucleoside (i.e., uridine, cytidine, guanosine, or adenosine) are modified. In another embodiment, the fraction of modified residues is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.7%. In another embodiment, the fraction is 0.8%. In another embodiment, the fraction is 0.9%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 7%. In another embodiment, the fraction is 8%. In another embodiment, the fraction is 9%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 55%. In another embodiment, the fraction is 60%. In another embodiment, the fraction is 65%. In another embodiment, the fraction is 70%. In another embodiment, the fraction is 75%. In another embodiment, the fraction is 80%. In another embodiment, the fraction is 85%. In another embodiment, the fraction is 90%. In another embodiment, the fraction is 91%. In another embodiment, the fraction is 92%. In another embodiment, the fraction is 93%. In another embodiment, the fraction is 94%. In another embodiment, the fraction is 95%. In another embodiment, the fraction is 96%. In another embodiment, the fraction is 97%. In another embodiment, the fraction is 98%. In another embodiment, the fraction is 99%. In another embodiment, the fraction is 100%. In another embodiment, the fraction of the given nucleotide that is modified is less than 8%. In another embodiment, the fraction is less than 10%. In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In some embodiments, the composition comprises a purified preparation of single-stranded nucleoside modified RNA. For example, in some embodiments, the purified preparation of single-stranded nucleoside modified RNA is substantially free of double stranded RNA (dsRNA). In some embodiments, the purified preparation is at least 90%, or at least 91%, or at least 92%, or at least 93% or at least 94%, or at least 95%, or at least 96%, or at least 97%, or at least 98%, or at least 99%, or at least 99.5%, or at least 99.9% single stranded nucleoside modified RNA, relative to all other nucleic acid molecules (DNA, dsRNA, etc.).

In another embodiment, a nucleoside-modified RNA of the present invention is translated in the cell more efficiently than an unmodified RNA molecule with the same sequence. In another embodiment, the nucleoside-modified RNA exhibits enhanced ability to be translated by a target cell. In another embodiment, translation is enhanced by a factor of 2-fold relative to its unmodified counterpart. In another embodiment, translation is enhanced by a 3-fold factor. In another embodiment, translation is enhanced by a 4-fold factor. In another embodiment, translation is enhanced by a 5-fold factor. In another embodiment, translation is enhanced by a 6-fold factor. In another embodiment, translation is enhanced by a 7-fold factor. In another embodiment, translation is enhanced by an 8-fold factor. In another embodiment, translation is enhanced by a 9-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts.

In another embodiment, the nucleoside-modified antigen-encoding RNA of the present invention induces a significantly more robust adaptive immune response as compared with an unmodified in vitro-synthesized RNA molecule of the same sequence. In another embodiment, the modified RNA molecule induces an adaptive immune response that is 2-fold greater than its unmodified counterpart. In another embodiment, the adaptive immune response is increased by a 3-fold factor. In another embodiment, the adaptive immune response is increased by a 4-fold factor. In another embodiment, the adaptive immune response is increased by a 5-fold factor. In another embodiment, the adaptive immune response is increased by a 6-fold factor. In another embodiment, the adaptive immune response is increased by a 7-fold factor. In another embodiment, the adaptive immune response is increased by an 8-fold factor. In another embodiment, the adaptive immune response is increased by a 9-fold factor. In another embodiment, the adaptive immune response is increased by a 10-fold factor. In another embodiment, the adaptive immune response is increased by a 15-fold factor. In another embodiment, the adaptive immune response is increased by a 20-fold factor. In another embodiment, the adaptive immune response is increased by a 50-fold factor. In another embodiment, the adaptive immune response is increased by a 100-fold factor. In another embodiment, the adaptive immune response is increased by a 200-fold factor. In another embodiment, the adaptive immune response is increased by a 500-fold factor. In another embodiment, the adaptive immune response is increased by a 1000-fold factor. In another embodiment, the adaptive immune response is increased by a 2000-fold factor. In another embodiment, the adaptive immune response is increased by another fold difference.

In another embodiment, "induces significantly more robust adaptive immune response" refers to a detectable increase in an adaptive immune response. In another embodiment, the term refers to a fold increase in the adaptive immune response (e.g., 1 of the fold increases enumerated above). In another embodiment, the term refers to an increase such that the nucleoside-modified RNA can be administered at a lower dose or frequency than an unmodified RNA molecule while still inducing a similarly effective adaptive immune response. In another embodiment, the increase is such that the nucleoside-modified RNA can be administered using a single dose to induce an effective adaptive immune response.

In another embodiment, the nucleoside-modified RNA of the present invention exhibits significantly less innate immunogenicity than an unmodified in vitro-synthesized RNA molecule of the same sequence. In another embodiment, the modified RNA molecule exhibits an innate immune response that is 2-fold less than its unmodified counterpart. In another embodiment, innate immunogenicity is reduced by a 3-fold factor. In another embodiment, innate immunogenicity is reduced by a 4-fold factor. In another embodiment, innate immunogenicity is reduced by a 5-fold factor. In another embodiment, innate immunogenicity is reduced by a 6-fold factor. In another embodiment, innate immunogenicity is reduced by a 7-fold factor. In another embodiment, innate immunogenicity is reduced by a 8-fold factor. In another embodiment, innate immunogenicity is reduced by a 9-fold factor. In another embodiment, innate immunogenicity is reduced by a 10-fold factor. In another embodiment, innate immunogenicity is reduced by a 15-fold factor. In another embodiment, innate immunogenicity is reduced by a 20-fold factor. In another embodiment, innate immunogenicity is reduced by a 50-fold factor. In another embodiment, innate immunogenicity is reduced by a 100-fold factor. In another embodiment, innate immunogenicity is reduced by a 200-fold factor. In another embodiment, innate immunogenicity is reduced by a 500-fold factor. In another embodiment, innate immunogenicity is reduced by a 1000-fold factor. In another embodiment, innate immunogenicity is reduced by a 2000-fold factor. In another embodiment, innate immunogenicity is reduced by another fold difference.

In another embodiment, "exhibits significantly less innate immunogenicity" refers to a detectable decrease in innate immunogenicity. In another embodiment, the term refers to a fold decrease in innate immunogenicity (e.g., 1 of the fold decreases enumerated above). In another embodiment, the term refers to a decrease such that an effective amount of the nucleoside-modified RNA can be administered without triggering a detectable innate immune response. In another embodiment, the term refers to a decrease such that the nucleoside-modified RNA can be repeatedly administered without eliciting an innate immune response sufficient to detectably reduce production of the protein encoded by the modified RNA. In another embodiment, the decrease is such that the nucleoside-modified RNA can be repeatedly administered without eliciting an innate immune response sufficient to eliminate detectable production of the protein encoded by the modified RNA.

Lipid Nanoparticle

In one embodiment, delivery of nucleoside-modified RNA comprises any suitable delivery method, including exemplary RNA transfection methods described elsewhere herein. In some embodiments, delivery of a nucleoside-modified RNA to a subject comprises mixing the nucleoside-modified RNA with a transfection reagent prior to the step of contacting. In another embodiment, a method of present invention further comprises administering nucleoside-modified RNA together with the transfection reagent. In another embodiment, the transfection reagent is a cationic lipid reagent. In another embodiment, the transfection reagent is a cationic polymer reagent.

In another embodiment, the transfection reagent is a lipid-based transfection reagent. In another embodiment, the transfection reagent is a protein-based transfection reagent. In another embodiment, the transfection reagent is a carbohydrate-based transfection reagent. In another embodiment, the transfection reagent is a cationic lipid-based transfection reagent. In another embodiment, the transfection reagent is a cationic polymer-based transfection reagent. In another embodiment, the transfection reagent is a polyethyleneimine based transfection reagent. In another embodiment, the transfection reagent is calcium phosphate. In another embodiment, the transfection reagent is Lipofectin®, Lipofectamine®, or TransIT®. In another embodiment, the transfection reagent is any other transfection reagent known in the art.

In another embodiment, the transfection reagent forms a liposome. Liposomes, in another embodiment, increase intracellular stability, increase uptake efficiency and improve biological activity. In another embodiment, liposomes are hollow spherical vesicles composed of lipids arranged in a similar fashion as those lipids, which make up the cell membrane. They have, in another embodiment, an internal aqueous space for entrapping water-soluble compounds and range in size from 0.05 to several microns in diameter. In another embodiment, liposomes can deliver RNA to cells in a biologically active form.

In one embodiment, the composition comprises a lipid nanoparticle (LNP) and one or more nucleic acid molecules described herein. For example, in one embodiment, the composition comprises an LNP and one or more nucleoside-modified RNA molecules encoding one or more antigens, adjuvants, or a combination thereof.

In some embodiments, the lipid nanoparticle is a particle having at least one dimension on the order of nanometers (e.g., 1-1,000 nm). In some embodiments, the lipid nanoparticle comprises one or more lipids. For example, in some embodiments, the lipid comprises a lipid of Formula (I), (II) or (III).

In some embodiments, lipid nanoparticles are included in a formulation comprising a nucleoside-modified RNA as described herein. In some embodiments, such lipid nanoparticles comprise a cationic lipid (e.g., a lipid of Formula (I), (II) or (III)) and one or more excipient selected from neutral lipids, charged lipids, steroids and polymer conjugated lipids (e.g., a pegylated lipid such as a pegylated lipid of structure (IV). In some embodiments, the nucleoside-modified RNA is encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells, e.g., an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In some embodiments, the nucleoside-modified RNA, when present in the lipid nanoparticles, is resistant in aqueous solution to degradation with a nuclease.

The LNP may comprise any lipid capable of forming a particle to which the one or more nucleic acid molecules are attached, or in which the one or more nucleic acid molecules are encapsulated.

In one embodiment, the LNP comprises one or more cationic lipids, and one or more stabilizing lipids. Stabilizing lipids include neutral lipids and pegylated lipids.

In one embodiment, the LNP comprises a cationic lipid. In some embodiments, the cationic lipid comprises any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl) cholesterol (DC-Chol), N-(1-(2,3-dioleoyloxy)propyl)-N-2-(sperminecarboxamido)ethyl)-N,N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy) propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate (DOSPA) and (DOPE), from GIBCO/BRL); and TRANSFECTAM© (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMIDMA, 1,2-dilinoleyloxy-N,N-dimethylaminopropane (DLinDMA), 1,2-dilinolenyloxy-N,N-dimethylaminopropane (DLenDMA).

In one embodiment, the cationic lipid is an amino lipid. Suitable amino lipids useful in the invention include those described in WO 2012/016184, incorporated herein by reference in its entirety. Representative amino lipids include, but are not limited to, 1,2-dilinoleyoxy-3-(dimethylamino) acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

Suitable amino lipids include those having the formula:

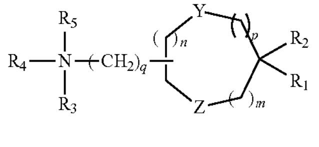

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl;

m, n, and p are either the same or different and independently either 0 or 1 with the proviso that m, n, and p are not simultaneously 0;

q is 0, 1, 2, 3, or 4; and

Y and Z are either the same or different and independently O, S, or NH.

In one embodiment, $R_1$ and $R_2$ are each linoleyl, and the amino lipid is a dilinoleyl amino lipid. In one embodiment, the amino lipid is a dilinoleyl amino lipid.

A representative useful dilinoleyl amino lipid has the formula:

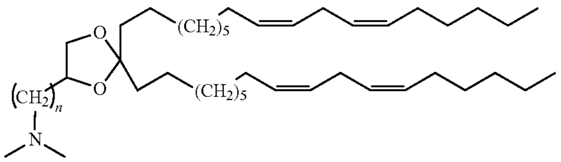

DLin-K-DMA wherein n is 0, 1, 2, 3, or 4.

In one embodiment, the cationic lipid is a DLin-K-DMA. In one embodiment, the cationic lipid is DLin-KC2-DMA (DLin-K-DMA above, wherein n is 2).

In one embodiment, the cationic lipid component of the LNPs has the structure of Formula (I):

(I)

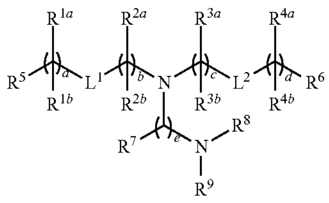

or a pharmaceutically acceptable salt, tautomer, prodrug or stereoisomer thereof, wherein:

$L^1$ and $L^2$ are each independently —O(C═O)—, —(C═O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2.

In some embodiments of Formula (I), at least one of $R^{1a}$, $R^{2a}$, $R^{3a}$ or $R^{4a}$ is $C_1$-$C_{12}$ alkyl, or at least one of $L^1$ or $L^2$ is —O(C═O)— or —(C═O)O—. In other embodiments, Ria and $R^{1b}$ are not isopropyl when a is 6 or n-butyl when a is 8.

In still further embodiments of Formula (I), at least one of $R^{1a}$, $R^{2a}$, $R^{3a}$ or $R^{4a}$ is $C_1$-$C_{12}$ alkyl, or at least one of $L^1$ or $L^2$ is —O(C═O)— or —(C═O)O—; and $R^{1a}$ and $R^{1b}$ are not isopropyl when a is 6 or n-butyl when a is 8.

In other embodiments of Formula (I), $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom; In some embodiments of Formula (I), any one of $L^1$ or $L^2$ may be —O(C═O)— or a carbon-carbon double bond. $L^1$ and $L^2$ may each be —O(C═O)— or may each be a carbon-carbon double bond.

In some embodiments of Formula (I), one of $L^1$ or $L^2$ is —O(C═O)—. In other embodiments, both $L^1$ and $L^2$ are —O(C═O)—.

In some embodiments of Formula (I), one of $L^1$ or $L^2$ is —(C═O)O—. In other embodiments, both $L^1$ and $L^2$ are —(C═O)O—.

In some other embodiments of Formula (I), one of $L^1$ or $L^2$ is a carbon-carbon double bond. In other embodiments, both $L^1$ and $L^2$ are a carbon-carbon double bond.

In still other embodiments of Formula (I), one of $L^1$ or $L^2$ is —O(C═O)— and the other of $L^1$ or $L^2$ is —(C═O)O—. In more embodiments, one of $L^1$ or $L^2$ is —O(C═O)— and the other of $L^1$ or $L^2$ is a carbon-carbon double bond. In yet more embodiments, one of L or $L^2$ is —(C═O)O— and the other of $L^1$ or $L^2$ is a carbon-carbon double bond.

It is understood that "carbon-carbon" double bond, as used throughout the specification, refers to one of the following structures:

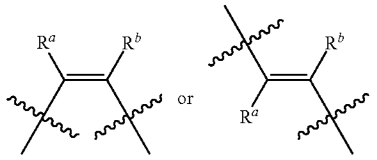

wherein $R^a$ and $R^b$ are, at each occurrence, independently H or a substituent. For example, in some embodiments $R^a$ and $R^b$ are, at each occurrence, independently H, $C_1$-$C_{12}$ alkyl or cycloalkyl, for example H or $C_1$-$C_{12}$ alkyl.

In other embodiments, the lipid compounds of Formula (I) have the following structure (Ia):

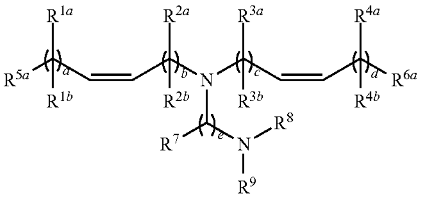
(Ia)

In other embodiments, the lipid compounds of Formula (I) have the following structure (Ib):

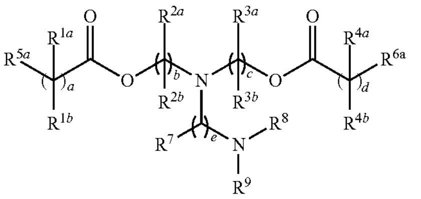
(Ib)

In yet other embodiments, the lipid compounds of Formula (I) have the following structure (Ic):

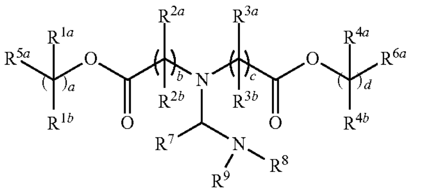
(Ic)

In some embodiments of the lipid compound of Formula (I), a, b, c and d are each independently an integer from 2 to 12 or an integer from 4 to 12. In other embodiments, a, b, c and d are each independently an integer from 8 to 12 or 5 to 9. In some embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some other embodiments of Formula (I), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some more embodiments of Formula (I), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some other embodiments of Formula (I), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments of Formula (I), a and d are the same. In some other embodiments, b and c are the same. In some other specific embodiments, a and d are the same and b and c are the same.

The sum of a and b and the sum of c and d in Formula (I) are factors which may be varied to obtain a lipid of Formula (I) having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such the sum of a and b and the sum of c and d is 12 or greater.

In some embodiments of Formula (I), e is 1. In other embodiments, e is 2.

The substituents at $R^{1a}$, $R^{2a}$, $R^{3a}$ and $R^{4a}$ of Formula (I) are not particularly limited. In some embodiments $R^{1a}$, $R^{2a}$, $R^{3a}$ and $R^{4a}$ are H at each occurrence. In some other embodiments at least one of $R^{1a}$, $R^{2a}$, $R^{3a}$ and $R^{4a}$ is $C_1$-$C_{12}$ alkyl. In some other embodiments at least one of $R^{1a}$, $R^{2a}$, $R^{3a}$ and $R^{4a}$ is $C_1$-$C_8$ alkyl. In some other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In some embodiments of Formula (I), $R^{1a}$, $R^{1b}$, $R^{4a}$ and $R^{4b}$ are $C_1$-$C_{12}$ alkyl at each occurrence.

In further embodiments of Formula (I), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In some embodiments of Formula (I), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$together with the carbon atom to which it is bound is taken together with an adjacent $R^{4b}$ and the carbon atom to which it is bound to form a carbon-carbon double bond.

The substituents at $R^5$ and $R^6$ of Formula (I) are not particularly limited in the foregoing embodiments. In some embodiments one or both of $R^5$ or $R^6$ is methyl. In some other embodiments one or both of $R^5$ or $R^6$ is cycloalkyl for example cyclohexyl. In these embodiments the cycloalkyl may be substituted or not substituted. In some other embodiments the cycloalkyl is substituted with $C_1$-$C_{12}$ alkyl, for example tert-butyl.

The substituents at $R^7$ are not particularly limited in the foregoing embodiments of Formula (I). In some embodiments at least one $R^7$ is H. In some other embodiments, $R^7$ is H at each occurrence. In some other embodiments $R^7$ is $C_1$-$C_{12}$ alkyl.

In some other of the foregoing embodiments of Formula (I), one of $R^8$ or $R^9$ is methyl. In other embodiments, both $R^8$ and $R^9$ are methyl.

In some different embodiments of Formula (I), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In various different embodiments, the lipid of Formula (I) has one of the structures set forth in Table 1 below.

TABLE 1

Representative Lipids of Formula (I).

| No. | Structure | Prep. Method |
|---|---|---|
| I-1 | 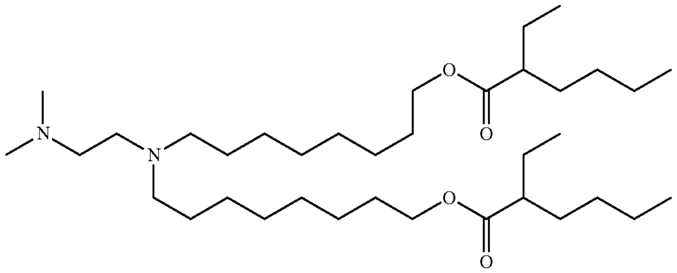 [SMILES: CCCCC(CC)C(=O)OCCCCCCCCN(CCCCCCCCOC(=O)C(CC)CCCC)CCN(C)C] | B |
| I-2 | 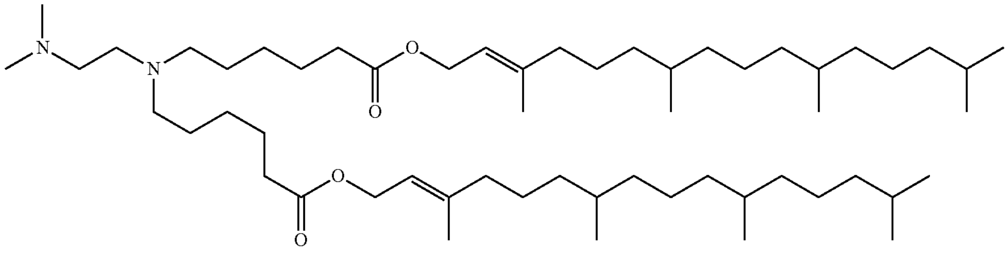 [SMILES: C/C(=C\COC(=O)CCCCCN(CCCCCC(=O)OC/C=C(\C)CCCC(C)CCCC(C)CCCC(C)C)CCN(C)C)CCCC(C)CCCC(C)CCCC(C)C] | A |
| I-3 | 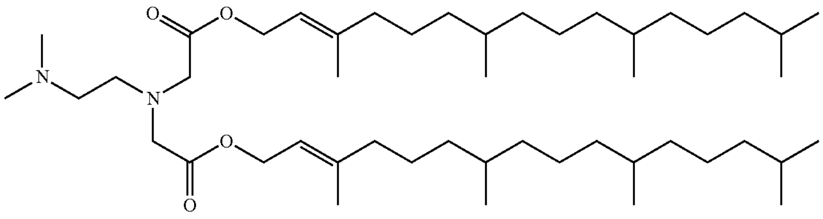 [SMILES: C/C(=C\COC(=O)CN(CCN(C)C)CC(=O)OC/C=C(\C)CCCC(C)CCCC(C)CCCC(C)C)CCCC(C)CCCC(C)CCCC(C)C] | A |
| I-4 | 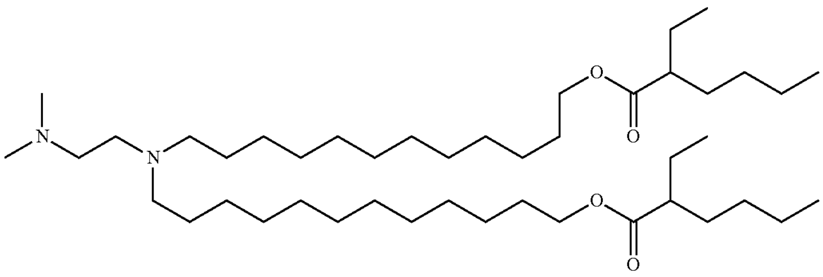 [SMILES: CCCCC(CC)C(=O)OCCCCCCCCCCCCN(CCCCCCCCCCCCOC(=O)C(CC)CCCC)CCN(C)C] | B |

TABLE 1-continued
| Representative Lipids of Formula (I). | | |
|---|---|---|
| No. | Structure | Prep. Method |
| I-5 | 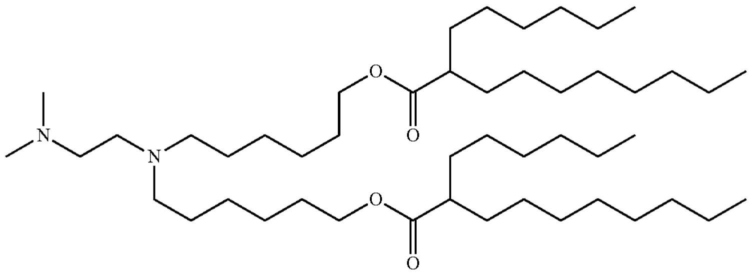 [SMILES: CCCCCCCCC(CCCCCC)C(=O)OCCCCCCN(CCCCCCOC(=O)C(CCCCCC)CCCCCCCC)CCN(C)C] | B |
| I-6 | 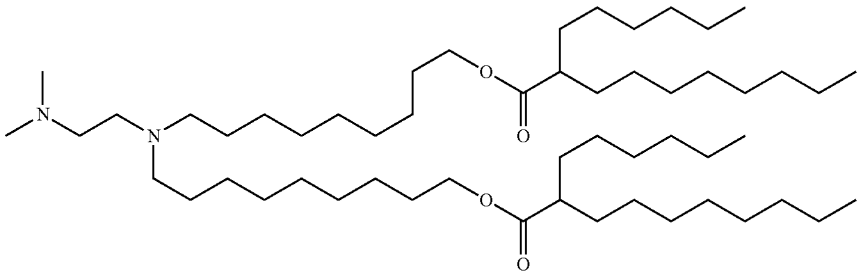 [SMILES: CCCCCCCCC(CCCCCC)C(=O)OCCCCCCCCCN(CCCCCCCCCOC(=O)C(CCCCCC)CCCCCCCC)CCN(C)C] | B |
| I-7 | 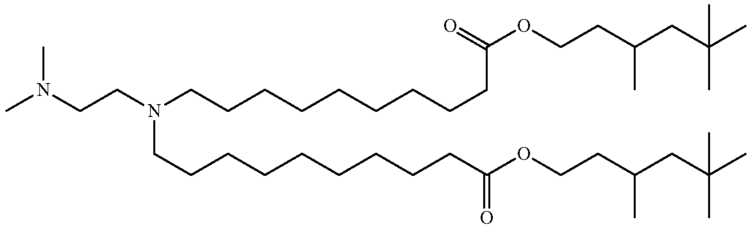 [SMILES: CC(CCOC(=O)CCCCCCCCCN(CCCCCCCCCC(=O)OCCC(C)CC(C)(C)C)CCN(C)C)CC(C)(C)C] | A |
| I-8 | 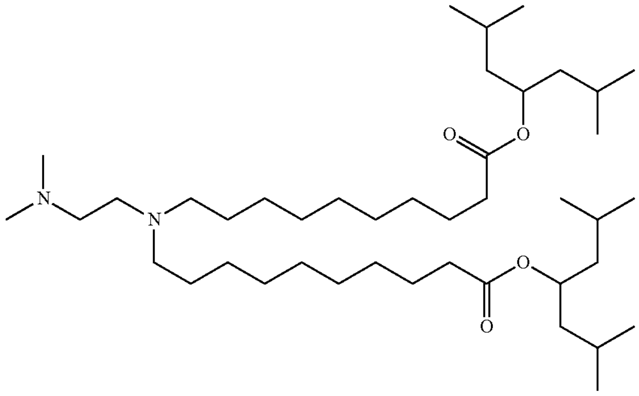 [SMILES: CC(C)CC(CC(C)C)OC(=O)CCCCCCCCCN(CCCCCCCCCC(=O)OC(CC(C)C)CC(C)C)CCN(C)C] | A |
| I-9 | 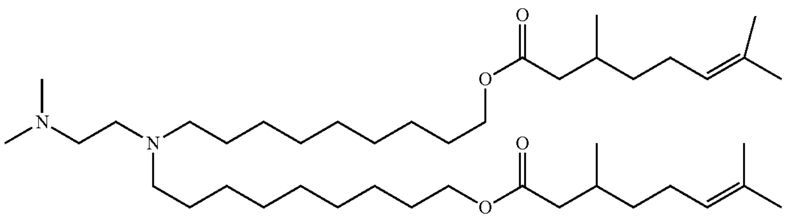 [SMILES: CC(C)=CCCC(C)CC(=O)OCCCCCCCCCN(CCCCCCCCCOC(=O)CC(C)CCC=C(C)C)CCN(C)C] | B |

TABLE 1-continued
| Representative Lipids of Formula (I). | | |
|---|---|---|
| No. | Structure | Prep. Method |
| I-10 | 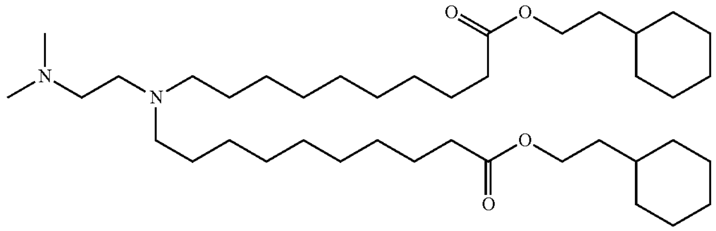 [SMILES: CN(C)CCN(CCCCCCCCCC(=O)OCCC1CCCCC1)CCCCCCCCCC(=O)OCCC1CCCCC1] | A |
| I-11 | 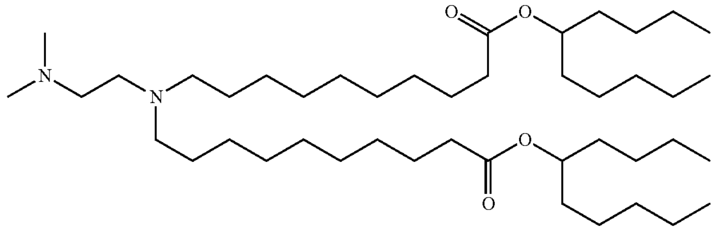 [SMILES: CCCCCC(CCCC)OC(=O)CCCCCCCCCN(CCCCCCCCCC(=O)OC(CCCC)CCCCC)CCN(C)C] | A |
| I-12 | 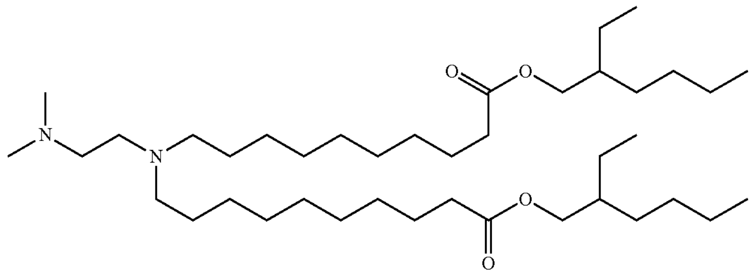 [SMILES: CCCCC(CC)COC(=O)CCCCCCCCCN(CCCCCCCCCC(=O)OCC(CC)CCCC)CCN(C)C] | A |
| I-13 | 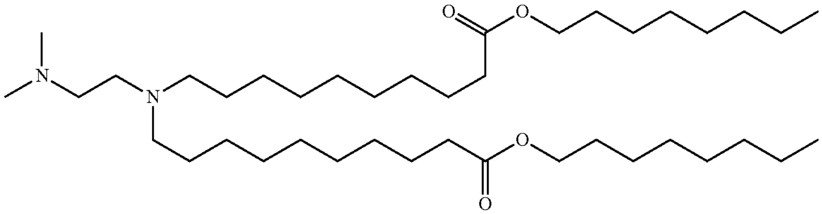 [SMILES: CCCCCCCCOC(=O)CCCCCCCCCN(CCCCCCCCCC(=O)OCCCCCCCC)CCN(C)C] | A |
| I-14 | 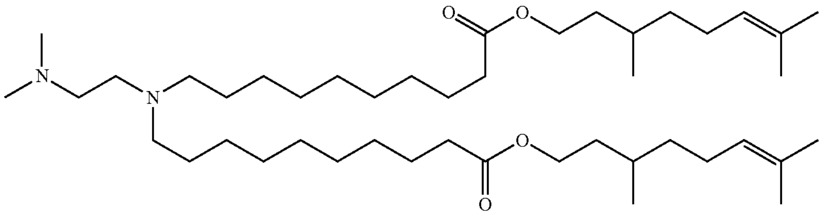 [SMILES: CC(C)=CCCC(C)CCOC(=O)CCCCCCCCCN(CCCCCCCCCC(=O)OCCC(C)CCC=C(C)C)CCN(C)C] | A |
| I-15 | 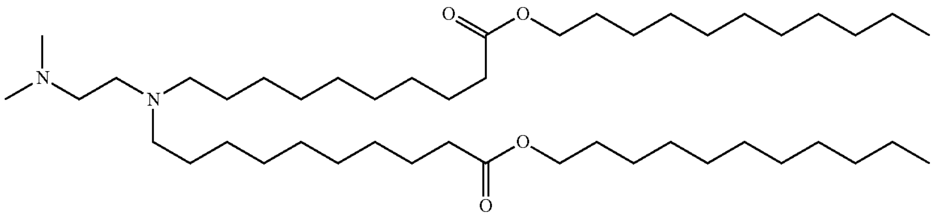 [SMILES: CCCCCCCCCCCOC(=O)CCCCCCCCCN(CCCCCCCCCC(=O)OCCCCCCCCCCC)CCN(C)C] | A |

TABLE 1-continued
Representative Lipids of Formula (I).
| No. | Structure | Prep. Method |
|---|---|---|
| I-16 | 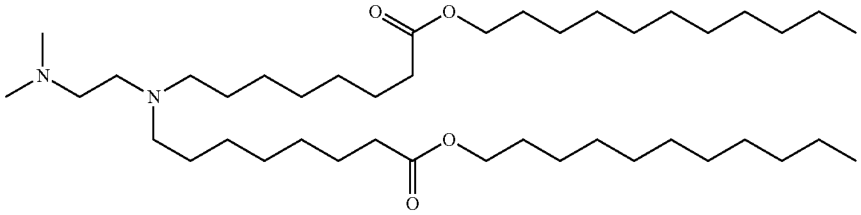 [SMILES: CCCCCCCCCCCOC(=O)CCCCCCCN(CCCCCCCC(=O)OCCCCCCCCCCC)CCN(C)C] | A |
| I-17 | 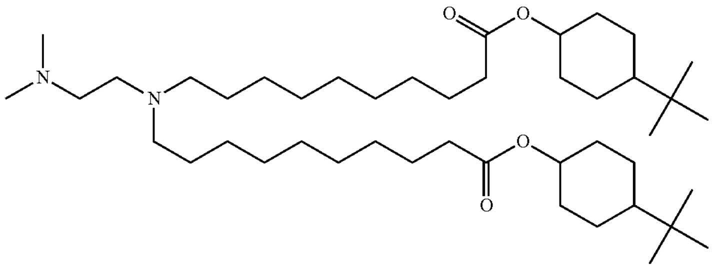 [SMILES: CN(C)CCN(CCCCCCCCCC(=O)OC1CCC(C(C)(C)C)CC1)CCCCCCCCCC(=O)OC1CCC(C(C)(C)C)CC1] | A |
| I-18 | 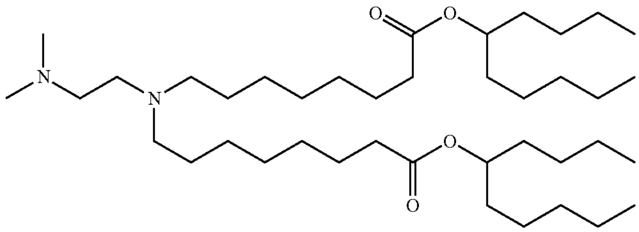 [SMILES: CCCCCC(CCCC)OC(=O)CCCCCCCN(CCCCCCCC(=O)OC(CCCC)CCCCC)CCN(C)C] | A |
| I-19 | 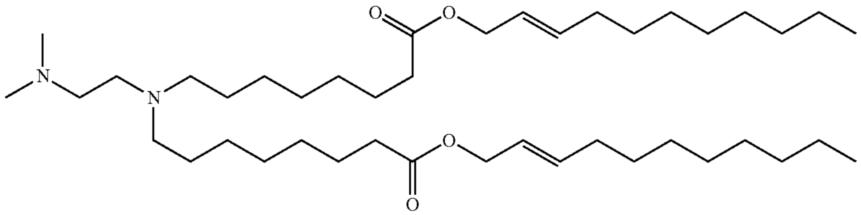 [SMILES: CCCCCCCC/C=C/COC(=O)CCCCCCCN(CCCCCCCC(=O)OC/C=C/CCCCCCCC)CCN(C)C] | A |
| I-20 | 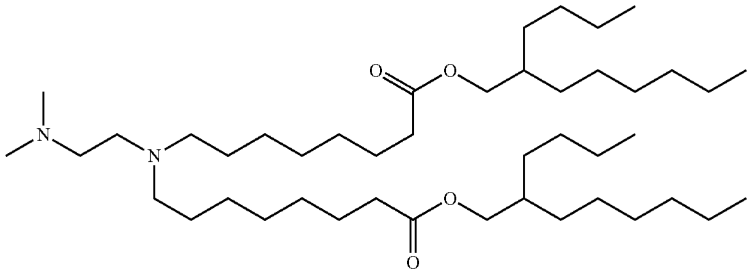 [SMILES: CCCCCCC(CCCC)COC(=O)CCCCCCCN(CCCCCCCC(=O)OCC(CCCC)CCCCCC)CCN(C)C] | A |
| I-21 | 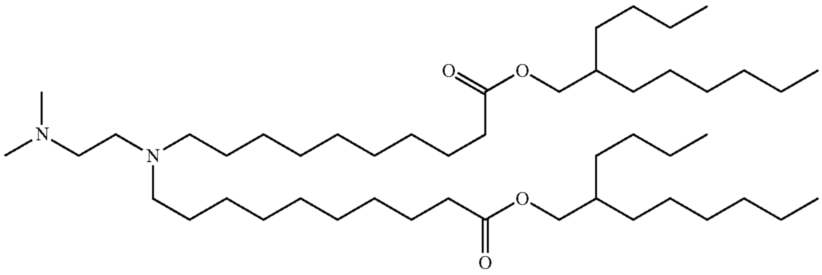 [SMILES: CCCCCCC(CCCC)COC(=O)CCCCCCCCCN(CCCCCCCCCC(=O)OCC(CCCC)CCCCCC)CCN(C)C] | A |

TABLE 1-continued
| Representative Lipids of Formula (I). | | |
|---|---|---|
| No. | Structure | Prep. Method |
| I-22 | 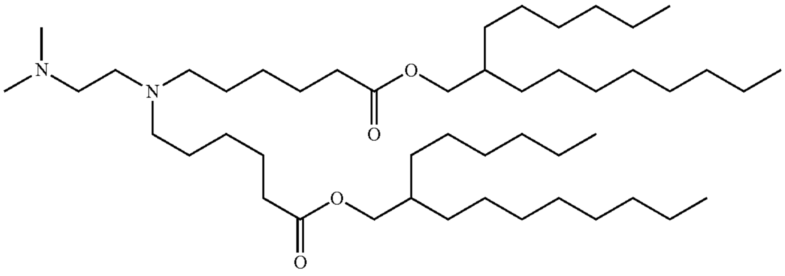 [SMILES: CCCCCCCCC(CCCCCC)COC(=O)CCCCCN(CCCCCC(=O)OCC(CCCCCC)CCCCCCCC)CCN(C)C] | A |
| I-23 | 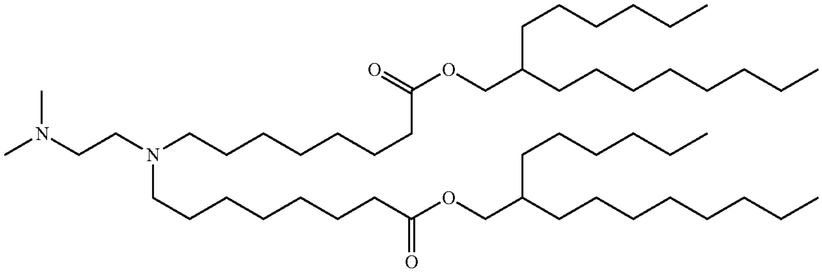 [SMILES: CCCCCCCCC(CCCCCC)COC(=O)CCCCCCCN(CCCCCCCC(=O)OCC(CCCCCC)CCCCCCCC)CCN(C)C] | A |
| I-24 | 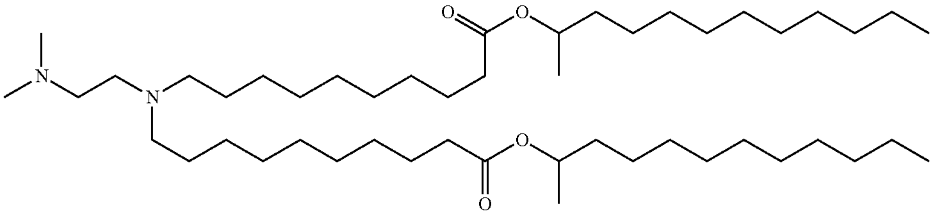 [SMILES: CCCCCCCCCCC(C)OC(=O)CCCCCCCCCN(CCCCCCCCCC(=O)OC(C)CCCCCCCCCC)CCN(C)C] | A |
| I-25 | 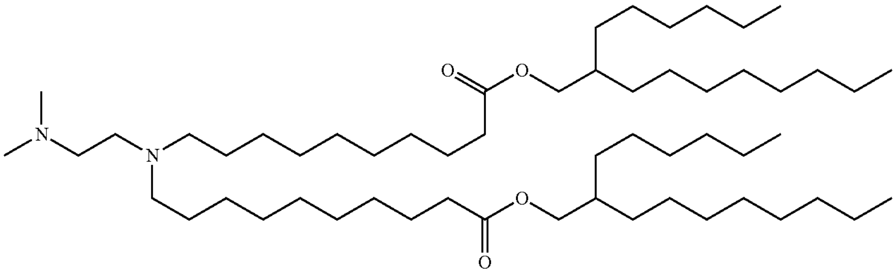 [SMILES: CCCCCCCCC(CCCCCC)COC(=O)CCCCCCCCCN(CCCCCCCCCC(=O)OCC(CCCCCC)CCCCCCCC)CCN(C)C] | A |
| I-26 | 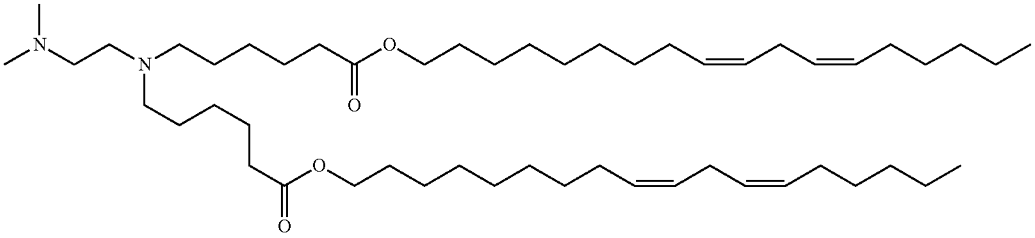 [SMILES: CCCCC/C=C\C/C=C\CCCCCCCCOC(=O)CCCCCN(CCCCCC(=O)OCCCCCCCC/C=C\C/C=C\CCCCC)CCN(C)C] | A |

TABLE 1-continued
| Representative Lipids of Formula (I). | | |
|---|---|---|
| No. | Structure | Prep. Method |
| I-27 | 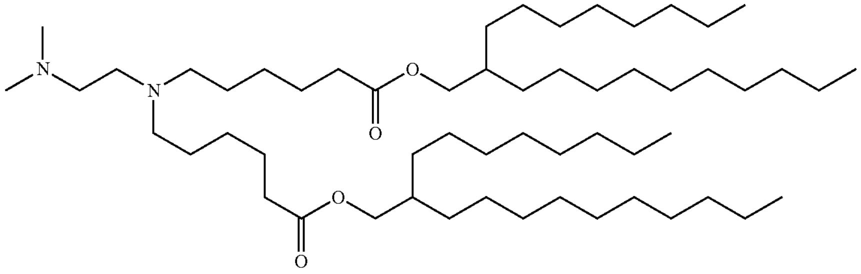 [SMILES: CCCCCCCCCCC(CCCCCCCC)COC(=O)CCCCCN(CCCCCC(=O)OCC(CCCCCCCC)CCCCCCCCCC)CCN(C)C] | A |
| I-28 | 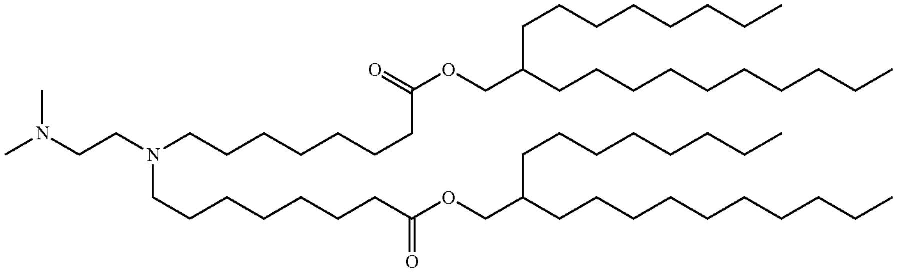 [SMILES: CCCCCCCCCCC(CCCCCCCC)COC(=O)CCCCCCCN(CCCCCCCC(=O)OCC(CCCCCCCC)CCCCCCCCCC)CCN(C)C] | A |
| I-29 | 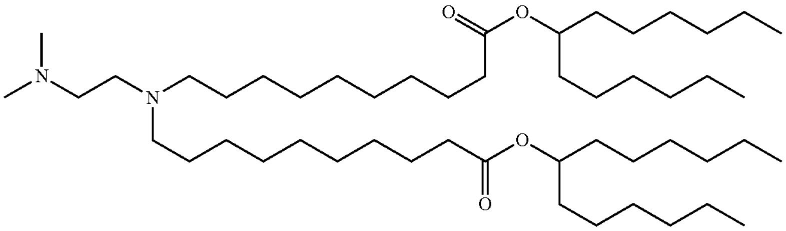 [SMILES: CCCCCCC(CCCCCC)OC(=O)CCCCCCCCCN(CCCCCCCCCC(=O)OC(CCCCCC)CCCCCC)CCN(C)C] | A |
| I-30 | 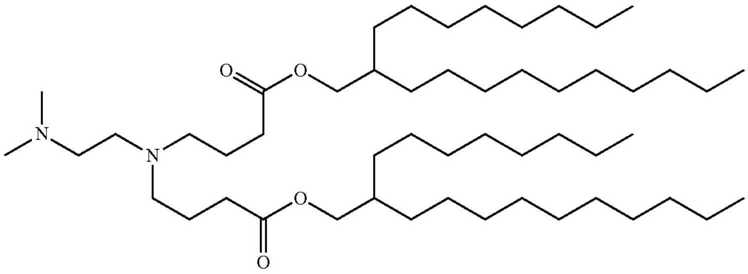 [SMILES: CCCCCCCCCCC(CCCCCCCC)COC(=O)CCCN(CCCC(=O)OCC(CCCCCCCC)CCCCCCCCCC)CCN(C)C] | A |
| I-31 | 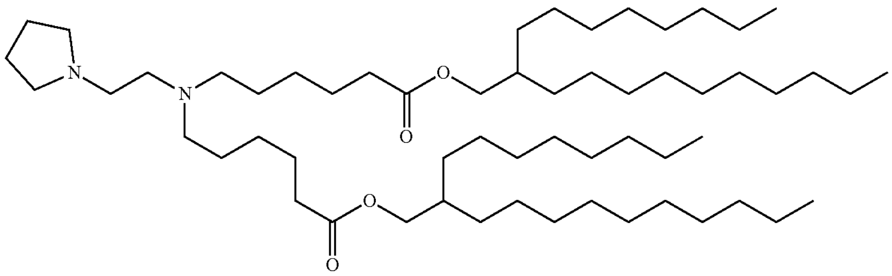 [SMILES: CCCCCCCCCCC(CCCCCCCC)COC(=O)CCCCCN(CCCCCC(=O)OCC(CCCCCCCC)CCCCCCCCCC)CCN1CCCC1] | C |

TABLE 1-continued
Representative Lipids of Formula (I).
| No. | Structure | Prep. Method |
|---|---|---|
| I-32 | 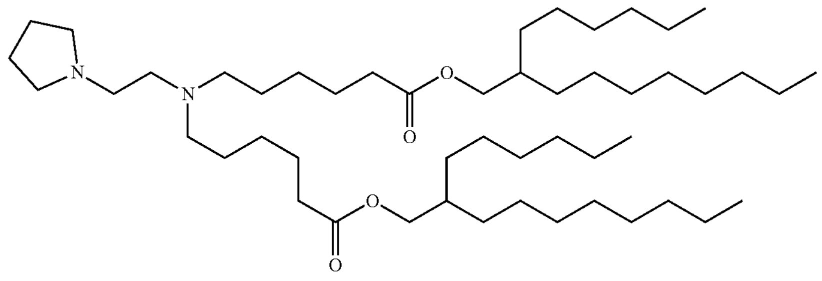 [SMILES: CCCCCCCCC(CCCCCC)COC(=O)CCCCCN(CCCCCC(=O)OCC(CCCCCC)CCCCCCCC)CCN1CCCC1] | C |
| I-33 | 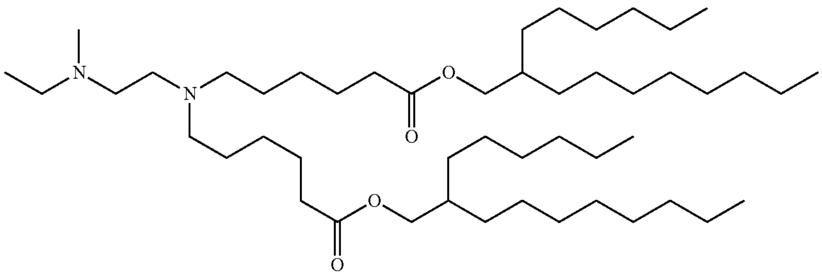 [SMILES: CCCCCCCCC(CCCCCC)COC(=O)CCCCCN(CCCCCC(=O)OCC(CCCCCC)CCCCCCCC)CCN(C)CC] | C |
| I-34 | 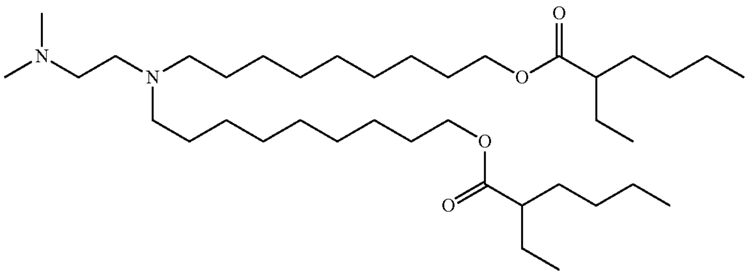 [SMILES: CCCCC(CC)C(=O)OCCCCCCCCCN(CCCCCCCCCOC(=O)C(CC)CCCC)CCN(C)C] | B |
| I-35 | 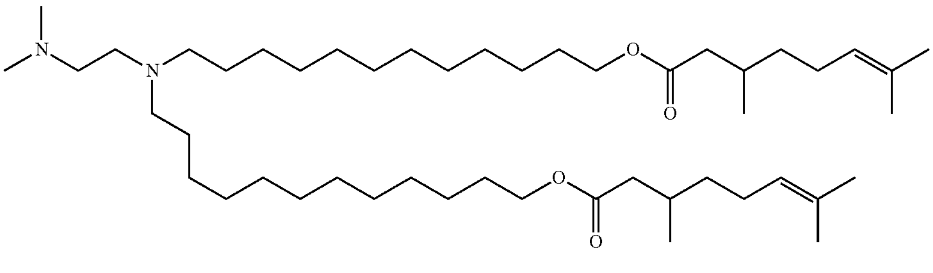 [SMILES: CC(C)=CCCC(C)CC(=O)OCCCCCCCCCCCCN(CCCCCCCCCCCCOC(=O)CC(C)CCC=C(C)C)CCN(C)C] | B |
| I-36 | 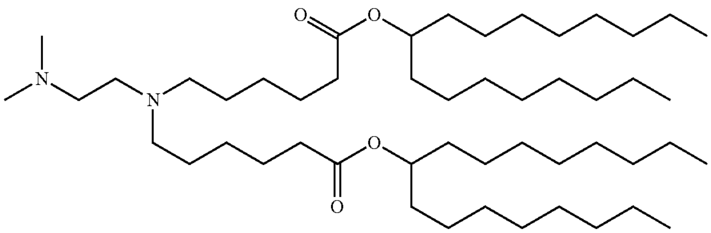 [SMILES: CCCCCCCCC(CCCCCCCC)OC(=O)CCCCCN(CCCCCC(=O)OC(CCCCCCCC)CCCCCCCC)CCN(C)C] | C |

TABLE 1-continued
| Representative Lipids of Formula (I). | | |
| --- | --- | --- |
| No. | Structure | Prep. Method |
| I-37 | 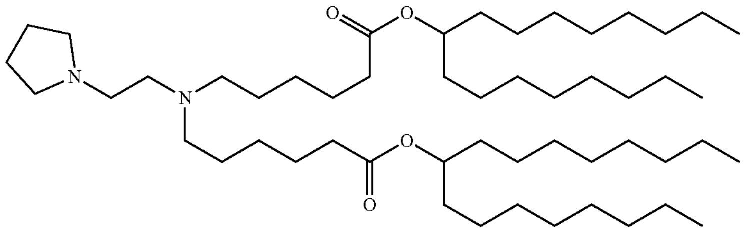 [SMILES: CCCCCCCCC(CCCCCCCC)OC(=O)CCCCCN(CCCCCC(=O)OC(CCCCCCCC)CCCCCCCC)CCN1CCCC1] | C |
| I-38 | 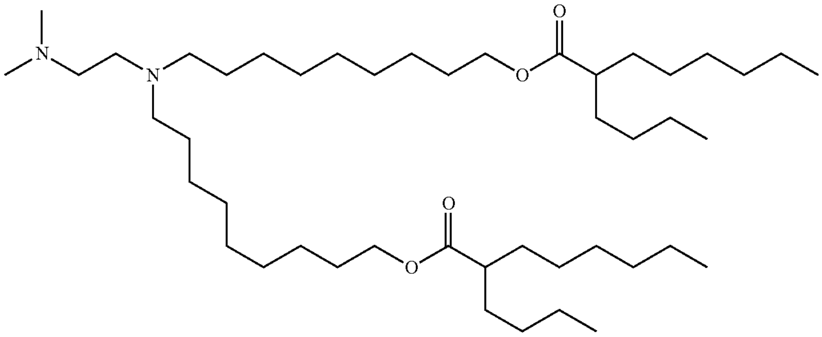 [SMILES: CCCCCCC(CCCC)C(=O)OCCCCCCCCCN(CCCCCCCCCOC(=O)C(CCCC)CCCCCC)CCN(C)C] | B |
| I-39 | 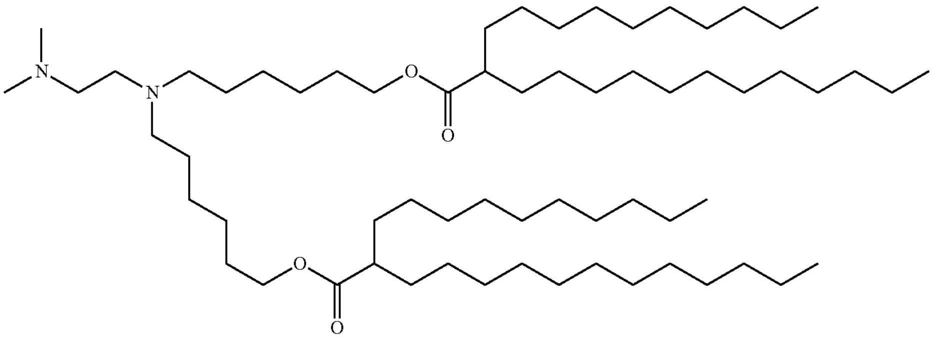 [SMILES: CCCCCCCCCCCCC(CCCCCCCCCC)C(=O)OCCCCCCN(CCCCCCOC(=O)C(CCCCCCCCCC)CCCCCCCCCCCC)CCN(C)C] | B |
| I-40 | 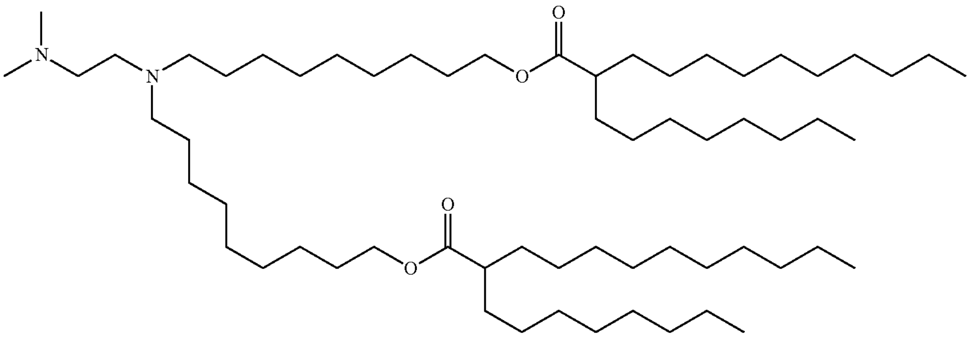 [SMILES: CCCCCCCCCCC(CCCCCCCC)C(=O)OCCCCCCCCCN(CCCCCCCCCOC(=O)C(CCCCCCCC)CCCCCCCCCC)CCN(C)C] | B |

TABLE 1-continued

Representative Lipids of Formula (I).

| No. | Structure | Prep. Method |
|---|---|---|
| I-41 | 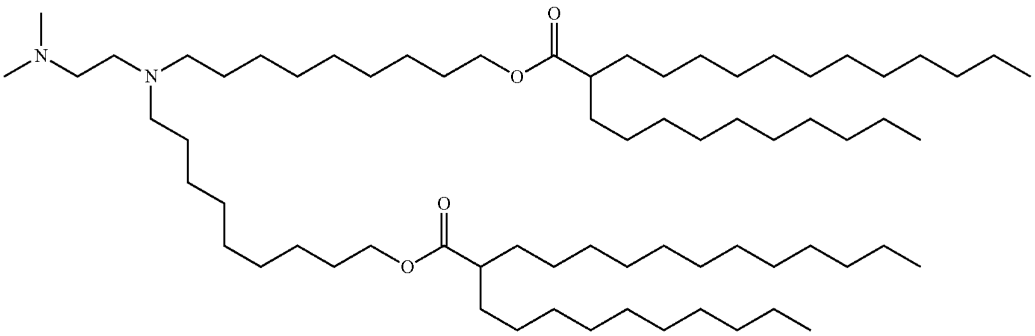 [SMILES: CCCCCCCCCCCCC(CCCCCCCCCC)C(=O)OCCCCCCCCCN(CCCCCCCCCOC(=O)C(CCCCCCCCCC)CCCCCCCCCCCC)CCN(C)C] | B |

In some embodiments, the LNPs comprise a lipid of Formula (I), a nucleoside-modified RNA and one or more excipients selected from neutral lipids, steroids and pegylated lipids. In some embodiments the lipid of Formula (I) is compound 1-5. In some embodiments the lipid of Formula (I) is compound 1-6.

In some other embodiments, the cationic lipid component of the LNPs has the structure of Formula (II):

(II)

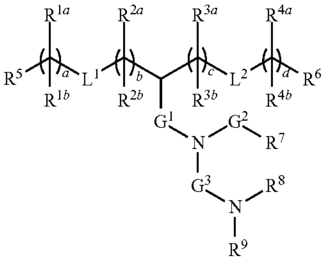

or a pharmaceutically acceptable salt, tautomer, prodrug or stereoisomer thereof, wherein:

$L^1$ and $L^2$ are each independently —O(C═O)—, —(C═O)O—, —C(═O)—, —O—, —$S(O)_x$—, —S—S—, —C(═O)S—, —SC(═O)—, —$NR^a$C(═O)—, —C(═O)$NR^a$—, —$NR^a$C(═O)$NR^a$, —OC(═O)$NR^a$—, —$NR^a$C(═O)O—, or a direct bond;

$G^1$ is $C_1$-$C_2$ alkylene, —(C═O)—, —O(C═O)—, —SC(═O)—, —$NR^a$C(═O)- or a direct bond;

$G^2$ is —C(═O)—, —(C═O)O—, —C(═O)S—, —C(═O)$NR^a$ or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either: (a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments of Formula (II), $L^1$ and $L^2$ are each independently —O(C═O)—, —(C═O)O— or a direct bond. In other embodiments, $G^1$ and $G^2$ are each independently —(C═O)— or a direct bond. In some different embodiments, $L^1$ and $L^2$ are each independently —O(C═O)—, —(C═O)O— or a direct bond; and $G^1$ and $G^2$ are each independently —(C═O)— or a direct bond.

In some different embodiments of Formula (II), $L^1$ and $L^2$ are each independently —C(═O)—, —O—, —$S(O)_x$—, —S—S—, —C(═O)S—, —SC(═O)—, —$NR^a$—, —$NR^a$C(═O)—, —C(═O)$NR^a$—, —$NR^a$C(═O)$NR^a$, —OC(═O)$NR^a$—, —$NR^a$C(═O)O—, —$NR^a$$S(O)_x$$NR^a$—, —$NR^a$$S(O)_x$— or —$S(O)_x$$NR^a$—.

In other of the foregoing embodiments of Formula (II), the lipid compound has one of the following structures (IIA) or (IIB):

(IIA)

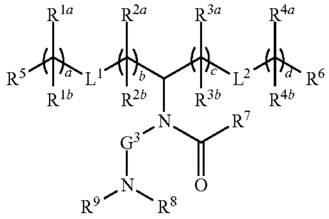

or (IIB)

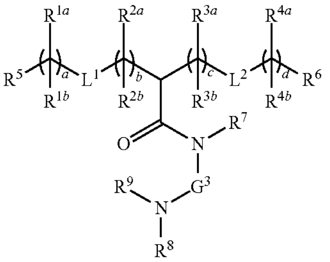

In some embodiments of Formula (II), the lipid compound has structure (IIA). In other embodiments, the lipid compound has structure (IIB).

In any of the foregoing embodiments of Formula (II), one of $L^1$ or $L^2$ is —O(C═O)—. For example, in some embodiments each of $L^1$ and $L^2$ are —O(C═O)—.

In some different embodiments of Formula (II), one of $L^1$ or $L^2$ is —(C═O)O—. For example, in some embodiments each of $L^1$ and $L^2$ is —(C═O)O—.

In different embodiments of Formula (II), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of Formula (II), for at least one occurrence of Ria and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of Formula (II), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of Formula (II), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of Formula (II), for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

In various other embodiments of Formula (II), the lipid compound has one of the following structures (IIC) or (IID):

(IIC)

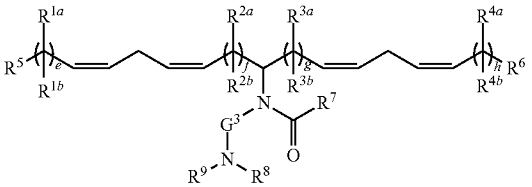

or (IID)

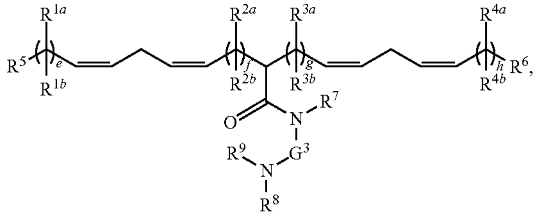

, wherein e, f, g and h are each independently an integer from 1 to 12.

In some embodiments of Formula (II), the lipid compound has structure (IIC). In other embodiments, the lipid compound has structure (IID).

In various embodiments of structures (IIC) or (IID), e, f, g and h are each independently an integer from 4 to 10.

In some embodiments of Formula (II), a, b, c and d are each independently an integer from 2 to 12 or an integer from 4 to 12. In other embodiments, a, b, c and d are each independently an integer from 8 to 12 or 5 to 9. In some embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of Formula (II), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of Formula (II), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some embodiments of Formula (II), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of Formula (II), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of Formula (II), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of Formula (II), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of Formula (II), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of Formula (II), a and d are the same. In some other embodiments, b and c are the same. In some other specific embodiments and a and d are the same and b and c are the same.

The sum of a and b and the sum of c and d of Formula (II) are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^{1a}$, $R^{2a}$, $R^{3a}$ and $R^{4a}$ of Formula (II) are not particularly limited. In some embodiments, at least one of $R^{1a}$, $R^{2a}$, $R^{3a}$ and $R^{4a}$ is H. In some embodiments $R^{1a}$, $R^{2a}$, $R^{3a}$ and $R^{4a}$ are H at each occurrence. In some other embodiments at least one of $R^{1a}$, $R^{2a}$, $R^{3a}$ and $R^{4a}$ is $C_1$-$C_{12}$ alkyl. In some other embodiments at least one of $R^{1a}$, $R^{2a}$, $R^{3a}$ and $R^{4a}$ is $C_1$-$C_8$ alkyl. In some other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In some embodiments of Formula (II), $R^{1a}$, $R^{1b}$, $R^{4a}$ and $R^{4b}$ are $C_1$-$C_{12}$ alkyl at each occurrence.

In further embodiments of Formula (II), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In some embodiments of Formula (II), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$together with the carbon atom to which it is bound is taken together with an adjacent $R^{4b}$ and the carbon atom to which it is bound to form a carbon-carbon double bond.

The substituents at $R^5$ and $R^6$ of Formula (II) are not particularly limited in the foregoing embodiments. In some embodiments one of $R^5$ or $R^6$ is methyl. In other embodiments each of $R^5$ or $R^6$ is methyl.

The substituents at $R^7$ of Formula (II) are not particularly limited in the foregoing embodiments. In some embodiments $R^7$ is $C_6$-$C_{16}$ alkyl. In some other embodiments, $R^7$ is $C_6$-$C_9$ alkyl. In some of these embodiments, $R^7$ is substituted with —(C═O)OR$^b$, —O(C═O)R$^b$, —C(═O)R$^b$, —OR$^b$, —S(O)$_x$R$^b$, —S—SR$^b$, —C(═O)SR$^b$, —SC(═O)R$^b$, —NR$^a$R$^b$, —NR$^a$C(═O)R$^b$, —C(═O)NR$^a$R$^b$, —NR$^a$C(═O)NR$^a$R$^b$, —OC(═O)NR$^a$R$^b$, —NR$^a$C(═O)OR$^b$, —NR$^a$S(O)$_x$NR$^a$R$^b$, —NR$^a$S(O)$_x$R$^b$ or —S(O)$_x$NR$^a$R$^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with —(C═O)OR$^b$ or —O(C═O)R$^b$.

In various of the foregoing embodiments of Formula (II), $R^b$ is branched $C_1$-$C_{15}$ alkyl. For example, in some embodiments $R^b$ has one of the following structures:

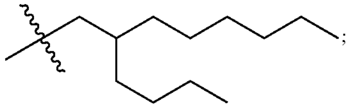
;
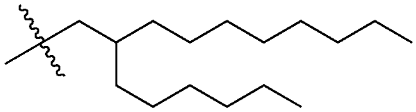
;
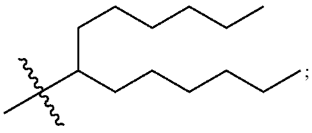
;
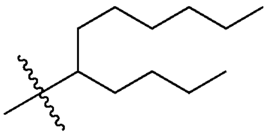
;
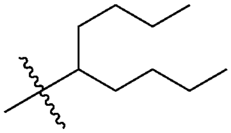
or
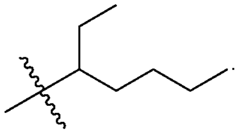
.

In some other of the foregoing embodiments of Formula (II), one of $R^8$ or $R^9$ is methyl. In other embodiments, both $R^8$ and $R^9$ are methyl.

In some different embodiments of Formula (II), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring. In some different embodiments of the foregoing, $R^8$ and $R^9$, together with the nitrogen atom to which they are attached, form a 6-membered heterocyclic ring, for example a piperazinyl ring.

In still other embodiments of the foregoing lipids of Formula (II), $G^3$ is $C_2$-$C_4$ alkylene, for example $C_3$ alkylene.

In various different embodiments, the lipid compound has one of the structures set forth in Table 2 below.
TABLE 2
Representative Lipids of Formula (II).
| No. | Structure | Prep. Method |
|---|---|---|
| II-1 | 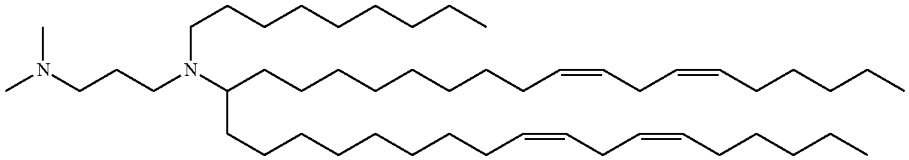 [SMILES: CCCCC/C=C\C/C=C\CCCCCCCCC(CCCCCCCC/C=C\C/C=C\CCCCC)N(CCCCCCCCC)CCCN(C)C] | D |
| II-2 | 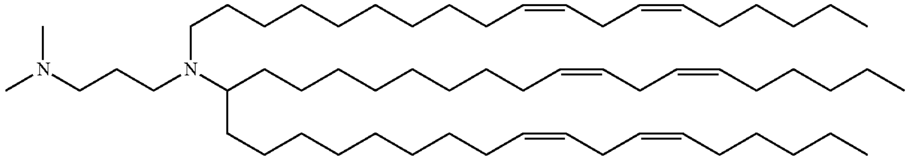 [SMILES: CCCCC/C=C\C/C=C\CCCCCCCCCN(CCCN(C)C)C(CCCCCCCC/C=C\C/C=C\CCCCC)CCCCCCCC/C=C\C/C=C\CCCCC] | D |
| II-3 | 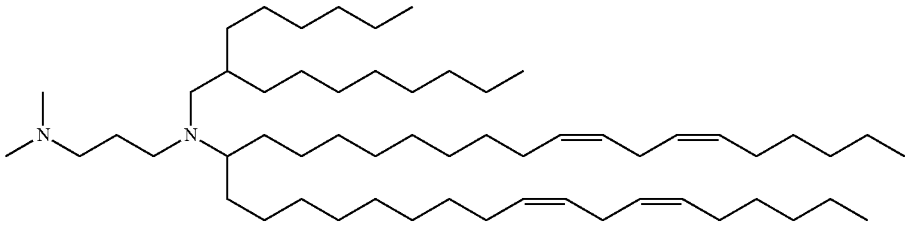 [SMILES: CCCCC/C=C\C/C=C\CCCCCCCCC(CCCCCCCC/C=C\C/C=C\CCCCC)N(CCCN(C)C)CC(CCCCCC)CCCCCCCC] | D |
| II-4 | 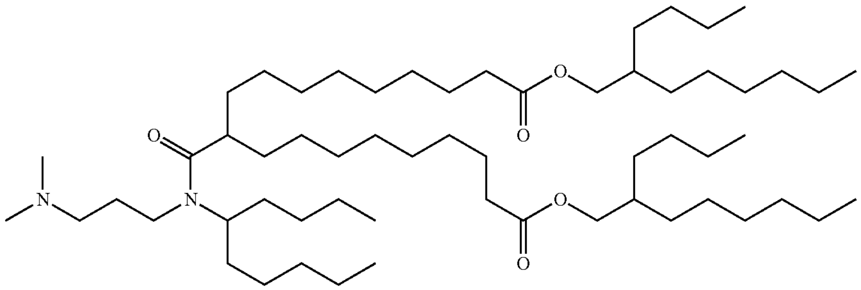 [SMILES: CCCCCCC(CCCC)COC(=O)CCCCCCCCC(CCCCCCCCC(=O)OCC(CCCC)CCCCCC)C(=O)N(CCCN(C)C)C(CCCC)CCCCC] | E |
| II-5 | 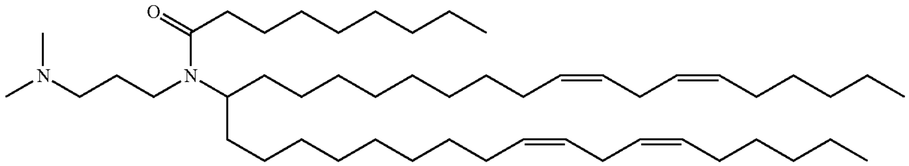 [SMILES: CCCCC/C=C\C/C=C\CCCCCCCCC(CCCCCCCC/C=C\C/C=C\CCCCC)N(CCCN(C)C)C(=O)CCCCCCCC] | D |
| II-6 | 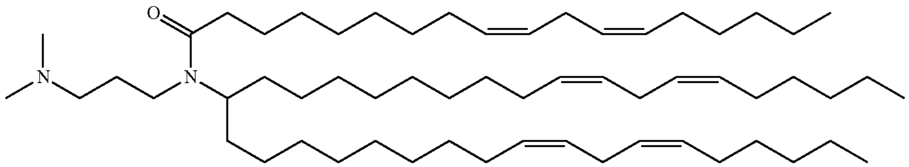 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC] | D |
| II-7 | 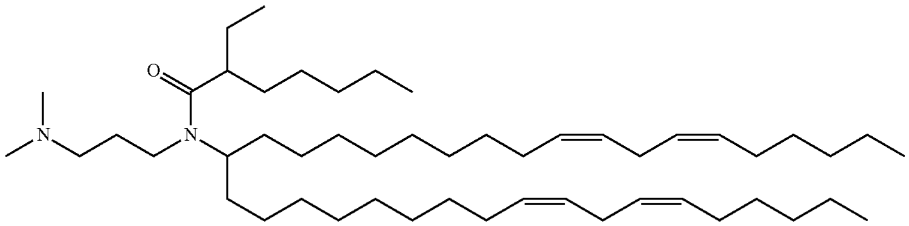 [SMILES: CCCCC/C=C\C/C=C\CCCCCCCCC(CCCCCCCC/C=C\C/C=C\CCCCC)N(CCCN(C)C)C(=O)C(CC)CCCCC] | D |

TABLE 2-continued
| Representative Lipids of Formula (II). | | |
|---|---|---|
| No. | Structure | Prep. Method |
| II-8 | 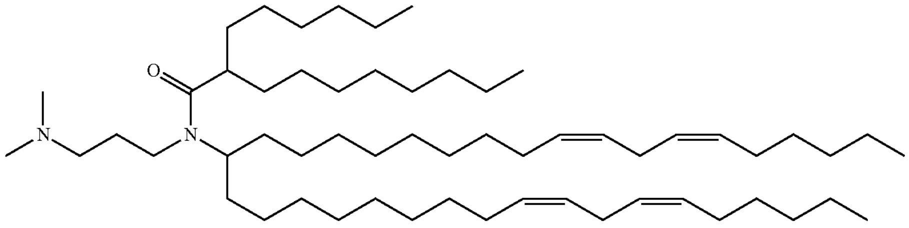 [SMILES: CCCCC/C=C\C/C=C\CCCCCCCCC(CCCCCCCC/C=C\C/C=C\CCCCC)N(CCCN(C)C)C(=O)C(CCCCCC)CCCCCCCC] | D |
| II-9 | 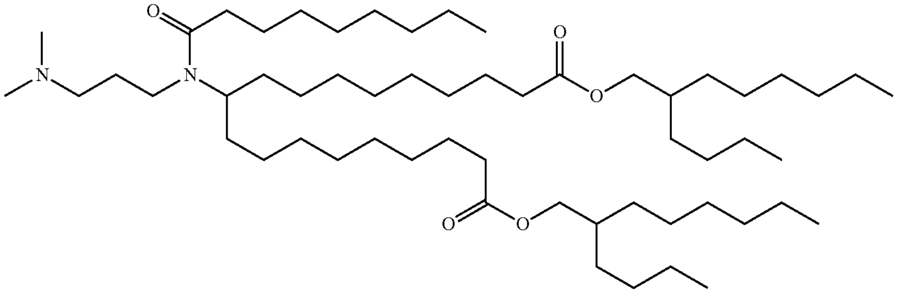 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] | D |
| II-10 | 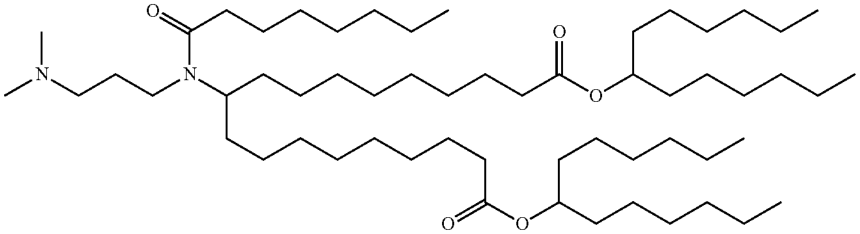 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC] | D |
| II-11 | 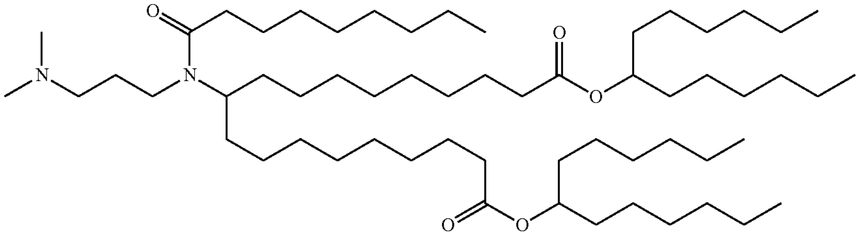 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] | D |
| II-12 | 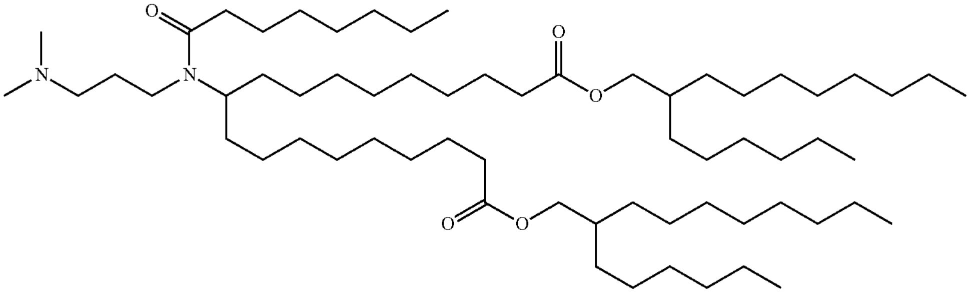 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] | D |

TABLE 2-continued
| Representative Lipids of Formula (II). | | |
|---|---|---|
| No. | Structure | Prep. Method |
| II-13 | 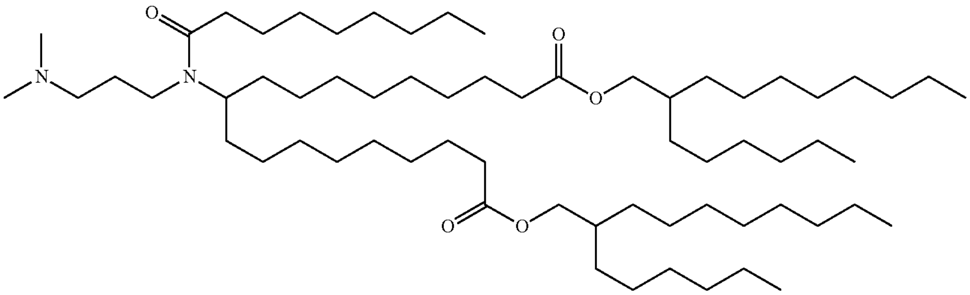 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC] | D |
| II-14 | 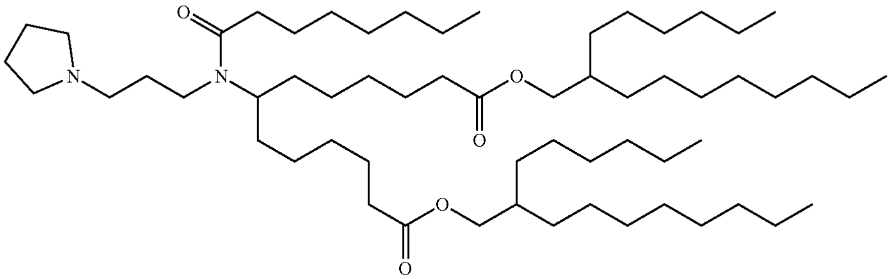 [SMILES: CCCCCCCCC(CCCCCC)COC(=O)CCCCCC(CCCCCC(=O)OCC(CCCCCC)CCCCCCCC)N(CCCN1CCCC1)C(=O)CCCCCCC] | D |
| II-15 | 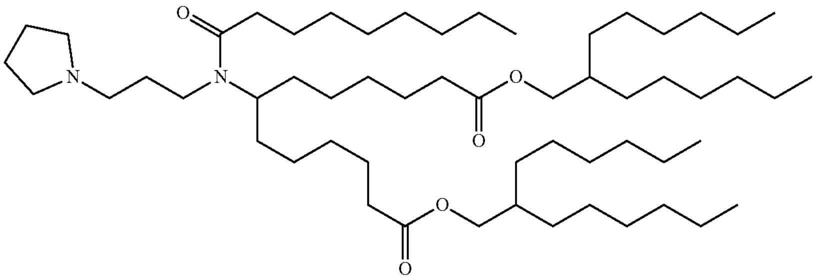 [SMILES: CCCCCCCCC(=O)N(CCCN1CCCC1)C(CCCCCC(=O)OCC(CCCCCC)CCCCCC)CCCCCC(=O)OCC(CCCCCC)CCCCCC] | D |
| II-16 | 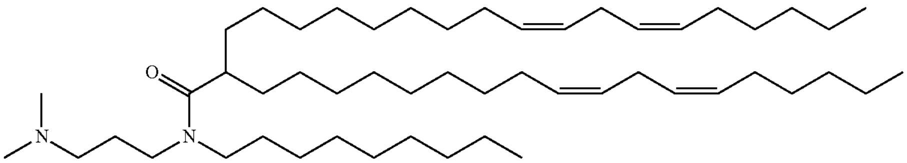 [SMILES: CCCCC/C=C\C/C=C\CCCCCCCCC(CCCCCCCC/C=C\C/C=C\CCCCC)C(=O)N(CCCCCCCCC)CCCN(C)C] | E |
| II-17 | 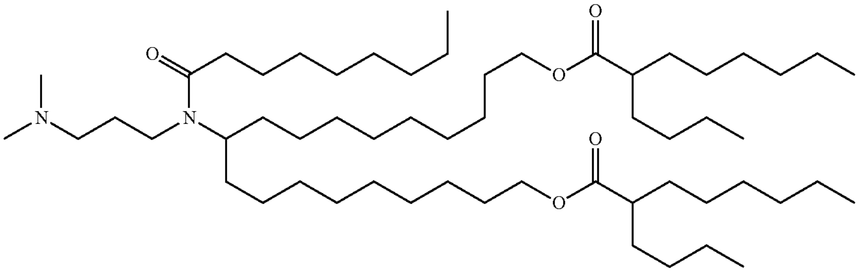 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC] | D |

TABLE 2-continued
Representative Lipids of Formula (II).
| No. | Structure | Prep. Method |
|---|---|---|
| II-18 | 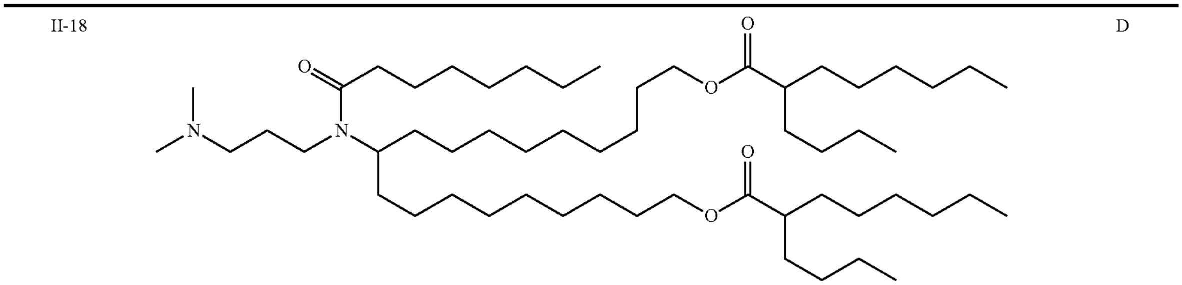 | D |
| II-19 | 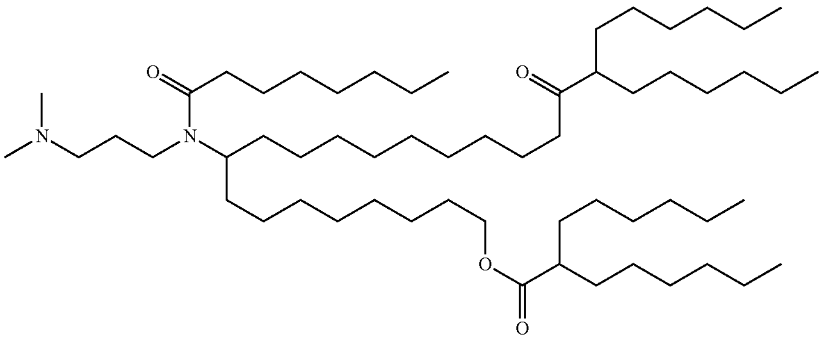 [SMILES: CCCCCCCC(=O)N(CCCN(C)C)C(CCCCCCCCCC(=O)C(CCCCCC)CCCCCC)CCCCCCCCOC(=O)C(CCCCCC)CCCCCC] | D |
| II-20 | 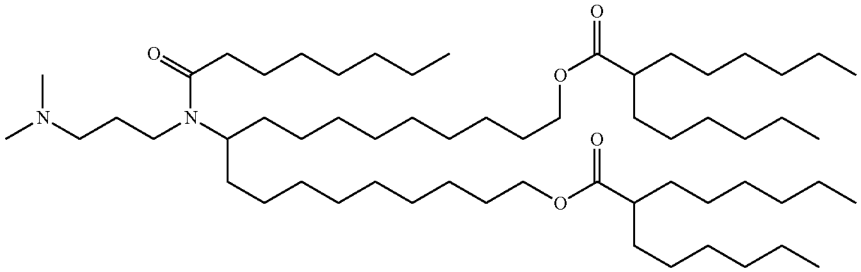 [SMILES: CCCCCCCC(=O)N(CCCN(C)C)C(CCCCCCCCCOC(=O)C(CCCCCC)CCCCCC)CCCCCCCCCOC(=O)C(CCCCCC)CCCCCC] | D |
| II-21 | 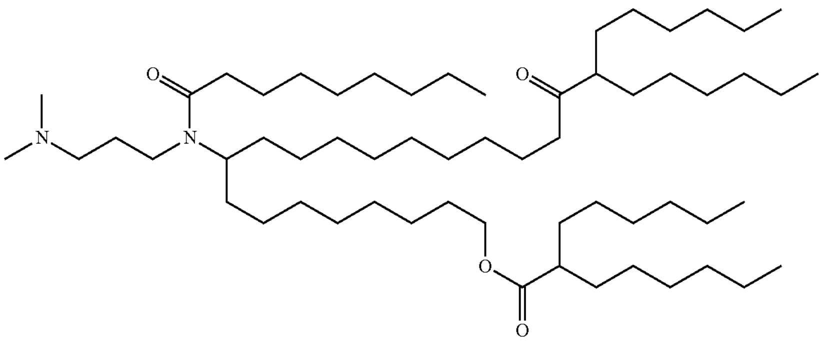 [SMILES: CCCCCCCCC(=O)N(CCCN(C)C)C(CCCCCCCCCC(=O)C(CCCCCC)CCCCCC)CCCCCCCCOC(=O)C(CCCCCC)CCCCCC] | D |
| II-22 | 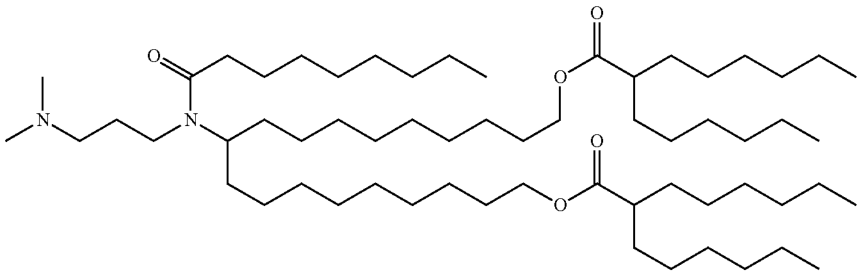 [SMILES: CCCCCCCCC(=O)N(CCCN(C)C)C(CCCCCCCCCOC(=O)C(CCCCCC)CCCCCC)CCCCCCCCCOC(=O)C(CCCCCC)CCCCCC] | D |

TABLE 2-continued
| Representative Lipids of Formula (II). | | |
|---|---|---|
| No. | Structure | Prep. Method |
| II-23 | 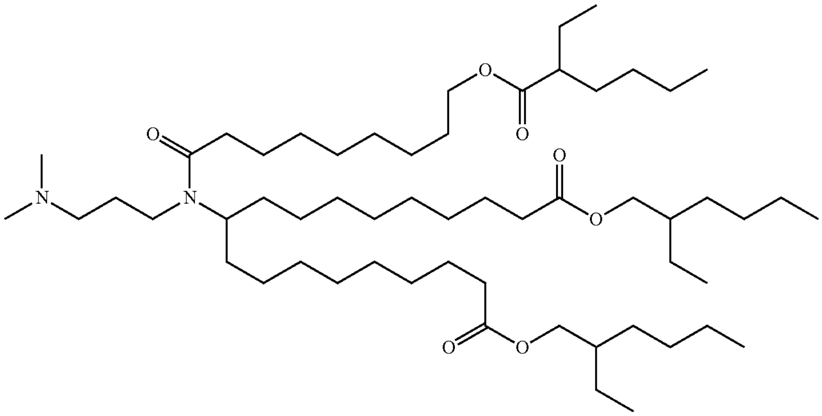 [SMILES: CCCCC(CC)COC(=O)CCCCCCCCC(CCCCCCCCC(=O)OCC(CC)CCCC)N(CCCN(C)C)C(=O)CCCCCCCCOC(=O)C(CC)CCCC] | D |
| II-24 | 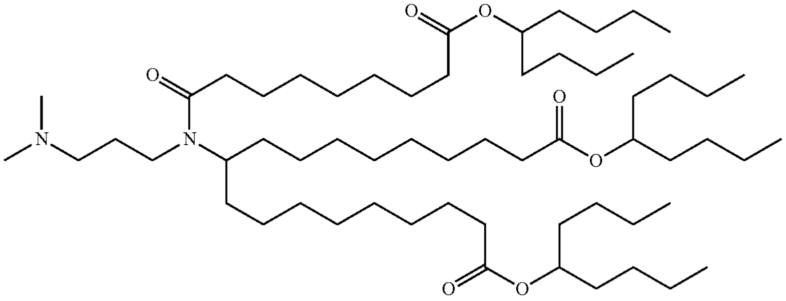 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] | D |
| II-25 | 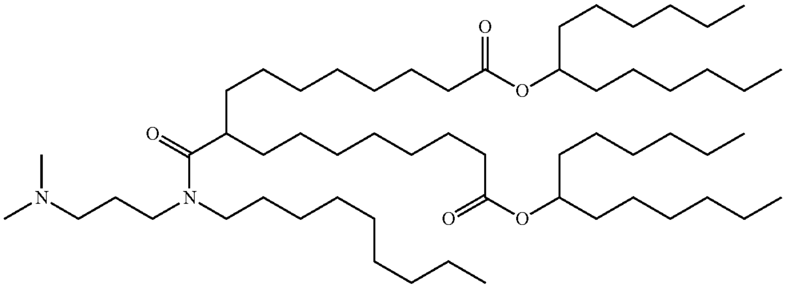 [SMILES: CCCCCCCCCN(CCCN(C)C)C(=O)C(CCCCCCCC(=O)OC(CCCCCC)CCCCCC)CCCCCCCC(=O)OC(CCCCCC)CCCCCC] | E |
| II-26 | 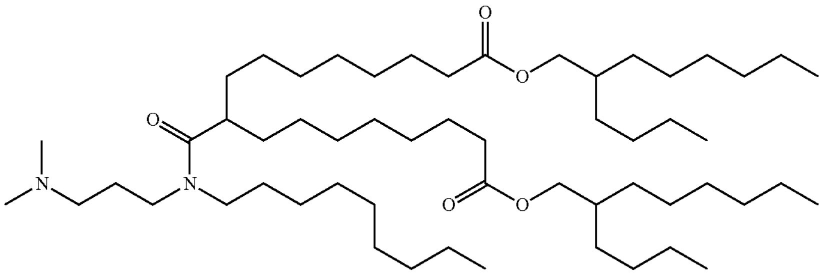 [SMILES: CCCCCCCCCN(CCCN(C)C)C(=O)C(CCCCCCCC(=O)OCC(CCCC)CCCCCC)CCCCCCCC(=O)OCC(CCCC)CCCCCC] | E |

TABLE 2-continued
| Representative Lipids of Formula (II). | | |
|---|---|---|
| No. | Structure | Prep. Method |
| II-27 | 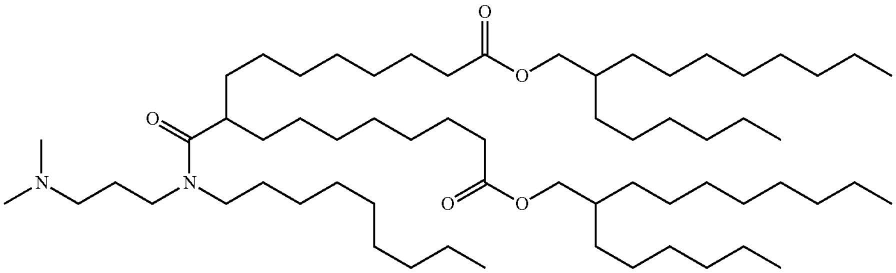 [SMILES: CCCCCCCCCN(CCCN(C)C)C(=O)C(CCCCCCCC(=O)OCC(CCCCCC)CCCCCCCC)CCCCCCCC(=O)OCC(CCCCCC)CCCCCCCC] | E |
| II-28 | 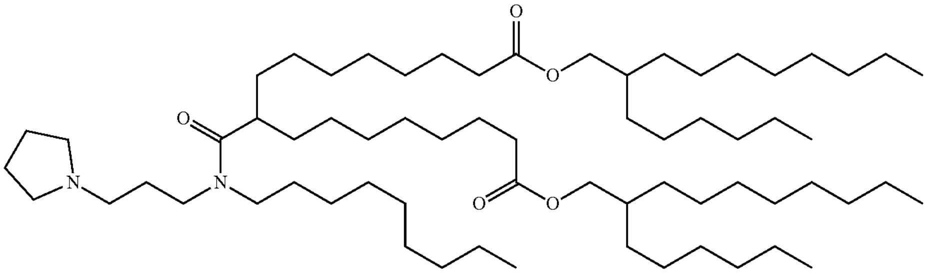 [SMILES: CCCCCCCCCN(CCCN1CCCC1)C(=O)C(CCCCCCCC(=O)OCC(CCCCCC)CCCCCCCC)CCCCCCCC(=O)OCC(CCCCCC)CCCCCCCC] | E |
| II-29 | 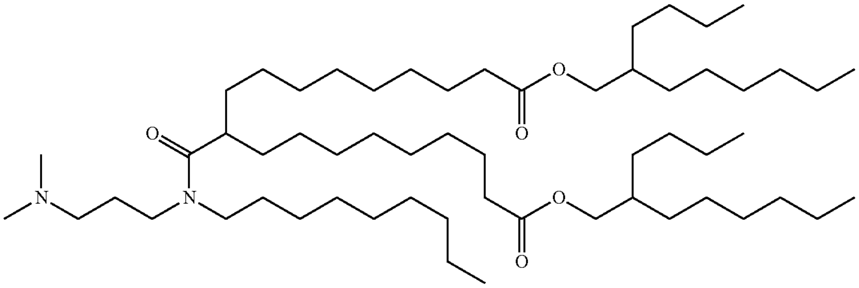 [SMILES: CCCCCCCCCN(CCCN(C)C)C(=O)C(CCCCCCCCC(=O)OCC(CCCC)CCCCCC)CCCCCCCCC(=O)OCC(CCCC)CCCCCC] | E |
| II-30 | 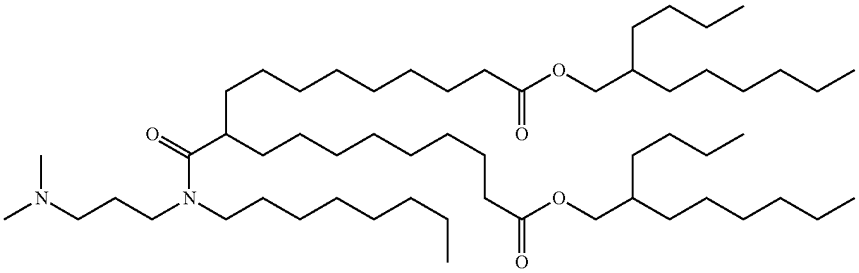 [SMILES: CCCCCCCCN(CCCN(C)C)C(=O)C(CCCCCCCCC(=O)OCC(CCCC)CCCCCC)CCCCCCCCC(=O)OCC(CCCC)CCCCCC] | E |
| II-31 | 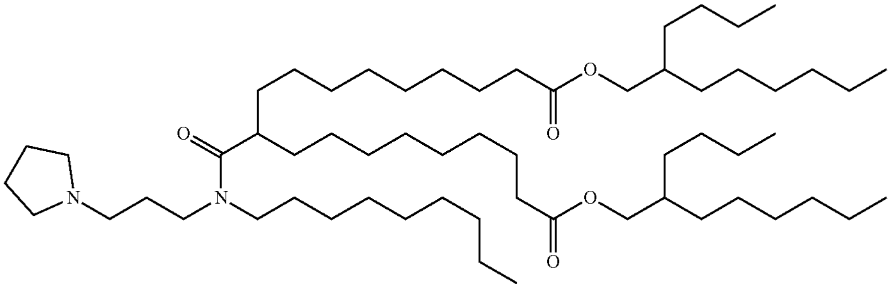 [SMILES: CCCCCCCCCN(CCCN1CCCC1)C(=O)C(CCCCCCCCC(=O)OCC(CCCC)CCCCCC)CCCCCCCCC(=O)OCC(CCCC)CCCCCC] | E |

TABLE 2-continued

| Representative Lipids of Formula (II). | | |
|---|---|---|
| No. | Structure | Prep. Method |
| II-32 | 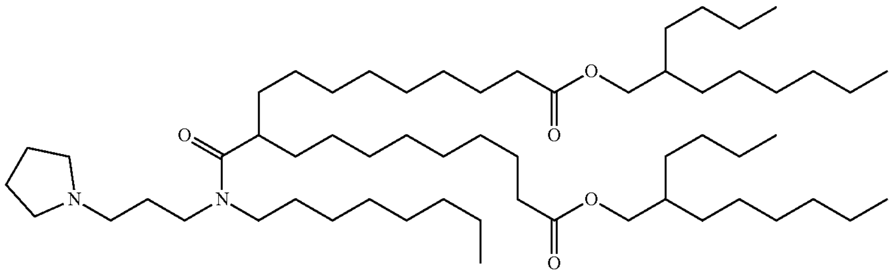 [SMILES: CCCCCCCCN(CCCN1CCCC1)C(=O)C(CCCCCCCCC(=O)OCC(CCCC)CCCCCC)CCCCCCCCC(=O)OCC(CCCC)CCCCCC] | E |
| II-33 | 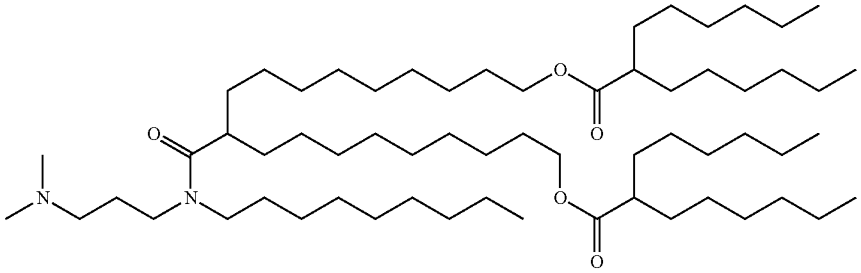 [SMILES: CCCCCCCCCN(CCCN(C)C)C(=O)C(CCCCCCCCCOC(=O)C(CCCCCC)CCCCCC)CCCCCCCCCOC(=O)C(CCCCCC)CCCCCC] | E |
| II-34 | 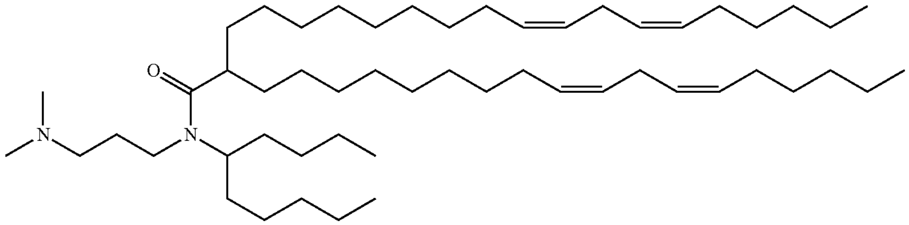 [SMILES: CCCCC/C=C\C/C=C\CCCCCCCCC(CCCCCCCC/C=C\C/C=C\CCCCC)C(=O)N(CCCN(C)C)C(CCCC)CCCCC] | E |
| II-35 | 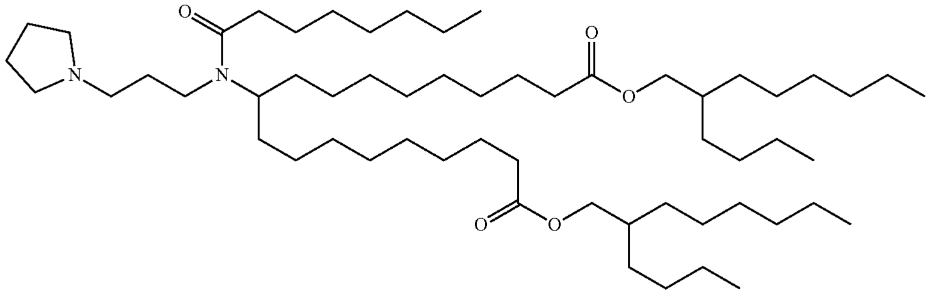 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC] | D |
| II-36 | 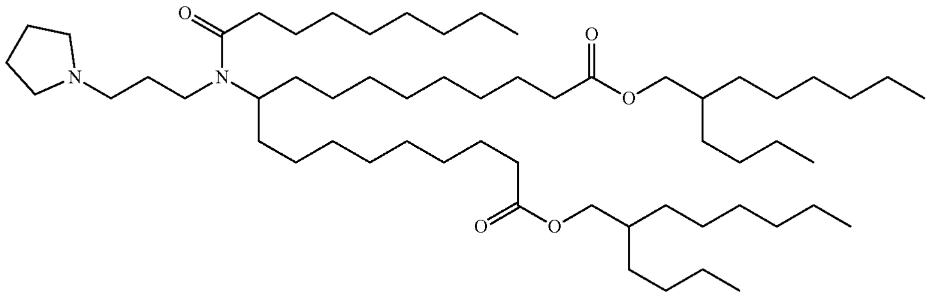 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC] | D |

In some embodiments, the LNPs comprise a lipid of Formula (II), a nucleoside-modified RNA and one or more excipient selected from neutral lipids, steroids and pegylated lipids. In some embodiments the lipid of Formula (II) is compound II-9. In some embodiments the lipid of Formula (II) is compound II-10. In some embodiments the lipid of Formula (II) is compound II-11. In some embodiments the lipid of Formula (II) is compound II-12. In some embodiments the lipid of Formula (II) is compound II-32.

In some other embodiments, the cationic lipid component of the LNPs has the structure of Formula (III):

(III)

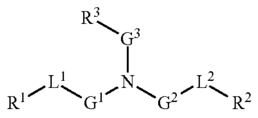

or a pharmaceutically acceptable salt, tautomer, prodrug or stereoisomer thereof, wherein:

one of $L^1$ or $L^2$ is —O(C═O)—, —(C═O)O—, —C(═O)—, —O—, —$S(O)_x$—, —S—S—, —C(═O)S—, SC(═O)—, —$NR^a$C(═O)—, —C(═O)$NR^a$—, $NR^a$C(═O)$NR^a$—, —OC(═O)$NR^a$— or —$NR^a$C(═O)O—, and the other of $L^1$ or $L^2$ is —O(C═O)—, —(C═O)O—, —C(═O)—, —O—, —$S(O)_x$—, —S—S—, —C(═O)S—, SC(═O)—, —$NR^a$C(═O)—, —C(═O)$NR^a$—, $NR^a$C(═O)$NR^a$—, —OC(═O)$NR^a$— or —$NR^a$C(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(═O)$OR^4$, —OC(═O)$R^4$ or —$NR^5$C(═O)$R^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the lipid has one of the following structures (IIIA) or (IIIB):

(IIIA)

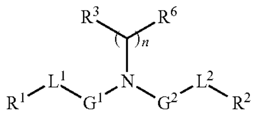

or (IIIB)

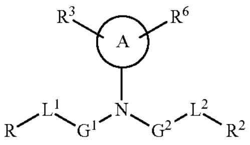

wherein:

A is a 3 to 8-membered cycloalkyl or cycloalkylene ring;

$R^6$ is, at each occurrence, independently H, OH or $C_1$-$C_{24}$ alkyl;

n is an integer ranging from 1 to 15.

In some of the foregoing embodiments of Formula (III), the lipid has structure (IIIA), and in other embodiments, the lipid has structure (IIIB).

In other embodiments of Formula (III), the lipid has one of the following structures (IIIC) or (IIID):

(IIIC)

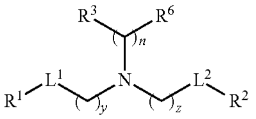

or (IIID)

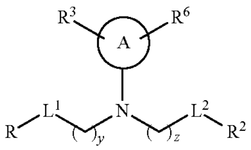

wherein y and z are each independently integers ranging from 1 to 12.

In any of the foregoing embodiments of Formula (III), one of $L^1$ or $L^2$ is —O(C═O)—. For example, in some embodiments each of $L^1$ and $L^2$ are —O(C═O)—. In some different embodiments of any of the foregoing, $L^1$ and $L^2$ are each independently —(C═O)O— or —O(C═O)—. For example, in some embodiments each of $L^1$ and $L^2$ is —(C═O)O—.

In some different embodiments of Formula (III), the lipid has one of the following structures (IIIE) or (IIIF):

(IIIE)

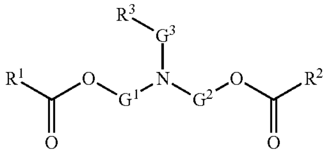

or (IIIF)

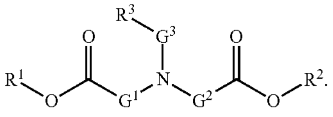

In some of the foregoing embodiments of Formula (III), the lipid has one of the following structures (IIIG), (IIIH), (IIII), or (IIIJ):

(IIIG)

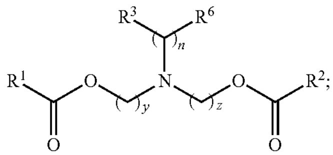

(IIIH)

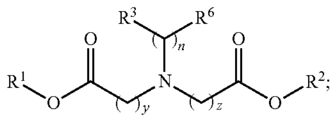

(IIII)

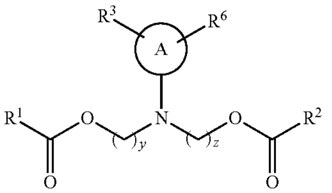

or

-continued (IIIJ)

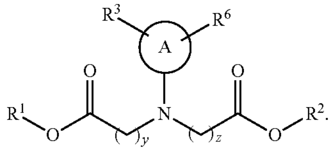

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R^2$ each, independently have the following structure:

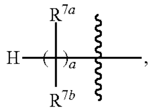, wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures:

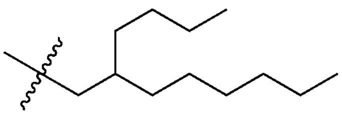;

-continued

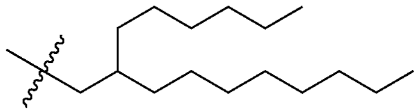;

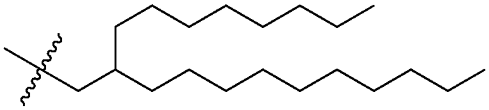;

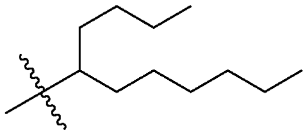;

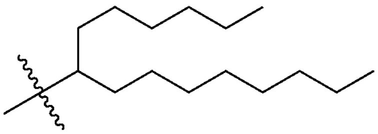;

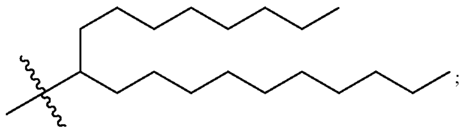;

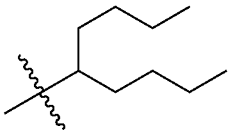; 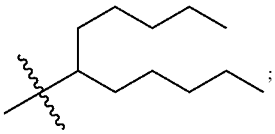;

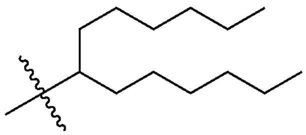;

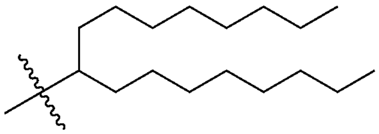.

In some of the foregoing embodiments of Formula (III), $R^3$ is OH, CN, —C(=O)O$R^4$, —OC(=O)$R^4$ or —NHC(=O)$R^4$. In some embodiments, $R^4$ is methyl or ethyl.

In various different embodiments, the cationic lipid of Formula (III) has one of the structures set forth in Table 3 below.

TABLE 3
| Representative Compounds of Formula (III). | | |
|---|---|---|
| No. | Structure | Prep. Method |
| III-1 | 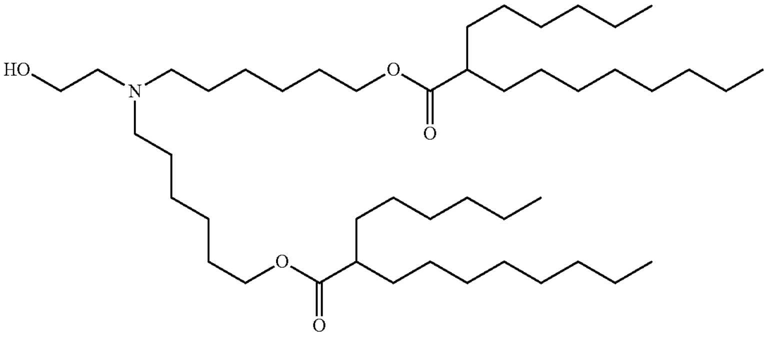 [SMILES: CCCCCCCCC(CCCCCC)C(=O)OCCCCCCN(CCO)CCCCCCOC(=O)C(CCCCCC)CCCCCCCC] | F |
| III-2 | 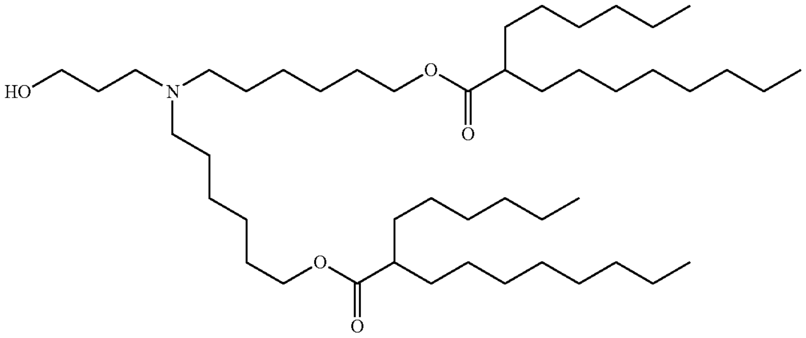 [SMILES: CCCCCCCCC(CCCCCC)C(=O)OCCCCCCN(CCCO)CCCCCCOC(=O)C(CCCCCC)CCCCCCCC] | F |
| III-3 | 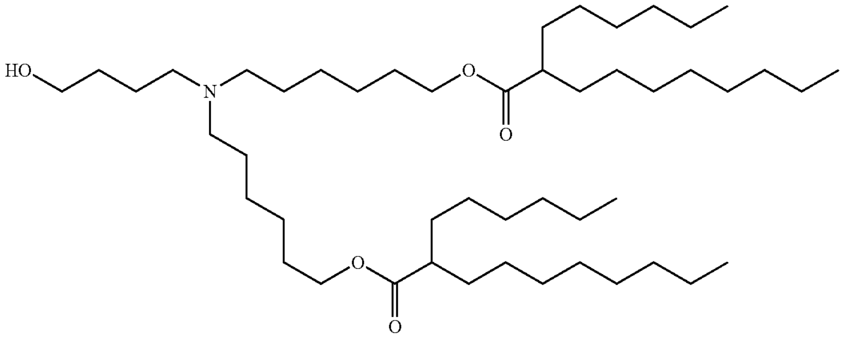 [SMILES: CCCCCCCCC(CCCCCC)C(=O)OCCCCCCN(CCCCO)CCCCCCOC(=O)C(CCCCCC)CCCCCCCC] | F |
| III-4 | 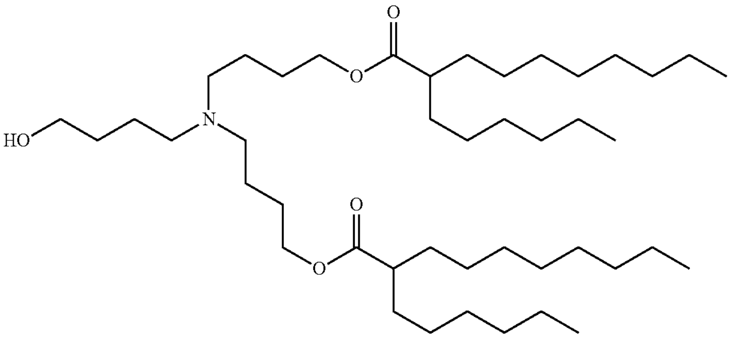 [SMILES: CCCCCCCCC(CCCCCC)C(=O)OCCCCN(CCCCO)CCCCOC(=O)C(CCCCCC)CCCCCCCC] | F |

TABLE 3-continued
| Representative Compounds of Formula (III). | | |
|---|---|---|
| No. | Structure | Prep. Method |
| III-5 | 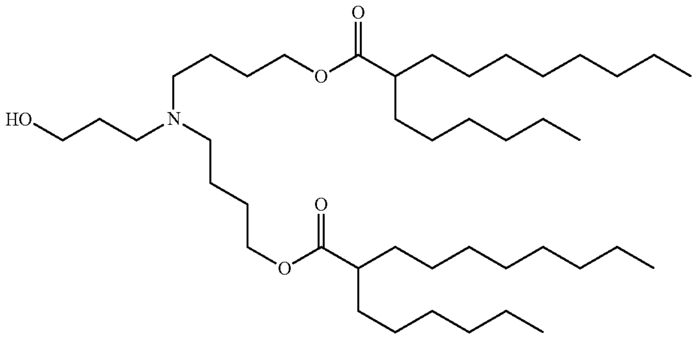 [SMILES: CCCCCCCCC(CCCCCC)C(=O)OCCCCN(CCCO)CCCCOC(=O)C(CCCCCC)CCCCCCCC] | F |
| III-6 | 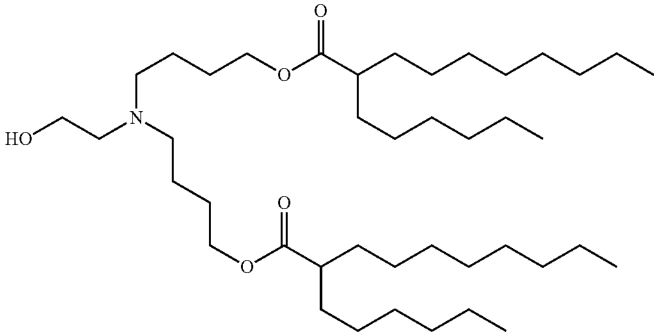 [SMILES: CCCCCCCCC(CCCCCC)C(=O)OCCCCN(CCO)CCCCOC(=O)C(CCCCCC)CCCCCCCC] | F |
| III-7 | 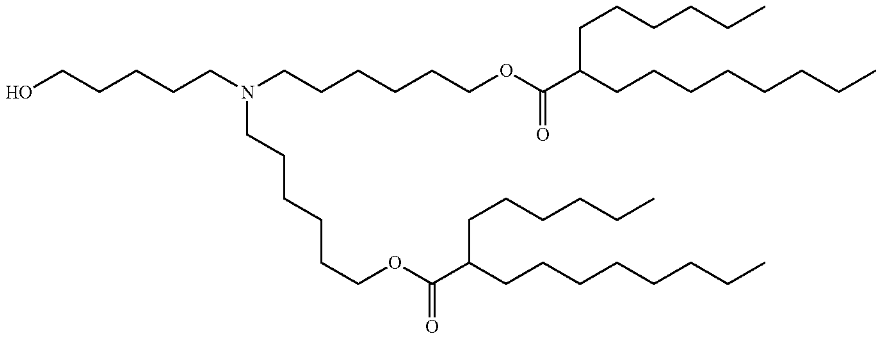 [SMILES: CCCCCCCCC(CCCCCC)C(=O)OCCCCCCN(CCCCCO)CCCCCCOC(=O)C(CCCCCC)CCCCCCCC] | F |
| III-8 | 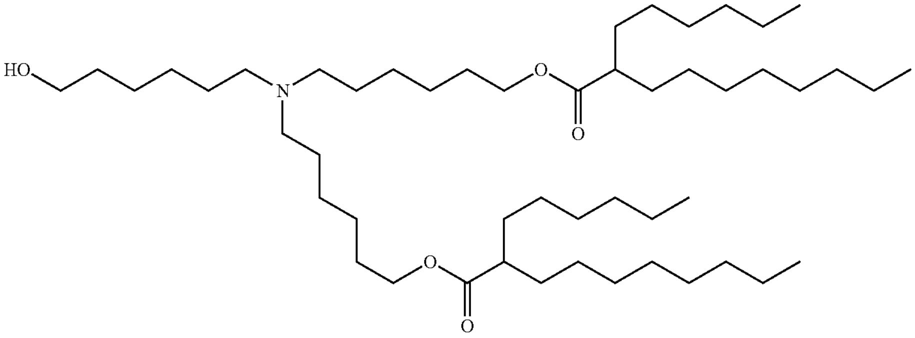 [SMILES: CCCCCCCCC(CCCCCC)C(=O)OCCCCCCN(CCCCCCO)CCCCCCOC(=O)C(CCCCCC)CCCCCCCC] | F |

TABLE 3-continued
| Representative Compounds of Formula (III). | | |
|---|---|---|
| No. | Structure | Prep. Method |
| III-9 | 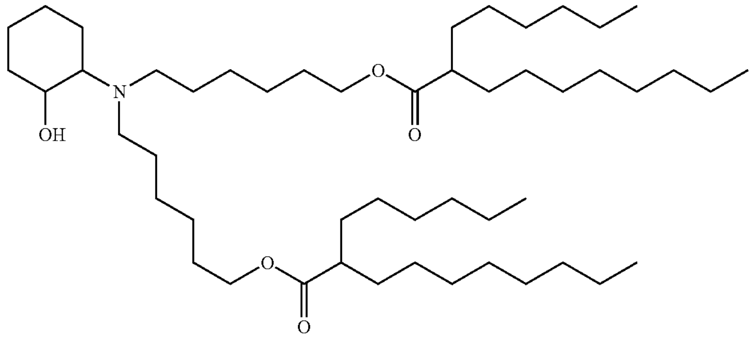 [SMILES: CCCCCCCCC(CCCCCC)C(=O)OCCCCCCN(CCCCCCOC(=O)C(CCCCCC)CCCCCCCC)C1CCCCC1O] | F |
| III-10 | 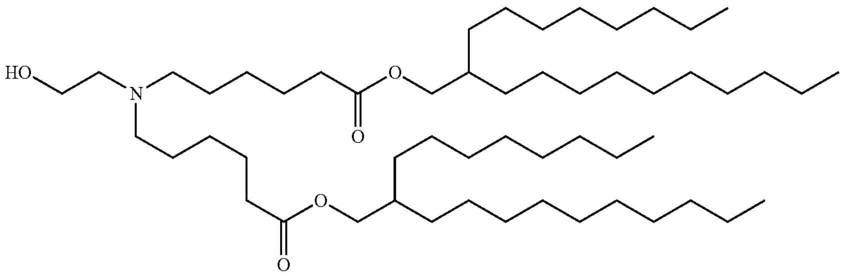 [SMILES: CCCCCCCCCCC(CCCCCCCC)COC(=O)CCCCCN(CCO)CCCCCC(=O)OCC(CCCCCCCC)CCCCCCCCCC] | F |
| III-11 | 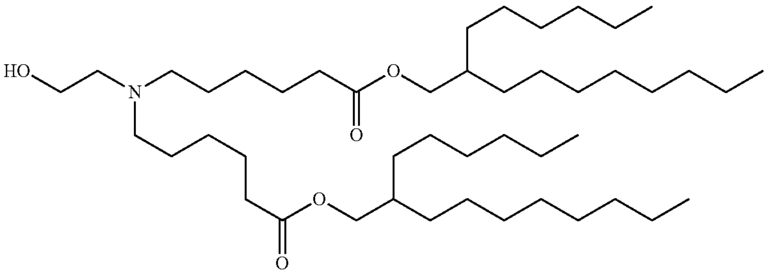 [SMILES: CCCCCCCCC(CCCCCC)COC(=O)CCCCCN(CCO)CCCCCC(=O)OCC(CCCCCC)CCCCCCCC] | F |
| III-12 | 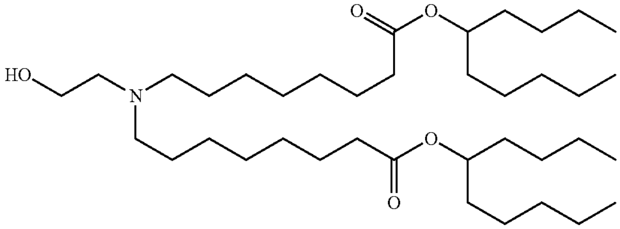 [SMILES: CCCCCC(CCCC)OC(=O)CCCCCCCN(CCO)CCCCCCCC(=O)OC(CCCC)CCCCC] | F |
| III-13 | 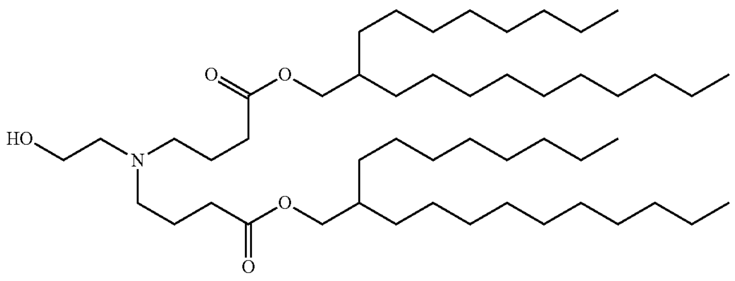 [SMILES: CCCCCCCCCCC(CCCCCCCC)COC(=O)CCCN(CCO)CCCC(=O)OCC(CCCCCCCC)CCCCCCCCCC] | F |

TABLE 3-continued
Representative Compounds of Formula (III).
| No. | Structure | Prep. Method |
|---|---|---|
| III-14 | 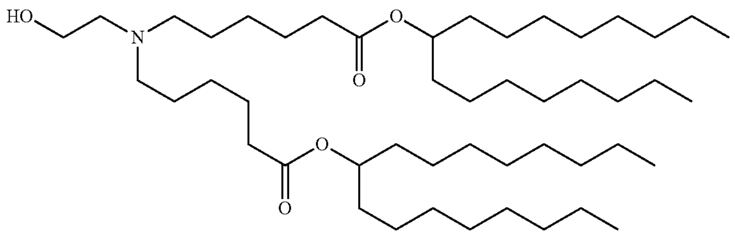 [SMILES: CCCCCCCCC(CCCCCCCC)OC(=O)CCCCCN(CCO)CCCCCC(=O)OC(CCCCCCCC)CCCCCCCC] | F |
| III-15 | 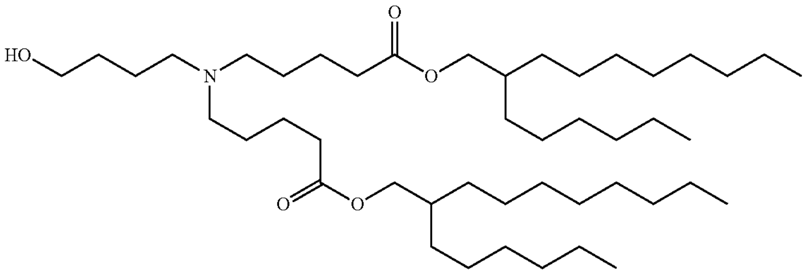 [SMILES: CCCCCCCCC(CCCCCC)COC(=O)CCCCN(CCCCO)CCCCC(=O)OCC(CCCCCC)CCCCCCCC] | F |
| Ill-16 | 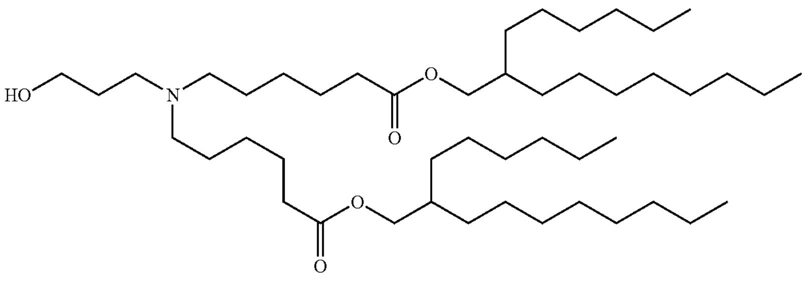 [SMILES: CCCCCCCCC(CCCCCC)COC(=O)CCCCCN(CCCO)CCCCCC(=O)OCC(CCCCCC)CCCCCCCC] | F |
| III-17 | 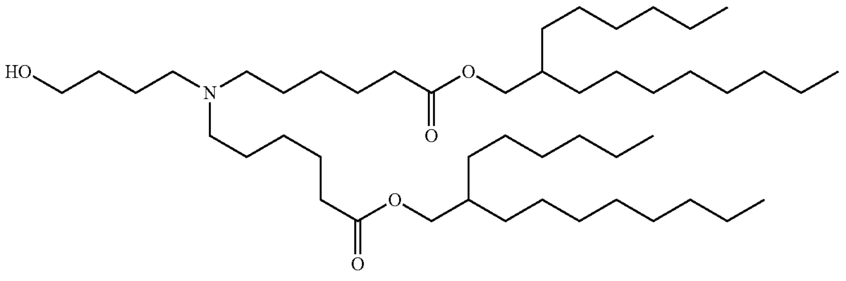 [SMILES: CCCCCCCCC(CCCCCC)COC(=O)CCCCCN(CCCCO)CCCCCC(=O)OCC(CCCCCC)CCCCCCCC] | F |
| III-18 | 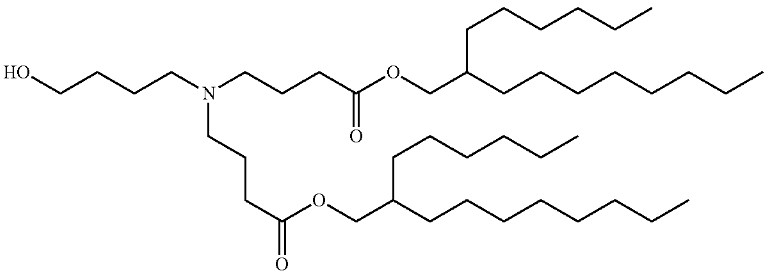 [SMILES: CCCCCCCCC(CCCCCC)COC(=O)CCCN(CCCCO)CCCC(=O)OCC(CCCCCC)CCCCCCCC] | F |

TABLE 3-continued
Representative Compounds of Formula (III).
| No. | Structure | Prep. Method |
| --- | --- | --- |
| III-19 | 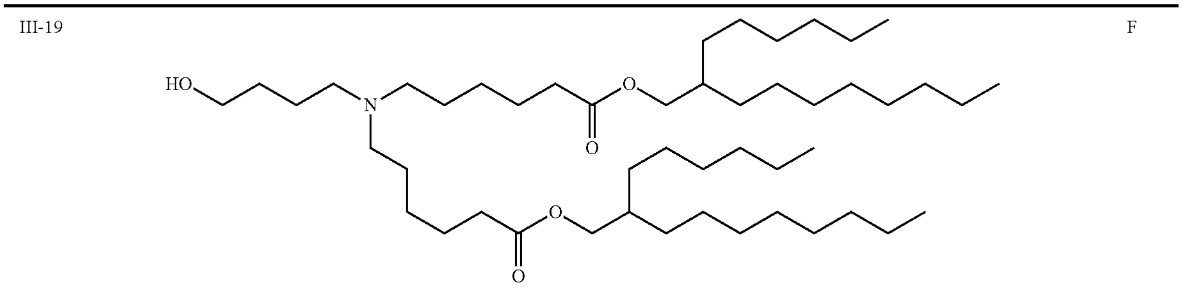 | F |
| III-20 | 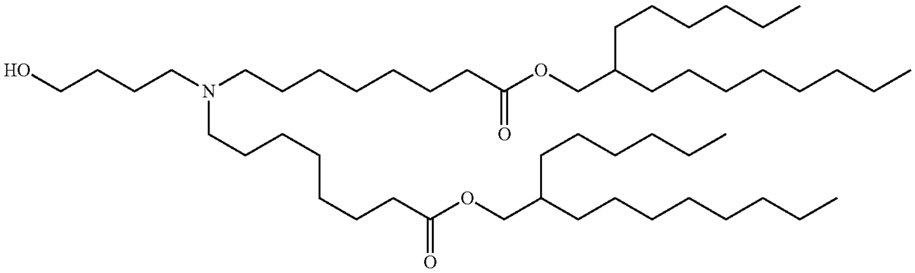 [SMILES: CCCCCCCCC(CCCCCC)COC(=O)CCCCCCCN(CCCCO)CCCCCCCC(=O)OCC(CCCCCC)CCCCCCCC] | F |
| III-21 | 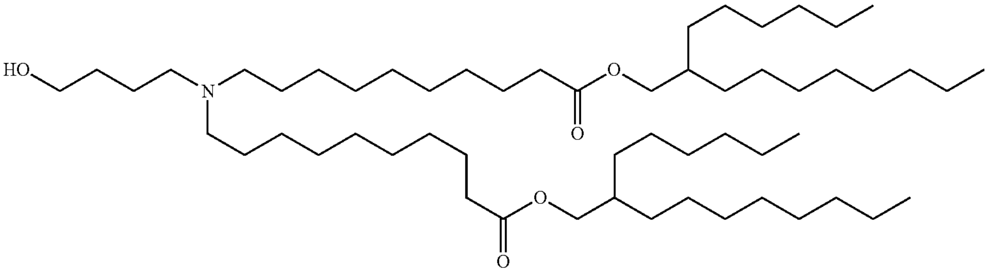 [SMILES: CCCCCCCCC(CCCCCC)COC(=O)CCCCCCCCCN(CCCCO)CCCCCCCCCC(=O)OCC(CCCCCC)CCCCCCCC] | F |
| III-22 | 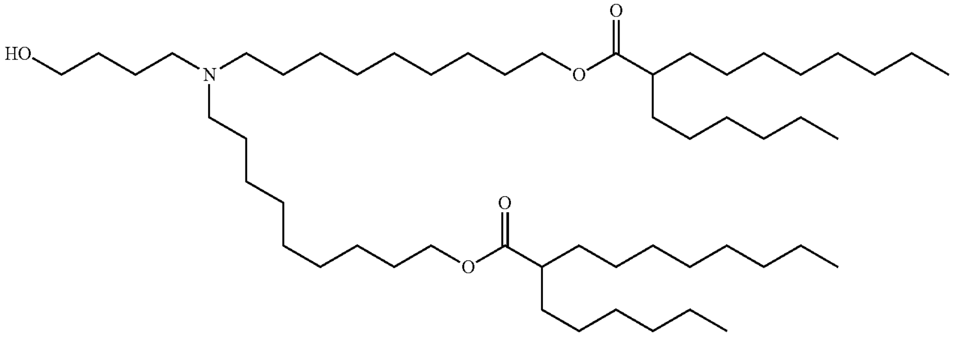 [SMILES: CCCCCCCCC(CCCCCC)C(=O)OCCCCCCCCCN(CCCCO)CCCCCCCCCOC(=O)C(CCCCCC)CCCCCCCC] | F |
| III-23 | 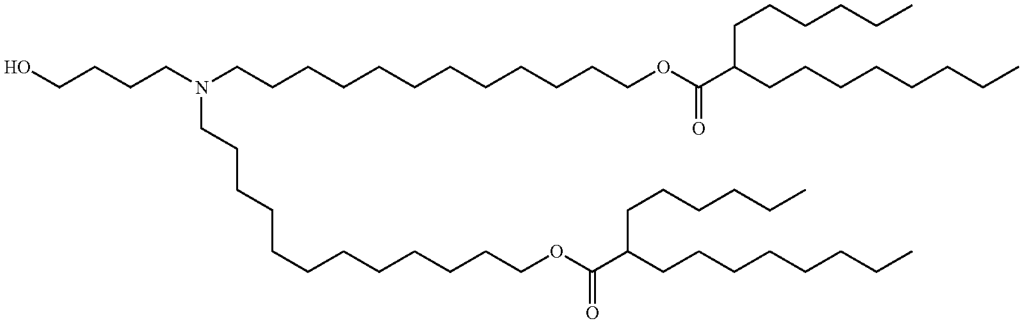 [SMILES: CCCCCCCCC(CCCCCC)C(=O)OCCCCCCCCCCCCN(CCCCO)CCCCCCCCCCCCOC(=O)C(CCCCCC)CCCCCCCC] | F |

TABLE 3-continued
| Representative Compounds of Formula (III). | | |
|---|---|---|
| No. | Structure | Prep. Method |
| III-24 | 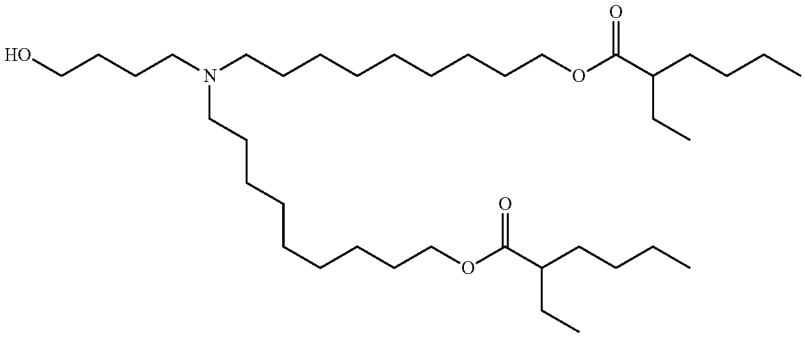 [SMILES: CCCCC(CC)C(=O)OCCCCCCCCCN(CCCCO)CCCCCCCCCOC(=O)C(CC)CCCC] | F |
| III-25 | 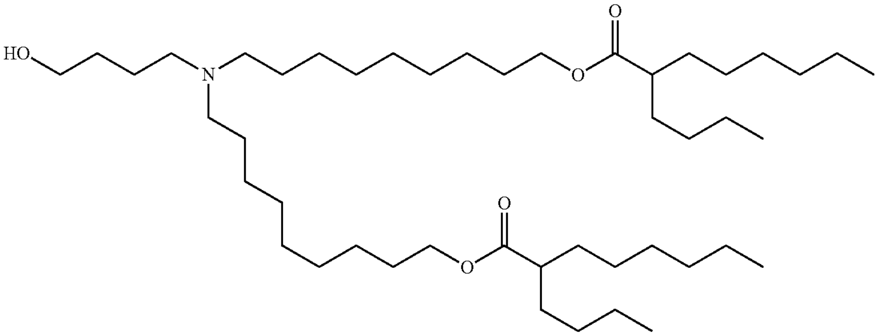 [SMILES: CCCCCCC(CCCC)C(=O)OCCCCCCCCCN(CCCCO)CCCCCCCCCOC(=O)C(CCCC)CCCCCC] | F |
| III-26 | 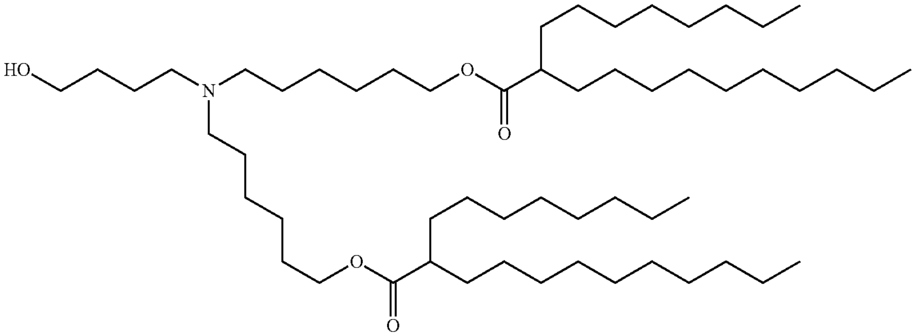 [SMILES: CCCCCCCCCCC(CCCCCCCC)C(=O)OCCCCCCN(CCCCO)CCCCCCOC(=O)C(CCCCCCCC)CCCCCCCCCC] | F |
| III-27 | 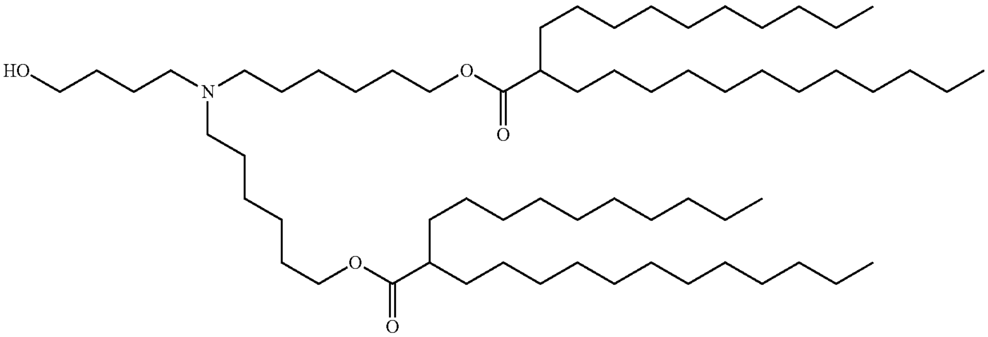 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] | F |

TABLE 3-continued
Representative Compounds of Formula (III).
| No. | Structure | Prep. Method |
|---|---|---|
| III-28 | 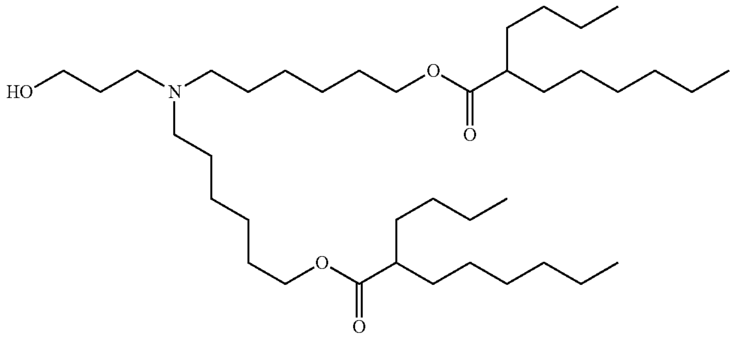 [SMILES: CCCCCCC(CCCC)C(=O)OCCCCCCN(CCCO)CCCCCCOC(=O)C(CCCC)CCCCCC] | F |
| III-29 | 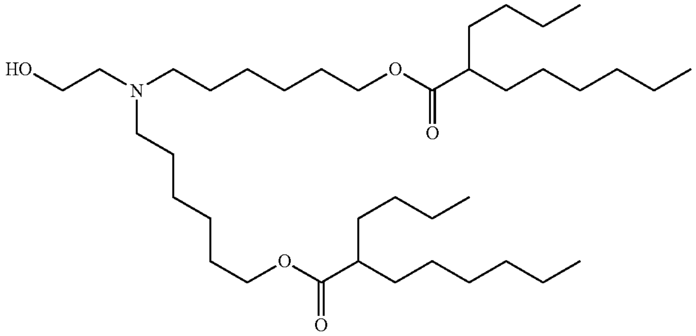 [SMILES: CCCCCCC(CCCC)C(=O)OCCCCCCN(CCO)CCCCCCOC(=O)C(CCCC)CCCCCC] | F |
| III-30 | 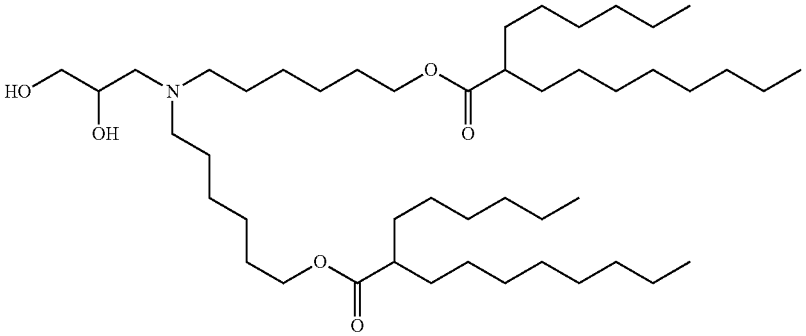 [SMILES: CCCCCCCCC(CCCCCC)C(=O)OCCCCCCN(CCCCCCOC(=O)C(CCCCCC)CCCCCCCC)CC(O)CO] | F |
| III-31 | 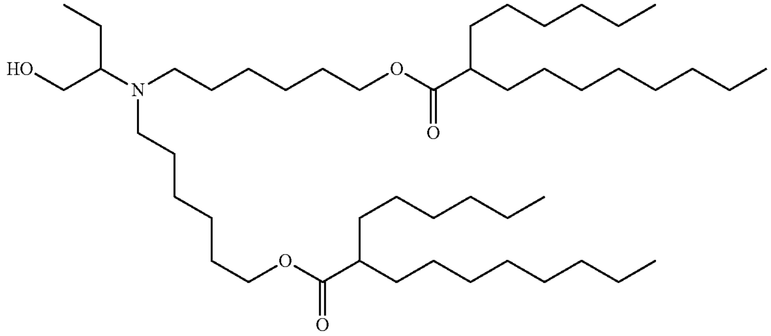 [SMILES: CCCCCCCCC(CCCCCC)C(=O)OCCCCCCN(CCCCCCOC(=O)C(CCCCCC)CCCCCCCC)C(CC)CO] | F |

TABLE 3-continued
Representative Compounds of Formula (III).
| No. | Structure | Prep. Method |
|---|---|---|
| III-32 | 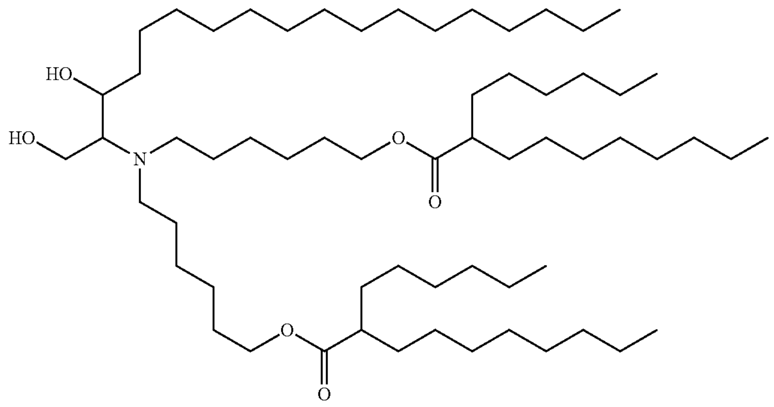 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] | F |
| III-33 | 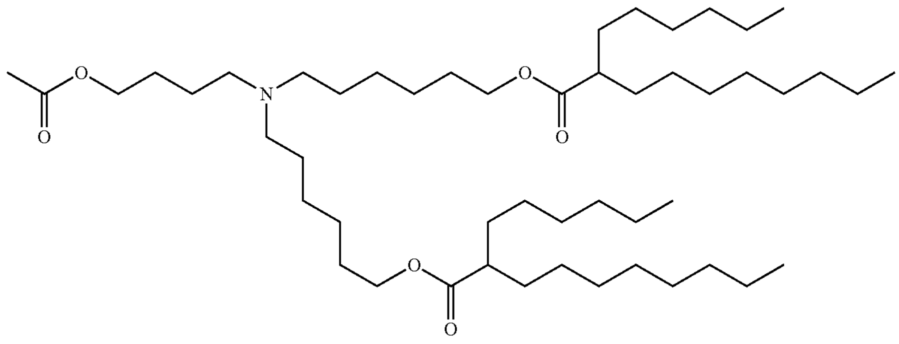 [SMILES: CCCCCCCCC(CCCCCC)C(=O)OCCCCCCN(CCCCCCOC(=O)C(CCCCCC)CCCCCCCC)CCCCOC(C)=O] | F |
| III-34 | 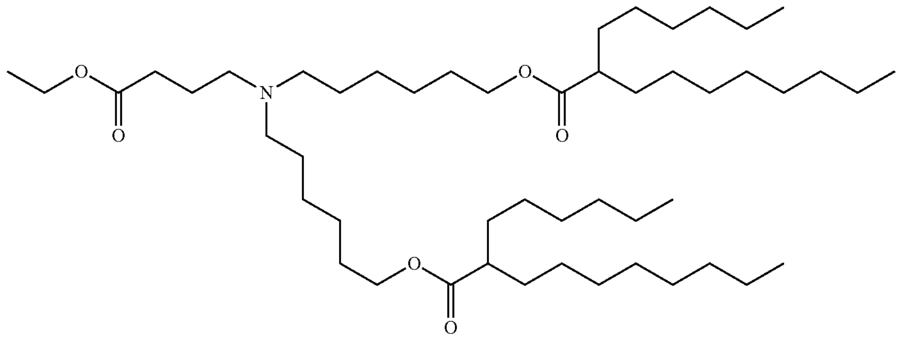 [SMILES: CCCCCCCCC(CCCCCC)C(=O)OCCCCCCN(CCCCCCOC(=O)C(CCCCCC)CCCCCCCC)CCCC(=O)OCC] | F |
| III-35 | 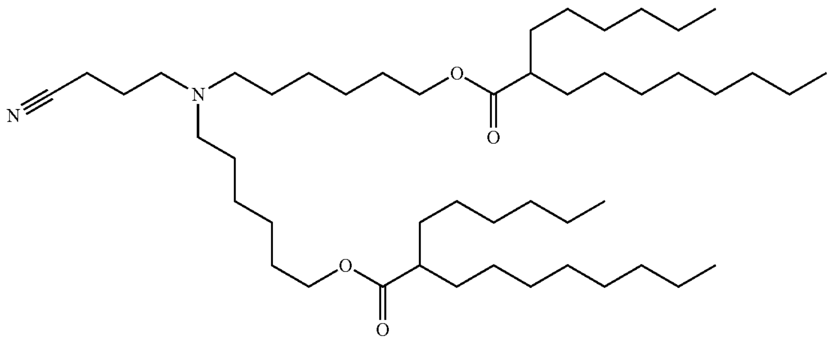 [SMILES: CCCCCCCCC(CCCCCC)C(=O)OCCCCCCN(CCCC#N)CCCCCCOC(=O)C(CCCCCC)CCCCCCCC] | F |

TABLE 3-continued

Representative Compounds of Formula (III).

| No. | Structure | Prep. Method |
|---|---|---|
| III-36 | 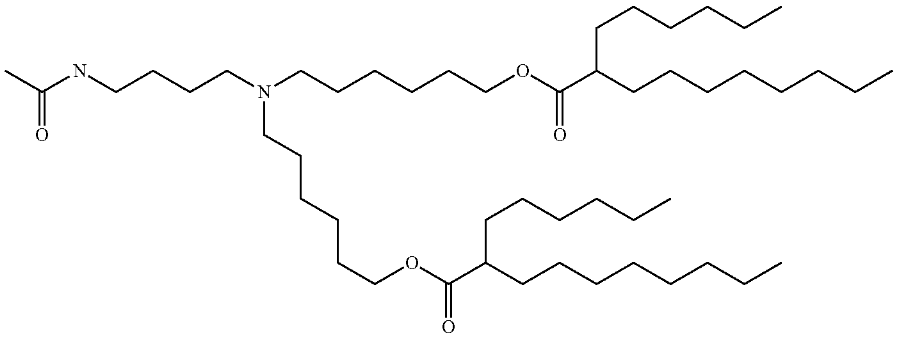 | F |

In some embodiments, the LNPs comprise a lipid of Formula (III), a nucleoside-modified RNA and one or more excipient selected from neutral lipids, steroids and pegylated lipids. In some embodiments the lipid of Formula (III) is compound III-3. In some embodiments the lipid of Formula (III) is compound III-7.

In some embodiments, the cationic lipid is present in the LNP in an amount from about 30 to about 95 mole percent. In one embodiment, the cationic lipid is present in the LNP in an amount from about 30 to about 70 mole percent. In one embodiment, the cationic lipid is present in the LNP in an amount from about 40 to about 60 mole percent. In one embodiment, the cationic lipid is present in the LNP in an amount of about 50 mole percent. In one embodiment, the LNP comprises only cationic lipids.

In some embodiments, the LNP comprises one or more additional lipids which stabilize the formation of particles during their formation.

Suitable stabilizing lipids include neutral lipids and anionic lipids.

Exemplary anionic lipids include, but are not limited to, phosphatidylglycerol, cardiolipin, diacylphosphatidylserine, diacylphosphatidic acid, N-dodecanoylphosphatidylethanolamines, N-succinylphosphatidylethanolamines, N-glutarylphosphatidylethanolamines, lysylphosphatidylglycerols, palmitoyloleyolphosphatidylglycerol (POPG), and other anionic modifying groups joined to neutral lipids.

Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). In one embodiment, the neutral lipid is 1,2-distearoyl-sn-glycero-3-phosphocholine (DSPC).

In some embodiments, the LNPs comprise a neutral lipid selected from DSPC, DPPC, DMPC, DOPC, POPC, DOPE and SM. In various embodiments, the molar ratio of the cationic lipid (e.g., lipid of Formula (I)) to the neutral lipid ranges from about 2:1 to about 8:1.

In various embodiments, the LNPs further comprise a steroid or steroid analogue. A "steroid" is a compound comprising the following carbon skeleton:

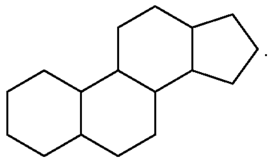 [SMILES: C1CCC2C(C1)CCC1C3CCCC3CCC21]

In some embodiments, the steroid or steroid analogue is cholesterol. In some of these embodiments, the molar ratio of the cationic lipid (e.g., lipid of Formula (I)) to cholesterol ranges from about 2:1 to 1:1.

In some embodiments, the LNP comprises glycolipids (e.g., monosialoganglioside $GM_1$). In some embodiments, the LNP comprises a sterol, such as cholesterol.

In some embodiments, the LNPs comprise a polymer conjugated lipid.

In some embodiments, the LNP comprises an additional, stabilizing-lipid which is a polyethylene glycol-lipid (pegylated lipid). Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol)$_{2000}$)carbamyl]-1,2-dimyristyloxlpropyl-3-amine (PEG-c-DMA). In one embodiment, the polyethylene glycol-lipid is PEG-c-DOMG). In other embodiments, the LNPs comprise a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(o-methoxy(polyethoxy)ethyl)butanedioate (PEG-S-DMG), a pegylated ceramide (PEG-cer), or a PEG dialkoxypropylcarbamate such as o-methoxy (polyethoxy)ethyl-N-(2,3-di(tetradecanoxy)propyl)carbamate or 2,3-di(tetradecanoxy)propyl-N-(o-methoxy(polyethoxy)ethyl)carbamate. In various embodiments, the molar ratio of the cationic lipid to the pegylated lipid ranges from about 100:1 to about 25:1.

In some embodiments, the LNPs comprise a pegylated lipid having the following structure (IV):

(IV)

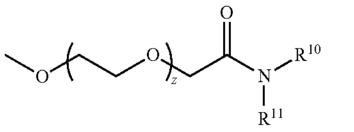

or a pharmaceutically acceptable salt, tautomer or stereoisomer thereof, wherein:

$R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has mean value ranging from 30 to 60.

In some of the foregoing embodiments of the pegylated lipid (IV), $R^{10}$ and $R^{11}$ are not both n-octadecyl when z is 42. In some other embodiments, $R^{10}$ and $R^{11}$ are each independently a straight or branched, saturated or unsaturated alkyl chain containing from to 18 carbon atoms. In some embodiments, $R^{10}$ and $R^{11}$ are each independently a straight or branched, saturated or unsaturated alkyl chain containing from 12 to 16 carbon atoms. In some embodiments, $R^{10}$ and $R^{11}$ are each independently a straight or branched, saturated or unsaturated alkyl chain containing 12 carbon atoms. In some embodiments, $R^{10}$ and $R^{11}$ are each independently a straight or branched, saturated or unsaturated alkyl chain containing 14 carbon atoms. In other embodiments, $R^{10}$ and $R^{11}$ are each independently a straight or branched, saturated or unsaturated alkyl chain containing 16 carbon atoms. In still more embodiments, $R^{10}$ and $R^{11}$ are each independently a straight or branched, saturated or unsaturated alkyl chain containing 18 carbon atoms. In still other embodiments, $R^{10}$ is a straight or branched, saturated or unsaturated alkyl chain containing 12 carbon atoms and $R^{11}$ is a straight or branched, saturated or unsaturated alkyl chain containing 14 carbon atoms.

In various embodiments, z spans a range that is selected such that the PEG portion of (II) has an average molecular weight of about 400 to about 6000 g/mol. In some embodiments, the average z is about 45.

In other embodiments, the pegylated lipid has one of the following structures:

(IVa)

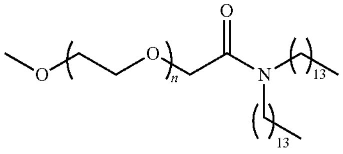

(IVb)

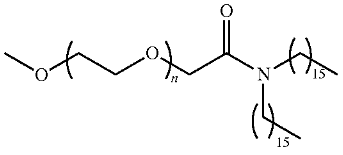

-continued (IVc)

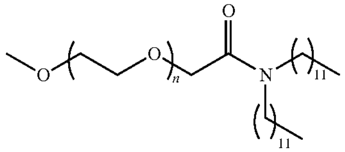

(IVd)

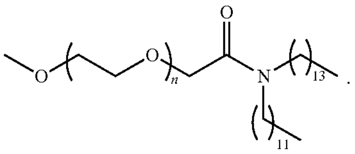

wherein n is an integer selected such that the average molecular weight of the pegylated lipid is about 2500 g/mol.

In some embodiments, the additional lipid is present in the LNP in an amount from about 1 to about 10 mole percent. In one embodiment, the additional lipid is present in the LNP in an amount from about 1 to about 5 mole percent. In one embodiment, the additional lipid is present in the LNP in about 1 mole percent or about 1.5 mole percent.

In some embodiments, the LNPs comprise a lipid of Formula (I), a nucleoside-modified RNA, a neutral lipid, a steroid and a pegylated lipid. In some embodiments the lipid of Formula (I) is compound I-6. In different embodiments, the neutral lipid is DSPC. In other embodiments, the steroid is cholesterol. In still different embodiments, the pegylated lipid is compound IVa.

In some embodiments, the LNP comprises one or more targeting moieties, which are capable of targeting the LNP to a cell or cell population. For example, in one embodiment, the targeting moiety is a ligand, which directs the LNP to a receptor found on a cell surface.

In some embodiments, the LNP comprises one or more internalization domains. For example, in one embodiment, the LNP comprises one or more domains, which bind to a cell to induce the internalization of the LNP. For example, in one embodiment, the one or more internalization domains bind to a receptor found on a cell surface to induce receptor-mediated uptake of the LNP. In some embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo.

Other exemplary LNPs and their manufacture are described in the art, for example in U.S. Patent Application Publication No. US20120276209, Semple et al., 2010, Nat Biotechnol., 28(2):172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids. 2, e139; Maier et al., 2013, Mol Ther., 21(8): 1570-1578; and Tam et al., 2013, Nanomedicine, 9(5): 665-74, each of which are incorporated by reference in their entirety.

The following Reaction Schemes illustrate methods to make lipids of Formula (I), (II) or (III).

GENERAL REACTION SCHEME 1

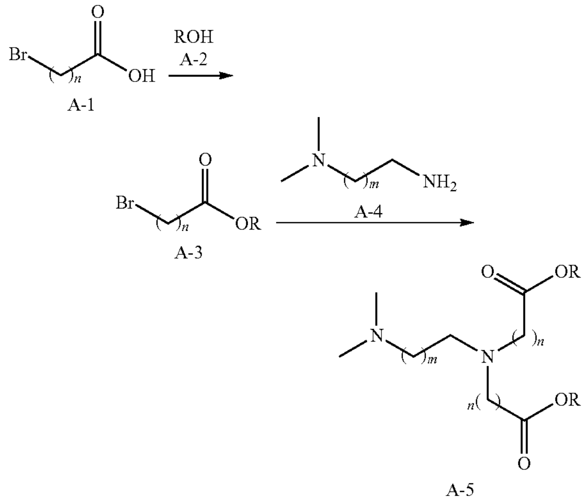

Embodiments of the lipid of Formula (I) (e.g., compound A-5) can be prepared according to General Reaction Scheme 1 ("Method A"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 1, compounds of structure A-1 can be purchased from commercial sources or prepared according to methods familiar to one of ordinary skill in the art. A mixture of A-1, A-2 and DMAP is treated with DCC to give the bromide A-3. A mixture of the bromide A-3, a base (e.g., N,N-diisopropylethylamine) and the N,N-dimethyldiamine A-4 is heated at a temperature and time sufficient to produce A-5 after any necessarily workup and or purification step.

GENERAL REACTION SCHEME 2

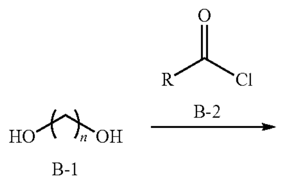

-continued

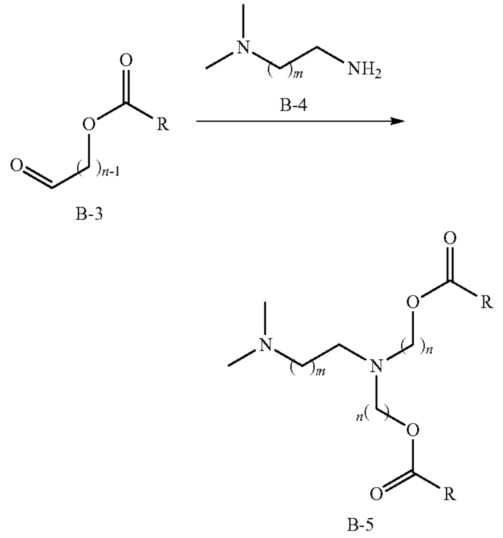

Other embodiments of the compound of Formula (I) (e.g., compound B-5) can be prepared according to General Reaction Scheme 2 ("Method B"), wherein R is a saturated or unsaturated $C_1$-$C_{24}$ alkyl or saturated or unsaturated cycloalkyl, m is 0 or 1 and n is an integer from 1 to 24. As shown in General Reaction Scheme 2, compounds of structure B-1 can be purchased from commercial sources or prepared according to methods familiar to one of ordinary skill in the art. A solution of B-1 (1 equivalent) is treated with acid chloride B-2 (1 equivalent) and a base (e.g., triethylamine). The crude product is treated with an oxidizing agent (e.g., pyridinium chlorochromate) and intermediate product B-3 is recovered. A solution of crude B-3, an acid (e.g., acetic acid), and N,N-dimethylaminoamine B-4 is then treated with a reducing agent (e.g., sodium triacetoxyborohydride) to obtain B-5 after any necessary work up and/or purification.

It should be noted that although starting materials A-1 and B-1 are depicted above as including only saturated methylene carbons, starting materials which include carbon-carbon double bonds may also be employed for preparation of compounds which include carbon-carbon double bonds.

GENERAL REACTION SCHEME 3

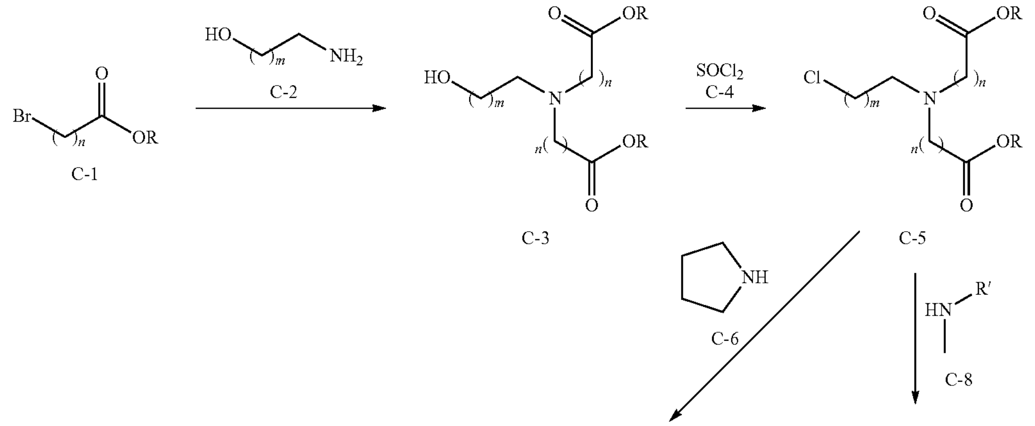

-continued

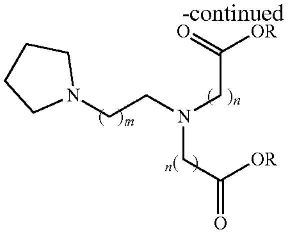

C-7

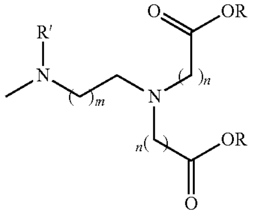

C-9

Different embodiments of the lipid of Formula (I) (e.g., compound C-7 or C9) can be prepared according to General Reaction Scheme 3 ("Method C"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 3, compounds of structure C-1 can be purchased from commercial sources or prepared according to methods familiar to one of ordinary skill in the art.

GENERAL REACTION SCHEME 4

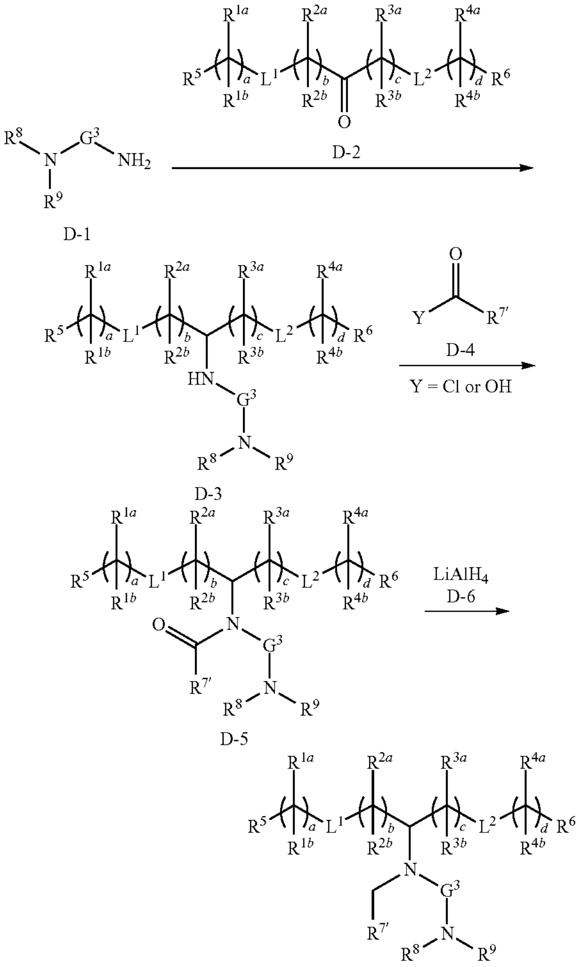

Embodiments of the compound of Formula (II) (e.g., compounds D-5 and D-7) can be prepared according to General Reaction Scheme 4 ("Method D"), wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^8$, $R^9$, $L^1$, $L^2$, $G^1$, $G^2$, $G^3$, a, b, c and d are as defined herein, and $R^{7'}$ represents $R^7$ or a $C_3$-$C_{19}$ alkyl. Referring to General Reaction Scheme 1, compounds of structure D-1 and D-2 can be purchased from commercial sources or prepared according to methods familiar to one of ordinary skill in the art. A solution of D-1 and D-2 is treated with a reducing agent (e.g., sodium triacetoxyborohydride) to obtain D-3 after any necessary work up. A solution of D-3 and a base (e.g. trimethylamine, DMAP) is treated with acyl chloride D-4 (or carboxylic acid and DCC) to obtain D-5 after any necessary work up and/or purification. D-5 can be reduced with LiAlH4 D-6 to give D-7 after any necessary work up and/or purification.

GENERAL REACTION SCHEME 5

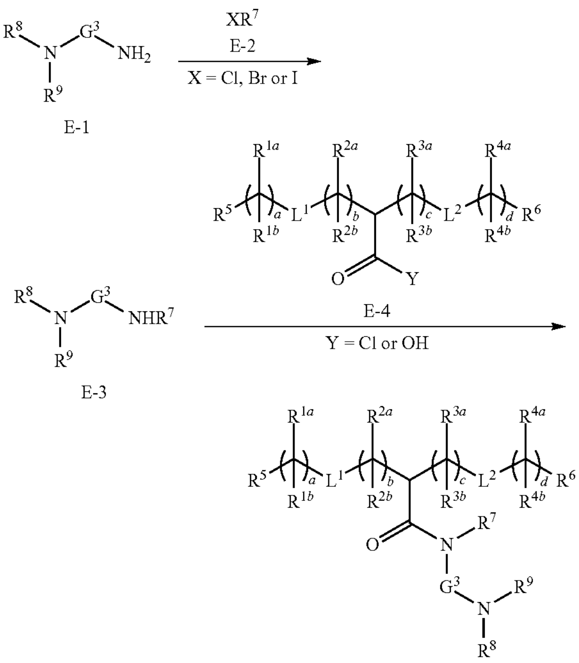

Embodiments of the lipid of Formula (II) (e.g., compound E-5) can be prepared according to General Reaction Scheme 5 ("Method E"), wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^7$, $R^8$, $R^9$, $L^1$, $L^2$, $G^3$, a, b, c and d are as defined herein. Referring to General Reaction Scheme 2, compounds of structure E-1 and E-2 can be purchased from commercial sources or prepared according to methods familiar to one of ordinary skill in the art. A mixture of E-1 (in excess), E-2 and a base (e.g., potassium carbonate) is heated to obtain E-3 after any necessary work up. A solution of E-3 and a base (e.g. trimethylamine, DMAP) is treated with acyl chloride E-4 (or carboxylic acid and DCC) to obtain E-5 after any necessary work up and/or purification.

GENERAL REACTION SCHEME 6

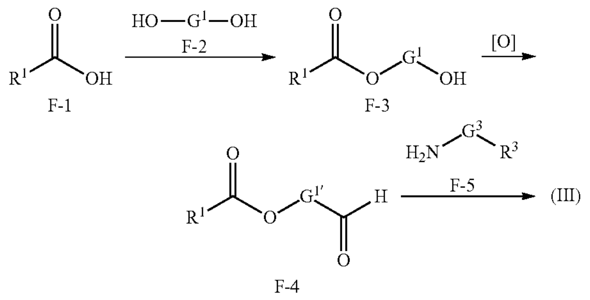

General Reaction Scheme 6 provides an exemplary method (Method F) for preparation of Lipids of Formula (III). $G^1$, $G^3$, $R^1$ and $R^3$ in General Reaction Scheme 6 are as defined herein for Formula (III), and G1' refers to a one-carbon shorter homologue of G1. Compounds of structure F-1 are purchased or prepared according to methods known in the art. Reaction of F-1 with diol F-2 under appropriate condensation conditions (e.g., DCC) yields ester/alcohol F-3, which can then be oxidized (e.g., PCC) to aldehyde F-4. Reaction of F-4 with amine F-5 under reductive amination conditions yields a lipid of Formula (III).

It should be noted that various alternative strategies for preparation of lipids of Formula (III) are available to those of ordinary skill in the art. For example, other lipids of Formula (III) wherein $L^1$ and $L^2$ are other than ester can be prepared according to analogous methods using the appropriate starting material. Further, General Reaction Scheme 6 depicts preparation of a lipids of Formula (III), wherein $G^1$ and $G^2$ are the same; however, this is not a required aspect of the invention and modifications to the above reaction scheme are possible to yield compounds wherein $G^1$ and $G^2$ are different.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—$R^{11}$ (where $R^{11}$ is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to subjects of all sorts. Modification of pharmaceutical compositions suitable for administration to humans in order to render the compositions suitable for administration to various subjects is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intravenous, intracerebroventricular, intradermal, intramuscular, or another route of administration. Other contemplated formulations include projected nanoparticles, liposomal preparations, resealed erythrocytes containing the active ingredient, and immunogenic-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient, which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intradermal, intrasternal injection, intratumoral, intravenous, intracerebroventricular and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers. In some embodiments, the formulation may comprise dry particles which comprise the active ingredient and which have a diameter in the range from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In some embodiments, such powders comprise particles wherein at least 98% of the particles by weight have a diameter greater than 0.5 nanometers and at least 95% of the particles by number have a diameter less than 7 nanometers. In some embodiments, at least 95% of the particles by weight have a diameter greater than 1 nanometer and at least 90% of the particles by number have a diameter less than 6 nanometers. In some embodiments, dry powder compositions include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in some instances having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Methods of Treatment or Prevention

The present invention provides methods of inducing an adaptive immune response against influenza virus in a subject comprising administering an effective amount of a composition comprising one or more isolated nucleic acids encoding one or more influenza virus antigens.

In one embodiment, the method provides immunity in the subject to influenza virus, influenza virus infection, or to a disease or disorder associated with influenza virus. The present invention thus provides a method of treating or preventing the infection, disease, or disorder associated with influenza virus.

In one embodiment, the composition is administered to a subject having an infection, disease, or disorder associated with influenza virus. In one embodiment, the composition is administered to a subject at risk for developing the infection, disease, or disorder associated with influenza virus. For example, the composition may be administered to a subject who is at risk for being in contact with influenza virus. In one embodiment, the composition is administered to a subject who lives in, traveled to, or is expected to travel to a geographic region in which influenza virus is prevalent. In one embodiment, the composition is administered to a subject who is in contact with or expected to be in contact with another person who lives in, traveled to, or is expected to travel to a geographic region in which influenza virus is prevalent. In one embodiment, the composition is administered to a subject who has knowingly been exposed to influenza virus through their occupation, or other contact.

In one embodiment, the method comprises administering a composition comprising one or more nucleoside-modified nucleic acid molecules encoding one or more influenza virus antigens. In one embodiment, the method comprises administering a composition comprising a first nucleoside-modified nucleic acid molecule encoding one or more influenza virus antigens and a second nucleoside-modified nucleic acid molecule encoding one or more influenza virus antigens. In one embodiment, the method comprises administering a composition comprising a one or more nucleoside-modified nucleic acid molecules encoding a plurality of lineage influenza virus antigens described herein.

In one embodiment, the method comprises administering one or more compositions, each composition comprising one or more nucleoside-modified nucleic acid molecules encoding one or more influenza virus antigens. In one embodiment, the method comprises administering a first composition comprising one or more nucleoside-modified nucleic acid molecules encoding one or more influenza virus antigens and administering a second composition comprising one or more nucleoside-modified nucleic acid molecules encoding one or more influenza virus antigens. In one embodiment, the method comprises administering a plurality of compositions, each composition comprising one or more nucleoside-modified nucleic acid molecules encoding one or more lineage influenza virus antigens described herein. In some embodiments, the method comprises a staggered administration of the plurality of compositions.

In some embodiments, the method comprises administering to subject a plurality of nucleoside-modified nucleic acid molecules encoding a plurality of influenza virus antigens, adjuvants, or a combination thereof.

In some embodiments, the method of the invention allows for sustained expression of the influenza virus antigen or adjuvant, described herein, for at least several days following administration. In some embodiments, the method of the invention allows for sustained expression of the influenza virus antigen or adjuvant, described herein, for at least 2 weeks following administration. In some embodiments, the method of the invention allows for sustained expression of the influenza virus antigen or adjuvant, described herein, for at least 1 month following administration. However, the method, in some embodiments, also provides for transient expression, as in some embodiments, the nucleic acid is not integrated into the subject genome.

In some embodiments, the method comprises administering nucleoside-modified RNA, which provides stable expression of the influenza virus antigen or adjuvant described herein. In some embodiments, administration of nucleoside-modified RNA results in little to no innate immune response, while inducing an effective adaptive immune response.

In some embodiments, the method provides sustained protection against influenza virus. For example, in some embodiments, the method provides sustained protection against influenza virus for more than 2 weeks. In some embodiments, the method provides sustained protection against influenza virus for 1 month or more. In some embodiments, the method provides sustained protection against influenza virus for 2 months or more. In some embodiments, the method provides sustained protection against influenza virus for 3 months or more. In some embodiments, the method provides sustained protection against influenza virus for 4 months or more. In some embodiments, the method provides sustained protection against influenza virus for 5 months or more. In some embodiments, the method provides sustained protection against influenza virus for 6 months or more. In some embodiments, the method provides sustained protection against influenza virus for 1 year or more.

In one embodiment, a single immunization of the composition induces a sustained protection against influenza virus for 1 month or more, 2 months or more, 3 months or more, 4 months or more, 5 months or more, 6 months or more, or 1 year or more.

Administration of the compositions of the invention in a method of treatment can be achieved in a number of different ways, using methods known in the art. In one embodiment, the method of the invention comprises systemic administration of the subject, including for example enteral or parenteral administration. In some embodiments, the method comprises intradermal delivery of the composition. In another embodiment, the method comprises intravenous delivery of the composition. In some embodiments, the method comprises intramuscular delivery of the composition. In one embodiment, the method comprises subcutaneous delivery of the composition. In one embodiment, the method comprises inhalation of the composition. In one embodiment, the method comprises intranasal delivery of the composition.

It will be appreciated that the composition of the invention may be administered to a subject either alone, or in conjunction with another agent.

The therapeutic and prophylactic methods of the invention thus encompass the use of pharmaceutical compositions encoding an influenza virus antigen, adjuvant, or a combination thereof, described herein to practice the methods of the invention. The pharmaceutical compositions useful for practicing the invention may be administered to deliver a dose of from 1 ng/kg/day and 100 mg/kg/day. In one embodiment, the invention envisions administration of a dose, which results in a concentration of the compound of the present invention from 10 nM and 10 μM in a mammal.

Typically, dosages which may be administered in a method of the invention to a mammal, such as a human, range in amount from 0.01 μg to about 50 mg per kilogram of body weight of the mammal, while the precise dosage administered will vary depending upon any number of factors, including but not limited to, the type of mammal and type of disease state being treated, the age of the mammal and the route of administration. In some embodiments, the dosage of the compound will vary from about 0.1 μg to about 10 mg per kilogram of body weight of the mammal. In some embodiments, the dosage will vary from about 1 μg to about 1 mg per kilogram of body weight of the mammal.

The composition may be administered to a mammal as frequently as several times daily, or it may be administered less frequently, such as once a day, once a week, once every two weeks, once a month, or even less frequently, such as once every several months, several years, or even less frequently, such as every 10-20 years, 15-30 years, or even less frequently, such as every 50-100 years. The frequency of the dose will be readily apparent to the skilled artisan and will depend upon any number of factors, such as, but not limited to, the type and severity of the disease being treated, the type and age of the mammal, etc.

In some embodiments, administration of an immunogenic composition or vaccine of the present invention may be performed by single administration or boosted by multiple administrations.

In one embodiment, the invention includes a method comprising administering one or more compositions encoding one or more influenza virus antigens or adjuvants described herein. In some embodiments, the method has an additive effect, wherein the overall effect of the administering the combination is approximately equal to the sum of the effects of administering each influenza virus antigen or adjuvant. In other embodiments, the method has a synergistic effect, wherein the overall effect of administering the combination is greater than the sum of the effects of administering each influenza virus antigen or adjuvant.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: A Multi-Targeting. Nucleoside-Modified mRNA Influenza Virus Vaccine Provided Broad Protection in Mice Nucleoside-modified mRNA-lipid nanoparticle (LNP) vaccines have recently emerged as vaccine vectors displaying many properties desirable for delivery of a universal influenza virus vaccine candidate (Scorza F B et al., 2018, Vaccines, 6:20). A single antigen from the virus can be expressed at high levels for an extended period of time, more closely mimicking the dynamics of viral infection (Pardi N et al., 2015, J. Control. Release., 217:345-351). The lack of a foreign vector prevents the adaptive immune system from recognizing the input, allowing the potential for multiple rounds of vaccination to achieve a substantial boosting of immune responses. Additionally, production of synthetic mRNA vaccines is egg independent, removing the reliance on embryonated chicken eggs for influenza virus vaccines. The mRNA vector utilized in this study has been modified to incorporate 1-methylpseudouridine (m1Ψ), which prevents recognition by RNA sensors, thereby avoiding excess inflammation and increasing protein (antigen) expression (Kariko K et al., 2005, Immunity, 645:165-175; Durbin A F et al., 2016, MBio, 7:648).

In this example, the technology of nucleoside-modified mRNA-LNP vaccines were harnessed to effectively deliver a universal influenza virus vaccine candidate that targets a combination of conserved antigens and provided broad protection in mice after administration of a single low dose.

The materials and methods employed in these experiments are now described.

Viruses, Cells, and Proteins:

Influenza A viruses utilized are described as follows. H1N1pdm (IVR-180): Recombinant influenza A virus with the HA and NA from A/Singapore/GP1908/2015 H1N1pdm virus and remaining proteins from A/Texas/1/1977 H3N2 virus. NC99: A/New Caledonia/20/1999 H1N1 virus. PR8: A/Puerto Rico/8/1934 H1N1 virus. cH6/1N5: Recombinant chimeric influenza A virus with an HA head domain from A/mallard/Sweden/81/2002 H6N1 virus, HA stalk domain from A/California/04/2009 H1N1pdm virus, NA from A/mallard/Sweden/86/2003 H12N5 virus, and remaining proteins from A/Puerto Rico/8/1934 H1N1 virus. H5N8: Recombinant influenza A virus containing a low pathogenic H5 HA, with the polybasic cleavage site removed, from the A/Vietnam/1203/2004 H5N1 virus, the N8 from A/mallard/Sweden/50/2002 H3N8 virus, and remaining proteins from A/Puerto Rico/8/1934 H1N1 virus.

Viruses were propagated in 10 day old embryonated chicken eggs (Charles River) after injection of 100 plaque forming units of influenza virus into each egg. Eggs were incubated at 37° C. for 48 hours, then left overnight at 4° C. Allantoic fluid was harvested from each egg and spun at 3000 g for 10 minutes at 4° C. to remove debris. Resulting supernatant was aliquoted and frozen at −80° C. to form a viral stock. To make purified stocks of virus, this supernatant was spun at 125,000 g for two hours at 4° C. in tubes containing 5 mL of a 30% sucrose solution. The resulting pellet was resuspended in phosphate buffered saline (PBS), aliquoted, and frozen at −80° C. to form a purified stock. Protein concentration was determined using a Bradford assay.

NIH/3T3 cells (ATCC) were cultured in Roswell Park Memorial Institute (RPMI) 1640 medium supplemented with 2 mM L-glutamine (Corning) and 10% fetal bovine serum (FBS; HyClone) and 100 units $mL^{-1}$ Penicillin and 100 μg $mL^{-1}$ Streptomycin (Gibco) (complete medium). The NIH/3T3 cell line was tested for *mycoplasma* contamination after receipt from ATCC and before expansion and cryopreservation. Madin-Darby Canine Kidney (MDCK) cells and HEK293T cells (ATCC) were cultured in Dulbecco's modified Eagle's medium (DMEM) supplemented with 10% FBS (Gibco), 100 units $mL^{-1}$ Penicillin and 100 μg $mL^{-1}$ Streptomycin (Gibco), and 1 mM 4-(2-hydroxyethyl)-1-piperazineethanesulfonic acid (HEPES; Gibco).

Expression plasmids (pcDNA3.1) were constructed for a stabilized, trimeric headless H1 (i.e., Mini HA) described by Impagliazzo et al. (Impagliazzo A et al., 2015, Science, 349:1301-1306), an N1 neuraminidase (A/Michigan/45/2015), or a viral NP (A/Michigan/45/2015) and synthesized by GenScript. The NA construct features an N-terminal signal peptide, a hexahistadine tag, and the vasodilator stimulating phosphoprotein (VASP) tetramerization domain followed by the NA ectodomain as described previously (Margine I et al., 2013, J. Vis. Exp., e51112). Mini HA and NP both feature a C-terminal hexahistidine purification tag. Plasmids were transfected into $6\times10^7$ Expi293F suspension cells (Life Technologies) using 4 μg $mL^{-1}$ polyethylenimine (PEI). Supernatants were harvested 96 hours post-transfection and recombinant protein was purified from the cell-free supernatant by affinity chromatography using nickel nitrilotriacetic acid agarose (Qiagen). Expression was confirmed by anti-HIS (Abcam) Western blot and when relevant, the multimerization of recombinant protein was confirmed by ELISA using monoclonal antibodies which recognize conformational epitopes (e.g., CR9114 and FI6). Expression levels were as follows: Mini HA 15-20 mg $L^{-1}$, N1 and NP both 1-0.5 mg $L^{-1}$.

Conservation Diagrams:

To determine the amino acid conservation of influenza virus proteins, data sets were established containing full length, complete influenza virus isolates by searching fludb.org. For H1N1 subtype variation, human isolates were chosen randomly to select one strain per year (n=49-52). Additionally, influenza virus isolates were chosen randomly to fairly spread the strains across the HA group 1 subtypes (H1, H2, H5, H6, H8, H9, H11, H12, H13, and H16), NA group 1 subtypes (N1, N4, N5, and N8), or across human, avian, and swine influenza A isolates for M2 and NP (n=50). Single nucleotide polymorphism scoring was performed based on a formula modified from Crooks et al. (Crooks G E et al., 2004, Genome Res., 14:1188-1190). In brief, a consensus sequence was produced based on the protein sequences analyzed and variation from consensus was scored based on the number and abundance of alleles or indels. These scores were used to color amino acid residues using PyMOL (Schrödinger).

mRNA Production:

Sequences of A/Michigan/45/2015 H1N1 influenza virus NA, NP, M2 (pUC-ccTEV-Michigan NA-A101, pUC-ccTEV-Michigan NP-A101, pUC-ccTEV-Michigan M2-A101), Crucell Mini HA #4900 (pUC-ccTEV-CRC HA-A101), or firefly luciferase (pUC-ccTEV-Luc2-A101) were codon-optimized, synthesized (GenScript) and cloned into the mRNA production plasmid. After ligation into expression vectors, mRNAs were produced using T7 RNA polymerase (Megascript, Ambion) on linearized plasmids. mRNAs were transcribed to contain 101 nucleotide-long poly(A) tails. mlW-5'-triphosphate (TriLink) instead of UTP was used to generate modified nucleoside-containing mRNA. Capping of the in vitro transcribed mRNAs was performed co-transcriptionally using the trinucleotide cap1 analog, CleanCap (TriLink). mRNA was purified by cellulose purification, as described (Baiersdorfer M et al., 2019, Mol. Ther. Nucleic Acids, 15:26-35). All mRNAs were analyzed by denaturing or native agarose gel electrophoresis and were stored frozen at −20° C.

LNP Formulation of the mRNA:

Cellulose purified mlW-containing RNAs were encapsulated in LNPs using a self-assembly process as previously described wherein an ethanolic lipid mixture of ionizable cationic lipid, phosphatidylcholine, cholesterol and polyethylene glycol-lipid was rapidly mixed with an aqueous solution containing mRNA at acidic pH (Pardi N et al., 2015, J. Control. Release, 217:345-351). The RNA-loaded particles were characterized and subsequently stored at −80° C. at a concentration of 1 μg $\mu L^{-1}$. The mean hydrodynamic diameter of these mRNA-LNP was ~80 nm with a polydispersity index of 0.02-0.06 and an encapsulation efficiency of ~95%.

mRNA Transfection:

Transfection of NIH/3T3 cells was performed utilizing TransIT-mRNA (Mirus Bio), according to the manufacturer's instructions: mRNA (0.3 g) was combined with TransIT-mRNA Reagent (0.34 μL) and Boost Reagent (0.22 μL) in 17 μL serum-free medium, and the complex was added to $3\times10^4$ cells in 183 μL complete medium. After overnight incubation at 37° C., NA and M2 mRNA-transfected cells were lysed for 30 minutes on ice in radio immunoprecipitation assay (RIPA) buffer (Sigma), Mini HA mRNA transfected cells were lysed with 1× NativePAGE Sample Buffer (Invitrogen), NP-transfected cells were collected for staining and flow cytometry analysis, all at 18 hours post transfection.

Western Blot Analyses of NA, M2, and Mini HA Protein Expression:

Whole-cell lysates obtained from $6\times10^4$ NA and M2 mRNA-transfected cells were assayed for NA and M2 protein by denaturing sodium dodecyl sulfate-polyacrylamide gel electrophoresis Western blot. Samples were combined with 4× Laemmli buffer (Bio-Rad) and incubated at 95° C. for 5 min, then separated on a 4%-15% precast polyacrylamide Mini-Protean TGX gel (Bio-Rad) for 1 hour at 120 V.

Whole-cell lysates obtained from $6\times10^4$ Mini HA mRNA-transfected cells were assayed for HA protein by Western blot under non-denaturing conditions. Samples were combined with 4× NativePAGE Sample Buffer, then separated on a NativePAGE 4-16% Bis-Tris Protein Gel (both from Invitrogen) for 1 hour at 150V, followed by 30 minutes at 250 V, all on ice. Transfer to polyvinylidene fluoride membrane was completed utilizing a Horizontal Semi-Dry Electro Blotter (Ellard Instrumentation) at 10 V for 1 hour.

For NA and M2, the membrane was blocked with 5% non-fat dry milk in Tris-buffered saline buffer containing 0.1% Tween-20 (TBS-T). For HA, the membrane was incubated in 8% acetic acid for 15 minutes to fix the proteins, followed by a 5 minutes rinse with methanol to remove background dye, before blocking in the same manner as with NA and M2. NA, M2, and HA proteins were probed by incubating with a 1:2,000 dilution of 4A5 (anti-NA)(Wohlbold T J et al., 2015, MBio, 6:e02556-14), E10 (anti-M2)(Bourmakina S V et al., 2005, J. Virol., 79:7926-7932), and KB2 (anti-HA)(Heaton N S et al., 2013, J. Virol., 87:8272-8281) mouse monoclonal antibodies at 1 mg $mL^{-1}$ overnight at 4° C., followed by incubation with a 1:5,000 dilution of donkey anti-mouse horseradish peroxidase (HRP)-IgG (Jackson ImmunoResearch Laboratories) secondary antibody for 1 hour at room temperature, all antibodies diluted in 5% non-fat dry milk in TBS-T. Blots were developed using Amersham ECL Western Blotting Detection Reagent on an Amersham Imager 600 (both from GE Healthcare) system.

Staining and Flow Cytometry Analyses of NP mRNA-Transfected NIH/3T3 Cells and Mouse Splenocytes:

$1.2\times10^5$ NP or Luc mRNA-transfected NIH/3T3 cells were incubated at 4° C. for 10 minutes with Cytofix/Cytoperm solution, then washed with 1× Perm/Wash buffer (both from BD Biosciences). Cells were then incubated at 4° C. for 30 minutes with 1:100 dilutions of an anti-NP mouse monoclonal antibody (BioXCell, BE0159) and washed again with 1× Perm/Wash. Finally, cells were incubated at 4° C. for 30 minutes with a 1:900 dilution of a goat anti-mouse (IgG+IgM) FITC-conjugated secondary antibody (Cayman Chemical). After an additional wash, cells were resuspended in FACS buffer (PBS with 2% FBS) and stored at 4° C. until analysis. The percentage of NP positive cells was detected on a modified LSR II flow cytometer (BD Biosciences). At least 25,000 events for each sample were recorded and data was analyzed with the FlowJo 10 software.

Spleen single-cell suspensions were made in complete RPMI 1640 medium. $3\times10^6$ cells per sample were stimulated for 6 hours at 37° C. 5% $CO_2$, in the presence of overlapping NA (BEI Resources, NR-19249) or NP (JPT peptides, PM-INFA-NPH2N2) peptide pools at 5 μg $mL^{-1}$ per peptide and an anti-CD28 antibody (1 μg $mL^{-1}$; clone 37.51; BD Biosciences). Golgi Plug (5 μg $mL^{-1}$; brefeldin A; BD Biosciences) and Golgi Stop (10 μg $mL^{-1}$; monensin; BD Biosciences) were added to each sample after 1 hour of stimulation. Unstimulated samples for each animal were included. A phorbol 12-myristate-13-acetate (10 μg $mL^{-1}$) and ionomycin (200 ng $mL^{-1}$; Sigma)-stimulated sample were included as a positive control.

After stimulation, cells were washed with PBS and stained with the LIVE/DEAD Fixable Aqua Dead Cell Stain Kit (Life Technologies) and then surface stained with the monoclonal antibodies (mAb) anti-CD4 PerCP/Cy5.5 (clone GK1.5; BioLegend) and anti-CD8 Pacific Blue (clone 53-6.7; BioLegend) for 30 minutes at 4° C. After surface staining, cells were washed with FACS buffer, fixed (PBS containing 1% paraformaldehyde), and permeabilized using the Cytofix/Cytoperm kit (BD Biosciences). Cells were intracellularly stained with anti-CD3 APC-Cy7 (clone SP34-2; BD Biosciences), anti-TNF-α PE-Cy7 (clone MP6-XT22; BD Biosciences), anti-IFN-γ AF700 (clone XMG1.2; BD Biosciences), and anti-IL-2 BV711 (clone JES6-5H4; BioLegend) mAbs for 30 minutes at 4° C. Next, the cells were washed with the permeabilization buffer, fixed as before, and stored at 4° C. until analysis.

Splenocytes were analyzed on a modified LSR II flow cytometer (BD Biosciences). 500,000 events were collected per specimen. After the gates for each function were created, the Boolean gate platform was used to create the full array of possible combinations, equating to seven response patterns when testing three functions. Data were analyzed with the FlowJo 10 program. Data were expressed by subtracting the percentages of the unstimulated stained cells from the percentages of the peptide pool stimulated stained samples.

Enzyme-Linked Immunosorbent Assays:

Flat-bottom, 96-well plates (Immulon 4 HBX (Thermo Fisher Scientific)) were coated with either recombinant protein at 2 μg $mL^{-1}$ or whole purified influenza virions at 5 μg $mL^{-1}$ to a volume of 50 μL per well. Plates were stored overnight at 4° C. The following morning, plates were washed three times with PBS containing 0.1% Tween 20 (Fisher Scientific) (PBS-T). 220 μL of blocking buffer (0.5% milk and 3% goat serum (Gibco) in PBS-T) was added to each well and plates were left at room temperature (RT) for one hour.

Blocking buffer was removed from wells, and fresh blocking buffer was added to ensure a final volume of 100 μL per well. Mouse sera were added and a three-fold serial dilution was performed in the plate leaving the first and last column blank to account for edge effects. The plate was stored at RT for two hours.

Plates were then washed with PBS-T three times and secondary antibody (horse radish peroxidase-linked polyclonal goat anti-mouse IgG (Abcam)) at a dilution of 1:15, 000 was added to each well to a final volume of 50 μL. Plates were left at RT for one hour, then washed four times with PBST with a shaking step included. 100 μL SigmaFast o-phenylenediamine dihydrochloride substrate (Sigma) was added and quenched with 50 μL of 3M hydrochloric acid (Fisher) after 10 minutes of development. Plates were read on a Synergy H1 hybrid multimode microplate reader (BioTek) at 490 nm. Data were analyzed using Prism 8.0 (GraphPad) and the area under the curve (AUC) was calculated using a baseline of the average of all control wells plus 3 times the standard deviation, or 0.07 if the baseline was lower than 0.07. All AUC values below one were adjusted to a value of one. Points showing no reactivity were nudged to ensure all lines were visible on a single graph.

For cell based ELISAs, $4\times10^4$ 293T cells were plated in serum-free DMEM in 96-well plates previously coated with poly-L-lysine (Sigma). After 24 hours of incubation, cells were transfected with 100 ng of pCAGGS vectored Mich15 M2 (catalytically inactive) using 0.3 μL of TransIT-LT1 (Mirus) per 100 ng DNA per well. Cells were incubated overnight at 37° C. and 5% $CO_2$. Cells were fixed with 3.7% paraformaldehyde (Fisher) in PBS for 24 hours at 4° C. before washing with PBS and blocking as above. The procedure was continued as described above, with gentle pipetting used to avoid dislodging cells from the plate.

mRNA Vaccination and Virus Challenge:

To determine the appropriate viral challenge dose, an infection using a dose escalation of infectious influenza virus was performed in female BALB/c mice aged six to eight weeks (Jackson labs). 3 mice were infected from each dose which ranged from 10 PFU to $10^5$ PFU in log intervals. Mice were anesthetized with a ketamine/xylazine mixture and 50 μL of virus at each dose was introduced through the intranasal route. Weight loss was monitored for 14 days and mice losing 25% of their initial body weight were humanly sacrificed. The dose at which 50% of mice succumbed to infection was determined as the $LD_{50}$ for future challenge studies.

Female BALB/c mice aged six to eight weeks were anesthetized and shaved to expose the skin of the back. After sterilization with 70% ethanol, mRNA vaccines diluted to 10 or 20 μg per 100 μL in PBS were injected intradermally into two sites distant from one another on the back to a total volume of 100 μL. Four weeks post vaccination, mice were anesthetized and infected with 50 μL of influenza virus intranasally. Additionally, mice were bled for serological analysis. Weight loss was monitored for 14 days and mice which lost more than 25% of initial body weight were humanely euthanized.

Passive Transfer of Sera and Splenocytes:

Female BALB/c mice aged six to eight weeks underwent a prime-boost regimen with 10 μg of mRNA vaccine per mouse with four-week intervals between both vaccinations and subsequent harvest. Mice were anesthetized, then a cardiac puncture was performed to gather whole blood. The blood was allowed to coagulate at room temperature for one hour before being placed at 4° C. for 30 minutes. Blood was then spun at 12,000 g for 10 minutes at 4° C. and sera were separated from remaining blood components and stored at 4° C. until further use. 200 μL of sera were transferred intraperitoneally into naïve mice two to six hours prior to influenza virus challenge. Mice were bled post-transfer, and sera were tested against the appropriate antigen by ELISA to ensure the transfer was successful. Spleens were dissected from euthanized mice and processed through a 70 m filter (Falcon) to dissociate cells, spleens and cells were placed in RPMI 1640 media (Gibco) on ice throughout this process. Red blood cells were lysed with ACK lysing buffer (Gibco) for 5 minutes before quenching with PBS. Cleared splenocytes were counted and 80 million cells were intravenously transferred into naïve mice two to four hours prior to influenza virus challenge.

Microneutralization Assay:

MDCK cells were plated at a concentration of $2.5\times10^4$ cells per well in 96-well dishes and incubated overnight at 37° C. and 5% $CO_2$. Serum samples were treated with a working dilution, following manufacturers guidelines, of receptor-destroying enzyme (RDE) (Seiken) at a ratio of 3:1 overnight in a 37° C. water bath. The following morning, RDE-treated serum was incubated with a 2.5% solution of Sodium Citrate (Fisher) at 56° C. for 30 minutes at a ratio of 3:4. To bring the sample to a 1 to 10 dilution, PBS was added at a final ratio of 3:7 with the solution. Assay buffer was made by adding 6-(1-tosylamido-2-phenyl) ethyl chloromethyl ketone (TPCK) treated trypsin at a concentration of 1 μg per mL to Ultra-MDCK media (Lonza). Sera were serially diluted 1:2 in a 96-well plate in assay buffer. Influenza virus IVR-180 was diluted to $100\times TCID_{50}$ in Ultra-MDCK media. 60 μL of diluted, RDE-treated sera were mixed with 60 μL of virus and allowed to shake at RT for 1 hour. In this time, MDCK cells were rinsed with PBS. 100 μL of the serum/virus mixture was then added to the cells and virus was allowed to adsorb to cells for 1 hour at 33° C. Virus/serum mixture was then removed and cells were washed with PBS before replacing with media containing serum at the same dilutions and incubating for 72 hours at 33° C. A hemagglutination assay was performed by mixing equal volumes of cell supernatant with 0.5% chicken red blood cells (Lampire). Wells in which red blood cells were agglutinated were determined to lack virus, determining the neutralization potential of the sera.

Antibody-Dependent Cell-Mediated Cytotoxicity Reporter Assay:

MDCK cells were plated in 96-well dishes at a concentration of $2.5\times10^4$ cells per well and incubated overnight at 37° C. and 5% $CO_2$. The next morning, influenza virus IVR-180 was diluted to $2.5\times10^5$ PFU per well in Ultra-MDCK media (an MOI of 5 assuming a doubling of cells) and MDCK cells were washed with PBS before the addition of 100 μL of diluted virus in the absence of TPCK-treated Trypsin.

Infection was allowed to proceed 24 hours at 37° C. Assay buffer was prepared by adding 4% Ultra Low-IgG FBS (Gibco) to RPMI-1640 (Gibco). Serum samples were serial diluted 3-fold in assay buffer starting at 1:25. Medium was removed from infected MDCK cells and 25 μL of warm assay buffer was added to each well along with 25 μL of diluted serum. ADCC effector cells (Jurkat cell line expressing the mouse FcγRIV cell-surface receptor (Promega)) were rapidly thawed and diluted in warm assay buffer to a concentration of $3\times10^6$ cells/mL ($7.5\times10^4$ cells per 25 μL) and 25 μL of cell dilution was added to each well and the mixture was allowed to incubate for 6 hours at 37° C. Cells and Bio-Glo Luciferase Substrate (Promega) were adjusted to RT, then 75 μL of luciferase substrate was added to each well and luminescence was immediately read on a Synergy H1 hybrid multimode microplate reader (BioTek). Fold change was calculated as relative luminescence unit of test wells divided by the average plus 3 times the standard deviation of background wells.

Figure 10:
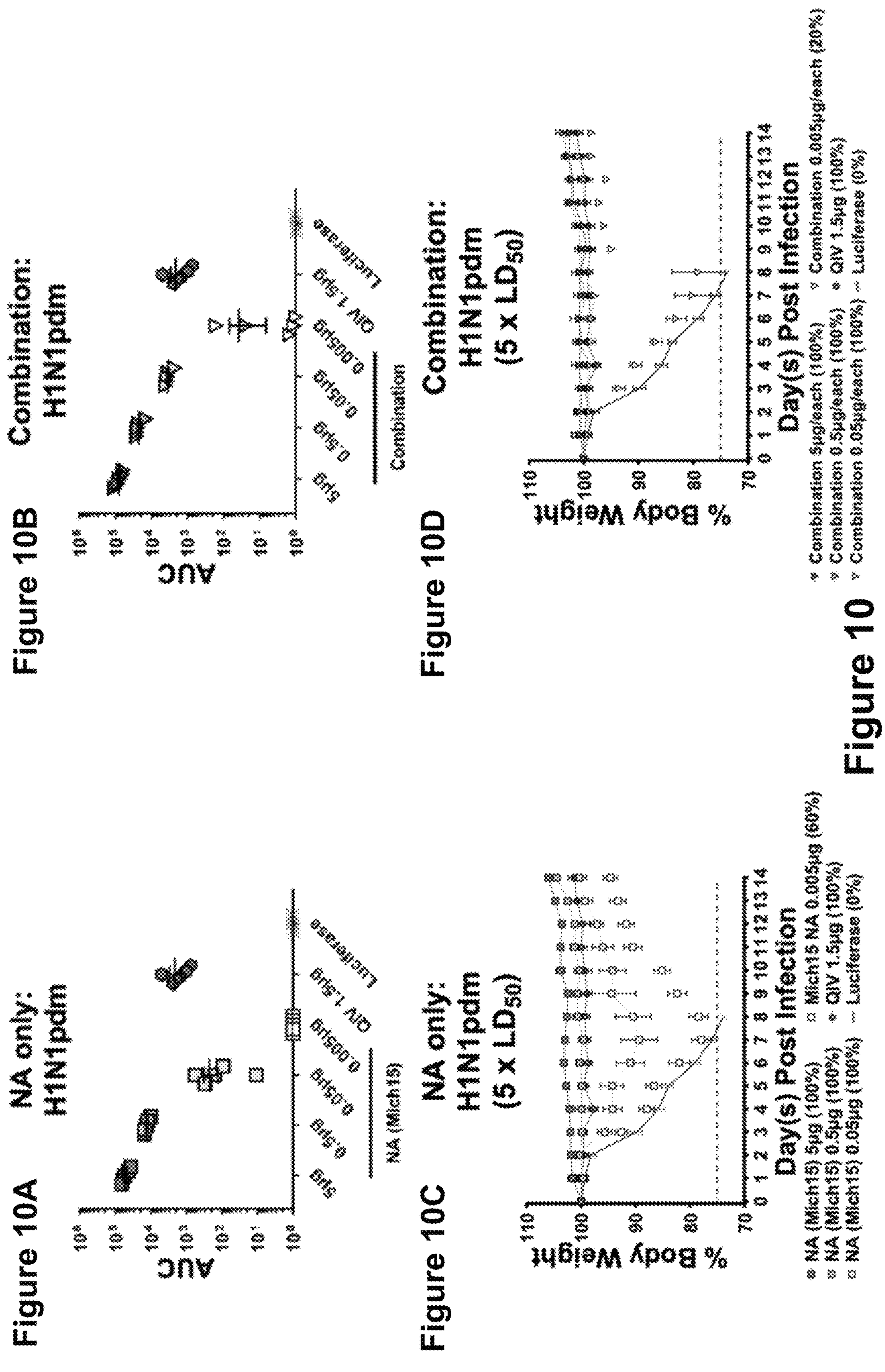
FIG. 10, comprising
Figure 14:
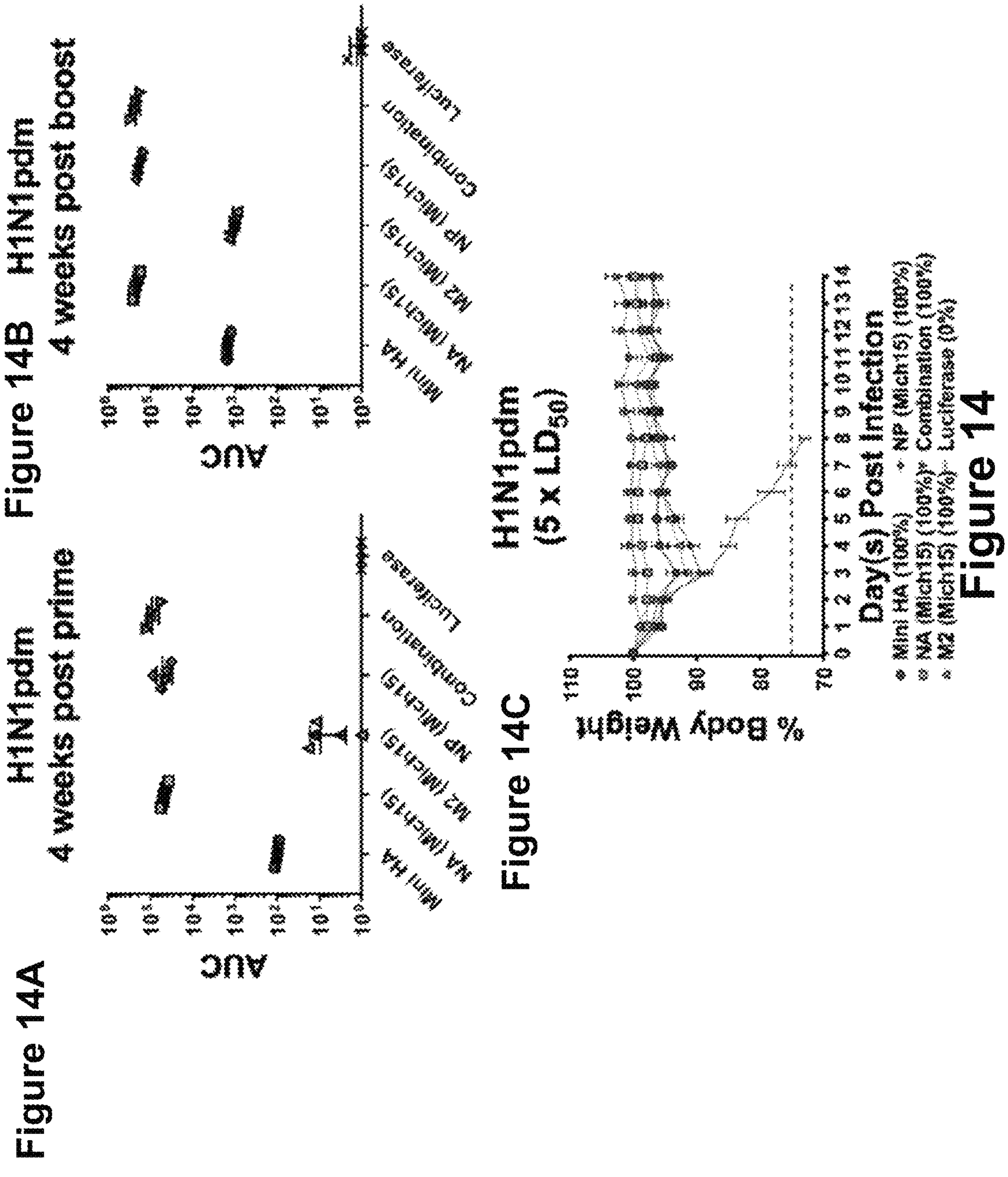
FIG. 14, comprising

Statistical Analyses:

Statistical analyses were performed using Prism 6.0 program (GraphPad Software, San Diego, CA-USA). FIG. 10: Data were compared with a Mann-Whitney (two-tailed) test. All p values <0.05 were considered statistically significant with a confidence interval of 95%. (*) p<0.05; () p<0.01; (*) p<0.001. FIG. 14: Data were compared using a two-way ANOVA test with Dunnett's correction for multiple comparisons. All adjusted p values <0.0332 were considered statistically significant with a confidence interval of 95%. (*) p<0.0332; () p<0.0021; (*) p<0.0002; (****) p<0.0001.

Selection of Universally Protective Influenza Virus Vaccine Antigens

To determine the extent of the variation in influenza virus proteins proposed as antigens for a combination universal influenza virus vaccine, conservation diagrams were produced. Human influenza virus isolates with complete genome sequences from within the H1N1 subtype were selected for each year available, dating back to 1918, to cover known variation. Across the H1N1 subtype, the HA stalk region remains conserved while the head domain showed substantial variability (FIG. 1), consistent with previous reports (Thyagarajan B et al., 2014, eLife, 3:e03300; Fulton B O et al., 2018, J. Virol., 655 92:e00754-18). The NA head showed a high degree of conservation, solidifying the rationale that vaccination with a high dose of NA protein can provide cross-reactive antibodies within the N1 subtype (Chen Y Q et al., 2018, Cell, 173:417-429; Wohlbold T J et al., 2015, MBio, 6:e02556). Both the M2 and NP proteins are highly conserved across the subtype, including the exposed M2 ectodomain.

Similarly, sequences were acquired for viruses spanning influenza HA group 1 viruses (H1, H2, H5, H6, H8, H9, H11, H12, H13, and H16) as well as NA group 1 viruses (N1, N4, N5, and N8) not limited by species tropism (Nachbagauer R et al., 2017, Nat. Immunol., 18:464-473; Krammer F et al., 2018, MBio, 9: e02332-17). The strong selective pressure on both of these molecules by antibody-mediated immunity was apparent in the small number of conserved domains within group 1 (FIG. 1). The HA stalk had some patches of conservation where broadly cross-reactive antibodies have been described to bind (Lee P S et al., 2015, Curr. Top. Microbiol. Immunol., 386:323-341). The NA active site was also well conserved within group 1 NAs (FIG. 1), and cross-reactive antibodies have been reported to bind this site (Stadlbauer D et al., 2019, Science, 366:499-504). Differences in M2 and NP are mostly found between species (Zhuang, Q et al., 2019, Virol. J., 16:85), therefore, sequences were selected from human, avian, and swine strains to model the breadth of influenza viruses of seasonal and pandemic concern (FIG. 1). Both M2 and NP proteins show high levels of conservation compared to the more exposed glycoproteins and were both previously studied as antigens for influenza virus vaccines (Schotsaert M et al., 2016, Sci. Rep., 6:24402; Lambe T et al., 2013, Sci. Rep., 3:1443; Antrobus R D et al., 2014, Mol. Ther., 22:668-674; Coughlan L et al., 2018, EBioMedicine, 29:146-154).

Therefore, the conservation profile and previous encouraging approaches supported the selection of these four proteins for a combination vaccination approach using nucleoside-modified mRNA-LNP vaccines. To elicit antibodies against the conserved HA stalk domain, a "Mini HA" construct based on the A/Brisbane/59/2007 H1N1 HA and designed to lack the highly variable globular head domain of HA was used (Impagliazzo A et al., 2015, Science, 349: 1301-1306). The wild-type, membrane-bound NA from A/Michigan/45/2015 H1N1pdm (Mich15) was used to match the currently circulating seasonal influenza virus strain. Similarly, the wild-type NP from Mich15 was used, which matched the currently circulating H1N1 viruses and was overall highly conserved. To elicit immune responses against M2, a construct (based on Mich15) with the amino acid residues 29-31 deleted was used. This mutation was introduced to render the ion-channel activity non-functional and to reduce potential cytotoxicity as a result of overexpression on the cell surface (Watanabe T et al., 2001, J. Virol., 75:5656-5662). Importantly, the mRNA approach enabled encoding of the full-length M2 ion channel, including the transmembrane region, which retained T-cell epitopes and leads to a more natural presentation of the antigen on the cell surface compared to previous vaccination approaches.

Figure 2:
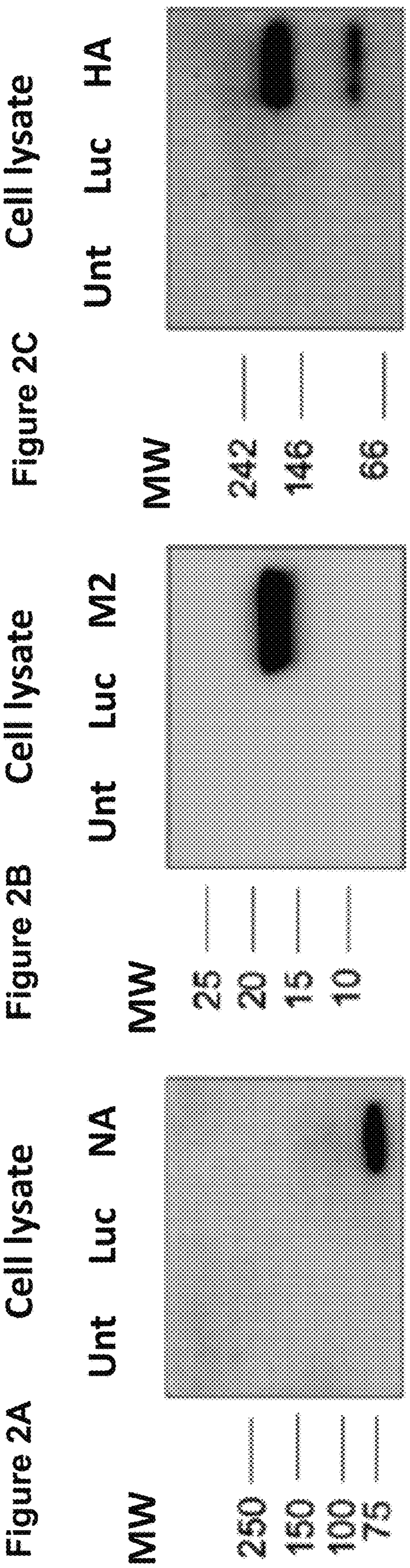
FIG. 2, comprising
Figure 3:
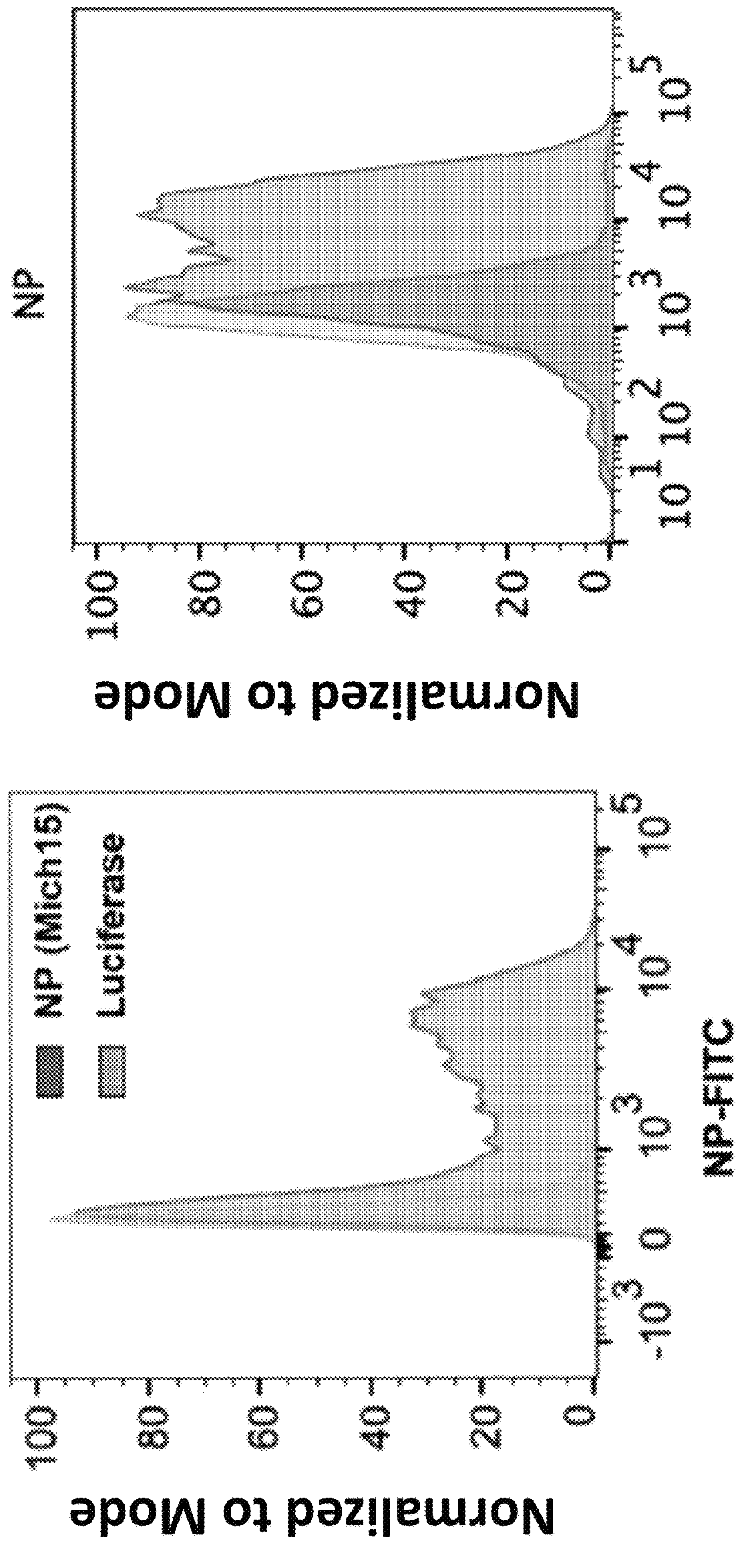
FIG. 3 depicts a representative characterization of nucleoprotein (NP) encoding mRNA by flow cytometry. NP mRNA was transfected into NIH/3T3 cells. Positive binding of the anti-NP antibody to NP-transfected cells (purple) relative to luciferase transfected cells (gray). Two independent experiments were performed with similar results.

Nucleoside-Modified mRNA-LNP Vaccination Elicited Robust Humoral Immune Responses Protein production from mRNAs encoding Mini HA, NA, and M2 immunogens was confirmed by Western blot analyses on cell lysates made from transfected NIH/3T3 cells (FIG. 2). Production of NP protein in NP mRNA-transfected NIH/3T3 cells was validated by flow cytometry (FIG. 3).

Figures 4, 4A, 4B, 4C:
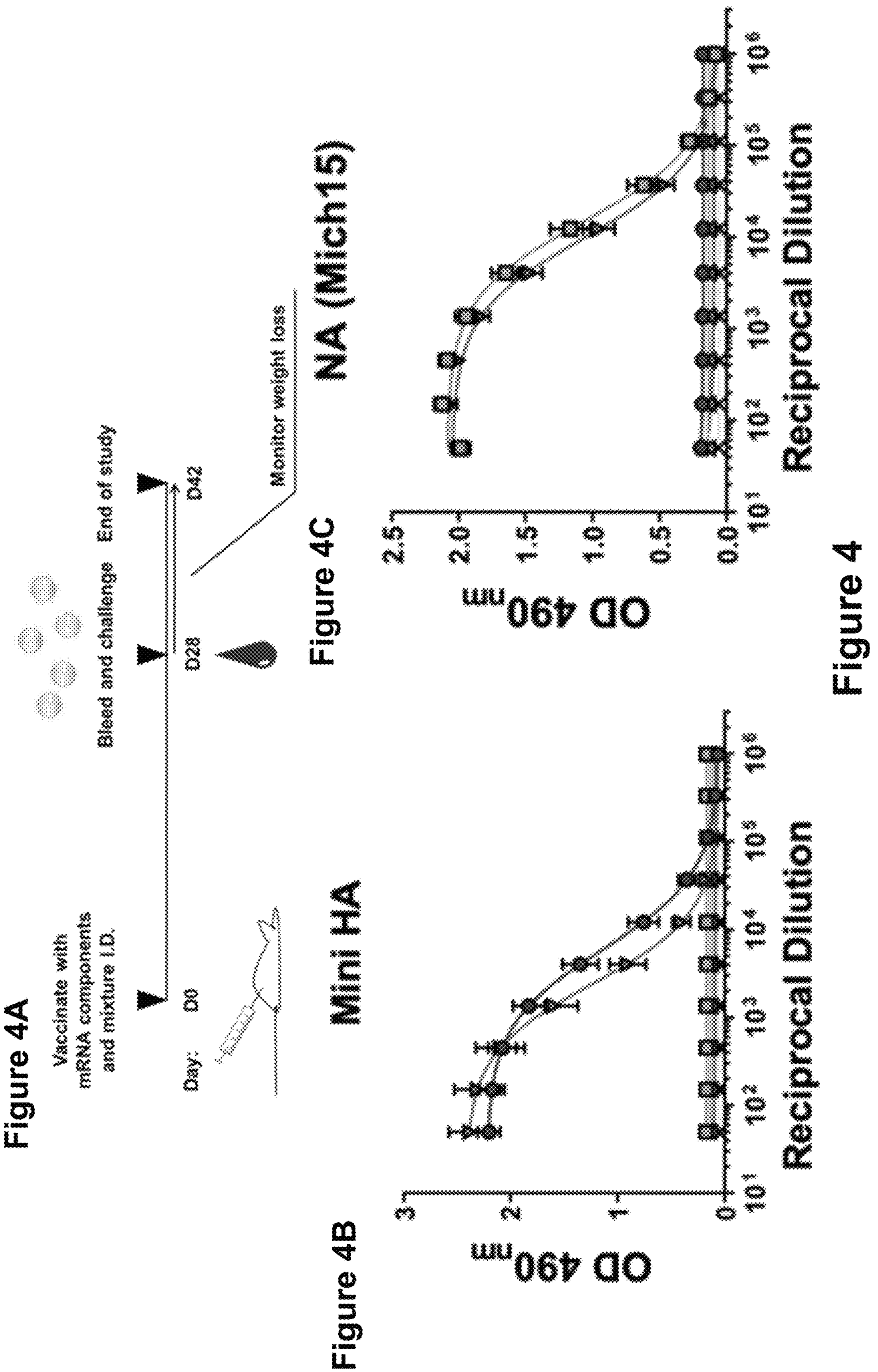
FIG. 4, comprising
FIG. 4A through FIG. 4G, depicts representative results demonstrating that nucleoside-modified mRNA-lipid nanoparticles (LNP) vaccines encoding conserved influenza virus antigens elicit robust immune responses in mice.

The titers elicited as well as specificity and functionality of serum antibodies produced 28 days after vaccination were then investigated. Mice were vaccinated with a single dose of nucleoside-modified mRNA-LNPs encoding different conserved influenza virus antigens (combined or individually) or an irrelevant formulation encoding firefly luciferase (Luc) (FIG. 4A). In enzyme-linked immunosorbent assays (ELISAs), the vaccines were shown to elicit potent antigen-specific antibodies, with similar results observed when the four constructs were administered individually or in combination (FIG. 4B through FIG. 4E).

Figures 4, 4D, 4E, 4F, 4G:
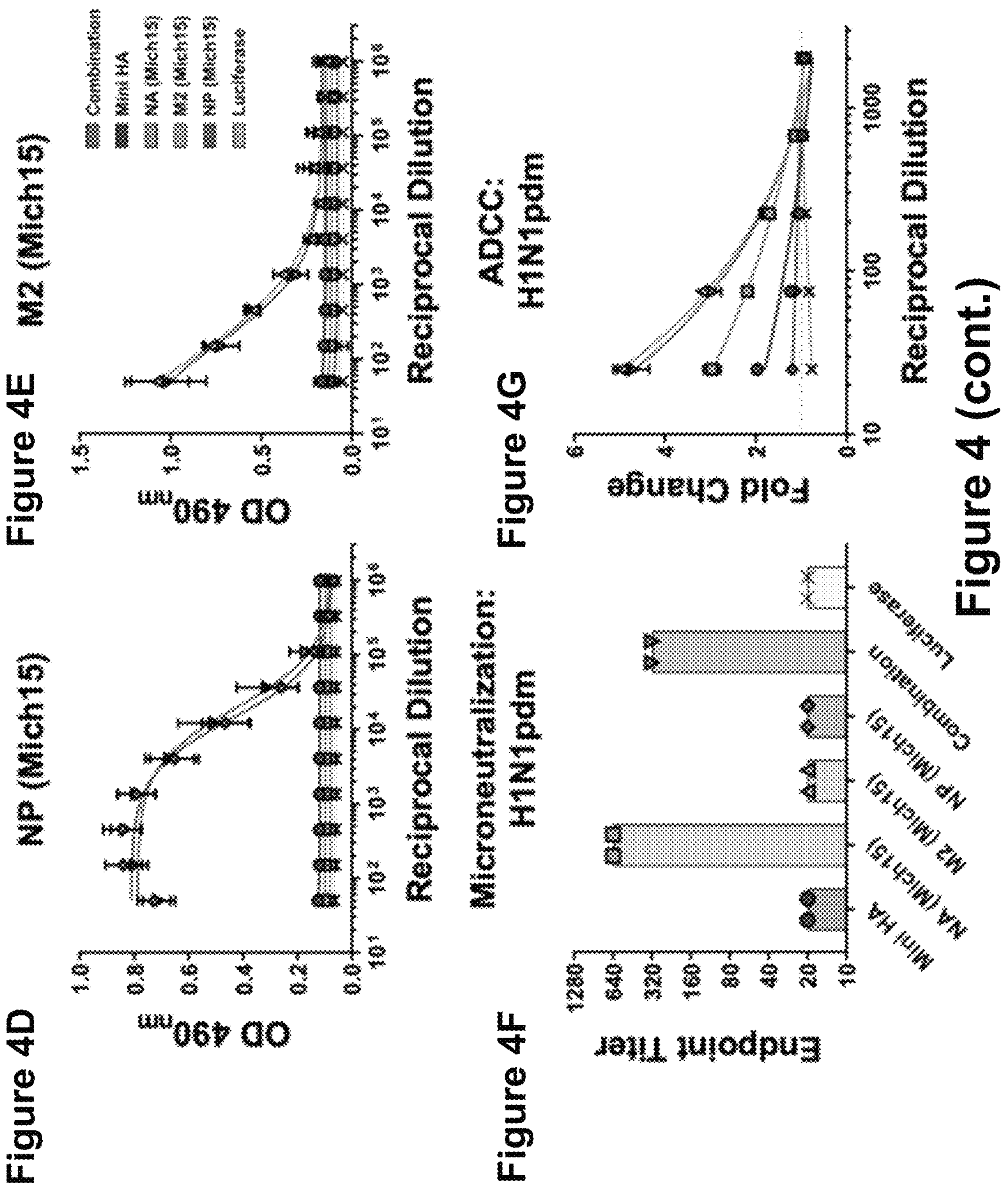

To further assess the functionality and potency of vaccine-elicited antibodies, a multicycle neutralization assay was performed using a vaccine strain for the current seasonal H1N1pdm virus (FIG. 4F). The NA component of the vaccine was found to elicit high neutralizing titers, even in the context of a combination approach. While NA-specific antibodies generally did not interfere with virus entry, the multicycle assay used can also detect antibodies that interfere with virus egress, which was the likely mechanism of action. In contrast, sera from the NP, M2, and Mini HA vaccination groups did not show neutralization in the assay. NP was not exposed on the virion surface and therefore did not elicit neutralizing antibodies. M2-specific antibodies have been previously shown to lack neutralizing functionality, but to mediate protection through Fc-functions (El Bakkouri K et al., 2011, J. Immunol., 186:1022-1031). While HA stalk antibodies can exhibit neutralizing activity, repeated administrations may be required to elicit these antibodies in a naïve animal model. Similar to M2-specific antibodies, HA stalk-specific antibodies have been shown to confer Fc-mediated protection in vivo (Jacobsen H et al., 2017, MBio, 8:e01463-17).

To assess the ability of serum antibodies to elicit Fc-mediated effector functions, a murine antibody dependent cell-mediated cytotoxicity (ADCC) reporter assay was utilized (Cheng Z J et al., 2014, J. Immunol. Methods, 414: 69-81; Choi A et al., 2019, Immunohorizons, 3:133-148). Sera from M2-encoded mRNA-LNP vaccinated mice showed the strongest activity in the ADCC reporter assay (FIG. 4G). Lower responses were observed in groups immunized with the monovalent NA or Mini HA mRNA-LNP vaccines and no activity was detected in mice given NP mRNA-LNP vaccine alone.

Figure 5:
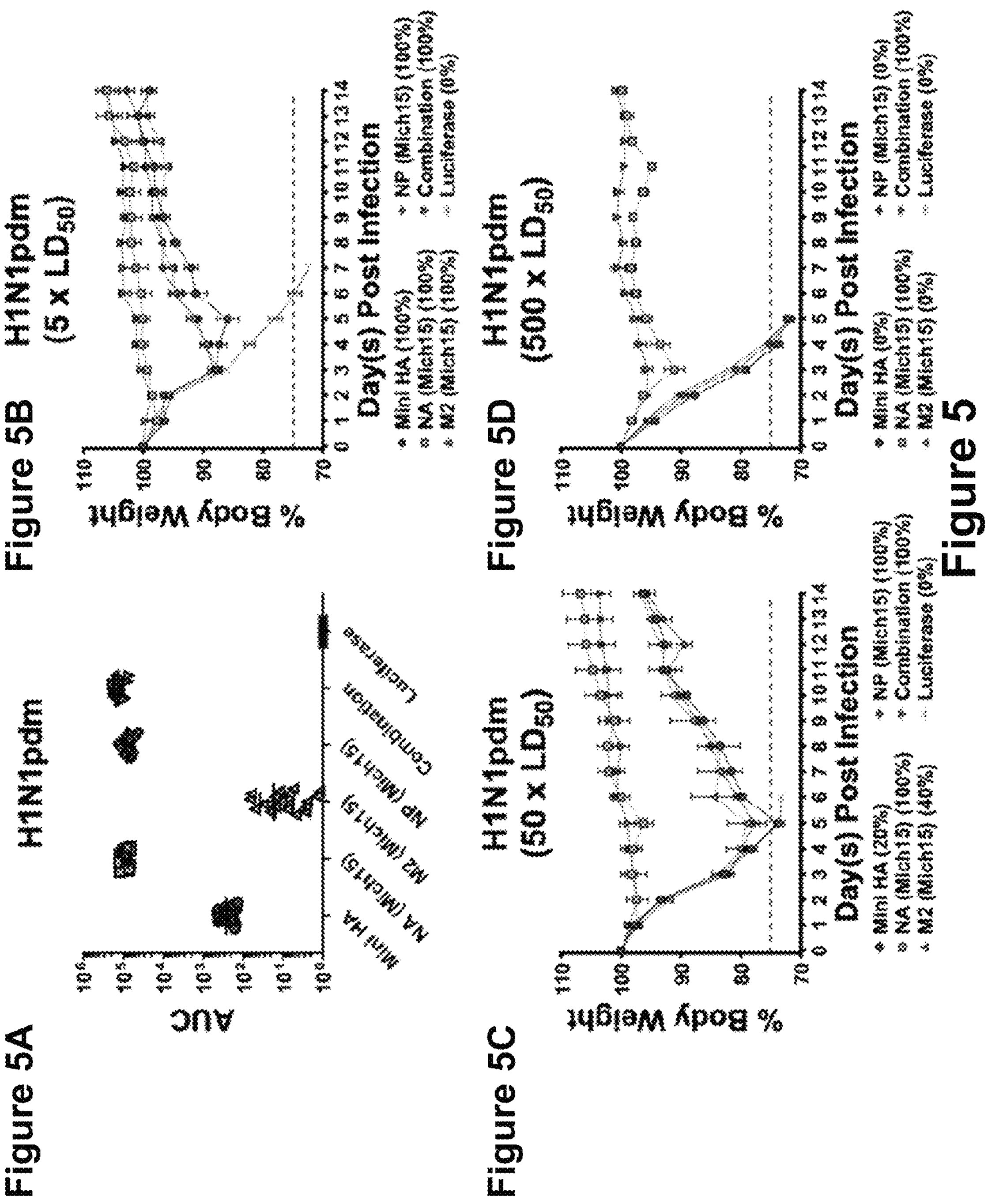
FIG. 5, comprising

In addition, the sera were tested against a purified stock of the H1N1pdm virus by ELISA in order to determine the binding of serum antibodies to virion particles rather than individual recombinant proteins (FIG. 5A). The strongest binding was observed in groups that received NA and NP vaccines, revealing a strong antibody response to the internal NP. Sera from Mini HA-vaccinated mice showed lower binding, again indicating that repeated vaccinations may be required for strong affinity maturation of HA stalk specific antibodies. Sera from M2-vaccinated mice showed the weakest reactivity to whole virus, likely due to the low prevalence of M2 on the virion surface (Lamb R A et al., 1985, Cell, 40:627-633). The combination vaccine did not result in higher reactivity to the virion, though antigen saturation may have been achieved by the NA and NP-specific antibodies.

Overall, the antibodies elicited by nucleoside-modified mRNA-LNP vaccines were antigen-specific, bind to virus, and show functionality in multiple assays.

Nucleoside-Modified mRNA-LNP Vaccinated Mice were Protected from Challenge with Influenza Virus Twenty-eight days after a single intradermal (I.D.) vaccination, mice were challenged with an influenza virus H1N1pdm challenge strain (FIG. 4A). All animals vaccinated with the monovalent or combined influenza virus vaccines survived challenge with five times the 50% lethal dose (LD50) of virus albeit with some morbidity in the Mini HA, M2, and NP groups (FIG. 5B). All mice vaccinated with Luc mRNA LNPs at the same dose did not survive infection. Due to a complete lack of morbidity in both the NA only and combination vaccine groups, additional challenge experiments with higher doses of virus (50× and 500×$LD_{50}$) were performed (FIG. 5C and FIG. 5D). Vaccination with Mini HA, M2, or NP alone conferred only partial protection at 50×$LD_{50}$ and did not protect at 500×$LD_{50}$. The NA-only vaccine prevented mortality in mice at both high dose challenges. A trend towards improved protection with the combination vaccine compared to NA-only was observed at the highest infection dose (FIG. 5D). However, this was strong support for NA-based protection in a vaccine-matched challenge virus setting.

Figure 6:
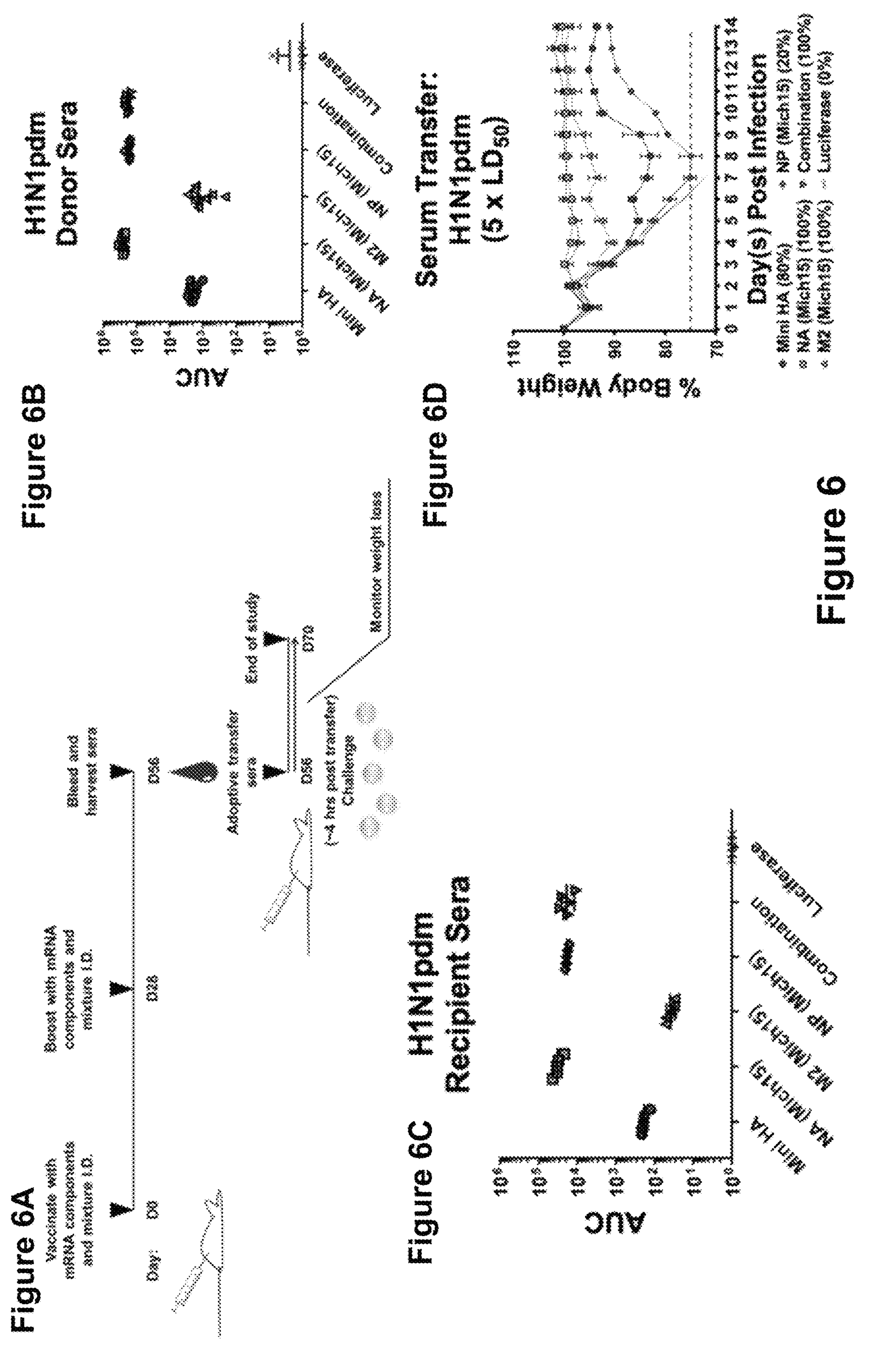
FIG. 6, comprising
Figures 8, 8A:
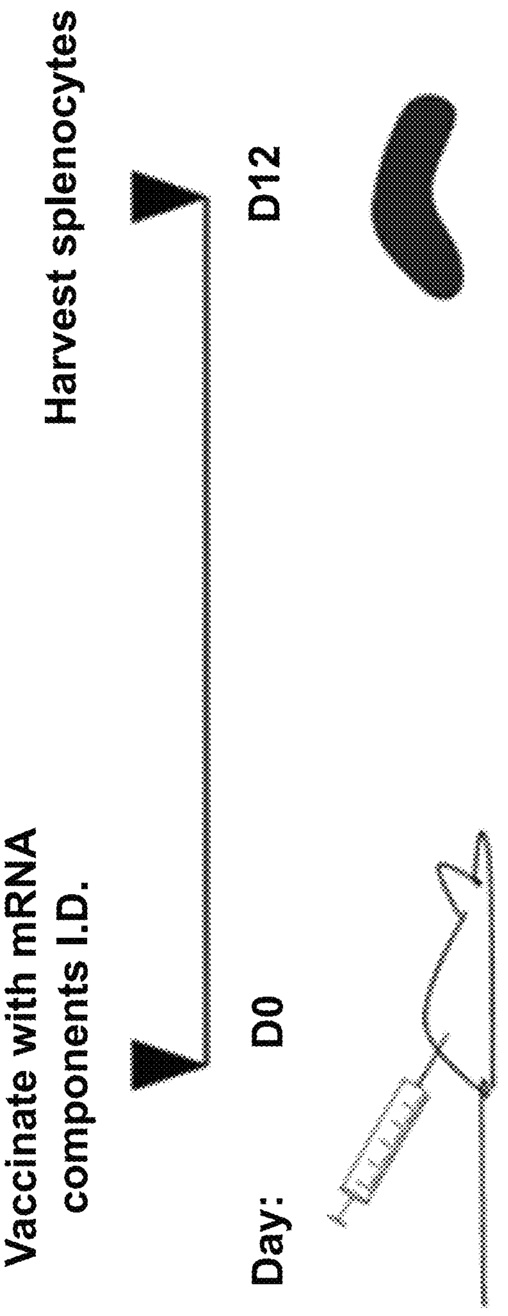
Figure 8:
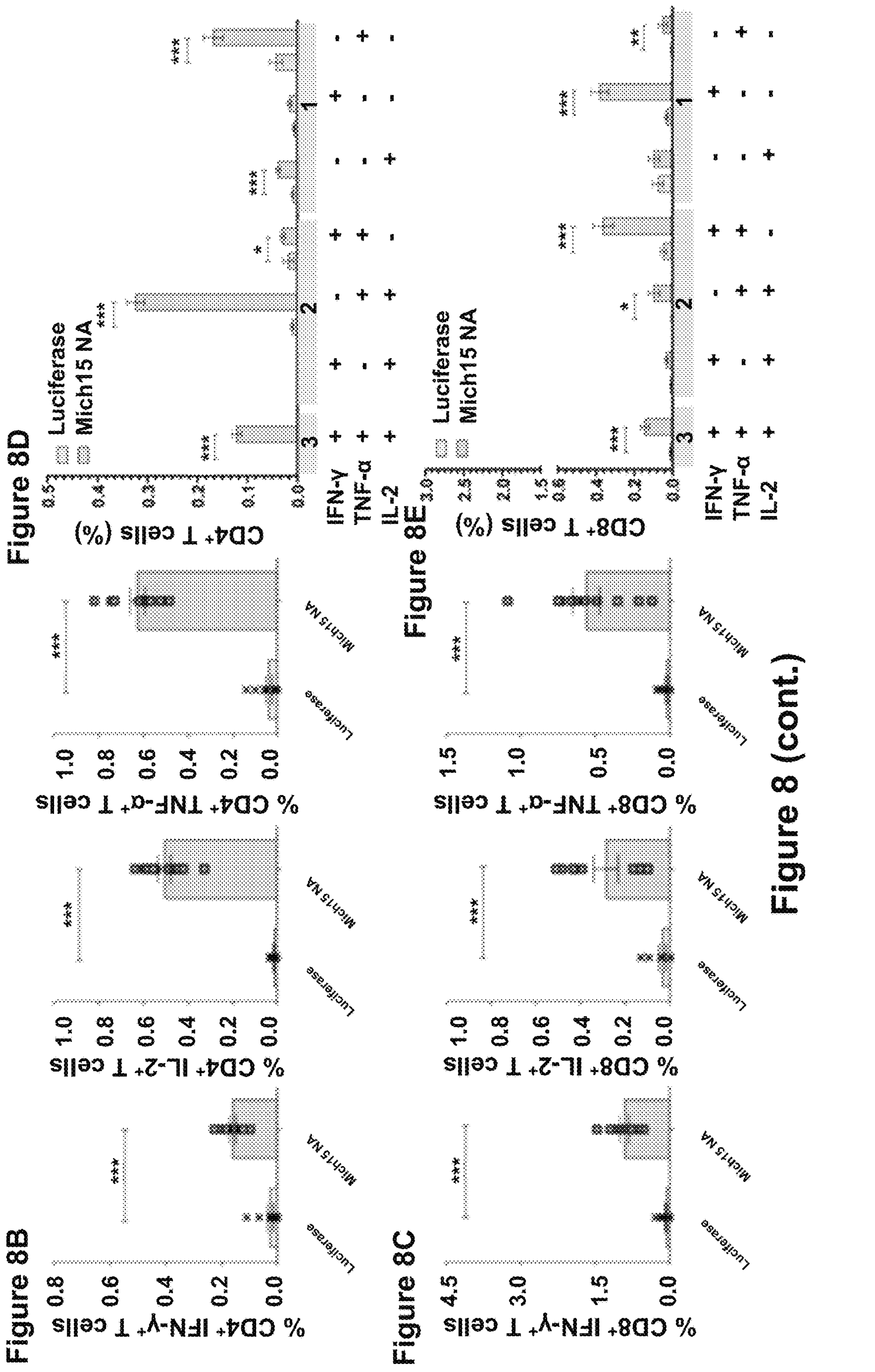
FIG. 8, comprising
Figure 8:
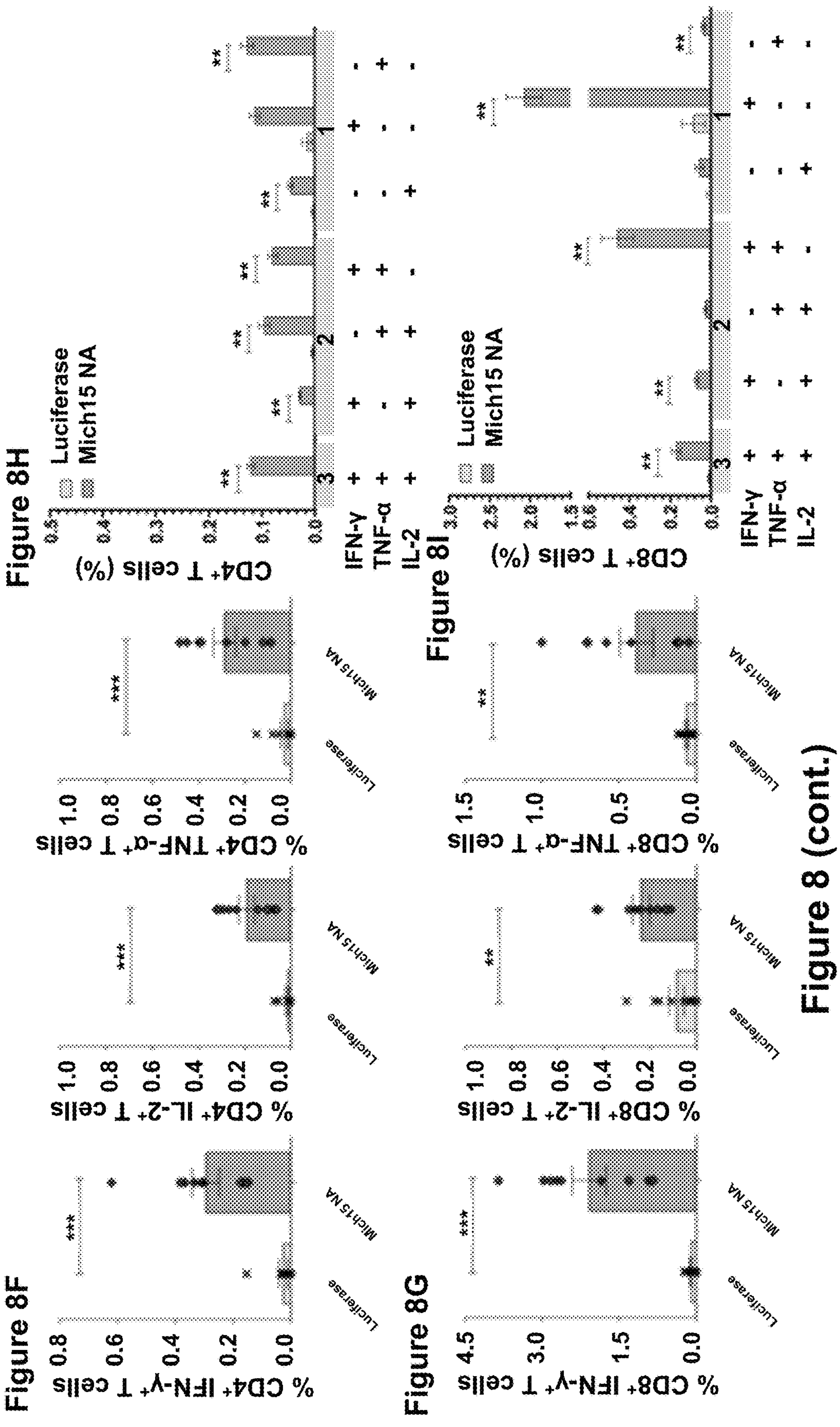
Figure 9:
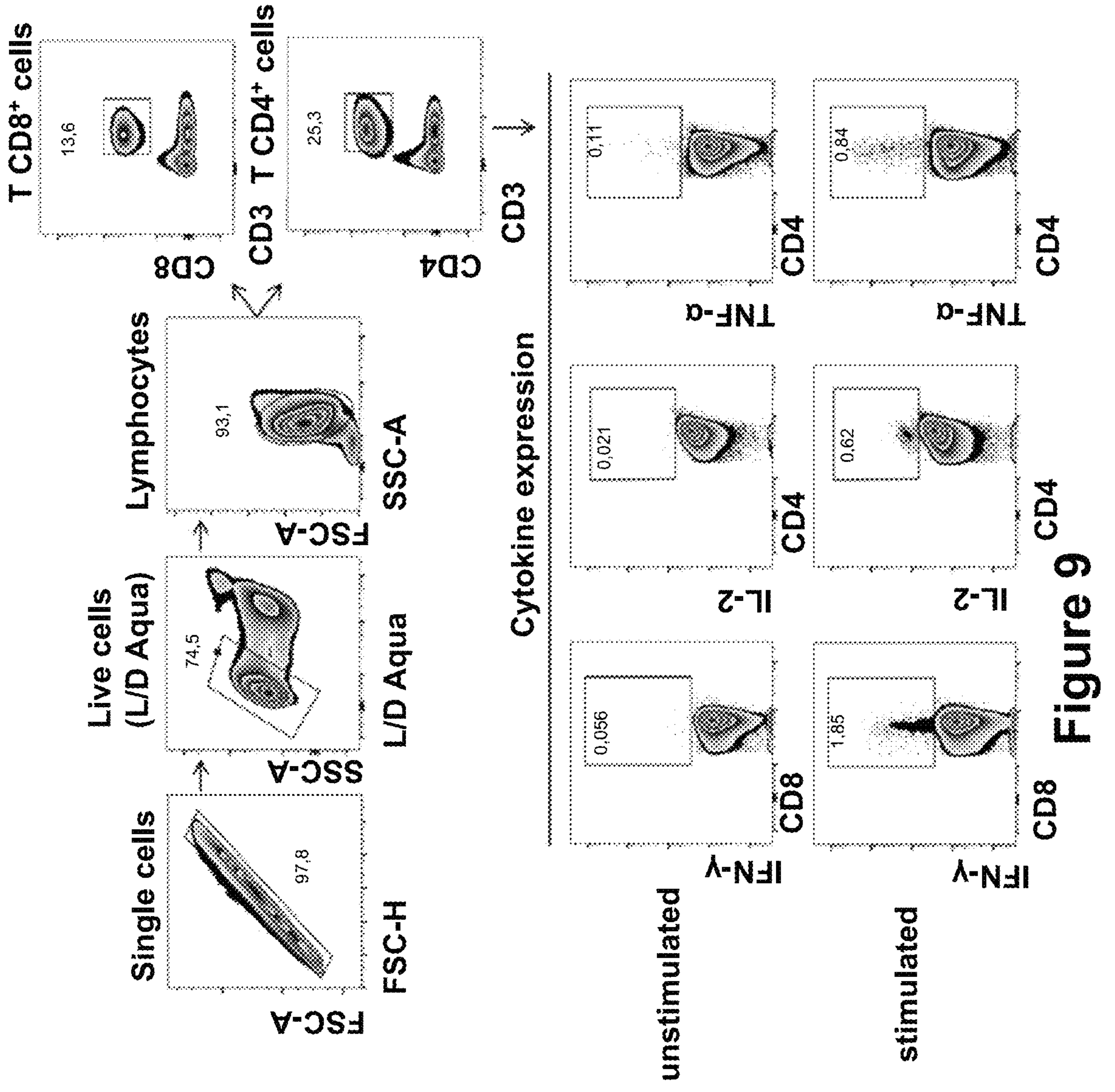
FIG. 9 depicts a flow cytometric gating strategy for the investigation of T cell responses in neuraminidase and nucleoprotein mRNA-LNP-immunized mice. Representative flow cytometry plots for unstimulated and peptide-stimulated samples are shown.

Nucleoside-Modified mRNA-LNP Vaccine-Induced Protection from Influenza Virus Challenge was Mediated Primarily by Antibodies To determine which component(s) of the immune system contributed to protection, an adoptive transfer system was established. Mice were vaccinated twice with 10 μg of mRNA-LNP vaccines (single and combined formulations) with four-week intervals between administrations to generate strong immune responses (FIG. 6A). Mice were then euthanized four weeks after the boost and a terminal bleed was performed to collect sera. Spleens were also extracted from immunized animals and splenocytes were isolated and pooled after red blood cell lysis for adoptive transfer experiments using naïve mice. Sera from the terminal bleeds was tested against purified H1N1pdm virus by ELISA and shown to be highly reactive (FIG. 6B). This serum was then pooled and transferred into naïve mice through intraperitoneal administration. Concurrently, additional groups of naïve mice were adoptively transferred 80 million splenocytes from the immune-primed hosts through the intravenous route. Two hours post transfer, sera from the recipient mice were harvested and subsequently tested by ELISA (FIG. 6C). The sera tested reacted similarly to the pre-transfer sera, though a loss of response was noted, due to the low volume (200 μl) of transfer relative to the total blood volume of a mouse (~2 ml). Animals were then challenged with 5×$LD_{50}$ of H1N1pdm virus and weight loss was monitored for 14 days. Animals that received serum from mice vaccinated with the combination of antigens or the NA component of the vaccine alone were protected from challenge (FIG. 6D), while those receiving Mini HA or M2 alone saw morbidity and partial protection. Mice that received sera from NP-immunized donors showed severe morbidity and mortality. After splenocyte transfer, all animals succumbed to infection (FIG. 7) with no protection from morbidity or mortality observed. These results show that immunity elicited by nucleoside-modified mRNA-LNP vaccines was primarily antibody-mediated. However, the approach may not be sensitive enough to detect cell-mediated protection, which likely contributed to the stronger protection observed for NP in the direct challenge setup.

To determine the induction of cellular immune responses elicited by vaccination with nucleoside modified mRNA-LNPs, analyses of T-cell repertoires were performed. The immune responses elicited in mice after vaccination with nucleoside-modified mRNA-LNPs has been previously reported to induce high frequencies of antigen-specific CD4+ helper T-cells which stimulate a strong germinal center B-cell reaction and subsequent antibody production (Pardi N et al., 2018, J. Exp. Med., 215:1571-1588). In line with these findings, polyfunctional CD4+ T-cell responses and strong CD8+ T-cell activation to NA were measured in mice 12 days after a single I.D. immunization with 20 g of NA mRNA-LNPs (FIG. 7A through FIG. 7E and FIG. 9). Potent NP-specific CD8+ T cell activation followed by I.D. administration of a single dose of 20 μg of NP mRNA-LNPs (FIG. 7F, FIG. 71, and FIG. 9) was also measured. Therefore, these cellular responses may be playing a role in combatting infection, but the adoptive transfer assay may not have been sensitive enough to detect protective cellular immunity (FIG. 6D).

Dose De-Escalation of Nucleoside-Modified mRNA-LNP Vaccines Showed Protection in the Nanogram Range after Administration of a Single Dose Mice were vaccinated with decreasing doses of either NA alone or NA in addition to the Mini HA, M2, and NP constructs (Combination). Matched, seasonal QIV was administered intramuscularly (I.M.) as a "standard of care". Twenty-eight days after vaccine administration, mice were bled and sera were analyzed by ELISA against purified H1N1pdm virus. Mice given NA alone showed responses to purified virus with a dose as low as 0.050 μg of mRNA, with responses reaching undetectable levels at the 0.005 μg dose (FIG. 9A). The sera from mice vaccinated with the combination vaccine were more reactive by ELISA at similar doses, which can be explained by the additional antigens administered in addition to the NA (FIG. 9B). Responses were consistently detectable at the 0.05 μg (per antigen) dose and two serum samples reacted above background at the 0.005 μg dose. Mice were then challenged with $5\times LD_{50}$ of H1N1pdm virus and weight loss was monitored for 14 days. All NA-vaccinated mice were protected from infection at the 0.5 μg dose, with no morbidity or mortality observed (FIG. 9C). Some morbidity was observed at the 0.05 μg dose, but all mice survived the challenge. At the 0.005 μg dose, mice either succumbed to the infection or lost nearly 25% of their body weight before recovering. In the combination vaccination group, the protection was more potent with no morbidity or mortality noted in mice immunized with 0.05 μg per antigen of mRNA-LNP vaccine (FIG. 9D). Four out of five mice given 0.005 μg for each antigen succumbed to infection. One mouse only lost 10% of initial body weight and was identified as the highest responder by ELISA.

In summary, vaccination with a single low dose of 0.05 μg of NA nucleoside-modified mRNA-LNP alone can protect animals from morbidity and mortality with an NA-matched challenge strain, while the addition of Mini HA, M2, and NP antigens further contribute to this protection to ameliorate morbidity at this dose.

Figure 11:
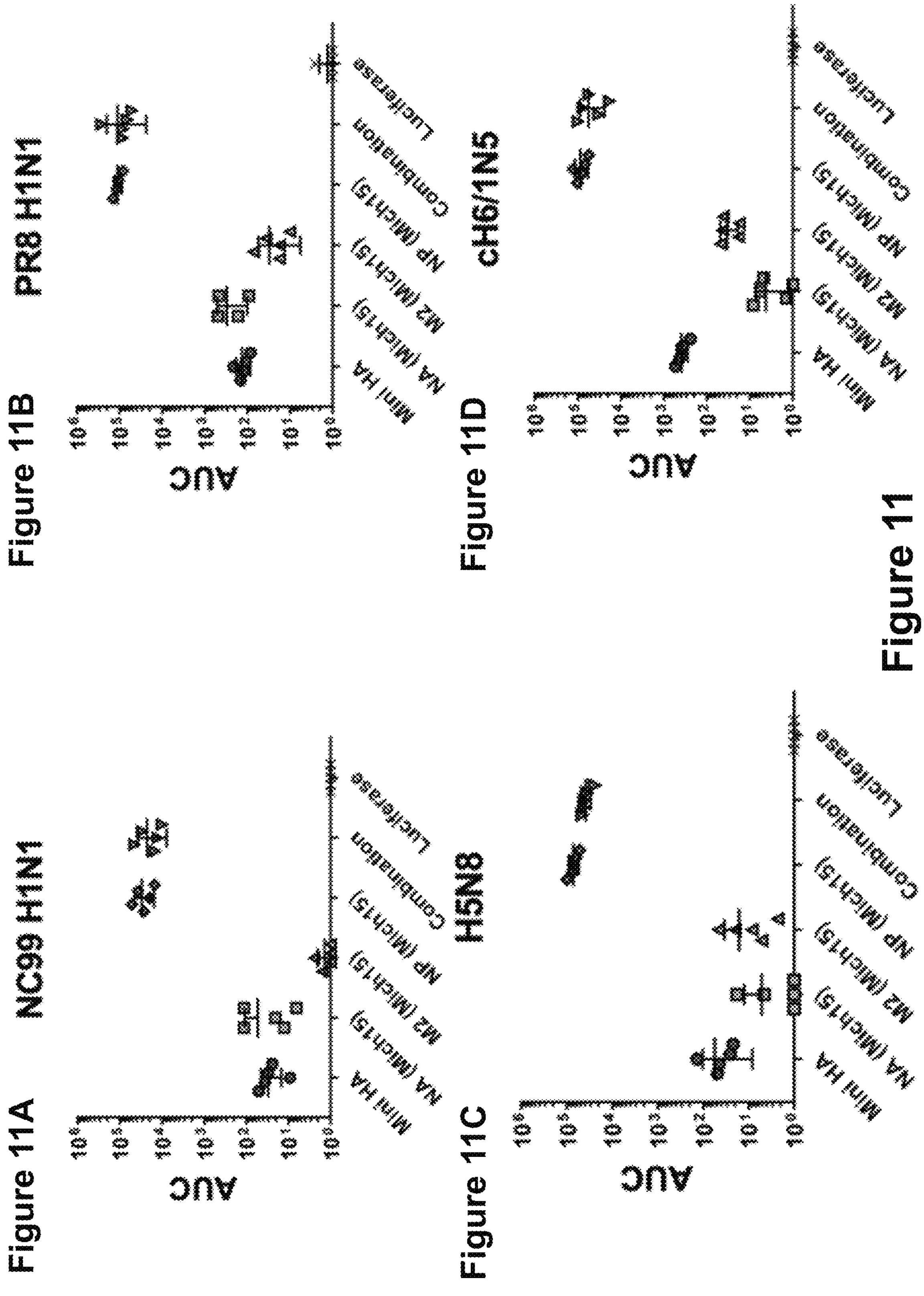
FIG. 11, comprising

A Single Immunization with Nucleoside-Modified mRNA-LNP Influenza Virus Vaccines Induced Protection from a Broad Range of Group 1 Influenza a Viruses To assess the potential of this vaccination approach to provide protection from group 1 influenza viruses, a broad panel of challenge viruses was utilized. Mice were vaccinated in a prime-only regimen, as described above. Twenty-eight days after vaccination, mice were bled to determine the reactivity of sera against the corresponding purified challenge virus by ELISA (FIG. 11). H1N1 subtype viruses isolated before the 2009 pandemic and also influenza viruses with avian glycoproteins were tested to determine the level of cross-reactivity (FIG. 12). A/New Caledonia/20/1999 H1N1 (NC99) and A/Puerto Rico/8/1934 H1N1 (PR8) viruses were chosen due to the relative distance of these viruses from one another within the pre-pandemic H1N1 subtype (Nachbagauer R et al., 2017, Nat. Immunol., 18:464-473). An influenza virus with an avian H6 head domain and H1N1pdm stalk domain coupled with an avian N5 glycoprotein (cH6/1N5) was selected along with a virus bearing a low-pathogenicity avian H5 and avian N8 (H5N8) to represent group 1 breadth of protection for both HA and NA.

Figure 13:
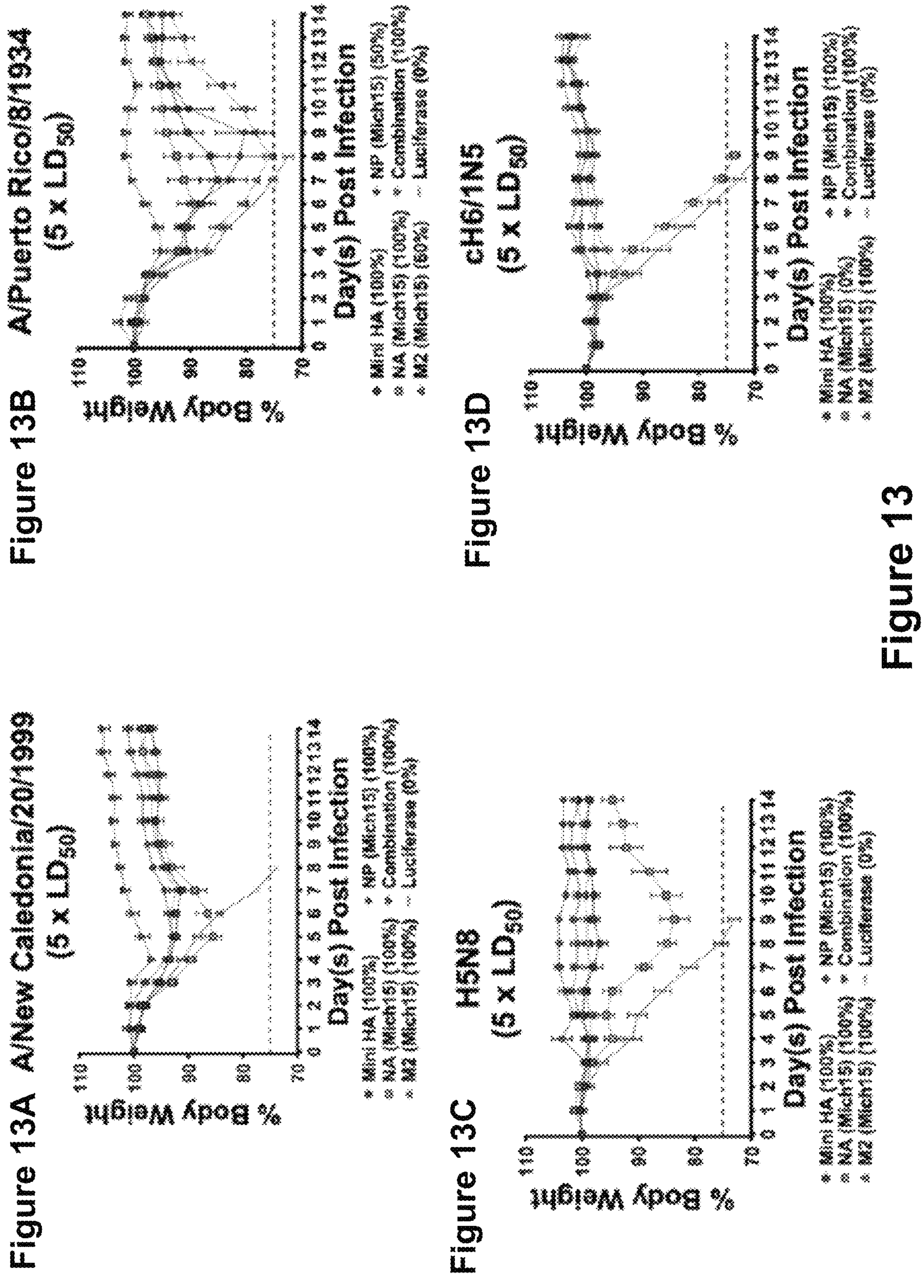
FIG. 13, comprising
Figures 13, 13E:
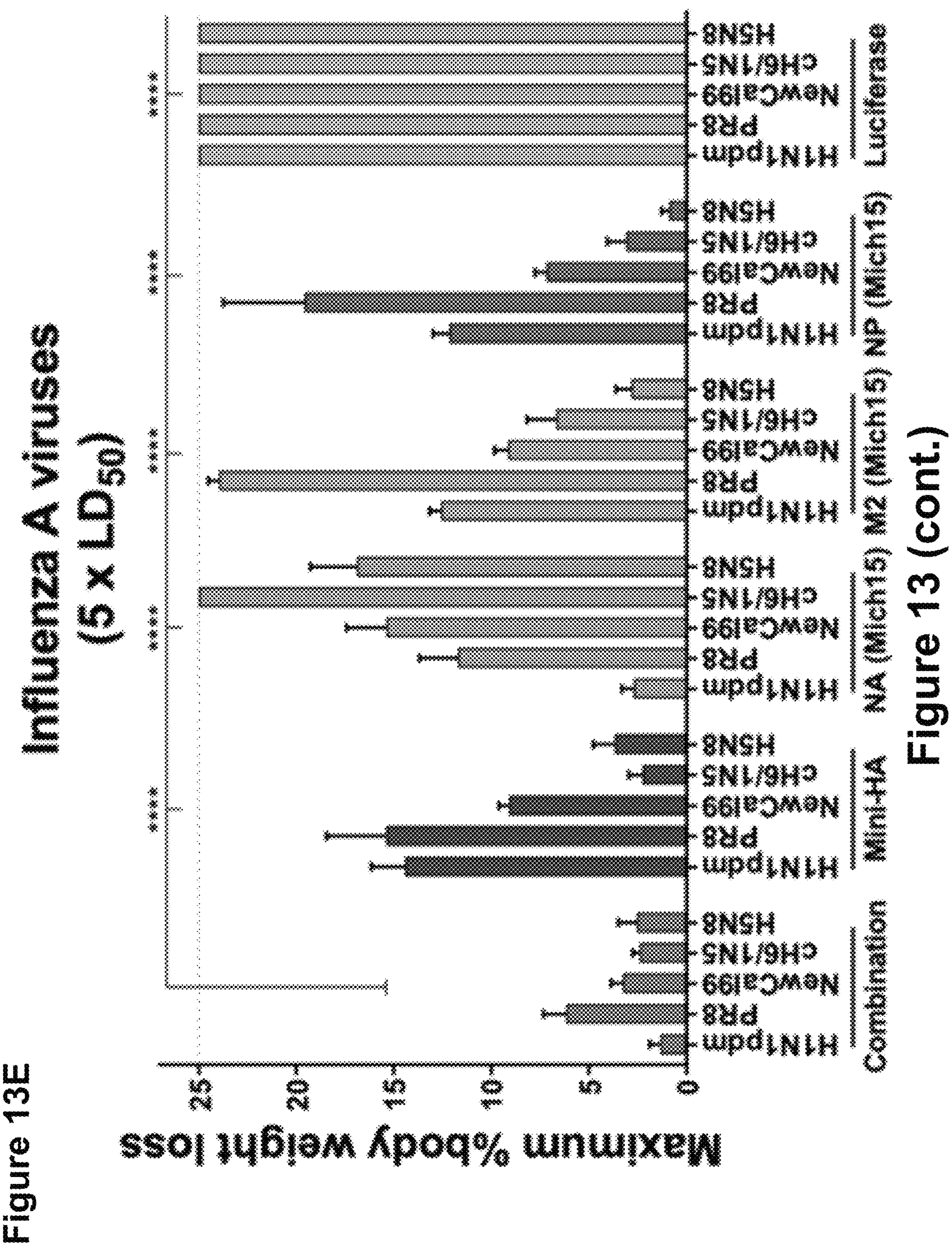

Mice were challenged with influenza viruses from this broad panel and weight loss was monitored to observe morbidity and mortality. For viruses of the H1N1 subtype, morbidity was observed in animals immunized with the single component vaccines, though all mice survived the challenge with NC99 virus (FIG. 13A) and some mortality was observed after challenge with PR8 virus (FIG. 13B). When given a combination of all four influenza virus antigens, mice showed limited morbidity (<5% initial body weight loss) and all survived viral challenge. To further evaluate the breadth of the vaccine response, viruses bearing avian glycoproteins were used for infection. Interestingly, protection mediated by the internal protein components of the vaccine (M2 and NP) as well as that stimulated by Mini HA alone were sufficient to protect mice from morbidity and mortality in infections with H5N8 or cH6/1N5 (FIG. 13C and FIG. 13D). NA-based responses resulted in complete mortality upon infection with cH6/1N5 and substantial morbidity with H5N8, though all mice survived the challenge. This minimal protection conferred to N5 and N8 bearing viruses was not surprising, as generally NA antibodies did not exceed subtype-specific breadth (Wohlbold T J et al., 2015, MBio, 6:e02556-14). Weight loss maxima for each individual mouse were compiled into a single graphic to better compare the potency and breadth of protective efficacy elicited by the nucleoside-modified mRNA-LNP vaccines (FIG. 13E).

Nucleoside-modified mRNA-LNP vaccines demonstrated great promise in multiple recent studies, as they induced protective immunity against critical infectious pathogens such as herpes simplex virus-2, human cytomegalovirus, influenza virus, Zika virus, and Ebola virus (Pardi N et al., 2018, J. Exp. Med., 215:1571-1588; Awasthi S et al., 2019, Sci. Immunol., 4:eaaw7083; Bahl K et al., 2017, Mol. Ther., 25:1316-1327; Pardi N et al., 2017, Nature, 543:248-251; Richner J M et al., 2017, Cell, 169:1114-1125; John S et al., 2018, Vaccine, 36:1689-1699; Meyer M et al., 2018, J. Infect. Dis., 217, 451-455; Pardi N et al., 2018, Nat. Commun., 9:3361). Nucleoside-modified influenza virus mRNA-LNP vaccines encoding a single full-length HA antigen were well-studied and induced durable protective immune responses (often after a single immunization) through the induction of potent T follicular helper cell and humoral immune responses in mice (Pardi N et al., 2018, J. Exp. Med., 215:1571-1588; Bahl K et al., 2017, Mol. Ther., 25:1316-1327; Pardi N et al., 2018, Nat. Commun., 9:3361; Lindgren G et al., 2017, Front. Immunol., 8:1539).

To broaden the protective efficacy of these vaccines, in the current study, a nucleoside-modified mRNA-LNP influenza virus vaccine was developed to elicit predominantly antibody-based protection to several conserved antigens (HA stalk, NA, M2, and NP) of the influenza virus. When multiple antigens were delivered in combination, no substantial differences in the magnitude of humoral immune responses were detected when compared to a single antigen delivered alone. This solidified the rationale that combining multiple individual mRNA-encoded antigens in a single administration increases the breadth of immune responses elicited by vaccination. Serum antibodies obtained after a single immunization with the combination vaccine were found to bind a diverse panel of influenza virus strains, including those from the pre-pandemic H1N1 subtype and those bearing glycoproteins from avian isolates. Mice were protected after a single dose of the combination vaccine against infection with seasonal influenza virus, heterologous challenge within the H1N1 subtype (NC99 and PR8), and heterosubtypic challenge with viruses bearing avian glycoproteins (H5N8 and cH6/1N5). Of note, the vast majority of previous influenza virus mRNA vaccine studies used 1-80 μg vaccine doses to induce protection in mice (Scorza F B et al., 2018, Vaccines, 6:20). The combined vaccine formulation induced protection from seasonal influenza virus challenge after administration of a single dose of 0.05 μg per antigen. This level of protection highlights the potential of this vaccine approach for further development as a universal influenza virus vaccine.

In addition to potency, the nucleoside-modified mRNA-LNP vaccine platform had critical advantages over conventional influenza virus vaccines, specifically: 1) rapid, scalable, sequence-independent production of synthetic mRNA vaccines that did not require eggs or cell lines and complicated purification procedures; 2) enormous flexibility of the mRNA vaccine technology that allowed combination of several antigen-encoding mRNAs into a single regimen that results in greater breadth of vaccine protection (Awasthi S et al., 2019, Sci. Immunol., 4:eaaw7083; John S et al., 2018, Vaccine, 36:1689-1699; Chahal J S et al., 2018, Proc. Natl. Acad. Sci. USA, 113:E4133-4142); 3) ability to use several influenza virus antigens (M2 and internal proteins) that can be expressed directly in the cytosol to better recapitulate the expression occurring during infection, which cannot be achieved through administration of recombinant proteins—the studies described herein showed that the nucleoside-modified mRNA-LNP vaccine platform enabled the use of M2 and NP (and possibly other antigens) for vaccination to induce broadly protective immune responses.

Individually, a single immunization with the Mini HA component provided protection from all H1N1 challenge strains as well as H5N8 and cH6/1N5 strains, highlighting the breadth of protection provided by the stalk-specific responses. The antibodies functioned to protect in the absence of neutralizing activity, measured by microneutralization assay, but did show low ADCC-reporter activity. A potential limitation was the likely requirement of affinity maturation for potent HA stalk responses, as demonstrated by the improvement of antibody responses after booster vaccination (FIG. 14). Importantly, most humans were already primed for HA stalk responses and respond more effectively to HA stalk based vaccines (Bernstein D I et al., 2019, Lancet. Infect. Dis., 20:80-91). An important benefit of using HA stalk-based constructs was the lack of an antibody response against the immunodominant variable head domain of the hemagglutinin, which was highly strain specific, while HA stalk antibodies have been shown to confer protection against very diverse strains (Krammer F et al., 2015, Nat. Rev., Drug Discov., 14:167-182).

Vaccination with NA outcompeted all other single components when challenge with a seasonal H1N1pdm strain was performed. Antibodies elicited by this antigen protected mice up to a challenge dose of 500 times the $LD_{50}$, and with the addition of the other vaccine components, no morbidity was observed (<5%). NA was the only vaccine component which elicited neutralizing antibodies in a multicycle microneutralization assay, and antibodies also were seen to induce modest ADCC activity. Importantly, the vaccine dose can be reduced to 0.05 μg and still elicit complete protection from mortality. Protection from morbidity was demonstrated when additional antigens were included in the vaccine regimen. This low dose of vaccination was promising, as a major limitation to mRNA vaccines has been side-effects associated with high doses of LNP causing inflammation at the injection site (Feldman R A et al., 2019, Vaccine, 37:3326-3334).

The M2 construct designed in this vaccine approach was mutated to ablate ion channel activity to prevent excess cytotoxicity when overexpressed in recipient cells (Watanabe T et al., 2001, J. Virol., 75:5656-5662). This approach allowed the delivery of the full-length M2 protein as an antigen, which maintains T-cell epitopes present in the transmembrane domain (Deng L et al., 2015, Vaccines, 3:105-136). Also, the intracellular expression of the M2 results in more efficient presentation of conformational epitopes. M2 was highly conserved and antibodies tested after vaccination with M2 alone were found to have high ADCC activity. Further, M2 alone prevented mortality in challenge with multiple influenza strains. Though protection was not complete against PR8 virus, morbidity was not observed after challenge with H5N8 or cH6/1N5 virus strains. Interestingly, these viruses all share the same M2 sequence, as well as NP where a similar phenomenon was observed. Although not bound by any particular theory, this was likely due to kinetics of viral replication, which also resulted in delayed weight loss for cH6/1N5 compared to PR8. The initial delay in viral replication may be sufficient for humoral and cellular immunity to clear infected cells before further viral spread occurs.

Due to the sizable global health burden incurred by influenza virus infection, the threat of pandemic outbreaks, and the limited effectiveness of current vaccines, novel vaccine platforms must be developed to mitigate or remove these dangers. The study described herein showed that a nucleoside-modified mRNA-LNP vaccine with the potential to deliver multiple influenza virus antigens can provide the breadth and potency of immune responses necessary to prevent influenza virus infection, warranting the development of this approach as a universal influenza virus vaccine candidate.

In summary, influenza viruses are respiratory pathogens of public health concern worldwide with up to 650,000 deaths occurring each year. Seasonal influenza virus vaccines are employed to prevent disease, but with limited effectiveness. Development of a universal influenza virus vaccine with the potential to elicit long-lasting, broadly cross-reactive immune responses was necessary for reducing influenza virus prevalence. In this study, lipid nanoparticle encapsulated, nucleoside-modified mRNA vaccines were utilized to deliver a combination of conserved influenza virus antigens (hemagglutinin stalk, neuraminidase, matrix-2 ion channel, and nucleoprotein) and induce strong immune responses with substantial breadth and potency in a murine model. The immunity conferred by nucleoside-modified mRNA-lipid nanoparticle vaccines provided protection from challenge with pandemic H1N1 virus at 500 times the median lethal dose after administration of a single immunization, and the vaccine was protective at low vaccine doses in the nanogram range. The broad protective potential of a single dose of combination vaccine was confirmed by challenge with a diverse panel of influenza A viruses. These findings support the advancement of nucleoside-modified mRNA-lipid nanoparticle vaccines expressing multiple conserved antigens as universal influenza virus vaccine candidates.

Example 2: Universal Influenza Vaccine Using Nucleoside-Modified DNA

Influenza virus infections cause significant morbidity and mortality every year, with even greater death tolls during pandemic outbreaks. Influenza virus outbreaks occur annually resulting in approximately 3 to 5 million cases of severe illness and up to 650,000 deaths every year (who.int/mediacentre/news/releases/2017/seasonal-flu/en/). Influenza viruses undergo constant changes in the antigenic characteristics of their envelope glycoproteins, HA and NA, which allows them to evade the human herd immunity. Around the equator, outbreaks occur during any time of the year, while in the Northern and Southern regions of the world, outbreaks occur mostly in the winter. Large outbreaks known as pandemics are less frequent. During the 20th century, three pandemics of influenza occurred: a) the Spanish influenza of 1918, b) the Asian influenza of 1958, and c) the Hong Kong influenza of 1968. The most recent pandemic occurred less than 10 years ago in 2009, when a new H1N1 strain was introduced into the human population. These pandemics resulted in millions of deaths. Since currently licensed influenza virus vaccines provide some level of protection only against the matched circulating influenza virus strains, development of novel vaccine platforms and immunization schemes that elicit broad and durable protection are urgently needed.

Current influenza virus vaccines preferentially target the immunodominant and constantly changing HA head domain, enabling the virus to escape from immune pressure. Thus, seasonal vaccines need to be reformulated and readministered annually. Recent studies have identified conserved viral regions such as the. membrane-proximal HA stalk, some regions of NA, NP, and the ectodomain of the ion channel M2 (M2e) that all represent potential vulnerabilities for influenza virus. Most seasonal vaccines elicit poor immune responses against these immunosubdominant regions. Unlike HA, NA, NP and M2e immunogens are much less studied and not specifically targeted by current vaccines. However, these viral domains are highly conserved between different virus strains and including them in a multivalent vaccine provides a feasible strategy to elicit broadly cross-protective immunity. Induction of durable and broadly protective immune responses in humans was challenging and may not be obtainable with current vaccination strategies. Novel, more potent vaccine platforms, such as mRNA vaccination may help to overcome this limitation.

Nucleic acid-based vaccines emerged as a promising alternative to conventional vaccine approaches. The first use of messenger RNA (mRNA) encoding a potentially therapeutic protein delivered in vivo occurred in 1990 when Wolff et al. demonstrated expression of reporter proteins after direct injection of mRNA to mice. Interestingly, these early promising results did not lead to substantial investment into developing mRNA therapeutics, largely owing to concerns associated with mRNA instability, high innate immunogenicity and inefficient in vivo delivery. Instead, the field pursued DNA-based and protein-based approaches. The use of mRNA has several beneficial features over subunit, killed and live-attenuated virus and DNA-based vaccines: 1) safety: as mRNA is a non-infectious, non-integrating platform, there is no potential risk of infection or insertional mutagenesis. Additionally, mRNA is degraded by normal cellular processes, and its in vivo half-life can be regulated through the use of various modifications and delivery methods. The inherent immunogenicity of the mRNA can be down-modulated to further increase the safety profile. 2) Efficacy: mRNA delivered therapeutically only results in transient translation that can be controlled by changes in the untranslated regions (UTRs), cap, poly(A) tail, or coding sequence. Various modifications can make mRNA more stable and highly translatable. Efficient in vivo delivery can be achieved by formulating mRNA into carrier molecules, allowing rapid uptake and expression in the cytoplasm. mRNA is the minimal genetic vector; therefore, anti-vector immunity can be avoided, and mRNA vaccines can be administered repeatedly. 3) Production: Influenza vaccines currently licensed by the FDA include three or four viral strains (one H1N1 influenza A, one H3N2 influenza A, and one or two influenza B viruses). Every year, the World Health Organization (WHO) recommends which strains to include in the seasonal vaccine. The WHO established the Global Influenza Surveillance Network in 1952 to monitor the spread of antigenically distinct viral strains. This surveillance team, consisting of over 135 National Influenza Centers in 105 countries, extensively characterizes ~8,000 viral isolates every year. Each viral isolate's genome is sequenced and antigenic profiles are determined through hemagglutination inhibition (HAI) assays using reference sera generated in ferrets. From an influenza virus vaccine perspective, the most critical advantages of mRNA vaccines are the rapid development and the ease of production. It is notable that these vaccines are not subject to cell culture and egg-adaptive mutations that commonly arise as conventional influenza virus vaccines are manufactured. Currently available seasonal influenza virus vaccines do not protect well against antigenically drifted viral strains and provide almost no protection against emerging pandemic strains. Production of conventional, FDA-approved vaccines against new pandemic viruses takes at least six months, leaving the population unprotected during this period1. On the contrary, once the genetic sequences of the target HA (or other) antigens are known, mRNA-LNP vaccines can potentially be produced within weeks.

To elicit antibodies against the conserved HA stalk domain, a "mini-HA" construct was used (as published in ncbi.nlm.nih.gov/pubmed/26303961). It is based on the AlBrisbane/59/2007 H1 N1 HA and designed to lack the highly variable globular head domain of HA. The wild-type, membrane-bound NA from NMichigan/45/2015 H1 N1 pdm was used to match the currently circulating seasonal influenza virus strains. Similarly, the wild-type NP from H1N1pdm was used, which matches the currently circulating H1N1 viruses. To elicit immune responses against M2, an H1N1pdm-based M2 construct with the amino acid residues 29-31 deleted was used. This mutation was introduced to render the ion-channel activity non-functional and to reduce potential cytotoxicity as a result of overexpression on the cell surface. Importantly, the mRNA approach enables the encoding of the full-length M2 ion channel, including the transmembrane region, which retains T-cell epitopes. This provides means towards a more natural presentation of the antigen on the cell surface compared to previous vaccination approaches.

Previous nucleoside-modified mRNA-LNP studies used single full-length HA-encoding mRNA-LNPs for vaccination. These vaccines induced potent immune responses in mice and ferrets. To broaden the protective efficacy of nucleoside-modified mRNA-LNP vaccines, in the current study, a nucleoside-modified mRNA-LNP influenza virus vaccine was developed to elicit protective antibodies to several conserved antigens (HA stalk, NA, M2, and NP) of the influenza virus. When multiple antigens were delivered in combination, protective immune responses were remarkable. This solidifies the rationale that combining multiple individual antigens in a single administration to increases the breadth of immune responses elicited by vaccination. Serum antibodies obtained after a single immunization of the combination preparation were found to bind a diverse panel of influenza virus strains, including those from the pre-pandemic H1 N1 subtype and those bearing glycoproteins from exotic avian isolates. Specifically, mice were protected by the combination vaccination approach against infection with seasonal influenza virus (H1N1pdm), with variants within the H1N1 subtype (NC99 and PRS), and with viruses bearing avian glycoproteins (H5NS and cH6/1 N5). Of note, the vast majority of previous influenza mRNA vaccine studies used up to 80 μg vaccine doses to induce protection in mice. Herein described combination vaccine induced protection from stringent, highly lethal H1 N1 pdm virus challenge after administration of a single dose of 50 ng of mRNA. This level of protection from morbidity and mortality highlights the potential of this vaccine approach for further development as a universal influenza virus vaccine.

The present study described the development of nucleoside-modified mRNA-LNP as a vaccine delivery system and found that it is a superior vaccine when directly compared to conventional inactivated pathogen, protein subunit or live virus vaccines. What makes this delivery approach truly innovative is that while showing clearly superior immune responses, it is not likely to have any of the potential adverse events associated with viral delivery systems. All of the components of the mRNA are physiological and degraded by cellular pathways. The LNPs that complex the mRNA have entered phase three clinical trials without adverse events (clinical trial number: NCT01960348). Additionally, non-replicating mRNA vaccines encode exclusively the specific antigen(s) of interest, which likely elicit more specific and desirable immune responses against the targeted pathogen.

Potent activation of Tfh cells is critical for generating high affinity, broadly protective antibodies, however, currently used vaccine adjuvants often do not elicit efficient Tfh cell immune responses. In contrast, nucleoside-modified mRNA-LNP vaccines induce extremely potent CD4 helper and, most importantly, Tfh cell responses The ability to induce such a potent Tfh response is novel and innovative and a goal of many vaccine development studies.

The stalk domain of influenza virus HA represents an attractive vaccine target, as antibodies against this conserved viral region are able to protect from antigenically distant influenza viruses. It was recently demonstrated that nucleoside-modified mRNA-LNP vaccines induced high titers of IgG that mediated durable HA inhibition after a single dose immunization. Importantly, substantial responses to the HA stalk was also observed. Additionally, a single immunization protected mice against homologous and heterologous viral challenges and two immunizations elicited protective immune responses against a heterosubtypic influenza virus strain. Monovalent mRNA-LNP vaccines encoding full-length HA immunogens was used in these studies, thus, although not bound by any particular theory, it was hypothesized that the use of the nucleoside-modified mRNA-LNP platform with optimized stalk-inducing headless HA immunogens alone or in combination with conserved NA, NP, and M2e sequences offer a novel, very innovative, superior platform with easy clinical use.

mRNA is currently in GMP production, as is its formulation in LNPs. mRNA vaccine antigens can be easily updated (weeks) and antigens encoded by mRNA are not at risk of acquiring mutations during the manufacturing process, as can occur with viruses grown in eggs. Although not bound by any particular theory, it was hypothesized that using these highly innovative findings result in an easily administered and safe influenza vaccine that generates long-lived and broad neutralizing responses with high potential to become a "universal influenza virus vaccine".

Figure 15:
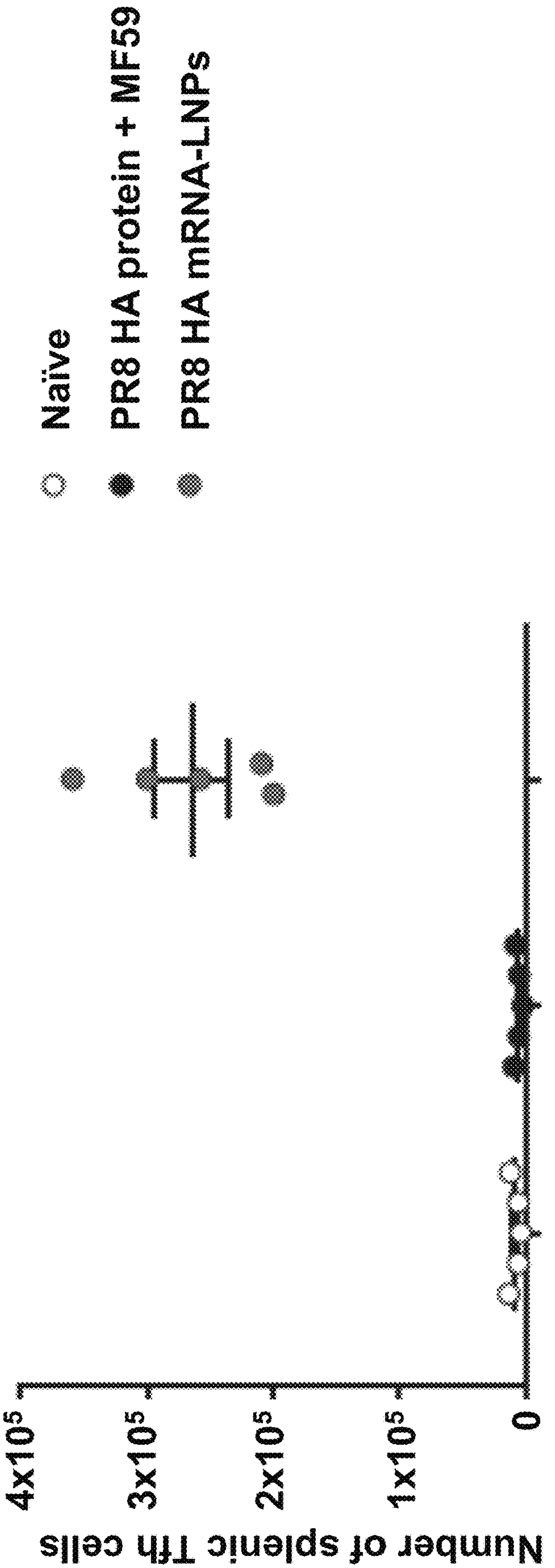
FIG. 15 depicts representative results demonstrating that a single immunization with nucleoside-modified PR8 HA mRNA-LNPs induces potent Tfh cell responses. 8 week-old female Balb/c mice were immunized i.m. with a single dose of 10 μg of MF59-adjuvanted recombinant PR8 HA protein or PR8 HA mRNA LNPs and the number of splenic Tfh cells (CD4+CXCR5+PD-1+) were determined by flow cytometry 12 days post immunization. Error bars are SEM. Each symbol represents one animal.

A Single Immunization with Full-Length PR8 HA-Encoding Nucleoside-Modified mRNA-LNPs Induces Potent T Follicular Helper (Tfh) Cell Responses in Mice Multiple studies demonstrated that the activation of Tfh cells is critical for durable, protective neutralizing antibody responses. It was recently demonstrated the lack of significant Tfh cell activation after immunization with adjuvanted recombinant A/PuertoRico/8/1934 (PR8) HA or inactivated PR8 virus vaccines. In contrast, it was found that a single immunization with 10 μg of PR8 HA nucleoside-modified mRNALNPs induced potent Tfh cell responses in mice (FIG. 15).

Nucleoside-Modified HA mRNA-LNP Vaccine-Induced Potent Tfh Cell Immune Responses are Associated with Durable HA Inhibition (HAI) Titers and Induction of HA Stalk-Specific Antibodies PR8 HA inhibition titers were followed in mice immunized with a single dose of 10 μg of PR8 HA mRNA-LNPs. Strikingly, high and stable HAI titers were measured over 20 weeks post immunization (FIG. 16), confirming the previous observations that nucleoside-modified mRNA-LNP influenza vaccines induce strong and durable antibody responses.

Figure 17:
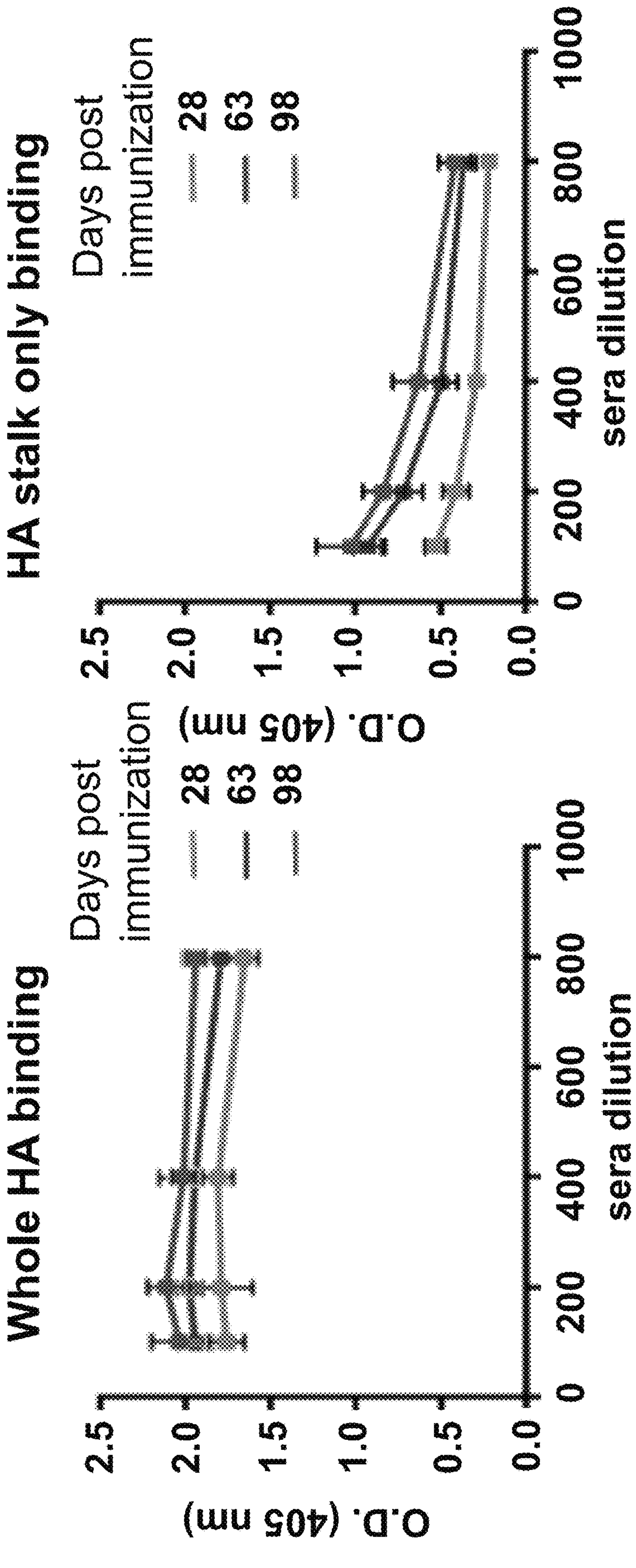
FIG. 17 depicts representative results demonstrating that a single immunization with nucleoside-modified PR8 HA mRNA-LNPs induces durable HA stalk-specific antibody responses. 8 week-old female Balb/c mice (n=5 per group) were intradermally immunized with 10 μg of PR8 HA mRNA-LNPs and binding to full-length H1 HA and to an H1 HA stalk probe were determined by ELISA. Error bars are SEM.

As discussed above, licensed influenza virus vaccines preferentially target the immunodominant and everchanging HA head domain and therefore, the virus can escape from immune pressure. The HA stalk domain is an attractive target for broadly protective/universal influenza virus vaccines as it is conserved and mutation in this region often result in a significant viral fitness loss. It was recently demonstrated that immunization with full-length PR8 or A/California/07/2009 (A/Cal09) HA nucleoside-modified mRNA-LNPs induced durable HA stalk-specific antibody responses in mice and ferrets (FIG. 17). These findings suggested that the potent Tfh cell immune responses are likely critical for the induction of cross-reactive HA stalk-specific antibodies that confer protection from antigenically distinct influenza virus subtypes. Indeed, it was found that a single immunization with A/Cal09 nucleoside-modified HA mRNA-LNP vaccines induced protection from the homologous (A/Cal09) and heterologous (PR8) influenza viruses and, most importantly, two immunizations protected mice from heterosubtypic (H5N1) virus challenge. These important findings serve as the basis for further development using optimized HA stalk immunogens and other fairly conserved influenza virus antigens (NA, NP and M2e) as mRNA vaccine regimens to further increase protective efficacy.

The data described above demonstrated that unlike MF59-adjuvanted PR8 HA recombinant protein vaccine, nucleoside-modified PR8 HA mRNA-LNP vaccine induced potent Tfh cell responses and high PR8 HAI titers. Most importantly, PR8 HA nucleoside-modified mRNA-LNP vaccination elicited durable HA stalk-specific immune responses after a single immunization. The three sections below describe the design and production of optimized mRNA immunogens against conserved regions of influenza virus, evaluate immunogenicity and protective efficacy of mRNA-LNP vaccine formulations in mice and test for selected regimens in ferrets, and determine the mechanisms of strong Tfh cell and humoral immune response activation by influenza mRNA-LNP vaccines.

Scientific Rigor:

Every mouse experiment is repeated three times with at least five mice per experiment. This is based on the extensive experience with the models. Smaller group sizes lead to excessive variability between individuals, necessitating additional experiments and ultimately greater animal usage. The mice are randomly and blindly assigned to the various experimental groups. To ensure rigor, serological experiments from each mouse and ferret study are performed in technical triplicates. Investigators assessing, measuring or quantifying experimental outcomes are blinded as well. The inter-operator variability are minimized by SOPs and specific training. All of the raw data points are included in the preliminary analysis. Data exclusions are only applied in exceptional cases, such as a sick mouse, fight wounds, partial treatment, contaminated samples, etc. The resulting data are compared using Student's paired/unpaired t-test, unless a non-Gaussian distribution is present, in which case a Mann-Whitney test is used. ANOVA tests variation within and between groups. A p value below 0.05 is considered significant. Four ferrets per group are tested in each experiment. This number is based on previous experience using the ferret model to study vaccination approaches and housing limitations due to animal size. Key experiments are repeated to increase the sample size and to improve statistical power.

Biological Variables:

Both sexes and littermate controls are always included in the experiments. If there are no differences between sexes, results may be combined. Animals are specific-pathogen-free (SPF) and bred in-house or purchased from commercial vendors. All mice are between 6 and 12 weeks old. Ferrets are 4 months old.

Design and Production of mRNA Immunogens for Conserved Regions of Influenza Virus It was demonstrated that nucleoside-modified mRNA-LNP influenza vaccines are a promising new vaccine class with great potential. However, there are multiple ways to improve the current influenza virus RNA vaccines, mainly through designing optimized vaccine regimens and increase the valency of the vaccines.

The overall goal of this study is to generate nucleoside-modified mRNA-LNP vaccines that elicit humoral and cellular immune responses against conserved epitopes of influenza virus. The highly conserved HA stalk domain is targeted to elicit broadly protective antibodies and aim to induce antibodies against the NAs of current seasonal viruses, which can provide broad protection against viruses that share the same NA subtype (including avian viruses). M2e antigens are also included against avian and human viruses, which can provide broad protective immunity against all influenza A viruses. Finally, NP-encoding mRNA-LNPs ins included for influenza A and B viruses to elicit broadly protective T cell responses against all influenza viruses. These vaccination approaches are tested individually and then combine the most potently protective immunogens to create a novel mRNA-based universal influenza virus vaccine.

Most influenza virus RNA vaccine studies used a single full-length HA as an immunogen. The herein described studies generate nucleoside-modified mRNAs encoding headless HA-ferritin particles that proved to be potent protein immunization regimens in mice and ferrets. Three different mRNAs encoding are made for influenza A group 1 (H1) and group 2 (H3) and influenza B headless HA-ferritin. Using these three immunogens, HA stalk-based broad protection against all influenza A and B strains may be achievable.

NA is a fairly conserved viral glycoprotein that was shown to contribute to protection from infection. Despite its potential to reduce morbidity and viral shedding, it is a largely ignored vaccine target. While NA-specific immunity is mainly restricted to a subtype, cross-protection within the subtype has been observed. For example, mice vaccinated with the NA of the PR8 laboratory strain were protected from challenge with both the 2009-pandemic H1N1 isolate as well as a potentially pandemic H5N1 virus. Three optimized mRNAs encoding for the subtypes of the currently human pathogenic viruses N1 (A/Michigan/45/2015 (H1N1) pdm09), N2 (A/Singapore/INFIMH-16-0019/2016 (H3N2)) and influenza B (B/Colorado/06/2017) virus NAs are designed. These NAs cover the current seasonal isolates (the largest contributor to annual overall influenza mortality) and may cross-protect against some potentially pandemic avian strains such as H5N1 and H7N2 as demonstrated by some human N1 and N2-specific antibodies. In contrast to the influenza B HAs, the NAs have not separated into antigenically distinct lineages and antibodies elicited against the selected strain are likely cross-protect against all current influenza B isolates.

T cell responses against highly conserved influenza virus antigens, particularly against NP, have been shown to contribute to vaccine protection. Therefore, NP-encoding nucleoside-modified mRNA-LNP vaccines are designed and their contribution to vaccine efficacy are evaluated. NP is a fairly conserved antigen that likely provide cross protection against a large number of influenza virus strains. Thus, influenza A group 1 and group 2 and influenza B NP mRNA-LNP vaccine regimens are generated.

M2e is a highly conserved viral antigen in both human and avian influenza A viruses and immune responses against it have been shown to correlate well with protection in preclinical and clinical settings. What makes it a very attractive vaccine antigen is that it is only 23 amino acids in length and it is almost invariant in all human epidemic strains regardless of subtype. As demonstrated in early studies, constructs containing several M2e sequences in tandem induced high titers of M2e-specific antibodies and improved protection from viral challenge. Thus, mRNAs encoding both avian and human M2e copies are produced, as described and evaluate the protective efficacy of these mRNA-LNP vaccines against seasonal and avian influenza A viruses. Protein production from each mRNA construct is confirmed using mRNA-transfected human embryonic kidney (HEK)293T cells for ELISA and Western blot analyses. Additionally, combined mRNA-LNP formulations are also tested by HEK293T cell transfection to confirm that all encoded proteins are translated from mRNAs.

Figure 18:
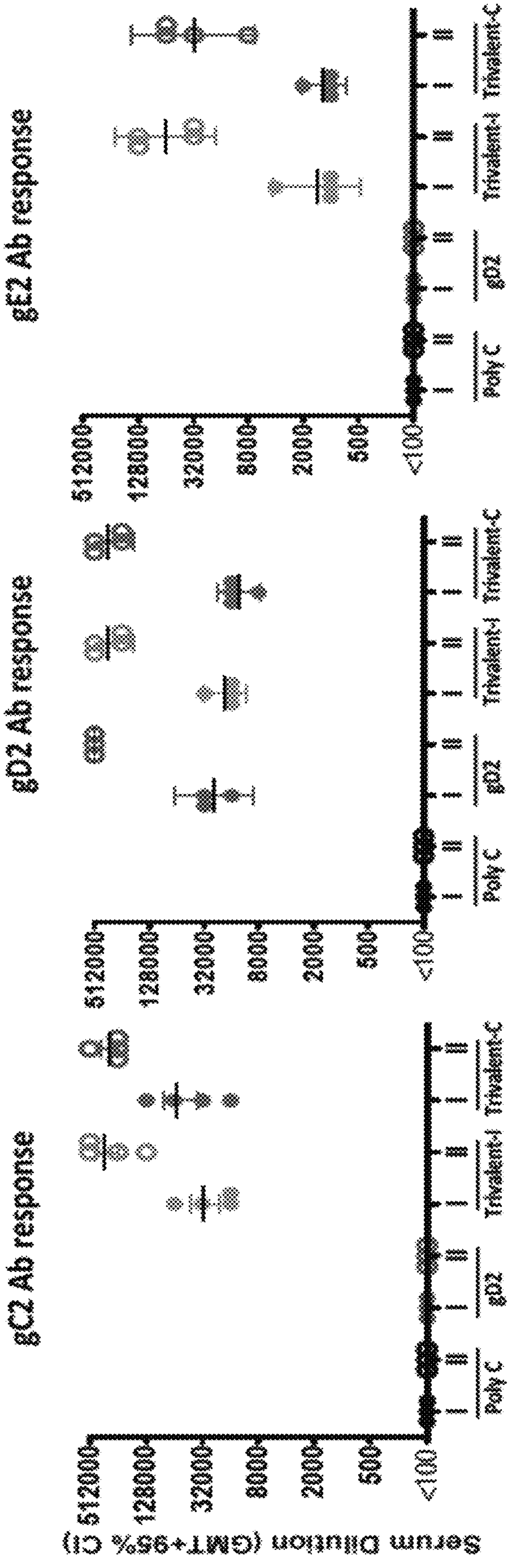
FIG. 18 representative results demonstrating that immunization with nucleoside-modified trivalent HSV-2 (gC2, gD2 and gE2) mRNA-LNP vaccines induces high levels of antigen-specific IgG titers. 8 week-old female Balb/c mice were intradermally immunized once (I) or twice (II) with 10 μg of HSV-2 monovalent gD2 or gC2-gD2-gE2 or trivalent gC2-gD2-gE2 mRNA-LNPs or control poly(C) RNA-LNPs and antigen-specific IgG titers were determined by ELISA. One group of mice (Trivalent-I) received each immunogen as monovalent vaccines at different intradermal sites. Another group of mice (Trivalent-C) received a combined trivalent vaccine. Error bars are SEM. Each symbol represents one animal.

Initially, monovalent mRNA-LNP vaccine formulations encoding the proposed influenza virus immunogens are made and evaluated and then combined the most protective regimens into a single formulation. It was previously observed that three different HSV-2 immunogen-encoding mRNAs were combined in a single vaccine and obtained the same level of antigen-specific IgG (FIG. 18) as when each was administered alone; thus, it is likely that no decrease in response when all influenza virus immunogen mRNAs (HA, NA, NP and M2e) are combined, although, this is directly tested. If a reduction is observed, the number of immunogens in a single vaccine is reduced and the response is evaluated.

Immunogenicity and Protective Efficacy of Nucleoside-Modified Influenza mRNA-LNP Vaccines in Mice and Ferrets The data described above (FIG. 15 though FIG. 17) demonstrated the ability of nucleoside-modified mRNA-LNP vaccines to induce potent Tfh cell and neutralizing antibody responses against influenza virus. The studies used monovalent full-length PR8 or A/Cal09 HA-encoding mRNA-LNP vaccines. Importantly, even these vaccines induced protection from homologous, heterologous and heterosubtypic viruses in mice after one or two immunizations. Therefore, although not bound by any particular theory, it was hypothesized that the use of optimized HA immunogens and the combination of four fairly conserved antigens (headless HA-ferritin, NA, NP and M2e) in multivalent vaccines result in significantly increased protective efficacy.

During the course of this study, nucleoside-modified mRNA-LNP formulations encoding influenza A group 1, influenza A group 2 and influenza B antigens (HA, NA, NP and M2e) are evaluated individually and in combined formulations. T and B cell immune responses and the short and long term protective efficacy of each vaccine are evaluated. The vast majority of influenza virus vaccines are administered i.m. and some (for example Fluzone) are injected i.d. It was recently demonstrated that nucleoside-modified mRNALNP vaccines work well after i.m. and i.d. delivery, however, i.d. delivery induced slightly stronger immune responses. Thus, the i.d. route is used to evaluate the influenza mRNA-LNP vaccine candidates.

Evaluation of T Cell Immune Responses in Mice:

Groups of ten Balb/c mice (five males and five females) are injected i.d. once with 10 μg (previously shown to elicit potent antibody responses) of nucleoside-modified mRNA-LNP vaccines and antigen-specific CD4+ and CD8+ T cell responses are evaluated in lymph node (LN) and spleen resident T cells by stimulation with overlapping peptide pools for each vaccine antigen followed by intracellular staining for IFN-γ, TNF-α and IL-2 (CD4) or IFN-γ, IL-2 and CD107a (CD8) 12 days post single immunization. T cell immune responses are also evaluated after two immunizations (4 week interval between vaccine administration, animals are sacrificed 12 days after administration of the second dose). Tfh cell immune responses are evaluated after one immunization by enumerating splenic CD4+CXCR5+ PD-1+ T cells 12 days after vaccine administration. In addition, splenocytes from individual antigen vaccinations, as well as from combined vaccination approaches are tested in killing assays of virus infected cells. This allows to quantify the level of T cell mediated killing elicited by each vaccination approach and to assess the benefits of combined vaccine approaches on the T cell response.

Evaluation of Antigen-Specific Humoral Immune Responses in Mice.

Figure 16:
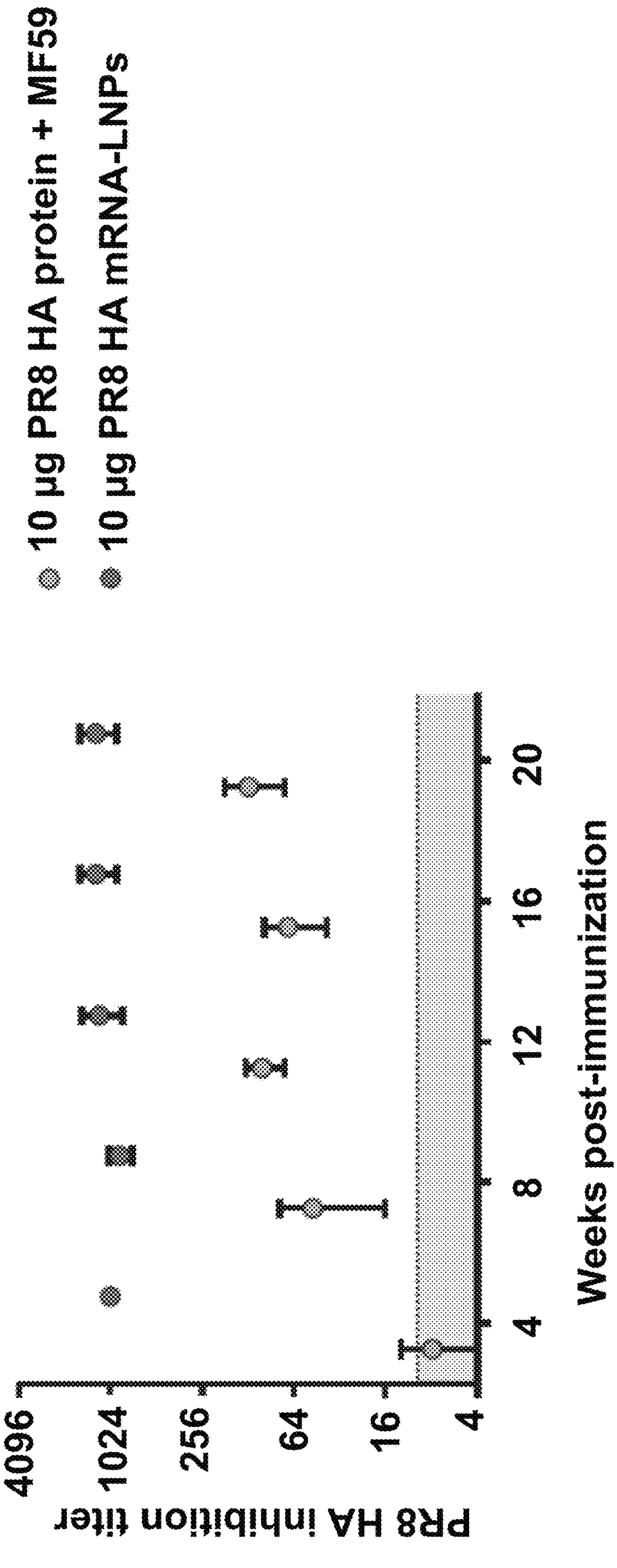
FIG. 16 depicts representative results demonstrating that a single immunization with nucleoside-modified PR8 HA mRNA-LNPs induces high and durable PR8 HAI titers. 8 week-old female Balb/c mice (n=5 per group) were immunized i.m. with a single dose of 10 μg of MF59-adjuvanted recombinant PR8 HA protein or PR8 HA mRNA-LNPs and PR8 HAI titers from serum samples were determined. Error bars indicate SEM.
Figure 19:
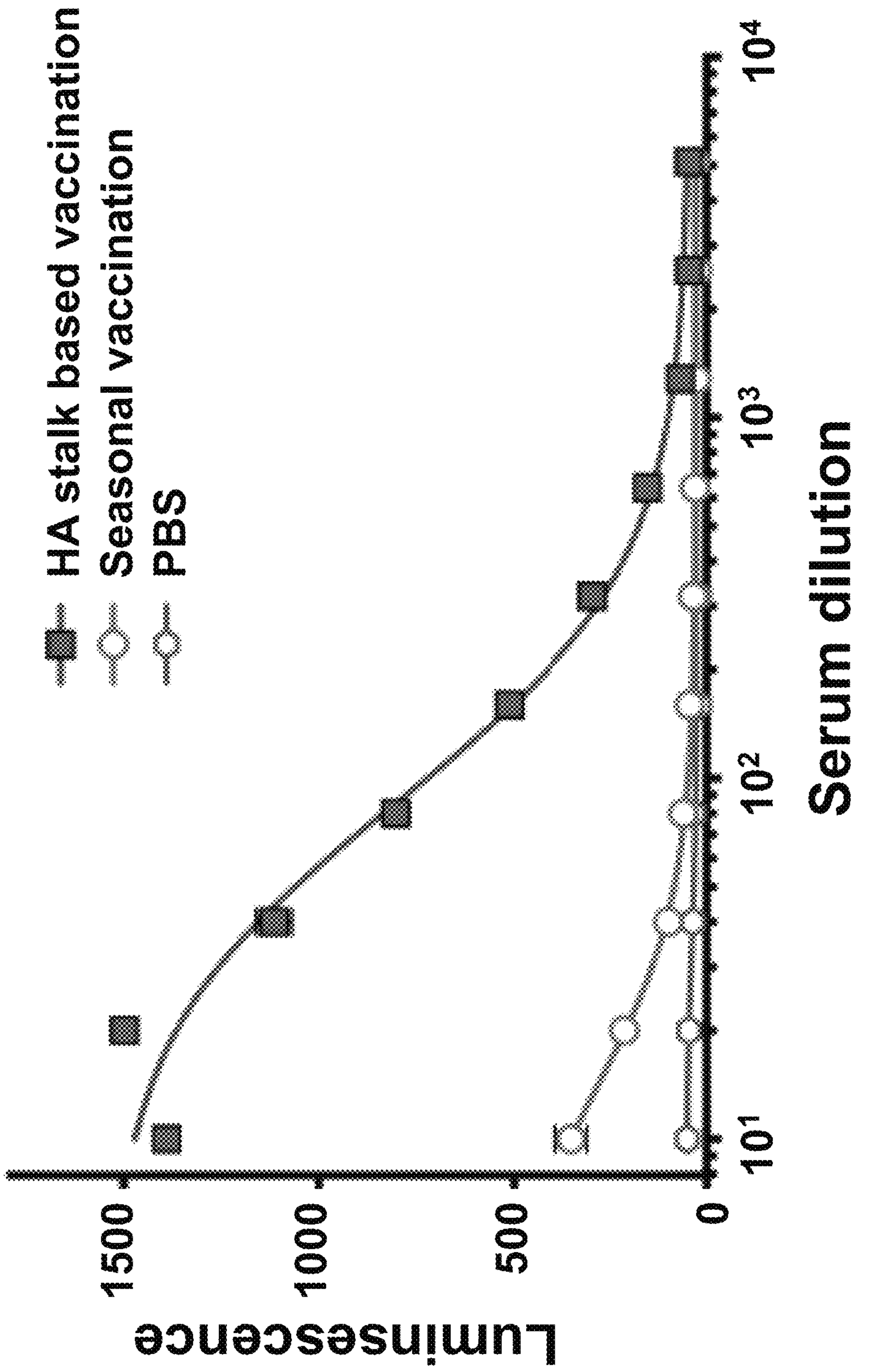
FIG. 19 depicts representative results demonstrating that mouse sera obtained from HA stalk-specific immunization are active in an ADCC reporter assay. 6-8 week-old female Balb/c mice were vaccinated with a vaccination strategy that elicits HA stalk antibodies (blue), seasonal influenza virus vaccine (green) or PBS (gray). Serum samples were tested in an ADCC reporter assay on H1N1pdm09-infected cells.
Figure 20:
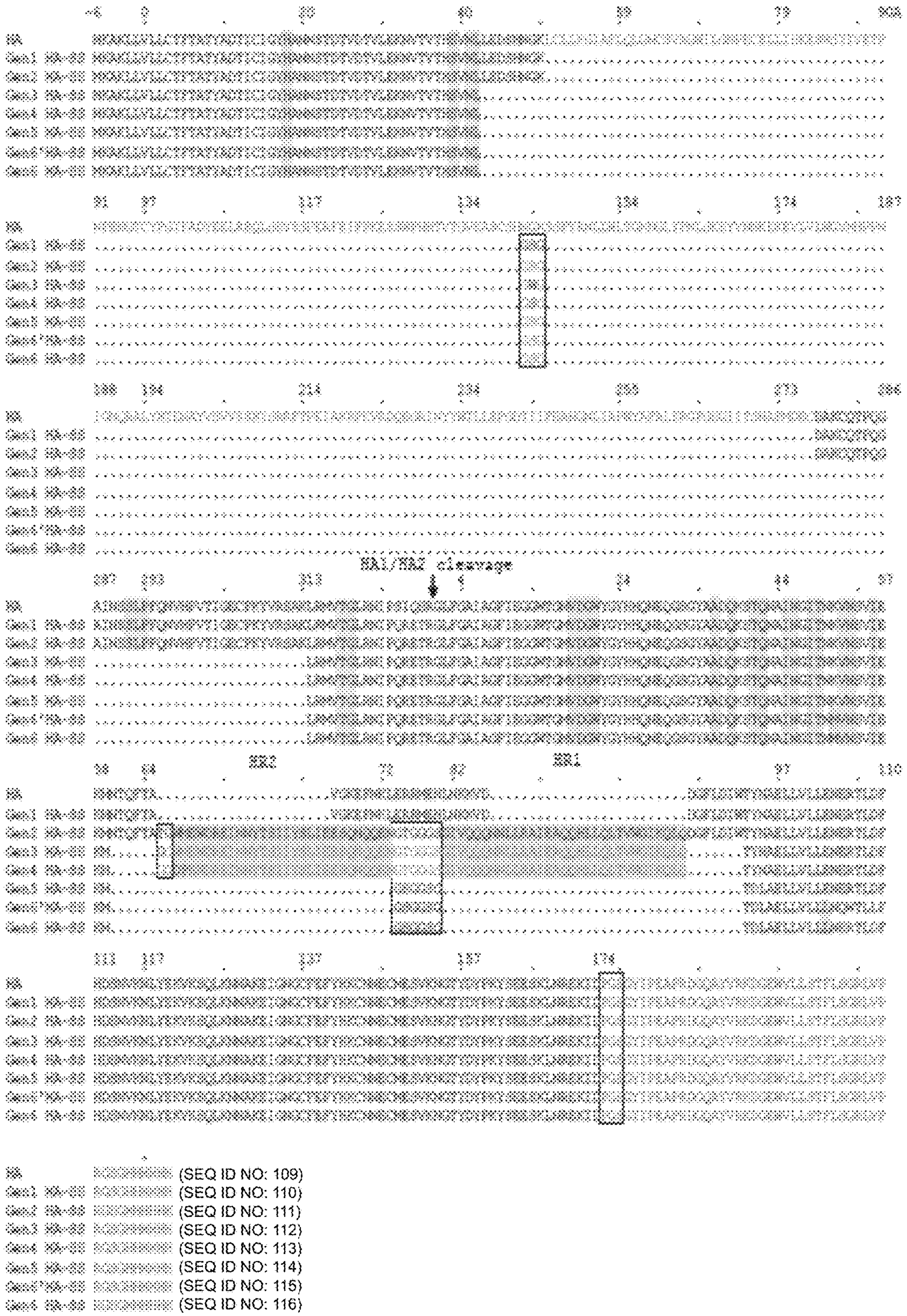
FIG. 20 depicts representative examples of mini HA amino acid sequences (SEQ ID NOs: 109-116).
Figure 21:
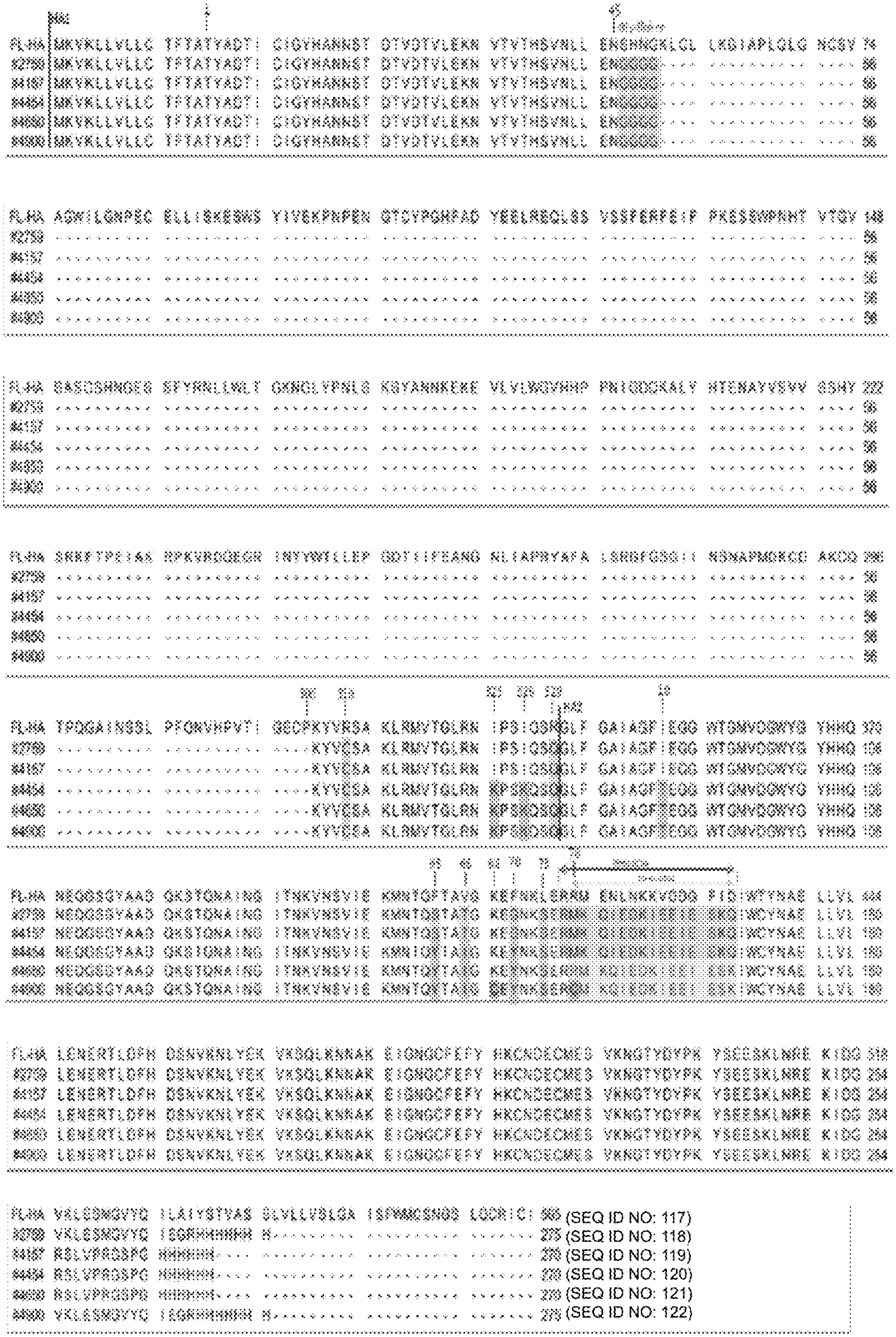
FIG. 21 depicts representative examples of HA amino acid sequences (SEQ ID NOs: 117-122).
Figure 22:
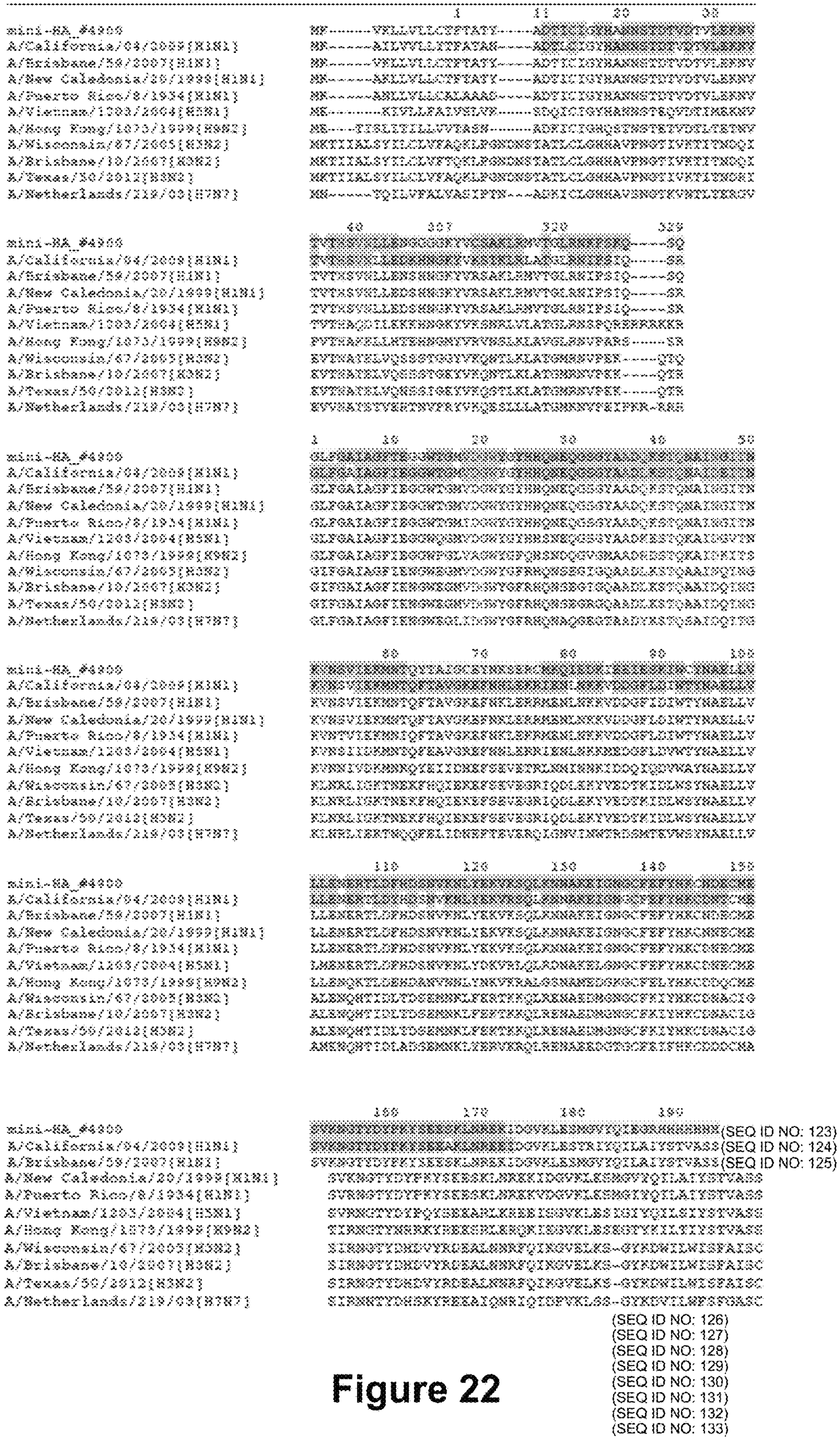
FIG. 22 depicts representative examples of mini HA amino acid sequences (SEQ ID NOs: 123-133).

Groups of ten Balb/c mice (five males and five females) are injected i.d. either once or twice (4 weeks apart) with 10 μg of mRNA-LNP vaccines and serum are collected at weeks 4, 8, 12, 16 and 20. Antigen-specific IgG titers are determined by ELISA. In addition, the breadth of the immune response is assessed by testing the sera against a variety of heterologous antigens (including a large panel of avian and human influenza virus antigens). As headless HA immunogens are used, antibodies that are active in hemagglutination inhibition assays (HAI) are not induced, which are therefore only performed against the challenge viruses to confirm that no HA head-specific responses are elicited. Neuraminidase inhibition (NAI) are measured and also perform in vitro microneutralization assays. Nucleoside-modified monovalent HA (full-length) mRNALNP vaccines induced very high HAI titers and protection against the homologous virus strain (FIG. 16). Interestingly, they displayed protective efficacy against heterologous and heterosubtypic influenza viruses in the absence of HAI titers against those viruses. The present study also demonstrated that HA mRNA-LNP vaccines induced HA stalk-specific antibodies. Taken together, it was suspected that HA stalk-specific antibodies likely have a critical role in influencing the protective efficacy of nucleoside-modified mRNA-LNP vaccines, but the underlying mechanisms are remained to be determined. As it was found that sera from A/Cal09 HA mRNALNP-immunized mice did not neutralize the H5N1 virus in vitro but the animals were protected from lethal H5N1 virus challenge, it is likely that HA stalk-specific antibodies act through various effector immune mechanisms to induce heterosubtypic vaccine protection. This is in line with the literature as several recent studies demonstrated that the potency of HA stalk-specific antibodies were often enhanced by Fc receptor-mediated mechanisms such as antibody-dependent cell-mediated cytotoxicity (ADCC) or complement-dependent cytotoxicity (CDC). Thus, ADCC reporter assays are performed on sera from headless HA-encoding mRNA-LNP-immunized mice by using a commercially available reporter system that utilizes engineered Jurkat cells to express a murine Fc-receptor known to trigger ADCC (mFcγRIV). A downstream cascade in activated cells leads to the expression of luciferase, which can be detected in a luminescent readout (FIG. 19).

Evaluation of Protective Vaccine Efficacy in Mice:

To assess the protective efficacy of each individual vaccination approach, groups of ten Balb/c mice (five males and five females) mice are vaccinated either once or twice for each vaccination approach and then challenged with a lethal dose of an influenza A group 1 (A/Netherlands/602/2009 (H1N1)), group 2 (A/Hong Kong/1/1968 (H3N2)) or influenza B virus strain (B/Malaysia/2506/2004) that contains wild type variants for the vaccine targets contained in the vaccine. A group of mice injected with an RNA vaccine encoding for firefly luciferase is included as a negative control. No influenza B challenges are performed for the M2e vaccine approach, since the target is not present in this virus group.

All the approaches that show a significant protective effect compared to the negative control group in these challenge studies, are included in a combined vaccination approach. To confirm the superiority of the combined vaccination approach over each individual vaccination approach, it is tested side-by-side against the individual immunization strategies in challenges against a panel of low-pathogenic PR8 reassortant viruses that express exotic variants of the vaccination targets (including A/Vietnam/1203/2004 (H5N1) and A/Shanghai/1/2013 (H7N9)). Influenza B viruses only circulate in humans. To show broad protection against these viruses, challenge viruses of both human lineages as well as older isolates are included, including an influenza B virus first isolated in 1940 (B/Lee/1940), which went through over 70 years of antigenic drift. To ensure that differences between the vaccination approaches are observed, highly lethal virus doses are used for the challenge.

Immunogenicity and Protective Efficacy of Nucleoside-Modified Influenza Virus mRNA-LNP Vaccines in Ferrets:

Ferrets are the gold standard models for testing influenza vaccines because they show similar clinical signs to humans after viral infection. Both type A and B human influenza viruses naturally infect ferrets. The best working immunization schemes and vaccine types from mouse studies are evaluated in ferrets. The magnitude and breadth of antibody responses as well as the protective efficacy are investigated.

Four 4-month old, castrated, and descended male Fitch ferrets are vaccinated with 50 μg (previously established mRNA dose for ferrets) of multivalent nucleoside-modified mRNA-LNP universal influenza virus vaccine and challenge them with human seasonal influenza virus isolates including A/Michigan/45/2015 (H1N1), A/Hong Kong/4801/2014 (H3N2) and B/Florida/04/2006. A control group that receives two human doses of an inactivated seasonal influenza virus vaccine is included (human standard of care control group). A group of animals injected with an mRNA vaccine encoding for firefly luciferase is included as a negative control. The number of vaccinations is determined based on the mouse experiments. It is unlikely that a single immunization elicits sterilizing immune responses thus, it is likely that ferrets need to be immunized 2 or 3 times. Human influenza viruses replicate well in the upper and lower respiratory tract, but are generally not lethal in the ferret model. Therefore, nasal washes on days 1 and 3 post-challenge are collected to observe differences in replication kinetics in the upper respiratory tract. On day 4 post-challenge, the ferrets are euthanized and tissues are collected to measure viral replication in the upper and lower respiratory tract.

Following challenges with human seasonal influenza viruses, the protective effect of the vaccine against highly pathogenic avian influenza viruses is also assessed. Additional groups of ferrets are vaccinated using the same vaccination regimen as used for seasonal influenza virus challenge. A positive control group for these experiments receives an adjuvanted, matched inactivated whole virus vaccination. Ferrets are then challenged with wild-type highly virulent avian influenza viruses including A/Vietnam/1203/2004 (H5N1) and A/Shanghai/1/2013 (H7N9). Since highly pathogenic wild type avian viruses are used, these experiments are performed in a biosafety level three setting. These viruses are lethal in ferrets and instead of comparing viral titers, weight-loss and survival after viral challenge are monitored. The protective effect of the vaccination are assessed based on decrease in weight-loss and increased survival. Observed protection against these highly pathogenic influenza viruses confirms that the vaccine elicits universal protection also against avian influenza viruses and can be used as a pandemic prophylaxis.

Both the cellular and humoral immune responses are assessed for each mRNA-LNP vaccine and the breadth of the antibody response is able to be estimated. While it is likely that each vaccination approach result in potent immune responses, it is possible that some vaccines elicit immune responses that show low reactivity in in vitro assays. A vaccination approach is not eliminated based on in vitro assay results, but are judged by the in vivo challenge outcomes, since the desired quality of the vaccination is to confer protection. A discrepancy between in vitro and in vivo results requires an optimization of the used in vitro assays to identify the correlate of protection. In addition, adoptive serum or T cell transfers with consecutive viral challenge can be performed to identify which component contributes most to the observed protection.

Since most of the approaches have been shown to be protective using different vaccination strategies, it is likely to observe protection for the individual vaccinations. However, it is possible that some vaccination approaches show different levels of protection for each sub-component. For example, significant NP-based protection against influenza A, but not against influenza B challenge strains, may be observed. In such a case, the sub-components can be individually tested in dose-escalation studies to identify a minimal protective dose, which provides means to adjust the combined vaccine accordingly.

A number of influenza A group 1 and influenza B virus challenge strains expressing wild-type variants of the vaccine targets are available for the murine challenge model. Recent H3N2 influenza virus isolates (influenza A group 2) do not readily infect mice, which seems to be primarily dependent on the surface glycoproteins. However, older reassortant viruses that are highly lethal in mice are available. Similar reassortants that express the appropriate NP and M2e proteins can be generated and used for the challenge studies. Since the HA and NA components elicit broad protection, they may also protect against older versions of the surface glycoproteins. In addition, a recent human H3N2 virus isolate is used for ferret challenge experiments.

It was expected to observe similar protection in the ferret model and the mouse model, based on previously performed influenza virus vaccination studies. However, the ferret challenge studies are first performed using less pathogenic human influenza virus isolates and confirm protection before advancing to highly pathogenic avian influenza viruses. If the protection observed against human viruses is not satisfactory, an additional immunization or higher vaccination doses can be tested. This is also highly informative for the translational potential of the vaccination and indicates if higher doses are required for human vaccination.

In conclusion, the present study described the development of novel broadly protective/universal influenza virus vaccines using the novel highly effective and safe nucleoside-modified mRNA-LNP vaccine platform that induced protective immune responses against various viral pathogens in small and large animals. Moreover, the use of optimized stalk-inducing headless HA immunogens with conserved NA, NP, and M2e sequences encoded as mRNAs is a novel, very innovative approach that can lead to the development of superior, broadly protective influenza virus vaccines.

In addition to potency, production of nucleoside-modified mRNA-LNP vaccines is easy and sequence-independent and does not require eggs or expensive cell culture and protein purifications systems. Both the mRNA and LNP components of the vaccine are currently in GMP production.

In summary, besides enhanced potency, the nucleoside modified mRNA-LNP vaccine platform has critical advantages over conventional influenza virus vaccines: 1) production of synthetic mRNA vaccines is rapid, scalable, sequence-independent and does not require eggs or cell lines or complex purification procedures; 2) the mRNA vaccine technology provides flexibility and allows the combination of several antigen-encoding mRNAs into a single regimen that results in greater breadth of vaccine protection; 3) in the past several influenza virus antigens (M2 and internal proteins) have been refractive to induce an effective protective response.—the present study showed that the mRNA-LNP vaccine platform enabled the use of M2 and NP (and other antigens) for vaccination to induce broad protection.

The present study also highlights the efficacy of a combination of multiple antigens to protect against a broad variety of influenza viruses in mice, which protects better than any individual components. Furthermore, a functionally inactive (non-toxic) M2 ion channel protein delivered as mRNA induces strong M2-directed immunity; and functionally active, membrane-bound NA provides protection against variant strains within the subtype. Moreover, the protection in mice was observed at doses as low as 50 ng of mRNA. Influenza A group 1-specific immunogens were tested and these studies are extended to various mutant versions of these immunogens to increase vaccine immunogenicity and safety and add influenza A group 2 and influenza B-specific immunogens.

Example 3: Antigen Modifications Improved Nucleoside-Modified mRNA-Based Influenza Virus Vaccines in Mice Influenza viruses cause over half a million deaths annually as well as millions of hospitalizations and subclinical infections (WHO, 2020, Influenza (Seasonal) Fact Sheet). Seasonal influenza virus vaccines confer suboptimal effectiveness due to poor immunogenicity or potential strain mismatches (CDC, 2019, Seasonal Influenza Vaccine Effectiveness, 2004-2019). To overcome these obstacles to ideal care, broadly protective influenza virus vaccines are currently being developed which offer the promise of superior and long-lasting immune responses (Nachbagauer R et al., 2020, Annu. Rev. Med., 71:315-327).

The influenza virus HA conserved stalk domain has been a target of several vaccine strategies and human clinical trials (Bernstein D I et al., 2020, Lancet. Infect. Dis., 20:80-91; Impagliazzo A et al., 2015, Science, 349:1301-1306; NIAID, 2019, Dose, safety, tolerability and immunogenicity of an influenza H1 stabilized stem ferritin vaccine, VRCFLUNPF099-00-VP, in healthy adults; Yassine H M et al., 2015, Nat. Med., 21:1065-1070), as this region has been found to elicit antibodies with the ability to cross-react with multiple influenza A and B viruses and act to confer protection through direct neutralization and Fc-mediated effector functions (DiLillo D J et al., 2014, Nat. Med., 20:143-151). Rationally designed vaccine candidates attempt to elicit this class of antibodies through sequential vaccination with chimeric HA proteins (Bernstein D I et al., 2020, Lancet. Infect. Dis., 20:80-91), headless HA stalk-only constructs (Impagliazzo A et al., 2015, Science, 349:1301-1306; Yassine H M et al., 2015, Nat. Med., 21:1065-1070), or hyperglycosylated HA head domain proteins (Eggink D et al., 2014, J. Virol., 88:699-704; Bajic G et al., 2019, Cell Host Microbe, 25:827-835).

The viral NA has gained momentum as a potential vaccine antigen due to its ability to elicit antibodies which potently neutralize within a subtype (Wohlbold T J et al., 2015, MBio., 6:e02556). Recently, broadly cross-reactive antibodies, which target the NA active site, have been discovered that can bind and inhibit influenza A and B viruses (Stadlbauer D et al., 2019, Science, 366:499-504). Strategies to supplement current influenza virus vaccines with NA components have been discussed to improve overall vaccine effectiveness (Krammer F et al., 2018, MBio., 9: e02332-17).

There have been several studies that have examined the potential of the extracellular domain of the matrix protein 2 (M2e) ion channel to serve as a universal influenza virus vaccine antigen (Deng L et al., 2015, Vaccines (Basel), 3:105-136; El Bakkouri, K et al., 2011, J. Immunol., 186: 1022-1031; Schotsaert M et al., 2016, Sci. Rep., 6:24402). The M2e region is highly conserved across influenza A viruses and is known to elicit non-neutralizing antibodies which confer protection through antibody-dependent cell-mediated cytotoxicity (ADCC) activity (El Bakkouri, K et al., 2011, J. Immunol., 186:1022-1031). The full length M2 protein is also known to contain several T-cell epitopes which may act to enhance antibody responses or stimulate cellular immune responses (Deng L et al., 2015, Vaccines (Basel), 3:105-136).

Strategies to stimulate broadly reactive cellular responses have also been investigated, often through the use of vectored expression of internal influenza virus proteins. Viral NP and matrix protein 1 (M1) proteins are favored antigens to stimulate cellular immunity due to the presence of highly conserved T-cell epitopes (Berthoud T K et al., 2011, Clin. Infect. Dis., 52:1-7). Broadly cross-reactive cellular responses have been shown to lead to clearance of infected cells, which leads to a reduction in symptoms and viral transmission (Topham D J et al., 1997, J. Immunol., 159: 5197-5200). Vaccines which utilize these antigens as targets are currently being tested in clinical trials (Lillie P J et al., 2012, Clin. Infect. Dis., 55:19-25).

Besides strain-specificity and limited potency, one of the major limitations of conventional influenza virus vaccine platforms is the difficulty with production in eggs or cell lines and the lack of flexibility to rapidly incorporate specific highly desired modifications (Houser K et al., 2015, Cell Host Microbe., 17:295-300). Next-generation vaccine technologies have pushed the field of influenza vaccine development forward by allowing delivery of conserved antigens and preferentially skewing the immune system to provoke desired responses. LNP-encapsulated nucleoside-modified mRNAs have recently been developed as a vaccine platform which offers not only exceptional potency, but also a rapid, scalable response to viral threats (Pardi N et al., 2015, J. Control. Release, 217:345-351; Alameh M G et al., 2020, Curr. Top. Microbiol. Immunol., 1-35). These vaccines have been shown to be effective against a variety of pathogens in preclinical studies (Alameh M G et al., 2020, Curr. Top. Microbiol. Immunol., 1-35), and several clinical studies are underway to prevent viral diseases including those caused by human cytomegalovirus (NCT04232280), respiratory syncytial virus (NCT04528719), severe acute respiratory syndrome-coronavirus 2 (NCT04470427 and NCT04537949) and others.

Importantly, several studies demonstrated that multiple vaccine antigens were formulated in mRNA-LNP for delivery in a single immunization (John S et al., 2018, Vaccine, 36:1689-1699; Awasthi S et al., 2019, Sci. Immunol., 4; Egan K P et al., 2020, PLoS Pathog., 16:e1008795; Freyn A W et al., 2020, Mol. Ther., 28:1569-1584), and this vaccine platform allows for easy alteration of the antigens they express through modification of the underlying sequence (Espeseth A S et al., 2020, NPJ Vaccines, 5:16). To improve on influenza virus vaccine targets, the present studies focused on altering protein functional domains by leveraging above described mutations.

The materials and methods employed in these experiments are now described.

Ethics Statement:

The herein described studies adhered to the "Guide for the Care and Use of Laboratory Animals" by the Committee on Care of Laboratory Animal Resources Commission on Life Sciences, National Research Council. Mouse studies were conducted under protocols approved by the Institutional Animal Care and Use Committees (IACUC) of the University of Pennsylvania (UPenn) and the Icahn School of Medicine at Mount Sinai (ISMMS). All animals were housed and cared for according to local, state, and federal policies in an Association for Assessment and Accreditation of Laboratory Animal Care International (AAALAC)-accredited facility.

Viruses, Cells, and Proteins:

Influenza A viruses A/Michigan/45/2015 H1N1pdm (Mich15), A/New Caledonia/20/1999 H1N1 (NC99), and IVR-180 (HA and NA from A/Singapore/GP1908/2015 H1N1pdm virus and non-glycoproteins from A/Texas/1/1977 H3N2) were utilized in this study. Viruses were grown in 10 day old embryonated chicken eggs (Charles River) for 48 hours at 37° C. before placing at 4° C. overnight. Allantoic fluid was harvested and cleared of debris through centrifugation at 4000×g for 10 minutes at 4° C. Cleared allantoic fluid, which was found to be hemagglutination positive (described below), was pooled, aliquoted, and stored at −80° C. until use. To purify and concentrate virus, pooled allantoic fluid was spun at 100,000×g for two hours at 4° C. over a 30% sucrose cushion. Viral pellets were resuspended in phosphate buffered saline (PBS), protein concentration was measured using a Bradford assay, and aliquots were frozen at −80° C. until use.

Madin-Darby canine kidney (MDCK) cells were grown in complete Dulbecco's modified Eagle's medium (10% FBS (Gibco), 100 units/mL penicillin and 100 μg/mL streptomycin (Gibco), and 1 mM 4-(2-hydroxyethyl)-1-piperazineethanesulfonic acid (HEPES; Gibco)) at 37° C. and 5% $CO_2$.

mRNA Production:

A/Michigan/45/2015 H1N1pdm virus segment sequences were utilized for antigen design. Codon-optimized HA, NA, NP, M1, and M2 were synthesized (Genscript) and mutations were included in the nucleotide sequence through polymerase chain reaction-guided amplification. Constructs were ligated into mRNA production vectors, vectors were linearized, and a T7-driven in vitro transcription reaction (Megascript, Ambion) was performed to generate mRNA with 101 nucleotide long poly(A) tails. Capping of mRNA was performed in concert with transcription through addition of a trinucleotide cap1 analog, CleanCap (TriLink) and m1'Ψ-5'-triphosphate (TriLink) was incorporated into the reaction instead of UTP. Cellulose-based purification of mRNA was performed as described (Baiersdorfer M et al., 2019, Mol. Ther. Nucleic Acids, 15:26-35). mRNAs were then checked on an agarose gel before storing at −20° C. (Baiersdorfer M et al., 2019, Mol. Ther. Nucleic Acids, 15:26-35).

Lipid Nanoparticle Formulation of mRNA:

Purified mRNAs were lipid nanoparticle formulated using a self-assembling ethanolic lipid mixture of an ionizable cationic lipid, phosphatidylcholine, cholesterol, and polyethylene glycol-lipid. This mixture was rapidly combined with an aqueous solution containing mRNA at acidic pH as previously described (Pardi N et al., 2015, J. Control. Release, 217:345-351). The ionizable cationic lipid (pKa in the range of 6.0-6.5, proprietary to Acuitas Therapeutics) and LNP composition are described in the patent application WO 2017/004143. The average hydrodynamic diameter was ~80 nm with a polydispersity index of 0.02-0.06 as measured by dynamic light scattering using a Zetasizer Nano ZS (Malvern Instruments Ltd, Malvern, UK) and an encapsulation efficiency of ~95% as determined using a Ribogreen assay.

mRNA Vaccination and Viral Challenge:

Female BALB/c mice aged six to eight weeks (Jackson Labs-ISMMS and Charles River Laboratories-UPenn) were utilized for this study. Mice were anesthetized with a low dose of ketamine/xylazine mixture (ISMMS) or isoflurane (UPenn) and shaved before intradermal delivery of mRNA-LNP vaccine diluted in PBS in two different spots on the back to a total volume of 100 μL.

The influenza virus challenge dose was determined through infection of mice with log-fold decreasing plaque forming units of virus. The median lethal dose ($LD_{50}$) was calculated based on survival of mice and the dose received and a challenge dose of $5\times LD_{50}$ was calculated. At the time of challenge, mice were anesthetized with a ketamine/xylazine mixture and weighed before $5\times LD_{50}$ of influenza virus was administered intranasally in 50 μL of PBS. Mice were weighed daily and were sacrificed if weight loss was greater than 25% of initial body weight or at the experimental end. All animal work was approved by the Icahn School of Medicine at Mount Sinai Institutional Animal Care and Use Committee.

Enzyme-Linked Immunosorbent Assays:

Immulon 4 HBX flat-bottomed, 96-well plates (Thermo Fisher) were coated with purified virus in PBS at a final concentration of 250 ng per well and allowed to incubate overnight at 4° C. The following morning, plates were washed three times with 0.1% Tween 20 (Fisher) in PBS (PBST) and blocked in Blocking Buffer (3% goat serum (Gibco) and 0.25% milk (Quality Biological) in PBST) for one hour at room temperature (RT). After removal of Blocking Buffer, samples were serial diluted three-fold in fresh Blocking Buffer and allowed to incubate at RT for two hours. Plates were then washed three times with PBST and goat anti-mouse IgG Fc horseradish peroxidase (HRP)-linked secondary antibody (Abcam, 97265) was added at a concentration of 1:15,000 in Blocking Buffer and incubated at RT for one hour. Plates were then washed four times with PBST with additional shaking and developed using SigmaFast o-phenylenediamine dihydrochloride substrate (OPD; Sigma) for 10 minutes before quenching with 3M HCl (Fisher). Plates were read on a Synergy H1 hybrid multimode microplate reader (BioTek) at 490 nm. Data were processed using Prism 8.0 (GraphPad) and area under the curve was calculated using a baseline of the average plus three times the standard deviation of negative wells or 0.07, whichever value was higher.

Hemagglutination Inhibition Assay:

Hemagglutination titer was determined through incubation of two-fold serial dilutions of virus in PBS with an equal volume of chicken red blood cells (RBCs) at 0.5% in PBS at 4° C. Titer was determined as the final dilution able to cause agglutination of RBCs which prevents a pellet from being formed.

Serum was treated with receptor destroying enzyme (RDE; Seiken) as per the manufacturer's instruction. Briefly, serum was incubated with RDE overnight at 37° C. then the reaction was quenched with 2.5% sodium citrate (Fisher) and heat inactivated at 56° C. for 30 minutes, then diluted to a final concentration of 1:10 in PBS. Serum was then serially diluted two-fold in PBS. Virus was diluted to four hemagglutination units in PBS and added to serum dilutions. The mixture was shaken for 30 minutes at RT then added to chicken RBCs at 0.5% in PBS and allowed to develop at 4° C. Endpoint titer was determined as the final reciprocal dilution able to prevent agglutination of RBCs, denoted visually by pelleted RBCs.

Microneutralization Assay:

Median tissue culture infectious dose ($TCID_{50}$) was determined for each virus utilized in this assay. MDCK cells were plated at $2.5\times10^4$ cells per well in tissue culture-treated 96 well dishes and allowed to culture overnight at 37° C. and 5% $CO_2$. The following morning, virus was serially diluted in half-log increments in assay buffer (Ultra MDCK media (Lonza) with 1 μg/mL 6-(1-tosylamido-2-phenyl) ethyl chloromethyl ketone (TPCK)-treated trypsin). Cells were washed with PBS and infected with viral dilutions for 72 hours at 33° C. A hemagglutination assay was performed by mixing 50 μL of supernatant from each well with 50 μL of 0.5% chicken RBCs (Lampire). The last dilution which was able to cause agglutination of RBCs was recorded and used to calculate $TCID_{50}$.

MDCK cells were plated in 96 well dishes at $2.5\times10^4$ cells/well. Serum samples were pooled and RDE treated as described above. Sera were then diluted two-fold in assay buffer before adding equal volumes of diluted sera with 100 $TCID_{50}$ of influenza virus diluted in assay buffer. This mixture was shaken at RT for 30 minutes before adding to PBS-washed MDCK cells and allowing virus to adsorb for one hour at 33° C. and 5% $CO_2$. Cells were washed with PBS and remaining sera were diluted in an equal volume assay buffer before adding to the corresponding wells. Infection was allowed to proceed before reading of the plate via hemagglutination assay. The last dilution which was able to cause agglutination of RBCs was determined as the endpoint titer.

Antibody-Dependent Cell-Mediated Cytotoxicity Reporter Assay:

MDCK cells were plated in white-walled, 96-well dishes (CoStar) to $2.5\times10^4$ cells/well in cDMEM and incubated overnight at 37° C. and 5% $CO_2$. The following morning, cells were washed with PBS and infected with influenza virus at a multiplicity of infection of five in the absence of TPCK-treated trypsin. Infection was allowed to proceed for 24 hours at 37° C. and 5% $CO_2$. Media was removed from cells and 25 μL of assay buffer (RPMI 16-40 with 4% Low IgG FBS (Gibco)) was added to each well. Serum was serially diluted three-fold in assay buffer and 25 μL was added to the infected cells. Effector ADCC cells expressing murine FcγRIV with an NFAT-driven luciferase cassette (Promega) were added to a final count of $3\times10^6$ cells/mL in 25 μL. The reaction was allowed to incubate for six hours at 37° C. and 5% $CO_2$ before normalizing to room temperature (RT). Bio-Glo luciferase substrate (Promega) was added to each well and luminescence was immediately read with a Synergy H1 hybrid multimode microplate reader (BioTek). Fold change was determined by dividing each well by the average of background wells plus three times the standard deviation. Regression curves were fit to the background corrected values and area under the curve was calculated with a baseline threshold of one in Prism 8.0 (GraphPad).

Neuraminidase Inhibition Assay:

Enzyme-linked lectin assays were performed to determine the amount of virus necessary for NI assays. Fetuin (Sigma-Aldrich) was coated in 96-well dishes at a final concentration of 25 μg/mL in 100 μL PBS and plates were stored overnight at 4° C. The following day, plates were washed three times with PBS-T and blocked with 5% BSA in PBS-T for one hour at RT. Virus was serially diluted two-fold in PBS with 1% BSA (Sigma-Aldrich) and added to blocked plates for two hours at 37° C. and 5% $CO_2$. Plates were then washed six times with PBS-T and 100 L of HRP-conjugated peanut agglutinin (PNA) at 5 μg/mL was added and plates were incubated for two hours at RT in the dark. After washing six times with PBS-T, 100 μL of SigmaFast OPD (Sigma) was added and allowed to develop for ten minutes before quenching with 3M HCl (Fisher). Plates were read on a Synergy H1 hybrid multimode microplate reader (BioTek) at 490 nm. Curves were fit using non-linear regression in Prism 8.0 (GraphPad) and the 90% effective concentration (EC90) was determined and used for subsequent neuraminidase inhibition assays.

96-well dishes were coated with 25 μg/mL fetuin in 100 μL PBS and stored overnight at 4° C. Sera were heat-treated at 56° C. before diluting two-fold in PBS with 1% BSA. Virus was diluted in PBS with 1% BSA based on the EC90 value and was added in equal volumes to the serum dilutions and incubated, shaking at RT for one and a half hours. Fetuin coated plates were washed and blocked for one hour at RT as described above. After removing blocking buffer, virus/serum mixture was added to the fetuin plates and incubated at 37° C. and 5% $CO_2$ for two hours. Plates were then washed six times with PBST and HRP-linked PNA was added for two hours at RT in the dark. Plates were washed again six times with PBST and developed as described above. Nonlinear regression curves were fit using Prism 8.0 (GraphPad) and EC50 values were determined.

Staining and Flow Cytometry Analysis of Mouse Splenocytes:

Single-cell suspensions of mouse splenocytes were generated in complete RPMI-1640 medium. $3\times10^6$ cells per sample were stimulated for six hours at 37° C. and 5% $CO_2$ in the presence of an overlapping M1 peptide pool (JPT Peptide Technologies, MP1/California H1N1) at 5 μg/mL and anti-CD28 antibody (BD Biosciences, clone 37.51) at 1 μg/mL. GolgiPlug (BD Biosciences, Brefeldin A) at 5 μg/mL and GolgiStop (BD Biosciences, Monensin) at g/mL were added to each sample one hour after the start of stimulation. Unstimulated samples for each animal were also included. A sample stimulated with phorbol 12-myristate-13-acetate (Sigma) at 10 μg/mL and ionomycin (Sigma) at 200 ng/mL was included as a positive control. After stimulation, cells were washed with PBS and stained with a LIVE/DEAD Fixable Aqua Dead Cell Stain Kit (Life Technologies) for ten minutes in the dark at RT. Cells were subsequently surface stained with unlabeled CD16/CD32 rat anti-mouse (BD Biosciences, clone 2.4G2) and anti-CD4 PerCP (peridinin chlorophyll protein)/Cy5.5 (BioLegend, clone GK1.5) and anti-CD8 Pacific Blue (BioLegend, clone 53-6.7) monoclonal antibodies (mAbs) for 30 minutes in the dark at 4° C. After surface staining, cells were washed with FACS buffer, fixed (PBS containing 1% paraformaldehyde), and permeabilized using a Permeabilization/Fixation Solution Kit (BD Biosciences). Cells were then intracellularly stained with anti-CD3 allophycocyanin (APC)-Cy7 (BD Biosciences, clone SP34-2), anti-tumor necrosis factor (TNF)-α phycoerythrin (PE)-Cy7 (BD Biosciences, clone MP6-XT22), anti-interferon (IFN)-γ Alexa Fluor 700 (AF700) (BD Biosciences, clone XMG1.2), and anti-interleukin (IL)-2 Brilliant Violet 711 (BV711) (BioLegend, clone JES6-5H4) mAbs for 30 minutes in the dark at 4° C. Finally, cells were washed with permeabilization buffer, fixed as before, and stored at 4° C. until analysis. Splenocytes were analyzed on a modified LSR II flow cytometer (BD Biosciences). 500,000 events were collected per specimen. After the gates for each function were developed, the Boolean gate platform was used to create the full array of possible combinations, equating to seven response patterns when testing three functions. Data was analyzed with the FlowJo 10 program. Data was expressed by subtracting frequencies of unstimulated stained cells from frequencies of peptide pool-stimulated stained samples.

Membrane-Anchored Hemagglutinin Antigens Outperformed Soluble Constructs

Vectored vaccine approaches provided the ability to display antigen in a native, membrane-bound form. To compare soluble and membrane-bound HA constructs, mRNA sequences were designed which either contained the full-length wild type A/Michigan/45/2015 H1N1pdm (Mich15)

Figure 23:
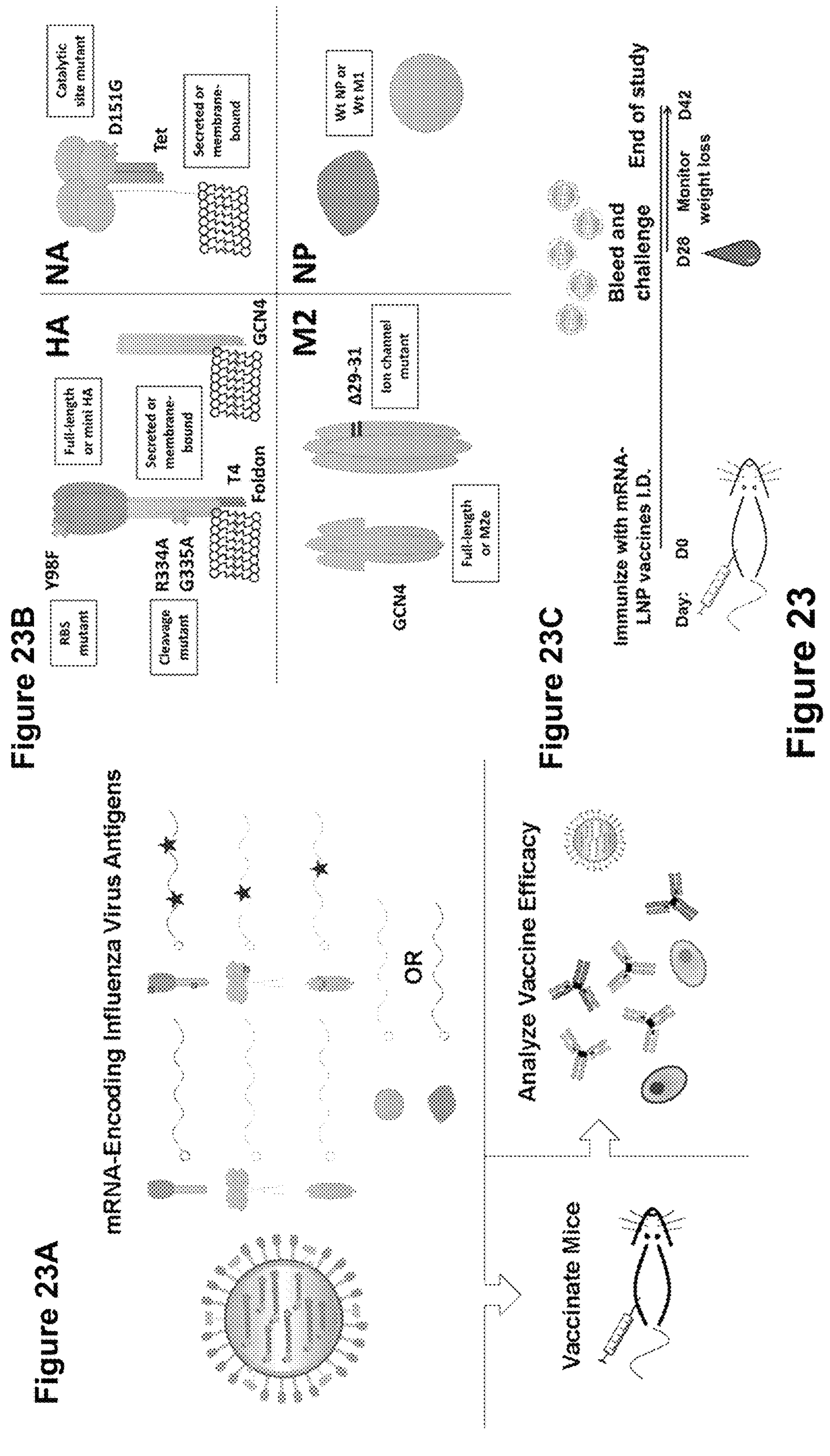
FIG. 23, comprising

HA sequence or had the transmembrane and cytosolic domains removed and replaced with a T4 foldon trimerization domain (FIG. 23B; Krammer F et al., 2012, PLoS One, 7:e43603).

Figure 24:
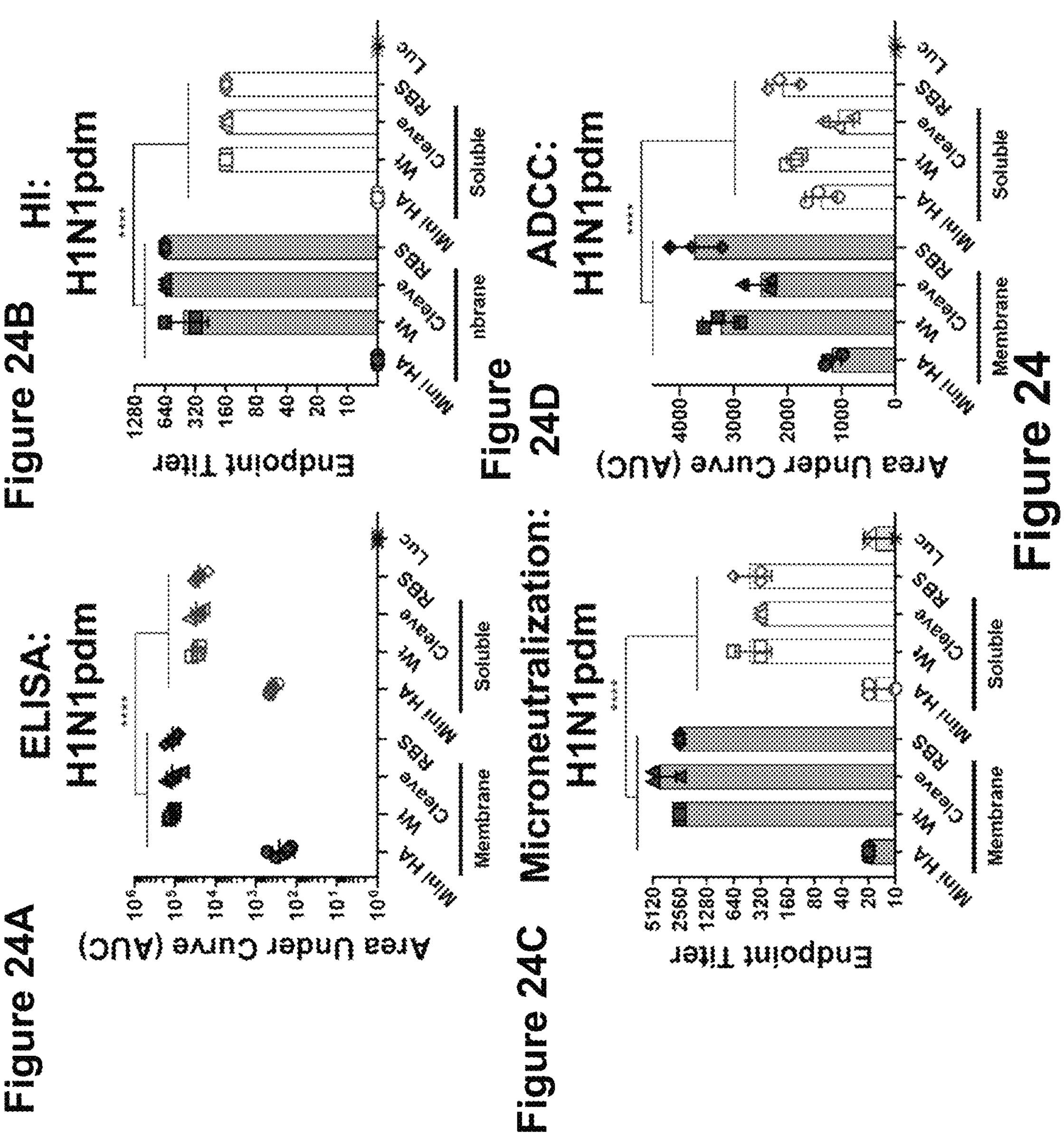
FIG. 24, comprising
Figure 25:
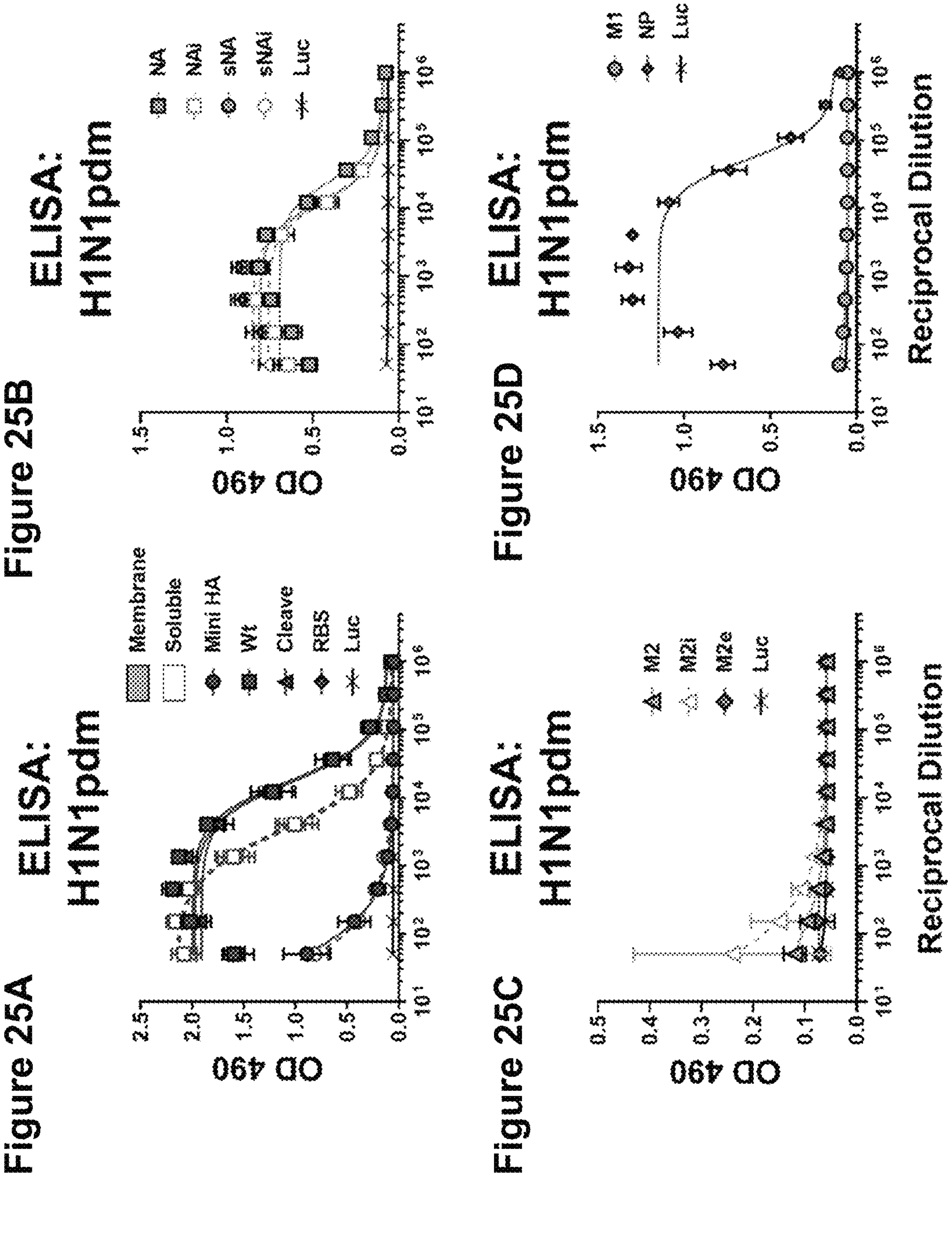
FIG. 25, comprising
Figures 26, 26A, 26B, 26C:
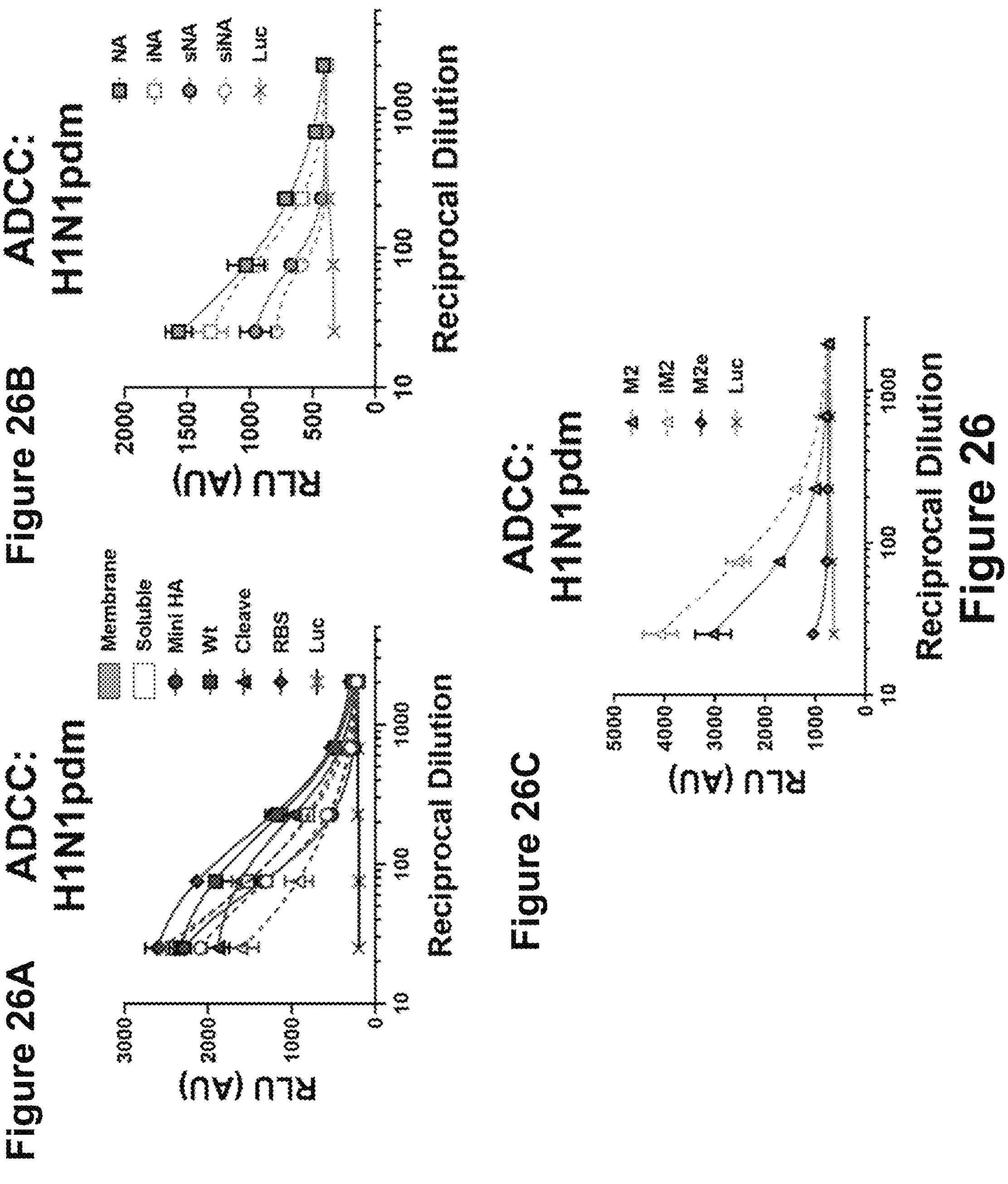

Further, to examine the effect of HA receptor binding activity on eliciting immune responses, an additional mutation (Y98F) was introduced in the receptor binding site (RBS) to reduce sialic acid binding (Martin J et al., 1998, Virology, 241:101-111). Also, mutation of the HA cleavage site (R334A and G335A) was performed to observe if reduction of proteolytic cleavage plays a role in antigen presentation or stability in the context of intradermal vaccination. Soluble and transmembrane domain-bearing constructs were also produced using the CR #4900 Mini HA, which was based on the conserved stalk domain of the A/Brisbane/59/2007 H1N1 influenza virus (Impagliazzo A et al., 2015, Science, 349:1301-1306). Mice were vaccinated intradermally (I.D.) with 20 g of a single mRNA-LNP construct and serum was obtained four weeks later for analysis (FIG. 23C). Sera were analyzed to determine antibody binding by enzyme-linked immunosorbent assay (ELISA; FIG. 24A and FIG. 25A), interference of HA receptor binding activity by hemagglutination inhibition (FIG. 24B), neutralization by a multi-cycle microneutralization assay (FIG. 24C), and antibody Fc-mediated effector functionality through an antibody-dependent cell-mediated cytotoxicity reporter assay (FIG. 24D and FIG. 26A). Mutation of the RBS and the HA cleavage site was not found to substantially impact antigenicity at the tested dose level. However, expression of HA as a full-length, membrane bound construct was found to significantly improve the quality of the antibody responses compared with soluble HAs. The responses elicited by Mini HA constructs were overall lower and no difference between membrane-bound and secreted HA was detected. However, these constructs were structurally designed as stable secreted antigens and the impact of introducing a transmembrane domain to these constructs is unclear. Further, it was noted that the Mini HA was based on the pre-pandemic A/Brisbane/59/2007 H1N1 while all other constructs were based on the post-pandemic Mich15 sequence which matched the viruses used for these assays.

Figures 24, 24E:
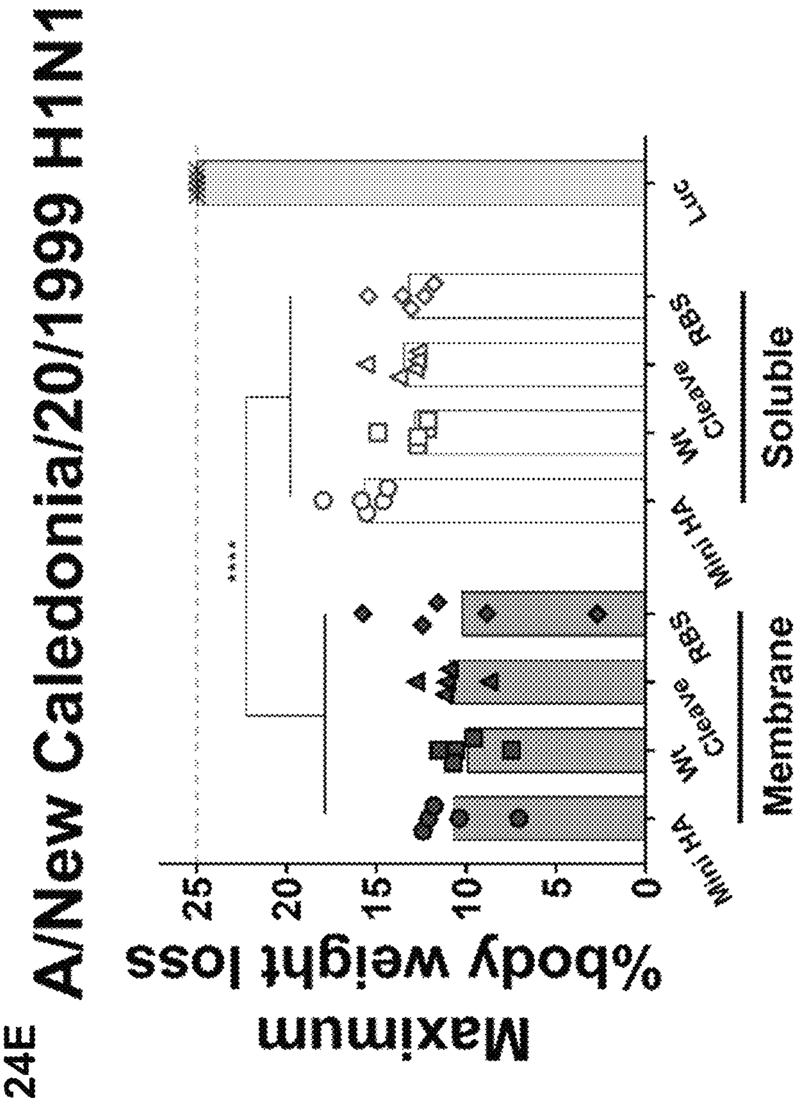

Four weeks after vaccination, mice were challenged with the pre-pandemic A/New Caledonia/20/1999 H1N1 (NC99) virus to observe differences in protection conferred by the membrane bound (FIG. 27A) and soluble (FIG. 27B) constructs based on body weight loss. Maximum percent body weight loss data was plotted (FIG. 24E) and demonstrated a significant increase in protection when HA constructs were expressed as full-length membrane bound protein. No substantial differences in weight loss were observed for any mutant relative to wild type antigen, demonstrating a lack of effect of functional mutation for altering HA immunogenicity at the tested dose. It is important to note that the influenza challenge virus NC99 is genetically more similar to the pre-pandemic Mini HA than to the post-pandemic Mich15-based constructs.

Alteration of Neuraminidase Catalytic Activity Reduced Reactogenicity

Figure 27:
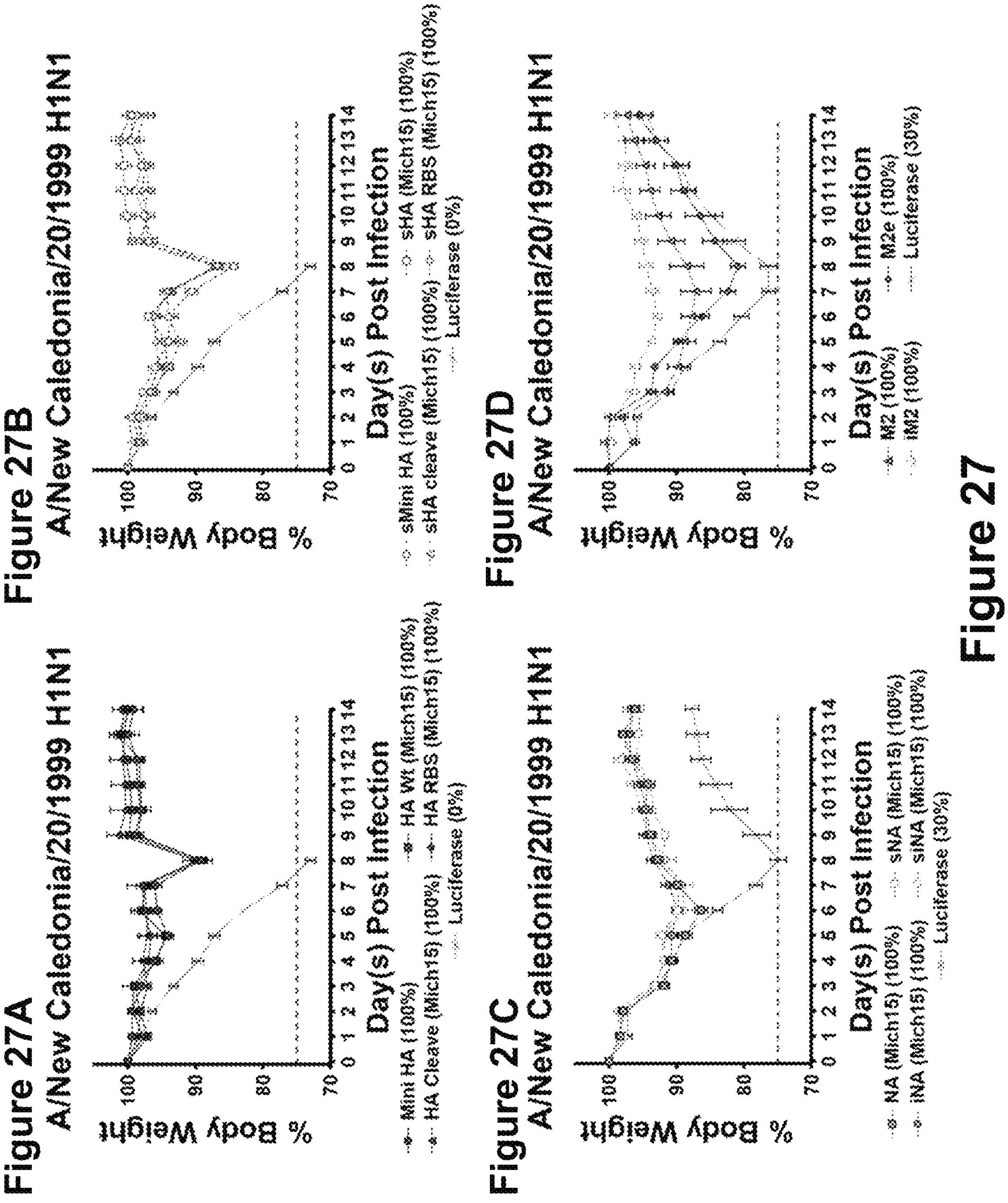
FIG. 27, comprising
Figure 28:
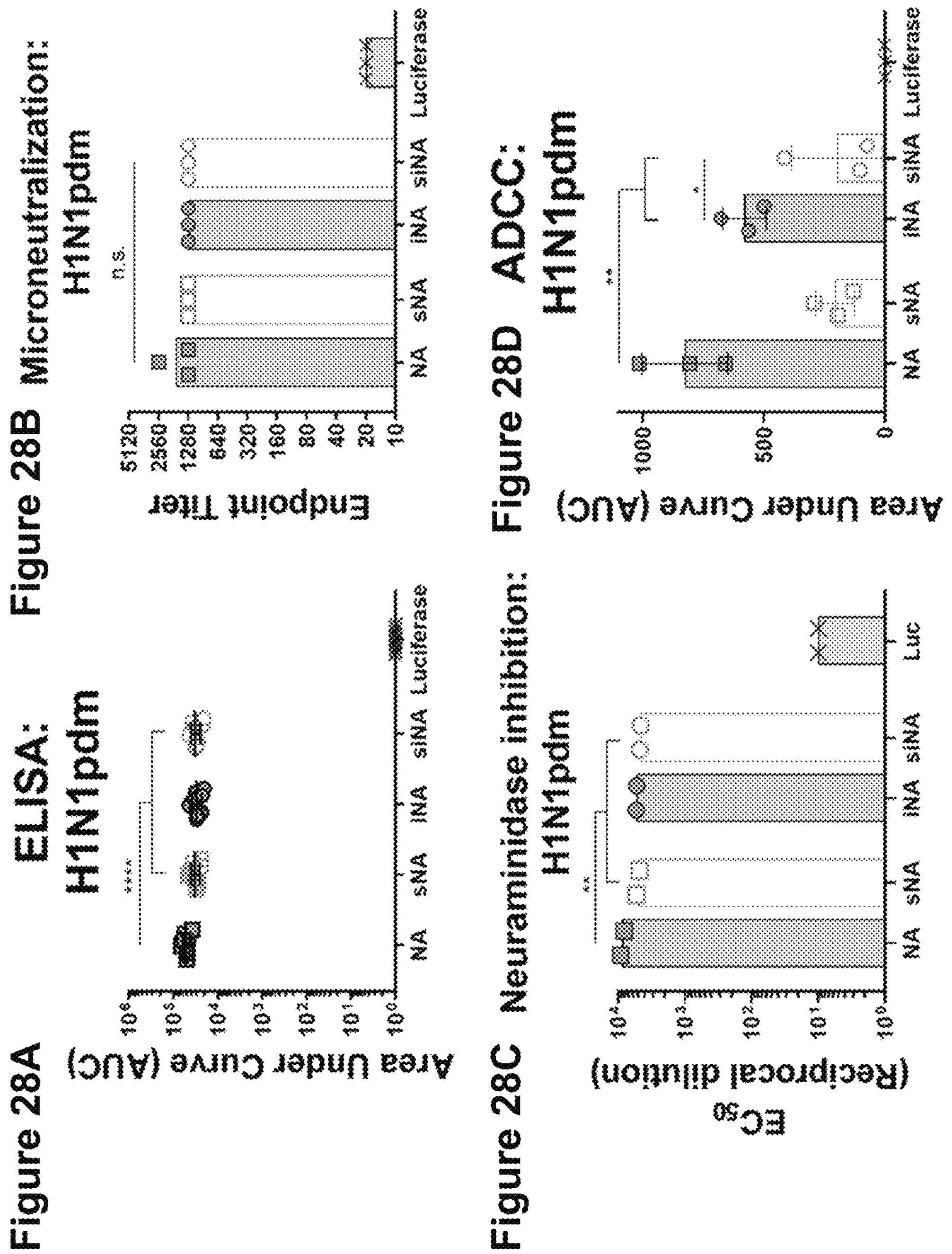
FIG. 28, comprising

The impact of mutation of the NA catalytic site was examined by introducing a D151G mutation into the mRNA sequence (FIG. 23B), which has been previously described to reduce functional activity (Zhu X et al., 2012, J. Virol., 86:13371-13383). In parallel, secreted forms of the NA head domain fused to a tetrabrachion tetramerization domain with or without the catalytic site mutant were tested (Margine I et al., 2013, J. Vis. Exp., e51112). Mice were immunized as described above with 20 μg of nucleoside-modified mRNA-LNP and serological assays were performed four weeks after vaccination. All constructs were found to elicit similar levels of antibodies by ELISA to a matched H1N1pdm influenza virus, though wild type NA elicited slightly higher responses (FIG. 28A and FIG. 25B). While neutralizing titers were similar between groups (FIG. 28B), neuraminidase inhibition measured by an enzyme-linked lectin assay (ELLA) showed again a trend to higher levels for the wild type construct (FIG. 28C). In an ADCC reporter assay, sera from mice immunized with membrane-bound constructs elicited stronger signals (FIG. 28D and FIG. 26B). To determine the impact of modifications on protection, mice were infected with the heterologous A/New Caledonia/20/1999 H1N1 virus strain. Maximal body weight loss was similar between groups, with no significant differences in protection observed (FIG. 28E and FIG. 27C).

Interestingly, reactogenicity in the form of lesions was observed when testing the wild type NA construct in an I.D. prime/boost regimen (10 μg of mRNA twice; three weeks apart). The lesions were only observed when testing NA antigens and only after booster vaccination (FIG. 28F), suggesting an involvement of adaptive immune responses. Importantly, it was found that mutating the catalytic site of the NA substantially reduced reactogenicity while the mutation did not substantially alter immunogenicity or conferred protection.

Expression of a Full-Length M2 with Ion Channel Activity Ablated Improved Immunogenicity mRNA and other vectored vaccines allow the expression of full-length transmembrane proteins. Comparison of full-length M2 mRNA-LNP with a construct expressing only the M2 ectodomain attached to a general control non-repressible 4 (GCN4) tetramerization domain (M2e) was performed through vaccination followed by serological analysis and challenge (De Filette M et al., 2008, J. Biol. Chem., 283: 11382-11387). Additionally, a full-length M2 encoding mRNA-LNP with amino acids 29-31 deleted (iM2) was also used (FIG. 23B), as this mutation has been previously shown to ablate ion channel activity (Watanabe T et al., 2001, J. Virol., 75:5656-5662).

Figures 29, 29A, 29B, 29C:
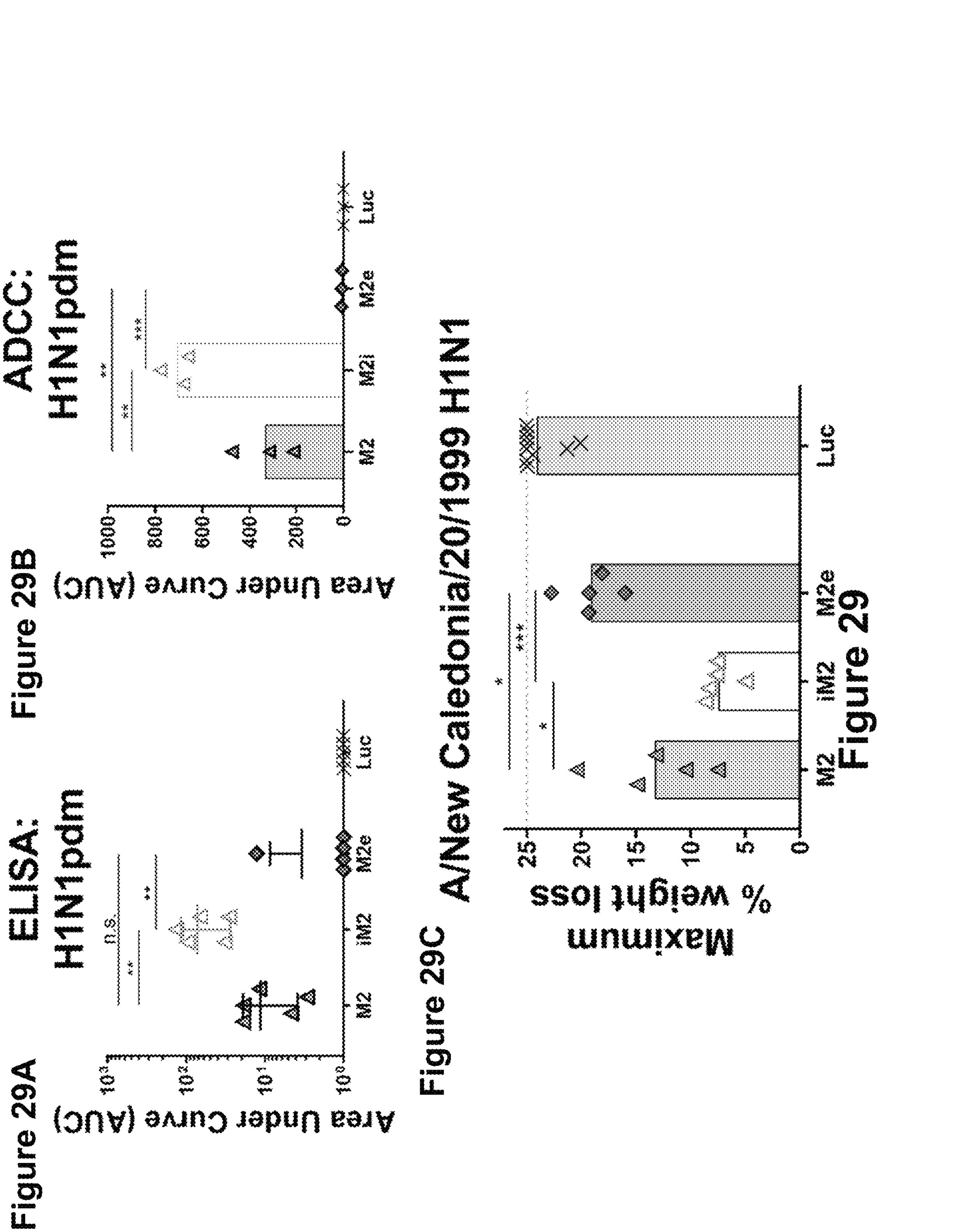
FIG. 29, comprising
FIG. 29A through FIG. 29C, depicts representative results demonstrating that ablation of full-length matrix protein 2 ion channel activity increased immunogenicity. Mice were vaccinated intradermally with 20 μg of mRNA-LNP expressing M2 constructs. Sera were collected four weeks after vaccination followed by challenge with NC99 H1N1 virus. One-way ANOVA with Tukey's correction for multiple comparisons was performed to determine statistical significance: * $p<0.033$,  $p<0.002$, * $p<0.0002$.

ELISA analysis revealed that iM2 vaccinated mice mounted significantly stronger responses to the target than the other constructs tested (FIG. 29A and FIG. 25C). This pattern persisted through functional examination of the elicited antibodies by ADCC reporter assays with iM2>M2>M2e (FIG. 29B and FIG. 26C). After challenge with the heterologous A/New Caledonia/20/1999 H1N1 strain, protection was examined through analysis of percent body weight loss as described above (FIG. 27D). Maximum percent body weight loss was found to be lowest in mice vaccinated with iM2, which showed significantly better protection than both other vaccine groups (FIG. 29C).

Figure 30:
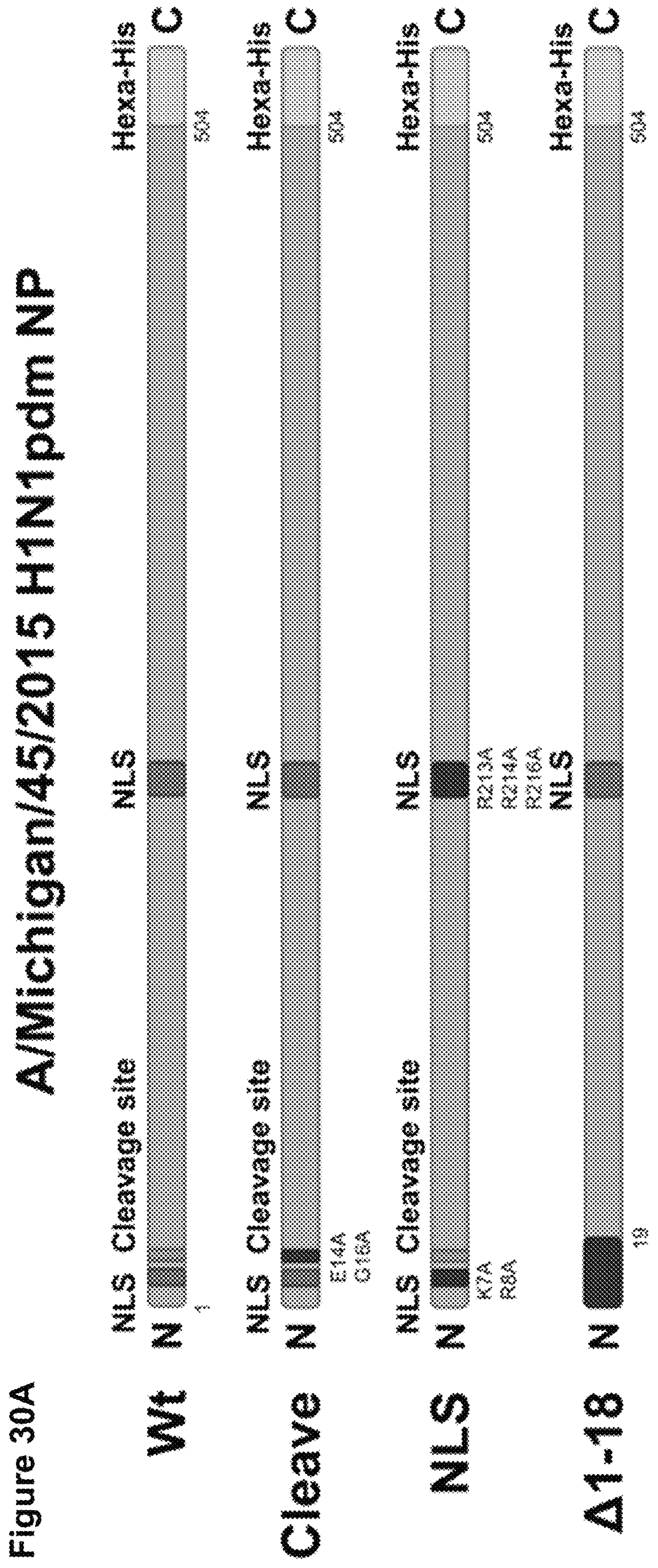
FIG. 30, comprising
Figure 30:
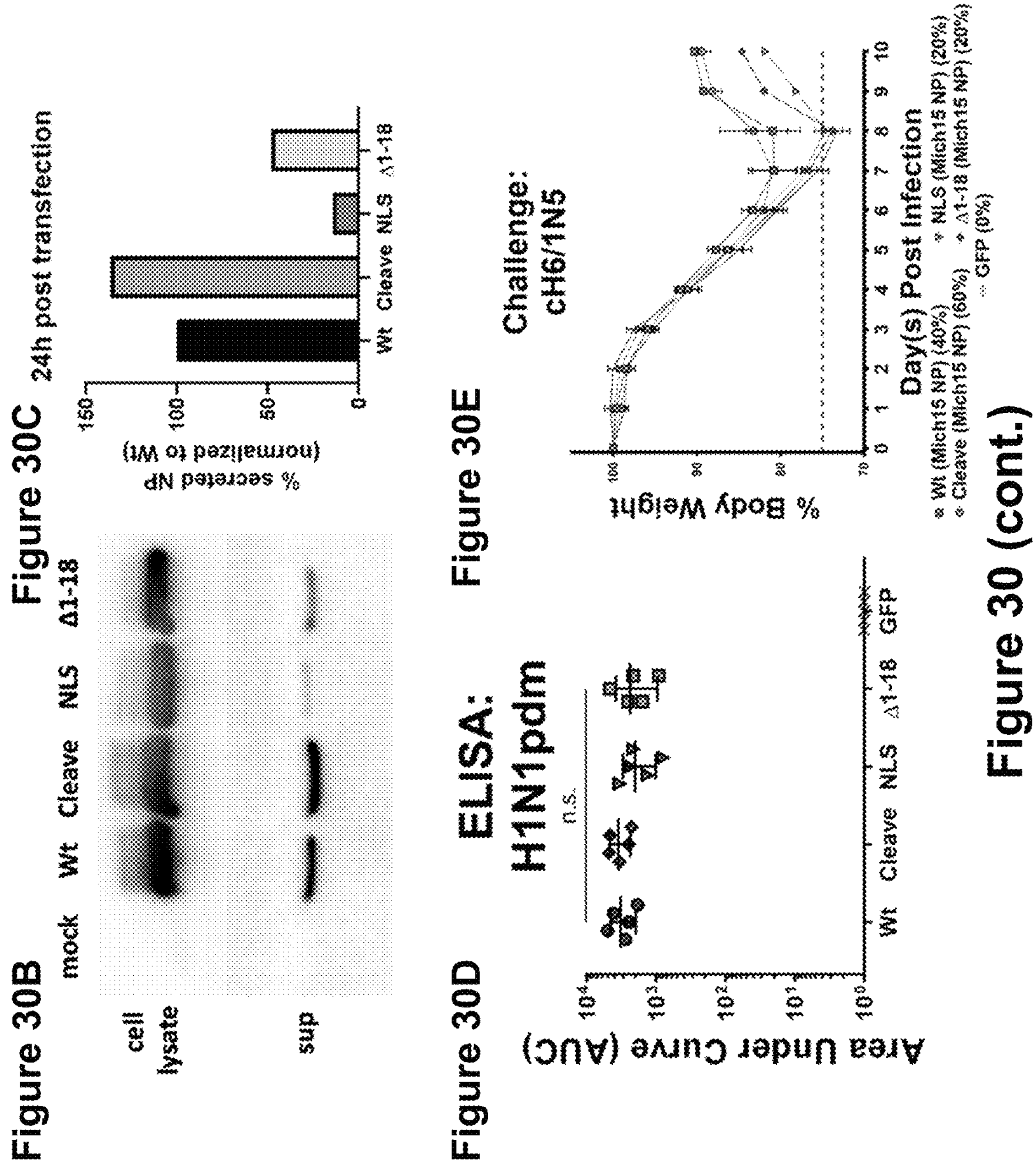

Nucleoprotein was a Superior Antigen to Matrix Protein 1 when Delivered by Nucleoside-Modified mRNA-LNP Internal proteins of the influenza virion have been utilized as targets to stimulate broadly reactive cellular responses through viral vectored approaches (Berthoud T K et al., 2011, Clin. Infect. Dis., 52:1-7; Antrobus R D et al., 2014, Mol. Ther., 22:668-674). To assess the ability of these antigens to confer protection after delivery through an mRNA-LNP, wild type NP and M1 (A/Michigan/45/2015 H1N1pdm) expressing vaccines were formulated. Vaccination was performed as described above followed by serological assessment and viral challenge. Modifications to the NP protein nuclear localization signal sequences to attempt to reduce antibody responses through reduced secretion were also tested, but did not translate to differences in vivo (FIG. 30).

Figures 27, 27E:
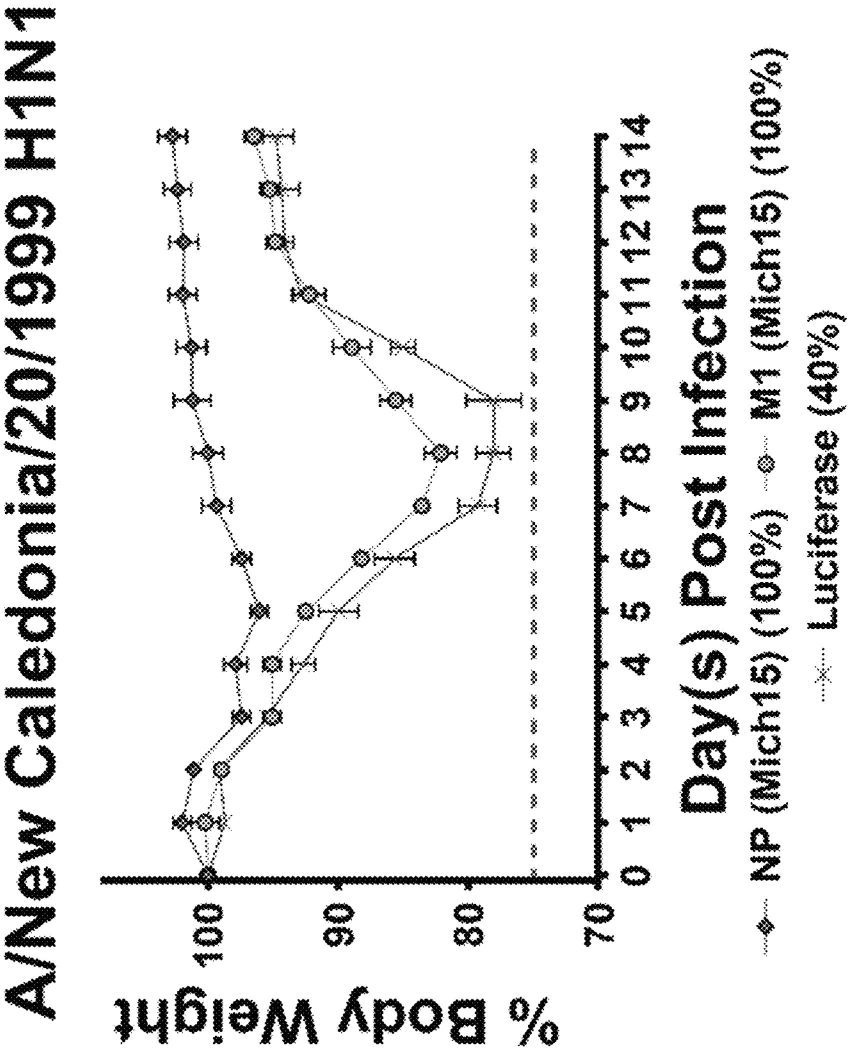
Figures 31, 31A, 31B, 31C:
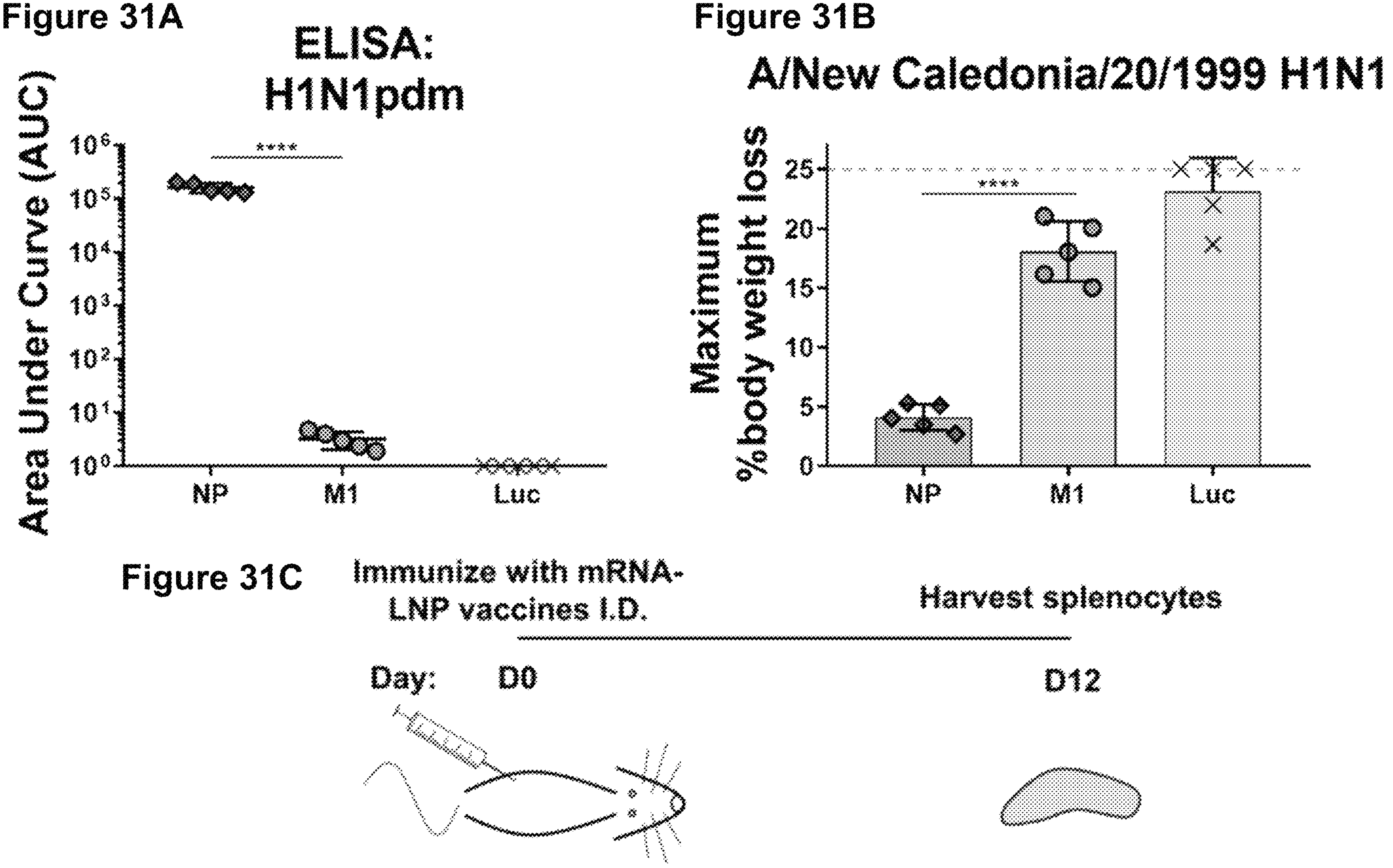
FIG. 31, comprising
FIG. 31A through FIG. 31G, depicts representative results demonstrating that nucleoside-modified mRNA-LNP delivery of nucleoprotein confers enhanced protection relative to matrix protein 1. Mice were vaccinated with 20 g nucleoside-modified mRNA-LNP I.D. and bled four weeks later for serological analysis before challenge with a heterologous H1N1 virus. Values from matrix protein 1 (M1)-immunized mice are compared to values from Luc-immunized animals (FIG. 31B through FIG. 31E). Each symbol represents one animal and error is shown as SD (n=mice/group). Data from two independent experiments are shown (n=5 mice/group/experiment).

The NP expressing construct was found to stimulate high levels of antibodies to a purified H1N1pdm target by ELISA, while humoral responses were negligible after vaccination with the M1 expressing mRNA-LNP (FIG. 31A and FIG. 25D). Survival after viral challenge was complete for both antigens (FIG. 31B), but the maximum percent body weight loss was significantly lower in mice receiving NP-expressing mRNA-LNP (FIG. 27E).

Figures 31, 31D, 31E, 31F, 31G:
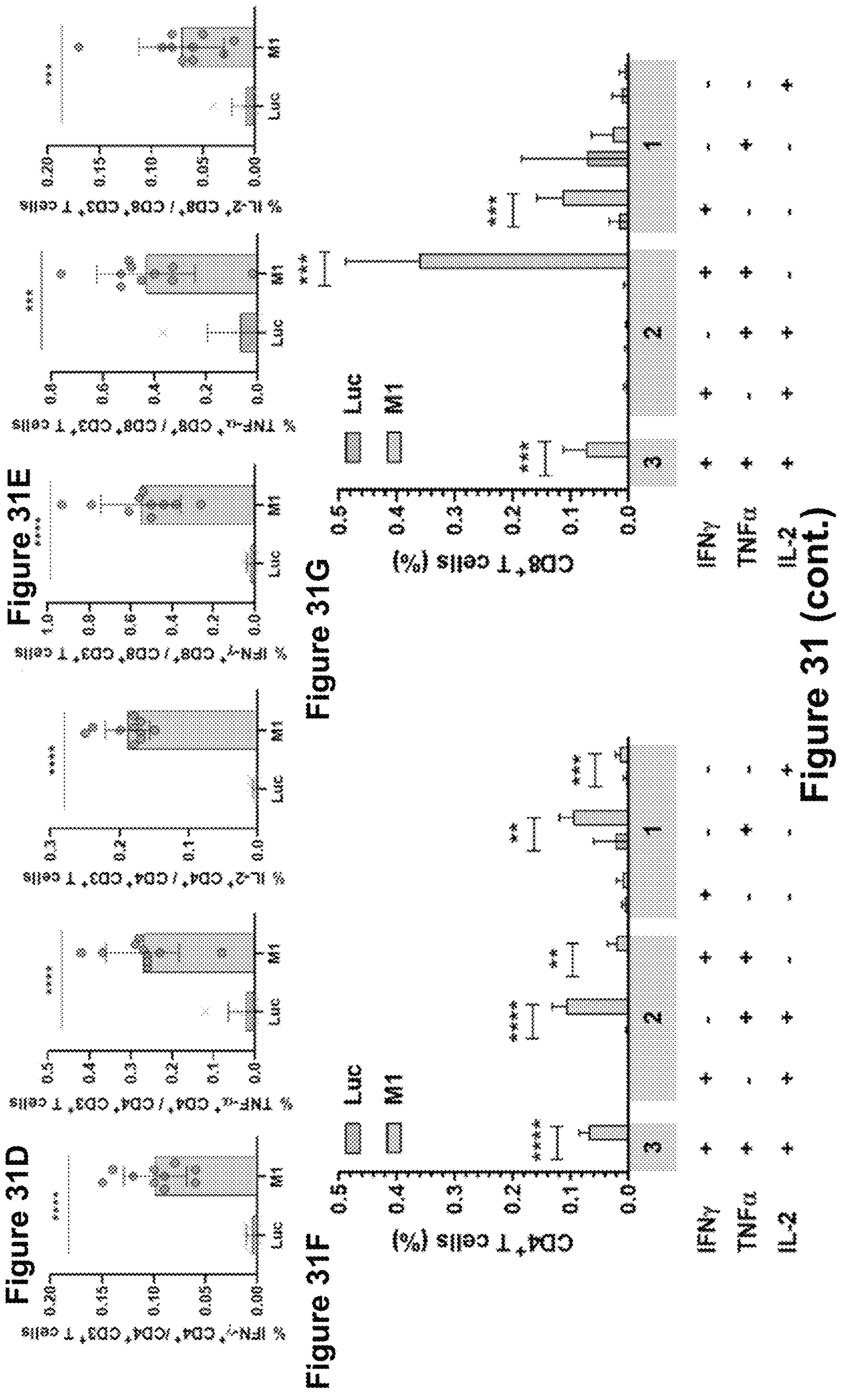
Figure 32:
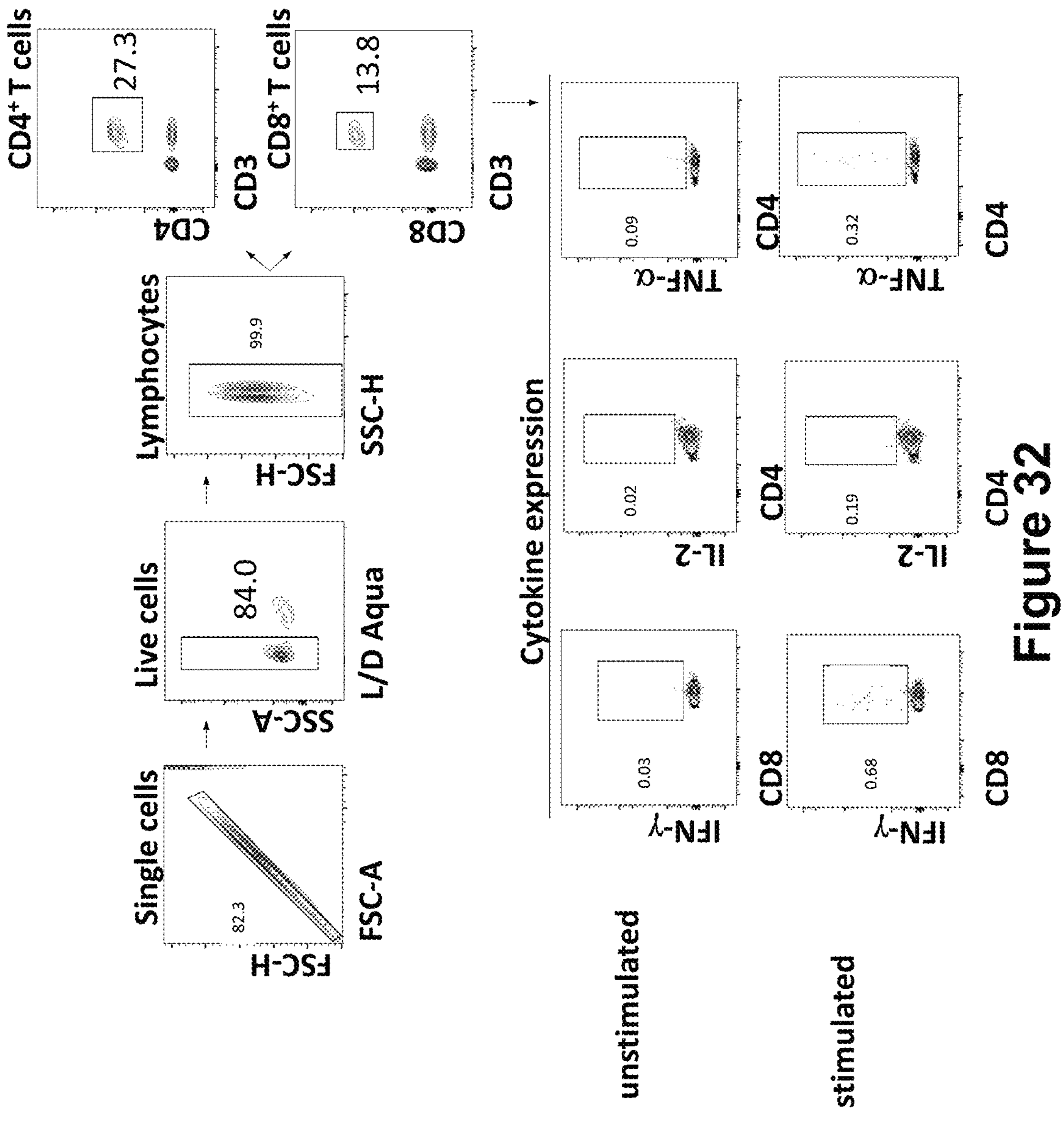
FIG. 32 depicts a schematic representation of flow cytometric gating strategy for the investigation of T-cell responses in matrix protein 1 mRNA-LNP-immunized mice. Representative flow cytometry plots for unstimulated and peptide-stimulated samples are shown.

Analysis of T-cell responses was performed for the M1-encoding mRNA-LNP to compare with previously published results on NP-expressing mRNA-LNP vaccination (Freyn A W et al., 2020, Mol. Ther., 28:1569-1584). Mice were vaccinated with 20 μg of M1 mRNA-LNP and spleens were harvested for analysis 12 days later (FIG. 31C). T-cells were stimulated with M1-specific peptides and flow cytometry was utilized with intracellular cytokine staining to determine antigen-specific T-cell activation. The proportion of cytokine-expressing T-cells out of total CD3+ cells was reported for both CD4+ and CD8+ populations (FIG. 31D, FIG. 31E, and FIG. 32). Also, polyfunctionality was assessed through Boolean gating to determine cell populations expressing multiple cytokines simultaneously (FIG. 31F and FIG. 31G). Both CD4+ and CD8+ T-cell responses were detected in M1 vaccinated mice. Compared to previously published data for NP-specific T-cell responses after mRNA-LNP vaccination, the CD8+M1-specific T-cell population was substantially weaker (Freyn A W et al., 2020, Mol. Ther., 28:1569-1584).

Antigen modification of vaccines has been commonly used to increase stability/immunogenicity of recombinantly expressed protein antigens (Graham B S et al., 2019, Annu. Rev. Med., 70:91-104). Expanding this process to include alteration of functional domains has been explored to determine the specific effects modifications have on immunogenicity and reactogenicity (Graham B S et al., 2019, Annu. Rev. Med., 70:91-104). Due to its fully synthetic nature, the nucleoside-modified mRNA-LNP technology enabled the rapid incorporations of changes to the protein target through modification of the underlying sequence. This procedure was applied to potentially broadly protective influenza virus vaccine antigens in an attempt to optimize each component.

It was found that vaccination with full-length HA with the intact transmembrane region elicited more functional and protective antibody responses than soluble constructs when delivered by nucleoside-modified mRNA-LNP. Although not bound by any particular theory, this was likely due to increased stabilization of the HA protein through this native domain rather than a foreign soluble trimerization domain or overexpression on the cell surface facilitating B-cell receptor crosslinking. Furthermore, accumulation of membrane-bound antigen on the cell surface facilitate more effective cross-linking of B cell receptors, resulting in stronger antibody responses. This beneficial effect is transferred to secreted antigens by polymerization through presentation on nanoparticles, such as ferritin (Yassine H M et al., 2015, Nat. Med., 21:1065-1070). Mutation of the HA RBS or cleavage site had little impact on immunogenicity in either secreted or membrane-bound form.

Furthermore, although not bound by any particular theory, it cannot exclude that reduction of receptor binding activity result in observable differences in immunogenicity at lower doses, as it may change antigen distribution due to reduced "stickiness". The Mini HA antigen also benefited from regrafting of the transmembrane domain as protection conferred was similar to the wild type antigen after heterologous challenge. The observed protective effect was similar for all constructs, but it is important to note that the Mini HA was closer in amino acid sequence to the pre-pandemic NC99 challenge virus than the post-pandemic Mich15-based constructs. Thus, although not bound by any particular theory, based on the decreased activity of sera from Mini HA-vaccinated mice in vitro, it was likely that the full-length antigens result in superior protection against challenge with matched strains.

Modification of the NA revealed little impact of diminished catalytic activity on immunogenicity of the antigen. Some advantage was seen for the wild type antigen in binding and functional assays, but the conferred protection by all tested antigens was similar. ADCC activity was most affected by antigen modification, with full length constructs showing an increase in reporter activity relative to their secreted counterparts. This indicated that epitopes targeted by antibodies that mediated ADCC activity were lost when the entire stalk domain was removed to design the soluble constructs. Interestingly, it was found that reactogenicity was substantially decreased when catalytic activity of the antigen was reduced. This finding is broadly applicable to improve safety of NA-based vaccines for a variety of platforms and applies more generally to antigens with enzymatic activity.

Analysis of M2 constructs revealed the benefit of preserving the entire transmembrane domain, which contained T-cell epitopes and was involved in presenting the appropriately folded conformation of the antigen to the cell surface. Although not bound by any particular theory, ablation of ion channel activity increased stimulated immune responses, most likely due to a decrease in toxicity that overexpression of active ion channels on the cell surface would impart. Expression of the soluble M2e construct showed poor immunogenicity in the context of delivery by mRNA-LNP, which is likely due to lack of appropriate conformation when expressed in vivo, or limited B cell receptor cross-linking in the context of a small, secreted antigen. The antigen was typically expressed in a bacterial system and highly purified to only maintain correctly folded tetrameric constructs (Schotsaert M et al., 2016, Sci. Rep., 6:24402). The lack of this quality control in vivo likely leads to expression of a majority of misfolded or inappropriate antigens, which prevent an optimal response. Also, delivering this antigen in a prime-boost regimen increase its potency.

Comparison of internal proteins previously selected for viral vectored vaccines revealed the benefit of delivery of NP by mRNA-LNP over M1. The level of protection conferred by NP was significantly higher than that seen through delivery of M1, and a comparison with previous data showed the stimulation of CD8+ T-cells was much greater after exposure to NP. Antibody responses to these antigens were significantly different, with very potent antibody responses observed against NP with little to no M1 response detected. This corroborates previous studies that found a low seroprevalence of M1-specific responses in the general population which suggests that M1 is a poor B-cell target (Cretescu L et al., 1978, Infect. Immun., 22:322-327). Functionality of NP-specific antibodies has been debated in the field, but potentially the combination of these responses with a potent T-cell response has led to effective protection from influenza virus challenge in a murine model.

In summary, modification of antigens has been shown to change immunogenicity and reactogenicity of universal influenza virus vaccine targets utilizing the nucleosidemodified mRNA-LNP vaccine platform. The dose of vaccination used in this study lead to high amounts of antigen expressed for each individual construct, which overwhelms some of the subtle effects mutation have had on immunogenicity if lower doses were utilized. Some of the findings in this study are broadly apply to other vaccine platforms and viral antigens. Structure-guided approaches to rational vaccine design tend to focus on stabilization of antigens or presentation of specific epitopes (Graham B S et al., 2019, Annu. Rev. Med., 70:91-104). Combining these efforts with modification of functional domains leads to improved antigen characteristics, which benefit general vaccine development.

Overall, the present studies demonstrated that protein modifications, such as mutating functional sites, changing secretion potential, and altering protein conformation, improved the safety and/or potency of mRNA-based influenza virus vaccines. Mice were vaccinated intradermally with wild type or mutant constructs of influenza virus HA, NA, M2, NP, or M1. Membrane-bound HA constructs elicited more potent and protective antibody responses than secreted forms. Altering the catalytic site of NA to reduce enzymatic activity, decreased reactogenicity while protective immunogenicity was maintained. Disruption of M2 ion channel activity improved immunogenicity and protective efficacy. A comparison of internal proteins NP and M1 revealed the superiority of NP in conferring protection from influenza virus challenge. These findings support the use of the nucleoside-modified mRNA platform for guided antigen design for influenza virus with extension to other pathogens.

Example 4: Sequence Listings

```
HA Sequences
1918 H1N1 - HA antigen Amino Acid sequence
                                                              (SEQ ID NO: 1)
MEARLLVLLC AFAATNADTI CIGYHANNST DTVDTVLEKN VTVTHSVNLL            050

EDSHNGKLCK LKGIAPLQLG KCNIAGWLLG NPECDLLLTA SSWSYIVETS            100

NSENGTCYPG DFIDYEELRE QLSSVSSFEK FEIFPKTSSW PNHETTKGVT            150

AACSYAGASS FYRNLLWLTK KGSSYPKLSK SYVNNKGKEV LVLWGVHHPP            200

TGTDQQSLYQ NADAYVSVGS SKYNRRFTPE IAARPKVRDQ AGRMNYYWTL            250

LEPGDTITFE ATGNLIAPWY AFALNRGSGS GIITSDAPVH DCNTKCQTPH            300

GAINSSLPFQ NIHPVTIGEC PKYVRSTKLR MATGLRNIPS IQSRGLFGAI            350

AGFIEGGWTG MIDGWYGYHH QNEQGSGYAA DQKSTQNAID GITNKVNSVI            400

EKMNTQFTAV GKEFNNLERR IENLNKKVDD GFLDIWTYNA ELLVLLENER            450

TLDFHDSNVR NLYEKVKSQL KNNAKEIGNG CFEFYHKCDD ACMESVRNGT            500

YDYPKYSEES KLNREEIDGV KLESMGVYQI LAIYSTVASS LVLLVSLGAI            550

SFWMCSNGSL QCRICI

1918 H1N1 - Optimized DNA sequence encoding the
nucleic acid sequence encoding HA antigen
                                                              (SEQ ID NO: 2)
ATGGAGGCCCGCCTGCTGGTGCTGCTGTGCGCCTTCGCCGCCACCAACGCCGACACCATCTGCATCGGCTA

CCACGCCAACAACTCCACCGACACCGTGGACACCGTGCTGGAGAAGAACGTGACCGTGACCCACTCCGTGA

ACCTGCTGGAGGACTCCCACAACGGCAAGCTGTGCAAGCTGAAGGGCATCGCCCCCCTGCAGCTGGGCAAG

TGCAACATCGCCGGCTGGCTGCTGGGCAACCCCGAGTGCGACCTGCTGCTGACCGCCTCCTCCTGGTCCTA

CATCGTGGAGACCTCCAACTCCGAGAACGGCACCTGCTACCCCGGCGACTTCATCGACTACGAGGAGCTGC

GCGAGCAGCTGTCCTCCGTGTCCTCCTTCGAGAAGTTCGAGATCTTCCCCAAGACCTCCTCCTGGCCCAAC

CACGAGACCACCAAGGGCGTGACCGCCGCCTGCTCCTACGCCGGCGCCTCCTCCTTCTACCGCAACCTGCT

GTGGCTGACCAAGAAGGGCTCCTCCTACCCCAAGCTGTCCAAGTCCTACGTGAACAACAAGGGCAAGGAGG

TGCTGGTGCTGTGGGGCGTGCACCACCCCCCCACCGGCACCGACCAGCAGTCCCTGTACCAGAACGCCGAC

GCCTACGTGTCCGTGGGCTCCTCCAAGTACAACCGCCGCTTCACCCCCGAGATCGCCGCCCGCCCCAAGGT

GCGCGACCAGGCCGGCCGCATGAACTACTACTGGACCCTGCTGGAGCCCGGCGACACCATCACCTTCGAGG

CCACCGGCAACCTGATCGCCCCCTGGTACGCCTTCGCCCTGAACCGCGGCTCCGGCTCCGGCATCATCACC

TCCGACGCCCCCGTGCACGACTGCAACACCAAGTGCCAGACCCCCCACGGCGCCATCAACTCCTCCCTGCC

CTTCCAGAACATCCACCCCGTGACCATCGGCGAGTGCCCCAAGTACGTGCGCTCCACCAAGCTGCGCATGG

CCACCGGCCTGCGCAACATCCCCTCCATCCAGTCCCGCGGCCTGTTCGGCGCCATCGCCGGCTTCATCGAG
```

-continued

GGCGGCTGGACCGGCATGATCGACGGCTGGTACGGCTACCACCACCAGAACGAGCAGGGCTCCGGCTACGC

CGCCGACCAGAAGTCCACCCAGAACGCCATCGACGGCATCACCAACAAGGTGAACTCCGTGATCGAGAAGA

TGAACACCCAGTTCACCGCCGTGGGCAAGGAGTTCAACAACCTGGAGCGCCGCATCGAGAACCTGAACAAG

AAGGTGGACGACGGCTTCCTGGACATCTGGACCTACAACGCCGAGCTGCTGGTGCTGCTGGAGAACGAGCG

CACCCTGGACTTCCACGACTCCAACGTGCGCAACCTGTACGAGAAGGTGAAGTCCCAGCTGAAGAACAACG

CCAAGGAGATCGGCAACGGCTGCTTCGAGTTCTACCACAAGTGCGACGACGCCTGCATGGAGTCCGTGCGC

AACGGCACCTACGACTACCCCAAGTACTCCGAGGAGTCCAAGCTGAACCGCGAGGAGATCGACGGCGTGAA

GCTGGAGTCCATGGGCGTGTACCAGATCCTGGCCATCTACTCCACCGTGGCCTCCTCCCTGGTGCTGCTGG

TGTCCCTGGGCGCCATCTCCTTCTGGATGTGCTCCAACGGCTCCCTGCAGTGCCGCATCTGCATC

1957 H2N2 - HA antigen Amino Acid sequence (SEQ ID NO: 3)

MAITYLILLF TAVRGDQICI GYHANNSTEK VDTILERNVT VTHAKDILEK 050

THNGKLCKLN GIPPLELGDC SIAGWLLGNP ECDRFLRVPE WSYIMEKENP 100

RYSLCYPGSF NDYEELKHLL SSVKHFEKVK ILPKDGWTQH TTTGGSMACA 150

VSGKPSFFRN MVWLTEKGQN YPVAKGSYNN TSGEQMLIIW GVHHPNDEAE 200

QRALYQKVGT YVSASTSTLN KRSTPEIAAR PKVNGLGSRM EFSWTLLDMW 250

DTINFESTGN LVAPEYGFKI SKRGSSGIMK TEGTLENCET KCQTPLGAIN 300

TTLPFHNVHP LTIGECPKYV KSEKLVLATG LRNIPQIESR GLFGAIAGFI 350

EGGWQGMVDG WYGYHHSNDQ GSGYAADKES TQKAFDGITN KVNSVIEKMN 400

TQFEAVGKEF SNLEKRLENL NKKMEDGFLD VWTYNAELLV LMENERTLDF 450

HDSNVKNLYD KVRMQLRDNV KELGNGCFEF YHKCDNECMD SVKNGTYDYP 500

KYEEESKLNR NEIKGVKLSS MGVYQILAIY ATVAGSLSLA IMMAGISFWM 550

CSNGSLQCRI CI

1957 H2N2 - Optimized DNA sequence encoding the nucleic acid sequence encoding HA antigen (SEQ ID NO: 4)

ATGGCCATCACCTACCTGATCCTGCTGTTCACCGCCGTGCGCGGCGACCAGATCTGCATCGGCTACCACGC

CAACAACTCCACCGAGAAGGTGGACACCATCCTGGAGCGCAACGTGACCGTGACCCACGCCAAGGACATCC

TGGAGAAGACCCACAACGGCAAGCTGTGCAAGCTGAACGGCATCCCCCCCCTGGAGCTGGGCGACTGCTCC

ATCGCCGGCTGGCTGCTGGGCAACCCCGAGTGCGACCGCTTCCTGCGCGTGCCCGAGTGGTCCTACATCAT

GGAGAAGGAGAACCCCCGCTACTCCCTGTGCTACCCCGGCTCCTTCAACGACTACGAGGAGCTGAAGCACC

TGCTGTCCTCCGTGAAGCACTTCGAGAAGGTGAAGATCCTGCCCAAGGACGGCTGGACCCAGCACACCACC

ACCGGCGGCTCCATGGCCTGCGCCGTGTCCGGCAAGCCCTCCTTCTTCCGCAACATGGTGTGGCTGACCGA

GAAGGGCCAGAACTACCCCGTGGCCAAGGGCTCCTACAACAACACCTCCGGCGAGCAGATGCTGATCATCT

GGGGCGTGCACCACCCCAACGACGAGGCCGAGCAGCGCGCCCTGTACCAGAAGGTGGGCACCTACGTGTCC

GCCTCCACCTCCACCCTGAACAAGCGCTCCACCCCCGAGATCGCCGCCCGCCCCAAGGTGAACGGCCTGGG

CTCCCGCATGGAGTTCTCCTGGACCCTGCTGGACATGTGGGACACCATCAACTTCGAGTCCACCGGCAACC

TGGTGGCCCCCGAGTACGGCTTCAAGATCTCCAAGCGCGGCTCCTCCGGCATCATGAAGACCGAGGGCACC

CTGGAGAACTGCGAGACCAAGTGCCAGACCCCCCTGGGCGCCATCAACACCACCCTGCCCTTCCACAACGT

GCACCCCCTGACCATCGGCGAGTGCCCCAAGTACGTGAAGTCCGAGAAGCTGGTGCTGGCCACCGGCCTGC

GCAACATCCCCCAGATCGAGTCCCGCGGCCTGTTCGGCGCCATCGCCGGCTTCATCGAGGGCGGCTGGCAG

GGCATGGTGGACGGCTGGTACGGCTACCACCACTCCAACGACCAGGGCTCCGGCTACGCCGCCGACAAGGA

GTCCACCCAGAAGGCCTTCGACGGCATCACCAACAAGGTGAACTCCGTGATCGAGAAGATGAACACCCAGT

-continued

TCGAGGCCGTGGGCAAGGAGTTCTCCAACCTGGAGAAGCGCCTGGAGAACCTGAACAAGAAGATGGAGGAC

GGCTTCCTGGACGTGTGGACCTACAACGCCGAGCTGCTGGTGCTGATGGAGAACGAGCGCACCCTGGACTT

CCACGACTCCAACGTGAAGAACCTGTACGACAAGGTGCGCATGCAGCTGCGCGACAACGTGAAGGAGCTGG

GCAACGGCTGCTTCGAGTTCTACCACAAGTGCGACAACGAGTGCATGGACTCCGTGAAGAACGGCACCTAC

GACTACCCCAAGTACGAGGAGGAGTCCAAGCTGAACCGCAACGAGATCAAGGGCGTGAAGCTGTCCTCCAT

GGGCGTGTACCAGATCCTGGCCATCTACGCCACCGTGGCCGGCTCCCTGTCCCTGGCCATCATGATGGCCG

GCATCTCCTTCTGGATGTGCTCCAACGGCTCCCTGCAGTGCCGCATCTGCATC

1968 H3N2 - HA antigen Amino Acid sequence (SEQ ID NO: 5)

MKTIIALSYI FCLALGQDLP GNDNSTATLC LGHHAVPNGT LVKTITDDQI 050

EVTNATELVQ SSSTGKICNN PHRILDGIDC TLIDALLGDP HCDVFQNETW 100

DLFVERSKAF SNCYPYDVPD YASLRSLVAS SGTLEFITEG FTWTGVTQNG 150

GSNACKRGPG SGFFSRLNWL TKSGSTYPVL NVTMPNNDNF DKLYIWGVHH 200

PSTNQEQTSL YVQASGRVTV STRRSQQTII PNIGSRPWVR GLSSRISIYW 250

TIVKPGDVLV INSNGNLIAP RGYFKMRTGK SSIMRSDAPI DTCISECITP 300

NGSIPNDKPF QNVNKITYGA CPKYVKQNTL KLATGMRNVP EKQTRGLFGA 350

IAGFIENGWE GMIDGWYGFR HQNSEGTGQA ADLKSTQAAI DQINGKLNRV 400

IEKTNEKFHQ IEKEFSEVEG RIQDLEKYVE DTKIDLWSYN AELLVALENQ 450

HTIDLTDSEM NKLFEKTRRQ LRENAEDMGN GCFKIYHKCD NACIESIRNG 500

TYDHDVYRDE ALNNRFQIKG VELKSGYKDW ILWISFAISC FLLCVVLLGF 550

IMWACQRGNI RCNICI

1968 H3N2 - Optimized DNA sequence encoding the
nucleic acid sequence encoding HA antigen (SEQ ID NO: 6)

ATGAAGACCATCATCGCCCTGTCCTACATCTTCTGCCTGGCCCTGGGCCAGGACCTGCCCGGCAACGACAA

CTCCACCGCCACCCTGTGCCTGGGCCACCACGCCGTGCCCAACGGCACCCTGGTGAAGACCATCACCGACG

ACCAGATCGAGGTGACCAACGCCACCGAGCTGGTGCAGTCCTCCTCCACCGGCAAGATCTGCAACAACCCC

CACCGCATCCTGGACGGCATCGACTGCACCCTGATCGACGCCCTGCTGGGCGACCCCCACTGCGACGTGTT

CCAGAACGAGACCTGGGACCTGTTCGTGGAGCGCTCCAAGGCCTTCTCCAACTGCTACCCCTACGACGTGC

CCGACTACGCCTCCCTGCGCTCCCTGGTGGCCTCCTCCGGCACCCTGGAGTTCATCACCGAGGGCTTCACC

TGGACCGGCGTGACCCAGAACGGCGGCTCCAACGCCTGCAAGCGCGGCCCCGGCTCCGGCTTCTTCTCCCG

CCTGAACTGGCTGACCAAGTCCGGCTCCACCTACCCCGTGCTGAACGTGACCATGCCCAACAACGACAACT

TCGACAAGCTGTACATCTGGGGCGTGCACCACCCCTCCACCAACCAGGAGCAGACCTCCCTGTACGTGCAG

GCCTCCGGCCGCGTGACCGTGTCCACCCGCCGCTCCCAGCAGACCATCATCCCCAACATCGGCTCCCGCCC

CTGGGTGCGCGGCCTGTCCTCCCGCATCTCCATCTACTGGACCATCGTGAAGCCCGGCGACGTGCTGGTGA

TCAACTCCAACGGCAACCTGATCGCCCCCCGCGGCTACTTCAAGATGCGCACCGGCAAGTCCTCCATCATG

CGCTCCGACGCCCCCATCGACACCTGCATCTCCGAGTGCATCACCCCCAACGGCTCCATCCCCAACGACAA

GCCCTTCCAGAACGTGAACAAGATCACCTACGGCGCCTGCCCCAAGTACGTGAAGCAGAACACCCTGAAGC

TGGCCACCGGCATGCGCAACGTGCCCGAGAAGCAGACCCGCGGCCTGTTCGGCGCCATCGCCGGCTTCATC

GAGAACGGCTGGGAGGGCATGATCGACGGCTGGTACGGCTTCCGCCACCAGAACTCCGAGGGCACCGGCCA

GGCCGCCGACCTGAAGTCCACCCAGGCCGCCATCGACCAGATCAACGGCAAGCTGAACCGCGTGATCGAGA

AGACCAACGAGAAGTTCCACCAGATCGAGAAGGAGTTCTCCGAGGTGGAGGGCCGCATCCAGGACCTGGAG

AAGTACGTGGAGGACACCAAGATCGACCTGTGGTCCTACAACGCCGAGCTGCTGGTGGCCCTGGAGAACCA

-continued

GCACACCATCGACCTGACCGACTCCGAGATGAACAAGCTGTTCGAGAAGACCCGCCGCCAGCTGCGCGAGA

ACGCCGAGGACATGGGCAACGGCTGCTTCAAGATCTACCACAAGTGCGACAACGCCTGCATCGAGTCCATC

CGCAACGGCACCTACGACCACGACGTGTACCGCGACGAGGCCCTGAACAACCGCTTCCAGATCAAGGGCGT

GGAGCTGAAGTCCGGCTACAAGGACTGGATCCTGTGGATCTCCTTCGCCATCTCCTGCTTCCTGCTGTGCG

TGGTGCTGCTGGGCTTCATCATGTGGGCCTGCCAGCGCGGCAACATCCGCTGCAACATCTGCATC

1977 H1N1 - HA antigen Amino Acid sequence (SEQ ID NO: 7)

MKAKLLVLLC ALSATDADTI CIGYHANNST DTVDTVLEKN VTVTHSVNLL 050

EDSHNGKLCR LKGIAPLQLG KCNIAGWILG NPECESLFSK KSWSYIAETP 100

NSENGTCYPG YFADYEELRE QLSSVSSFER FEIFPKERSW PKHNVTRGVT 150

ASCSHKGKSS FYRNLLWLTE KNGSYPNLSK SYVNNKEKEV LVLWGVHHPS 200

NIEDQKTIYR KENAYVSVVS SNYNRRFTPE IAERPKVRGQ AGRINYYWTL 250

LEPGDTIIFE ANGNLIAPWH AFALNRGFGS GIITSNASMD ECDTKCQTPQ 300

GAINSSLPFQ NIHPVTIGEC PKYVRSTKLR MVTGLRNIPS IQSRGLFGAI 350

AGFIEGGWTG MIDGWYGYHH QNEQGSGYAA DQKSTQNAIN GITNKVNSVI 400

EKMNTQFTAV GKEFNKLEKR MENLNKKVDD GFLDIWTYNA ELLVLLENER 450

TLDFHDSNVK NLYEKVKSQL KNNAKEIGNG CFEFYHKCNN ECMESVKNGT 500

YDYPKYSEES KLNREKIDGV KLESMGVYQI LAIYSTVASS LVLLVSLGAI 550

SFWMCSNGSL QCRICI

1977 H1N1 - Optimized DNA sequence encoding the
nucleic acid sequence encoding HA antigen (SEQ ID NO: 8)

ATGAAGGCCAAGCTGCTGGTGCTGCTGTGCGCCCTGTCCGCCACCGACGCCGACACCATCTGCATCGGCTA

CCACGCCAACAACTCCACCGACACCGTGGACACCGTGCTGGAGAAGAACGTGACCGTGACCCACTCCGTGA

ACCTGCTGGAGGACTCCCACAACGGCAAGCTGTGCCGCCTGAAGGGCATCGCCCCCCTGCAGCTGGGCAAG

TGCAACATCGCCGGCTGGATCCTGGGCAACCCCGAGTGCGAGTCCCTGTTCTCCAAGAAGTCCTGGTCCTA

CATCGCCGAGACCCCCAACTCCGAGAACGGCACCTGCTACCCCGGCTACTTCGCCGACTACGAGGAGCTGC

GCGAGCAGCTGTCCTCCGTGTCCTCCTTCGAGCGCTTCGAGATCTTCCCCAAGGAGCGCTCCTGGCCCAAG

CACAACGTGACCCGCGGCGTGACCGCCTCCTGCTCCCACAAGGGCAAGTCCTCCTTCTACCGCAACCTGCT

GTGGCTGACCGAGAAGAACGGCTCCTACCCCAACCTGTCCAAGTCCTACGTGAACAACAAGGAGAAGGAGG

TGCTGGTGCTGTGGGGCGTGCACCACCCCTCCAACATCGAGGACCAGAAGACCATCTACCGCAAGGAGAAC

GCCTACGTGTCCGTGGTGTCCTCCAACTACAACCGCCGCTTCACCCCCGAGATCGCCGAGCGCCCCAAGGT

GCGCGGCCAGGCCGGCCGCATCAACTACTACTGGACCCTGCTGGAGCCCGGCGACACCATCATCTTCGAGG

CCAACGGCAACCTGATCGCCCCCTGGCACGCCTTCGCCCTGAACCGCGGCTTCGGCTCCGGCATCATCACC

TCCAACGCCTCCATGGACGAGTGCGACACCAAGTGCCAGACCCCCCAGGGCGCCATCAACTCCTCCCTGCC

CTTCCAGAACATCCACCCCGTGACCATCGGCGAGTGCCCCAAGTACGTGCGCTCCACCAAGCTGCGCATGG

TGACCGGCCTGCGCAACATCCCCTCCATCCAGTCCCGCGGCCTGTTCGGCGCCATCGCCGGCTTCATCGAG

GGCGGCTGGACCGGCATGATCGACGGCTGGTACGGCTACCACCACCAGAACGAGCAGGGCTCCGGCTACGC

CGCCGACCAGAAGTCCACCCAGAACGCCATCAACGGCATCACCAACAAGGTGAACTCCGTGATCGAGAAGA

TGAACACCCAGTTCACCGCCGTGGGCAAGGAGTTCAACAAGCTGGAGAAGCGCATGGAGAACCTGAACAAG

AAGGTGGACGACGGCTTCCTGGACATCTGGACCTACAACGCCGAGCTGCTGGTGCTGCTGGAGAACGAGCG

CACCCTGGACTTCCACGACTCCAACGTGAAGAACCTGTACGAGAAGGTGAAGTCCCAGCTGAAGAACAACG

CCAAGGAGATCGGCAACGGCTGCTTCGAGTTCTACCACAAGTGCAACAACGAGTGCATGGAGTCCGTGAAG

-continued

AACGGCACCTACGACTACCCCAAGTACTCCGAGGAGTCCAAGCTGAACCGCGAGAAGATCGACGGCGTGAA

GCTGGAGTCCATGGGCGTGTACCAGATCCTGGCCATCTACTCCACCGTGGCCTCCTCCCTGGTGCTGCTGG

TGTCCCTGGGCGCCATCTCCTTCTGGATGTGCTCCAACGGCTCCCTGCAGTGCCGCATCTGCATC

2007 H1N1 - HA antigen Amino Acid sequence (SEQ ID NO: 9)

MKVKLLVLLC TFTATYADTI CIGYHANNST DTVDTVLEKN VTVTHSVNLL 050

ENSHNGKLCL LKGIAPLQLG NCSVAGWILG NPECELLISK ESWSYIVEKP 100

NPENGTCYPG HFADYEELRE QLSSVSSFER FEIFPKESSW PNHTVTGVSA 150

SCSHNGESSF YRNLLWLTGK NGLYPNLSKS YANNKEKEVL VLWGVHHPPN 200

IGVQKALYHT ENAYVSVVSS HYSRKFTPEI AKRPKVRDQE GRINYYWTLL 250

EPGDTIIFEA NGNLIAPRYA FALSRGFGSG IINSNAPMDK CDAKCQTPQG 300

AINSSLPFQN VHPVTIGECP KYVRSAKLRM VTGLRNIPSI QSRGLFGAIA 350

GFIEGGWTGM VDGWYGYHHQ NEQGSGYAAD QKSTQNAING ITNKVNSVIE 400

KMNTQFTAVG KEFNKLERRM ENLNKKVDDG FIDIWTYNAE LLVLLENERT 450

LDFHDSNVKN LYEKVKSQLK NNAKEIGNGC FEFYHKCNDE CMESVKNGTY 500

DYPKYSEESK LNREKIDGVK LESMGVYQIL AIYSTVASSL VLLVSLGAIS 550

FWMCSNGSLQ CRICI

2007 H1N1 - Optimized DNA sequence encoding the nucleic acid sequence encoding HA antigen (SEQ ID NO: 10)

ATGAAGGTGAAGCTGCTGGTGCTGCTGTGCACCTTCACCGCCACCTACGCCGACACCATCTGCATCGGCTA

CCACGCCAACAACTCCACCGACACCGTGGACACCGTGCTGGAGAAGAACGTGACCGTGACCCACTCCGTGA

ACCTGCTGGAGAACTCCCACAACGGCAAGCTGTGCCTGCTGAAGGGCATCGCCCCCCTGCAGCTGGGCAAC

TGCTCCGTGGCCGGCTGGATCCTGGGCAACCCCGAGTGCGAGCTGCTGATCTCCAAGGAGTCCTGGTCCTA

CATCGTGGAGAAGCCCAACCCCGAGAACGGCACCTGCTACCCCGGCCACTTCGCCGACTACGAGGAGCTGC

GCGAGCAGCTGTCCTCCGTGTCCTCCTTCGAGCGCTTCGAGATCTTCCCCAAGGAGTCCTCCTGGCCCAAC

CACACCGTGACCGGCGTGTCCGCCTCCTGCTCCCACAACGGCGAGTCCTCCTTCTACCGCAACCTGCTGTG

GCTGACCGGCAAGAACGGCCTGTACCCCAACCTGTCCAAGTCCTACGCCAACAACAAGGAGAAGGAGGTGC

TGGTGCTGTGGGGCGTGCACCACCCCCCCAACATCGGCGTGCAGAAGGCCCTGTACCACACCGAGAACGCC

TACGTGTCCGTGGTGTCCTCCCACTACTCCCGCAAGTTCACCCCCGAGATCGCCAAGCGCCCCAAGGTGCG

CGACCAGGAGGGCCGCATCAACTACTACTGGACCCTGCTGGAGCCCGGCGACACCATCATCTTCGAGGCCA

ACGGCAACCTGATCGCCCCCCGCTACGCCTTCGCCCTGTCCCGCGGCTTCGGCTCCGGCATCATCAACTCC

AACGCCCCCATGGACAAGTGCGACGCCAAGTGCCAGACCCCCCAGGGCGCCATCAACTCCTCCCTGCCCTT

CCAGAACGTGCACCCCGTGACCATCGGCGAGTGCCCCAAGTACGTGCGCTCCGCCAAGCTGCGCATGGTGA

CCGGCCTGCGCAACATCCCCTCCATCCAGTCCCGCGGCCTGTTCGGCGCCATCGCCGGCTTCATCGAGGGC

GGCTGGACCGGCATGGTGGACGGCTGGTACGGCTACCACCACCAGAACGAGCAGGGCTCCGGCTACGCCGC

CGACCAGAAGTCCACCCAGAACGCCATCAACGGCATCACCAACAAGGTGAACTCCGTGATCGAGAAGATGA

ACACCCAGTTCACCGCCGTGGGCAAGGAGTTCAACAAGCTGGAGCGCCGCATGGAGAACCTGAACAAGAAG

GTGGACGACGGCTTCATCGACATCTGGACCTACAACGCCGAGCTGCTGGTGCTGCTGGAGAACGAGCGCAC

CCTGGACTTCCACGACTCCAACGTGAAGAACCTGTACGAGAAGGTGAAGTCCCAGCTGAAGAACAACGCCA

AGGAGATCGGCAACGGCTGCTTCGAGTTCTACCACAAGTGCAACGACGAGTGCATGGAGTCCGTGAAGAAC

GGCACCTACGACTACCCCAAGTACTCCGAGGAGTCCAAGCTGAACCGCGAGAAGATCGACGGCGTGAAGCT

-continued

GGAGTCCATGGGCGTGTACCAGATCCTGGCCATCTACTCCACCGTGGCCTCCTCCCTGGTGCTGCTGGTGT

CCCTGGGCGCCATCTCCTTCTGGATGTGCTCCAACGGCTCCCTGCAGTGCCGCATCTGCATC

2009 H1N1 - HA antigen Amino Acid sequence (SEQ ID NO: 11)

MKAILVVLLY TFATANADTL CIGYHANNST DTVDTVLEKN VTVTHSVNLL 050

EDKHNGKLCK LRGVAPLHLG KCNIAGWILG NPECESLSTA SSWSYIVETP 100

SSDNGTCYPG DFIDYEELRE QLSSVSSFER FEIFPKTSSW PNHDSNKGVT 150

AACPHAGAKS FYKNLIWLVK KGNSYPKLSK SYINDKGKEV LVLWGIHHPS 200

TSADQQSLYQ NADTYVFVGS SRYSKKFKPE IAIRPKVRDQ EGRMNYYWTL 250

VEPGDKITFE ATGNLVVPRY AFAMERNAGS GIIISDTPVH DCNTTCQTPK 300

GAINTSLPFQ NIHPITIGKC PKYVKSTKLR LATGLRNIPS IQSRGLFGAI 350

AGFIEGGWTG MVDGWYGYHH QNEQGSGYAA DLKSTQNAID EITNKVNSVI 400

EKMNTQFTAV GKEFNHLEKR IENLNKKVDD GFLDIWTYNA ELLVLLENER 450

TLDYHDSNVK NLYEKVRSQL KNNAKEIGNG CFEFYHKCDN TCMESVKNGT 500

YDYPKYSEEA KLNREEIDGV KLESTRIYQI LAIYSTVASS LVLVVSLGAI 550

SFWMCSNGSL QCRICI

2009 H1N1 - Optimized DNA sequence encoding the nucleic acid sequence encoding HA antigen (SEQ ID NO: 12)

ATGAAGGCCATCCTGGTGGTGCTGCTGTACACCTTCGCCACCGCCAACGCCGACACCCTGTGCATCGGCTA

CCACGCCAACAACTCCACCGACACCGTGGACACCGTGCTGGAGAAGAACGTGACCGTGACCCACTCCGTGA

ACCTGCTGGAGGACAAGCACAACGGCAAGCTGTGCAAGCTGCGCGGCGTGGCCCCCCTGCACCTGGGCAAG

TGCAACATCGCCGGCTGGATCCTGGGCAACCCCGAGTGCGAGTCCCTGTCCACCGCCTCCTCCTGGTCCTA

CATCGTGGAGACCCCCTCCTCCGACAACGGCACCTGCTACCCCGGCGACTTCATCGACTACGAGGAGCTGC

GCGAGCAGCTGTCCTCCGTGTCCTCCTTCGAGCGCTTCGAGATCTTCCCCAAGACCTCCTCCTGGCCCAAC

CACGACTCCAACAAGGGCGTGACCGCCGCCTGCCCCCACGCCGGCGCCAAGTCCTTCTACAAGAACCTGAT

CTGGCTGGTGAAGAAGGGCAACTCCTACCCCAAGCTGTCCAAGTCCTACATCAACGACAAGGGCAAGGAGG

TGCTGGTGCTGTGGGGCATCCACCACCCCTCCACCTCCGCCGACCAGCAGTCCCTGTACCAGAACGCCGAC

ACCTACGTGTTCGTGGGCTCCTCCCGCTACTCCAAGAAGTTCAAGCCCGAGATCGCCATCCGCCCCAAGGT

GCGCGACCAGGAGGGCCGCATGAACTACTACTGGACCCTGGTGGAGCCCGGCGACAAGATCACCTTCGAGG

CCACCGGCAACCTGGTGGTGCCCCGCTACGCCTTCGCCATGGAGCGCAACGCCGGCTCCGGCATCATCATC

TCCGACACCCCCGTGCACGACTGCAACACCACCTGCCAGACCCCCAAGGGCGCCATCAACACCTCCCTGCC

CTTCCAGAACATCCACCCCATCACCATCGGCAAGTGCCCCAAGTACGTGAAGTCCACCAAGCTGCGCCTGG

CCACCGGCCTGCGCAACATCCCCTCCATCCAGTCCCGCGGCCTGTTCGGCGCCATCGCCGGCTTCATCGAG

GGCGGCTGGACCGGCATGGTGGACGGCTGGTACGGCTACCACCACCAGAACGAGCAGGGCTCCGGCTACGC

CGCCGACCTGAAGTCCACCCAGAACGCCATCGACGAGATCACCAACAAGGTGAACTCCGTGATCGAGAAGA

TGAACACCCAGTTCACCGCCGTGGGCAAGGAGTTCAACCACCTGGAGAAGCGCATCGAGAACCTGAACAAG

AAGGTGGACGACGGCTTCCTGGACATCTGGACCTACAACGCCGAGCTGCTGGTGCTGCTGGAGAACGAGCG

CACCCTGGACTACCACGACTCCAACGTGAAGAACCTGTACGAGAAGGTGCGCTCCCAGCTGAAGAACAACG

CCAAGGAGATCGGCAACGGCTGCTTCGAGTTCTACCACAAGTGCGACAACACCTGCATGGAGTCCGTGAAG

AACGGCACCTACGACTACCCCAAGTACTCCGAGGAGGCCAAGCTGAACCGCGAGGAGATCGACGGCGTGAA

GCTGGAGTCCACCCGCATCTACCAGATCCTGGCCATCTACTCCACCGTGGCCTCCTCCCTGGTGCTGGTGG

TGTCCCTGGGCGCCATCTCCTTCTGGATGTGCTCCAACGGCTCCCTGCAGTGCCGCATCTGCATC

-continued

2015 H1N1 - HA antigen Amino Acid sequence (SEQ ID NO: 13)

MAISGVPVLGFFIIAVLMSAQESWADTLCIGYHANNSTDTVDTVLEKNVTVTHSVNLLEDKHNGKLCKLRG

VAPLHLGKCNIAGWILGNPECESLSTASSWSYIVETSNSDNGTCYPGDFINYEELREQLSSVSSFERFEIF

PKTSSWPNHDSNKGVTAACPHAGAKSFYKNLIWLVKKGNSYPKLNQSYINDKGKEVLVLWGIHHPSTTADQ

QSLYQNADAYVFVGTSRYSKKFKPEIATRPKVRDQEGRMNYYWTLVEPGDKITFEATGNLVVPRYAFTMER

NAGSGIIISDTPVHDCNTTCQTPEGAINTSLPFQNIHPITIGKCPKYVKSTKLRLATGLRNVPSIQSRGLF

GAIAGFIEGGWTGMVDGWYGYHHQNEQGSGYAADLKSTQNAIDKITNKVNSVIEKMNTQFTAVGKEFNHLE

KRIENLNKKVDDGFLDIWTYNAELLVLLENERTLDYHDSNVKNLYEKVRNQLKNNAKEIGNGCFEFYHKCD

NTCMESVKNGTYDYPKYSEEAKLNREKIDGVKLESTRIYQILAIYSTVASSLVLVVSLGAISFWMCSNGSL

QCRICI

2015 H1N1 - Optimized DNA sequence encoding the nucleic acid sequence encoding HA antigen (SEQ ID NO: 14)

ATGGCCATCTCCGGCGTGCCCGTGCTGGGCTTCTTCATCATCGCCGTGCTGATGTCCGCCCAGGAGTCCTG

GGCCGACACCCTGTGCATCGGCTACCACGCCAACAACTCCACCGACACCGTGGACACCGTGCTGGAGAAGA

ACGTGACCGTGACCCACTCCGTGAACCTGCTGGAGGACAAGCACAACGGCAAGCTGTGCAAGCTGCGCGGC

GTGGCCCCCCTGCACCTGGGCAAGTGCAACATCGCCGGCTGGATCCTGGGCAACCCCGAGTGCGAGTCCCT

GTCCACCGCCTCCTCCTGGTCCTACATCGTGGAGACCTCCAACTCCGACAACGGCACCTGCTACCCCGGCG

ACTTCATCAACTACGAGGAGCTGCGCGAGCAGCTGTCCTCCGTGTCCTCCTTCGAGCGgTTCGAGATCTTC

CCCAAGACCTCCTCCTGGCCCAACCACGACTCCAACAAGGGCGTGACCGCCGCCTGCCCCCACGCCGGCGC

CAAGTCCTTCTACAAGAACCTGATCTGGCTGGTGAAGAAGGGCAACTCCTACCCCAAGCTGAACCAGTCCT

ACATCAACGACAAGGGCAAGGAGGTGCTGGTGCTGTGGGGCATCCACCACCCCTCCACCACCGCCGACCAG

CAGTCCCTGTACCAGAACGCCGACGCCTACGTGTTCGTGGGCACCTCCCGCTACTCCAAGAAGTTCAAGCC

CGAGATCGCCACCCGCCCCAAGGTGCGCGACCAGGAGGGCCGCATGAACTACTACTGGACCCTGGTGGAGC

CCGGCGACAAGATCACCTTCGAGGCCACCGGCAACCTGGTGGTGCCCCGCTACGCCTTCACCATGGAGCGC

AACGCCGGCTCCGGCATCATCATCTCCGACACCCCCGTGCACGACTGCAACACCACCTGCCAGACCCCCGA

GGGCGCCATCAACACCTCCCTGCCCTTCCAGAACATCCACCCCATCACCATCGGCAAGTGCCCCAAGTACG

TGAAGTCCACCAAGCTGCGCCTGGCCACCGGCCTGCGCAACGTGCCCTCCATCCAGTCCCGCGGCCTGTTC

GGCGCCATCGCCGGCTTCATCGAGGGCGGCTGGACCGGCATGGTGGACGGCTGGTACGGCTACCACCACCA

GAACGAGCAGGGCTCCGGCTACGCCGCCGACCTGAAGTCCACCCAGAACGCCATCGACAAGATCACCAACA

AGGTGAACTCCGTGATCGAGAAGATGAACACCCAGTTCACCGCCGTGGGCAAGGAGTTCAACCACCTGGAG

AAGCGCATCGAGAACCTGAACAAGAAGGTGGACGACGGCTTCCTGGACATCTGGACCTACAACGCCGAGCT

GCTGGTGCTGCTGGAGAACGAGCGCACCCTGGACTACCACGACTCCAACGTGAAGAACCTGTACGAGAAGG

TGCGCAACCAGCTGAAGAACAACGCCAAGGAGATCGGCAACGGCTGCTTCGAGTTCTACCACAAGTGCGAC

AACACCTGCATGGAGTCCGTGAAGAACGGCACCTACGACTACCCCAAGTACTCCGAGGAGGCCAAGCTGAA

CCGCGAGAAGATCGACGGCGTGAAGCTGGAGTCCACCCGCATCTACCAGATCCTGGCCATCTACTCCACCG

TGGCCTCCTCCCTGGTGCTGGTGGTGTCCCTGGGCGCCATCTCCTTCTGGATGTGCTCCAACGGCTCCCTG

CAGTGCCGCATCTGCATC

2017 H3N2 - HA antigen Amino Acid sequence (SEQ ID NO: 15)

MKTIIALSCI LCLVFAQKIP GNDNSTATLC LGHHAVPNGT IVKTITNDRI 050

EVTNATELVQ NSSIGEICDS PHQILDGENC TLIDALLGDP QCDGFQNKKW 100

DLFVERNKAY SNCYPYDVPD YASLRSLVAS SGTLEFNNES FNWAGVTQNG 150

-continued

TSSSCIRGSK SSFFSRLNWL THLNSKYPAL NVTMPNNEQF DKLYIWGVHH 200

PGTDKNQISL YAQSSGRITV STKRSQQAVI PNIGSRPRIR DIPSRISIYW 250

TIVKPGDILL IXSTGNLIAP RGYFKIRSGK SSIMRSDAPI GKCKSECITP 300

NGSIPNDKPF QNVNRITYGA CPRYVKQSTL KLATGMRNVP ERQTRGIFGA 350

IAGFIENGWE GMVDGWYGFR HQNSEGRGQA ADLKSTQAAI DQINGKLNRL 400

IGKTNEKFHQ IEKEFSEVEG RIQDLEKYVE DTKIDLWSYN AELLVALENQ 450

HTIDLTDSEM NKLFEKTKKQ LRENAEDMGN GCFKIYHKCD NACMGSIRNG 500

TYDHNVYRDE ALNNRFQIKG VELKSGYKDW ILWISFAISC FLLCVALLGF 550

IMWACQKGNI RCNICI

2017 H3N2 - Optimized DNA sequence encoding the
nucleic acid sequence encoding HA antigen (SEQ ID NO: 16)

ATGAAGACCATCATCGCCCTGTCCTGCATCCTGTGCCTGGTGTTCGCCCAGAAGATCCCCGGCAACGACAA

CTCCACCGCCACCCTGTGCCTGGGCCACCACGCCGTGCCCAACGGCACCATCGTGAAGACCATCACCAACG

ACCGCATCGAGGTGACCAACGCCACCGAGCTGGTGCAGAACTCCTCCATCGGCGAGATCTGCGACTCCCCC

CACCAGATCCTGGACGGCGAGAACTGCACCCTGATCGACGCCCTGCTGGGCGACCCCCAGTGCGACGGCTT

CCAGAACAAGAAGTGGGACCTGTTCGTGGAGCGCAACAAGGCCTACTCCAACTGCTACCCCTACGACGTGC

CCGACTACGCCTCCCTGCGCTCCCTGGTGGCCTCCTCCGGCACCCTGGAGTTCAACAACGAGTCCTTCAAC

TGGGCCGGCGTGACCCAGAACGGCACCTCCTCCTCCTGCATCCGCGGCTCCAAGTCCTCCTTCTTCTCCCG

CCTGAACTGGCTGACCCACCTGAACTCCAAGTACCCCGCCCTGAACGTGACCATGCCCAACAACGAGCAGT

TCGACAAGCTGTACATCTGGGGCGTGCACCACCCCGGCACCGACAAGAACCAGATCTCCCTGTACGCCCAG

TCCTCCGGCCGCATCACCGTGTCCACCAAGCGCTCCCAGCAGGCCGTGATCCCCAACATCGGCTCCCGCCC

CCGCATCCGCGACATCCCCTCCCGCATCTCCATCTACTGGACCATCGTGAAGCCCGGCGACATCCTGCTGA

TCNNNTCCACCGGCAACCTGATCGCCCCCCGCGGCTACTTCAAGATCCGCTCCGGCAAGTCCTCCATCATG

CGCTCCGACGCCCCCATCGGCAAGTGCAAGTCCGAGTGCATCACCCCCAACGGCTCCATCCCCAACGACAA

GCCCTTCCAGAACGTGAACCGCATCACCTACGGCGCCTGCCCCCGCTACGTGAAGCAGTCCACCCTGAAGC

TGGCCACCGGCATGCGCAACGTGCCCGAGCGCCAGACCCGCGGCATCTTCGGCGCCATCGCCGGCTTCATC

GAGAACGGCTGGGAGGGCATGGTGGACGGCTGGTACGGCTTCCGCCACCAGAACTCCGAGGGCCGCGGCCA

GGCCGCCGACCTGAAGTCCACCCAGGCCGCCATCGACCAGATCAACGGCAAGCTGAACCGCCTGATCGGCA

AGACCAACGAGAAGTTCCACCAGATCGAGAAGGAGTTCTCCGAGGTGGAGGGCCGCATCCAGGACCTGGAG

AAGTACGTGGAGGACACCAAGATCGACCTGTGGTCCTACAACGCCGAGCTGCTGGTGGCCCTGGAGAACCA

GCACACCATCGACCTGACCGACTCCGAGATGAACAAGCTGTTCGAGAAGACCAAGAAGCAGCTGCGCGAGA

ACGCCGAGGACATGGGCAACGGCTGCTTCAAGATCTACCACAAGTGCGACAACGCCTGCATGGGCTCCATC

CGCAACGGCACCTACGACCACAACGTGTACCGCGACGAGGCCCTGAACAACCGCTTCCAGATCAAGGGCGT

GGAGCTGAAGTCCGGCTACAAGGACTGGATCCTGTGGATCTCCTTCGCCATCTCCTGCTTCCTGCTGTGCG

TGGCCCTGCTGGGCTTCATCATGTGGGCCTGCCAGAAGGGCAACATCCGCTGCAACATCTGCATC

2017 Influenza B (Victoria lineage) - HA antigen
Amino Acid sequence (SEQ ID NO: 17)

MKAIIVLLMV VTSSADRICT GITSSNSPHV VKTATQGEVN VTGVIPLTTT 050

PTKSHFANLK GTETRGKLCP KCLNCTDLDV ALGRPKCTGK IPSARVSILH 100

EVRPVTSGCF PIMHDRTKIR QLPNLLRGYE HVRLSTHNVI NAEGAPGGPY 150

KIGTSGSCPN ITNGNGFFAT MAWAVPDKNK TATNPLTIEV PYVCTEGEDQ 200

-continued

ITVWGFHSDX ETQMAKLYGD SKPQKFTSSA NGVTTHYVSQ IGGFPNQTED 250

GGLPQSGRIV VDYMVQKSGK TGTITYQRGI LLPQKVWCAS GRSKVIKGSL 300

PLIGEADCLH EKYGGLNKSK PYYTGEHAKA IGNCPIWVKT PLKLANGTKY 350

RPPAKLLKER GFFGAIAGFL EGGWEGMIAG WHGYTSHGAH GVAVAADLKS 400

TQEAINKITK NLNSLSELEV KNLQRLSGAM DELHNEILEL DEKVDDLRAD 450

TISSQIELAV LLSNEGIINS EDEHLLALER KLKKMLGPSA VEIGNGCFET 500

KHKCNQTCLD KIAAGTFDAG EFSLPTFDSL NITAASLNDD GLDNHTILLY 550

YSTAASSLAV TLMIAIFVVY MVSRDNVSCS ICL

2017 Influenza B (Victoria lineage) - Optimized
DNA sequence encoding the nucleic acid sequence
encoding HA antigen (SEQ ID NO: 18)

ATGAAGGCCATCATCGTGCTGCTGATGGTGGTGACCTCCTCCGCCGACCGCATCTGCACCGGCATCACCTC

CTCCAACTCCCCCCACGTGGTGAAGACCGCCACCCAGGGCGAGGTGAACGTGACCGGCGTGATCCCCCTGA

CCACCACCCCCACCAAGTCCCACTTCGCCAACCTGAAGGGCACCGAGACCCGCGGCAAGCTGTGCCCCAAG

TGCCTGAACTGCACCGACCTGGACGTGGCCCTGGGCCGCCCCAAGTGCACCGGCAAGATCCCCTCCGCCCG

CGTGTCCATCCTGCACGAGGTGCGCCCCGTGACCTCCGGCTGCTTCCCCATCATGCACGACCGCACCAAGA

TCCGCCAGCTGCCCAACCTGCTGCGCGGCTACGAGCACGTGCGCCTGTCCACCCACAACGTGATCAACGCC

GAGGGCGCCCCCGGCGGCCCCTACAAGATCGGCACCTCCGGCTCCTGCCCCAACATCACCAACGGCAACGG

CTTCTTCGCCACCATGGCCTGGGCCGTGCCCGACAAGAACAAGACCGCCACCAACCCCCTGACCATCGAGG

TGCCCTACGTGTGCACCGAGGGCGAGGACCAGATCACCGTGTGGGGCTTCCACTCCGACNNNGAGACCCAG

ATGGCCAAGCTGTACGGCGACTCCAAGCCCCAGAAGTTCACCTCCTCCGCCAACGGCGTGACCACCCACTA

CGTGTCCCAGATCGGCGGCTTCCCCAACCAGACCGAGGACGGCGGCCTGCCCCAGTCCGGCCGCATCGTGG

TGGACTACATGGTGCAGAAGTCCGGCAAGACCGGCACCATCACCTACCAGCGCGGCATCCTGCTGCCCCAG

AAGGTGTGGTGCGCCTCCGGCCGCTCCAAGGTGATCAAGGGCTCCCTGCCCCTGATCGGCGAGGCCGACTG

CCTGCACGAGAAGTACGGCGGCCTGAACAAGTCCAAGCCCTACTACACCGGCGAGCACGCCAAGGCCATCG

GCAACTGCCCCATCTGGGTGAAGACCCCCCTGAAGCTGGCCAACGGCACCAAGTACCGCCCCCCCGCCAAG

CTGCTGAAGGAGCGCGGCTTCTTCGGCGCCATCGCCGGCTTCCTGGAGGGCGGCTGGGAGGGCATGATCGC

CGGCTGGCACGGCTACACCTCCCACGGCGCCCACGGCGTGGCCGTGGCCGCCGACCTGAAGTCCACCCAGG

AGGCCATCAACAAGATCACCAAGAACCTGAACTCCCTGTCCGAGCTGGAGGTGAAGAACCTGCAGCGCCTG

TCCGGCGCCATGGACGAGCTGCACAACGAGATCCTGGAGCTGGACGAGAAGGTGGACGACCTGCGCGCCGA

CACCATCTCCTCCCAGATCGAGCTGGCCGTGCTGCTGTCCAACGAGGGCATCATCAACTCCGAGGACGAGC

ACCTGCTGGCCCTGGAGCGCAAGCTGAAGAAGATGCTGGGCCCCTCCGCCGTGGAGATCGGCAACGGCTGC

TTCGAGACCAAGCACAAGTGCAACCAGACCTGCCTGGACAAGATCGCCGCCGGCACCTTCGACGCCGGCGA

GTTCTCCCTGCCCACCTTCGACTCCCTGAACATCACCGCCGCCTCCCTGAACGACGACGGCCTGGACAACC

ACACCATCCTGCTGTACTACTCCACCGCCGCCTCCTCCCTGGCCGTGACCCTGATGATCGCCATCTTCGTG

GTGTACATGGTGTCCCGCGACAACGTGTCCTGCTCCATCTGCCTG

2013 Influenza B (Yamagata lineage) - Sequence
only on GISAID - HA antigen Amino Acid sequence (SEQ ID NO: 19)

MKAIIVLLMV VTSNADRICT GITSSNSPHV VKTATQGEVN VTGVIPLTTT PTKSYFANLK

GTRTRGKLCP DCLNCTDLDV ALGRPMCVGT TPSAKASILH EVRPVTSGCF PIMHDRTKIR

QLPNLLRGYE KIRLSTQNVI DAEKAPGGPY RLGTSGSCPN ATSKIGFFAT MAWAVPKDNY

KNATNPLTVE VPYICTEGED QITVWGFHSD NKXQMKSLYG DSNPQKFTSS ANGVTTHYVS

-continued

QIGDFPDQTE DGGLPQSGRI VVDYMMQKPG KTGTIVYQRG VLLPQKVWCA SGRSKVIKGS

LPLIGEADCL HEEYGGLNKS KPYYTGKHAK AIGNCPIWVK TPLKLANGTK YRPPAKLLKE

RGFFGAIAGF LEGGWEGMIA GWHGYTSHGA HGVAVAADLK STQEAINKIT KNLNSLSELE

VKNLQRLSGA MDELHNEILE LDEKVDDLRA DTISSQIELA VLLSNEGIIN SEDEHLLALE

RKLKKMLGPS AVDIGNGCFE TKHKCNQTCL DRIAAGTFNA GEFSLPTFDS LNITAASLND

DGLDNHTILL YYSTAASSLA VTLMLAIFIV YMVSRDNVSC SICL

2013 Influenza B (Yamagata lineage) - Sequence only on GISAID - Optimized DNA sequence encoding the nucleic acid sequence encoding HA antigen (SEQ ID NO: 20)

ATGAAGGCCATCATCGTGCTGCTGATGGTGGTGACCTCCAACGCCGACCGCATCTGCACCGGCATCACCTC

CTCCAACTCCCCCCACGTGGTGAAGACCGCCACCCAGGGCGAGGTGAACGTGACCGGCGTGATCCCCCTGA

CCACCACCCCCACCAAGTCCTACTTCGCCAACCTGAAGGGCACCCGCACCCGCGGCAAGCTGTGCCCCGAC

TGCCTGAACTGCACCGACCTGGACGTGGCCCTGGGCCGCCCCATGTGCGTGGGCACCACCCCCTCCGCCAA

GGCCTCCATCCTGCACGAGGTGCGCCCCGTGACCTCCGGCTGCTTCCCCATCATGCACGACCGCACCAAGA

TCCGCCAGCTGCCCAACCTGCTGCGCGGCTACGAGAAGATCCGCCTGTCCACCCAGAACGTGATCGACGCC

GAGAAGGCCCCCGGCGGCCCCTACCGCCTGGGCACCTCCGGCTCCTGCCCCAACGCCACCTCCAAGATCGG

CTTCTTCGCCACCATGGCCTGGGCCGTGCCCAAGGACAACTACAAGAACGCCACCAACCCCCTGACCGTGG

AGGTGCCCTACATCTGCACCGAGGGCGAGGACCAGATCACCGTGTGGGGCTTCCACTCCGACAACAAGNNN

CAGATGAAGTCCCTGTACGGCGACTCCAACCCCCAGAAGTTCACCTCCTCCGCCAACGGCGTGACCACCCA

CTACGTGTCCCAGATCGGCGACTTCCCCGACCAGACCGAGGACGGCGGCCTGCCCCAGTCCGGCCGCATCG

TGGTGGACTACATGATGCAGAAGCCCGGCAAGACCGGCACCATCGTGTACCAGCGCGGCGTGCTGCTGCCC

CAGAAGGTGTGGTGCGCCTCCGGCCGCTCCAAGGTGATCAAGGGCTCCCTGCCCCTGATCGGCGAGGCCGA

CTGCCTGCACGAGGAGTACGGCGGCCTGAACAAGTCCAAGCCCTACTACACCGGCAAGCACGCCAAGGCCA

TCGGCAACTGCCCCATCTGGGTGAAGACCCCCCTGAAGCTGGCCAACGGCACCAAGTACCGCCCCCCCGCC

AAGCTGCTGAAGGAGCGCGGCTTCTTCGGCGCCATCGCCGGCTTCCTGGAGGGCGGCTGGGAGGGCATGAT

CGCCGGCTGGCACGGCTACACCTCCCACGGCGCCCACGGCGTGGCCGTGGCCGCCGACCTGAAGTCCACCC

AGGAGGCCATCAACAAGATCACCAAGAACCTGAACTCCCTGTCCGAGCTGGAGGTGAAGAACCTGCAGCGC

CTGTCCGGCGCCATGGACGAGCTGCACAACGAGATCCTGGAGCTGGACGAGAAGGTGGACGACCTGCGCGC

CGACACCATCTCCTCCCAGATCGAGCTGGCCGTGCTGCTGTCCAACGAGGGCATCATCAACTCCGAGGACG

AGCACCTGCTGGCCCTGGAGCGCAAGCTGAAGAAGATGCTGGGCCCCTCCGCCGTGGACATCGGCAACGGC

TGCTTCGAGACCAAGCACAAGTGCAACCAGACCTGCCTGGACCGCATCGCCGCCGGCACCTTCAACGCCGG

CGAGTTCTCCCTGCCCACCTTCGACTCCCTGAACATCACCGCCGCCTCCCTGAACGACGACGGCCTGGACA

ACCACACCATCCTGCTGTACTACTCCACCGCCGCCTCCTCCCTGGCCGTGACCCTGATGCTGGCCATCTTC

ATCGTGTACATGGTGTCCCGCGACAACGTGTCCTGCTCCATCTGCCTG

2015 H5N1 - HA antigen Amino Acid sequence (SEQ ID NO: 21)

MEKIVLLFAT ISLVKSDHIC IGYHANNSTE QVDTIMEKNV TVTHAQDILE 050

KTHNGKLCDL NGVKPLILKD CSVAGWLLGN PWCDEFINVP EWSYIVEKAN 100

PVNGLCYPGN FNDYEELKHL LSRINHFEKI QIIPKDSWSD HEASKGGSAA 150

CSYQGKSSFF RNVVWLIKKN DTYPTIKKDY NNTNREDLLV LWGIHHPNDK 200

AEQITLYQNP TTYISIGTST LNQRLVPKIA TRSKINGQSG RIDFFWTILK 250

PNDAIHFESN GNFIAPEYAY KIVKKGDSTI MRSEVEYGNC NTRCQTPVGA 300

INSSMPFHNI HPLTIGECPK YVKSNKLVLA TGLRNSPQRE RRRKRGLFGA 350

-continued

KAGFIEGGWQ GMVDGWYGYH HSNEQGSGYA ADKESTQKAI DGVTNKVNSI 400

IDKMNTQFEA VGREFNNLER RIENLNKKME DGFLDVWTYN AELLVLMENE 450

RTLDFHDSNV KNLYDKVRLQ LKDNAKELGN GCFEFYHKCN NECMESVRNG 500

TYDYPQYSEE ARLKREEISG VKLESIGVYQ ILSIYSTVAS SLVLAIMMAG 550

LSLWMCSNGS LQCRICI

2015 H5N1 - Optimized DNA sequence encoding the nucleic acid sequence encoding HA antigen (SEQ ID NO: 22)

ATGGAGAAGATCGTGCTGCTGTTCGCCACCATCTCCCTGGTGAAGTCCGACCACATCTGCATCGGCTACCA

CGCCAACAACTCCACCGAGCAGGTGGACACCATCATGGAGAAGAACGTGACCGTGACCCACGCCCAGGACA

TCCTGGAGAAGACCCACAACGGCAAGCTGTGCGACCTGAACGGCGTGAAGCCCCTGATCCTGAAGGACTGC

TCCGTGGCCGGCTGGCTGCTGGGCAACCCCTGGTGCGACGAGTTCATCAACGTGCCCGAGTGGTCCTACAT

CGTGGAGAAGGCCAACCCCGTGAACGGCCTGTGCTACCCCGGCAACTTCAACGACTACGAGGAGCTGAAGC

ACCTGCTGTCCCGCATCAACCACTTCGAGAAGATCCAGATCATCCCCAAGGACTCCTGGTCCGACCACGAG

GCCTCCAAGGGCGGCTCCGCCGCCTGCTCCTACCAGGGCAAGTCCTCCTTCTTCCGCAACGTGGTGTGGCT

GATCAAGAAGAACGACACCTACCCCACCATCAAGAAGGACTACAACAACACCAACCGCGAGGACCTGCTGG

TGCTGTGGGGCATCCACCACCCCAACGACAAGGCCGAGCAGATCACCCTGTACCAGAACCCCACCACCTAC

ATCTCCATCGGCACCTCCACCCTGAACCAGCGCCTGGTGCCCAAGATCGCCACCCGCTCCAAGATCAACGG

CCAGTCCGGCCGCATCGACTTCTTCTGGACCATCCTGAAGCCCAACGACGCCATCCACTTCGAGTCCAACG

GCAACTTCATCGCCCCCGAGTACGCCTACAAGATCGTGAAGAAGGGCGACTCCACCATCATGCGCTCCGAG

GTGGAGTACGGCAACTGCAACACCCGCTGCCAGACCCCCGTGGGCGCCATCAACTCCTCCATGCCCTTCCA

CAACATCCACCCCCTGACCATCGGCGAGTGCCCCAAGTACGTGAAGTCCAACAAGCTGGTGCTGGCCACCG

GCCTGCGCAACTCCCCCCAGCGCGAGCGCCGCCGCAAGCGCGGCCTGTTCGGCGCCAAGGCCGGCTTCATC

GAGGGCGGCTGGCAGGGCATGGTGGACGGCTGGTACGGCTACCACCACTCCAACGAGCAGGGCTCCGGCTA

CGCCGCCGACAAGGAGTCCACCCAGAAGGCCATCGACGGCGTGACCAACAAGGTGAACTCCATCATCGACA

AGATGAACACCCAGTTCGAGGCCGTGGGCCGCGAGTTCAACAACCTGGAGCGCCGCATCGAGAACCTGAAC

AAGAAGATGGAGGACGGCTTCCTGGACGTGTGGACCTACAACGCCGAGCTGCTGGTGCTGATGGAGAACGA

GCGCACCCTGGACTTCCACGACTCCAACGTGAAGAACCTGTACGACAAGGTGCGCCTGCAGCTGAAGGACA

ACGCCAAGGAGCTGGGCAACGGCTGCTTCGAGTTCTACCACAAGTGCAACAACGAGTGCATGGAGTCCGTG

CGCAACGGCACCTACGACTACCCCCAGTACTCCGAGGAGGCCCGCCTGAAGCGCGAGGAGATCTCCGGCGT

GAAGCTGGAGTCCATCGGCGTGTACCAGATCCTGTCCATCTACTCCACCGTGGCCTCCTCCCTGGTGCTGG

CCATCATGATGGCCGGCCTGTCCCTGTGGATGTGCTCCAACGGCTCCCTGCAGTGCCGCATCTGCATC

2017 H7N9 - HA antigen Amino Acid sequence (SEQ ID NO: 23)

MNTQILVFAL IAIIPTNADK ICLGHHAVSN GTKVDTLTER GVEVVNATET 050

VERTNIPRIC SKGKRTVDLG QCGLLGTITG PPQCDQFLEF SADLIIERRE 100

GSDFCYPGKF VNEEALRQIL RESGGIDKEA MGFTYNGIRT NGVTSACRRS 150

GSSFYAEMKW LLSNTDNATF PQMTKSYKNT RKSPAIIVWG IHHSVSTAEQ 200

TKLYGSGNKL VTVGSSNYQQ SFVPSPGARP QVNGLSGRID FHWLILNPND 250

TVTFSFNGAF IAPDRASFLR GKSMGIQSGV QVDANCEGDC YHSGGTIISN 300

LPFQNIDSRA VGKCPRYVKQ RSLLLATGMK NVPEIPKGRG LFGAIAGFIE 350

NGWEGLIDGW YGFRHQNAQG EGTAADYKST QSAIDQIAGK LNRLIAKTNQ 400

QFELIDNEFN EVEKQIGNVI NWTRDSITEV WSYNAELLIA MENQHTIDLA 450

-continued

DSEMDKLYER VKRQLRENAE EDGTGCFEIF HKCDDDCMAS IRNNTYDHRK 500

YREEAMQNRI QIDPVKLSSG YKDVILWFSF GASCFILLAV VMGLVFICVK 550

NGNMRCTICI

2017 H7N9 - Optimized DNA sequence encoding the nucleic acid sequence encoding HA antigen (SEQ ID NO: 24)

ATGAACACCCAGATCCTGGTGTTCGCCCTGATCGCCATCATCCCCACCAACGCCGACAAGATCTGCCTGGG

CCACCACGCCGTGTCCAACGGCACCAAGGTGGACACCCTGACCGAGCGCGGCGTGGAGGTGGTGAACGCCA

CCGAGACCGTGGAGCGCACCAACATCCCCCGCATCTGCTCCAAGGGCAAGCGCACCGTGGACCTGGGCCAG

TGCGGCCTGCTGGGCACCATCACCGGCCCCCCCCAGTGCGACCAGTTCCTGGAGTTCTCCGCCGACCTGAT

CATCGAGCGCCGCGAGGGCTCCGACTTCTGCTACCCCGGCAAGTTCGTGAACGAGGAGGCCCTGCGCCAGA

TCCTGCGCGAGTCCGGCGGCATCGACAAGGAGGCCATGGGCTTCACCTACAACGGCATCCGCACCAACGGC

GTGACCTCCGCCTGCCGCCGCTCCGGCTCCTCCTTCTACGCCGAGATGAAGTGGCTGCTGTCCAACACCGA

CAACGCCACCTTCCCCCAGATGACCAAGTCCTACAAGAACACCCGCAAGTCCCCCGCCATCATCGTGTGGG

GCATCCACCACTCCGTGTCCACCGCCGAGCAGACCAAGCTGTACGGCTCCGGCAACAAGCTGGTGACCGTG

GGCTCCTCCAACTACCAGCAGTCCTTCGTGCCCTCCCCCGGCGCCCGCCCCCAGGTGAACGGCCTGTCCGG

CCGCATCGACTTCCACTGGCTGATCCTGAACCCCAACGACACCGTGACCTTCTCCTTCAACGGCGCCTTCA

TCGCCCCCGACCGCGCCTCCTTCCTGCGCGGCAAGTCCATGGGCATCCAGTCCGGCGTGCAGGTGGACGCC

AACTGCGAGGGCGACTGCTACCACTCCGGCGGCACCATCATCTCCAACCTGCCCTTCCAGAACATCGACTC

CCGCGCCGTGGGCAAGTGCCCCCGCTACGTGAAGCAGCGCTCCCTGCTGCTGGCCACCGGCATGAAGAACG

TGCCCGAGATCCCCAAGGGCCGCGGCCTGTTCGGCGCCATCGCCGGCTTCATCGAGAACGGCTGGGAGGGC

CTGATCGACGGCTGGTACGGCTTCCGCCACCAGAACGCCCAGGGCGAGGGCACCGCCGCCGACTACAAGTC

CACCCAGTCCGCCATCGACCAGATCGCCGGCAAGCTGAACCGCCTGATCGCCAAGACCAACCAGCAGTTCG

AGCTGATCGACAACGAGTTCAACGAGGTGGAGAAGCAGATCGGCAACGTGATCAACTGGACCCGCGACTCC

ATCACCGAGGTGTGGTCCTACAACGCCGAGCTGCTGATCGCCATGGAGAACCAGCACACCATCGACCTGGC

CGACTCCGAGATGGACAAGCTGTACGAGCGCGTGAAGCGCCAGCTGCGCGAGAACGCCGAGGAGGACGGCA

CCGGCTGCTTCGAGATCTTCCACAAGTGCGACGACGACTGCATGGCCTCCATCCGCAACAACACCTACGAC

CACCGCAAGTACCGCGAGGAGGCCATGCAGAACCGCATCCAGATCGACCCCGTGAAGCTGTCCTCCGGCTA

CAAGGACGTGATCCTGTGGTTCTCCTTCGGCGCCTCCTGCTTCATCCTGCTGGCCGTGGTGATGGGCCTGG

TGTTCATCTGCGTGAAGAACGGCAACATGCGCTGCACCATCTGCATC

2013 H10N8 - HA antigen Amino Acid sequence (SEQ ID NO: 25)

MYKIVVIIAL LGAVKGLDKI CLGHHAVANG TIVKTLTNEQ EEVTNATETV 050

ESTGINRLCM KGRKHKDLGN CHPIGMLIGT PACDLHLTGM WDTLIERENA 100

IAYCYPGATV NVEALRQKIM ESGGINKIST GFTYGSSINS AGTTRACMRN 150

GGNSFYAELK WLVSKSKGQN FPQTTNTYRN TDTAEHLIMW GIHHPSSTQE 200

KNDLYGTQSL SISVGSSTYR NNFVPVVGAG PQVNGQSGRI DFHWTLVQPG 250

DNITFSHNGG LIAPSRVSKL IGRGLGIQSD APIDNNCESK CFWRGGSINT 300

RLPFQNLSPR TVGQCPKYVN RRSLMLATGM RNVPELIQGR GLFGAIAGFL 350

ENGWEGMVDG WYGFRHQNAQ GTGQAADYKS TQAAIDQITG KLNRLVEKTN 400

TEFESIESEF SEIEHQIGNV INWTKDSITD IWTYQAELLV AMENQHTIDM 450

ADSEMLNLYE RVRKQLRQNA EEDGKGCFEI YHACDDSCME SIRNNTYDHS 500

-continued

QYREEALLNR LNINPVTLSS GYKDIILWFS FGASCFVLLA VVMGLFFFCL 550

KNGNMRCTIC I

2013 H10N8 - Optimized DNA sequence encoding the nucleic acid sequence encoding HA antigen (SEQ ID NO: 26)

ATGTACAAGATCGTGGTGATCATCGCCCTGCTGGGCGCCGTGAAGGGCCTGGACAAGATCTGCCTGGGCCA

CCACGCCGTGGCCAACGGCACCATCGTGAAGACCCTGACCAACGAGCAGGAGGAGGTGACCAACGCCACCG

AGACCGTGGAGTCCACCGGCATCAACCGCCTGTGCATGAAGGGCCGCAAGCACAAGGACCTGGGCAACTGC

CACCCCATCGGCATGCTGATCGGCACCCCCGCCTGCGACCTGCACCTGACCGGCATGTGGGACACCCTGAT

CGAGCGCGAGAACGCCATCGCCTACTGCTACCCCGGCGCCACCGTGAACGTGGAGGCCCTGCGCCAGAAGA

TCATGGAGTCCGGCGGCATCAACAAGATCTCCACCGGCTTCACCTACGGCTCCTCCATCAACTCCGCCGGC

ACCACCCGCGCCTGCATGCGCAACGGCGGCAACTCCTTCTACGCCGAGCTGAAGTGGCTGGTGTCCAAGTC

CAAGGGCCAGAACTTCCCCCAGACCACCAACACCTACCGCAACACCGACACCGCCGAGCACCTGATCATGT

GGGGCATCCACCACCCCTCCTCCACCCAGGAGAAGAACGACCTGTACGGCACCCAGTCCCTGTCCATCTCC

GTGGGCTCCTCCACCTACCGCAACAACTTCGTGCCCGTGGTGGGCGCCGGCCCCCAGGTGAACGGCCAGTC

CGGCCGCATCGACTTCCACTGGACCCTGGTGCAGCCCGGCGACAACATCACCTTCTCCCACAACGGCGGCC

TGATCGCCCCCTCCCGCGTGTCCAAGCTGATCGGCCGCGGCCTGGGCATCCAGTCCGACGCCCCCATCGAC

AACAACTGCGAGTCCAAGTGCTTCTGGCGCGGCGGCTCCATCAACACCCGCCTGCCCTTCCAGAACCTGTC

CCCCCGCACCGTGGGCCAGTGCCCCAAGTACGTGAACCGCCGCTCCCTGATGCTGGCCACCGGCATGCGCA

ACGTGCCCGAGCTGATCCAGGGCCGCGGCCTGTTCGGCGCCATCGCCGGCTTCCTGGAGAACGGCTGGGAG

GGCATGGTGGACGGCTGGTACGGCTTCCGCCACCAGAACGCCCAGGGCACCGGCCAGGCCGCCGACTACAA

GTCCACCCAGGCCGCCATCGACCAGATCACCGGCAAGCTGAACCGCCTGGTGGAGAAGACCAACACCGAGT

TCGAGTCCATCGAGTCCGAGTTCTCCGAGATCGAGCACCAGATCGGCAACGTGATCAACTGGACCAAGGAC

TCCATCACCGACATCTGGACCTACCAGGCCGAGCTGCTGGTGGCCATGGAGAACCAGCACACCATCGACAT

GGCCGACTCCGAGATGCTGAACCTGTACGAGCGCGTGCGCAAGCAGCTGCGCCAGAACGCCGAGGAGGACG

GCAAGGGCTGCTTCGAGATCTACCACGCCTGCGACGACTCCTGCATGGAGTCCATCCGCAACAACACCTAC

GACCACTCCCAGTACCGCGAGGAGGCCCTGCTGAACCGCCTGAACATCAACCCCGTGACCCTGTCCTCCGG

CTACAAGGACATCATCCTGTGGTTCTCCTTCGGCGCCTCCTGCTTCGTGCTGCTGGCCGTGGTGATGGGCC

TGTTCTTCTTCTGCCTGAAGAACGGCAACATGCGCTGCACCATCTGCATC

Mini HA domain - HA antigen Amino Acid sequence (SEQ ID NO: 27)

MKVKLLVLLCTFTATYADTICIGYHANNSTDTVDTVLEKNVTVTHSVNLLENGGGGKYVCSAKLRMVTGLR

NKPSKQSQGLFGAIAGFTEGGWTGMVDGWYGYHHQNEQGSGYAADQKSTQNAINGITNKVNSVIEKMNTQY

TAIGCEYNKSERCMKQIEDKIEEIESKIWCYNAELLVLLENERTLDFHDSNVKNLYEKVKSQLKNNAKEIG

NGCFEFYHKCNDECMESVKNGTYDYPKYSEESKLNREKIDGVKLESMGVYQIEGR

Mini HA domain - Optimized DNA sequence encoding the nucleic acid sequence encoding HA antigen (SEQ ID NO: 28)

ATGAAGGTGAAGCTGCTGGTGCTGCTGTGCACCTTCACCGCCACCTACGCCGACACCATCTGCATCGGCTA

CCACGCCAACAACTCCACCGACACCGTGGACACCGTGCTGGAGAAGAACGTGACCGTGACCCACTCCGTGA

ACCTGCTGGAGAACGGCGGCGGCGGCAAGTACGTGTGCTCCGCCAAGCTGCGCATGGTGACCGGCCTGCGC

AACAAGCCCTCCAAGCAGTCCCAGGGCCTGTTCGGCGCCATCGCCGGCTTCACCGAGGGCGGCTGGACCGG

CATGGTGGACGGCTGGTACGGCTACCACCACCAGAACGAGCAGGGCTCCGGCTACGCCGCCGACCAGAAGT

CCACCCAGAACGCCATCAACGGCATCACCAACAAGGTGAACTCCGTGATCGAGAAGATGAACACCCAGTAC

-continued

ACCGCCATCGGCTGCGAGTACAACAAGTCCGAGCGgTGCATGAAGCAGATCGAGGACAAGATCGAGGAGAT

CGAGTCCAAGATCTGGTGCTACAACGCCGAGCTGCTGGTGCTGCTGGAGAACGAGCGCACCCTGGACTTCC

ACGACTCCAACGTGAAGAACCTGTACGAGAAGGTGAAGTCCCAGCTGAAGAACAACGCCAAGGAGATCGGC

AACGGCTGCTTCGAGTTCTACCACAAGTGCAACGACGAGTGCATGGAGTCCGTGAAGAACGGCACCTACGA

CTACCCCAAGTACTCCGAGGAGTCCAAGCTGAACCGCGAGAAGATCGACGGCGTGAAGCTGGAGTCCATGG

GCGTGTACCAGATCGAGGGCCGC

NA Sequence
1918 H1N1 - NA antigen Amino Acid sequence (SEQ ID NO: 29)

MNPNQKIITI GSICMVVGII SLILQIGNII SIWVSHSIQT GNQNHPETCN 050

QSIITYENNT WVNQTYVNIS NTNVVAGQDA TSVILTGNSS LCPISGWAIY 100

SKDNGIRIGS KGDVFVIREP FISCSHLECR TFFLTQGALL NDKHSNGTVK 150

DRSPYRTLMS CPVGEAPSPY NSRFESVAWS ASACHDGMGW LTIGISGPDN 200

GAVAVLKYNG IITDTIKSWR NNILRTQESE CACVNGSCFT IMTDGPSNGQ 250

ASYKILKIEK GKVTKSIELN APNYHYEECS CYPDTGKVMC VCRDNWHGSN 300

RPWVSFDQNL DYQIGYICSG VFGDNPRPND GTGSCGPVSS NGANGIKGFS 350

FRYDNGVWIG RTKSTSSRSG FEMIWDPNGW TETDSSFSVR QDIVAITDWS 400

GYSGSFVQHP ELTGLDCMRP CFWVELIRGQ PKENTIWTSG SSISFCGVNS 450

DTVGWSWPDG AELPFSIDK

1918 H1N1 - Optimized DNA sequence encoding
the nucleic acid sequence encoding NA antigen (SEQ ID NO: 30)

ATGAACCCCAACCAGAAGATCATCACCATCGGCTCCATCTGCATGGTGGTGGGCATCATCTCCCTGATCCT

GCAGATCGGCAACATCATCTCCATCTGGGTGTCCCACTCCATCCAGACCGGCAACCAGAACCACCCCGAGA

CCTGCAACCAGTCCATCATCACCTACGAGAACAACACCTGGGTGAACCAGACCTACGTGAACATCTCCAAC

ACCAACGTGGTGGCCGGCCAGGACGCCACCTCCGTGATCCTGACCGGCAACTCCTCCCTGTGCCCCATCTC

CGGCTGGGCCATCTACTCCAAGGACAACGGCATCCGCATCGGCTCCAAGGGCGACGTGTTCGTGATCCGCG

AGCCCTTCATCTCCTGCTCCCACCTGGAGTGCCGCACCTTCTTCCTGACCCAGGGCGCCCTGCTGAACGAC

AAGCACTCCAACGGCACCGTGAAGGACCGCTCCCCCTACCGCACCCTGATGTCCTGCCCCGTGGGCGAGGC

CCCCTCCCCCTACAACTCCCGCTTCGAGTCCGTGGCCTGGTCCGCCTCCGCCTGCCACGACGGCATGGGCT

GGCTGACCATCGGCATCTCCGGCCCCGACAACGGCGCCGTGGCCGTGCTGAAGTACAACGGCATCATCACC

GACACCATCAAGTCCTGGCGCAACAACATCCTGCGCACCCAGGAGTCCGAGTGCGCCTGCGTGAACGGCTC

CTGCTTCACCATCATGACCGACGGCCCCTCCAACGGCCAGGCCTCCTACAAGATCCTGAAGATCGAGAAGG

GCAAGGTGACCAAGTCCATCGAGCTGAACGCCCCCAACTACCACTACGAGGAGTGCTCCTGCTACCCCGAC

ACCGGCAAGGTGATGTGCGTGTGCCGCGACAACTGGCACGGCTCCAACCGCCCCTGGGTGTCCTTCGACCA

GAACCTGGACTACCAGATCGGCTACATCTGCTCCGGCGTGTTCGGCGACAACCCCCGCCCCAACGACGGCA

CCGGCTCCTGCGGCCCCGTGTCCTCCAACGGCGCCAACGGCATCAAGGGCTTCTCCTTCCGCTACGACAAC

GGCGTGTGGATCGGCCGCACCAAGTCCACCTCCTCCCGCTCCGGCTTCGAGATGATCTGGGACCCCAACGG

CTGGACCGAGACCGACTCCTCCTTCTCCGTGCGCCAGGACATCGTGGCCATCACCGACTGGTCCGGCTACT

CCGGCTCCTTCGTGCAGCACCCCGAGCTGACCGGCCTGGACTGCATGCGCCCCTGCTTCTGGGTGGAGCTG

ATCCGCGGCCAGCCCAAGGAGAACACCATCTGGACCTCCGGCTCCTCCATCTCCTTCTGCGGCGTGAACTC

CGACACCGTGGGCTGGTCCTGGCCCGACGGCGCCGAGCTGCCCTTCTCCATCGACAAG

-continued

1957 H2N2 - NA antigen Amino Acid sequence (SEQ ID NO: 31)

MNPNQKIITI GSVSLIIATV CFLMQIAILV TTVTLHFKQH ECDSPASNQV 050

MPCEPIIIER NITEIVYLNN TTIEKEICPK VVEYRNWSKP QCQITGFAPF 100

SKDNSIRLSA GGDIWVTREP YVSCDPGKCY QFALGQGTTL DNKHSNDTIH 150

DRIPHRTLLM NELGVPFHLG TRQVCVAWSS SSCHDGKAWL HVCVTGDDKN 200

ATASFIYDGR LVDSIGSWSQ NILRTQESEC VCINGTCTVV MTDGSASGRA 250

DTRILFIEEG KIVHISPLSG SAQHVEECSC YPRYPDVRCI CRDNWKGSNR 300

PVIDINMEDY SIDSSYVCSG LVGDTPRNDD RSSNSNCRNP NNERGNPGVK 350

GWAFDNGDDV WMGRTISKDL RSGYETFKVI GGWSTPNSKS QINRQVIVDS 400

NNWSGYSGIF SVEGKSCINR CFYVELIRGR QQETRVWWTS NSIVVFCGTS 450

GTYGTGSWPD GANINFMPI

1957 H2N2 - Optimized DNA sequence encoding the nucleic acid sequence encoding NA antigen (SEQ ID NO: 32)

ATGAACCCCAACCAGAAGATCATCACCATCGGCTCCGTGTCCCTGATCATCGCCACCGTGTGCTTCCTGAT

GCAGATCGCCATCCTGGTGACCACCGTGACCCTGCACTTCAAGCAGCACGAGTGCGACTCCCCCGCCTCCA

ACCAGGTGATGCCCTGCGAGCCCATCATCATCGAGCGCAACATCACCGAGATCGTGTACCTGAACAACACC

ACCATCGAGAAGGAGATCTGCCCCAAGGTGGTGGAGTACCGCAACTGGTCCAAGCCCCAGTGCCAGATCAC

CGGCTTCGCCCCCTTCTCCAAGGACAACTCCATCCGCCTGTCCGCCGGCGGCGACATCTGGGTGACCCGCG

AGCCCTACGTGTCCTGCGACCCCGGCAAGTGCTACCAGTTCGCCCTGGGCCAGGGCACCACCCTGGACAAC

AAGCACTCCAACGACACCATCCACGACCGCATCCCCCACCGCACCCTGCTGATGAACGAGCTGGGCGTGCC

CTTCCACCTGGGCACCCGCCAGGTGTGCGTGGCCTGGTCCTCCTCCTCCTGCCACGACGGCAAGGCCTGGC

TGCACGTGTGCGTGACCGGCGACGACAAGAACGCCACCGCCTCCTTCATCTACGACGGCCGCCTGGTGGAC

TCCATCGGCTCCTGGTCCCAGAACATCCTGCGCACCCAGGAGTCCGAGTGCGTGTGCATCAACGGCACCTG

CACCGTGGTGATGACCGACGGCTCCGCCTCCGGCCGCGCCGACACCCGCATCCTGTTCATCGAGGAGGGCA

AGATCGTGCACATCTCCCCCCTGTCCGGCTCCGCCCAGCACGTGGAGGAGTGCTCCTGCTACCCCCGCTAC

CCCGACGTGCGCTGCATCTGCCGCGACAACTGGAAGGGCTCCAACCGCCCCGTGATCGACATCAACATGGA

GGACTACTCCATCGACTCCTCCTACGTGTGCTCCGGCCTGGTGGGCGACACCCCCCGCAACGACGACCGCT

CCTCCAACTCCAACTGCCGCAACCCCAACAACGAGCGCGGCAACCCCGGCGTGAAGGGCTGGGCCTTCGAC

AACGGCGACGACGTGTGGATGGGCCGCACCATCTCCAAGGACCTGCGCTCCGGCTACGAGACCTTCAAGGT

GATCGGCGGCTGGTCCACCCCCAACTCCAAGTCCCAGATCAACCGCCAGGTGATCGTGGACTCCAACAACT

GGTCCGGCTACTCCGGCATCTTCTCCGTGGAGGGCAAGTCCTGCATCAACCGCTGCTTCTACGTGGAGCTG

ATCCGCGGCCGCCAGCAGGAGACCCGCGTGTGGTGGACCTCCAACTCCATCGTGGTGTTCTGCGGCACCTC

CGGCACCTACGGCACCGGCTCCTGGCCCGACGGCGCCAACATCAACTTCATGCCCATC

1968 H3N2 - NA antigen Amino Acid sequence (SEQ ID NO: 33)

MNPNQKIITI GSVSLTIATV CFLMQIAILV TTVTLHFKQY ECDSPASNQV 050

MPCEPIIIER NITEIVYLNN TTIEKEICPK VVEYRNWSKP QCQITGFAPF 100

SKDNSIRLSA GGDIWVTREP YVSCDHGKCY QFALGQGTTL DNKHSNDTIH 150

DRIPHRTLLM NELGVPFHLG TRQVCIAWSS SSCHDGKAWL HVCITGDDKN 200

ATASFIYDGR LVDSIGSWSQ NILRTQESEC VCINGTCTVV MTDGSASGRA 250

DTRILFIEEG KIVHISPLSG SAQHVEECSC YPRYPGVRCI CRDNWKGSNR 300

PVIDINMEDY SIDSSYVCSG LVGDTPRNDD RSSNSNCRNP NNERGNQGVK 350

-continued

GWAFDNGDDV WMGRTISKDL RSGYETFKVI GGWSTPNSKS QINRQVIVDS 400

DNRSGYSGIF SVEGKSCINR CFYVELIRGR KQETRVWWTS NSIVVFCGTS 450

GTYGTGSWPD GANINFMPI

1968 H3N2 - Optimized DNA sequence encoding the nucleic acid sequence encoding NA antigen (SEQ ID NO: 34)

ATGAACCCCAACCAGAAGATCATCACCATCGGCTCCGTGTCCCTGACCATCGCCACCGTGTGCTTCCTGAT

GCAGATCGCCATCCTGGTGACCACCGTGACCCTGCACTTCAAGCAGTACGAGTGCGACTCCCCCGCCTCCA

ACCAGGTGATGCCCTGCGAGCCCATCATCATCGAGCGCAACATCACCGAGATCGTGTACCTGAACAACACC

ACCATCGAGAAGGAGATCTGCCCCAAGGTGGTGGAGTACCGCAACTGGTCCAAGCCCCAGTGCCAGATCAC

CGGCTTCGCCCCCTTCTCCAAGGACAACTCCATCCGCCTGTCCGCCGGCGGCGACATCTGGGTGACCCGCG

AGCCCTACGTGTCCTGCGACCACGGCAAGTGCTACCAGTTCGCCCTGGGCCAGGGCACCACCCTGGACAAC

AAGCACTCCAACGACACCATCCACGACCGCATCCCCCACCGCACCCTGCTGATGAACGAGCTGGGCGTGCC

CTTCCACCTGGGCACCCGCCAGGTGTGCATCGCCTGGTCCTCCTCCTCCTGCCACGACGGCAAGGCCTGGC

TGCACGTGTGCATCACCGGCGACGACAAGAACGCCACCGCCTCCTTCATCTACGACGGCCGCCTGGTGGAC

TCCATCGGCTCCTGGTCCCAGAACATCCTGCGCACCCAGGAGTCCGAGTGCGTGTGCATCAACGGCACCTG

CACCGTGGTGATGACCGACGGCTCCGCCTCCGGCCGCGCCGACACCCGCATCCTGTTCATCGAGGAGGGCA

AGATCGTGCACATCTCCCCCCTGTCCGGCTCCGCCCAGCACGTGGAGGAGTGCTCCTGCTACCCCCGCTAC

CCCGGCGTGCGCTGCATCTGCCGCGACAACTGGAAGGGCTCCAACCGCCCCGTGGTGGACATCAACATGGA

GGACTACTCCATCGACTCCTCCTACGTGTGCTCCGGCCTGGTGGGCGACACCCCCCGCAACGACGACCGCT

CCTCCAACTCCAACTGCCGCAACCCCAACAACGAGCGCGGCAACCAGGGCGTGAAGGGCTGGGCCTTCGAC

AACGGCGACGACGTGTGGATGGGCCGCACCATCTCCAAGGACCTGCGCTCCGGCTACGAGACCTTCAAGGT

GATCGGCGGCTGGTCCACCCCCAACTCCAAGTCCCAGATCAACCGCCAGGTGATCGTGGACTCCGACAACC

GCTCCGGCTACTCCGGCATCTTCTCCGTGGAGGGCAAGTCCTGCATCAACCGCTGCTTCTACGTGGAGCTG

ATCCGCGGCCGCAAGCAGGAGACCCGCGTGTGGTGGACCTCCAACTCCATCGTGGTGTTCTGCGGCACCTC

CGGCACCTACGGCACCGGCTCCTGGCCCGACGGCGCCAACATCAACTTCATGCCCATC

1977 H1N1 - NA antigen Amino Acid sequence (SEQ ID NO: 35)

MNPNQKIITI GSICMAIGII SLILQIGNII SIWVSHSIQT GSQNHTGICN 050

QRIITYENST WVNQTYVNIS NTNVVAGKDT TSMTLAGNSS LCPIRGWAIY 100

SKDNSIRIGS KGDVFVIREP FISCSHLECR TFFLTQGALL NDKHSNGTVK 150

DRSPYRALMS CPIGEAPSPY NSRFESVAWS ASACHDGMGW LTIGISGPDD 200

GAVAVLKYNG IITETIKSWR KQILRTQESE CVCVNGSCFT IMTDGPSDGP 250

ASYRIFKIEK GKITKSIELD APNSHYEECS CYPDTGTVMC VCRDNWHGSN 300

RPWVSFNQNL DYQIGYICSG VFGDNPRPKD GKGSCDPVNV DGADGVKGFS 350

YRYGNGVWIG RTKSNSSRKG FEMIWDPNGW TDTDSNFLVK QDVVAMTDWS 400

GYSGSFVQHP ELTGLDCMRP CFWVELIRGR PREKTTIWTS GSSISFCGVN 450

SDTVNWSWPD GAELPFTIDK

1977 H1N1 - Optimized DNA sequence encoding the nucleic acid sequence encoding NA antigen (SEQ ID NO: 36)

ATGAACCCCAACCAGAAGATCATCACCATCGGCTCCATCTGCATGGCCATCGGCATCATCTCCCTGATCCT

GCAGATCGGCAACATCATCTCCATCTGGGTGTCCCACTCCATCCAGACCGGCTCCCAGAACCACACCGGCA

TCTGCAACCAGCGCATCATCACCTACGAGAACTCCACCTGGGTGAACCAGACCTACGTGAACATCTCCAAC

-continued

ACCAACGTGGTGGCCGGCAAGGACACCACCTCCATGACCCTGGCCGGCAACTCCTCCCTGTGCCCCATCCG

CGGCTGGGCCATCTACTCCAAGGACAACTCCATCCGCATCGGCTCCAAGGGCGACGTGTTCGTGATCCGCG

AGCCCTTCATCTCCTGCTCCCACCTGGAGTGCCGCACCTTCTTCCTGACCCAGGGCGCCCTGCTGAACGAC

AAGCACTCCAACGGCACCGTGAAGGACCGCTCCCCCTACCGCGCCCTGATGTCCTGCCCCATCGGCGAGGC

CCCCTCCCCCTACAACTCCCGCTTCGAGTCCGTGGCCTGGTCCGCCTCCGCCTGCCACGACGGCATGGGCT

GGCTGACCATCGGCATCTCCGGCCCCGACGACGGCGCCGTGGCCGTGCTGAAGTACAACGGCATCATCACC

GAGACCATCAAGTCCTGGCGCAAGCAGATCCTGCGCACCCAGGAGTCCGAGTGCGTGTGCGTGAACGGCTC

CTGCTTCACCATCATGACCGACGGCCCCTCCGACGGCCCCGCCTCCTACCGCATCTTCAAGATCGAGAAGG

GCAAGATCACCAAGTCCATCGAGCTGGACGCCCCCAACTCCCACTACGAGGAGTGCTCCTGCTACCCCGAC

ACCGGCACCGTGATGTGCGTGTGCCGCGACAACTGGCACGGCTCCAACCGCCCCTGGGTGTCCTTCAACCA

GAACCTGGACTACCAGATCGGCTACATCTGCTCCGGCGTGTTCGGCGACAACCCCCGCCCCAAGGACGGCA

AGGGCTCCTGCGACCCCGTGAACGTGGACGGCGCCGACGGCGTGAAGGGCTTCTCCTACCGCTACGGCAAC

GGCGTGTGGATCGGCCGCACCAAGTCCAACTCCTCCCGCAAGGGCTTCGAGATGATCTGGGACCCCAACGG

CTGGACCGACACCGACTCCAACTTCCTGGTGAAGCAGGACGTGGTGGCCATGACCGACTGGTCCGGCTACT

CCGGCTCCTTCGTGCAGCACCCCGAGCTGACCGGCCTGGACTGCATGCGCCCCTGCTTCTGGGTGGAGCTG

ATCCGCGGCCGCCCCCGCGAGAAGACCACCATCTGGACCTCCGGCTCCTCCATCTCCTTCTGCGGCGTGAA

CTCCGACACCGTGAACTGGTCCTGGCCCGACGGCGCCGAGCTGCCCTTCACCATCGACAAG

2007 H1N1 - NA antigen Amino Acid sequence (SEQ ID NO: 37)

MNPNQKIITI GSISIAIGII SLMLQIGNII SIWASHSIQT GSQNNTGICN 050

QRIITYENST WVNHTYVNIN NTNVVAGEDK TSVTLAGNSS LCSISGWAIY 100

TKDNSIRIGS KGDVFVIREP FISCSHLECR TFFLTQGALL NDKHSNGTVK 150

DRSPYRALMS CPLGEAPSPY NSKFESVAWS ASACHDGMGW LTIGISGPDN 200

GAVAVLKYNG IITGTIKSWK KQILRTQESE CVCMNGSCFT IMTDGPSNKA 250

ASYKIFKIEK GKVTKSIELN APNFHYEECS CYPDTGIVMC VCRDNWHGSN 300

RPWVSFNQNL DYQIGYICSG VFGDNPRPED GEGSCNPVTV DGANGVKGFS 350

YKYDNGVWIG RTKSNRLRKG FEMIWDPNGW TNTDSDFSVK QDVVAITDWS 400

GYSGSFVQHP ELTGLDCIRP CFWVELVRGL PRENTTIWTS GSSISFCGVN 450

SDTANWSWPD GAELPFTIDK

2007 H1N1 - Optimized DNA sequence encoding the nucleic acid sequence encoding NA antigen (SEQ ID NO: 38)

ATGAACCCCAACCAGAAGATCATCACCATCGGCTCCATCTCCATCGCCATCGGCATCATCTCCCTGATGCT

GCAGATCGGCAACATCATCTCCATCTGGGCCTCCCACTCCATCCAGACCGGCTCCCAGAACAACACCGGCA

TCTGCAACCAGCGCATCATCACCTACGAGAACTCCACCTGGGTGAACCACACCTACGTGAACATCAACAAC

ACCAACGTGGTGGCCGGCGAGGACAAGACCTCCGTGACCCTGGCCGGCAACTCCTCCCTGTGCTCCATCTC

CGGCTGGGCCATCTACACCAAGGACAACTCCATCCGCATCGGCTCCAAGGGCGACGTGTTCGTGATCCGCG

AGCCCTTCATCTCCTGCTCCCACCTGGAGTGCCGCACCTTCTTCCTGACCCAGGGCGCCCTGCTGAACGAC

AAGCACTCCAACGGCACCGTGAAGGACCGCTCCCCCTACCGCGCCCTGATGTCCTGCCCCCTGGGCGAGGC

CCCCTCCCCCTACAACTCCAAGTTCGAGTCCGTGGCCTGGTCCGCCTCCGCCTGCCACGACGGCATGGGCT

GGCTGACCATCGGCATCTCCGGCCCCGACAACGGCGCCGTGGCCGTGCTGAAGTACAACGGCATCATCACC

GGCACCATCAAGTCCTGGAAGAAGCAGATCCTGCGCACCCAGGAGTCCGAGTGCGTGTGCATGAACGGCTC

CTGCTTCACCATCATGACCGACGGCCCCTCCAACAAGGCCGCCTCCTACAAGATCTTCAAGATCGAGAAGG

-continued

GCAAGGTGACCAAGTCCATCGAGCTGAACGCCCCCAACTTCCACTACGAGGAGTGCTCCTGCTACCCCGAC

ACCGGCATCGTGATGTGCGTGTGCCGCGACAACTGGCACGGCTCCAACCGCCCCTGGGTGTCCTTCAACCA

GAACCTGGACTACCAGATCGGCTACATCTGCTCCGGCGTGTTCGGCGACAACCCCCGCCCCGAGGACGGCG

AGGGCTCCTGCAACCCCGTGACCGTGGACGGCGCCAACGGCGTGAAGGGCTTCTCCTACAAGTACGACAAC

GGCGTGTGGATCGGCCGCACCAAGTCCAACCGCCTGCGCAAGGGCTTCGAGATGATCTGGGACCCCAACGG

CTGGACCAACACCGACTCCGACTTCTCCGTGAAGCAGGACGTGGTGGCCATCACCGACTGGTCCGGCTACT

CCGGCTCCTTCGTGCAGCACCCCGAGCTGACCGGCCTGGACTGCATCCGCCCCTGCTTCTGGGTGGAGCTG

GTGCGCGGCCTGCCCCGCGAGAACACCACCATCTGGACCTCCGGCTCCTCCATCTCCTTCTGCGGCGTGAA

CTCCGACACCGCCAACTGGTCCTGGCCCGACGGCGCCGAGCTGCCCTTCACCATCGACAAG

2009 H1N1 - NA antigen Amino Acid sequence (SEQ ID NO: 39)

MNPNQKIITI GSVCMTIGMA NLILQIGNII SIWISHSIQL GNQNQIETCN 050

QSVITYENNT WVNQTYVNIS NTNFAAGQSV VSVKLAGNSS LCPVSGWAIY 100

SKDNSVRIGS KGDVFVIREP FISCSPLECR TFFLTQGALL NDKHSNGTIK 150

DRSPYRTLMS CPIGEVPSPY NSRFESVAWS ASACHDGINW LTIGISGPDN 200

GAVAVLKYNG IITDTIKSWR NNILRTQESE CACVNGSCFT VMTDGPSNGQ 250

ASYKIFRIEK GKIVKSVEMN APNYHYEECS CYPDSSEITC VCRDNWHGSN 300

RPWVSFNQNL EYQIGYICSG IFGDNPRPND KTGSCGPVSS NGANGVKGFS 350

FKYGNGVWIG RTKSISSRNG FEMIWDPNGW TGTDNNFSIK QDIVGINEWS 400

GYSGSFVQHP ELTGLDCIRP CFWVELIRGR PKENTIWTSG SSISFCGVNS 450

DTVGWSWPDG AELPFTIDK

2009 H1N1 - Optimized DNA sequence encoding the
nucleic acid sequence encoding NA antigen (SEQ ID NO: 40)

ATGAACCCCAACCAGAAGATCATCACCATCGGCTCCGTGTGCATGACCATCGGCATGGCCAACCTGATCCT

GCAGATCGGCAACATCATCTCCATCTGGATCTCCCACTCCATCCAGCTGGGCAACCAGAACCAGATCGAGA

CCTGCAACCAGTCCGTGATCACCTACGAGAACAACACCTGGGTGAACCAGACCTACGTGAACATCTCCAAC

ACCAACTTCGCCGCCGGCCAGTCCGTGGTGTCCGTGAAGCTGGCCGGCAACTCCTCCCTGTGCCCCGTGTC

CGGCTGGGCCATCTACTCCAAGGACAACTCCGTGCGCATCGGCTCCAAGGGCGACGTGTTCGTGATCCGCG

AGCCCTTCATCTCCTGCTCCCCCCTGGAGTGCCGCACCTTCTTCCTGACCCAGGGCGCCCTGCTGAACGAC

AAGCACTCCAACGGCACCATCAAGGACCGCTCCCCCTACCGCACCCTGATGTCCTGCCCCATCGGCGAGGT

GCCCTCCCCCTACAACTCCCGCTTCGAGTCCGTGGCCTGGTCCGCCTCCGCCTGCCACGACGGCATCAACT

GGCTGACCATCGGCATCTCCGGCCCCGACAACGGCGCCGTGGCCGTGCTGAAGTACAACGGCATCATCACC

GACACCATCAAGTCCTGGCGCAACAACATCCTGCGCACCCAGGAGTCCGAGTGCGCCTGCGTGAACGGCTC

CTGCTTCACCGTGATGACCGACGGCCCCTCCAACGGCCAGGCCTCCTACAAGATCTTCCGCATCGAGAAGG

GCAAGATCGTGAAGTCCGTGGAGATGAACGCCCCCAACTACCACTACGAGGAGTGCTCCTGCTACCCCGAC

TCCTCCGAGATCACCTGCGTGTGCCGCGACAACTGGCACGGCTCCAACCGCCCCTGGGTGTCCTTCAACCA

GAACCTGGAGTACCAGATCGGCTACATCTGCTCCGGCATCTTCGGCGACAACCCCCGCCCCAACGACAAGA

CCGGCTCCTGCGGCCCCGTGTCCTCCAACGGCGCCAACGGCGTGAAGGGCTTCTCCTTCAAGTACGGCAAC

GGCGTGTGGATCGGCCGCACCAAGTCCATCTCCTCCCGCAACGGCTTCGAGATGATCTGGGACCCCAACGG

CTGGACCGGCACCGACAACAACTTCTCCATCAAGCAGGACATCGTGGGCATCAACGAGTGGTCCGGCTACT

CCGGCTCCTTCGTGCAGCACCCCGAGCTGACCGGCCTGGACTGCATCCGCCCCTGCTTCTGGGTGGAGCTG

-continued

ATCCGCGGCCGCCCCAAGGAGAACACCATCTGGACCTCCGGCTCCTCCATCTCCTTCTGCGGCGTGAACTC

CGACACCGTGGGCTGGTCCTGGCCCGACGGCGCCGAGCTGCCCTTCACCATCGACAAG

2015 H1N1 - NA antigen Amino Acid sequence (SEQ ID NO: 41)

MNPNQKIITI GSICMTIGMA NLILQIGXII SIWVSHSIQI GNQSQIETCN 050

QSVITYENNT WVNQTYVNIS NTNFAAGQSV VSVKLAGNSS LCPVSGWAIY 100

SKDNSVRIGS KGDVFVIREP FISCSPLECR TFFLTQGALL NDKHSNGTIK 150

DRSPYRTLMS CPIGEVPSPY NSRFESVAWS ASACHDGINW LTIGISGPDS 200

GAVAVLKYNG IITDTIKSWR NNILRTQESE CACVNGSCFT IMTDGPSDGQ 250

ASYKIFRIEK GKIIKSVEMK APNYHYEECS CYPDSSEITC VCRDNWHGSN 300

RPWVSFNQNL EYQMGYICSG VFGDNPRPND KTGSCGPVSS NGANGVKGFS 350

FKYGNGVWIG RTKSISSRKG FEMIWDPNGW TGTDNKFSIK QDIVGINEWS 400

GYSGSFVQHP ELTGLDCIRP CFWVELIRGR PEENTIWTSG SSISFCGVNS 450

DTVGWSWPDG AELPFTIDK

2015 H1N1 - Optimized DNA sequence encoding the
nucleic acid sequence encoding NA antigen (SEQ ID NO: 42)

ATGAACCCCAACCAGAAGATCATCACCATCGGCTCCATCTGCATGACCATCGGCATGGCCAACCTGATCCT

GCAGATCGGCNNNATCATCTCCATCTGGGTGTCCCACTCCATCCAGATCGGCAACCAGTCCCAGATCGAGA

CCTGCAACCAGTCCGTGATCACCTACGAGAACAACACCTGGGTGAACCAGACCTACGTGAACATCTCCAAC

ACCAACTTCGCCGCCGGCCAGTCCGTGGTGTCCGTGAAGCTGGCCGGCAACTCCTCCCTGTGCCCCGTGTC

CGGCTGGGCCATCTACTCCAAGGACAACTCCGTGCGCATCGGCTCCAAGGGCGACGTGTTCGTGATCCGCG

AGCCCTTCATCTCCTGCTCCCCCCTGGAGTGCCGCACCTTCTTCCTGACCCAGGGCGCCCTGCTGAACGAC

AAGCACTCCAACGGCACCATCAAGGACCGCTCCCCCTACCGCACCCTGATGTCCTGCCCCATCGGCGAGGT

GCCCTCCCCCTACAACTCCCGCTTCGAGTCCGTGGCCTGGTCCGCCTCCGCCTGCCACGACGGCATCAACT

GGCTGACCATCGGCATCTCCGGCCCCGACTCCGGCGCCGTGGCCGTGCTGAAGTACAACGGCATCATCACC

GACACCATCAAGTCCTGGCGCAACAACATCCTGCGCACCCAGGAGTCCGAGTGCGCCTGCGTGAACGGCTC

CTGCTTCACCATCATGACCGACGGCCCCTCCGACGGCCAGGCCTCCTACAAGATCTTCCGCATCGAGAAGG

GCAAGATCATCAAGTCCGTGGAGATGAAGGCCCCCAACTACCACTACGAGGAGTGCTCCTGCTACCCCGAC

TCCTCCGAGATCACCTGCGTGTGCCGCGACAACTGGCACGGCTCCAACCGCCCCTGGGTGTCCTTCAACCA

GAACCTGGAGTACCAGATGGGCTACATCTGCTCCGGCGTGTTCGGCGACAACCCCCGCCCCAACGACAAGA

CCGGCTCCTGCGGCCCCGTGTCCTCCAACGGCGCCAACGGCGTGAAGGGCTTCTCCTTCAAGTACGGCAAC

GGCGTGTGGATCGGCCGCACCAAGTCCATCTCCTCCCGCAAGGGCTTCGAGATGATCTGGGACCCCAACGG

CTGGACCGGCACCGACAACAAGTTCTCCATCAAGCAGGACATCGTGGGCATCAACGAGTGGTCCGGCTACT

CCGGCTCCTTCGTGCAGCACCCCGAGCTGACCGGCCTGGACTGCATCCGCCCCTGCTTCTGGGTGGAGCTG

ATCCGCGGCCGCCCCGAGGAGAACACCATCTGGACCTCCGGCTCCTCCATCTCCTTCTGCGGCGTGAACTC

CGACACCGTGGGCTGGTCCTGGCCCGACGGCGCCGAGCTGCCCTTCACCATCGACAAG

2017 H3N2 - NA antigen Amino Acid sequence (SEQ ID NO: 43)

MNPNQKIITI GSVSLTISTI CFFMQIAILI TTVTLHFKQY EFNSPPNNQV 050

MLCEPTIIER NITEIVYLTN TTIEREICPK PAEYRNWSKP QCGITGFAPF 100

SKDNSIRLSA GGDIWVTREP YVSCDPDKCY QFALGQGTTI NNVHSNNTAR 150

DRTPHRTLLM NELGVPFHLG TKQVCIAWSS SSCHDGKAWL HVCITGDDKN 200

ATASFIYNGR LVDSVVSWSK DILRTQESEC VCINGTCTVV MTDGNATGKA 250

-continued

DTKILFIEEG KIVHTSKLSG SAQHVEECSC YPRYPGVRCV CRDNWKGSNR 300

PIVDINIKDH SIVSSYVCSG LVGDTPRKTD SSSSSHCLNP NNEKGGHGVK 350

GWAFDDGNDV WMGRTINETS RLGYETFKVV EGWSNPKSKL QINRQVIVDR 400

GDRSGYSGIF SVEGKSCINR CFYVELIRGR KEETEVLWTS NSIVVFCGTS 450

GTYGTGSWPD GADLNLMHI

2017 H3N2 - Optimized DNA sequence encoding the
nucleic acid sequence encoding NA antigen (SEQ ID NO: 44)

ATGAACCCCAACCAGAAGATCATCACCATCGGCTCCGTGTCCCTGACCATCTCCACCATCTGCTTCTTCAT

GCAGATCGCCATCCTGATCACCACCGTGACCCTGCACTTCAAGCAGTACGAGTTCAACTCCCCCCCCAACA

ACCAGGTGATGCTGTGCGAGCCCACCATCATCGAGCGCAACATCACCGAGATCGTGTACCTGACCAACACC

ACCATCGAGCGCGAGATCTGCCCCAAGCCCGCCGAGTACCGCAACTGGTCCAAGCCCCAGTGCGGCATCAC

CGGCTTCGCCCCCTTCTCCAAGGACAACTCCATCCGCCTGTCCGCCGGCGGCGACATCTGGGTGACCCGCG

AGCCCTACGTGTCCTGCGACCCCGACAAGTGCTACCAGTTCGCCCTGGGCCAGGGCACCACCATCAACAAC

GTGCACTCCAACAACACCGCCCGCGACCGCACCCCCCACCGCACCCTGCTGATGAACGAGCTGGGCGTGCC

CTTCCACCTGGGCACCAAGCAGGTGTGCATCGCCTGGTCCTCCTCCTCCTGCCACGACGGCAAGGCCTGGC

TGCACGTGTGCATCACCGGCGACGACAAGAACGCCACCGCCTCCTTCATCTACAACGGCCGCCTGGTGGAC

TCCGTGGTGTCCTGGTCCAAGGACATCCTGCGCACCCAGGAGTCCGAGTGCGTGTGCATCAACGGCACCTG

CACCGTGGTGATGACCGACGGCAACGCCACCGGCAAGGCCGACACCAAGATCCTGTTCATCGAGGAGGGCA

AGATCGTGCACACCTCCAAGCTGTCCGGCTCCGCCCAGCACGTGGAGGAGTGCTCCTGCTACCCCCGCTAC

CCCGGCGTGCGCTGCGTGTGCCGCGACAACTGGAAGGGCTCCAACCGCCCCATCGTGGACATCAACATCAA

GGACCACTCCATCGTGTCCTCCTACGTGTGCTCCGGCCTGGTGGGCGACACCCCCCGCAAGACCGACTCCT

CCTCCTCCTCCCACTGCCTGAACCCCAACAACGAGAAGGGCGGCCACGGCGTGAAGGGCTGGGCCTTCGAC

GACGGCAACGACGTGTGGATGGGCCGCACCATCAACGAGACCTCCCGCCTGGGCTACGAGACCTTCAAGGT

GGTGGAGGGCTGGTCCAACCCCAAGTCCAAGCTGCAGATCAACCGCCAGGTGATCGTGGACCGCGGCGACC

GCTCCGGCTACTCCGGCATCTTCTCCGTGGAGGGCAAGTCCTGCATCAACCGCTGCTTCTACGTGGAGCTG

ATCCGCGGCCGCAAGGAGGAGACCGAGGTGCTGTGGACCTCCAACTCCATCGTGGTGTTCTGCGGCACCTC

CGGCACCTACGGCACCGGCTCCTGGCCCGACGGCGCCGACCTGAACCTGATGCACATC

2017 Influenza B (Victoria lineage) - NA antigen
Amino Acid sequence (SEQ ID NO: 45)

MLPSTIQTLT LFLTSGGVLL SLYVSASLSY LLYSDILLKF SPTEITAPTM 050

PLDCANASNV QAVNRSATKG VTLLLPEPEW TYPRLSCPGS TFQKALLISP 100

HRFGETKGNS APLIIREPFV ACGPNECKHF ALTHYAAQPG GYYNGTRGDR 150

NKLRHLISVK LGKIPTVENS IFHMAAWSGS ACHDGKEWTY IGVDGPDNNA 200

LLKVKYGEAY TDTYHSYANN ILRTQESACN CIGGNCYLMI TDGSASGVSE 250

CRFLKIREGR IIKEIFPTGR VKHTEECTCG FASNKTIECA CRDNRYTAKR 300

PFVKLNVETD TAEIRLMCTD TYLDTPRPND GSITGPCESD GDKGSGGIKG 350

GFVHQRMKSK IGRWYSRTMS QTERMGMGLY VKYGGDPWAD SDALAFSGVM 400

VSMKEPGWYS FGFEIKDKKC DVPCIGIEMV HDGGKETWHS AATAIYCLMG 450

SGQLLWDTVT GVDMAL

-continued

2017 Influenza B (Victoria lineage) - Optimized DNA sequence encoding the nucleic acid sequence encoding NA antigen (SEQ ID NO: 46)

ATGCTGCCCTCCACCATCCAGACCCTGACCCTGTTCCTGACCTCCGGCGGCGTGCTGCTGTCCCTGTACGT

GTCCGCCTCCCTGTCCTACCTGCTGTACTCCGACATCCTGCTGAAGTTCTCCCCCACCGAGATCACCGCCC

CCACCATGCCCCTGGACTGCGCCAACGCCTCCAACGTGCAGGCCGTGAACCGCTCCGCCACCAAGGGCGTG

ACCCTGCTGCTGCCCGAGCCCGAGTGGACCTACCCCCGCCTGTCCTGCCCCGGCTCCACCTTCCAGAAGGC

CCTGCTGATCTCCCCCCACCGCTTCGGCGAGACCAAGGGCAACTCCGCCCCCCTGATCATCCGCGAGCCCT

TCGTGGCCTGCGGCCCCAACGAGTGCAAGCACTTCGCCCTGACCCACTACGCCGCCCAGCCCGGCGGCTAC

TACAACGGCACCCGCGGCGACCGCAACAAGCTGCGCCACCTGATCTCCGTGAAGCTGGGCAAGATCCCCAC

CGTGGAGAACTCCATCTTCCACATGGCCGCCTGGTCCGGCTCCGCCTGCCACGACGGCAAGGAGTGGACCT

ACATCGGCGTGGACGGCCCCGACAACAACGCCCTGCTGAAGGTGAAGTACGGCGAGGCCTACACCGACACC

TACCACTCCTACGCCAACAACATCCTGCGCACCCAGGAGTCCGCCTGCAACTGCATCGGCGGCAACTGCTA

CCTGATGATCACCGACGGCTCCGCCTCCGGCGTGTCCGAGTGCCGCTTCCTGAAGATCCGCGAGGGCCGCA

TCATCAAGGAGATCTTCCCCACCGGCCGCGTGAAGCACACCGAGGAGTGCACCTGCGGCTTCGCCTCCAAC

AAGACCATCGAGTGCGCCTGCCGCGACAACCGCTACACCGCCAAGCGCCCCTTCGTGAAGCTGAACGTGGA

GACCGACACCGCCGAGATCCGCCTGATGTGCACCGACACCTACCTGGACACCCCCCGCCCCAACGACGGCT

CCATCACCGGCCCCTGCGAGTCCGACGGCGACAAGGGCTCCGGCGGCATCAAGGGCGGCTTCGTGCACCAG

CGCATGAAGTCCAAGATCGGCCGCTGGTACTCCCGCACCATGTCCCAGACCGAGCGCATGGGCATGGGCCT

GTACGTGAAGTACGGCGGCGACCCCTGGGCCGACTCCGACGCCCTGGCCTTCTCCGGCGTGATGGTGTCCA

TGAAGGAGCCCGGCTGGTACTCCTTCGGCTTCGAGATCAAGGACAAGAAGTGCGACGTGCCCTGCATCGGC

ATCGAGATGGTGCACGACGGCGGCAAGGAGACCTGGCACTCCGCCGCCACCGCCATCTACTGCCTGATGGG

CTCCGGCCAGCTGCTGTGGGACACCGTGACCGGCGTGGACATGGCCCTG

2013 Influenza B (Yamagata lineage) - Sequence only on GISAID - NA antigen Amino Acid sequence (SEQ ID NO: 47)

0001 MLPSTIQTLT LFLTSGGVLL SLYVSASLSY LLYSDILLKF SRTEVTAPIM PLDCANASNV

QAVNRSATKG VTPLLPEPEW

0081 TYPRLSCPGS TFQKALLISP HRFGETKGNS APLIIREPFI ACGPKECKHF ALTHYAAQPG

GYYNGTREDR NKLRHLISVK

0161 LGKIPTVENS IFHMAAWSGS ACHDGREWTY IGVDGPDSNA LLKIKYGEAY TDTYHSYAKN

ILRTQESACN CIGGDCYLMI

0241 TDGPASGISE CRFLKIREGR IIKEIFPTGR VKHTEECTCG FASNKTIECA CRDNSYTAKR

PFVKLNVETD TAEIRLMCTK

0321 TYLDTPRPND GSITGPCESD GDEGSGGIKG GFVHQRMASK IGRWYSRTMS KTKRMGMGLY

VKYDGDPWTD SEALALSGVM

0401 VSMEEPGWYS FGFEIKDKKC DVPCIGIEMV HDGGKTTWHS AATAIYCLMG SGQLLWDTVT

GVNMTL

2013 Influenza B (Yamagata lineage) - Sequence only on GISAID - Optimized DNA sequence encoding the nucleic acid sequence encoding NA antigen (SEQ ID NO: 48)

ATGCTGCCCTCCACCATCCAGACCCTGACCCTGTTCCTGACCTCCGGCGGCGTGCTGCTGTCCCTGTACGT

GTCCGCCTCCCTGTCCTACCTGCTGTACTCCGACATCCTGCTGAAGTTCTCCCGCACCGAGGTGACCGCCC

CCATCATGCCCCTGGACTGCGCCAACGCCTCCAACGTGCAGGCCGTGAACCGCTCCGCCACCAAGGGCGTG

-continued

ACCCCCCTGCTGCCCGAGCCCGAGTGGACCTACCCCCGCCTGTCCTGCCCCGGCTCCACCTTCCAGAAGGC

CCTGCTGATCTCCCCCCACCGCTTCGGCGAGACCAAGGGCAACTCCGCCCCCCTGATCATCCGCGAGCCCT

TCATCGCCTGCGGCCCCAAGGAGTGCAAGCACTTCGCCCTGACCCACTACGCCGCCCAGCCCGGCGGCTAC

TACAACGGCACCCGCGAGGACCGCAACAAGCTGCGCCACCTGATCTCCGTGAAGCTGGGCAAGATCCCCAC

CGTGGAGAACTCCATCTTCCACATGGCCGCCTGGTCCGGCTCCGCCTGCCACGACGGCCGCGAGTGGACCT

ACATCGGCGTGGACGGCCCCGACTCCAACGCCCTGCTGAAGATCAAGTACGGCGAGGCCTACACCGACACC

TACCACTCCTACGCCAAGAACATCCTGCGCACCCAGGAGTCCGCCTGCAACTGCATCGGCGGCGACTGCTA

CCTGATGATCACCGACGGCCCCGCCTCCGGCATCTCCGAGTGCCGCTTCCTGAAGATCCGCGAGGGCCGCA

TCATCAAGGAGATCTTCCCCACCGGCCGCGTGAAGCACACCGAGGAGTGCACCTGCGGCTTCGCCTCCAAC

AAGACCATCGAGTGCGCCTGCCGCGACAACTCCTACACCGCCAAGCGCCCCTTCGTGAAGCTGAACGTGGA

GACCGACACCGCCGAGATCCGCCTGATGTGCACCAAGACCTACCTGGACACCCCCCGCCCCAACGACGGCT

CCATCACCGGCCCCTGCGAGTCCGACGGCGACGAGGGCTCCGGCGGCATCAAGGGCGGCTTCGTGCACCAG

CGCATGGCCTCCAAGATCGGCCGCTGGTACTCCCGCACCATGTCCAAGACCAAGCGCATGGGCATGGGCCT

GTACGTGAAGTACGACGGCGACCCCTGGACCGACTCCGAGGCCCTGGCCCTGTCCGGCGTGATGGTGTCCA

TGGAGGAGCCCGGCTGGTACTCCTTCGGCTTCGAGATCAAGGACAAGAAGTGCGACGTGCCCTGCATCGGC

ATCGAGATGGTGCACGACGGCGGCAAGACCACCTGGCACTCCGCCGCCACCGCCATCTACTGCCTGATGGG

CTCCGGCCAGCTGCTGTGGGACACCGTGACCGGCGTGAACATGACCCTG

2015 H5N1 - NA antigen Amino Acid sequence (SEQ ID NO: 49)

MNPNQKIITI GSICMIIGIV SLMLQIGNMI SILVSHSIQT GNQHQAEPIR 050

NTNFLTENAV ASITLTGSSS LCPIRGWAVH SKDNSIRIGS KGDVFVIREP 100

FISCSHMECR TFFLTHGALL NDKHSNGTVK DRSPHRTLMS CPVGEAPSPY 150

NSRFESVAWS ASACHDGTSW LTIGISGPDN GAVAVLKYNG IITDTIKSWR 200

NNILRTQESE CACVNGSCFT VMTDGPSNGQ ASYKIFKIEK GKVVKSVELN 250

APNYHYEECS CYPDSGEIMC VCRDNWHGSN RPWVTFNQNL EYQIGYICSG 300

VFGDNPRPND GTGSCGPMSL NGAYGIKGFS FKYGNGVWIG RTKSTNSRSG 350

FEMIWDPNGW TGTDSEFSVK QDIVAITDWS GYSGSFVQHP ELTGLDCIRP 400

CFWVELIRGR PKESTIWTSG SSISFCGVNS DTVSWSWPDG AELPFTIDK

2015 H5N1 - Optimized DNA sequence encoding the nucleic acid sequence encoding NA antigen (SEQ ID NO: 50)

ATGAACCCCAACCAGAAGATCATCACCATCGGCTCCATCTGCATGATCATCGGCATCGTGTCCCTGATGCT

GCAGATCGGCAACATGATCTCCATCCTGGTGTCCCACTCCATCCAGACCGGCAACCAGCACCAGGCCGAGC

CCATCCGCAACACCAACTTCCTGACCGAGAACGCCGTGGCCTCCATCACCCTGACCGGCTCCTCCTCCCTG

TGCCCCATCCGCGGCTGGGCCGTGCACTCCAAGGACAACTCCATCCGCATCGGCTCCAAGGGCGACGTGTT

CGTGATCCGCGAGCCCTTCATCTCCTGCTCCCACATGGAGTGCCGCACCTTCTTCCTGACCCACGGCGCCC

TGCTGAACGACAAGCACTCCAACGGCACCGTGAAGGACCGCTCCCCCCACCGCACCCTGATGTCCTGCCCC

GTGGGCGAGGCCCCCTCCCCCTACAACTCCCGCTTCGAGTCCGTGGCCTGGTCCGCCTCCGCCTGCCACGA

CGGCACCTCCTGGCTGACCATCGGCATCTCCGGCCCCGACAACGGCGCCGTGGCCGTGCTGAAGTACAACG

GCATCATCACCGACACCATCAAGTCCTGGCGCAACAACATCCTGCGCACCCAGGAGTCCGAGTGCGCCTGC

GTGAACGGCTCCTGCTTCACCGTGATGACCGACGGCCCCTCCAACGGCCAGGCCTCCTACAAGATCTTCAA

GATCGAGAAGGGCAAGGTGGTGAAGTCCGTGGAGCTGAACGCCCCCAACTACCACTACGAGGAGTGCTCCT

GCTACCCCGACTCCGGCGAGATCATGTGCGTGTGCCGCGACAACTGGCACGGCTCCAACCGCCCCTGGGTG

-continued

ACCTTCAACCAGAACCTGGAGTACCAGATCGGCTACATCTGCTCCGGCGTGTTCGGCGACAACCCCCGCCC

CAACGACGGCACCGGCTCCTGCGGCCCCATGTCCCTGAACGGCGCCTACGGCATCAAGGGCTTCTCCTTCA

AGTACGGCAACGGCGTGTGGATCGGCCGCACCAAGTCCACCAACTCCCGCTCCGGCTTCGAGATGATCTGG

GACCCCAACGGCTGGACCGGCACCGACTCCGAGTTCTCCGTGAAGCAGGACATCGTGGCCATCACCGACTG

GTCCGGCTACTCCGGCTCCTTCGTGCAGCACCCCGAGCTGACCGGCCTGGACTGCATCCGCCCCTGCTTCT

GGGTGGAGCTGATCCGCGGCCGCCCCAAGGAGTCCACCATCTGGACCTCCGGCTCCTCCATCTCCTTCTGC

GGCGTGAACTCCGACACCGTGTCCTGGTCCTGGCCCGACGGCGCCGAGCTGCCCTTCACCATCGACAAG

2017 H7N9 - NA antigen Amino Acid sequence (SEQ ID NO: 51)

MNPNQKILCT SATAITIGAI AVLIGIANLG LNIGLHLKPG CNCSHSQPEI 050

TNTSQTIINN YYSETNITNI QMEERTSKNF NNLTKGLCTI NSWHIYGKDN 100

AVRIGESSDV LVTREPYVSC DPDECRFYAL SQGTTIRGKH SNGTIHDRSQ 150

YRALISWPLS SPPTVYNSRV ECIGWSSTSC HDGKSRMSIC ISGPNNNASA 200

VVWYNRRPVA EINTWARNIL RTQESECVCH NGICPVVFTD GSATGPADTR 250

IYYFKEGKIL KWESLTGTAK HVEECSCYGE RTGITCTCRD NWQGSNRPVI 300

QIDPVAMTHT SQYICSPVLT DNPRPNDPNI GKCNDPYPGN NNNGIKGFSY 350

LDGDNTWLGR TISTASRSGY EVLKVPNALT DDRSKPIQGQ TIVLNADWSG 400

YSGSFMDYWA DGDCYRACFY VELIRGRPKE DKVWWTSNSI VSMCSSTEFL 450

GQWNWPDGAK IEYFL

2017 H7N9 - Optimized DNA sequence encoding
the nucleic acid sequence encoding NA antigen (SEQ ID NO: 52)

ATGAACCCCAACCAGAAGATCCTGTGCACCTCCGCCACCGCCATCACCATCGGCGCCATCGCCGTGCTGAT

CGGCATCGCCAACCTGGGCCTGAACATCGGCCTGCACCTGAAGCCCGGCTGCAACTGCTCCCACTCCCAGC

CCGAGATCACCAACACCTCCCAGACCATCATCAACAACTACTACTCCGAGACCAACATCACCAACATCCAG

ATGGAGGAGCGCACCTCCAAGAACTTCAACAACCTGACCAAGGGCCTGTGCACCATCAACTCCTGGCACAT

CTACGGCAAGGACAACGCCGTGCGCATCGGCGAGTCCTCCGACGTGCTGGTGACCCGCGAGCCCTACGTGT

CCTGCGACCCCGACGAGTGCCGCTTCTACGCCCTGTCCCAGGGCACCACCATCCGCGGCAAGCACTCCAAC

GGCACCATCCACGACCGCTCCCAGTACCGCGCCCTGATCTCCTGGCCCCTGTCCTCCCCCCCCACCGTGTA

CAACTCCCGCGTGGAGTGCATCGGCTGGTCCTCCACCTCCTGCCACGACGGCAAGTCCCGCATGTCCATCT

GCATCTCCGGCCCCAACAACAACGCCTCCGCCGTGGTGTGGTACAACCGCCGCCCCGTGGCCGAGATCAAC

ACCTGGGCCCGCAACATCCTGCGCACCCAGGAGTCCGAGTGCGTGTGCCACAACGGCATCTGCCCCGTGGT

GTTCACCGACGGCTCCGCCACCGGCCCCGCCGACACCCGCATCTACTACTTCAAGGAGGGCAAGATCCTGA

AGTGGGAGTCCCTGACCGGCACCGCCAAGCACGTGGAGGAGTGCTCCTGCTACGGCGAGCGCACCGGCATC

ACCTGCACCTGCCGCGACAACTGGCAGGGCTCCAACCGCCCCGTGATCCAGATCGACCCCGTGGCCATGAC

CCACACCTCCCAGTACATCTGCTCCCCCGTGCTGACCGACAACCCCCGCCCCAACGACCCCAACATCGGCA

AGTGCAACGACCCCTACCCCGGCAACAACAACAACGGCATCAAGGGCTTCTCCTACCTGGACGGCGACAAC

ACCTGGCTGGGCCGCACCATCTCCACCGCCTCCCGCTCCGGCTACGAGGTGCTGAAGGTGCCCAACGCCCT

GACCGACGACCGCTCCAAGCCCATCCAGGGCCAGACCATCGTGCTGAACGCCGACTGGTCCGGCTACTCCG

GCTCCTTCATGGACTACTGGGCCGACGGCGACTGCTACCGCGCCTGCTTCTACGTGGAGCTGATCCGCGGC

CGCCCCAAGGAGGACAAGGTGTGGTGGACCTCCAACTCCATCGTGTCCATGTGCTCCTCCACCGAGTTCCT

GGGCCAGTGGAACTGGCCCGACGGCGCCAAGATCGAGTACTTCCTG

-continued

2013 H10N8 - NA antigen Amino Acid sequence (SEQ ID NO: 53)

MNPNQKIITI GSVSLGLVIL NILLHIVSIT VTVLVLPGNG NNESCNETVI 050

REYNETVRVE KVTQWHNTNV IEYIERPEND HFMNNTEALC DAKGFAPFSK 100

DNGIRIGSRG HVFVIREPFV SCSPTECRTF FLTQGSLLND KHSNGTVKDR 150

SPYRTLMSVE IGQSPNVYQA RFEAVAWSAT ACHDGKKWMT IGVTGPDAKA 200

VAVVHYGGIP TDVINSWAGD ILRTQESSCT CIQGECFWVM TDGPANRQAQ 250

YRAFKAKQGK IVGQAEISFN GGHIEECSCY PNEGKVECVC KDNWTGTNRP 300

VLVISPDLSY RVGYLCAGLP SDTPRGEDSQ FTGSCTSPMG NQGYGVKGFG 350

FRQGNDVWMG RTISRTSRSG FEILKVRNGW VQNSKEQIKR QVVVDNLNWS 400

GYSGSFTLPA ELTKRNCLVP CFWVEMIRGN PEEKTIWTSS SSIVMCGVDH 450

EIADWSWHDG AILPFDIDKM

2013 H10N8 - Optimized DNA sequence encoding the nucleic acid sequence encoding NA antigen (SEQ ID NO: 54)

ATGAACCCCAACCAGAAGATCATCACCATCGGCTCCGTGTCCCTGGGCCTGGTGATCCTGAACATCCTGCT

GCACATCGTGTCCATCACCGTGACCGTGCTGGTGCTGCCCGGCAACGGCAACAACGAGTCCTGCAACGAGA

CCGTGATCCGCGAGTACAACGAGACCGTGCGCGTGGAGAAGGTGACCCAGTGGCACAACACCAACGTGATC

GAGTACATCGAGCGCCCCGAGAACGACCACTTCATGAACAACACCGAGGCCCTGTGCGACGCCAAGGGCTT

CGCCCCCTTCTCCAAGGACAACGGCATCCGCATCGGCTCCCGCGGCCACGTGTTCGTGATCCGCGAGCCCT

TCGTGTCCTGCTCCCCCACCGAGTGCCGCACCTTCTTCCTGACCCAGGGCTCCCTGCTGAACGACAAGCAC

TCCAACGGCACCGTGAAGGACCGCTCCCCCTACCGCACCCTGATGTCCGTGGAGATCGGCCAGTCCCCCAA

CGTGTACCAGGCCCGCTTCGAGGCCGTGGCCTGGTCCGCCACCGCCTGCCACGACGGCAAGAAGTGGATGA

CCATCGGCGTGACCGGCCCCGACGCCAAGGCCGTGGCCGTGGTGCACTACGGCGGCATCCCCACCGACGTG

ATCAACTCCTGGGCCGGCGACATCCTGCGCACCCAGGAGTCCTCCTGCACCTGCATCCAGGGCGAGTGCTT

CTGGGTGATGACCGACGGCCCCGCCAACCGCCAGGCCCAGTACCGCGCCTTCAAGGCCAAGCAGGGCAAGA

TCGTGGGCCAGGCCGAGATCTCCTTCAACGGCGGCCACATCGAGGAGTGCTCCTGCTACCCCAACGAGGGC

AAGGTGGAGTGCGTGTGCAAGGACAACTGGACCGGCACCAACCGCCCCGTGCTGGTGATCTCCCCCGACCT

GTCCTACCGCGTGGGCTACCTGTGCGCCGGCCTGCCCTCCGACACCCCCCGCGGCGAGGACTCCCAGTTCA

CCGGCTCCTGCACCTCCCCCATGGGCAACCAGGGCTACGGCGTGAAGGGCTTCGGCTTCCGCCAGGGCAAC

GACGTGTGGATGGGCCGCACCATCTCCCGCACCTCCCGCTCCGGCTTCGAGATCCTGAAGGTGCGCAACGG

CTGGGTGCAGAACTCCAAGGAGCAGATCAAGCGCCAGGTGGTGGTGGACAACCTGAACTGGTCCGGCTACT

CCGGCTCCTTCACCCTGCCCGCCGAGCTGACCAAGCGCAACTGCCTGGTGCCCTGCTTCTGGGTGGAGATG

ATCCGCGGCAACCCCGAGGAGAAGACCATCTGGACCTCCTCCTCCTCCATCGTGATGTGCGGCGTGGACCA

CGAGATCGCCGACTGGTCCTGGCACGACGGCGCCATCCTGCCCTTCGACATCGACAAGATG

NP Sequence

1918 H1N1 - NP antigen Amino Acid sequence (SEQ ID NO: 55)

MASQGTKRSY EQMETDGERQ NATEIRASVG RMIGGIGRFY IQMCTELKLS 050

DYEGRLIQNS ITIERMVLSA FDERRNKYLE EHPSAGKDPK KTGGPIYRRI 100

DGKWMRELIL YDKEEIRRIW RQANNGEDAT AGLTHMMIWH SNLNDATYQR 150

TRALVRTGMD PRMCSLMQGS TLPRRSGAAG AAVKGVGTMV MELIRMIKRG 200

INDRNFWRGE NGRRTRIAYE RMCNILKGKF QTAAQRAMMD QVRESRNPGN 250

AEIEDLIFLA RSALILRGSV AHKSCLPACV YGPAVASGYD FEREGYSLVG 300

-continued

IDPFRLLQNS QVYSLIRPNE NPAHKSQLVW MACHSAAFED LRVSSFIRGT 350

RVVPRGKLST RGVQIASNEN METMDSSTLE LRSRYWAIRT RSGGNTNQQR 400

ASAGQISVQP TFSVQRNLPF ERATIMAAFT GNTEGRTSDM RTEIIRMMEG 450

ARPEDVSFQG RGVFELSDEK ATSPIVPSFD MSNEGSYFFG DNAEEYDN 498

1918 H1N1 - Optimized DNA sequence encoding
the nucleic acid sequence encoding NP antigen (SEQ ID NO: 56)

ATGGCCTCCCAGGGCACCAAGCGCTCCTACGAGCAGATGGAGACCGACGGCGAGCGCCAGAACGCCACCGA

GATCCGCGCCTCCGTGGGCCGCATGATCGGCGGCATCGGCCGCTTCTACATCCAGATGTGCACCGAGCTGA

AGCTGTCCGACTACGAGGGCCGCCTGATCCAGAACTCCATCACCATCGAGCGCATGGTGCTGTCCGCCTTC

GACGAGCGCCGCAACAAGTACCTGGAGGAGCACCCCTCCGCCGGCAAGGACCCCAAGAAGACCGGCGGCCC

CATCTACCGCCGCATCGACGGCAAGTGGATGCGCGAGCTGATCCTGTACGACAAGGAGGAGATCCGCCGCA

TCTGGCGCCAGGCCAACAACGGCGAGGACGCCACCGCCGGCCTGACCCACATGATGATCTGGCACTCCAAC

CTGAACGACGCCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCGTGGGCACCATGG

TGATGGAGCTGATCCGCATGATCAAGCGCGGCATCAACGACCGCAACTTCTGGCGCGGCGAGAACGGCCGC

CGCACCCGCATCGCCTACGAGCGCATGTGCAACATCCTGAAGGGCAAGTTCCAGACCGCCGCCCAGCGCGC

CATGATGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGTGTACGGCCCCGCC

GTGGCCTCCGGCTACGACTTCGAGCGCGAGGGCTACTCCCTGGTGGGCATCGACCCCTTCCGCCTGCTGCA

GAACTCCCAGGTGTACTCCCTGATCCGCCCCAACGAGAACCCCGCCCACAAGTCCCAGCTGGTGTGGATGG

CCTGCCACTCCGCCGCCTTCGAGGACCTGCGCGTGTCCTCCTTCATCCGCGGCACCCGCGTGGTGCCCCGC

GGCAAGCTGTCCACCCGCGGCGTGCAGATCGCCTCCAACGAGAACATGGAGACCATGGACTCCTCCACCCT

GGAGCTGCGCTCCCGCTACTGGGCCATCCGCACCCGCTCCGGCGGCAACACCAACCAGCAGCGCGCCTCCG

CCGGCCAGATCTCCGTGCAGCCCACCTTCTCCGTGCAGCGCAACCTGCCCTTCGAGCGCGCCACCATCATG

GCCGCCTTCACCGGCAACACCGAGGGCCGCACCTCCGACATGCGCACCGAGATCATCCGCATGATGGAGTC

CGCCCGCCCCGAGGACGTGTCCTTCCAGGGCCGCGGCGTGTTCGAGCTGTCCGACGAGAAGGCCACCTCCC

CCATCGTGCCCTCCTTCGACATGTCCAACGAGGGCTCCTACTTCTTCGGCGACAACGCCGAGGAGTACGAC

AAC

1957 H2N2 - NP antigen Amino Acid sequence (SEQ ID NO: 57)

MASQGTKRSY EQMETDGERQ NATEIRASVG KMIDGIGRFY IQMCTELKLS 050

DYEGRLIQNS LTIERMVLSA FDERRNKYLE EHPSAGKDPK KTGGPIYKRV 100

DGKWMRELVL YDKEEIRRIW RQANNGDDAT AGLTHMMIWH SNLNDTTYQR 150

TRALVRTGMD PRMCSLMQGS TLPRRSGAAG AAVKGVGTMV MELIRMIKRG 200

INDRNFWRGE NGRKTRSAYE RMCNILKGKF QTAAQRAMMD QVRESRNPGN 250

AEIEDLIFLA RSALILRGSV AHKSCLPACV YGPAVASGYV FEKEGYSLVG 300

IDPFKLLQNS QVYSLIRPNE NPAHKSQLVW MACNSAAFED LRVLSFIRGT 350

KVSPRGKLST RGVQIASNEN MDTMESSTLE LRSRYWAIRT RSGGNTNQQR 400

ASAGQISVQP AFSVQRNLPF DKPTIMAAFT GNTEGRTSDM RAEIIRMMEG 450

AKPEEMSFQG RGVFELSDEK ATNPIVPSFD MSNEGSYFFG DNAEEYDN 498

-continued

1957 H2N2 - Optimized DNA sequence encoding the nucleic acid sequence encoding NP antigen (SEQ ID NO: 58)

ATGGCCTCCCAGGGCACCAAGCGCTCCTACGAGCAGATGGAGACCGACGGCGAGCGCCAGAACGCCACCGA

GATCCGCGCCTCCGTGGGCAAGATGATCGACGGCATCGGCCGCTTCTACATCCAGATGTGCACCGAGCTGA

AGCTGTCCGACTACGAGGGCCGCCTGATCCAGAACTCCCTGACCATCGAGCGCATGGTGCTGTCCGCCTTC

GACGAGCGCCGCAACAAGTACCTGGAGGAGCACCCCTCCGCCGGCAAGGACCCCAAGAAGACCGGCGGCCC

CATCTACAAGCGCGTGGACGGCAAGTGGATGCGCGAGCTGGTGCTGTACGACAAGGAGGAGATCCGCCGCA

TCTGGCGCCAGGCCAACAACGGCGACGACGCCACCGCCGGCCTGACCCACATGATGATCTGGCACTCCAAC

CTGAACGACACCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCGTGGGCACCATGG

TGATGGAGCTGATCCGCATGATCAAGCGCGGCATCAACGACCGCAACTTCTGGCGCGGCGAGAACGGCCGC

AAGACCCGCTCCGCCTACGAGCGCATGTGCAACATCCTGAAGGGCAAGTTCCAGACCGCCGCCCAGCGCGC

CATGATGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGTGTACGGCCCCGCC

GTGGCCTCCGGCTACGTGTTCGAGAAGGAGGGCTACTCCCTGGTGGGCATCGACCCCTTCAAGCTGCTGCA

GAACTCCCAGGTGTACTCCCTGATCCGCCCCAACGAGAACCCCGCCCACAAGTCCCAGCTGGTGTGGATGG

CCTGCAACTCCGCCGCCTTCGAGGACCTGCGCGTGCTGTCCTTCATCCGCGGCACCAAGGTGTCCCCCCGC

GGCAAGCTGTCCACCCGCGGCGTGCAGATCGCCTCCAACGAGAACATGGACACCATGGAGTCCTCCACCCT

GGAGCTGCGCTCCCGCTACTGGGCCATCCGCACCCGCTCCGGCGGCAACACCAACCAGCAGCGCGCCTCCG

CCGGCCAGATCTCCGTGCAGCCCGCCTTCTCCGTGCAGCGCAACCTGCCCTTCGACAAGCCCACCATCATG

GCCGCCTTCACCGGCAACACCGAGGGCCGCACCTCCGACATGCGCGCCGAGATCATCCGCATGATGGAGGG

CGCCAAGCCCGAGGAGATGTCCTTCCAGGGCCGCGGCGTGTTCGAGCTGTCCGACGAGAAGGCCACCAACC

CCATCGTGCCCTCCTTCGACATGTCCAACGAGGGCTCCTACTTCTTCGGCGACAACGCCGAGGAGTACGAC

AAC

1968 H3N2 - NP antigen Amino Acid sequence (SEQ ID NO: 59)

MASQGTKRSY EQMETDGERQ NATEIRASVG KMIDGIGRFY IQMCTELKLS 050

DYEGRLIQNS LTIERMVLSA FDERRNKYLE EHPSAGKDPK KTGGPIYKRV 100

DRKWMRELVL YDKEEIRRIW RQANNGDDAT AGLTHMMIWH SNLNDTTYQR 150

TRALVRTGMD PRMCSLMQGS TLPRRSGAAG AAVKGVGTMV MELIRMIKRG 200

INDRNFWRGE NGRKTRSAYE RMCNILKGKF QTAAQRAMMD QVRESRNPGN 250

AEIEDLIFLA RSALILRGSV AHKSCLPACV YGPAVASGYD FEKEGYSLVG 300

IDPFKLLQNS QVYSLIRPNE NPAHKSQLVW MACNSAAFED LRVLSFIRGT 350

KVSPRGKLST RGVQIASNEN MDAMESSTLE LRSRYWAIRT RSGGNTNQQR 400

ASAGQISVQP AFSVQRNLPF DKPTIMAAFT GNTEGRTSDM RAEIIRMMEG 450

AKPEEMSFQG RGVFELSDER AANPIVPSFD MSNEGSYFFG DNAEEYDN 498

1968 H3N2 - Optimized DNA sequence encoding the nucleic acid sequence encoding NP antigen (SEQ ID NO: 60)

ATGGCCTCCCAGGGCACCAAGCGCTCCTACGAGCAGATGGAGACCGACGGCGAGCGCCAGAACGCCACCGA

GATCCGCGCCTCCGTGGGCAAGATGATCGACGGCATCGGCCGCTTCTACATCCAGATGTGCACCGAGCTGA

AGCTGTCCGACTACGAGGGCCGCCTGATCCAGAACTCCCTGACCATCGAGCGCATGGTGCTGTCCGCCTTC

GACGAGCGCCGCAACAAGTACCTGGAGGAGCACCCCTCCGCCGGCAAGGACCCCAAGAAGACCGGCGGCCC

-continued

CATCTACAAGCGCGTGGACCGCAAGTGGATGCGCGAGCTGGTGCTGTACGACAAGGAGGAGATCCGCCGCA

TCTGGCGCCAGGCCAACAACGGCGACGACGCCACCGCCGGCCTGACCCACATGATGATCTGGCACTCCAAC

CTGAACGACACCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCGTGGGCACCATGG

TGATGGAGCTGATCCGCATGATCAAGCGCGGCATCAACGACCGCAACTTCTGGCGCGGCGAGAACGGCCGC

AAGACCCGCTCCGCCTACGAGCGCATGTGCAACATCCTGAAGGGCAAGTTCCAGACCGCCGCCCAGCGCGC

CATGATGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGTGTACGGCCCCGCC

GTGGCCTCCGGCTACGACTTCGAGAAGGAGGGCTACTCCCTGGTGGGCATCGACCCCTTCAAGCTGCTGCA

GAACTCCCAGGTGTACTCCCTGATCCGCCCCAACGAGAACCCCGCCCACAAGTCCCAGCTGGTGTGGATGG

CCTGCAACTCCGCCGCCTTCGAGGACCTGCGCGTGCTGTCCTTCATCCGCGGCACCAAGGTGTCCCCCCGC

GGCAAGCTGTCCACCCGCGGCGTGCAGATCGCCTCCAACGAGAACATGGACGCCATGGAGTCCTCCACCCT

GGAGCTGCGCTCCCGCTACTGGGCCATCCGCACCCGCTCCGGCGGCAACACCAACCAGCAGCGCGCCTCCG

CCGGCCAGATCTCCGTGCAGCCCGCCTTCTCCGTGCAGCGCAACCTGCCCTTCGACAAGCCCACCATCATG

GCCGCCTTCACCGGCAACACCGAGGGCCGCACCTCCGACATGCGCGCCGAGATCATCCGCATGATGGAGGG

CGCCAAGCCCGAGGAGATGTCCTTCCAGGGCCGCGGCGTGTTCGAGCTGTCCGACGAGCGCGCCGCCAACC

CCATCGTGCCCTCCTTCGACATGTCCAACGAGGGCTCCTACTTCTTCGGCGACAACGCCGAGGAGTACGAC

AAC

1977 H1N1 - NP antigen Amino Acid sequence (SEQ ID NO: 61)

MASQGTKRSY EQMETDGERQ NATEIRASVG KMIDGIGRFY IQMCTELKLS 050

DYEGRLIQNS LTIERMVLSA FDERRNKYLE EHPSAGKDPK KTGGPIYKRV 100

DGKWMRELVL YDKEEIRRIW RQANNGDDAT AGLTHMMIWH SNLNDTTYQR 150

TRALVRTGMD PRMCSLMQGS TLPRRSGAAG AAVKGVGTMV LELIRMIKRG 200

INDRNFWRGE NGRKTRIAYE RMCNILKGKF QTAAQRAMMD QVRESRNPGN 250

AEIEDLIFLA RSALILRGSV AHKSCLPACV YGPAVASGYN FEKEGYSLVG 300

IDPFKLLQTS QVYSLIRPNE NPAHKSQLVW MACNSAAFED LRVSSFIRGT 350

KVIPRGKLST RGVQIASNEN MDTMGSSTLE LRSRYWAIRT RSGGNTNQQR 400

ASAGQISIQP TFSVQRNLPF DKTTIMAAFT GNAEGRTSDM RAEIIKMMES 450

ARPEEVSFQG RGVFELSDER AANPIVPSFD MSNEGSYFFG DNAEEYDN 498

1977 H1N1 - Optimized DNA sequence encoding the nucleic acid sequence encoding NP antigen (SEQ ID NO: 62)

ATGGCCTCCCAGGGCACCAAGCGCTCCTACGAGCAGATGGAGACCGACGGCGAGCGCCAGAACGCCACCGA

GATCCGCGCCTCCGTGGGCAAGATGATCGACGGCATCGGCCGCTTCTACATCCAGATGTGCACCGAGCTGA

AGCTGTCCGACTACGAGGGCCGCCTGATCCAGAACTCCCTGACCATCGAGCGCATGGTGCTGTCCGCCTTC

GACGAGCGCCGCAACAAGTACCTGGAGGAGCACCCCTCCGCCGGCAAGGACCCCAAGAAGACCGGCGGCCC

CATCTACAAGCGCGTGGACGGCAAGTGGATGCGCGAGCTGGTGCTGTACGACAAGGAGGAGATCCGCCGCA

TCTGGCGCCAGGCCAACAACGGCGACGACGCCACCGCCGGCCTGACCCACATGATGATCTGGCACTCCAAC

CTGAACGACACCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCGTGGGCACCATGG

TGCTGGAGCTGATCCGCATGATCAAGCGCGGCATCAACGACCGCAACTTCTGGCGCGGCGAGAACGGCCGC

AAGACCCGCATCGCCTACGAGCGCATGTGCAACATCCTGAAGGGCAAGTTCCAGACCGCCGCCCAGCGCGC

-continued

CATGATGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGTGTACGGCCCCGCC

GTGGCCTCCGGCTACAACTTCGAGAAGGAGGGCTACTCCCTGGTGGGCATCGACCCCTTCAAGCTGCTGCA

GACCTCCCAGGTGTACTCCCTGATCCGCCCCAACGAGAACCCCGCCCACAAGTCCCAGCTGGTGTGGATGG

CCTGCAACTCCGCCGCCTTCGAGGACCTGCGCGTGTCCTCCTTCATCCGCGGCACCAAGGTGATCCCCCGC

GGCAAGCTGTCCACCCGCGGCGTGCAGATCGCCTCCAACGAGAACATGGACACCATGGGCTCCTCCACCCT

GGAGCTGCGCTCCCGCTACTGGGCCATCCGCACCCGCTCCGGCGGCAACACCAACCAGCAGCGCGCCTCCG

CCGGCCAGATCTCCATCCAGCCCACCTTCTCCGTGCAGCGCAACCTGCCCTTCGACAAGACCACCATCATG

GCCGCCTTCACCGGCAACGCCGAGGGCCGCACCTCCGACATGCGCGCCGAGATCATCAAGATGATGGAGTC

CGCCCGCCCCGAGGAGGTGTCCTTCCAGGGCCGCGGCGTGTTCGAGCTGTCCGACGAGCGCGCCGCCAACC

CCATCGTGCCCTCCTTCGACATGTCCAACGAGGGCTCCTACTTCTTCGGCGACAACGCCGAGGAGTACGAC

AAC

2007 H1N1 - NP antigen Amino Acid sequence (SEQ ID NO: 63)

MASQGTKRSY EQMETDGERQ NATEIRASVG RMIGGIGRFY IQMCTELKLN 050

DYEGRLIQNS LTIERMVLSA FDERRNKYLE EHPSAGKDPK KTGGPIYKRV 100

DGKWVRELVL YDKEEIRRIW RQANNGDDAT AGLTHIMIWH SNLNDTTYQR 150

TRALVRTGMD PRMCSLMQGS TLPRRSGAAG AAVKGVGTMV LELIRMIKRG 200

INDRNFWRGE NGRKTRIAYE RMCNILKGKF QTAAQKAMMD QVRESRNPGN 250

AEIEDLTFLA RSALILRGSV AHKSCLPACV YGPAVASGYD FEKEGYSLVG 300

VDPFKLLQTS QVYSLIRPNE NPAHKSQLVW MACNSAAFED LRVSSFIRGT 350

RVLPRGKLST RGVQIASNEN MDAIVSSTLE LRSRYWAIRT RSGGNTNQQR 400

ASAGQISTQP TFSVQRNLPF DKATIMAAFS GNTEGRTSDM RAEIIKMMES 450

ARPEEVSFQG RGVFELSDER ATNPIVPSFD MSNEGSYFFG DNAEEYDN 498

2007 H1N1 - Optimized DNA sequence encoding the
nucleic acid sequence encoding NP antigen (SEQ ID NO: 64)

ATGGCCTCCCAGGGCACCAAGCGCTCCTACGAGCAGATGGAGACCGACGGCGAGCGCCAGAACGCCACCGA

GATCCGCGCCTCCGTGGGCCGCATGATCGGCGGCATCGGCCGCTTCTACATCCAGATGTGCACCGAGCTGA

AGCTGAACGACTACGAGGGCCGCCTGATCCAGAACTCCCTGACCATCGAGCGCATGGTGCTGTCCGCCTTC

GACGAGCGCCGCAACAAGTACCTGGAGGAGCACCCCTCCGCCGGCAAGGACCCCAAGAAGACCGGCGGCCC

CATCTACAAGCGCGTGGACGGCAAGTGGGTGCGCGAGCTGGTGCTGTACGACAAGGAGGAGATCCGCCGCA

TCTGGCGCCAGGCCAACAACGGCGACGACGCCACCGCCGGCCTGACCCACATCATGATCTGGCACTCCAAC

CTGAACGACACCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCGTGGGCACCATGG

TGCTGGAGCTGATCCGCATGATCAAGCGCGGCATCAACGACCGCAACTTCTGGCGCGGCGAGAACGGCCGC

AAGACCCGCATCGCCTACGAGCGCATGTGCAACATCCTGAAGGGCAAGTTCCAGACCGCCGCCCAGAAGGC

CATGATGGACCAGGTGCGCGAGTCCCGCAACCCCGGCAACGCCGAGATCGAGGACCTGACCTTCCTGGCCC

GCTCCGCCCTGATCCTGCGCGGCTCCGTGGCCCACAAGTCCTGCCTGCCCGCCTGCGTGTACGGCCCCGCC

GTGGCCTCCGGCTACGACTTCGAGAAGGAGGGCTACTCCCTGGTGGGCGTGGACCCCTTCAAGCTGCTGCA

GACCTCCCAGGTGTACTCCCTGATCCGCCCCAACGAGAACCCCGCCCACAAGTCCCAGCTGGTGTGGATGG

CCTGCAACTCCGCCGCCTTCGAGGACCTGCGCGTGTCCTCCTTCATCCGCGGCACCCGCGTGCTGCCCCGC

GGCAAGCTGTCCACCCGCGGCGTGCAGATCGCCTCCAACGAGAACATGGACGCCATCGTGTCCTCCACCCT

-continued

GGAGCTGCGCTCCCGCTACTGGGCCATCCGCACCCGCTCCGGCGGCAACACCAACCAGCAGCGCGCCTCCG

CCGGCCAGATCTCCACCCAGCCCACCTTCTCCGTGCAGCGCAACCTGCCCTTCGACAAGGCCACCATCATG

GCCGCCTTCTCCGGCAACACCGAGGGCCGCACCTCCGACATGCGCGCCGAGATCATCAAGATGATGGAGTC

CGCCCGCCCCGAGGAGGTGTCCTTCCAGGGCCGCGGCGTGTTCGAGCTGTCCGACGAGCGCGCCACCAACC

CCATCGTGCCCTCCTTCGACATGTCCAACGAGGGCTCCTACTTCTTCGGCGACAACGCCGAGGAGTACGAC

AAC

2009 H1N1 - NP antigen Amino Acid sequence (SEQ ID NO: 65)

MASQGTKRSY EQMETGGERQ DATEIRASVG RMIGGIGRFY IQMCTELKLS 050

DYDGRLIQNS ITIERMVLSA FDERRNKYLE EHPSAGKDPK KTGGPIYRRV 100

DGKWMRELIL YDKEEIRRVW RQANNGEDAT AGLTHIMIWH SNLNDATYQR 150

TRALVRTGMD PRMCSLMQGS TLPRRSGAAG AAVKGVGTIA MELIRMIKRG 200

INDRNFWRGE NGRRTRVAYE RMCNILKGKF QTAAQRAMMD QVRESRNPGN 250

AEIEDLIFLA RSALILRGSV AHKSCLPACV YGLAVASGHD FEREGYSLVG 300

IDPFKLLQNS QVVSLMRPNE NPAHKSQLVW MACHSAAFED LRVSSFIRGK 350

KVIPRGKLST RGVQIASNEN VETMDSNTLE LRSRYWAIRT RSGGNTNQQK 400

ASAGQISVQP TFSVQRNLPF ERATVMAAFS GNNEGRTSDM RTEVIRMMES 450

AKPEDLSFQG RGVFELSDEK ATNPIVPSFD MSNEGSYFFG DNAEEYDS 498

2009 H1N1 - Optimized DNA sequence encoding the nucleic acid sequence encoding NP antigen (SEQ ID NO: 66)

ATGGCCTCCCAGGGCACCAAGCGCTCCTACGAGCAGATGGAGACCGGCGGCGAGCGCCAGGACGCCACCGA

GATCCGCGCCTCCGTGGGCCGCATGATCGGCGGCATCGGCCGCTTCTACATCCAGATGTGCACCGAGCTGA

AGCTGTCCGACTACGACGGCCGCCTGATCCAGAACTCCATCACCATCGAGCGCATGGTGCTGTCCGCCTTC

GACGAGCGCCGCAACAAGTACCTGGAGGAGCACCCCTCCGCCGGCAAGGACCCCAAGAAGACCGGCGGCCC

CATCTACCGCCGCGTGGACGGCAAGTGGATGCGCGAGCTGATCCTGTACGACAAGGAGGAGATCCGCCGCG

TGTGGCGCCAGGCCAACAACGGCGAGGACGCCACCGCCGGCCTGACCCACATCATGATCTGGCACTCCAAC

CTGAACGACGCCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCGTGGGCACCATCG

CCATGGAGCTGATCCGCATGATCAAGCGCGGCATCAACGACCGCAACTTCTGGCGCGGCGAGAACGGCCGC

CGCACCCGCGTGGCCTACGAGCGCATGTGCAACATCCTGAAGGGCAAGTTCCAGACCGCCGCCCAGCGCGC

CATGATGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGTGTACGGCCTGGCC

GTGGCCTCCGGCCACGACTTCGAGCGCGAGGGCTACTCCCTGGTGGGCATCGACCCCTTCAAGCTGCTGCA

GAACTCCCAGGTGGTGTCCCTGATGCGCCCCAACGAGAACCCCGCCCACAAGTCCCAGCTGGTGTGGATGG

CCTGCCACTCCGCCGCCTTCGAGGACCTGCGCGTGTCCTCCTTCATCCGCGGCAAGAAGGTGATCCCCCGC

GGCAAGCTGTCCACCCGCGGCGTGCAGATCGCCTCCAACGAGAACGTGGAGACCATGGACTCCAACACCCT

GGAGCTGCGCTCCCGCTACTGGGCCATCCGCACCCGCTCCGGCGGCAACACCAACCAGCAGAAGGCCTCCG

CCGGCCAGATCTCCGTGCAGCCCACCTTCTCCGTGCAGCGCAACCTGCCCTTCGAGCGCGCCACCGTGATG

GCCGCCTTCTCCGGCAACAACGAGGGCCGCACCTCCGACATGCGCACCGAGGTGATCCGCATGATGGAGTC

CGCCAAGCCCGAGGACCTGTCCTTCCAGGGCCGCGGCGTGTTCGAGCTGTCCGACGAGAAGGCCACCAACC

CCATCGTGCCCTCCTTCGACATGTCCAACGAGGGCTCCTACTTCTTCGGCGACAACGCCGAGGAGTACGAC

TCC

-continued

2015 H1N1 - NP antigen Amino Acid sequence (SEQ ID NO: 67)

MASQGTKRSY EQMETGGERQ DTTEIRASVG RMIGGIGRFY IQMCTELKLS 050

DYDGRLIQNS ITIERMVLSA FDERRNKYLE EHPSAGKDPK KTGGPIYRRI 100

DGKWTRELIL YDKEEIRRVW RQANNGEDAT AGLTHIMIWH SNLNDATYQR 150

TRALVRTGMD PRMCSLMQGS TLPRRSGAAG AAVKGVGTIA MELIRMIKRG 200

INDRNFWRGE NGRRTRVAYE RMCNILKGKF QTAAQRAMMD QVRESRNPGN 250

AEIEDLIFLA RSALILRGSV AHKSCLPACV YGLAVASGHD FEREGYSLVG 300

IDPFKLLQNS QVVSLMRPNE NPAHKSQLVW MACHSAAFED LRVSSFIRGK 350

KVIPRGKLST RGVQIASNEN VETMDSNTLE LRSRYWAIRT RSGGNTNQQK 400

ASAGQISVQP TFSVQRNLPF ERATVMAAFS GNNEGRTSDM RTEVIRMMES 450

AKPEDLSFQG RGVFELSDEK ATNPIVPSFD MSNEGSYFFG DNAEEYDN 498

2015 H1N1 - Optimized DNA sequence encoding the
nucleic acid sequence encoding NP antigen (SEQ ID NO: 68)

ATGGCCTCCCAGGGCACCAAGCGCTCCTACGAGCAGATGGAGACCGGCGGCGAGCGCCAGGACACCACCGA

GATCCGCGCCTCCGTGGGCCGCATGATCGGCGGCATCGGCCGCTTCTACATCCAGATGTGCACCGAGCTGA

AGCTGTCCGACTACGACGGCCGCCTGATCCAGAACTCCATCACCATCGAGCGCATGGTGCTGTCCGCCTTC

GACGAGCGCCGCAACAAGTACCTGGAGGAGCACCCCTCCGCCGGCAAGGACCCCAAGAAGACCGGCGGCCC

CATCTACCGCCGCATCGACGGCAAGTGGACCCGCGAGCTGATCCTGTACGACAAGGAGGAGATCCGCCGCG

TGTGGCGCCAGGCCAACAACGGCGAGGACGCCACCGCCGGCCTGACCCACATCATGATCTGGCACTCCAAC

CTGAACGACGCCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCGTGGGCACCATCG

CCATGGAGCTGATCCGCATGATCAAGCGCGGCATCAACGACCGCAACTTCTGGCGCGGCGAGAACGGCCGC

CGCACCCGCGTGGCCTACGAGCGCATGTGCAACATCCTGAAGGGCAAGTTCCAGACCGCCGCCCAGCGCGC

CATGATGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGTGTACGGCCTGGCC

GTGGCCTCCGGCCACGACTTCGAGCGCGAGGGCTACTCCCTGGTGGGCATCGACCCCTTCAAGCTGCTGCA

GAACTCCCAGGTGGTGTCCCTGATGCGCCCCAACGAGAACCCCGCCCACAAGTCCCAGCTGGTGTGGATGG

CCTGCCACTCCGCCGCCTTCGAGGACCTGCGCGTGTCCTCCTTCATCCGCGGCAAGAAGGTGATCCCCCGC

GGCAAGCTGTCCACCCGCGGCGTGCAGATCGCCTCCAACGAGAACGTGGAGACCATGGACTCCAACACCCT

GGAGCTGCGCTCCCGCTACTGGGCCATCCGCACCCGCTCCGGCGGCAACACCAACCAGCAGAAGGCCTCCG

CCGGCCAGATCTCCGTGCAGCCCACCTTCTCCGTGCAGCGCAACCTGCCCTTCGAGCGCGCCACCGTGATG

GCCGCCTTCTCCGGCAACAACGAGGGCCGCACCTCCGACATGCGCACCGAGGTGATCCGCATGATGGAGTC

CGCCAAGCCCGAGGACCTGTCCTTCCAGGGCCGCGGCGTGTTCGAGCTGTCCGACGAGAAGGCCACCAACC

CCATCGTGCCCTCCTTCGACATGTCCAACGAGGGCTCCTACTTCTTCGGCGACAACGCCGAGGAGTACGAC

AAC

2017 H3N2 - NP antigen Amino Acid sequence (SEQ ID NO: 69)

MASQGTKRSY EQMETDGDRQ NATEIRASVG KMIDGIGRFY IQMCTELKLS 050

DHEGRLIQNS LTIEKMVLSA FDERRNKYLE EHPSAGKDPK KTGGPIYRRV 100

DXKWMRELVL YDKEEIRRIW RQANNGEDAT SGLTHIMIWH SNLNDATYQR 150

TRALVRTGMD PRMCSLMQGS TLPRRSGAAG AAVKGIGTMV MELIRMVKRG 200

INDRNFWRGE NGRKTRSAYE RMCNILKGKF QTAAQRAMVD QVRESRNPGN 250

-continued

AEIEDLIFLA RSALILRGSV AHKSCLPACA YGPAVSSGYD FEKEGYSLVG 300

IDPFKLLQNS QIYSLIRPNE NPAHKSQLVW MACHSAAFED LRLLSFIRGT 350

KVSPRGKLST RGVQIASNEN MDNMGSSTLE LRSGYWAIRT RSGGNTNQQR 400

ASAGQTSVQP TFSVQRNLPF EKSTIMAAFT GNTEGRTSDM RAEIIRMMEG 450

AKPEEVSFRG RGVFELSDEK AANPIVPSFD MSNEGSYFFG DNAEEYDN 498

2017 H3N2 - Optimized DNA sequence encoding the nucleic acid sequence encoding NP antigen (SEQ ID NO: 70)

ATGGCCTCCCAGGGCACCAAGCGCTCCTACGAGCAGATGGAGACCGACGGCGACCGCCAGAACGCCACCGA

GATCCGCGCCTCCGTGGGCAAGATGATCGACGGCATCGGCCGCTTCTACATCCAGATGTGCACCGAGCTGA

AGCTGTCCGACCACGAGGGCCGCCTGATCCAGAACTCCCTGACCATCGAGAAGATGGTGCTGTCCGCCTTC

GACGAGCGCCGCAACAAGTACCTGGAGGAGCACCCCTCCGCCGGCAAGGACCCCAAGAAGACCGGCGGCCC

CATCTACCGCCGCGTGGACNNNAAGTGGATGCGCGAGCTGGTGCTGTACGACAAGGAGGAGATCCGCCGCA

TCTGGCGCCAGGCCAACAACGGCGAGGACGCCACCTCCGGCCTGACCCACATCATGATCTGGCACTCCAAC

CTGAACGACGCCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCATCGGCACCATGG

TGATGGAGCTGATCCGCATGGTGAAGCGCGGCATCAACGACCGCAACTTCTGGCGCGGCGAGAACGGCCGC

AAGACCCGCTCCGCCTACGAGCGCATGTGCAACATCCTGAAGGGCAAGTTCCAGACCGCCGCCCAGCGCGC

CATGGTGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGCCTACGGCCCCGCC

GTGTCCTCCGGCTACGACTTCGAGAAGGAGGGCTACTCCCTGGTGGGCATCGACCCCTTCAAGCTGCTGCA

GAACTCCCAGATCTACTCCCTGATCCGCCCCAACGAGAACCCCGCCCACAAGTCCCAGCTGGTGTGGATGG

CCTGCCACTCCGCCGCCTTCGAGGACCTGCGCCTGCTGTCCTTCATCCGCGGCACCAAGGTGTCCCCCCGC

GGCAAGCTGTCCACCCGCGGCGTGCAGATCGCCTCCAACGAGAACATGGACAACATGGGCTCCTCCACCCT

GGAGCTGCGCTCCGGCTACTGGGCCATCCGCACCCGCTCCGGCGGCAACACCAACCAGCAGCGCGCCTCCG

CCGGCCAGACCTCCGTGCAGCCCACCTTCTCCGTGCAGCGCAACCTGCCCTTCGAGAAGTCCACCATCATG

GCCGCCTTCACCGGCAACACCGAGGGCCGCACCTCCGACATGCGCGCCGAGATCATCCGCATGATGGAGGG

CGCCAAGCCCGAGGAGGTGTCCTTCCGCGGCCGCGGCGTGTTCGAGCTGTCCGACGAGAAGGCCGCCAACC

CCATCGTGCCCTCCTTCGACATGTCCAACGAGGGCTCCTACTTCTTCGGCGACAACGCCGAGGAGTACGAC

AAC

2017 Influenza B (Victoria lineage) - NP antigen Amino Acid sequence (SEQ ID NO: 71)

MSNMDIDGMN TGTIDKTPEE ITSGTSGTTR PIIRPATLAP PSNKRTRNPS 050

PERATTSSED DVGRKAQKKQ TPTEIKKSVY NMVVKLGEFY NQMMVKAGLN 100

DDMERNLIQN AHAVERILLA ATDDKKTEFQ KKKNARDVKE GKEEIDHNKT 150

GGTFYKMVRD DKTIYFSPIR ITFLKEEVKT MYKTTMGSDG FSGLNHIMIG 200

HSQMNDVCFQ RSKALKRVGL DPSLISTFAG STVPRRSGAT GVAIKGGGTL 250

VAEAIRFIGR AMADRGLLRD IKAKTAYEKI LLNLKNKCSA PQQKALVDQV 300

IGSRNPGIAD IEDLTLLARS MVVVRPSVAS KVVLPISIYA KIPQLGFNVE 350

EYSMVGYEAM ALYNMATPVS ILRMGDDAKD KSQLFFMSCF GAAYEDLRVL 400

SALTGTEFKP RSALKCKGFH VPAKEQVEGM GAALMSIKLQ FWAPMTRSGG 450

-continued

NEVGGDGGSG QISCSPVFAV ERPIALSKQA VRRMLSMNIE GRDADVKGNL 500

LKMMNDSMAK KTSGNAFIGK KMFQISDKNK TNPIEIPIKQ TIPNFFFGRD 550

TAEDYDDLDY 560

2017 Influenza B (Victoria lineage) - Optimized DNA sequence encoding the nucleic acid sequence encoding NP antigen (SEQ ID NO: 72)

ATGTCCAACATGGACATCGACGGCATGAACACCGGCACCATCGACAAGACCCCCGAGGAGATCACCTCCGG

CACCTCCGGCACCACCCGCCCCATCATCCGCCCCGCCACCCTGGCCCCCCCCTCCAACAAGCGCACCCGCA

ACCCCTCCCCCGAGCGCGCCACCACCTCCTCCGAGGACGACGTGGGCCGCAAGGCCCAGAAGAAGCAGACC

CCCACCGAGATCAAGAAGTCCGTGTACAACATGGTGGTGAAGCTGGGCGAGTTCTACAACCAGATGATGGT

GAAGGCCGGCCTGAACGACGACATGGAGCGCAACCTGATCCAGAACGCCCACGCCGTGGAGCGCATCCTGC

TGGCCGCCACCGACGACAAGAAGACCGAGTTCCAGAAGAAGAAGAACGCCCGCGACGTGAAGGAGGGCAAG

GAGGAGATCGACCACAACAAGACCGGCGGCACCTTCTACAAGATGGTGCGCGACGACAAGACCATCTACTT

CTCCCCCATCCGCATCACCTTCCTGAAGGAGGAGGTGAAGACCATGTACAAGACCACCATGGGCTCCGACG

GCTTCTCCGGCCTGAACCACATCATGATCGGCCACTCCCAGATGAACGACGTGTGCTTCCAGCGCTCCAAG

GCCCTGAAGCGCGTGGGCCTGGACCCCTCCCTGATCTCCACCTTCGCCGGCTCCACCGTGCCCCGCCGCTC

CGGCGCCACCGGCGTGGCCATCAAGGGCGGCGGCACCCTGGTGGCCGAGGCCATCCGCTTCATCGGCCGCG

CCATGGCCGACCGCGGCCTGCTGCGCGACATCAAGGCCAAGACCGCCTACGAGAAGATCCTGCTGAACCTG

AAGAACAAGTGCTCCGCCCCCCAGCAGAAGGCCCTGGTGGACCAGGTGATCGGCTCCCGCAACCCCGGCAT

CGCCGACATCGAGGACCTGACCCTGCTGGCCCGCTCCATGGTGGTGGTGCGCCCCTCCGTGGCCTCCAAGG

TGGTGCTGCCCATCTCCATCTACGCCAAGATCCCCCAGCTGGGCTTCAACGTGGAGGAGTACTCCATGGTG

GGCTACGAGGCCATGGCCCTGTACAACATGGCCACCCCCGTGTCCATCCTGCGCATGGGCGACGACGCCAA

GGACAAGTCCCAGCTGTTCTTCATGTCCTGCTTCGGCGCCGCCTACGAGGACCTGCGCGTGCTGTCCGCCC

TGACCGGCACCGAGTTCAAGCCCCGCTCCGCCCTGAAGTGCAAGGGCTTCCACGTGCCCGCCAAGGAGCAG

GTGGAGGGCATGGGCGCCGCCCTGATGTCCATCAAGCTGCAGTTCTGGGCCCCCATGACCCGCTCCGGCGG

CAACGAGGTGGGCGGCGACGGCGGCTCCGGCCAGATCTCCTGCTCCCCCGTGTTCGCCGTGGAGCGCCCCA

TCGCCCTGTCCAAGCAGGCCGTGCGCCGCATGCTGTCCATGAACATCGAGGGCCGCGACGCCGACGTGAAG

GGCAACCTGCTGAAGATGATGAACGACTCCATGGCCAAGAAGACCTCCGGCAACGCCTTCATCGGCAAGAA

GATGTTCCAGATCTCCGACAAGAACAAGACCAACCCCATCGAGATCCCCATCAAGCAGACCATCCCCAACT

TCTTCTTCGGCCGCGACACCGCCGAGGACTACGACGACCTGGACTAC

2013 Influenza B (Yamagata lineage) - Sequence only on GISAID - NP antigen Amino Acid sequence (SEQ ID NO: 73)

0001 MSNMDIDGIN TGTIDKTPEE ITSGTSGTTR PIIRPATLAP PSNKRTRNPS PERATTSSED

DVGRKTQKKQ TPTEIKKSVY

0081 NMVVKLGEFY NQMMVKAGLN DDMERNLIQN AYAVERILLA ATDDKKTEFQ KKKNARDVKE

GKEEIDHNKT GGTFYKMVRD

0161 DKTIYFSPIR ITFLKEEVKT MYKTTMGSDG FSGLNHIMIG HSQMNDVCFQ RSKALKRVGL

DPSLISTFAG STVPRRSGAT

0241 GVAIKGGGTL VAEAIRFIGR AMADRGLLRD IKAKTAYEKI LLNLKNKCSA PQQKALVDQV

IGSRNPGIAD IEDLTLLARS

0321 MVVVRPSVAS KVVLPISIYA KIPQLGFNVE EYSMVGYEAM ALYNMATPVS ILRMGDDAKD

KSQLFFMSCF GAAYEDLRVL

-continued

0401 SALTGTEFKP RSALKCKGFH VPAKEQVEGM GAALMSIKLQ FWAPMTRSGG NEAGGDGGSG

QISCSPVFAV ERPIALSKQA

0481 VRRMLSMNIE GRDADVKGNL LKMMNDSMAK KTSGNAFIGK KMFQISDKNK TNPIEIPIKQ

TIPNFFFGRD TAEDYDDLDY

2013 Influenza B (Yamagata lineage) - Sequence only on GISAID - Optimized DNA sequence encoding the nucleic acid sequence encoding NP antigen (SEQ ID NO: 74)

ATGTCCAACATGGACATCGACGGCATCAACACCGGCACCATCGACAAGACCCCCGAGGAGATCACCTCCGG

CACCTCCGGCACCACCCGCCCCATCATCCGCCCCGCCACCCTGGCCCCCCCCTCCAACAAGCGCACCCGCA

ACCCCTCCCCCGAGCGCGCCACCACCTCCTCCGAGGACGACGTGGGCCGCAAGACCCAGAAGAAGCAGACC

CCCACCGAGATCAAGAAGTCCGTGTACAACATGGTGGTGAAGCTGGGCGAGTTCTACAACCAGATGATGGT

GAAGGCCGGCCTGAACGACGACATGGAGCGCAACCTGATCCAGAACGCCTACGCCGTGGAGCGCATCCTGC

TGGCCGCCACCGACGACAAGAAGACCGAGTTCCAGAAGAAGAAGAACGCCCGCGACGTGAAGGAGGGCAAG

GAGGAGATCGACCACAACAAGACCGGCGGCACCTTCTACAAGATGGTGCGCGACGACAAGACCATCTACTT

CTCCCCCATCCGCATCACCTTCCTGAAGGAGGAGGTGAAGACCATGTACAAGACCACCATGGGCTCCGACG

GCTTCTCCGGCCTGAACCACATCATGATCGGCCACTCCCAGATGAACGACGTGTGCTTCCAGCGCTCCAAG

GCCCTGAAGCGCGTGGGCCTGGACCCCTCCCTGATCTCCACCTTCGCCGGCTCCACCGTGCCCCGCCGCTC

CGGCGCCACCGGCGTGGCCATCAAGGGCGGCGGCACCCTGGTGGCCGAGGCCATCCGCTTCATCGGCCGCG

CCATGGCCGACCGCGGCCTGCTGCGCGACATCAAGGCCAAGACCGCCTACGAGAAGATCCTGCTGAACCTG

AAGAACAAGTGCTCCGCCCCCCAGCAGAAGGCCCTGGTGGACCAGGTGATCGGCTCCCGCAACCCCGGCAT

CGCCGACATCGAGGACCTGACCCTGCTGGCCCGCTCCATGGTGGTGGTGCGCCCCTCCGTGGCCTCCAAGG

TGGTGCTGCCCATCTCCATCTACGCCAAGATCCCCCAGCTGGGCTTCAACGTGGAGGAGTACTCCATGGTG

GGCTACGAGGCCATGGCCCTGTACAACATGGCCACCCCCGTGTCCATCCTGCGCATGGGCGACGACGCCAA

GGACAAGTCCCAGCTGTTCTTCATGTCCTGCTTCGGCGCCGCCTACGAGGACCTGCGCGTGCTGTCCGCCC

TGACCGGCACCGAGTTCAAGCCCCGCTCCGCCCTGAAGTGCAAGGGCTTCCACGTGCCCGCCAAGGAGCAG

GTGGAGGGCATGGGCGCCGCCCTGATGTCCATCAAGCTGCAGTTCTGGGCCCCCATGACCCGCTCCGGCGG

CAACGAGGCCGGCGGCGACGGCGGCTCCGGCCAGATCTCCTGCTCCCCCGTGTTCGCCGTGGAGCGCCCCA

TCGCCCTGTCCAAGCAGGCCGTGCGCCGCATGCTGTCCATGAACATCGAGGGCCGCGACGCCGACGTGAAG

GGCAACCTGCTGAAGATGATGAACGACTCCATGGCCAAGAAGACCTCCGGCAACGCCTTCATCGGCAAGAA

GATGTTCCAGATCTCCGACAAGAACAAGACCAACCCCATCGAGATCCCCATCAAGCAGACCATCCCCAACT

TCTTCTTCGGCCGCGACACCGCCGAGGACTACGACGACCTGGACTAC

2015 H5N1 - NP antigen Amino Acid sequence (SEQ ID NO: 75)

MASQGTKRSY EQMETGGERQ NATEIRASVG RMVSGIGRFY IQMCTELKLS 050

DYEGRLIQNS ITIERMVLSA FDERRNRYLE EHPSAGKDPK KTGGPIYRRR 100

DGKWVRELIL YDKEEIRRIW RQANNGEDAT AGLTHLMIWH SNLNDATYQR 150

TRALVRTGMD PRMCSLMQGS TLPRRSGAAG AAVKGVGTMV MELIRMIKRG 200

INDRNFWRGE NGRRTRIAYE RMCNILKGKF QTAAQRAMMD QVRESRNPGN 250

AEIEDLIFLA RSALILRGSV AHKSCLPACV YGLAVASGYD FEREGYSLVG 300

IDPFRLLQNS QVFSLIRPNE NPAHKSQLVW MACHSAAFED LRVSSFIRGT 350

RVIPRGQLST RGVQIASNEN MEAMDSNTLE LRSRYWAIRT RSGGNTNQQR 400

-continued

ASAGQISIQP TFSVQRNLPF ERATIMAAFT GNTEGRTSDM RTEIIRMMES 450

ARPEDVSFQG RGVFELSDEK ATNPIVPSFD MNNEGSYFFG DNAEEYDN 498

2015 H5N1 - Optimized DNA sequence encoding the nucleic acid sequence encoding NP antigen (SEQ ID NO: 76)

ATGGCCTCCCAGGGCACCAAGCGCTCCTACGAGCAGATGGAGACCGGCGGCGAGCGCCAGAACGCCACCGA

GATCCGCGCCTCCGTGGGCCGCATGGTGTCCGGCATCGGCCGCTTCTACATCCAGATGTGCACCGAGCTGA

AGCTGTCCGACTACGAGGGCCGCCTGATCCAGAACTCCATCACCATCGAGCGCATGGTGCTGTCCGCCTTC

GACGAGCGCCGCAACCGCTACCTGGAGGAGCACCCCTCCGCCGGCAAGGACCCCAAGAAGACCGGCGGCCC

CATCTACCGCCGCCGCGACGGCAAGTGGGTGCGCGAGCTGATCCTGTACGACAAGGAGGAGATCCGCCGCA

TCTGGCGCCAGGCCAACAACGGCGAGGACGCCACCGCCGGCCTGACCCACCTGATGATCTGGCACTCCAAC

CTGAACGACGCCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCGTGGGCACCATGG

TGATGGAGCTGATCCGCATGATCAAGCGCGGCATCAACGACCGCAACTTCTGGCGCGGCGAGAACGGCCGC

CGCACCCGCATCGCCTACGAGCGCATGTGCAACATCCTGAAGGGCAAGTTCCAGACCGCCGCCCAGCGCGC

CATGATGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGTGTACGGCCTGGCC

GTGGCCTCCGGCTACGACTTCGAGCGCGAGGGCTACTCCCTGGTGGGCATCGACCCCTTCCGCCTGCTGCA

GAACTCCCAGGTGTTCTCCCTGATCCGCCCCAACGAGAACCCCGCCCACAAGTCCCAGCTGGTGTGGATGG

CCTGCCACTCCGCCGCCTTCGAGGACCTGCGCGTGTCCTCCTTCATCCGCGGCACCCGCGTGATCCCCCGC

GGCCAGCTGTCCACCCGCGGCGTGCAGATCGCCTCCAACGAGAACATGGAGGCCATGGACTCCAACACCCT

GGAGCTGCGCTCCCGCTACTGGGCCATCCGCACCCGCTCCGGCGGCAACACCAACCAGCAGCGCGCCTCCG

CCGGCCAGATCTCCATCCAGCCCACCTTCTCCGTGCAGCGCAACCTGCCCTTCGAGCGCGCCACCATCATG

GCCGCCTTCACCGGCAACACCGAGGGCCGCACCTCCGACATGCGCACCGAGATCATCCGCATGATGGAGTC

CGCCCGCCCCGAGGACGTGTCCTTCCAGGGCCGCGGCGTGTTCGAGCTGTCCGACGAGAAGGCCACCAACC

CCATCGTGCCCTCCTTCGACATGAACAACGAGGGCTCCTACTTCTTCGGCGACAACGCCGAGGAGTACGAC

AAC

2017 H7N9 - NP antigen Amino Acid sequence (SEQ ID NO: 77)

MASQGTKRSY EQMETGGERQ NATEIRASVG RMVSGIGRFY IQMCTELKLS 050

DNEGRLIQNS ITIERMVLSA FDERRNRYLE EHPSSGKDPK KTGGPIYRRR 100

DGKWVRELIL YDKEEIRRIW RQANNGEDAT AGLTHLMIWH SNLNDATYQR 150

TRALVRTGMD PRMCSLMQGS TLPRRSGAAG AAVKGIGTMV MELVRMIKRG 200

INDRNFWRGE NGRRTRIAYE RMCNILKGKF QTAAQRAMMD QVRESRNPGN 250

AEIEDLIFLA RSALILRGSV AXKSCLPACV YGLAVASGYD FEREGYSLVG 300

IDPFRLLQNS QVFSLIRPNE NPAHKSQLVW MACHSAAFED LRVSSFIKGT 350

KMVPRGQLST RGVQIASNEN MEAMDSNTLE LRSRYWAIRT RSGGNTNQQR 400

ASAGQVSVQP TFSVQRNLPF ERATIMAAFT GNTEGRTSDM RTEIIRMMES 450

ARPEDVSFQG RGVFELSDEK ATNPIVPSFD MNNEGSYFFG DNAEEYDN 498

2017 H7N9 - Optimized DNA sequence encoding the nucleic acid sequence encoding NP antigen (SEQ ID NO: 78)

ATGGCCTCCCAGGGCACCAAGCGCTCCTACGAGCAGATGGAGACCGGCGGCGAGCGCCAGAACGCCACCGA

GATCCGCGCCTCCGTGGGCCGCATGGTGTCCGGCATCGGCCGCTTCTACATCCAGATGTGCACCGAGCTGA

-continued

AGCTGTCCGACAACGAGGGCCGCCTGATCCAGAACTCCATCACCATCGAGCGCATGGTGCTGTCCGCCTTC

GACGAGCGCCGCAACCGCTACCTGGAGGAGCACCCCTCCTCCGGCAAGGACCCCAAGAAGACCGGCGGCCC

CATCTACCGCCGCCGCGACGGCAAGTGGGTGCGCGAGCTGATCCTGTACGACAAGGAGGAGATCCGCCGCA

TCTGGCGCCAGGCCAACAACGGCGAGGACGCCACCGCCGGCCTGACCCACCTGATGATCTGGCACTCCAAC

CTGAACGACGCCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCATCGGCACCATGG

TGATGGAGCTGGTGCGCATGATCAAGCGCGGCATCAACGACCGCAACTTCTGGCGCGGCGAGAACGGCCGC

CGCACCCGCATCGCCTACGAGCGCATGTGCAACATCCTGAAGGGCAAGTTCCAGACCGCCGCCCAGCGCGC

CATGATGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCNNNAAGTCCTGCCTGCCCGCCTGCGTGTACGGCCTGGCC

GTGGCCTCCGGCTACGACTTCGAGCGCGAGGGCTACTCCCTGGTGGGCATCGACCCCTTCCGCCTGCTGCA

GAACTCCCAGGTGTTCTCCCTGATCCGCCCCAACGAGAACCCCGCCCACAAGTCCCAGCTGGTGTGGATGG

CCTGCCACTCCGCCGCCTTCGAGGACCTGCGCGTGTCCTCCTTCATCAAGGGCACCAAGATGGTGCCCCGC

GGCCAGCTGTCCACCCGCGGCGTGCAGATCGCCTCCAACGAGAACATGGAGGCCATGGACTCCAACACCCT

GGAGCTGCGCTCCCGCTACTGGGCCATCCGCACCCGCTCCGGCGGCAACACCAACCAGCAGCGCGCCTCCG

CCGGCCAGGTGTCCGTGCAGCCCACCTTCTCCGTGCAGCGCAACCTGCCCTTCGAGCGCGCCACCATCATG

GCCGCCTTCACCGGCAACACCGAGGGCCGCACCTCCGACATGCGCACCGAGATCATCCGCATGATGGAGTC

CGCCCGCCCCGAGGACGTGTCCTTCCAGGGCCGCGGCGTGTTCGAGCTGTCCGACGAGAAGGCCACCAACC

CCATCGTGCCCTCCTTCGACATGAACAACGAGGGCTCCTACTTCTTCGGCGACAACGCCGAGGAGTACGAC

AAC

2013 H10N8 - NP antigen Amino Acid sequence (SEQ ID NO: 79)

MASQGTKRSY EQMETGGERQ NATEIRASVG RMVSGIGRFY IQMCTELKLS 050

DNEGRLIQNS ITIERMVLSA FDERRNRYLE EHPSAGKDPK KTGGPIYRRR 100

DGKWVRELIL YDKEEIRRIW RQANNGEDAT AGLTHLMIWH SNLNDATYQR 150

TRALVRTGMD PRMCSLMQGS TLPRRSGAAG AAVKGIGTMV MELIRMVKRG 200

INDRNFWRGE NGRRTRVAYE RMCNILKGKF QTAAQRAMVD QVRESRNPGN 250

AEIEDLIFLA RSALILRGSV AHKSCLPACV YGLAVASGYD FEREGYSLVG 300

IDPFRLLQNS QVFSLIRPNE NPAHKSQLVW MACHSAAFED LRVSSFIRGT 350

RMVPRGQLST RGVQIASNEN MEAMDSNTLE LRSRYWAIRT RSGGNTNQQR 400

ASAGQISVQP TFSVQRNLPF ERATIMAAFT GNTEGRTSDM RTEIIRMMES 450

ARPEDVSFQG RGVFELSDKK ATNPIVPSFD MSNEGSYFFG DNAEEYDN 498

2013 H10N8 - Optimized DNA sequence encoding the
nucleic acid sequence encoding NP antigen (SEQ ID NO: 80)

ATGGCCTCCCAGGGCACCAAGCGCTCCTACGAGCAGATGGAGACCGGCGGCGAGCGCCAGAACGCCACCGA

GATCCGCGCCTCCGTGGGCCGCATGGTGTCCGGCATCGGCCGCTTCTACATCCAGATGTGCACCGAGCTGA

AGCTGTCCGACAACGAGGGCCGCCTGATCCAGAACTCCATCACCATCGAGCGCATGGTGCTGTCCGCCTTC

GACGAGCGCCGCAACCGCTACCTGGAGGAGCACCCCTCCGCCGGCAAGGACCCCAAGAAGACCGGCGGCCC

CATCTACCGCCGCCGCGACGGCAAGTGGGTGCGCGAGCTGATCCTGTACGACAAGGAGGAGATCCGCCGCA

TCTGGCGCCAGGCCAACAACGGCGAGGACGCCACCGCCGGCCTGACCCACCTGATGATCTGGCACTCCAAC

CTGAACGACGCCACCTACCAGCGCACCCGCGCCCTGGTGCGCACCGGCATGGACCCCCGCATGTGCTCCCT

GATGCAGGGCTCCACCCTGCCCCGCCGCTCCGGCGCCGCCGGCGCCGCCGTGAAGGGCATCGGCACCATGG

-continued

TGATGGAGCTGATCCGCATGGTGAAGCGCGGCATCAACGACCGCAACTTCTGGCGCGGCGAGAACGGCCGC

CGCACCCGCGTGGCCTACGAGCGCATGTGCAACATCCTGAAGGGCAAGTTCCAGACCGCCGCCCAGCGCGC

CATGGTGGACCAGGTGCGCGAGTCCCGCAACCCCGGCAACGCCGAGATCGAGGACCTGATCTTCCTGGCCC

GCTCCGCCCTGATCCTGCGCGGCTCCGTGGCCCACAAGTCCTGCCTGCCCGCCTGCGTGTACGGCCTGGCC

GTGGCCTCCGGCTACGACTTCGAGCGCGAGGGCTACTCCCTGGTGGGCATCGACCCCTTCCGCCTGCTGCA

GAACTCCCAGGTGTTCTCCCTGATCCGCCCCAACGAGAACCCCGCCCACAAGTCCCAGCTGGTGTGGATGG

CCTGCCACTCCGCCGCCTTCGAGGACCTGCGCGTGTCCTCCTTCATCCGCGGCACCCGCATGGTGCCCCGC

GGCCAGCTGTCCACCCGCGGCGTGCAGATCGCCTCCAACGAGAACATGGAGGCCATGGACTCCAACACCCT

GGAGCTGCGCTCCCGCTACTGGGCCATCCGCACCCGCTCCGGCGGCAACACCAACCAGCAGCGCGCCTCCG

CCGGCCAGATCTCCGTGCAGCCCACCTTCTCCGTGCAGCGCAACCTGCCCTTCGAGCGCGCCACCATCATG

GCCGCCTTCACCGGCAACACCGAGGGCCGCACCTCCGACATGCGCACCGAGATCATCCGCATGATGGAGTC

CGCCCGCCCCGAGGACGTGTCCTTCCAGGGCCGCGGCGTGTTCGAGCTGTCCGACAAGAAGGCCACCAACC

CCATCGTGCCCTCCTTCGACATGTCCAACGAGGGCTCCTACTTCTTCGGCGACAACGCCGAGGAGTACGAC

AAC

M2 Sequence
1918 H1N1 - M2 ion channel antigen Amino
Acid sequence (SEQ ID NO: 81)

MSLLTEVETP TRNEWGCRCN DSSDPLVIAA SIIGILHLIL WILDRLFFKC 50

IYRRLKYGLK RGPSTEGVPE SMREEYRKEQ QSAVDVDDGH FVNIELE

1918 H1N1 - Optimized DNA sequence encoding the
nucleic acid sequence encoding M2 ion channel antigen (SEQ ID NO: 82)

ATGTCCCTGCTGACCGAGGTGGAGACCCCCACCCGCAACGAGTGGGGCTGCCGCTGCAACGACTCCTCCGA

CCCCCTGGTGATCGCCGCCTCCATCATCGGCATCCTGCACCTGATCCTGTGGATCCTGGACCGCCTGTTCT

TCAAGTGCATCTACCGCCGCCTGAAGTACGGCCTGAAGCGCGGCCCCTCCACCGAGGGCGTGCCCGAGTCC

ATGCGCGAGGAGTACCGCAAGGAGCAGCAGTCCGCCGTGGACGTGGACGACGGCCACTTCGTGAACATCGA

GCTGGAG

1957 H2N2 - M2 ion channel antigen Amino
Acid sequence (SEQ ID NO: 83)

MSLLTEVETP IRNEWGCRCN DSSDPLVVAA SIIGILHLIL WILDRLFFKC 50

IYRFFKHGLK RGPSTEGVPE SMREEYRKEQ QSAVDADDSH FVSIELE 97

1957 H2N2 - Optimized DNA sequence encoding the
nucleic acid sequence encoding M2 ion channel
antigen (SEQ ID NO: 84)

ATGTCCCTGCTGACCGAGGTGGAGACCCCCATCCGCAACGAGTGGGGCTGCCGCTGCAACGACTCCTCCGA

CCCCCTGGTGGTGGCCGCCTCCATCATCGGCATCCTGCACCTGATCCTGTGGATCCTGGACCGCCTGTTCT

TCAAGTGCATCTACCGCTTCTTCAAGCACGGCCTGAAGCGCGGCCCCTCCACCGAGGGCGTGCCCGAGTCC

ATGCGCGAGGAGTACCGCAAGGAGCAGCAGTCCGCCGTGGACGCCGACGACTCCCACTTCGTGTCCATCGA

GCTGGAG

1968 H3N2 - M2 ion channel antigen Amino
Acid sequence (SEQ ID NO: 85)

MSLLTEVETP IRNEWGCRCN DSSDPLVVAA SIIGILHLIL WILDRLFFKC 50

IYRFFEHGLK RGPSTEGVPE SMREEYRKEQ QSAVDADDSH FVSIELE 97

-continued

1968 H3N2 - Optimized DNA sequence encoding the nucleic acid sequence encoding M2 ion channel antigen (SEQ ID NO: 86)

ATGTCCCTGCTGACCGAGGTGGAGACCCCCATCCGCAACGAGTGGGGCTGCCGCTGCAACGACTCCTCCGA

CCCCCTGGTGGTGGCCGCCTCCATCATCGGCATCCTGCACCTGATCCTGTGGATCCTGGACCGCCTGTTCT

TCAAGTGCATCTACCGCTTCTTCGAGCACGGCCTGAAGCGCGGCCCCTCCACCGAGGGCGTGCCCGAGTCC

ATGCGCGAGGAGTACCGCAAGGAGCAGCAGTCCGCCGTGGACGCCGACGACTCCCACTTCGTGTCCATCGA

GCTGGAG

1977 H1N1 - M2 ion channel antigen Amino Acid sequence (SEQ ID NO: 87)

MSLLTEVETP IRNEWGCRCN DSSDPLVVAA SIIGILHLIL WILDRLFFKC 50

IYRLFKHGLK RGPSTEGVPE SMREEYRKEQ QNAVDADDSH FVNIELE

1977 H1N1 - Optimized DNA sequence encoding the nucleic acid sequence encoding M2 ion channel antigen (SEQ ID NO: 88)

ATGTCCCTGCTGACCGAGGTGGAGACCCCCATCCGCAACGAGTGGGGCTGCCGCTGCAACGACTCCTCCGA

CCCCCTGGTGGTGGCCGCCTCCATCATCGGCATCCTGCACCTGATCCTGTGGATCCTGGACCGCCTGTTCT

TCAAGTGCATCTACCGCCTGTTCAAGCACGGCCTGAAGCGCGGCCCCTCCACCGAGGGCGTGCCCGAGTCC

ATGCGCGAGGAGTACCGCAAGGAGCAGCAGAACGCCGTGGACGCCGACGACTCCCACTTCGTGAACATCGA

GCTGGAG

2007 H1N1 - M2 ion channel antigen Amino Acid sequence (SEQ ID NO: 89)

MSLLTEVETP IRNEWGCRCN DSSDPLVVAA SIIGIVHLIL WIIDRLFSKS 50

IYRIFKHGLK RGPSTEGVPE SMREEYREEQ QNAVDADDDH FVSIELE 97

2007 H1N1 - Optimized DNA sequence encoding the nucleic acid sequence encoding M2 ion channel antigen (SEQ ID NO: 90)

ATGTCCCTGCTGACCGAGGTGGAGACCCCCATCCGCAACGAGTGGGGCTGCCGCTGCAACGACTCCTCCGA

CCCCCTGGTGGTGGCCGCCTCCATCATCGGCATCGTGCACCTGATCCTGTGGATCATCGACCGCCTGTTCT

CCAAGTCCATCTACCGCATCTTCAAGCACGGCCTGAAGCGCGGCCCCTCCACCGAGGGCGTGCCCGAGTCC

ATGCGCGAGGAGTACCGCGAGGAGCAGCAGAACGCCGTGGACGCCGACGACGACCACTTCGTGTCCATCGA

GCTGGAG

2009 H1N1 - M2 ion channel antigen Amino Acid sequence (SEQ ID NO: 91)

MSLLTEVETP TRSEWECRCS DSSDPLVIAA NIIGILHLIL WITDRLFFKC 50

IYRRFKYGLK RGPSTEGVPE SMREEYQQEQ QSAVDVDDGH FVNIELE

2009 H1N1 - Optimized DNA sequence encoding the nucleic acid sequence encoding M2 ion channel antigen (SEQ ID NO: 92)

ATGTCCCTGCTGACCGAGGTGGAGACCCCCACCCGCTCCGAGTGGGAGTGCCGCTGCTCCGACTCCTCCGA

CCCCCTGGTGATCGCCGCCAACATCATCGGCATCCTGCACCTGATCCTGTGGATCACCGACCGCCTGTTCT

TCAAGTGCATCTACCGCCGCTTCAAGTACGGCCTGAAGCGCGGCCCCTCCACCGAGGGCGTGCCCGAGTCC

ATGCGCGAGGAGTACCAGCAGGAGCAGCAGTCCGCCGTGGACGTGGACGACGGCCACTTCGTGAACATCGA

GCTGGAG

-continued

2015 H1N1 - M2 ion channel antigen Amino Acid sequence (SEQ ID NO: 93)

MSLLTEVETP TRSEWECRCS GSSDPLVIAA NIIGILHLIL WITDRLFFKC 50

IYRRFKYGLK RGPSTEGVPE SMREEYQQEQ QSAVDVDDGH FVNIELE

2015 H1N1 - Optimized DNA sequence encoding the nucleic acid sequence encoding M2 ion channel antigen (SEQ ID NO: 94)

ATGTCCCTGCTGACCGAGGTGGAGACCCCCACCCGCTCCGAGTGGGAGTGCCGCTGCTCCGGCTCCTCCGA

CCCCCTGGTGATCGCCGCCAACATCATCGGCATCCTGCACCTGATCCTGTGGATCACCGACCGCCTGTTCT

TCAAGTGCATCTACCGCCGCTTCAAGTACGGCCTGAAGCGCGGCCCCTCCACCGAGGGCGTGCCCGAGTCC

ATGCGCGAGGAGTACCAGCAGGAGCAGCAGTCCGCCGTGGACGTGGACGACGGCCACTTCGTGAACATCGA

GCTGGAG

2017 H3N2 - M2 ion channel antigen Amino Acid sequence (SEQ ID NO: 95)

MSLLTEVETP IRNEWGCRCN DSSDPLIVAA NIIGILHLIL WILDRLFFKC 50

VCRLFKHGLK RGPSTEGVPE SMREEYRKEQ QNAVDADDSH FVSIELE

2017 H3N2 - Optimized DNA sequence encoding the nucleic acid sequence encoding M2 ion channel antigen (SEQ ID NO: 96)

ATGTCCCTGCTGACCGAGGTGGAGACCCCCATCCGCAACGAGTGGGGCTGCCGCTGCAACGACTCCTCCGA

CCCCCTGATCGTGGCCGCCAACATCATCGGCATCCTGCACCTGATCCTGTGGATCCTGGACCGCCTGTTCT

TCAAGTGCGTGTGCCGCCTGTTCAAGCACGGCCTGAAGCGCGGCCCCTCCACCGAGGGCGTGCCCGAGTCC

ATGCGCGAGGAGTACCGCAAGGAGCAGCAGAACGCCGTGGACGCCGACGACTCCCACTTCGTGTCCATCGA

GCTGGAG

2017 Influenza B (Victoria lineage) - M2 ion channel antigen Amino Acid sequence (SEQ ID NO: 97)

MLEPFQILTI CSFILSALHF MAWTIGHLNQ IKRGINMKIR IKGPNKETIT 050

REVSILRHSY QKEIQAKETM KEVLSDNMEV LNDHIIIEGL SAEEIIKMGE 100

TVLEIEELH

2017 Influenza B (Victoria lineage) - Optimized DNA sequence encoding the nucleic acid sequence encoding M2 ion channel antigen (SEQ ID NO: 98)

ATGCTGGAGCCCTTCCAGATCCTGACCATCTGCTCCTTCATCCTGTCCGCCCTGCACTTCATGGCCTGGAC

CATCGGCCACCTGAACCAGATCAAGCGCGGCATCAACATGAAGATCCGCATCAAGGGCCCCAACAAGGAGA

CCATCACCCGCGAGGTGTCCATCCTGCGCCACTCCTACCAGAAGGAGATCCAGGCCAAGGAGACCATGAAG

GAGGTGCTGTCCGACAACATGGAGGTGCTGAACGACCACATCATCATCGAGGGCCTGTCCGCCGAGGAGAT

CATCAAGATGGGCGAGACCGTGCTGGAGATCGAGGAGCTGCAC

2013 Influenza B (Yamagata lineage) - Sequence only on GISAID - M2 ion channel antigen Amino Acid sequence (SEQ ID NO: 99)

0001 MFEPFQILSI CSFILSALHF MAWTIGHLNQ IKRGVNMKIR IKGPNKETIN REVSILRHSY

QKEIQAKEAM KEVLSDNMEV

0081 LSDHIVIEGL SAEEIIKMGE TVLEVEESH

-continued

2013 Influenza B (Yamagata lineage) - Sequence only on GISAID - Optimized DNA sequence encoding the nucleic acid sequence encoding M2 ion channel antigen (SEQ ID NO: 100)

ATGTTCGAGCCCTTCCAGATCCTGTCCATCTGCTCCTTCATCCTGTCCGCCCTGCACTTCATGGCCTGGAC

CATCGGCCACCTGAACCAGATCAAGCGCGGCGTGAACATGAAGATCCGCATCAAGGGCCCCAACAAGGAGA

CCATCAACCGCGAGGTGTCCATCCTGCGCCACTCCTACCAGAAGGAGATCCAGGCCAAGGAGGCCATGAAG

GAGGTGCTGTCCGACAACATGGAGGTGCTGTCCGACCACATCGTGATCGAGGGCCTGTCCGCCGAGGAGAT

CATCAAGATGGGCGAGACCGTGCTGGAGGTGGAGGAGTCCCAC

2015 H5N1 - M2 ion channel antigen Amino Acid sequence (SEQ ID NO: 101)

MSLLTEVETL TKTGWECNCS GSSDPLGVAA NIIGILHLIL WILDRLFFKC 50

IYRRFRYGLK GGPSTEGIPE SMREEYRQEQ QNAVDVDDGH FVNIELE

2015 H5N1 - Optimized DNA sequence encoding the nucleic acid sequence encoding M2 ion channel antigen (SEQ ID NO: 102)

ATGTCCCTGCTGACCGAGGTGGAGACCCTGACCAAGACCGGCTGGGAGTGCAACTGCTCCGGCTCCTCCGA

CCCCCTGGGCGTGGCCGCCAACATCATCGGCATCCTGCACCTGATCCTGTGGATCCTGGACCGCCTGTTCT

TCAAGTGCATCTACCGCCGCTTCCGCTACGGCCTGAAGGGCGGCCCCTCCACCGAGGGCATCCCCGAGTCC

ATGCGCGAGGAGTACCGCCAGGAGCAGCAGAACGCCGTGGACGTGGACGACGGCCACTTCGTGAACATCGA

GCTGGAG

2017 H7N9 - M2 ion channel antigen Amino Acid sequence (SEQ ID NO: 103)

MSLLTEVETP TRTGWECNCS GSSDPFVVAA NIIGILHLIL WILDRLFFKC 50

IYRRFKYGLK RGPSTEGMPE SMREEYRQEQ QNAVDVDDGH FVNIELK

2017 H7N9 - Optimized DNA sequence encoding the nucleic acid sequence encoding M2 ion channel antigen (SEQ ID NO: 104)

ATGTCCCTGCTGACCGAGGTGGAGACCCCCACCCGCACCGGCTGGGAGTGCAACTGCTCCGGCTCCTCCGA

CCCCTTCGTGGTGGCCGCCAACATCATCGGCATCCTGCACCTGATCCTGTGGATCCTGGACCGCCTGTTCT

TCAAGTGCATCTACCGCCGCTTCAAGTACGGCCTGAAGCGCGGCCCCTCCACCGAGGGCATGCCCGAGTCC

ATGCGCGAGGAGTACCGCCAGGAGCAGCAGAACGCCGTGGACGTGGACGACGGCCACTTCGTGAACATCGA

GCTGAAG

2013 H10N8 - M2 ion channel antigen Amino Acid sequence (SEQ ID NO: 105)

MSLLTEVETL TKTGWECNCS GSSDPLVVAA NIIGILHLIL WILDRLFFKC 50

IYRRFKYGLK RGPSTEGMPE SMREEYRQEQ QNAVDVDDGH FVNIELK

2013 H10N8 - Optimized DNA sequence encoding the nucleic acid sequence encoding M2 ion channel antigen (SEQ ID NO: 106)

ATGTCCCTGCTGACCGAGGTGGAGACCCTGACCAAGACCGGCTGGGAGTGCAACTGCTCCGGCTCCTCCGA

CCCCCTGGTGGTGGCCGCCAACATCATCGGCATCCTGCACCTGATCCTGTGGATCCTGGACCGCCTGTTCT

TCAAGTGCATCTACCGCCGCTTCAAGTACGGCCTGAAGCGCGGCCCCTCCACCGAGGGCATGCCCGAGTCC

ATGCGCGAGGAGTACCGCCAGGAGCAGCAGAACGCCGTGGACGTGGACGACGGCCACTTCGTGAACATCGA

GCTGAAG

-continued

M1 Sequences
M1 antigen Amino Acid sequence
(SEQ ID NO: 107)
MSLLTEVETYVLSIIPSGPLKAEIAQRLESVFAGKNTDLEALMEWLKTRPILSPLTKGILGFVFTLTVPSE

RGLQRRRFIQNALNGNGDPNNMDRAVKLYKKLKREITFHGAKEVSLSYSTGALASCMGLIYNRMGTVTTEA

AFGLVCATCEQIADSQHRSHRQMATTTNPLIRHENRMVLASTTAKAMEQVAGSSEQAAEAMEVANKTRQMV

HAMRTIGTHPSSSAGLRDDLLENLQAYQKRMGVQMQRFK

Optimized DNA sequence encoding the nucleic
acid sequence encoding M1 antigen
(SEQ ID NO: 108)
ATGTCCCTGCTGACCGAGGTGGAGACCTACGTGCTGTCCATCATCCCCTCCGGCCCCCTGAAGGCCGAGAT

CGCCCAGCGCCTGGAGTCCGTGTTCGCCGGCAAGAACACCGACCTGGAGGCCCTGATGGAGTGGCTGAAGA

CCCGCCCCATCCTGTCCCCCCTGACCAAGGGCATCCTGGGCTTCGTGTTCACCCTGACCGTGCCCTCCGAG

CGCGGCCTGCAGCGCCGCCGCTTCATCCAGAACGCCCTGAACGGCAACGGCGACCCCAACAACATGGACCG

CGCCGTGAAGCTGTACAAGAAGCTGAAGCGCGAGATCACCTTCCACGGCGCCAAGGAGGTGTCCCTGTCCT

ACTCCACCGGCGCCCTGGCCTCCTGCATGGGCCTGATCTACAACCGCATGGGCACCGTGACCACCGAGGCC

GCCTTCGGCCTGGTGTGCGCCACCTGCGAGCAGATCGCCGACTCCCAGCACCGCTCCCACCGCCAGATGGC

CACCACCACCAACCCCCTGATCCGCCACGAGAACCGCATGGTGCTGGCCTCCACCACCGCCAAGGCCATGG

AGCAGGTGGCCGGCTCCTCCGAGCAGGCCGCCGAGGCCATGGAGGTGGCCAACAAGACCCGCCAGATGGTG

CACGCCATGCGCACCATCGGCACCCACCCCTCCTCCTCCGCCGGCCTGCGCGACGACCTGCTGGAGAACCT

GCAGGCCTACCAGAAGCGCATGGGCGTGCAGATGCAGCGgTTCAAG

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for inducing an immune response against one or more influenza viruses in a subject, the composition comprising a combination of isolated nucleoside-modified RNA molecules encoding at least four influenza viral antigens selected from:

a) a full length HA antigen or a fragment thereof comprising at least the HA-stalk domain or HA-head domain, b) a full length NA antigen or a fragment thereof comprising at least the NA-stalk domain or NA-head domain, c) a full length NP antigen or a fragment thereof, d) a full length M1 antigen or a fragment thereof, and e) a full length M2 ion channel antigen or a fragment thereof comprising at least the M2 ion channel-extracellular domain or M2 ion channel-intracellular domain, and further wherein the isolated nucleoside-modified RNA molecules comprise RNA molecules in which all of the uridines have been replaced with pseudouridine or 1-methyl pseudouridine.

2. The composition of claim 1, wherein the composition comprises at least four influenza virus antigens comprising amino acid sequences selected from the group consisting of:

a) an HA antigen comprising an amino acid sequence selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, and any combination thereof;

b) an NA antigen comprising an amino acid sequence selected from the group consisting of: SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, and any combination thereof;

c) an NP antigen comprising an amino acid sequence selected from the group consisting of: SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, and any combination thereof;

d) an M2 ion channel antigen comprising an amino acid sequence selected from the group consisting of: SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, and any combination thereof; and e) an M1 antigen comprises an amino acid sequence as set forth in SEQ ID NO: 107 and any combination thereof.

3. The composition of claim 1, wherein the at least one influenza virus antigen is a combination of a HA-stalk domain comprising an amino acid sequence as set forth in SEQ ID NO: 27, full length NA antigen comprising an amino acid sequence as set forth in SEQ ID NO: 41, full length NP antigen comprising an amino acid sequence as set forth in SEQ ID NO: 67, and full length M2 ion channel antigen comprising an amino acid sequence as set forth in SEQ ID NO: 93.

4. The composition of claim 1, wherein the composition comprises at least four nucleoside-modified RNA molecules comprising nucleic acid sequences that are encoded by a combination of at least four DNA sequences sequence selected from the group consisting of:

a) at least one nucleoside-modified RNA comprises a nucleic acid sequence that is encoded by a DNA sequence comprising at least one nucleotide sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, and SEQ ID NO: 28;

b) at least one nucleoside-modified RNA comprises a nucleic acid sequence that is encoded by a DNA sequence comprising at least one nucleotide sequence selected from the group consisting of: SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, and SEQ ID NO: 54;

c) at least one nucleoside-modified RNA comprises a nucleic acid sequence that is encoded by a DNA sequence comprising at least one nucleotide sequence selected from the group consisting of: SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, and SEQ ID NO: 80;

d) at least one nucleoside-modified RNA comprises a nucleic acid sequence that is encoded by a DNA sequence comprising at least one nucleotide sequence selected from the group consisting of: SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, and SEQ ID NO: 106; and e) at least one nucleoside-modified RNA comprises a nucleic acid sequence that is encoded by a DNA sequence comprising at least one nucleotide sequence as set forth in SEQ ID NO: 108.

5. The composition of claim 4, wherein the at least one nucleoside-modified RNA comprises a nucleic acid sequence that is encoded by a DNA sequence comprising a combination of a nucleotide sequence as set forth in SEQ ID NO: 28, nucleotide sequence as set forth in SEQ ID NO: 42, nucleotide sequence as set forth in SEQ ID NO: 68, and nucleotide sequence as set forth in SEQ ID NO: 94.

6. The composition of claim 1, wherein the composition further comprises an adjuvant, or wherein the at least one nucleoside-modified RNA further encodes at least one adjuvant.

7. The composition of claim 1, wherein the composition further comprises a lipid nanoparticle (LNP), or wherein the at least one nucleoside-modified RNA is encapsulated within an LNP.

8. The composition of claim 1, wherein the at least one isolated nucleoside-modified RNA is a purified nucleoside-modified mRNA.

9. A method of inducing an immune response against influenza virus in a subject comprising administering to the subject an effective amount of a composition of claim 1.

10. The method of claim 9, wherein the at least one influenza virus antigen is selected from the group consisting of a full length HA antigen or a fragment thereof, HA-stalk domain or a fragment thereof, HA-head domain or a fragment thereof, full length NA antigen or a fragment thereof, NA-stalk domain or a fragment thereof, NA-head domain or a fragment thereof, full length NP antigen or a fragment thereof, full length M1 antigen or a fragment thereof, full length M2 ion channel antigen or a fragment thereof, M2 ion channel-extracellular domain or a fragment thereof, M2 ion channel-intracellular domain or a fragment thereof, and any combination thereof.

11. The method of claim 10, wherein the at least one influenza virus antigen comprises an amino acid sequence selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, and any combination thereof.

12. The method of claim 10, wherein the at least one influenza virus antigen is a combination of a HA-stalk domain comprising an amino acid sequence as set forth in SEQ ID NO: 27, full length NA antigen comprising an amino acid sequence as set forth in SEQ ID NO: 41, full length NP antigen comprising an amino acid sequence as set forth in SEQ ID NO: 67, and full length M2 ion channel antigen comprising an amino acid sequence as set forth in SEQ ID NO: 93.

13. The method of claim 9, wherein the at least one nucleoside-modified RNA comprises a nucleic acid sequence that is encoded by a DNA sequence comprising at least one nucleotide sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, and SEQ ID NO: 108.

14. The method of claim 13, wherein the at least one nucleoside-modified RNA comprises a nucleic acid sequence that is encoded by a DNA sequence comprising a combination of a nucleotide sequence as set forth in SEQ ID NO: 28, nucleotide sequence as set forth in SEQ ID NO: 42, nucleotide sequence as set forth in SEQ ID NO: 68, and nucleotide sequence as set forth in SEQ ID NO: 94.

15. The method of claim 9, wherein the method further comprises administering to the subject an effective amount of an adjuvant.

16. The method of claim 9, wherein the at least one nucleoside-modified RNA is a purified nucleoside-modified mRNA, and further wherein the mRNA molecule comprises at least one selected from the group consisting of pseudouridine and 1-methyl-pseudouridine.

17. The method of claim 9, wherein the influenza virus is selected from the group consisting of an influenza virus A, influenza virus B, influenza virus C, influenza virus D, and any combination thereof.

18. The method of claim 9, wherein the method treats or prevents an infection, disease, disorder, or any combination thereof associated with influenza virus in the subject.

* * * * *

SEQUENCE LISTING

<160> NUMBER OF SEQ ID NOS: 133

<210> SEQ ID NO 1
<211> LENGTH: 566
<212> TYPE: PRT
<213> ORGANISM: Artificial Sequence
<220> FEATURE:
<223> OTHER INFORMATION: 1918 H1N1 - HA antigen Amino Acid sequence

<400> SEQUENCE: 1

```
Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110
```

-continued

```
Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
```

```
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 2
<211> LENGTH: 1698
<212> TYPE: DNA
<213> ORGANISM: Artificial Sequence
<220> FEATURE:
<223> OTHER INFORMATION: 1918 H1N1 - Optimized DNA sequence encoding the nucleic acid sequence encoding HA antigen

<400> SEQUENCE: 2

```
atggaggccc gcctgctggt gctgctgtgc gccttcgccg ccaccaacgc cgacaccatc     60

tgcatcggct accacgccaa caactccacc gacaccgtgg acaccgtgct ggagaagaac    120

gtgaccgtga cccactccgt gaacctgctg gaggactccc acaacggcaa gctgtgcaag    180

ctgaagggca tcgccccccct gcagctgggc aagtgcaaca tcgccggctg gctgctgggc    240

aaccccgagt gcgacctgct gctgaccgcc tcctcctggt cctacatcgt ggagacctcc    300

aactccgaga acggcacctg ctaccccggc gacttcatcg actacgagga gctgcgcgag    360

cagctgtcct ccgtgtcctc cttcgagaag ttcgagatct tccccaagac ctcctcctgg    420

cccaaccacg agaccaccaa gggcgtgacc gccgcctgct cctacgccgg cgcctcctcc    480

ttctaccgca acctgctgtg gctgaccaag aagggctcct cctaccccaa gctgtccaag    540

tcctacgtga acaacaaggg caaggaggtg ctggtgctgt ggggcgtgca ccaccccccc    600

accggcaccg accagcagtc cctgtaccag aacgccgacg cctacgtgtc cgtgggctcc    660

tccaagtaca accgccgctt caccccccgag atcgccgccc gccccaaggt gcgcgaccag    720

gccggccgca tgaactacta ctggaccctg ctggagcccg gcgacaccat caccttcgag    780

gccaccggca acctgatcgc cccctggtac gccttcgccc tgaaccgcgg ctccggctcc    840

ggcatcatca cctccgacgc ccccgtgcac gactgcaaca ccaagtgcca gacccccccac    900

ggcgccatca actcctccct gcccttccag aacatccacc ccgtgaccat cggcgagtgc    960

cccaagtacg tgcgctccac caagctgcgc atggccaccg gcctgcgcaa catcccctcc   1020

atccagtccc gcggcctgtt cggcgccatc gccggcttca tcgagggcgg ctggaccggc   1080

atgatcgacg gctggtacgg ctaccaccac cagaacgagc agggctccgg ctacgccgcc   1140

gaccagaagt ccacccagaa cgccatcgac ggcatcacca acaaggtgaa ctccgtgatc   1200

gagaagatga acacccagtt caccgccgtg ggcaaggagt tcaacaacct ggagcgccgc   1260

atcgagaacc tgaacaagaa ggtggacgac ggcttcctgg acatctggac ctacaacgcc   1320

gagctgctgg tgctgctgga gaacgagcgc accctggact tccacgactc caacgtgcgc   1380

aacctgtacg agaaggtgaa gtcccagctg aagaacaacg ccaaggagat cggcaacggc   1440

tgcttcgagt tctaccacaa gtgcgacgac gcctgcatgg agtccgtgcg caacggcacc   1500

tacgactacc ccaagtactc cgaggagtcc aagctgaacc gcgaggagat cgacggcgtg   1560

aagctggagt ccatgggcgt gtaccagatc ctggccatct actccaccgt ggcctcctcc   1620

ctggtgctgc tggtgtccct gggcgccatc tccttctgga tgtgctccaa cggctccctg   1680

cagtgccgca tctgcatc                                                 1698
```

<210> SEQ ID NO 3

<211> LENGTH: 562
<212> TYPE: PRT
<213> ORGANISM: Artificial Sequence
<220> FEATURE:
<223> OTHER INFORMATION: 1957 H2N2 - HA antigen Amino Acid sequence

<400> SEQUENCE: 3

```
Met Ala Ile Thr Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Phe Leu Arg Val Pro Glu Trp Ser Tyr Ile Met Glu
                85                  90                  95

Lys Glu Asn Pro Arg Tyr Ser Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Gly Trp Thr Gln His Thr Thr Thr Gly
    130                 135                 140

Gly Ser Met Ala Cys Ala Val Ser Gly Lys Pro Ser Phe Phe Arg Asn
145                 150                 155                 160

Met Val Trp Leu Thr Glu Lys Gly Gln Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Ala Glu Gln Arg Ala Leu Tyr Gln Lys Val
        195                 200                 205

Gly Thr Tyr Val Ser Ala Ser Thr Ser Thr Leu Asn Lys Arg Ser Thr
    210                 215                 220

Pro Glu Ile Ala Ala Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Val Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Ile Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380
```

```
Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Lys Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asn Glu Cys Met Asp Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 4
<211> LENGTH: 1686
<212> TYPE: DNA
<213> ORGANISM: Artificial Sequence
<220> FEATURE:
<223> OTHER INFORMATION: 1957 H2N2 - Optimized DNA sequence encoding the
      nucleic acid sequence encoding HA antigen

<400> SEQUENCE: 4

atggccatca cctacctgat cctgctgttc accgccgtgc gcggcgacca gatctgcatc      60

ggctaccacg ccaacaactc caccgagaag gtggacacca tcctggagcg caacgtgacc     120

gtgacccacg ccaaggacat cctggagaag acccacaacg gcaagctgtg caagctgaac     180

ggcatccccc ccctggagct gggcgactgc tccatcgccg gctggctgct gggcaacccc     240

gagtgcgacc gcttcctgcg cgtgcccgag tggtcctaca tcatggagaa ggagaacccc     300

cgctactccc tgtgctaccc cggctccttc aacgactacg aggagctgaa gcacctgctg     360

tcctccgtga agcacttcga gaaggtgaag atcctgccca aggacggctg gacccagcac     420

accaccaccg gcggctccat ggcctgcgcc gtgtccggca agccctcctt cttccgcaac     480

atggtgtggc tgaccgagaa gggccagaac taccccgtgg ccaagggctc ctacaacaac     540

acctccggcg agcagatgct gatcatctgg ggcgtgcacc accccaacga cgaggccgag     600

cagcgcgccc tgtaccagaa ggtgggcacc tacgtgtccg cctccacctc caccctgaac     660

aagcgctcca cccccgagat cgccgcccgc cccaaggtga acggcctggg ctcccgcatg     720

gagttctcct ggaccctgct ggacatgtgg gacaccatca acttcgagtc caccggcaac     780

ctggtggccc ccgagtacgg cttcaagatc tccaagcgcg gctcctccgg catcatgaag     840

accgagggca ccctggagaa ctgcgagacc aagtgccaga ccccccctggg cgccatcaac     900

accaccctgc ccttccacaa cgtgcacccc ctgaccatcg gcgagtgccc caagtacgtg     960
```

-continued

```
aagtccgaga agctggtgct ggccaccggc ctgcgcaaca tcccccagat cgagtcccgc   1020

ggcctgttcg gcgccatcgc cggcttcatc gagggcggct ggcagggcat ggtggacggc   1080

tggtacggct accaccactc caacgaccag ggctccggct acgccgccga caaggagtcc   1140

acccagaagg ccttcgacgg catcaccaac aaggtgaact ccgtgatcga gaagatgaac   1200

acccagttcg aggccgtggg caaggagttc tccaacctgg agaagcgcct ggagaacctg   1260

aacaagaaga tggaggacgg cttcctggac gtgtggacct acaacgccga gctgctggtg   1320

ctgatggaga acgagcgcac cctggacttc cacgactcca acgtgaagaa cctgtacgac   1380

aaggtgcgca tgcagctgcg cgacaacgtg aaggagctgg gcaacggctg cttcgagttc   1440

taccacaagt gcgacaacga gtgcatggac tccgtgaaga acggcaccta cgactacccc   1500

aagtacgagg aggagtccaa gctgaaccgc aacgagatca agggcgtgaa gctgtcctcc   1560

atgggcgtgt accagatcct ggccatctac gccaccgtgg ccggctccct gtccctggcc   1620

atcatgatgg ccggcatctc cttctggatg tgctccaacg gctccctgca gtgccgcatc   1680

tgcatc                                                              1686
```

```
<210> SEQ ID NO 5
<211> LENGTH: 566
<212> TYPE: PRT
<213> ORGANISM: Artificial Sequence
<220> FEATURE:
<223> OTHER INFORMATION: 1968 H3N2 - HA antigen Amino Acid sequence

<400> SEQUENCE: 5

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
```

```
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565
```

<210> SEQ ID NO 6
<211> LENGTH: 1698
<212> TYPE: DNA
<213> ORGANISM: Artificial Sequence
<220> FEATURE:
<223> OTHER INFORMATION: 1968 H3N2 - Optimized DNA sequence encoding the nucleic acid sequence encoding HA antigen

<400> SEQUENCE: 6

```
atgaagacca tcatcgccct gtcctacatc ttctgcctgg ccctgggcca ggacctgccc      60

ggcaacgaca actccaccgc caccctgtgc ctgggccacc acgccgtgcc caacggcacc     120
```

```
ctggtgaaga ccatcaccga cgaccagatc gaggtgacca acgccaccga gctggtgcag    180

tcctcctcca ccggcaagat ctgcaacaac ccccaccgca tcctggacgg catcgactgc    240

accctgatcg acgccctgct gggcgacccc cactgcgacg tgttccagaa cgagacctgg    300

gacctgttcg tggagcgctc caaggccttc tccaactgct acccctacga cgtgcccgac    360

tacgcctccc tgcgctccct ggtggcctcc tccggcaccc tggagttcat caccgagggc    420

ttcacctgga ccggcgtgac ccagaacggc ggctccaacg cctgcaagcg cggccccggc    480

tccggcttct tctcccgcct gaactggctg accaagtccg gctccaccta ccccgtgctg    540

aacgtgacca tgcccaacaa cgacaacttc gacaagctgt acatctgggg cgtgcaccac    600

ccctccacca accaggagca gacctccctg tacgtgcagg cctccggccg cgtgaccgtg    660

tccacccgcc gctcccagca gaccatcatc cccaacatcg gctcccgccc ctgggtgcgc    720

ggcctgtcct cccgcatctc catctactgg accatcgtga agcccggcga cgtgctggtg    780

atcaactcca acggcaacct gatcgccccc cgcggctact tcaagatgcg caccggcaag    840

tcctccatca tgcgctccga cgcccccatc gacacctgca tctccgagtg catcaccccc    900

aacggctcca tccccaacga caagcccttc cagaacgtga acaagatcac ctacggcgcc    960

tgccccaagt acgtgaagca gaacaccctg aagctggcca ccggcatgcg caacgtgccc   1020

gagaagcaga cccgcggcct gttcggcgcc atcgccggct tcatcgagaa cggctgggag   1080

ggcatgatcg acggctggta cggcttccgc caccagaact ccgagggcac cggccaggcc   1140

gccgacctga agtccaccca ggccgccatc gaccagatca acggcaagct gaaccgcgtg   1200

atcgagaaga ccaacgagaa gttccaccag atcgagaagg agttctccga ggtggagggc   1260

cgcatccagg acctggagaa gtacgtggag gacaccaaga tcgacctgtg gtcctacaac   1320

gccgagctgc tggtggccct ggagaaccag cacaccatcg acctgaccga ctccgagatg   1380

aacaagctgt tcgagaagac ccgccgccag ctgcgcgaga acgccgagga catgggcaac   1440

ggctgcttca agatctacca caagtgcgac aacgcctgca tcgagtccat ccgcaacggc   1500

acctacgacc acgacgtgta ccgcgacgag gccctgaaca accgcttcca gatcaagggc   1560

gtggagctga agtccggcta caaggactgg atcctgtgga tctccttcgc catctcctgc   1620

ttcctgctgt gcgtggtgct gctgggcttc atcatgtggg cctgccagcg cggcaacatc   1680

cgctgcaaca tctgcatc                                                  1698
```

<210> SEQ ID NO 7
<211> LENGTH: 566
<212> TYPE: PRT
<213> ORGANISM: Artificial Sequence
<220> FEATURE:
<223> OTHER INFORMATION: 1977 H1N1 - HA antigen Amino Acid sequence

<400> SEQUENCE: 7

```
Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80
```

```
Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Val Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp His Ala Phe
            260                 265                 270

Ala Leu Asn Arg Gly Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495
```

-continued

```
Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 8
<211> LENGTH: 1698
<212> TYPE: DNA
<213> ORGANISM: Artificial Sequence
<220> FEATURE:
<223> OTHER INFORMATION: 1977 H1N1 - Optimized DNA sequence encoding the nucleic acid sequence encoding HA antigen

<400> SEQUENCE: 8

```
atgaaggcca agctgctggt gctgctgtgc gccctgtccg ccaccgacgc cgacaccatc     60

tgcatcggct accacgccaa caactccacc gacaccgtgg acaccgtgct ggagaagaac    120

gtgaccgtga cccactccgt gaacctgctg gaggactccc acaacggcaa gctgtgccgc    180

ctgaagggca tcgcccccct gcagctgggc aagtgcaaca tcgccggctg gatcctgggc    240

aaccccgagt gcgagtccct gttctccaag aagtcctggt cctacatcgc cgagaccccc    300

aactccgaga acggcacctg ctaccccggc tacttcgccg actacgagga gctgcgcgag    360

cagctgtcct ccgtgtcctc cttcgagcgc ttcgagatct tccccaagga gcgctcctgg    420

cccaagcaca acgtgacccg cggcgtgacc gcctcctgct cccacaaggg caagtcctcc    480

ttctaccgca acctgctgtg gctgaccgag aagaacggct cctaccccaa cctgtccaag    540

tcctacgtga acaacaagga gaaggaggtg ctggtgctgt ggggcgtgca ccacccctcc    600

aacatcgagg accagaagac catctaccgc aaggagaacg cctacgtgtc cgtggtgtcc    660

tccaactaca accgccgctt cacccccgag atcgccgagc gccccaaggt gcgcggccag    720

gccggccgca tcaactacta ctggaccctg ctggagcccg gcgacaccat catcttcgag    780

gccaacggca acctgatcgc cccctggcac gccttcgccc tgaaccgcgg cttcggctcc    840

ggcatcatca cctccaacgc ctccatggac gagtgcgaca ccaagtgcca gaccccccag    900

ggcgccatca actcctccct gcccttccag aacatccacc ccgtgaccat cggcgagtgc    960

cccaagtacg tgcgctccac caagctgcgc atggtgaccg gcctgcgcaa catcccctcc   1020

atccagtccc gcggcctgtt cggcgccatc gccggcttca tcgagggcgg ctggaccggc   1080

atgatcgacg gctggtacgg ctaccaccac cagaacgagc agggctccgg ctacgccgcc   1140

gaccagaagt ccacccagaa cgccatcaac ggcatcacca acaaggtgaa ctccgtgatc   1200

gagaagatga acacccagtt caccgccgtg ggcaaggagt tcaacaagct ggagaagcgc   1260

atggagaacc tgaacaagaa ggtggacgac ggcttcctgg acatctggac ctacaacgcc   1320

gagctgctgg tgctgctgga gaacgagcgc accctggact tccacgactc caacgtgaag   1380

aacctgtacg agaaggtgaa gtcccagctg aagaacaacg ccaaggagat cggcaacggc   1440

tgcttcgagt tctaccacaa gtgcaacaac gagtgcatgg agtccgtgaa gaacggcacc   1500

tacgactacc ccaagtactc cgaggagtcc aagctgaacc gcgagaagat cgacggcgtg   1560

aagctggagt ccatgggcgt gtaccagatc ctggccatct actccaccgt ggcctcctcc   1620
```

```
ctggtgctgc tggtgtccct gggcgccatc tccttctgga tgtgctccaa cggctccctg   1680

cagtgccgca tctgcatc                                                 1698


<210> SEQ ID NO 9
<211> LENGTH: 565
<212> TYPE: PRT
<213> ORGANISM: Artificial Sequence
<220> FEATURE:
<223> OTHER INFORMATION: 2007 H1N1 - HA antigen Amino Acid sequence

<400> SEQUENCE: 9

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Val Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
```

```
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 10
<211> LENGTH: 1695
<212> TYPE: DNA
<213> ORGANISM: Artificial Sequence
<220> FEATURE:
<223> OTHER INFORMATION: 2007 H1N1 - Optimized DNA sequence encoding the
      nucleic acid sequence encoding HA antigen

<400> SEQUENCE: 10

atgaaggtga agctgctggt gctgctgtgc accttcaccg ccacctacgc cgacaccatc     60

tgcatcggct accacgccaa caactccacc gacaccgtgg acaccgtgct ggagaagaac    120

gtgaccgtga cccactccgt gaacctgctg gagaactccc acaacggcaa gctgtgcctg    180

ctgaagggca tcgccccccct gcagctgggc aactgctccg tggccggctg gatcctgggc    240

aaccccgagt gcgagctgct gatctccaag gagtcctggt cctacatcgt ggagaagccc    300

aaccccgaga acggcacctg ctaccccggc cacttcgccg actacgagga gctgcgcgag    360

cagctgtcct ccgtgtcctc cttcgagcgc ttcgagatct tccccaagga gtcctcctgg    420

cccaaccaca ccgtgaccgg cgtgtccgcc tcctgctccc acaacggcga gtcctccttc    480

taccgcaacc tgctgtggct gaccggcaag aacggcctgt accccaacct gtccaagtcc    540

tacgccaaca acaaggagaa ggaggtgctg gtgctgtggg gcgtgcacca cccccccaac    600

atcggcgtgc agaaggccct gtaccacacc gagaacgcct acgtgtccgt ggtgtcctcc    660

cactactccc gcaagttcac ccccgagatc gccaagcgcc ccaaggtgcg cgaccaggag    720
```

-continued

```
ggccgcatca actactactg gaccctgctg gagcccggcg acaccatcat cttcgaggcc    780

aacggcaacc tgatcgcccc ccgctacgcc ttcgccctgt cccgcggctt cggctccggc    840

atcatcaact ccaacgcccc catggacaag tgcgacgcca agtgccagac cccccagggc    900

gccatcaact cctccctgcc cttccagaac gtgcaccccg tgaccatcgg cgagtgcccc    960

aagtacgtgc gctccgccaa gctgcgcatg gtgaccggcc tgcgcaacat cccctccatc   1020

cagtcccgcg gcctgttcgg cgccatcgcc ggcttcatcg agggcggctg gaccggcatg   1080

gtggacggct ggtacggcta ccaccaccag aacgagcagg gctccggcta cgccgccgac   1140

cagaagtcca cccagaacgc catcaacggc atcaccaaca aggtgaactc cgtgatcgag   1200

aagatgaaca cccagttcac cgccgtgggc aaggagttca acaagctgga gcgccgcatg   1260

gagaacctga acaagaaggt ggacgacggc ttcatcgaca tctggaccta caacgccgag   1320

ctgctggtgc tgctggagaa cgagcgcacc ctggacttcc acgactccaa cgtgaagaac   1380

ctgtacgaga aggtgaagtc ccagctgaag aacaacgcca aggagatcgg caacggctgc   1440

ttcgagttct accacaagtg caacgacgag tgcatggagt ccgtgaagaa cggcacctac   1500

gactacccca agtactccga ggagtccaag ctgaaccgcg agaagatcga cggcgtgaag   1560

ctggagtcca tgggcgtgta ccagatcctg gccatctact ccaccgtggc ctcctccctg   1620

gtgctgctgg tgtccctggg cgccatctcc ttctggatgt gctccaacgg ctccctgcag   1680

tgccgcatct gcatc                                                    1695


<210> SEQ ID NO 11
<211> LENGTH: 566
<212> TYPE: PRT
<213> ORGANISM: Artificial Sequence
<220> FEATURE:
<223> OTHER INFORMATION: 2009 H1N1 - HA antigen Amino Acid sequence

<400> SEQUENCE: 11

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190
```

```
Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 12
<211> LENGTH: 1698
<212> TYPE: DNA
<213> ORGANISM: Artificial Sequence
<220> FEATURE:

-continued

<223> OTHER INFORMATION: 2009 H1N1 - Optimized DNA sequence encoding the nucleic acid sequence encoding HA antigen

<400> SEQUENCE: 12

```
atgaaggcca tcctggtggt gctgctgtac accttcgcca ccgccaacgc cgacaccctg     60

tgcatcggct accacgccaa caactccacc gacaccgtgg acaccgtgct ggagaagaac    120

gtgaccgtga cccactccgt gaacctgctg gaggacaagc acaacggcaa gctgtgcaag    180

ctgcgcggcg tggcccccct gcacctgggc aagtgcaaca tcgccggctg gatcctgggc    240

aaccccgagt gcgagtccct gtccaccgcc tcctcctggt cctacatcgt ggagaccccc    300

tcctccgaca acggcacctg ctaccccggc gacttcatcg actacgagga gctgcgcgag    360

cagctgtcct ccgtgtcctc cttcgagcgc ttcgagatct tccccaagac ctcctcctgg    420

cccaaccacg actccaacaa gggcgtgacc gccgcctgcc cccacgccgg cgccaagtcc    480

ttctacaaga acctgatctg gctggtgaag aagggcaact cctaccccaa gctgtccaag    540

tcctacatca acgacaaggg caaggaggtg ctggtgctgt ggggcatcca ccacccctcc    600

acctccgccg accagcagtc cctgtaccag aacgccgaca cctacgtgtt cgtgggctcc    660

tcccgctact ccaagaagtt caagcccgag atcgccatcc gccccaaggt gcgcgaccag    720

gagggccgca tgaactacta ctggaccctg gtggagcccg gcgacaagat caccttcgag    780

gccaccggca acctggtggt gccccgctac gccttcgcca tggagcgcaa cgccggctcc    840

ggcatcatca tctccgacac ccccgtgcac gactgcaaca ccacctgcca gacccccaag    900

ggcgccatca acacctccct gcccttccag aacatccacc ccatcaccat cggcaagtgc    960

cccaagtacg tgaagtccac caagctgcgc ctggccaccg gcctgcgcaa catcccctcc   1020

atccagtccc gcggcctgtt cggcgccatc gccggcttca tcgagggcgg ctggaccggc   1080

atggtggacg gctggtacgg ctaccaccac cagaacgagc agggctccgg ctacgccgcc   1140

gacctgaagt ccacccagaa cgccatcgac gagatcacca acaaggtgaa ctccgtgatc   1200

gagaagatga acacccagtt caccgccgtg ggcaaggagt tcaaccacct ggagaagcgc   1260

atcgagaacc tgaacaagaa ggtggacgac ggcttcctgg acatctggac ctacaacgcc   1320

gagctgctgg tgctgctgga gaacgagcgc accctggact accacgactc caacgtgaag   1380

aacctgtacg agaaggtgcg ctcccagctg aagaacaacg ccaaggagat cggcaacggc   1440

tgcttcgagt tctaccacaa gtgcgacaac acctgcatgg agtccgtgaa gaacggcacc   1500

tacgactacc ccaagtactc cgaggaggcc aagctgaacc gcgaggagat cgacggcgtg   1560

aagctggagt ccacccgcat ctaccagatc ctggccatct actccaccgt ggcctcctcc   1620

ctggtgctgg tggtgtccct gggcgccatc tccttctgga tgtgctccaa cggctccctg   1680

cagtgccgca tctgcatc                                                 1698
```

<210> SEQ ID NO 13
<211> LENGTH: 574
<212> TYPE: PRT
<213> ORGANISM: Artificial Sequence
<220> FEATURE:
<223> OTHER INFORMATION: 2015 H1N1 - HA antigen Amino Acid sequence

<400> SEQUENCE: 13

```
Met Ala Ile Ser Gly Val Pro Val Leu Gly Phe Phe Ile Ile Ala Val
1               5                   10                  15

Leu Met Ser Ala Gln Glu Ser Trp Ala Asp Thr Leu Cys Ile Gly Tyr
            20                  25                  30
```

```
His Ala Asn Asn Ser Thr Asp Thr Val Asp Thr Val Leu Glu Lys Asn
        35                  40                  45

Val Thr Val Thr His Ser Val Asn Leu Leu Glu Asp Lys His Asn Gly
    50                  55                  60

Lys Leu Cys Lys Leu Arg Gly Val Ala Pro Leu His Leu Gly Lys Cys
65                  70                  75                  80

Asn Ile Ala Gly Trp Ile Leu Gly Asn Pro Glu Cys Glu Ser Leu Ser
                85                  90                  95

Thr Ala Ser Ser Trp Ser Tyr Ile Val Glu Thr Ser Asn Ser Asp Asn
            100                 105                 110

Gly Thr Cys Tyr Pro Gly Asp Phe Ile Asn Tyr Glu Glu Leu Arg Glu
        115                 120                 125

Gln Leu Ser Ser Val Ser Ser Phe Glu Arg Phe Glu Ile Phe Pro Lys
    130                 135                 140

Thr Ser Ser Trp Pro Asn His Asp Ser Asn Lys Gly Val Thr Ala Ala
145                 150                 155                 160

Cys Pro His Ala Gly Ala Lys Ser Phe Tyr Lys Asn Leu Ile Trp Leu
                165                 170                 175

Val Lys Lys Gly Asn Ser Tyr Pro Lys Leu Asn Gln Ser Tyr Ile Asn
            180                 185                 190

Asp Lys Gly Lys Glu Val Leu Val Leu Trp Gly Ile His His Pro Ser
        195                 200                 205

Thr Thr Ala Asp Gln Gln Ser Leu Tyr Gln Asn Ala Asp Ala Tyr Val
    210                 215                 220

Phe Val Gly Thr Ser Arg Tyr Ser Lys Lys Phe Lys Pro Glu Ile Ala
225                 230                 235                 240

Thr Arg Pro Lys Val Arg Asp Gln Glu Gly Arg Met Asn Tyr Tyr Trp
                245                 250                 255

Thr Leu Val Glu Pro Gly Asp Lys Ile Thr Phe Glu Ala Thr Gly Asn
            260                 265                 270

Leu Val Val Pro Arg Tyr Ala Phe Thr Met Glu Arg Asn Ala Gly Ser
        275                 280                 285

Gly Ile Ile Ile Ser Asp Thr Pro Val His Asp Cys Asn Thr Thr Cys
    290                 295                 300

Gln Thr Pro Glu Gly Ala Ile Asn Thr Ser Leu Pro Phe Gln Asn Ile
305                 310                 315                 320

His Pro Ile Thr Ile Gly Lys Cys Pro Lys Tyr Val Lys Ser Thr Lys
                325                 330                 335

Leu Arg Leu Ala Thr Gly Leu Arg Asn Val Pro Ser Ile Gln Ser Arg
            340                 345                 350

Gly Leu Phe Gly Ala Ile Ala Gly Phe Ile Glu Gly Gly Trp Thr Gly
        355                 360                 365

Met Val Asp Gly Trp Tyr Gly Tyr His His Gln Asn Glu Gln Gly Ser
    370                 375                 380

Gly Tyr Ala Ala Asp Leu Lys Ser Thr Gln Asn Ala Ile Asp Lys Ile
385                 390                 395                 400

Thr Asn Lys Val Asn Ser Val Ile Glu Lys Met Asn Thr Gln Phe Thr
                405                 410                 415

Ala Val Gly Lys Glu Phe Asn His Leu Glu Lys Arg Ile Glu Asn Leu
            420                 425                 430

Asn Lys Lys Val Asp Asp Gly Phe Leu Asp Ile Trp Thr Tyr Asn Ala
        435                 440                 445

Glu Leu Leu Val Leu Leu Glu Asn Glu Arg Thr Leu Asp Tyr His Asp
```

```
    450                 455                 460

Ser Asn Val Lys Asn Leu Tyr Glu Lys Val Arg Asn Gln Leu Lys Asn
465                 470                 475                 480

Asn Ala Lys Glu Ile Gly Asn Gly Cys Phe Glu Phe Tyr His Lys Cys
                485                 490                 495

Asp Asn Thr Cys Met Glu Ser Val Lys Asn Gly Thr Tyr Asp Tyr Pro
            500                 505                 510

Lys Tyr Ser Glu Glu Ala Lys Leu Asn Arg Glu Lys Ile Asp Gly Val
        515                 520                 525

Lys Leu Glu Ser Thr Arg Ile Tyr Gln Ile Leu Ala Ile Tyr Ser Thr
    530                 535                 540

Val Ala Ser Ser Leu Val Leu Val Val Ser Leu Gly Ala Ile Ser Phe
545                 550                 555                 560

Trp Met Cys Ser Asn Gly Ser Leu Gln Cys Arg Ile Cys Ile
                565                 570


<210> SEQ ID NO 14
<211> LENGTH: 1722
<212> TYPE: DNA
<213> ORGANISM: Artificial Sequence
<220> FEATURE:
<223> OTHER INFORMATION: 2015 H1N1 - Optimized DNA sequence encoding the
      nucleic acid sequence encoding HA antigen

<400> SEQUENCE: 14

atggccatct ccggcgtgcc cgtgctgggc ttcttcatca tcgccgtgct gatgtccgcc      60

caggagtcct gggccgacac cctgtgcatc ggctaccacg ccaacaactc caccgacacc     120

gtggacaccg tgctggagaa gaacgtgacc gtgacccact ccgtgaacct gctggaggac     180

aagcacaacg gcaagctgtg caagctgcgc ggcgtggccc ccctgcacct gggcaagtgc     240

aacatcgccg gctggatcct gggcaacccc gagtgcgagt ccctgtccac cgcctcctcc     300

tggtcctaca tcgtggagac ctccaactcc gacaacggca cctgctaccc cggcgacttc     360

atcaactacg aggagctgcg cgagcagctg tcctccgtgt cctccttcga gcggttcgag     420

atcttcccca agacctcctc ctggcccaac cacgactcca acaagggcgt gaccgccgcc     480

tgcccccacg ccggcgccaa gtccttctac aagaacctga tctggctggt gaagaagggc     540

aactcctacc ccaagctgaa ccagtcctac atcaacgaca agggcaagga ggtgctggtg     600

ctgtggggca tccaccaccc ctccaccacc gccgaccagc agtccctgta ccagaacgcc     660

gacgcctacg tgttcgtggg cacctcccgc tactccaaga agttcaagcc cgagatcgcc     720

acccgcccca aggtgcgcga ccaggagggc cgcatgaact actactggac cctggtggag     780

cccggcgaca agatcacctt cgaggccacc ggcaacctgg tggtgccccg ctacgccttc     840

accatggagc gcaacgccgg ctccggcatc atcatctccg acacccccgt gcacgactgc     900

aacaccacct gccagacccc cgagggcgcc atcaacacct ccctgccctt ccagaacatc     960

caccccatca ccatcggcaa gtgccccaag tacgtgaagt ccaccaagct gcgcctggcc    1020

accggcctgc gcaacgtgcc ctccatccag tcccgcggcc tgttcggcgc catcgccggc    1080

ttcatcgagg gcggctggac cggcatggtg gacggctggt acggctacca ccaccagaac    1140

gagcagggct ccggctacgc cgccgacctg aagtccaccc agaacgccat cgacaagatc    1200

accaacaagg tgaactccgt gatcgagaag atgaacaccc agttcaccgc cgtgggcaag    1260

gagttcaacc acctggagaa gcgcatcgag aacctgaaca agaaggtgga cgacggcttc    1320

ctggacatct ggacctacaa cgccgagctg ctggtgctgc tggagaacga gcgcaccctg    1380
```

gactaccacg actccaacgt gaagaacctg tacgagaagg tgcgcaacca gctgaagaac 1440
aacgccaagg agatcggcaa cggctgcttc gagttctacc acaagtgcga caacacctgc 1500
atggagtccg tgaagaacgg cacctacgac taccccaagt actccgagga ggccaagctg 1560
aaccgcgaga agatcgacgg cgtgaagctg gagtccaccc gcatctacca gatcctggcc 1620
atctactcca ccgtggcctc ctccctggtg ctggtggtgt ccctgggcgc catctccttc 1680
tggatgtgct ccaacggctc cctgcagtgc cgcatctgca tc 1722

<210> SEQ ID NO 15
<211> LENGTH: 566
<212> TYPE: PRT
<213> ORGANISM: Artificial Sequence
<220> FEATURE:
<223> OTHER INFORMATION: 2017 H3N2 - HA antigen Amino Acid sequence
<220> FEATURE:
<221> NAME/KEY: misc_feature
<222> LOCATION: (262)..(262)
<223> OTHER INFORMATION: Xaa can be any naturally occurring amino acid

<400> SEQUENCE: 15

Met Lys Thr Ile Ile Ala Leu Ser Cys Ile Leu Cys Leu Val Phe Ala
1               5                   10                  15

Gln Lys Ile Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Asn Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Ala
    130                 135                 140

Gly Val Thr Gln Asn Gly Thr Ser Ser Ser Cys Ile Arg Gly Ser Lys
145                 150                 155                 160

Ser Ser Phe Phe Ser Arg Leu Asn Trp Leu Thr His Leu Asn Ser Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asn Gln Ile
        195                 200                 205

Ser Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Xaa Ser Thr Gly Asn Leu Ile Ala Pro Arg Gly
            260                 265                 270

Tyr Phe Lys Ile Arg Ser Gly Lys Ser Ser Ile Met Arg Ser Asp Ala

```
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Arg Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Met Gly Ser
                485                 490                 495

Ile Arg Asn Gly Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 16
<211> LENGTH: 1698
<212> TYPE: DNA
<213> ORGANISM: Artificial Sequence
<220> FEATURE:
<223> OTHER INFORMATION: 2017 H3N2 - Optimized DNA sequence encoding the nucleic acid sequence encoding HA antigen
<220> FEATURE:
<221> NAME/KEY: misc_feature
<222> LOCATION: (784)..(786)
<223> OTHER INFORMATION: any nucleotide

<400> SEQUENCE: 16

```
atgaagacca tcatcgccct gtcctgcatc ctgtgcctgg tgttcgccca gaagatcccc      60

ggcaacgaca actccaccgc caccctgtgc ctgggccacc acgccgtgcc caacggcacc     120

atcgtgaaga ccatcaccaa cgaccgcatc gaggtgacca acgccaccga gctggtgcag     180

aactcctcca tcggcgagat ctgcgactcc ccccaccaga tcctggacgg cgagaactgc     240
```

```
accctgatcg acgccctgct gggcgacccc cagtgcgacg gcttccagaa caagaagtgg    300

gacctgttcg tggagcgcaa caaggcctac tccaactgct acccctacga cgtgcccgac    360

tacgcctccc tgcgctccct ggtggcctcc tccggcaccc tggagttcaa caacgagtcc    420

ttcaactggg ccggcgtgac ccagaacggc acctcctcct cctgcatccg cggctccaag    480

tcctccttct tctcccgcct gaactggctg acccacctga actccaagta ccccgccctg    540

aacgtgacca tgcccaacaa cgagcagttc gacaagctgt acatctgggg cgtgcaccac    600

cccggcaccg acaagaacca gatctccctg tacgcccagt cctccggccg catcaccgtg    660

tccaccaagc gctcccagca ggccgtgatc cccaacatcg gctcccgccc ccgcatccgc    720

gacatcccct cccgcatctc catctactgg accatcgtga agcccggcga catcctgctg    780

atcnnntcca ccggcaacct gatcgccccc cgcggctact tcaagatccg ctccggcaag    840

tcctccatca tgcgctccga cgcccccatc ggcaagtgca agtccgagtg catcaccccc    900

aacggctcca tccccaacga caagcccttc cagaacgtga accgcatcac ctacggcgcc    960

tgcccccgct acgtgaagca gtccaccctg aagctggcca ccggcatgcg caacgtgccc   1020

gagcgccaga cccgcggcat cttcggcgcc atcgccggct tcatcgagaa cggctgggag   1080

ggcatggtgg acggctggta cggcttccgc caccagaact ccgagggccg cggccaggcc   1140

gccgacctga agtccaccca ggccgccatc gaccagatca acggcaagct gaaccgcctg   1200

atcggcaaga ccaacgagaa gttccaccag atcgagaagg agttctccga ggtggagggc   1260

cgcatccagg acctggagaa gtacgtggag gacaccaaga tcgacctgtg gtcctacaac   1320

gccgagctgc tggtggccct ggagaaccag cacaccatcg acctgaccga ctccgagatg   1380

aacaagctgt tcgagaagac caagaagcag ctgcgcgaga acgccgagga catgggcaac   1440

ggctgcttca agatctacca caagtgcgac aacgcctgca tgggctccat ccgcaacggc   1500

acctacgacc acaacgtgta ccgcgacgag gccctgaaca accgcttcca gatcaagggc   1560

gtggagctga agtccggcta caaggactgg atcctgtgga tctccttcgc catctcctgc   1620

ttcctgctgt gcgtggccct gctgggcttc atcatgtggg cctgccagaa gggcaacatc   1680

cgctgcaaca tctgcatc                                                1698
```

```
<210> SEQ ID NO 17
<211> LENGTH: 583
<212> TYPE: PRT
<213> ORGANISM: Artificial Sequence
<220> FEATURE:
<223> OTHER INFORMATION: 2017 Influenza B (Victoria lineage) - HA
      antigen Amino Acid sequence
<220> FEATURE:
<221> NAME/KEY: misc_feature
<222> LOCATION: (210)..(210)
<223> OTHER INFORMATION: Xaa can be any naturally occurring amino acid

<400> SEQUENCE: 17

Met Lys Ala Ile Ile Val Leu Leu Met Val Val Thr Ser Ser Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80
```

```
Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Val Arg Leu Ser Thr His Asn Val Ile Asn Ala Glu Gly
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Asp Lys Asn Lys Thr Ala Thr Asn Pro Leu Thr Ile Glu Val Pro Tyr
            180                 185                 190

Val Cys Thr Glu Gly Glu Asp Gln Ile Thr Val Trp Gly Phe His Ser
        195                 200                 205

Asp Xaa Glu Thr Gln Met Ala Lys Leu Tyr Gly Asp Ser Lys Pro Gln
    210                 215                 220

Lys Phe Thr Ser Ser Ala Asn Gly Val Thr Thr His Tyr Val Ser Gln
225                 230                 235                 240

Ile Gly Gly Phe Pro Asn Gln Thr Glu Asp Gly Gly Leu Pro Gln Ser
                245                 250                 255

Gly Arg Ile Val Val Asp Tyr Met Val Gln Lys Ser Gly Lys Thr Gly
            260                 265                 270

Thr Ile Thr Tyr Gln Arg Gly Ile Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Glu Ile Gly Asn Gly
                485                 490                 495
```

```
Cys Phe Glu Thr Lys His Lys Cys Asn Gln Thr Cys Leu Asp Lys Ile
            500                 505                 510

Ala Ala Gly Thr Phe Asp Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Val Val Tyr Met Val Ser Arg Asp Asn
                565                 570                 575

Val Ser Cys Ser Ile Cys Leu
            580


<210> SEQ ID NO 18
<211> LENGTH: 1749
<212> TYPE: DNA
<213> ORGANISM: Artificial Sequence
<220> FEATURE:
<223> OTHER INFORMATION: 2017 Influenza B (Victoria lineage) - Optimized
      DNA sequence encoding the nucleic acid sequence encoding HA
      antigen
<220> FEATURE:
<221> NAME/KEY: misc_feature
<222> LOCATION: (628)..(630)
<223> OTHER INFORMATION: any nucleotide

<400> SEQUENCE: 18

atgaaggcca tcatcgtgct gctgatggtg gtgacctcct ccgccgaccg catctgcacc     60

ggcatcacct cctccaactc cccccacgtg gtgaagaccg ccacccaggg cgaggtgaac    120

gtgaccggcg tgatccccct gaccaccacc cccaccaagt cccacttcgc caacctgaag    180

ggcaccgaga cccgcggcaa gctgtgcccc aagtgcctga actgcaccga cctggacgtg    240

gccctgggcc gccccaagtg caccggcaag atcccctccg cccgcgtgtc catcctgcac    300

gaggtgcgcc ccgtgacctc cggctgcttc cccatcatgc acgaccgcac caagatccgc    360

cagctgccca acctgctgcg cggctacgag cacgtgcgcc tgtccaccca caacgtgatc    420

aacgccgagg gcgcccccgg cggcccctac aagatcggca cctccggctc ctgccccaac    480

atcaccaacg gcaacggctt cttcgccacc atggcctggg ccgtgcccga caagaacaag    540

accgccacca accccctgac catcgaggtg ccctacgtgt gcaccgaggg cgaggaccag    600

atcaccgtgt ggggcttcca ctccgacnnn gagacccaga tggccaagct gtacggcgac    660

tccaagcccc agaagttcac ctcctccgcc aacggcgtga ccacccacta cgtgtcccag    720

atcggcggct tccccaacca gaccgaggac ggcggcctgc cccagtccgg ccgcatcgtg    780

gtggactaca tggtgcagaa gtccggcaag accggcacca tcacctacca gcgcggcatc    840

ctgctgcccc agaaggtgtg gtgcgcctcc ggccgctcca aggtgatcaa gggctccctg    900

cccctgatcg gcgaggccga ctgcctgcac gagaagtacg gcggcctgaa caagtccaag    960

ccctactaca ccggcgagca cgccaaggcc atcggcaact gccccatctg ggtgaagacc   1020

cccctgaagc tggccaacgg caccaagtac cgcccccccg ccaagctgct gaaggagcgc   1080

ggcttcttcg gcgccatcgc cggcttcctg gagggcggct gggagggcat gatcgccggc   1140

tggcacggct acacctccca cggcgcccac ggcgtggccg tggccgccga cctgaagtcc   1200

acccaggagg ccatcaacaa gatcaccaag aacctgaact ccctgtccga gctggaggtg   1260

aagaacctgc agcgcctgtc cggcgccatg gacgagctgc acaacgagat cctggagctg   1320

gacgagaagg tggacgacct gcgcgccgac accatctcct cccagatcga gctggccgtg   1380
```

```
ctgctgtcca acgagggcat catcaactcc gaggacgagc acctgctggc cctggagcgc   1440

aagctgaaga agatgctggg cccctccgcc gtggagatcg gcaacggctg cttcgagacc   1500

aagcacaagt gcaaccagac ctgcctggac aagatcgccg ccggcacctt cgacgccggc   1560

gagttctccc tgcccacctt cgactccctg aacatcaccg ccgcctccct gaacgacgac   1620

ggcctggaca accacaccat cctgctgtac tactccaccg ccgcctcctc cctggccgtg   1680

accctgatga tcgccatctt cgtggtgtac atggtgtccc gcgacaacgt gtcctgctcc   1740

atctgcctg                                                           1749


<210> SEQ ID NO 19
<211> LENGTH: 584
<212> TYPE: PRT
<213> ORGANISM: Artificial Sequence
<220> FEATURE:
<223> OTHER INFORMATION: 2013 Influenza B (Yamagata lineage) - Sequence
      only on GISAID - HA antigen Amino Acid sequence
<220> FEATURE:
<221> NAME/KEY: misc_feature
<222> LOCATION: (213)..(213)
<223> OTHER INFORMATION: Xaa can be any naturally occurring amino acid

<400> SEQUENCE: 19

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Lys Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Xaa Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
```

-continued

```
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Glu Tyr Gly Gly Leu Asn Lys Ser
305                 310                 315                 320

Lys Pro Tyr Tyr Thr Gly Lys His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580


<210> SEQ ID NO 20
<211> LENGTH: 1752
<212> TYPE: DNA
<213> ORGANISM: Artificial Sequence
<220> FEATURE:
<223> OTHER INFORMATION: 2013 Influenza B (Yamagata lineage) - Sequence
      only on GISAID - Optimized DNA sequence encoding the nucleic acid
      sequence encoding HA antigen
<220> FEATURE:
<221> NAME/KEY: misc_feature
<222> LOCATION: (637)..(639)
<223> OTHER INFORMATION: any nucleotide

<400> SEQUENCE: 20

atgaaggcca tcatcgtgct gctgatggtg gtgacctcca acgccgaccg catctgcacc     60
```

-continued

```
ggcatcacct cctccaactc cccccacgtg gtgaagaccg ccacccaggg cgaggtgaac    120
gtgaccggcg tgatccccct gaccaccacc cccaccaagt cctacttcgc caacctgaag    180
ggcacccgca cccgcggcaa gctgtgcccc gactgcctga actgcaccga cctggacgtg    240
gccctgggcc gccccatgtg cgtgggcacc accccctccg ccaaggcctc catcctgcac    300
gaggtgcgcc ccgtgacctc cggctgcttc cccatcatgc acgaccgcac caagatccgc    360
cagctgccca acctgctgcg cggctacgag aagatccgcc tgtccaccca gaacgtgatc    420
gacgccgaga aggcccccgg cggcccctac cgcctgggca cctccggctc ctgccccaac    480
gccacctcca agatcggctt cttcgccacc atggcctggg ccgtgcccaa ggacaactac    540
aagaacgcca ccaaccccct gaccgtggag gtgccctaca tctgcaccga gggcgaggac    600
cagatcaccg tgtggggctt ccactccgac aacaagnnnc agatgaagtc cctgtacggc    660
gactccaacc cccagaagtt cacctcctcc gccaacggcg tgaccaccca ctacgtgtcc    720
cagatcggcg acttccccga ccagaccgag gacggcggcc tgccccagtc cggccgcatc    780
gtggtggact acatgatgca gaagcccggc aagaccggca ccatcgtgta ccagcgcggc    840
gtgctgctgc cccagaaggt gtggtgcgcc tccggccgct ccaaggtgat caagggctcc    900
ctgcccctga tcggcgaggc cgactgcctg cacgaggagt acggcggcct gaacaagtcc    960
aagccctact acaccggcaa gcacgccaag gccatcggca actgccccat ctgggtgaag   1020
acccccctga agctggccaa cggcaccaag taccgccccc ccgccaagct gctgaaggag   1080
cgcggcttct tcggcgccat cgccggcttc ctggagggcg gctgggaggg catgatcgcc   1140
ggctggcacg gctacacctc ccacggcgcc cacggcgtgg ccgtggccgc cgacctgaag   1200
tccacccagg aggccatcaa caagatcacc aagaacctga actccctgtc cgagctggag   1260
gtgaagaacc tgcagcgcct gtccggcgcc atggacgagc tgcacaacga gatcctggag   1320
ctggacgaga aggtggacga cctgcgcgcc gacaccatct cctcccagat cgagctggcc   1380
gtgctgctgt ccaacgaggg catcatcaac tccgaggacg agcacctgct ggccctggag   1440
cgcaagctga agaagatgct gggcccctcc gccgtggaca tcggcaacgg ctgcttcgag   1500
accaagcaca agtgcaacca gacctgcctg gaccgcatcg ccgccggcac cttcaacgcc   1560
ggcgagttct ccctgcccac cttcgactcc ctgaacatca ccgccgcctc cctgaacgac   1620
gacggcctgg acaaccacac catcctgctg tactactcca ccgccgcctc ctccctggcc   1680
gtgaccctga tgctggccat cttcatcgtg tacatggtgt cccgcgacaa cgtgtcctgc   1740
tccatctgcc tg                                                       1752
```

<210> SEQ ID NO 21
<211> LENGTH: 567
<212> TYPE: PRT
<213> ORGANISM: Artificial Sequence
<220> FEATURE:
<223> OTHER INFORMATION: 2015 H5N1 - HA antigen Amino Acid sequence

<400> SEQUENCE: 21

```
Met Glu Lys Ile Val Leu Leu Phe Ala Thr Ile Ser Leu Val Lys Ser
1               5                   10                  15

Asp His Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
```

```
    50                  55                  60

Pro Leu Ile Leu Lys Asp Cys Ser Val Ala Gly Trp Leu Leu Gly Asn
65                  70                  75                  80

Pro Trp Cys Asp Glu Phe Ile Asn Val Pro Glu Trp Ser Tyr Ile Val
                85                  90                  95

Glu Lys Ala Asn Pro Val Asn Gly Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asp Ser Trp Ser Asp His Glu Ala Ser
    130                 135                 140

Lys Gly Gly Ser Ala Ala Cys Ser Tyr Gln Gly Lys Ser Ser Phe Phe
145                 150                 155                 160

Arg Asn Val Val Trp Leu Ile Lys Lys Asn Asp Thr Tyr Pro Thr Ile
                165                 170                 175

Lys Lys Asp Tyr Asn Asn Thr Asn Arg Glu Asp Leu Leu Val Leu Trp
            180                 185                 190

Gly Ile His His Pro Asn Asp Lys Ala Glu Gln Ile Thr Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Ile Asn Gly Gln Ser Gly
225                 230                 235                 240

Arg Ile Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Arg Ser Glu Val Glu Tyr Gly
        275                 280                 285

Asn Cys Asn Thr Arg Cys Gln Thr Pro Val Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Arg Arg Arg Lys Arg Gly Leu Phe Gly Ala Lys Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Lys Asp Asn Ala Lys Glu Leu Gly Asn
465                 470                 475                 480
```

```
Gly Cys Phe Glu Phe Tyr His Lys Cys Asn Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Val
        515                 520                 525

Tyr Gln Ile Leu Ser Ile Tyr Ser Thr Val Ala Ser Ser Leu Val Leu
    530                 535                 540

Ala Ile Met Met Ala Gly Leu Ser Leu Trp Met Cys Ser Asn Gly Ser
545                 550                 555                 560

Leu Gln Cys Arg Ile Cys Ile
                565
```

<210> SEQ ID NO 22
<211> LENGTH: 1701
<212> TYPE: DNA
<213> ORGANISM: Artificial Sequence
<220> FEATURE:
<223> OTHER INFORMATION: 2015 H5N1 - Optimized DNA sequence encoding the nucleic acid sequence encoding HA antigen

<400> SEQUENCE: 22

```
atggagaaga tcgtgctgct gttcgccacc atctccctgg tgaagtccga ccacatctgc     60

atcggctacc acgccaacaa ctccaccgag caggtggaca ccatcatgga gaagaacgtg    120

accgtgaccc acgcccagga catcctggag aagacccaca acggcaagct gtgcgacctg    180

aacggcgtga agcccctgat cctgaaggac tgctccgtgg ccggctggct gctgggcaac    240

ccctggtgcg acgagttcat caacgtgccc gagtggtcct acatcgtgga gaaggccaac    300

cccgtgaacg gcctgtgcta ccccggcaac ttcaacgact acgaggagct gaagcacctg    360

ctgtcccgca tcaaccactt cgagaagatc cagatcatcc ccaaggactc ctggtccgac    420

cacgaggcct ccaagggcgg ctccgccgcc tgctcctacc agggcaagtc ctccttcttc    480

cgcaacgtgg tgtggctgat caagaagaac gacacctacc ccaccatcaa gaaggactac    540

aacaacacca accgcgagga cctgctggtg ctgtggggca tccaccaccc caacgacaag    600

gccgagcaga tcaccctgta ccagaacccc accacctaca tctccatcgg cacctccacc    660

ctgaaccagc gcctggtgcc caagatcgcc acccgctcca agatcaacgg ccagtccggc    720

cgcatcgact tcttctggac catcctgaag cccaacgacg ccatccactt cgagtccaac    780

ggcaacttca tcgcccccga gtacgcctac aagatcgtga agaagggcga ctccaccatc    840

atgcgctccg aggtggagta cggcaactgc aacacccgct gccagacccc cgtgggcgcc    900

atcaactcct ccatgccctt ccacaacatc caccccctga ccatcggcga gtgccccaag    960

tacgtgaagt ccaacaagct ggtgctggcc accggcctgc gcaactcccc ccagcgcgag   1020

cgccgccgca agcgcggcct gttcggcgcc aaggccggct tcatcgaggg cggctggcag   1080

ggcatggtgg acggctggta cggctaccac cactccaacg agcagggctc cggctacgcc   1140

gccgacaagg agtccaccca gaaggccatc gacggcgtga ccaacaaggt gaactccatc   1200

atcgacaaga tgaacaccca gttcgaggcc gtgggccgcg agttcaacaa cctggagcgc   1260

cgcatcgaga acctgaacaa gaagatggag gacggcttcc tggacgtgtg gacctacaac   1320

gccgagctgc tggtgctgat ggagaacgag cgcaccctgg acttccacga ctccaacgtg   1380

aagaacctgt acgacaaggt gcgcctgcag ctgaaggaca acgccaagga gctgggcaac   1440

ggctgcttcg agttctacca caagtgcaac aacgagtgca tggagtccgt gcgcaacggc   1500
```

```
acctacgact acccccagta ctccgaggag gcccgcctga agcgcgagga gatctccggc   1560

gtgaagctgg agtccatcgg cgtgtaccag atcctgtcca tctactccac cgtggcctcc   1620

tccctggtgc tggccatcat gatggccggc ctgtccctgt ggatgtgctc caacggctcc   1680

ctgcagtgcc gcatctgcat c                                             1701


<210> SEQ ID NO 23
<211> LENGTH: 560
<212> TYPE: PRT
<213> ORGANISM: Artificial Sequence
<220> FEATURE:
<223> OTHER INFORMATION: 2017 H7N9 - HA antigen Amino Acid sequence

<400> SEQUENCE: 23

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asp Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Phe Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Asn Gly Ile Arg Thr Asn Gly Val Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Thr Phe Pro Gln Met Thr Lys Ser
                165                 170                 175

Tyr Lys Asn Thr Arg Lys Ser Pro Ala Ile Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320
```

```
Arg Ser Leu Leu Leu Ala Thr Gly Met Lys Asn Val Pro Glu Ile Pro
            325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Ala Gly Lys Leu Asn Arg Leu Ile Ala Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Ile Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Arg Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Val Val Met Gly Leu
    530                 535                 540

Val Phe Ile Cys Val Lys Asn Gly Asn Met Arg Cys Thr Ile Cys Ile
545                 550                 555                 560
```

<210> SEQ ID NO 24
<211> LENGTH: 1680
<212> TYPE: DNA
<213> ORGANISM: Artificial Sequence
<220> FEATURE:
<223> OTHER INFORMATION: 2017 H7N9 - Optimized DNA sequence encoding the nucleic acid sequence encoding HA antigen

<400> SEQUENCE: 24

```
atgaacaccc agatcctggt gttcgccctg atcgccatca tccccaccaa cgccgacaag     60

atctgcctgg gccaccacgc cgtgtccaac ggcaccaagg tggacaccct gaccgagcgc    120

ggcgtggagg tggtgaacgc caccgagacc gtggagcgca ccaacatccc ccgcatctgc    180

tccaagggca agcgcaccgt ggacctgggc cagtgcggcc tgctgggcac catcaccggc    240

ccccccccagt gcgaccagtt cctggagttc tccgccgacc tgatcatcga gcgccgcgag    300

ggctccgact tctgctaccc cggcaagttc gtgaacgagg aggccctgcg ccagatcctg    360

cgcgagtccg gcggcatcga caaggaggcc atgggcttca cctacaacgg catccgcacc    420

aacggcgtga cctccgcctg ccgccgctcc ggctcctcct tctacgccga gatgaagtgg    480

ctgctgtcca acaccgacaa cgccaccttc ccccagatga ccaagtccta caagaacacc    540

cgcaagtccc ccgccatcat cgtgtggggc atccaccact ccgtgtccac cgccgagcag    600

accaagctgt acggctccgg caacaagctg gtgaccgtgg gctcctccaa ctaccagcag    660

tccttcgtgc cctcccccgg cgcccgcccc caggtgaacg gcctgtccgg ccgcatcgac    720
```

```
ttccactggc tgatcctgaa ccccaacgac accgtgacct tctccttcaa cggcgccttc    780

atcgcccccg accgcgcctc cttcctgcgc ggcaagtcca tgggcatcca gtccggcgtg    840

caggtggacg ccaactgcga gggcgactgc taccactccg gcggcaccat catctccaac    900

ctgcccttcc agaacatcga ctcccgcgcc gtgggcaagt gcccccgcta cgtgaagcag    960

cgctccctgc tgctggccac cggcatgaag aacgtgcccg agatccccaa gggccgcggc   1020

ctgttcggcg ccatcgccgg cttcatcgag aacggctggg agggcctgat cgacggctgg   1080

tacggcttcc gccaccagaa cgcccagggc gagggcaccg ccgccgacta caagtccacc   1140

cagtccgcca tcgaccagat cgccggcaag ctgaaccgcc tgatcgccaa gaccaaccag   1200

cagttcgagc tgatcgacaa cgagttcaac gaggtggaga agcagatcgg caacgtgatc   1260

aactggaccc gcgactccat caccgaggtg tggtcctaca acgccgagct gctgatcgcc   1320

atggagaacc agcacaccat cgacctggcc gactccgaga tggacaagct gtacgagcgc   1380

gtgaagcgcc agctgcgcga gaacgccgag gaggacggca ccggctgctt cgagatcttc   1440

cacaagtgcg acgacgactg catggcctcc atccgcaaca acacctacga ccaccgcaag   1500

taccgcgagg aggccatgca gaaccgcatc cagatcgacc ccgtgaagct gtcctccggc   1560

tacaaggacg tgatcctgtg gttctccttc ggcgcctcct gcttcatcct gctggccgtg   1620

gtgatgggcc tggtgttcat ctgcgtgaag aacggcaaca tgcgctgcac catctgcatc   1680
```

```
<210> SEQ ID NO 25
<211> LENGTH: 561
<212> TYPE: PRT
<213> ORGANISM: Artificial Sequence
<220> FEATURE:
<223> OTHER INFORMATION: 2013 H10N8 - HA antigen Amino Acid sequence

<400> SEQUENCE: 25

Met Tyr Lys Ile Val Val Ile Ile Ala Leu Leu Gly Ala Val Lys Gly
1               5                   10                  15

Leu Asp Lys Ile Cys Leu Gly His His Ala Val Ala Asn Gly Thr Ile
            20                  25                  30

Val Lys Thr Leu Thr Asn Glu Gln Glu Glu Val Thr Asn Ala Thr Glu
        35                  40                  45

Thr Val Glu Ser Thr Gly Ile Asn Arg Leu Cys Met Lys Gly Arg Lys
    50                  55                  60

His Lys Asp Leu Gly Asn Cys His Pro Ile Gly Met Leu Ile Gly Thr
65                  70                  75                  80

Pro Ala Cys Asp Leu His Leu Thr Gly Met Trp Asp Thr Leu Ile Glu
                85                  90                  95

Arg Glu Asn Ala Ile Ala Tyr Cys Tyr Pro Gly Ala Thr Val Asn Val
            100                 105                 110

Glu Ala Leu Arg Gln Lys Ile Met Glu Ser Gly Gly Ile Asn Lys Ile
        115                 120                 125

Ser Thr Gly Phe Thr Tyr Gly Ser Ser Ile Asn Ser Ala Gly Thr Thr
    130                 135                 140

Arg Ala Cys Met Arg Asn Gly Gly Asn Ser Phe Tyr Ala Glu Leu Lys
145                 150                 155                 160

Trp Leu Val Ser Lys Ser Lys Gly Gln Asn Phe Pro Gln Thr Thr Asn
                165                 170                 175

Thr Tyr Arg Asn Thr Asp Thr Ala Glu His Leu Ile Met Trp Gly Ile
            180                 185                 190
```

```
His His Pro Ser Ser Thr Gln Glu Lys Asn Asp Leu Tyr Gly Thr Gln
        195                 200                 205

Ser Leu Ser Ile Ser Val Gly Ser Ser Thr Tyr Arg Asn Asn Phe Val
    210                 215                 220

Pro Val Val Gly Ala Gly Pro Gln Val Asn Gly Gln Ser Gly Arg Ile
225                 230                 235                 240

Asp Phe His Trp Thr Leu Val Gln Pro Gly Asp Asn Ile Thr Phe Ser
                245                 250                 255

His Asn Gly Gly Leu Ile Ala Pro Ser Arg Val Ser Lys Leu Ile Gly
            260                 265                 270

Arg Gly Leu Gly Ile Gln Ser Asp Ala Pro Ile Asp Asn Asn Cys Glu
        275                 280                 285

Ser Lys Cys Phe Trp Arg Gly Gly Ser Ile Asn Thr Arg Leu Pro Phe
    290                 295                 300

Gln Asn Leu Ser Pro Arg Thr Val Gly Gln Cys Pro Lys Tyr Val Asn
305                 310                 315                 320

Arg Arg Ser Leu Met Leu Ala Thr Gly Met Arg Asn Val Pro Glu Leu
                325                 330                 335

Ile Gln Gly Arg Gly Leu Phe Gly Ala Ile Ala Gly Phe Leu Glu Asn
            340                 345                 350

Gly Trp Glu Gly Met Val Asp Gly Trp Tyr Gly Phe Arg His Gln Asn
        355                 360                 365

Ala Gln Gly Thr Gly Gln Ala Ala Asp Tyr Lys Ser Thr Gln Ala Ala
    370                 375                 380

Ile Asp Gln Ile Thr Gly Lys Leu Asn Arg Leu Val Glu Lys Thr Asn
385                 390                 395                 400

Thr Glu Phe Glu Ser Ile Glu Ser Glu Phe Ser Glu Ile Glu His Gln
                405                 410                 415

Ile Gly Asn Val Ile Asn Trp Thr Lys Asp Ser Ile Thr Asp Ile Trp
            420                 425                 430

Thr Tyr Gln Ala Glu Leu Leu Val Ala Met Glu Asn Gln His Thr Ile
        435                 440                 445

Asp Met Ala Asp Ser Glu Met Leu Asn Leu Tyr Glu Arg Val Arg Lys
    450                 455                 460

Gln Leu Arg Gln Asn Ala Glu Glu Asp Gly Lys Gly Cys Phe Glu Ile
465                 470                 475                 480

Tyr His Ala Cys Asp Asp Ser Cys Met Glu Ser Ile Arg Asn Asn Thr
                485                 490                 495

Tyr Asp His Ser Gln Tyr Arg Glu Glu Ala Leu Leu Asn Arg Leu Asn
            500                 505                 510

Ile Asn Pro Val Thr Leu Ser Ser Gly Tyr Lys Asp Ile Ile Leu Trp
        515                 520                 525

Phe Ser Phe Gly Ala Ser Cys Phe Val Leu Leu Ala Val Val Met Gly
    530                 535                 540

Leu Phe Phe Phe Cys Leu Lys Asn Gly Asn Met Arg Cys Thr Ile Cys
545                 550                 555                 560

Ile
```

<210> SEQ ID NO 26
<211> LENGTH: 1683
<212> TYPE: DNA
<213> ORGANISM: Artificial Sequence
<220> FEATURE:
<223> OTHER INFORMATION: 2013 H10N8 - Optimized DNA sequence encoding
the nucleic acid sequence encoding HA antigen

<400> SEQUENCE: 26

```
atgtacaaga tcgtggtgat catcgccctg ctgggcgccg tgaagggcct ggacaagatc     60
tgcctgggcc accacgccgt ggccaacggc accatcgtga agaccctgac caacgagcag    120
gaggaggtga ccaacgccac cgagaccgtg gagtccaccg gcatcaaccg cctgtgcatg    180
aagggccgca agcacaagga cctgggcaac tgccacccca tcggcatgct gatcggcacc    240
cccgcctgcg acctgcacct gaccggcatg tgggacaccc tgatcgagcg cgagaacgcc    300
atcgcctact gctaccccgg cgccaccgtg aacgtggagg ccctgcgcca gaagatcatg    360
gagtccggcg gcatcaacaa gatctccacc ggcttcacct acggctcctc catcaactcc    420
gccggcacca cccgcgcctg catgcgcaac ggcggcaact ccttctacgc cgagctgaag    480
tggctggtgt ccaagtccaa gggccagaac ttcccccaga ccaccaacac ctaccgcaac    540
accgacaccg ccgagcacct gatcatgtgg ggcatccacc acccctcctc cacccaggag    600
aagaacgacc tgtacggcac ccagtccctg tccatctccg tgggctcctc cacctaccgc    660
aacaacttcg tgcccgtggt gggcgccggc ccccaggtga acggccagtc cggccgcatc    720
gacttccact ggaccctggt gcagcccggc gacaacatca ccttctccca caacggcggc    780
ctgatcgccc cctcccgcgt gtccaagctg atcggccgcg gcctgggcat ccagtccgac    840
gcccccatcg acaacaactg cgagtccaag tgcttctggc gcggcggctc catcaacacc    900
cgcctgccct tccagaacct gtcccccgc accgtgggcc agtgccccaa gtacgtgaac    960
cgccgctccc tgatgctggc caccggcatg cgcaacgtgc ccgagctgat ccagggccgc   1020
ggcctgttcg gcgccatcgc cggcttcctg gagaacggct gggagggcat ggtggacggc   1080
tggtacggct tccgccacca gaacgcccag ggcaccggcc aggccgccga ctacaagtcc   1140
acccaggccg ccatcgacca gatcaccggc aagctgaacc gcctggtgga gaagaccaac   1200
accgagttcg agtccatcga gtccgagttc tccgagatcg agcaccagat cggcaacgtg   1260
atcaactgga ccaaggactc catcaccgac atctggacct accaggccga gctgctggtg   1320
gccatggaga accagcacac catcgacatg gccgactccg agatgctgaa cctgtacgag   1380
cgcgtgcgca agcagctgcg ccagaacgcc gaggaggacg gcaagggctg cttcgagatc   1440
taccacgcct gcgacgactc ctgcatggag tccatccgca acaacaccta cgaccactcc   1500
cagtaccgcg aggaggccct gctgaaccgc ctgaacatca accccgtgac cctgtcctcc   1560
ggctacaagg acatcatcct gtggttctcc ttcggcgcct cctgcttcgt gctgctggcc   1620
gtggtgatgg gcctgttctt cttctgcctg aagaacggca acatgcgctg caccatctgc   1680
atc                                                                 1683
```

<210> SEQ ID NO 27
<211> LENGTH: 268
<212> TYPE: PRT
<213> ORGANISM: Artificial Sequence
<220> FEATURE:
<223> OTHER INFORMATION: Mini HA domain - HA antigen Amino Acid sequence

<400> SEQUENCE: 27

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45
```

```
Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Ile Gly Cys Glu Tyr Asn Lys Ser Glu Arg Cys Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Glu Gly Arg
            260                 265
```

<210> SEQ ID NO 28
<211> LENGTH: 804
<212> TYPE: DNA
<213> ORGANISM: Artificial Sequence
<220> FEATURE:
<223> OTHER INFORMATION: Mini HA domain - Optimized DNA sequence
      encoding the nucleic acid sequence encoding HA antigen

<400> SEQUENCE: 28

```
atgaaggtga agctgctggt gctgctgtgc accttcaccg ccacctacgc cgacaccatc     60

tgcatcggct accacgccaa caactccacc gacaccgtgg acaccgtgct ggagaagaac    120

gtgaccgtga cccactccgt gaacctgctg gagaacggcg gcggcggcaa gtacgtgtgc    180

tccgccaagc tgcgcatggt gaccggcctg cgcaacaagc cctccaagca gtcccagggc    240

ctgttcggcg ccatcgccgg cttcaccgag ggcggctgga ccggcatggt ggacggctgg    300

tacggctacc accaccagaa cgagcagggc tccggctacg ccgccgacca gaagtccacc    360

cagaacgcca tcaacggcat caccaacaag gtgaactccg tgatcgagaa gatgaacacc    420

cagtacaccg ccatcggctg cgagtacaac aagtccgagc ggtgcatgaa gcagatcgag    480

gacaagatcg aggagatcga gtccaagatc tggtgctaca acgccgagct gctggtgctg    540

ctggagaacg agcgcaccct ggacttccac gactccaacg tgaagaacct gtacgagaag    600

gtgaagtccc agctgaagaa caacgccaag gagatcggca acggctgctt cgagttctac    660

cacaagtgca acgacgagtg catggagtcc gtgaagaacg gcacctacga ctaccccaag    720

tactccgagg agtccaagct gaaccgcgag aagatcgacg gcgtgaagct ggagtccatg    780
```

ggcgtgtacc agatcgaggg ccgc 804

<210> SEQ ID NO 29
<211> LENGTH: 469
<212> TYPE: PRT
<213> ORGANISM: Artificial Sequence
<220> FEATURE:
<223> OTHER INFORMATION: 1918 H1N1 - NA antigen Amino Acid sequence

<400> SEQUENCE: 29

```
Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Val Ser His Ser Ile Gln Thr Gly Asn Gln Asn His Pro Glu Thr
        35                  40                  45

Cys Asn Gln Ser Ile Ile Thr Tyr Glu Asn Asn Thr Trp Val Asn Gln
    50                  55                  60

Thr Tyr Val Asn Ile Ser Asn Thr Asn Val Val Ala Gly Gln Asp Ala
65                  70                  75                  80

Thr Ser Val Ile Leu Thr Gly Asn Ser Ser Leu Cys Pro Ile Ser Gly
                85                  90                  95

Trp Ala Ile Tyr Ser Lys Asp Asn Gly Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Val Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asn Gly Gln Ala Ser Tyr Lys Ile Leu
                245                 250                 255

Lys Ile Glu Lys Gly Lys Val Thr Lys Ser Ile Glu Leu Asn Ala Pro
            260                 265                 270

Asn Tyr His Tyr Glu Glu Cys Ser Cys Tyr Pro Asp Thr Gly Lys Val
        275                 280                 285

Met Cys Val Cys Arg Asp Asn Trp His Gly Ser Asn Arg Pro Trp Val
    290                 295                 300

Ser Phe Asp Gln Asn Leu Asp Tyr Gln Ile Gly Tyr Ile Cys Ser Gly
305                 310                 315                 320

Val Phe Gly Asp Asn Pro Arg Pro Asn Asp Gly Thr Gly Ser Cys Gly
                325                 330                 335

Pro Val Ser Ser Asn Gly Ala Asn Gly Ile Lys Gly Phe Ser Phe Arg
            340                 345                 350
```

-continued

```
Tyr Asp Asn Gly Val Trp Ile Gly Arg Thr Lys Ser Thr Ser Ser Arg
        355                 360                 365

Ser Gly Phe Glu Met Ile Trp Asp Pro Asn Gly Trp Thr Glu Thr Asp
    370                 375                 380

Ser Ser Phe Ser Val Arg Gln Asp Ile Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Ile Arg Gly Gln Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Ser Ile Asp Lys
465


<210> SEQ ID NO 30
<211> LENGTH: 1407
<212> TYPE: DNA
<213> ORGANISM: Artificial Sequence
<220> FEATURE:
<223> OTHER INFORMATION: 1918 H1N1 - Optimized DNA sequence encoding the
      nucleic acid sequence encoding NA antigen

<400> SEQUENCE: 30

atgaacccca accagaagat catcaccatc ggctccatct gcatggtggt gggcatcatc      60

tccctgatcc tgcagatcgg caacatcatc tccatctggg tgtcccactc catccagacc     120

ggcaaccaga accaccccga gacctgcaac cagtccatca tcacctacga gaacaacacc     180

tgggtgaacc agacctacgt gaacatctcc aacaccaacg tggtggccgg ccaggacgcc     240

acctccgtga tcctgaccgg caactcctcc ctgtgcccca tctccggctg ggccatctac     300

tccaaggaca acggcatccg catcggctcc aagggcgacg tgttcgtgat ccgcgagccc     360

ttcatctcct gctcccacct ggagtgccgc accttcttcc tgacccaggg cgccctgctg     420

aacgacaagc actccaacgg caccgtgaag gaccgctccc cctaccgcac cctgatgtcc     480

tgccccgtgg gcgaggcccc ctccccctac aactcccgct tcgagtccgt ggcctggtcc     540

gcctccgcct gccacgacgg catgggctgg ctgaccatcg gcatctccgg ccccgacaac     600

ggcgccgtgg ccgtgctgaa gtacaacggc atcatcaccg acaccatcaa gtcctggcgc     660

aacaacatcc tgcgcaccca ggagtccgag tgcgcctgcg tgaacggctc ctgcttcacc     720

atcatgaccg acggcccctc caacggccag gcctcctaca agatcctgaa gatcgagaag     780

ggcaaggtga ccaagtccat cgagctgaac gcccccaact accactacga ggagtgctcc     840

tgctaccccg acaccggcaa ggtgatgtgc gtgtgccgcg acaactggca cggctccaac     900

cgcccctggg tgtccttcga ccagaacctg gactaccaga tcggctacat ctgctccggc     960

gtgttcggcg acaacccccg ccccaacgac ggcaccggct cctgcggccc cgtgtcctcc    1020

aacggcgcca acggcatcaa gggcttctcc ttccgctacg acaacggcgt gtggatcggc    1080

cgcaccaagt ccacctcctc ccgctccggc ttcgagatga tctgggaccc caacggctgg    1140

accgagaccg actcctcctt ctccgtgcgc caggacatcg tggccatcac cgactggtcc    1200

ggctactccg gctccttcgt gcagcacccc gagctgaccg gcctggactg catgcgcccc    1260

tgcttctggg tggagctgat ccgcggccag cccaaggaga acaccatctg gacctccggc    1320
```

```
tcctccatct ccttctgcgg cgtgaactcc gacaccgtgg gctggtcctg gcccgacggc   1380

gccgagctgc ccttctccat cgacaag                                       1407


<210> SEQ ID NO 31
<211> LENGTH: 469
<212> TYPE: PRT
<213> ORGANISM: Artificial Sequence
<220> FEATURE:
<223> OTHER INFORMATION: 1957 H2N2 - NA antigen Amino Acid sequence

<400> SEQUENCE: 31

Met Asn Pro Asn Gln Lys Ile Ile Thr Ile Gly Ser Val Ser Leu Ile
1               5                   10                  15

Ile Ala Thr Val Cys Phe Leu Met Gln Ile Ala Ile Leu Val Thr Thr
            20                  25                  30

Val Thr Leu His Phe Lys Gln His Glu Cys Asp Ser Pro Ala Ser Asn
        35                  40                  45

Gln Val Met Pro Cys Glu Pro Ile Ile Ile Glu Arg Asn Ile Thr Glu
    50                  55                  60

Ile Val Tyr Leu Asn Asn Thr Thr Ile Glu Lys Glu Ile Cys Pro Lys
65                  70                  75                  80

Val Val Glu Tyr Arg Asn Trp Ser Lys Pro Gln Cys Gln Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Gly Lys
        115                 120                 125

Cys Tyr Gln Phe Ala Leu Gly Gln Gly Thr Thr Leu Asp Asn Lys His
    130                 135                 140

Ser Asn Asp Thr Ile His Asp Arg Ile Pro His Arg Thr Leu Leu Met
145                 150                 155                 160

Asn Glu Leu Gly Val Pro Phe His Leu Gly Thr Arg Gln Val Cys Val
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asp
        195                 200                 205

Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Arg Ser Ser Asn Ser Asn
                325                 330                 335

Cys Arg Asn Pro Asn Asn Glu Arg Gly Asn Pro Gly Val Lys Gly Trp
            340                 345                 350
```

Ala Phe Asp Asn Gly Asp Asp Val Trp Met Gly Arg Thr Ile Ser Lys
355 360 365

Asp Leu Arg Ser Gly Tyr Glu Thr Phe Lys Val Ile Gly Gly Trp Ser
370 375 380

Thr Pro Asn Ser Lys Ser Gln Ile Asn Arg Gln Val Ile Val Asp Ser
385 390 395 400

Asn Asn Trp Ser Gly Tyr Ser Gly Ile Phe Ser Val Glu Gly Lys Ser
405 410 415

Cys Ile Asn Arg Cys Phe Tyr Val Glu Leu Ile Arg Gly Arg Gln Gln
420 425 430

Glu Thr Arg Val Trp Trp Thr Ser Asn Ser Ile Val Val Phe Cys Gly
435 440 445

Thr Ser Gly Thr Tyr Gly Thr Gly Ser Trp Pro Asp Gly Ala Asn Ile
450 455 460

Asn Phe Met Pro Ile
465

<210> SEQ ID NO 32
<211> LENGTH: 1407
<212> TYPE: DNA
<213> ORGANISM: Artificial Sequence
<220> FEATURE:
<223> OTHER INFORMATION: 1957 H2N2 - Optimized DNA sequence encoding the nucleic acid sequence encoding NA antigen

<400> SEQUENCE: 32
atgaacccca accagaagat catcaccatc ggctccgtgt ccctgatcat cgccaccgtg 60
tgcttcctga tgcagatcgc catcctggtg accaccgtga ccctgcactt caagcagcac 120
gagtgcgact cccccgcctc caaccaggtg atgccctgcg agcccatcat catcgagcgc 180
aacatcaccg agatcgtgta cctgaacaac accaccatcg agaaggagat ctgccccaag 240
gtggtggagt accgcaactg gtccaagccc cagtgccaga tcaccggctt cgccccctc 300 tccaaggaca actccatccg cctgtccgcc ggcggcgaca tctgggtgac ccgcgagccc 360
tacgtgtcct gcgaccccgg caagtgctac cagttcgccc tgggccaggg caccaccctg 420
gacaacaagc actccaacga caccatccac gaccgcatcc cccaccgcac cctgctgatg 480
aacgagctgg gcgtgccctt ccacctgggc acccgccagg tgtgcgtggc ctggtcctcc 540
tcctcctgcc acgacggcaa ggcctggctg cacgtgtgcg tgaccggcga cgacaagaac 600
gccaccgcct ccttcatcta cgacggccgc ctggtggact ccatcggctc ctggtcccag 660
aacatcctgc gcacccagga gtccgagtgc gtgtgcatca acggcacctg caccgtggtg 720
atgaccgacg gctccgcctc cggccgcgcc gacacccgca tcctgttcat cgaggagggc 780
aagatcgtgc acatctcccc cctgtccggc tccgcccagc acgtggagga gtgctcctgc 840
tacccccgct accccgacgt gcgctgcatc tgccgcgaca actggaaggg ctccaaccgc 900
cccgtgatcg acatcaacat ggaggactac tccatcgact cctcctacgt gtgctccggc 960
ctggtgggcg acacccccg caacgacgac cgctcctcca actccaactg ccgcaacccc 1020
aacaacgagc gcggcaaccc cggcgtgaag ggctgggcct tcgacaacgg cgacgacgtg 1080
tggatgggcc gcaccatctc caaggacctg cgctccggct acgagacctt caaggtgatc 1140
ggcggctggt ccacccccaa ctccaagtcc cagatcaacc gccaggtgat cgtggactcc 1200
aacaactggt ccggctactc cggcatcttc tccgtggagg gcaagtcctg catcaaccgc 1260
tgcttctacg tggagctgat ccgcggccgc cagcaggaga cccgcgtgtg gtggacctcc 1320
aactccatcg tggtgttctg cggcacctcc ggcacctacg gcaccggctc ctggcccgac 1380
ggcgccaaca tcaacttcat gcccatc 1407

<210> SEQ ID NO 33
<211> LENGTH: 469
<212> TYPE: PRT
<213> ORGANISM: Artificial Sequence
<220> FEATURE:
<223> OTHER INFORMATION: 1968 H3N2 - NA antigen Amino Acid sequence

<400> SEQUENCE: 33

Met Asn Pro Asn Gln Lys Ile Ile Thr Ile Gly Ser Val Ser Leu Thr
1 5 10 15

Ile Ala Thr Val Cys Phe Leu Met Gln Ile Ala Ile Leu Val Thr Thr
20 25 30

Val Thr Leu His Phe Lys Gln Tyr Glu Cys Asp Ser Pro Ala Ser Asn
35 40 45

Gln Val Met Pro Cys Glu Pro Ile Ile Ile Glu Arg Asn Ile Thr Glu
50 55 60

Ile Val Tyr Leu Asn Asn Thr Thr Ile Glu Lys Glu Ile Cys Pro Lys
65 70 75 80

Val Val Glu Tyr Arg Asn Trp Ser Lys Pro Gln Cys Gln Ile Thr Gly
85 90 95

Phe Ala Pro Phe Ser Lys Asp Asn Ser Ile Arg Leu Ser Ala Gly Gly
100 105 110

Asp Ile Trp Val Thr Arg Glu Pro Tyr Val Ser Cys Asp His Gly Lys
115 120 125

Cys Tyr Gln Phe Ala Leu Gly Gln Gly Thr Thr Leu Asp Asn Lys His
130 135 140

Ser Asn Asp Thr Ile His Asp Arg Ile Pro His Arg Thr Leu Leu Met
145 150 155 160

Asn Glu Leu Gly Val Pro Phe His Leu Gly Thr Arg Gln Val Cys Ile
165 170 175

Ala Trp Ser Ser Ser Ser Cys His Asp Gly Lys Ala Trp Leu His Val
180 185 190

Cys Ile Thr Gly Asp Asp Lys Asn Ala Thr Ala Ser Phe Ile Tyr Asp
195 200 205

Gly Arg Leu Val Asp Ser Ile Gly Ser Trp Ser Gln Asn Ile Leu Arg
210 215 220

Thr Gln Glu Ser Glu Cys Val Cys Ile Asn Gly Thr Cys Thr Val Val
225 230 235 240

Met Thr Asp Gly Ser Ala Ser Gly Arg Ala Asp Thr Arg Ile Leu Phe
245 250 255

Ile Glu Glu Gly Lys Ile Val His Ile Ser Pro Leu Ser Gly Ser Ala
260 265 270

Gln His Val Glu Glu Cys Ser Cys Tyr Pro Arg Tyr Pro Gly Val Arg
275 280 285

Cys Ile Cys Arg Asp Asn Trp Lys Gly Ser Asn Arg Pro Val Val Asp
290 295 300

Ile Asn Met Glu Asp Tyr Ser Ile Asp Ser Ser Tyr Val Cys Ser Gly
305 310 315 320

Leu Val Gly Asp Thr Pro Arg Asn Asp Asp Arg Ser Ser Asn Ser Asn
325 330 335

Cys Arg Asn Pro Asn Asn Glu Arg Gly Asn Gln Gly Val Lys Gly Trp

```
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Ile Asn Arg Gln Val Ile Val Asp Ser
385                 390                 395                 400

Asp Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465


<210> SEQ ID NO 34
<211> LENGTH: 1407
<212> TYPE: DNA
<213> ORGANISM: Artificial Sequence
<220> FEATURE:
<223> OTHER INFORMATION: 1968 H3N2 - Optimized DNA sequence encoding the
      nucleic acid sequence encoding NA antigen

<400> SEQUENCE: 34

atgaacccca accagaagat catcaccatc ggctccgtgt ccctgaccat cgccaccgtg      60

tgcttcctga tgcagatcgc catcctggtg accaccgtga ccctgcactt caagcagtac     120

gagtgcgact cccccgcctc caaccaggtg atgccctgcg agcccatcat catcgagcgc     180

aacatcaccg agatcgtgta cctgaacaac accaccatcg agaaggagat ctgccccaag     240

gtggtggagt accgcaactg gtccaagccc cagtgccaga tcaccggctt cgccccette     300

tccaaggaca actccatccg cctgtccgcc ggcggcgaca tctgggtgac ccgcgagccc     360

tacgtgtcct gcgaccacgg caagtgctac cagttcgccc tgggccaggg caccaccctg     420

gacaacaagc actccaacga caccatccac gaccgcatcc cccaccgcac cctgctgatg     480

aacgagctgg gcgtgccctt ccacctgggc acccgccagg tgtgcatcgc ctggtcctcc     540

tcctcctgcc acgacggcaa ggcctggctg cacgtgtgca tcaccggcga cgacaagaac     600

gccaccgcct ccttcatcta cgacggccgc ctggtggact ccatcggctc ctggtcccag     660

aacatcctgc gcacccagga gtccgagtgc gtgtgcatca acggcacctg caccgtggtg     720

atgaccgacg gctccgcctc cggccgcgcc gacacccgca tcctgttcat cgaggagggc     780

aagatcgtgc acatctcccc cctgtccggc tccgcccagc acgtggagga gtgctcctgc     840

taccccgct accccggcgt gcgctgcatc tgccgcgaca actggaaggg ctccaaccgc     900

cccgtggtgg acatcaacat ggaggactac tccatcgact cctcctacgt gtgctccggc     960

ctggtgggcg acaccccccg caacgacgac cgctcctcca actccaactg ccgcaacccc    1020

aacaacgagc gcggcaacca gggcgtgaag ggctgggcct tcgacaacgg cgacgacgtg    1080

tggatgggcc gcaccatctc caaggacctg cgctccggct acgagacctt caaggtgatc    1140

ggcggctggt ccaccccaa ctccaagtcc cagatcaacc gccaggtgat cgtggactcc    1200

gacaaccgct ccggctactc cggcatcttc tccgtggagg gcaagtcctg catcaaccgc    1260
```

-continued

```
tgcttctacg tggagctgat ccgcggccgc aagcaggaga cccgcgtgtg gtggacctcc   1320

aactccatcg tggtgttctg cggcacctcc ggcacctacg gcaccggctc ctggcccgac   1380

ggcgccaaca tcaacttcat gcccatc                                        1407


<210> SEQ ID NO 35
<211> LENGTH: 470
<212> TYPE: PRT
<213> ORGANISM: Artificial Sequence
<220> FEATURE:
<223> OTHER INFORMATION: 1977 H1N1 - NA antigen Amino Acid sequence

<400> SEQUENCE: 35

Met Asn Pro Asn Gln Lys Ile Ile Thr Ile Gly Ser Ile Cys Met Ala
1               5                   10                  15

Ile Gly Ile Ile Ser Leu Ile Leu Gln Ile Gly Asn Ile Ile Ser Ile
            20                  25                  30

Trp Val Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
    50                  55                  60

Thr Tyr Val Asn Ile Ser Asn Thr Asn Val Val Ala Gly Lys Asp Thr
65                  70                  75                  80

Thr Ser Met Thr Leu Ala Gly Asn Ser Ser Leu Cys Pro Ile Arg Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asp Gly Ala Val Ala Val Leu Lys Tyr
        195                 200                 205

Asn Gly Ile Ile Thr Glu Thr Ile Lys Ser Trp Arg Lys Gln Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asp Gly Pro Ala Ser Tyr Arg Ile Phe
                245                 250                 255

Lys Ile Glu Lys Gly Lys Ile Thr Lys Ser Ile Glu Leu Asp Ala Pro
            260                 265                 270

Asn Ser His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Lys Gly Ser Cys Asp
                325                 330                 335
```

```
Pro Val Asn Val Asp Gly Ala Asp Gly Val Lys Gly Phe Ser Tyr Arg
            340                 345                 350

Tyr Gly Asn Gly Val Trp Ile Gly Arg Thr Lys Ser Asn Ser Ser Arg
        355                 360                 365

Lys Gly Phe Glu Met Ile Trp Asp Pro Asn Gly Trp Thr Asp Thr Asp
    370                 375                 380

Ser Asn Phe Leu Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Ile Arg Gly Arg Pro Arg
            420                 425                 430

Glu Lys Thr Thr Ile Trp Thr Ser Gly Ser Ser Ile Ser Phe Cys Gly
        435                 440                 445

Val Asn Ser Asp Thr Val Asn Trp Ser Trp Pro Asp Gly Ala Glu Leu
    450                 455                 460

Pro Phe Thr Ile Asp Lys
465                 470
```

<210> SEQ ID NO 36
<211> LENGTH: 1410
<212> TYPE: DNA
<213> ORGANISM: Artificial Sequence
<220> FEATURE:
<223> OTHER INFORMATION: 1977 H1N1 - Optimized DNA sequence encoding the nucleic acid sequence encoding NA antigen

<400> SEQUENCE: 36

```
atgaacccca accagaagat catcaccatc ggctccatct gcatggccat cggcatcatc     60

tccctgatcc tgcagatcgg caacatcatc tccatctggg tgtcccactc catccagacc    120

ggctcccaga accacaccgg catctgcaac cagcgcatca tcacctacga gaactccacc    180

tgggtgaacc agacctacgt gaacatctcc aacaccaacg tggtggccgg caaggacacc    240

acctccatga ccctggccgg caactcctcc ctgtgcccca tccgcggctg ggccatctac    300

tccaaggaca actccatccg catcggctcc aagggcgacg tgttcgtgat ccgcgagccc    360

ttcatctcct gctcccacct ggagtgccgc accttcttcc tgacccaggg cgccctgctg    420

aacgacaagc actccaacgg caccgtgaag gaccgctccc cctaccgcgc cctgatgtcc    480

tgccccatcg gcgaggcccc ctccccctac aactcccgct tcgagtccgt ggcctggtcc    540

gcctccgcct gccacgacgg catgggctgg ctgaccatcg gcatctccgg ccccgacgac    600

ggcgccgtgg ccgtgctgaa gtacaacggc atcatcaccg agaccatcaa gtcctggcgc    660

aagcagatcc tgcgcaccca ggagtccgag tgcgtgtgcg tgaacggctc ctgcttcacc    720

atcatgaccg acggcccctc cgacggcccc gcctcctacc gcatcttcaa gatcgagaag    780

ggcaagatca ccaagtccat cgagctggac gcccccaact cccactacga ggagtgctcc    840

tgctaccccg acaccggcac cgtgatgtgc gtgtgccgcg acaactggca cggctccaac    900

cgcccctggg tgtccttcaa ccagaacctg gactaccaga tcggctacat ctgctccggc    960

gtgttcggcg acaacccccg ccccaaggac ggcaagggct cctgcgaccc cgtgaacgtg   1020

gacggcgccg acggcgtgaa gggcttctcc taccgctacg gcaacggcgt gtggatcggc   1080

cgcaccaagt ccaactcctc ccgcaagggc ttcgagatga tctgggaccc caacggctgg   1140

accgacaccg actccaactt cctggtgaag caggacgtgg tggccatgac cgactggtcc   1200

ggctactccg gctccttcgt gcagcacccc gagctgaccg gcctggactg catgcgcccc   1260
```

```
tgcttctggg tggagctgat ccgcggccgc ccccgcgaga agaccaccat ctggacctcc   1320

ggctcctcca tctccttctg cggcgtgaac tccgacaccg tgaactggtc ctggcccgac   1380

ggcgccgagc tgcccttcac catcgacaag                                    1410


<210> SEQ ID NO 37
<211> LENGTH: 470
<212> TYPE: PRT
<213> ORGANISM: Artificial Sequence
<220> FEATURE:
<223> OTHER INFORMATION: 2007 H1N1 - NA antigen Amino Acid sequence

<400> SEQUENCE: 37

Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
            20                  25                  30

Trp Ala Ser His Ser Ile Gln Thr Gly Ser Gln Asn Asn Thr Gly Ile
        35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Glu Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Gly Thr Ile Lys Ser Trp Lys Lys Gln Ile Leu
    210                 215                 220

Arg Thr Gln Glu Ser Glu Cys Val Cys Met Asn Gly Ser Cys Phe Thr
225                 230                 235                 240

Ile Met Thr Asp Gly Pro Ser Asn Lys Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Phe His Tyr Glu Glu Cys Ser Cys Tyr Pro Asp Thr Gly Ile Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Glu Asp Gly Glu Gly Ser Cys Asn
                325                 330                 335
```

```
Pro Val Thr Val Asp Gly Ala Asn Gly Val Lys Gly Phe Ser Tyr Lys
            340                 345                 350

Tyr Asp Asn Gly Val Trp Ile Gly Arg Thr Lys Ser Asn Arg Leu Arg
        355                 360                 365

Lys Gly Phe Glu Met Ile Trp Asp Pro Asn Gly Trp Thr Asn Thr Asp
    370                 375                 380

Ser Asp Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465                 470


<210> SEQ ID NO 38
<211> LENGTH: 1410
<212> TYPE: DNA
<213> ORGANISM: Artificial Sequence
<220> FEATURE:
<223> OTHER INFORMATION: 2007 H1N1 - Optimized DNA sequence encoding the
      nucleic acid sequence encoding NA antigen

<400> SEQUENCE: 38

atgaacccca accagaagat catcaccatc ggctccatct ccatcgccat cggcatcatc      60

tccctgatgc tgcagatcgg caacatcatc tccatctggg cctcccactc catccagacc     120

ggctcccaga acaacaccgg catctgcaac cagcgcatca tcacctacga gaactccacc     180

tgggtgaacc acacctacgt gaacatcaac aacaccaacg tggtggccgg cgaggacaag     240

acctccgtga ccctggccgg caactcctcc ctgtgctcca tctccggctg ggccatctac     300

accaaggaca actccatccg catcggctcc aagggcgacg tgttcgtgat ccgcgagccc     360

ttcatctcct gctcccacct ggagtgccgc accttcttcc tgacccaggg cgccctgctg     420

aacgacaagc actccaacgg caccgtgaag gaccgctccc cctaccgcgc cctgatgtcc     480

tgccccctgg gcgaggcccc ctccccctac aactccaagt tcgagtccgt ggcctggtcc     540

gcctccgcct gccacgacgg catgggctgg ctgaccatcg gcatctccgg ccccgacaac     600

ggcgccgtgg ccgtgctgaa gtacaacggc atcatcaccg gcaccatcaa gtcctggaag     660

aagcagatcc tgcgcaccca ggagtccgag tgcgtgtgca tgaacggctc ctgcttcacc     720

atcatgaccg acggcccctc caacaaggcc gcctcctaca agatcttcaa gatcgagaag     780

ggcaaggtga ccaagtccat cgagctgaac gcccccaact tccactacga ggagtgctcc     840

tgctaccccg acaccggcat cgtgatgtgc gtgtgccgcg acaactggca cggctccaac     900

cgcccctggg tgtccttcaa ccagaacctg gactaccaga tcggctacat ctgctccggc     960

gtgttcggcg acaacccccg ccccgaggac ggcgagggct cctgcaaccc cgtgaccgtg    1020

gacggcgcca acggcgtgaa gggcttctcc tacaagtacg acaacggcgt gtggatcggc    1080

cgcaccaagt ccaaccgcct gcgcaagggc ttcgagatga tctgggaccc caacggctgg    1140

accaacaccg actccgactt ctccgtgaag caggacgtgg tggccatcac cgactggtcc    1200
```

```
ggctactccg gctccttcgt gcagcacccc gagctgaccg gcctggactg catccgcccc   1260

tgcttctggg tggagctggt gcgcggcctg ccccgcgaga acaccaccat ctggacctcc   1320

ggctcctcca tctccttctg cggcgtgaac tccgacaccg ccaactggtc ctggcccgac   1380

ggcgccgagc tgcccttcac catcgacaag                                    1410
```

```
<210> SEQ ID NO 39
<211> LENGTH: 469
<212> TYPE: PRT
<213> ORGANISM: Artificial Sequence
<220> FEATURE:
<223> OTHER INFORMATION: 2009 H1N1 - NA antigen Amino Acid sequence

<400> SEQUENCE: 39

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
```

-continued

```
            325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 40
<211> LENGTH: 1407
<212> TYPE: DNA
<213> ORGANISM: Artificial Sequence
<220> FEATURE:
<223> OTHER INFORMATION: 2009 H1N1 - Optimized DNA sequence encoding the
      nucleic acid sequence encoding NA antigen

<400> SEQUENCE: 40

atgaacccca accagaagat catcaccatc ggctccgtgt gcatgaccat cggcatggcc     60

aacctgatcc tgcagatcgg caacatcatc tccatctgga tctcccactc catccagctg    120

ggcaaccaga accagatcga gacctgcaac cagtccgtga tcacctacga gaacaacacc    180

tgggtgaacc agacctacgt gaacatctcc aacaccaact tcgccgccgg ccagtccgtg    240

gtgtccgtga agctggccgg caactcctcc ctgtgccccg tgtccggctg ggccatctac    300

tccaaggaca actccgtgcg catcggctcc aagggcgacg tgttcgtgat ccgcgagccc    360

ttcatctcct gctccccccct ggagtgccgc accttcttcc tgacccaggg cgccctgctg    420

aacgacaagc actccaacgg caccatcaag gaccgctccc cctaccgcac cctgatgtcc    480

tgccccatcg gcgaggtgcc ctccccctac aactcccgct tcgagtccgt ggcctggtcc    540

gcctccgcct gccacgacgg catcaactgg ctgaccatcg gcatctccgg ccccgacaac    600

ggcgccgtgg ccgtgctgaa gtacaacggc atcatcaccg acaccatcaa gtcctggcgc    660

aacaacatcc tgcgcaccca ggagtccgag tgcgcctgcg tgaacggctc ctgcttcacc    720

gtgatgaccg acggcccctc caacggccag gcctcctaca agatcttccg catcgagaag    780

ggcaagatcg tgaagtccgt ggagatgaac gcccccaact accactacga ggagtgctcc    840

tgctaccccg actcctccga gatcacctgc gtgtgccgcg acaactggca cggctccaac    900

cgcccctggg tgtccttcaa ccagaacctg gagtaccaga tcggctacat ctgctccggc    960

atcttcggcg acaacccccg ccccaacgac aagaccggct cctgcggccc cgtgtcctcc   1020

aacggcgcca acggcgtgaa gggcttctcc ttcaagtacg gcaacggcgt gtggatcggc   1080

cgcaccaagt ccatctcctc ccgcaacggc ttcgagatga tctgggaccc caacggctgg   1140

accggcaccg acaacaactt ctccatcaag caggacatcg tgggcatcaa cgagtggtcc   1200
```

ggctactccg gctccttcgt gcagcacccc gagctgaccg gcctggactg catccgcccc 1260
tgcttctggg tggagctgat ccgcggccgc cccaaggaga acaccatctg gacctccggc 1320
tcctccatct ccttctgcgg cgtgaactcc gacaccgtgg gctggtcctg gcccgacggc 1380
gccgagctgc ccttcaccat cgacaag 1407

<210> SEQ ID NO 41
<211> LENGTH: 469
<212> TYPE: PRT
<213> ORGANISM: Artificial Sequence
<220> FEATURE:
<223> OTHER INFORMATION: 2015 H1N1 - NA antigen Amino Acid sequence
<220> FEATURE:
<221> NAME/KEY: misc_feature
<222> LOCATION: (28)..(28)
<223> OTHER INFORMATION: Xaa can be any naturally occurring amino acid

<400> SEQUENCE: 41

Met Asn Pro Asn Gln Lys Ile Ile Thr Ile Gly Ser Ile Cys Met Thr
1 5 10 15

Ile Gly Met Ala Asn Leu Ile Leu Gln Ile Gly Xaa Ile Ile Ser Ile
20 25 30

Trp Val Ser His Ser Ile Gln Ile Gly Asn Gln Ser Gln Ile Glu Thr
35 40 45

Cys Asn Gln Ser Val Ile Thr Tyr Glu Asn Asn Thr Trp Val Asn Gln
50 55 60

Thr Tyr Val Asn Ile Ser Asn Thr Asn Phe Ala Ala Gly Gln Ser Val
65 70 75 80

Val Ser Val Lys Leu Ala Gly Asn Ser Ser Leu Cys Pro Val Ser Gly
85 90 95

Trp Ala Ile Tyr Ser Lys Asp Asn Ser Val Arg Ile Gly Ser Lys Gly
100 105 110

Asp Val Phe Val Ile Arg Glu Pro Phe Ile Ser Cys Ser Pro Leu Glu
115 120 125

Cys Arg Thr Phe Phe Leu Thr Gln Gly Ala Leu Leu Asn Asp Lys His
130 135 140

Ser Asn Gly Thr Ile Lys Asp Arg Ser Pro Tyr Arg Thr Leu Met Ser
145 150 155 160

Cys Pro Ile Gly Glu Val Pro Ser Pro Tyr Asn Ser Arg Phe Glu Ser
165 170 175

Val Ala Trp Ser Ala Ser Ala Cys His Asp Gly Ile Asn Trp Leu Thr
180 185 190

Ile Gly Ile Ser Gly Pro Asp Ser Gly Ala Val Ala Val Leu Lys Tyr
195 200 205

Asn Gly Ile Ile Thr Asp Thr Ile Lys Ser Trp Arg Asn Asn Ile Leu
210 215 220

Arg Thr Gln Glu Ser Glu Cys Ala Cys Val Asn Gly Ser Cys Phe Thr
225 230 235 240

Ile Met Thr Asp Gly Pro Ser Asp Gly Gln Ala Ser Tyr Lys Ile Phe
245 250 255

Arg Ile Glu Lys Gly Lys Ile Ile Lys Ser Val Glu Met Lys Ala Pro
260 265 270

Asn Tyr His Tyr Glu Glu Cys Ser Cys Tyr Pro Asp Ser Ser Glu Ile
275 280 285

Thr Cys Val Cys Arg Asp Asn Trp His Gly Ser Asn Arg Pro Trp Val
290 295 300

```
Ser Phe Asn Gln Asn Leu Glu Tyr Gln Met Gly Tyr Ile Cys Ser Gly
305                 310                 315                 320

Val Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Asn Lys Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 42
<211> LENGTH: 1407
<212> TYPE: DNA
<213> ORGANISM: Artificial Sequence
<220> FEATURE:
<223> OTHER INFORMATION: 2015 H1N1 - Optimized DNA sequence encoding the
      nucleic acid sequence encoding NA antigen
<220> FEATURE:
<221> NAME/KEY: misc_feature
<222> LOCATION: (82)..(84)
<223> OTHER INFORMATION: any nucleotide

<400> SEQUENCE: 42

atgaacccca accagaagat catcaccatc ggctccatct gcatgaccat cggcatggcc     60

aacctgatcc tgcagatcgg cnnnatcatc tccatctggg tgtcccactc catccagatc    120

ggcaaccagt cccagatcga gacctgcaac cagtccgtga tcacctacga gaacaacacc    180

tgggtgaacc agacctacgt gaacatctcc aacaccaact tcgccgccgg ccagtccgtg    240

gtgtccgtga agctggccgg caactcctcc ctgtgccccg tgtccggctg ggccatctac    300

tccaaggaca actccgtgcg catcggctcc aagggcgacg tgttcgtgat ccgcgagccc    360

ttcatctcct gctcccccct ggagtgccgc accttcttcc tgacccaggg cgccctgctg    420

aacgacaagc actccaacgg caccatcaag gaccgctccc cctaccgcac cctgatgtcc    480

tgccccatcg gcgaggtgcc ctccccctac aactcccgct tcgagtccgt ggcctggtcc    540

gcctccgcct gccacgacgg catcaactgg ctgaccatcg gcatctccgg ccccgactcc    600

ggcgccgtgg ccgtgctgaa gtacaacggc atcatcaccg acaccatcaa gtcctggcgc    660

aacaacatcc tgcgcaccca ggagtccgag tgcgcctgcg tgaacggctc ctgcttcacc    720

atcatgaccg acggcccctc cgacggccag gcctcctaca agatcttccg catcgagaag    780

ggcaagatca tcaagtccgt ggagatgaag gcccccaact accactacga ggagtgctcc    840

tgctaccccg actcctccga gatcacctgc gtgtgccgcg acaactggca cggctccaac    900
```

```
cgcccctggg tgtccttcaa ccagaacctg gagtaccaga tgggctacat ctgctccggc    960

gtgttcggcg acaaccccg  ccccaacgac aagaccggct cctgcggccc cgtgtcctcc   1020

aacggcgcca acggcgtgaa gggcttctcc ttcaagtacg gcaacggcgt gtggatcggc   1080

cgcaccaagt ccatctcctc ccgcaagggc ttcgagatga tctgggaccc caacggctgg   1140

accggcaccg acaacaagtt ctccatcaag caggacatcg tgggcatcaa cgagtggtcc   1200

ggctactccg gctccttcgt gcagcacccc gagctgaccg gcctggactg catccgcccc   1260

tgcttctggg tggagctgat ccgcggccgc cccgaggaga acaccatctg gacctccggc   1320

tcctccatct ccttctgcgg cgtgaactcc gacaccgtgg gctggtcctg gcccgacggc   1380

gccgagctgc ccttcaccat cgacaag                                       1407
```

<210> SEQ ID NO 43
<211> LENGTH: 469
<212> TYPE: PRT
<213> ORGANISM: Artificial Sequence
<220> FEATURE:
<223> OTHER INFORMATION: 2017 H3N2 - NA antigen Amino Acid sequence

<400> SEQUENCE: 43

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Arg Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Ile Asn Asn Val His
    130                 135                 140

Ser Asn Asn Thr Ala Arg Asp Arg Thr Pro His Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Lys Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270
```

-continued

```
Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Thr Asp Ser Ser Ser Ser Ser His
                325                 330                 335

Cys Leu Asn Pro Asn Asn Glu Lys Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Val Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Leu
    450                 455                 460

Asn Leu Met His Ile
465
```

<210> SEQ ID NO 44
<211> LENGTH: 1407
<212> TYPE: DNA
<213> ORGANISM: Artificial Sequence
<220> FEATURE:
<223> OTHER INFORMATION: 2017 H3N2 - Optimized DNA sequence encoding the nucleic acid sequence encoding NA antigen

<400> SEQUENCE: 44

```
atgaacccca accagaagat catcaccatc ggctccgtgt ccctgaccat ctccaccatc      60

tgcttcttca tgcagatcgc catcctgatc accaccgtga ccctgcactt caagcagtac     120

gagttcaact cccccccaa caaccaggtg atgctgtgcg agcccaccat catcgagcgc     180

aacatcaccg agatcgtgta cctgaccaac accaccatcg agcgcgagat ctgccccaag     240

cccgccgagt accgcaactg gtccaagccc cagtgcggca tcaccggctt cgccccettc     300

tccaaggaca actccatccg cctgtccgcc ggcggcgaca tctgggtgac ccgcgagccc     360

tacgtgtcct gcgaccccga caagtgctac cagttcgccc tgggccaggg caccaccatc     420

aacaacgtgc actccaacaa caccgcccgc gaccgcaccc cccaccgcac cctgctgatg     480

aacgagctgg gcgtgccctt ccacctgggc accaagcagg tgtgcatcgc ctggtcctcc     540

tcctcctgcc acgacggcaa ggcctggctg cacgtgtgca tcaccggcga cgacaagaac     600

gccaccgcct ccttcatcta caacggccgc ctggtggact ccgtggtgtc ctggtccaag     660

gacatcctgc gcacccagga gtccgagtgc gtgtgcatca acggcacctg caccgtggtg     720

atgaccgacg gcaacgccac cggcaaggcc gacaccaaga tcctgttcat cgaggagggc     780

aagatcgtgc acacctccaa gctgtccggc tccgcccagc acgtggagga gtgctcctgc     840

taccccgct accccggcgt gcgctgcgtg tgccgcgaca actggaaggg ctccaaccgc     900
```

```
cccatcgtgg acatcaacat caaggaccac tccatcgtgt cctcctacgt gtgctccggc    960

ctggtgggcg acaccccccg caagaccgac tcctcctcct cctcccactg cctgaacccc   1020

aacaacgaga agggcggcca cggcgtgaag ggctgggcct tcgacgacgg caacgacgtg   1080

tggatgggcc gcaccatcaa cgagacctcc cgcctgggct acgagacctt caaggtggtg   1140

gagggctggt ccaaccccaa gtccaagctg cagatcaacc gccaggtgat cgtggaccgc   1200

ggcgaccgct ccggctactc cggcatcttc tccgtggagg gcaagtcctg catcaaccgc   1260

tgcttctacg tggagctgat ccgcggccgc aaggaggaga ccgaggtgct gtggacctcc   1320

aactccatcg tggtgttctg cggcacctcc ggcacctacg gcaccggctc ctggcccgac   1380

ggcgccgacc tgaacctgat gcacatc                                       1407
```

```
<210> SEQ ID NO 45
<211> LENGTH: 466
<212> TYPE: PRT
<213> ORGANISM: Artificial Sequence
<220> FEATURE:
<223> OTHER INFORMATION: 2017 Influenza B (Victoria lineage) - NA
      antigen Amino Acid sequence

<400> SEQUENCE: 45

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Val Ala Cys Gly Pro Asn Glu Cys Lys
        115                 120                 125

His Phe Ala Leu Thr His Tyr Ala Ala Gln Pro Gly Gly Tyr Tyr Asn
    130                 135                 140

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Val Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Ile Lys Glu Ile Phe Pro Thr Gly Arg Val Lys
```

```
            260                 265                 270

His Thr Glu Glu Cys Thr Cys Gly Phe Ala Ser Asn Lys Thr Ile Glu
        275                 280                 285

Cys Ala Cys Arg Asp Asn Arg Tyr Thr Ala Lys Arg Pro Phe Val Lys
    290                 295                 300

Leu Asn Val Glu Thr Asp Thr Ala Glu Ile Arg Leu Met Cys Thr Asp
305                 310                 315                 320

Thr Tyr Leu Asp Thr Pro Arg Pro Asn Asp Gly Ser Ile Thr Gly Pro
                325                 330                 335

Cys Glu Ser Asp Gly Asp Lys Gly Ser Gly Gly Ile Lys Gly Gly Phe
            340                 345                 350

Val His Gln Arg Met Lys Ser Lys Ile Gly Arg Trp Tyr Ser Arg Thr
        355                 360                 365

Met Ser Gln Thr Glu Arg Met Gly Met Gly Leu Tyr Val Lys Tyr Gly
    370                 375                 380

Gly Asp Pro Trp Ala Asp Ser Asp Ala Leu Ala Phe Ser Gly Val Met
385                 390                 395                 400

Val Ser Met Lys Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465
```

<210> SEQ ID NO 46
<211> LENGTH: 1398
<212> TYPE: DNA
<213> ORGANISM: Artificial Sequence
<220> FEATURE:
<223> OTHER INFORMATION: 2017 Influenza B (Victoria lineage) - Optimized DNA sequence encoding the nucleic acid sequence encoding NA antigen

<400> SEQUENCE: 46

```
atgctgccct ccaccatcca gaccctgacc ctgttcctga cctccggcgg cgtgctgctg     60

tccctgtacg tgtccgcctc cctgtcctac ctgctgtact ccgacatcct gctgaagttc    120

tcccccaccg agatcaccgc ccccaccatg cccctggact gcgccaacgc ctccaacgtg    180

caggccgtga accgctccgc caccaagggc gtgaccctgc tgctgcccga gcccgagtgg    240

acctaccccc gcctgtcctg ccccggctcc accttccaga aggccctgct gatctccccc    300

caccgcttcg gcgagaccaa gggcaactcc gccccctga tcatccgcga gcccttcgtg    360

gcctgcggcc ccaacgagtg caagcacttc gccctgaccc actacgccgc ccagcccggc    420

ggctactaca acggcacccg cggcgaccgc aacaagctgc gccacctgat ctccgtgaag    480

ctgggcaaga tccccaccgt ggagaactcc atcttccaca tggccgcctg gtccggctcc    540

gcctgccacg acggcaagga gtggacctac atcggcgtgg acggccccga caacaacgcc    600

ctgctgaagg tgaagtacgg cgaggcctac accgacacct accactccta cgccaacaac    660

atcctgcgca cccaggagtc cgcctgcaac tgcatcggcg gcaactgcta cctgatgatc    720

accgacggct ccgcctccgg cgtgtccgag tgccgcttcc tgaagatccg cgagggccgc    780
```

atcatcaagg agatcttccc caccggccgc gtgaagcaca ccgaggagtg cacctgcggc 840
ttcgcctcca acaagaccat cgagtgcgcc tgccgcgaca accgctacac cgccaagcgc 900
cccttcgtga agctgaacgt ggagaccgac accgccgaga tccgcctgat gtgcaccgac 960
acctacctgg acaccccccg ccccaacgac ggctccatca ccggcccctg cgagtccgac 1020
ggcgacaagg gctccggcgg catcaagggc ggcttcgtgc accagcgcat gaagtccaag 1080
atcggccgct ggtactcccg caccatgtcc cagaccgagc gcatgggcat gggcctgtac 1140
gtgaagtacg gcggcgaccc ctgggccgac tccgacgccc tggccttctc cggcgtgatg 1200
gtgtccatga aggagcccgg ctggtactcc ttcggcttcg agatcaagga caagaagtgc 1260
gacgtgccct gcatcggcat cgagatggtg cacgacggcg gcaaggagac ctggcactcc 1320
gccgccaccg ccatctactg cctgatgggc tccggccagc tgctgtggga caccgtgacc 1380
ggcgtggaca tggccctg 1398

<210> SEQ ID NO 47
<211> LENGTH: 466
<212> TYPE: PRT
<213> ORGANISM: Artificial Sequence
<220> FEATURE:
<223> OTHER INFORMATION: 2013 Influenza B (Yamagata lineage) - Sequence only on GISAID - NA antigen Amino Acid sequence

<400> SEQUENCE: 47

Met Leu Pro Ser Thr Ile Gln Thr Leu Thr Leu Phe Leu Thr Ser Gly
1 5 10 15

Gly Val Leu Leu Ser Leu Tyr Val Ser Ala Ser Leu Ser Tyr Leu Leu
20 25 30

Tyr Ser Asp Ile Leu Leu Lys Phe Ser Arg Thr Glu Val Thr Ala Pro
35 40 45

Ile Met Pro Leu Asp Cys Ala Asn Ala Ser Asn Val Gln Ala Val Asn
50 55 60

Arg Ser Ala Thr Lys Gly Val Thr Pro Leu Leu Pro Glu Pro Glu Trp
65 70 75 80

Thr Tyr Pro Arg Leu Ser Cys Pro Gly Ser Thr Phe Gln Lys Ala Leu
85 90 95

Leu Ile Ser Pro His Arg Phe Gly Glu Thr Lys Gly Asn Ser Ala Pro
100 105 110

Leu Ile Ile Arg Glu Pro Phe Ile Ala Cys Gly Pro Lys Glu Cys Lys
115 120 125

His Phe Ala Leu Thr His Tyr Ala Ala Gln Pro Gly Gly Tyr Tyr Asn
130 135 140

Gly Thr Arg Glu Asp Arg Asn Lys Leu Arg His Leu Ile Ser Val Lys
145 150 155 160

Leu Gly Lys Ile Pro Thr Val Glu Asn Ser Ile Phe His Met Ala Ala
165 170 175

Trp Ser Gly Ser Ala Cys His Asp Gly Arg Glu Trp Thr Tyr Ile Gly
180 185 190

Val Asp Gly Pro Asp Ser Asn Ala Leu Leu Lys Ile Lys Tyr Gly Glu
195 200 205

Ala Tyr Thr Asp Thr Tyr His Ser Tyr Ala Lys Asn Ile Leu Arg Thr
210 215 220

Gln Glu Ser Ala Cys Asn Cys Ile Gly Gly Asp Cys Tyr Leu Met Ile
225 230 235 240

Thr Asp Gly Pro Ala Ser Gly Ile Ser Glu Cys Arg Phe Leu Lys Ile

```
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Lys
305                 310                 315                 320

Thr Tyr Leu Asp Thr Pro Arg Pro Asn Asp Gly Ser Ile Thr Gly Pro
                325                 330                 335

Cys Glu Ser Asp Gly Asp Glu Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Thr Thr Trp His Ser Ala Ala Thr Ala Ile Tyr Cys Leu
        435                 440                 445

Met Gly Ser Gly Gln Leu Leu Trp Asp Thr Val Thr Gly Val Asn Met
    450                 455                 460

Thr Leu
465
```

<210> SEQ ID NO 48
<211> LENGTH: 1398
<212> TYPE: DNA
<213> ORGANISM: Artificial Sequence
<220> FEATURE:
<223> OTHER INFORMATION: 2013 Influenza B (Yamagata lineage) - Sequence only on GISAID - Optimized DNA sequence encoding the nucleic acid sequence encoding NA antigen

<400> SEQUENCE: 48

```
atgctgccct ccaccatcca gaccctgacc ctgttcctga cctccggcgg cgtgctgctg     60

tccctgtacg tgtccgcctc cctgtcctac ctgctgtact ccgacatcct gctgaagttc    120

tcccgcaccg aggtgaccgc cccatcatg cccctggact gcgccaacgc ctccaacgtg    180

caggccgtga accgctccgc caccaagggc gtgacccccc tgctgcccga gcccgagtgg    240

acctaccccc gcctgtcctg ccccggctcc accttccaga aggccctgct gatctccccc    300

caccgcttcg gcgagaccaa gggcaactcc gccccccctga tcatccgcga gcccttcatc    360

gcctgcggcc ccaaggagtg caagcacttc gccctgaccc actacgccgc ccagcccggc    420

ggctactaca acggcacccg cgaggaccgc aacaagctgc gccacctgat ctccgtgaag    480

ctgggcaaga tccccaccgt ggagaactcc atcttccaca tggccgcctg gtccggctcc    540

gcctgccacg acggccgcga gtggacctac atcggcgtgg acggccccga ctccaacgcc    600

ctgctgaaga tcaagtacgg cgaggcctac accgacacct accactccta cgccaagaac    660

atcctgcgca cccaggagtc cgcctgcaac tgcatcggcg gcgactgcta cctgatgatc    720
```

accgacggcc ccgcctccgg catctccgag tgccgcttcc tgaagatccg cgagggccgc 780
atcatcaagg agatcttccc caccggccgc gtgaagcaca ccgaggagtg cacctgcggc 840
ttcgcctcca acaagaccat cgagtgcgcc tgccgcgaca actcctacac cgccaagcgc 900
cccttcgtga agctgaacgt ggagaccgac accgccgaga tccgcctgat gtgcaccaag 960
acctacctgg acaccccccg ccccaacgac ggctccatca ccggcccctg cgagtccgac 1020
ggcgacgagg gctccggcgg catcaagggc ggcttcgtgc accagcgcat ggcctccaag 1080
atcggccgct ggtactcccg caccatgtcc aagaccaagc gcatgggcat gggcctgtac 1140
gtgaagtacg acggcgaccc ctggaccgac tccgaggccc tggccctgtc cggcgtgatg 1200
gtgtccatgg aggagcccgg ctggtactcc ttcggcttcg agatcaagga caagaagtgc 1260
gacgtgccct gcatcggcat cgagatggtg cacgacggcg gcaagaccac ctggcactcc 1320
gccgccaccg ccatctactg cctgatgggc tccggccagc tgctgtggga caccgtgacc 1380
ggcgtgaaca tgaccctg 1398

<210> SEQ ID NO 49
<211> LENGTH: 449
<212> TYPE: PRT
<213> ORGANISM: Artificial Sequence
<220> FEATURE:
<223> OTHER INFORMATION: 2015 H5N1 - NA antigen Amino Acid sequence

<400> SEQUENCE: 49

Met Asn Pro Asn Gln Lys Ile Ile Thr Ile Gly Ser Ile Cys Met Ile
1 5 10 15

Ile Gly Ile Val Ser Leu Met Leu Gln Ile Gly Asn Met Ile Ser Ile
20 25 30

Leu Val Ser His Ser Ile Gln Thr Gly Asn Gln His Gln Ala Glu Pro
35 40 45

Ile Arg Asn Thr Asn Phe Leu Thr Glu Asn Ala Val Ala Ser Ile Thr
50 55 60

Leu Thr Gly Ser Ser Ser Leu Cys Pro Ile Arg Gly Trp Ala Val His
65 70 75 80

Ser Lys Asp Asn Ser Ile Arg Ile Gly Ser Lys Gly Asp Val Phe Val
85 90 95

Ile Arg Glu Pro Phe Ile Ser Cys Ser His Met Glu Cys Arg Thr Phe
100 105 110

Phe Leu Thr His Gly Ala Leu Leu Asn Asp Lys His Ser Asn Gly Thr
115 120 125

Val Lys Asp Arg Ser Pro His Arg Thr Leu Met Ser Cys Pro Val Gly
130 135 140

Glu Ala Pro Ser Pro Tyr Asn Ser Arg Phe Glu Ser Val Ala Trp Ser
145 150 155 160

Ala Ser Ala Cys His Asp Gly Thr Ser Trp Leu Thr Ile Gly Ile Ser
165 170 175

Gly Pro Asp Asn Gly Ala Val Ala Val Leu Lys Tyr Asn Gly Ile Ile
180 185 190

Thr Asp Thr Ile Lys Ser Trp Arg Asn Asn Ile Leu Arg Thr Gln Glu
195 200 205

Ser Glu Cys Ala Cys Val Asn Gly Ser Cys Phe Thr Val Met Thr Asp
210 215 220

Gly Pro Ser Asn Gly Gln Ala Ser Tyr Lys Ile Phe Lys Ile Glu Lys
225 230 235 240

```
Gly Lys Val Val Lys Ser Val Glu Leu Asn Ala Pro Asn Tyr His Tyr
                245                 250                 255

Glu Glu Cys Ser Cys Tyr Pro Asp Ser Gly Glu Ile Met Cys Val Cys
            260                 265                 270

Arg Asp Asn Trp His Gly Ser Asn Arg Pro Trp Val Thr Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Met Ser Leu
305                 310                 315                 320

Asn Gly Ala Tyr Gly Ile Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Gly Thr Asp Ser Glu Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
            420                 425                 430

Val Ser Trp Ser Trp Pro Asp Gly Ala Glu Leu Pro Phe Thr Ile Asp
        435                 440                 445

Lys
```

<210> SEQ ID NO 50
<211> LENGTH: 1347
<212> TYPE: DNA
<213> ORGANISM: Artificial Sequence
<220> FEATURE:
<223> OTHER INFORMATION: 2015 H5N1 - Optimized DNA sequence encoding the nucleic acid sequence encoding NA antigen

<400> SEQUENCE: 50

```
atgaacccca accagaagat catcaccatc ggctccatct gcatgatcat cggcatcgtg      60

tccctgatgc tgcagatcgg caacatgatc tccatcctgg tgtcccactc catccagacc     120

ggcaaccagc accaggccga gcccatccgc aacaccaact tcctgaccga gaacgccgtg     180

gcctccatca ccctgaccgg ctcctcctcc ctgtgcccca tccgcggctg ggccgtgcac     240

tccaaggaca actccatccg catcggctcc aagggcgacg tgttcgtgat ccgcgagccc     300

ttcatctcct gctcccacat ggagtgccgc accttcttcc tgacccacgg cgccctgctg     360

aacgacaagc actccaacgg caccgtgaag gaccgctccc cccaccgcac cctgatgtcc     420

tgccccgtgg gcgaggcccc ctccccctac aactcccgct tcgagtccgt ggcctggtcc     480

gcctccgcct gccacgacgg cacctcctgg ctgaccatcg gcatctccgg ccccgacaac     540

ggcgccgtgg ccgtgctgaa gtacaacggc atcatcaccg acaccatcaa gtcctggcgc     600

aacaacatcc tgcgcaccca ggagtccgag tgcgcctgcg tgaacggctc ctgcttcacc     660

gtgatgaccg acggcccctc caacggccag gcctcctaca agatcttcaa gatcgagaag     720

ggcaaggtgg tgaagtccgt ggagctgaac gcccccaact accactacga ggagtgctcc     780
```

```
tgctaccccg actccggcga gatcatgtgc gtgtgccgcg acaactggca cggctccaac    840

cgcccctggg tgaccttcaa ccagaacctg gagtaccaga tcggctacat ctgctccggc    900

gtgttcggcg acaacccccg ccccaacgac ggcaccggct cctgcggccc catgtccctg    960

aacggcgcct acggcatcaa gggcttctcc ttcaagtacg gcaacggcgt gtggatcggc   1020

cgcaccaagt ccaccaactc ccgctccggc ttcgagatga tctgggaccc caacggctgg   1080

accggcaccg actccgagtt ctccgtgaag caggacatcg tggccatcac cgactggtcc   1140

ggctactccg gctccttcgt gcagcacccc gagctgaccg gcctggactg catccgcccc   1200

tgcttctggg tggagctgat ccgcggccgc cccaaggagt ccaccatctg gacctccggc   1260

tcctccatct ccttctgcgg cgtgaactcc gacaccgtgt cctggtcctg gcccgacggc   1320

gccgagctgc ccttcaccat cgacaag                                       1347
```

```
<210> SEQ ID NO 51
<211> LENGTH: 465
<212> TYPE: PRT
<213> ORGANISM: Artificial Sequence
<220> FEATURE:
<223> OTHER INFORMATION: 2017 H7N9 - NA antigen Amino Acid sequence

<400> SEQUENCE: 51

Met Asn Pro Asn Gln Lys Ile Leu Cys Thr Ser Ala Thr Ala Ile Thr
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
        35                  40                  45

Glu Ile Thr Asn Thr Ser Gln Thr Ile Ile Asn Asn Tyr Tyr Ser Glu
    50                  55                  60

Thr Asn Ile Thr Asn Ile Gln Met Glu Glu Arg Thr Ser Lys Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220

Ser Glu Cys Val Cys His Asn Gly Ile Cys Pro Val Val Phe Thr Asp
225                 230                 235                 240

Gly Ser Ala Thr Gly Pro Ala Asp Thr Arg Ile Tyr Tyr Phe Lys Glu
                245                 250                 255

Gly Lys Ile Leu Lys Trp Glu Ser Leu Thr Gly Thr Ala Lys His Val
```

```
            260                 265                 270

Glu Glu Cys Ser Cys Tyr Gly Glu Arg Thr Gly Ile Thr Cys Thr Cys
        275                 280                 285

Arg Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Asn Gly Ile Lys Gly Phe Ser Tyr Leu Asp
            340                 345                 350

Gly Asp Asn Thr Trp Leu Gly Arg Thr Ile Ser Thr Ala Ser Arg Ser
        355                 360                 365

Gly Tyr Glu Val Leu Lys Val Pro Asn Ala Leu Thr Asp Asp Arg Ser
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Asp Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465
```

<210> SEQ ID NO 52
<211> LENGTH: 1395
<212> TYPE: DNA
<213> ORGANISM: Artificial Sequence
<220> FEATURE:
<223> OTHER INFORMATION: 2017 H7N9 - Optimized DNA sequence encoding the nucleic acid sequence encoding NA antigen

<400> SEQUENCE: 52

```
atgaacccca accagaagat cctgtgcacc tccgccaccg ccatcaccat cggcgccatc      60

gccgtgctga tcggcatcgc caacctgggc ctgaacatcg gcctgcacct gaagcccggc     120

tgcaactgct cccactccca gcccgagatc accaacacct cccagaccat catcaacaac     180

tactactccg agaccaacat caccaacatc cagatggagg agcgcacctc caagaacttc     240

aacaacctga ccaagggcct gtgcaccatc aactcctggc acatctacgg caaggacaac     300

gccgtgcgca tcggcgagtc ctccgacgtg ctggtgaccc gcgagcccta cgtgtcctgc     360

gaccccgacg agtgccgctt ctacgccctg tcccagggca ccaccatccg cggcaagcac     420

tccaacggca ccatccacga ccgctcccag taccgcgccc tgatctcctg gcccctgtcc     480

tcccccccca ccgtgtacaa ctcccgcgtg gagtgcatcg gctggtcctc cacctcctgc     540

cacgacggca agtcccgcat gtccatctgc atctccggcc ccaacaacaa cgcctccgcc     600

gtggtgtggt acaaccgccg ccccgtggcc gagatcaaca cctgggcccg caacatcctg     660

cgcacccagg agtccgagtg cgtgtgccac aacggcatct gccccgtggt gttcaccgac     720

ggctccgcca ccggccccgc cgacacccgc atctactact tcaaggaggg caagatcctg     780

aagtgggagt ccctgaccgg caccgccaag cacgtggagg agtgctcctg ctacggcgag     840
```

```
cgcaccggca tcacctgcac ctgccgcgac aactggcagg gctccaaccg ccccgtgatc    900

cagatcgacc ccgtggccat gacccacacc tcccagtaca tctgctcccc cgtgctgacc    960

gacaaccccc gccccaacga ccccaacatc ggcaagtgca acgacccccta ccccggcaac  1020

aacaacaacg gcatcaaggg cttctcctac ctggacggcg acaacacctg gctgggccgc   1080

accatctcca ccgcctcccg ctccggctac gaggtgctga aggtgcccaa cgccctgacc   1140

gacgaccgct ccaagcccat ccagggccag accatcgtgc tgaacgccga ctggtccggc   1200

tactccggct ccttcatgga ctactgggcc gacggcgact gctaccgcgc ctgcttctac   1260

gtggagctga tccgcggccg ccccaaggag gacaaggtgt ggtggacctc caactccatc   1320

gtgtccatgt gctcctccac cgagttcctg ggccagtgga actggcccga cggcgccaag   1380

atcgagtact tcctg                                                    1395
```

<210> SEQ ID NO 53
<211> LENGTH: 470
<212> TYPE: PRT
<213> ORGANISM: Artificial Sequence
<220> FEATURE:
<223> OTHER INFORMATION: 2013 H10N8 - NA antigen Amino Acid sequence

<400> SEQUENCE: 53

```
Met Asn Pro Asn Gln Lys Ile Ile Thr Ile Gly Ser Val Ser Leu Gly
1               5                   10                  15

Leu Val Ile Leu Asn Ile Leu Leu His Ile Val Ser Ile Thr Val Thr
            20                  25                  30

Val Leu Val Leu Pro Gly Asn Gly Asn Asn Glu Ser Cys Asn Glu Thr
        35                  40                  45

Val Ile Arg Glu Tyr Asn Glu Thr Val Arg Val Glu Lys Val Thr Gln
    50                  55                  60

Trp His Asn Thr Asn Val Ile Glu Tyr Ile Glu Arg Pro Glu Asn Asp
65                  70                  75                  80

His Phe Met Asn Asn Thr Glu Ala Leu Cys Asp Ala Lys Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Thr Glu Cys Arg
        115                 120                 125

Thr Phe Phe Leu Thr Gln Gly Ser Leu Leu Asn Asp Lys His Ser Asn
    130                 135                 140

Gly Thr Val Lys Asp Arg Ser Pro Tyr Arg Thr Leu Met Ser Val Glu
145                 150                 155                 160

Ile Gly Gln Ser Pro Asn Val Tyr Gln Ala Arg Phe Glu Ala Val Ala
                165                 170                 175

Trp Ser Ala Thr Ala Cys His Asp Gly Lys Lys Trp Met Thr Ile Gly
            180                 185                 190

Val Thr Gly Pro Asp Ala Lys Ala Val Ala Val Val His Tyr Gly Gly
        195                 200                 205

Ile Pro Thr Asp Val Ile Asn Ser Trp Ala Gly Asp Ile Leu Arg Thr
    210                 215                 220

Gln Glu Ser Ser Cys Thr Cys Ile Gln Gly Glu Cys Phe Trp Val Met
225                 230                 235                 240

Thr Asp Gly Pro Ala Asn Arg Gln Ala Gln Tyr Arg Ala Phe Lys Ala
                245                 250                 255
```

-continued

```
Lys Gln Gly Lys Ile Val Gly Gln Ala Glu Ile Ser Phe Asn Gly Gly
            260                 265                 270

His Ile Glu Glu Cys Ser Cys Tyr Pro Asn Glu Gly Lys Val Glu Cys
        275                 280                 285

Val Cys Lys Asp Asn Trp Thr Gly Thr Asn Arg Pro Val Leu Val Ile
    290                 295                 300

Ser Pro Asp Leu Ser Tyr Arg Val Gly Tyr Leu Cys Ala Gly Leu Pro
305                 310                 315                 320

Ser Asp Thr Pro Arg Gly Glu Asp Ser Gln Phe Thr Gly Ser Cys Thr
                325                 330                 335

Ser Pro Met Gly Asn Gln Gly Tyr Gly Val Lys Gly Phe Gly Phe Arg
            340                 345                 350

Gln Gly Asn Asp Val Trp Met Gly Arg Thr Ile Ser Arg Thr Ser Arg
        355                 360                 365

Ser Gly Phe Glu Ile Leu Lys Val Arg Asn Gly Trp Val Gln Asn Ser
    370                 375                 380

Lys Glu Gln Ile Lys Arg Gln Val Val Val Asp Asn Leu Asn Trp Ser
385                 390                 395                 400

Gly Tyr Ser Gly Ser Phe Thr Leu Pro Ala Glu Leu Thr Lys Arg Asn
                405                 410                 415

Cys Leu Val Pro Cys Phe Trp Val Glu Met Ile Arg Gly Asn Pro Glu
            420                 425                 430

Glu Lys Thr Ile Trp Thr Ser Ser Ser Ser Ile Val Met Cys Gly Val
        435                 440                 445

Asp His Glu Ile Ala Asp Trp Ser Trp His Asp Gly Ala Ile Leu Pro
    450                 455                 460

Phe Asp Ile Asp Lys Met
465                 470
```

<210> SEQ ID NO 54
<211> LENGTH: 1410
<212> TYPE: DNA
<213> ORGANISM: Artificial Sequence
<220> FEATURE:
<223> OTHER INFORMATION: 2013 H10N8 - Optimized DNA sequence encoding the nucleic acid sequence encoding NA antigen

<400> SEQUENCE: 54

```
atgaacccca accagaagat catcaccatc ggctccgtgt ccctgggcct ggtgatcctg     60

aacatcctgc tgcacatcgt gtccatcacc gtgaccgtgc tggtgctgcc cggcaacggc    120

aacaacgagt cctgcaacga gaccgtgatc cgcgagtaca acgagaccgt gcgcgtggag    180

aaggtgaccc agtggcacaa caccaacgtg atcgagtaca tcgagcgccc cgagaacgac    240

cacttcatga acaacaccga ggccctgtgc gacgccaagg gcttcgcccc cttctccaag    300

gacaacggca tccgcatcgg ctcccgcggc cacgtgttcg tgatccgcga gcccttcgtg    360

tcctgctccc ccaccgagtg ccgcaccttc ttcctgaccc agggctccct gctgaacgac    420

aagcactcca acggcaccgt gaaggaccgc tccccctacc gcaccctgat gtccgtggag    480

atcggccagt cccccaacgt gtaccaggcc cgcttcgagg ccgtggcctg gtccgccacc    540

gcctgccacg acggcaagaa gtggatgacc atcggcgtga ccggccccga cgccaaggcc    600

gtggccgtgg tgcactacgg cggcatcccc accgacgtga tcaactcctg ggccggcgac    660

atcctgcgca cccaggagtc ctcctgcacc tgcatccagg gcgagtgctt ctgggtgatg    720

accgacggcc ccgccaaccg ccaggcccag taccgcgcct tcaaggccaa gcagggcaag    780
```

```
atcgtgggcc aggccgagat ctccttcaac ggcggccaca tcgaggagtg ctcctgctac     840

cccaacgagg gcaaggtgga gtgcgtgtgc aaggacaact ggaccggcac caaccgcccc     900

gtgctggtga tctcccccga cctgtcctac cgcgtgggct acctgtgcgc cggcctgccc     960

tccgacaccc cccgcggcga ggactcccag ttcaccggct cctgcacctc ccccatgggc    1020

aaccagggct acggcgtgaa gggcttcggc ttccgccagg gcaacgacgt gtggatgggc    1080

cgcaccatct cccgcacctc ccgctccggc ttcgagatcc tgaaggtgcg caacggctgg    1140

gtgcagaact ccaaggagca gatcaagcgc caggtggtgg tggacaacct gaactggtcc    1200

ggctactccg gctccttcac cctgcccgcc gagctgacca agcgcaactg cctggtgccc    1260

tgcttctggg tggagatgat ccgcggcaac cccgaggaga agaccatctg gacctcctcc    1320

tcctccatcg tgatgtgcgg cgtggaccac gagatcgccg actggtcctg gcacgacggc    1380

gccatcctgc ccttcgacat cgacaagatg                                     1410
```

<210> SEQ ID NO 55
<211> LENGTH: 498
<212> TYPE: PRT
<213> ORGANISM: Artificial Sequence
<220> FEATURE:
<223> OTHER INFORMATION: 1918 H1N1 - NP antigen Amino Acid sequence

<400> SEQUENCE: 55

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Ile Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255
```

-continued

```
Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Lys Leu Ser Thr Arg Gly Val Gln Ile Ala Ser Asn
        355                 360                 365

Glu Asn Met Glu Thr Met Asp Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 56
<211> LENGTH: 1494
<212> TYPE: DNA
<213> ORGANISM: Artificial Sequence
<220> FEATURE:
<223> OTHER INFORMATION: 1918 H1N1 - Optimized DNA sequence encoding the
      nucleic acid sequence encoding NP antigen

<400> SEQUENCE: 56

atggcctccc agggcaccaa gcgctcctac gagcagatgg agaccgacgg cgagcgccag      60

aacgccaccg agatccgcgc ctccgtgggc cgcatgatcg gcggcatcgg ccgcttctac     120

atccagatgt gcaccgagct gaagctgtcc gactacgagg gccgcctgat ccagaactcc     180

atcaccatcg agcgcatggt gctgtccgcc ttcgacgagc gccgcaacaa gtacctggag     240

gagcacccct ccgccggcaa ggaccccaag aagaccggcg gccccatcta ccgccgcatc     300

gacggcaagt ggatgcgcga gctgatcctg tacgacaagg aggagatccg ccgcatctgg     360

cgccaggcca acaacggcga ggacgccacc gccggcctga cccacatgat gatctggcac     420

tccaacctga acgacgccac ctaccagcgc acccgcgccc tggtgcgcac cggcatggac     480

ccccgcatgt gctccctgat gcagggctcc accctgcccc gccgctccgg cgccgccggc     540

gccgccgtga agggcgtggg caccatggtg atggagctga tccgcatgat caagcgcggc     600
```

atcaacgacc gcaacttctg gcgcggcgag aacggccgcc gcacccgcat cgcctacgag 660
cgcatgtgca acatcctgaa gggcaagttc cagaccgccg cccagcgcgc catgatggac 720
caggtgcgcg agtcccgcaa ccccggcaac gccgagatcg aggacctgat cttcctggcc 780
cgctccgccc tgatcctgcg cggctccgtg gcccacaagt cctgcctgcc cgcctgcgtg 840
tacggccccg ccgtggcctc cggctacgac ttcgagcgcg agggctactc cctggtgggc 900
atcgacccct tccgcctgct gcagaactcc caggtgtact ccctgatccg ccccaacgag 960
aaccccgccc acaagtccca gctggtgtgg atggcctgcc actccgccgc cttcgaggac 1020
ctgcgcgtgt cctccttcat ccgcggcacc cgcgtggtgc cccgcggcaa gctgtccacc 1080
cgcggcgtgc agatcgcctc caacgagaac atggagacca tggactcctc caccctggag 1140
ctgcgctccc gctactgggc catccgcacc cgctccggcg gcaacaccaa ccagcagcgc 1200
gcctccgccg gccagatctc cgtgcagccc accttctccg tgcagcgcaa cctgcccttc 1260
gagcgcgcca ccatcatggc cgccttcacc ggcaacaccg agggccgcac ctccgacatg 1320
cgcaccgaga tcatccgcat gatggagtcc gcccgccccg aggacgtgtc cttccagggc 1380
cgcggcgtgt tcgagctgtc cgacgagaag gccacctccc ccatcgtgcc ctccttcgac 1440
atgtccaacg agggctccta cttcttcggc gacaacgccg aggagtacga caac 1494

<210> SEQ ID NO 57
<211> LENGTH: 498
<212> TYPE: PRT
<213> ORGANISM: Artificial Sequence
<220> FEATURE:
<223> OTHER INFORMATION: 1957 H2N2 - NP antigen Amino Acid sequence

<400> SEQUENCE: 57

Met Ala Ser Gln Gly Thr Lys Arg Ser Tyr Glu Gln Met Glu Thr Asp
1 5 10 15

Gly Glu Arg Gln Asn Ala Thr Glu Ile Arg Ala Ser Val Gly Lys Met
20 25 30

Ile Asp Gly Ile Gly Arg Phe Tyr Ile Gln Met Cys Thr Glu Leu Lys
35 40 45

Leu Ser Asp Tyr Glu Gly Arg Leu Ile Gln Asn Ser Leu Thr Ile Glu
50 55 60

Arg Met Val Leu Ser Ala Phe Asp Glu Arg Arg Asn Lys Tyr Leu Glu
65 70 75 80

Glu His Pro Ser Ala Gly Lys Asp Pro Lys Lys Thr Gly Gly Pro Ile
85 90 95

Tyr Lys Arg Val Asp Gly Lys Trp Met Arg Glu Leu Val Leu Tyr Asp
100 105 110

Lys Glu Glu Ile Arg Arg Ile Trp Arg Gln Ala Asn Asn Gly Asp Asp
115 120 125

Ala Thr Ala Gly Leu Thr His Met Met Ile Trp His Ser Asn Leu Asn
130 135 140

Asp Thr Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Val Gly Thr Met Val Met Glu
180 185 190

Leu Ile Arg Met Ile Lys Arg Gly Ile Asn Asp Arg Asn Phe Trp Arg
195 200 205

```
Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Val Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Ala Phe Ser Val Gln Arg
                405                 410                 415

Asn Leu Pro Phe Asp Lys Pro Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Met Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 58
<211> LENGTH: 1494
<212> TYPE: DNA
<213> ORGANISM: Artificial Sequence
<220> FEATURE:
<223> OTHER INFORMATION: 1957 H2N2 - Optimized DNA sequence encoding the
      nucleic acid sequence encoding NP antigen

<400> SEQUENCE: 58

atggcctccc agggcaccaa gcgctcctac gagcagatgg agaccgacgg cgagcgccag      60

aacgccaccg agatccgcgc ctccgtgggc aagatgatcg acggcatcgg ccgcttctac     120

atccagatgt gcaccgagct gaagctgtcc gactacgagg gccgcctgat ccagaactcc     180

ctgaccatcg agcgcatggt gctgtccgcc ttcgacgagc gccgcaacaa gtacctggag     240

gagcacccct ccgccggcaa ggaccccaag aagaccggcg gccccatcta caagcgcgtg     300

gacggcaagt ggatgcgcga gctggtgctg tacgacaagg aggagatccg ccgcatctgg     360
```

```
cgccaggcca acaacggcga cgacgccacc gccggcctga cccacatgat gatctggcac    420

tccaacctga acgacaccac ctaccagcgc acccgcgccc tggtgcgcac cggcatggac    480

ccccgcatgt gctccctgat gcagggctcc accctgcccc gccgctccgg cgccgccggc    540

gccgccgtga agggcgtggg caccatggtg atggagctga tccgcatgat caagcgcggc    600

atcaacgacc gcaacttctg gcgcggcgag aacggccgca agacccgctc cgcctacgag    660

cgcatgtgca acatcctgaa gggcaagttc cagaccgccg cccagcgcgc catgatggac    720

caggtgcgcg agtcccgcaa ccccggcaac gccgagatcg aggacctgat cttcctggcc    780

cgctccgccc tgatcctgcg cggctccgtg gcccacaagt cctgcctgcc cgcctgcgtg    840

tacggccccg ccgtggcctc cggctacgtg ttcgagaagg agggctactc cctggtgggc    900

atcgacccct tcaagctgct gcagaactcc caggtgtact ccctgatccg ccccaacgag    960

aaccccgccc acaagtccca gctggtgtgg atggcctgca actccgccgc cttcgaggac   1020

ctgcgcgtgc tgtccttcat ccgcggcacc aaggtgtccc cccgcggcaa gctgtccacc   1080

cgcggcgtgc agatcgcctc caacgagaac atggacacca tggagtcctc caccctggag   1140

ctgcgctccc gctactgggc catccgcacc cgctccggcg gcaacaccaa ccagcagcgc   1200

gcctccgccg gccagatctc cgtgcagccc gccttctccg tgcagcgcaa cctgcccttc   1260

gacaagccca ccatcatggc cgccttcacc ggcaacaccg agggccgcac ctccgacatg   1320

cgcgccgaga tcatccgcat gatggagggc gccaagcccg aggagatgtc cttccagggc   1380

cgcggcgtgt tcgagctgtc cgacgagaag gccaccaacc ccatcgtgcc ctccttcgac   1440

atgtccaacg agggctccta cttcttcggc gacaacgccg aggagtacga caac         1494
```

<210> SEQ ID NO 59
<211> LENGTH: 498
<212> TYPE: PRT
<213> ORGANISM: Artificial Sequence
<220> FEATURE:
<223> OTHER INFORMATION: 1968 H3N2 - NP antigen Amino Acid sequence

<400> SEQUENCE: 59

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Arg Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
```

```
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Ala Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Ala Phe Ser Val Gln Arg
                405                 410                 415

Asn Leu Pro Phe Asp Lys Pro Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Met Ser Phe Gln Gly Arg Gly Val Phe
    450                 455                 460

Glu Leu Ser Asp Glu Arg Ala Ala Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 60
<211> LENGTH: 1494
<212> TYPE: DNA
<213> ORGANISM: Artificial Sequence
<220> FEATURE:
<223> OTHER INFORMATION: 1968 H3N2 - Optimized DNA sequence encoding the nucleic acid sequence encoding NP antigen

<400> SEQUENCE: 60

```
atggcctccc agggcaccaa gcgctcctac gagcagatgg agaccgacgg cgagcgccag      60

aacgccaccg agatccgcgc ctccgtgggc aagatgatcg acggcatcgg ccgcttctac     120
```

```
atccagatgt gcaccgagct gaagctgtcc gactacgagg gccgcctgat ccagaactcc    180
ctgaccatcg agcgcatggt gctgtccgcc ttcgacgagc gccgcaacaa gtacctggag    240
gagcacccct ccgccggcaa ggaccccaag aagaccggcg gccccatcta caagcgcgtg    300
gaccgcaagt ggatgcgcga gctggtgctg tacgacaagg aggagatccg ccgcatctgg    360
cgccaggcca acaacggcga cgacgccacc gccggcctga cccacatgat gatctggcac    420
tccaacctga acgacaccac ctaccagcgc acccgcgccc tggtgcgcac cggcatggac    480
ccccgcatgt gctccctgat gcagggctcc accctgcccc gccgctccgg cgccgccggc    540
gccgccgtga agggcgtggg caccatggtg atggagctga tccgcatgat caagcgcggc    600
atcaacgacc gcaacttctg gcgcggcgag aacggccgca agacccgctc cgcctacgag    660
cgcatgtgca acatcctgaa gggcaagttc cagaccgccg cccagcgcgc catgatggac    720
caggtgcgcg agtcccgcaa ccccggcaac gccgagatcg aggacctgat cttcctggcc    780
cgctccgccc tgatcctgcg cggctccgtg gcccacaagt cctgcctgcc cgcctgcgtg    840
tacggccccg ccgtggcctc cggctacgac ttcgagaagg agggctactc cctggtgggc    900
atcgacccct tcaagctgct gcagaactcc caggtgtact ccctgatccg ccccaacgag    960
aaccccgccc acaagtccca gctggtgtgg atggcctgca actccgccgc cttcgaggac   1020
ctgcgcgtgc tgtccttcat ccgcggcacc aaggtgtccc cccgcggcaa gctgtccacc   1080
cgcggcgtgc agatcgcctc caacgagaac atggacgcca tggagtcctc caccctggag   1140
ctgcgctccc gctactgggc catccgcacc cgctccggcg gcaacaccaa ccagcagcgc   1200
gcctccgccg gccagatctc cgtgcagccc gccttctccg tgcagcgcaa cctgcccttc   1260
gacaagccca ccatcatggc cgccttcacc ggcaacaccg agggccgcac ctccgacatg   1320
cgcgccgaga tcatccgcat gatggagggc gccaagcccg aggagatgtc cttccagggc   1380
cgcggcgtgt tcgagctgtc cgacgagcgc gccgccaacc ccatcgtgcc ctccttcgac   1440
atgtccaacg agggctccta cttcttcggc gacaacgccg aggagtacga caac         1494
```

<210> SEQ ID NO 61
<211> LENGTH: 498
<212> TYPE: PRT
<213> ORGANISM: Artificial Sequence
<220> FEATURE:
<223> OTHER INFORMATION: 1977 H1N1 - NP antigen Amino Acid sequence

<400> SEQUENCE: 61

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125
```

```
Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Leu Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asn Phe Glu Lys Glu Gly Tyr Ser Leu Val Gly Ile Asp Pro Phe
    290                 295                 300

Lys Leu Leu Gln Thr Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Ser Ser Phe Ile Arg Gly Thr Lys Val
            340                 345                 350

Ile Pro Arg Gly Lys Leu Ser Thr Arg Gly Val Gln Ile Ala Ser Asn
        355                 360                 365

Glu Asn Met Asp Thr Met Gly Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Lys Thr Thr Ile Met Ala Ala Phe Thr Gly Asn
            420                 425                 430

Ala Glu Gly Arg Thr Ser Asp Met Arg Ala Glu Ile Ile Lys Met Met
        435                 440                 445

Glu Ser Ala Arg Pro Glu Glu Val Ser Phe Gln Gly Arg Gly Val Phe
    450                 455                 460

Glu Leu Ser Asp Glu Arg Ala Ala Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 62
<211> LENGTH: 1494
<212> TYPE: DNA
<213> ORGANISM: Artificial Sequence
<220> FEATURE:
<223> OTHER INFORMATION: 1977 H1N1 - Optimized DNA sequence encoding the nucleic acid sequence encoding NP antigen

<400> SEQUENCE: 62

```
atggcctccc agggcaccaa gcgctcctac gagcagatgg agaccgacgg cgagcgccag     60
aacgccaccg agatccgcgc ctccgtgggc aagatgatcg acggcatcgg ccgcttctac    120
atccagatgt gcaccgagct gaagctgtcc gactacgagg gccgcctgat ccagaactcc    180
ctgaccatcg agcgcatggt gctgtccgcc ttcgacgagc gccgcaacaa gtacctggag    240
gagcacccct ccgccggcaa ggaccccaag aagaccggcg gccccatcta caagcgcgtg    300
gacggcaagt ggatgcgcga gctggtgctg tacgacaagg aggagatccg ccgcatctgg    360
cgccaggcca acaacggcga cgacgccacc gccggcctga cccacatgat gatctggcac    420
tccaacctga acgacaccac ctaccagcgc acccgcgccc tggtgcgcac cggcatggac    480
ccccgcatgt gctccctgat gcagggctcc accctgcccc gccgctccgg cgccgccggc    540
gccgccgtga agggcgtggg caccatggtg ctggagctga tccgcatgat caagcgcggc    600
atcaacgacc gcaacttctg gcgcggcgag aacggccgca agacccgcat cgcctacgag    660
cgcatgtgca acatcctgaa gggcaagttc cagaccgccg cccagcgcgc catgatggac    720
caggtgcgcg agtcccgcaa ccccggcaac gccgagatcg aggacctgat cttcctggcc    780
cgctccgccc tgatcctgcg cggctccgtg gcccacaagt cctgcctgcc cgcctgcgtg    840
tacggccccg ccgtggcctc cggctacaac ttcgagaagg agggctactc cctggtgggc    900
atcgacccct tcaagctgct gcagacctcc caggtgtact ccctgatccg ccccaacgag    960
aaccccgccc acaagtccca gctggtgtgg atggcctgca actccgccgc cttcgaggac   1020
ctgcgcgtgt cctccttcat ccgcggcacc aaggtgatcc cccgcggcaa gctgtccacc   1080
cgcggcgtgc agatcgcctc caacgagaac atggacacca tgggctcctc caccctggag   1140
ctgcgctccc gctactgggc catccgcacc cgctccggcg gcaacaccaa ccagcagcgc   1200
gcctccgccg gccagatctc catccagccc accttctccg tgcagcgcaa cctgcccttc   1260
gacaagacca ccatcatggc cgccttcacc ggcaacgccg agggccgcac ctccgacatg   1320
cgcgccgaga tcatcaagat gatggagtcc gcccgccccg aggaggtgtc cttccagggc   1380
cgcggcgtgt tcgagctgtc cgacgagcgc gccgccaacc ccatcgtgcc ctccttcgac   1440
atgtccaacg agggctccta cttcttcggc gacaacgccg aggagtacga caac         1494
```

<210> SEQ ID NO 63
<211> LENGTH: 498
<212> TYPE: PRT
<213> ORGANISM: Artificial Sequence
<220> FEATURE:
<223> OTHER INFORMATION: 2007 H1N1 - NP antigen Amino Acid sequence

<400> SEQUENCE: 63

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Asn Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80
```

-continued

```
Glu His Pro Ser Ala Gly Lys Asp Pro Lys Lys Thr Gly Gly Pro Ile
                85                  90                  95

Tyr Lys Arg Val Asp Gly Lys Trp Val Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Ile Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Leu Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Ile Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Val Asp Pro Phe
    290                 295                 300

Lys Leu Leu Gln Thr Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Ser Ser Phe Ile Arg Gly Thr Arg Val
            340                 345                 350

Leu Pro Arg Gly Lys Leu Ser Thr Arg Gly Val Gln Ile Ala Ser Asn
        355                 360                 365

Glu Asn Met Asp Ala Ile Val Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Thr Gln Pro Thr Phe Ser Val Gln Arg
                405                 410                 415

Asn Leu Pro Phe Asp Lys Ala Thr Ile Met Ala Ala Phe Ser Gly Asn
            420                 425                 430

Thr Glu Gly Arg Thr Ser Asp Met Arg Ala Glu Ile Ile Lys Met Met
        435                 440                 445

Glu Ser Ala Arg Pro Glu Glu Val Ser Phe Gln Gly Arg Gly Val Phe
    450                 455                 460

Glu Leu Ser Asp Glu Arg Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 64
<211> LENGTH: 1494
<212> TYPE: DNA
<213> ORGANISM: Artificial Sequence
<220> FEATURE:
<223> OTHER INFORMATION: 2007 H1N1 - Optimized DNA sequence encoding the nucleic acid sequence encoding NP antigen

<400> SEQUENCE: 64
atggcctccc agggcaccaa gcgctcctac gagcagatgg agaccgacgg cgagcgccag 60
aacgccaccg agatccgcgc ctccgtgggc cgcatgatcg gcggcatcgg ccgcttctac 120
atccagatgt gcaccgagct gaagctgaac gactacgagg gccgcctgat ccagaactcc 180
ctgaccatcg agcgcatggt gctgtccgcc ttcgacgagc gccgcaacaa gtacctggag 240
gagcacccct ccgccggcaa ggaccccaag aagaccggcg gccccatcta caagcgcgtg 300
gacggcaagt gggtgcgcga gctggtgctg tacgacaagg aggagatccg ccgcatctgg 360
cgccaggcca acaacggcga cgacgccacc gccggcctga cccacatcat gatctggcac 420
tccaacctga acgacaccac ctaccagcgc acccgcgccc tggtgcgcac cggcatggac 480
ccccgcatgt gctccctgat gcagggctcc accctgcccc gccgctccgg cgccgccggc 540
gccgccgtga agggcgtggg caccatggtg ctggagctga tccgcatgat caagcgcggc 600
atcaacgacc gcaacttctg gcgcggcgag aacggccgca agacccgcat cgcctacgag 660
cgcatgtgca acatcctgaa gggcaagttc cagaccgccg cccagaaggc catgatggac 720
caggtgcgcg agtcccgcaa ccccggcaac gccgagatcg aggacctgac cttcctggcc 780
cgctccgccc tgatcctgcg cggctccgtg gcccacaagt cctgcctgcc cgcctgcgtg 840
tacggccccg ccgtggcctc cggctacgac ttcgagaagg agggctactc cctggtgggc 900
gtggacccct tcaagctgct gcagacctcc caggtgtact ccctgatccg ccccaacgag 960
aaccccgccc acaagtccca gctggtgtgg atggcctgca actccgccgc cttcgaggac 1020
ctgcgcgtgt cctccttcat ccgcggcacc cgcgtgctgc ccgcgcggcaa gctgtccacc 1080 cgcggcgtgc agatcgcctc caacgagaac atggacgcca tcgtgtcctc caccctggag 1140
ctgcgctccc gctactgggc catccgcacc cgctccggcg gcaacaccaa ccagcagcgc 1200
gcctccgccg gccagatctc cacccagccc accttctccg tgcagcgcaa cctgcccttc 1260
gacaaggcca ccatcatggc cgccttctcc ggcaacaccg agggccgcac ctccgacatg 1320
cgcgccgaga tcatcaagat gatggagtcc gcccgccccg aggaggtgtc cttccagggc 1380
cgcggcgtgt tcgagctgtc cgacgagcgc gccaccaacc ccatcgtgcc ctccttcgac 1440
atgtccaacg agggctccta cttcttcggc gacaacgccg aggagtacga caac 1494

<210> SEQ ID NO 65
<211> LENGTH: 498
<212> TYPE: PRT
<213> ORGANISM: Artificial Sequence
<220> FEATURE:
<223> OTHER INFORMATION: 2009 H1N1 - NP antigen Amino Acid sequence

<400> SEQUENCE: 65

Met Ala Ser Gln Gly Thr Lys Arg Ser Tyr Glu Gln Met Glu Thr Gly
1 5 10 15

Gly Glu Arg Gln Asp Ala Thr Glu Ile Arg Ala Ser Val Gly Arg Met
20 25 30

Ile Gly Gly Ile Gly Arg Phe Tyr Ile Gln Met Cys Thr Glu Leu Lys

```
        35                  40                  45

Leu Ser Asp Tyr Asp Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Ile Leu Tyr Asp
            100                 105                 110

Lys Glu Glu Ile Arg Arg Val Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Ile Ala Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Val Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
    290                 295                 300

Lys Leu Leu Gln Asn Ser Gln Val Val Ser Leu Met Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Lys Lys Val
            340                 345                 350

Ile Pro Arg Gly Lys Leu Ser Thr Arg Gly Val Gln Ile Ala Ser Asn
        355                 360                 365

Glu Asn Val Glu Thr Met Asp Ser Asn Thr Leu Glu Leu Arg Ser Arg
    370                 375                 380

Tyr Trp Ala Ile Arg Thr Arg Ser Gly Gly Asn Thr Asn Gln Gln Lys
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Val Met Ala Ala Phe Ser Gly Asn
            420                 425                 430

Asn Glu Gly Arg Thr Ser Asp Met Arg Thr Glu Val Ile Arg Met Met
        435                 440                 445

Glu Ser Ala Lys Pro Glu Asp Leu Ser Phe Gln Gly Arg Gly Val Phe
    450                 455                 460
```

Glu Leu Ser Asp Glu Lys Ala Thr Asn Pro Ile Val Pro Ser Phe Asp
465 470 475 480

Met Ser Asn Glu Gly Ser Tyr Phe Phe Gly Asp Asn Ala Glu Glu Tyr
485 490 495

Asp Ser

<210> SEQ ID NO 66
<211> LENGTH: 1494
<212> TYPE: DNA
<213> ORGANISM: Artificial Sequence
<220> FEATURE:
<223> OTHER INFORMATION: 2009 H1N1 - Optimized DNA sequence encoding the nucleic acid sequence encoding NP antigen

<400> SEQUENCE: 66
atggcctccc agggcaccaa gcgctcctac gagcagatgg agaccggcgg cgagcgccag 60
gacgccaccg agatccgcgc ctccgtgggc cgcatgatcg gcggcatcgg ccgcttctac 120
atccagatgt gcaccgagct gaagctgtcc gactacgacg gccgcctgat ccagaactcc 180
atcaccatcg agcgcatggt gctgtccgcc ttcgacgagc gccgcaacaa gtacctggag 240
gagcacccct ccgccggcaa ggaccccaag aagaccggcg gccccatcta ccgccgcgtg 300
gacggcaagt ggatgcgcga gctgatcctg tacgacaagg aggagatccg ccgcgtgtgg 360
cgccaggcca acaacggcga ggacgccacc gccggcctga cccacatcat gatctggcac 420
tccaacctga acgacgccac ctaccagcgc acccgcgccc tggtgcgcac cggcatggac 480
ccccgcatgt gctccctgat gcagggctcc accctgcccc gccgctccgg cgccgccggc 540
gccgccgtga agggcgtggg caccatcgcc atggagctga tccgcatgat caagcgcggc 600
atcaacgacc gcaacttctg gcgcggcgag aacggccgcc gcacccgcgt ggcctacgag 660
cgcatgtgca acatcctgaa gggcaagttc cagaccgccg cccagcgcgc catgatggac 720
caggtgcgcg agtcccgcaa ccccggcaac gccgagatcg aggacctgat cttcctggcc 780
cgctccgccc tgatcctgcg cggctccgtg gcccacaagt cctgcctgcc cgcctgcgtg 840
tacggcctgg ccgtggcctc cggccacgac ttcgagcgcg agggctactc cctggtgggc 900
atcgacccct tcaagctgct gcagaactcc caggtggtgt ccctgatgcg ccccaacgag 960
aaccccgccc acaagtccca gctggtgtgg atggcctgcc actccgccgc cttcgaggac 1020
ctgcgcgtgt cctccttcat ccgcggcaag aaggtgatcc cccgcggcaa gctgtccacc 1080
cgcggcgtgc agatcgcctc caacgagaac gtggagacca tggactccaa caccctggag 1140
ctgcgctccc gctactgggc catccgcacc cgctccggcg gcaacaccaa ccagcagaag 1200
gcctccgccg gccagatctc cgtgcagccc accttctccg tgcagcgcaa cctgcccttc 1260
gagcgcgcca ccgtgatggc cgccttctcc ggcaacaacg agggccgcac ctccgacatg 1320
cgcaccgagg tgatccgcat gatggagtcc gccaagcccg aggacctgtc cttccagggc 1380
cgcggcgtgt tcgagctgtc cgacgagaag gccaccaacc ccatcgtgcc ctccttcgac 1440
atgtccaacg agggctccta cttcttcggc gacaacgccg aggagtacga ctcc 1494

<210> SEQ ID NO 67
<211> LENGTH: 498
<212> TYPE: PRT
<213> ORGANISM: Artificial Sequence
<220> FEATURE:
<223> OTHER INFORMATION: 2015 H1N1 - NP antigen Amino Acid sequence

<400> SEQUENCE: 67

```
Met Ala Ser Gln Gly Thr Lys Arg Ser Tyr Glu Gln Met Glu Thr Gly
1               5                   10                  15

Gly Glu Arg Gln Asp Thr Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Asp Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Ile Asp Gly Lys Trp Thr Arg Glu Leu Ile Leu Tyr Asp
            100                 105                 110

Lys Glu Glu Ile Arg Arg Val Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Ile Ala Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Val Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
    290                 295                 300

Lys Leu Leu Gln Asn Ser Gln Val Val Ser Leu Met Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Lys Lys Val
            340                 345                 350

Ile Pro Arg Gly Lys Leu Ser Thr Arg Gly Val Gln Ile Ala Ser Asn
        355                 360                 365

Glu Asn Val Glu Thr Met Asp Ser Asn Thr Leu Glu Leu Arg Ser Arg
    370                 375                 380

Tyr Trp Ala Ile Arg Thr Arg Ser Gly Gly Asn Thr Asn Gln Gln Lys
385                 390                 395                 400

Ala Ser Ala Gly Gln Ile Ser Val Gln Pro Thr Phe Ser Val Gln Arg
                405                 410                 415
```

```
Asn Leu Pro Phe Glu Arg Ala Thr Val Met Ala Ala Phe Ser Gly Asn
            420                 425                 430

Asn Glu Gly Arg Thr Ser Asp Met Arg Thr Glu Val Ile Arg Met Met
        435                 440                 445

Glu Ser Ala Lys Pro Glu Asp Leu Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 68
<211> LENGTH: 1494
<212> TYPE: DNA
<213> ORGANISM: Artificial Sequence
<220> FEATURE:
<223> OTHER INFORMATION: 2015 H1N1 - Optimized DNA sequence encoding the
      nucleic acid sequence encoding NP antigen

<400> SEQUENCE: 68

atggcctccc agggcaccaa gcgctcctac gagcagatgg agaccggcgg cgagcgccag      60

gacaccaccg agatccgcgc ctccgtgggc cgcatgatcg gcggcatcgg ccgcttctac     120

atccagatgt gcaccgagct gaagctgtcc gactacgacg gccgcctgat ccagaactcc     180

atcaccatcg agcgcatggt gctgtccgcc ttcgacgagc gccgcaacaa gtacctggag     240

gagcacccct ccgccggcaa ggaccccaag aagaccggcg gccccatcta ccgccgcatc     300

gacggcaagt ggacccgcga gctgatcctg tacgacaagg aggagatccg ccgcgtgtgg     360

cgccaggcca acaacggcga ggacgccacc gccggcctga cccacatcat gatctggcac     420

tccaacctga acgacgccac ctaccagcgc acccgcgccc tggtgcgcac cggcatggac     480

ccccgcatgt gctccctgat gcagggctcc accctgcccc gccgctccgg cgccgccggc     540

gccgccgtga agggcgtggg caccatcgcc atggagctga tccgcatgat caagcgcggc     600

atcaacgacc gcaacttctg gcgcggcgag aacggccgcc gcacccgcgt ggcctacgag     660

cgcatgtgca acatcctgaa gggcaagttc cagaccgccg cccagcgcgc catgatggac     720

caggtgcgcg agtcccgcaa ccccggcaac gccgagatcg aggacctgat cttcctggcc     780

cgctccgccc tgatcctgcg cggctccgtg gcccacaagt cctgcctgcc cgcctgcgtg     840

tacggcctgg ccgtggcctc cggccacgac ttcgagcgcg agggctactc cctggtgggc     900

atcgacccct tcaagctgct gcagaactcc caggtggtgt ccctgatgcg ccccaacgag     960

aaccccgccc acaagtccca gctggtgtgg atggcctgcc actccgccgc cttcgaggac    1020

ctgcgcgtgt cctccttcat ccgcggcaag aaggtgatcc cccgcggcaa gctgtccacc    1080

cgcggcgtgc agatcgcctc caacgagaac gtggagacca tggactccaa caccctggag    1140

ctgcgctccc gctactgggc catccgcacc cgctccggcg gcaacaccaa ccagcagaag    1200

gcctccgccg gccagatctc cgtgcagccc accttctccg tgcagcgcaa cctgcccttc    1260

gagcgcgcca ccgtgatggc cgccttctcc ggcaacaacg agggccgcac ctccgacatg    1320

cgcaccgagg tgatccgcat gatggagtcc gccaagcccg aggacctgtc cttccagggc    1380

cgcggcgtgt tcgagctgtc cgacgagaag gccaccaacc ccatcgtgcc ctccttcgac    1440

atgtccaacg agggctccta cttcttcggc gacaacgccg aggagtacga caac          1494
```

```
<210> SEQ ID NO 69
<211> LENGTH: 498
<212> TYPE: PRT
<213> ORGANISM: Artificial Sequence
<220> FEATURE:
<223> OTHER INFORMATION: 2017 H3N2 - NP antigen Amino Acid sequence
<220> FEATURE:
<221> NAME/KEY: misc_feature
<222> LOCATION: (102)..(102)
<223> OTHER INFORMATION: Xaa can be any naturally occurring amino acid

<400> SEQUENCE: 69

Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp His Glu Gly Arg Leu Ile Gln Asn Ser Leu Thr Ile Glu
    50                  55                  60

Lys Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Xaa Lys Trp Met Arg Glu Leu Val Leu Tyr Asp
            100                 105                 110

Lys Glu Glu Ile Arg Arg Ile Trp Arg Gln Ala Asn Asn Gly Glu Asp
        115                 120                 125

Ala Thr Ser Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ala Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350
```

-continued

```
Ser Pro Arg Gly Lys Leu Ser Thr Arg Gly Val Gln Ile Ala Ser Asn
        355                 360                 365

Glu Asn Met Asp Asn Met Gly Ser Ser Thr Leu Glu Leu Arg Ser Gly
    370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Ala Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 70
<211> LENGTH: 1494
<212> TYPE: DNA
<213> ORGANISM: Artificial Sequence
<220> FEATURE:
<223> OTHER INFORMATION: 2017 H3N2 - Optimized DNA sequence encoding the
      nucleic acid sequence encoding NP antigen
<220> FEATURE:
<221> NAME/KEY: misc_feature
<222> LOCATION: (304)..(306)
<223> OTHER INFORMATION: any nucleotide

<400> SEQUENCE: 70

atggcctccc agggcaccaa gcgctcctac gagcagatgg agaccgacgg cgaccgccag      60

aacgccaccg agatccgcgc ctccgtgggc aagatgatcg acggcatcgg ccgcttctac     120

atccagatgt gcaccgagct gaagctgtcc gaccacgagg gccgcctgat ccagaactcc     180

ctgaccatcg agaagatggt gctgtccgcc ttcgacgagc gccgcaacaa gtacctggag     240

gagcacccct ccgccggcaa ggaccccaag aagaccggcg gccccatcta ccgccgcgtg     300

gacnnnaagt ggatgcgcga gctggtgctg tacgacaagg aggagatccg ccgcatctgg     360

cgccaggcca acaacggcga ggacgccacc tccggcctga cccacatcat gatctggcac     420

tccaacctga acgacgccac ctaccagcgc acccgcgccc tggtgcgcac cggcatggac     480

ccccgcatgt gctccctgat gcagggctcc accctgcccc gccgctccgg cgccgccggc     540

gccgccgtga agggcatcgg caccatggtg atggagctga tccgcatggt gaagcgcggc     600

atcaacgacc gcaacttctg gcgcggcgag aacggccgca agacccgctc cgcctacgag     660

cgcatgtgca acatcctgaa gggcaagttc cagaccgccg cccagcgcgc catggtggac     720

caggtgcgcg agtcccgcaa ccccggcaac gccgagatcg aggacctgat cttcctggcc     780

cgctccgccc tgatcctgcg cggctccgtg gcccacaagt cctgcctgcc cgcctgcgcc     840

tacggccccg ccgtgtcctc cggctacgac ttcgagaagg agggctactc cctggtgggc     900

atcgacccct tcaagctgct gcagaactcc cagatctact ccctgatccg ccccaacgag     960

aaccccgccc acaagtccca gctggtgtgg atggcctgcc actccgccgc cttcgaggac    1020

ctgcgcctgc tgtccttcat ccgcggcacc aaggtgtccc cccgcggcaa gctgtccacc    1080
```

cgcggcgtgc agatcgcctc caacgagaac atggacaaca tgggctcctc caccctggag 1140
ctgcgctccg gctactgggc catccgcacc cgctccggcg gcaacaccaa ccagcagcgc 1200
gcctccgccg gccagacctc cgtgcagccc accttctccg tgcagcgcaa cctgcccttc 1260
gagaagtcca ccatcatggc cgccttcacc ggcaacaccg agggccgcac ctccgacatg 1320
cgcgccgaga tcatccgcat gatggagggc gccaagcccg aggaggtgtc cttccgcggc 1380
cgcggcgtgt tcgagctgtc cgacgagaag gccgccaacc ccatcgtgcc ctccttcgac 1440
atgtccaacg agggctccta cttcttcggc gacaacgccg aggagtacga caac 1494

<210> SEQ ID NO 71
<211> LENGTH: 560
<212> TYPE: PRT
<213> ORGANISM: Artificial Sequence
<220> FEATURE:
<223> OTHER INFORMATION: 2017 Influenza B (Victoria lineage) - NP antigen Amino Acid sequence.

<400> SEQUENCE: 71

Met Ser Asn Met Asp Ile Asp Gly Met Asn Thr Gly Thr Ile Asp Lys
1 5 10 15

Thr Pro Glu Glu Ile Thr Ser Gly Thr Ser Gly Thr Thr Arg Pro Ile
20 25 30

Ile Arg Pro Ala Thr Leu Ala Pro Pro Ser Asn Lys Arg Thr Arg Asn
35 40 45

Pro Ser Pro Glu Arg Ala Thr Thr Ser Ser Glu Asp Asp Val Gly Arg
50 55 60

Lys Ala Gln Lys Lys Gln Thr Pro Thr Glu Ile Lys Lys Ser Val Tyr
65 70 75 80

Asn Met Val Val Lys Leu Gly Glu Phe Tyr Asn Gln Met Met Val Lys
85 90 95

Ala Gly Leu Asn Asp Asp Met Glu Arg Asn Leu Ile Gln Asn Ala His
100 105 110

Ala Val Glu Arg Ile Leu Leu Ala Ala Thr Asp Asp Lys Lys Thr Glu
115 120 125

Phe Gln Lys Lys Lys Asn Ala Arg Asp Val Lys Glu Gly Lys Glu Glu
130 135 140

Ile Asp His Asn Lys Thr Gly Gly Thr Phe Tyr Lys Met Val Arg Asp
145 150 155 160

Asp Lys Thr Ile Tyr Phe Ser Pro Ile Arg Ile Thr Phe Leu Lys Glu
165 170 175

Glu Val Lys Thr Met Tyr Lys Thr Thr Met Gly Ser Asp Gly Phe Ser
180 185 190

Gly Leu Asn His Ile Met Ile Gly His Ser Gln Met Asn Asp Val Cys
195 200 205

Phe Gln Arg Ser Lys Ala Leu Lys Arg Val Gly Leu Asp Pro Ser Leu
210 215 220

Ile Ser Thr Phe Ala Gly Ser Thr Val Pro Arg Arg Ser Gly Ala Thr
225 230 235 240

Gly Val Ala Ile Lys Gly Gly Gly Thr Leu Val Ala Glu Ala Ile Arg
245 250 255

Phe Ile Gly Arg Ala Met Ala Asp Arg Gly Leu Leu Arg Asp Ile Lys
260 265 270

Ala Lys Thr Ala Tyr Glu Lys Ile Leu Leu Asn Leu Lys Asn Lys Cys
275 280 285

```
Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
        515                 520                 525

Asn Lys Thr Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560
```

<210> SEQ ID NO 72
<211> LENGTH: 1680
<212> TYPE: DNA
<213> ORGANISM: Artificial Sequence
<220> FEATURE:
<223> OTHER INFORMATION: 2017 Influenza B (Victoria lineage) - Optimized DNA sequence encoding the nucleic acid sequence encoding NP antigen

<400> SEQUENCE: 72

```
atgtccaaca tggacatcga cggcatgaac accggcacca tcgacaagac ccccgaggag      60

atcacctccg gcacctccgg caccacccgc cccatcatcc gccccgccac cctggccccc     120

ccctccaaca agcgcacccg caacccctcc cccgagcgcg ccaccacctc ctccgaggac     180

gacgtgggcc gcaaggccca gaagaagcag acccccaccg agatcaagaa gtccgtgtac     240

aacatggtgg tgaagctggg cgagttctac aaccagatga tggtgaaggc cggcctgaac     300

gacgacatgg agcgcaacct gatccagaac gcccacgccg tggagcgcat cctgctggcc     360

gccaccgacg acaagaagac cgagttccag aagaagaaga acgcccgcga cgtgaaggag     420

ggcaaggagg agatcgacca caacaagacc ggcggcacct tctacaagat ggtgcgcgac     480
```

```
gacaagacca tctacttctc ccccatccgc atcaccttcc tgaaggagga ggtgaagacc    540

atgtacaaga ccaccatggg ctccgacggc ttctccggcc tgaaccacat catgatcggc    600

cactcccaga tgaacgacgt gtgcttccag cgctccaagg ccctgaagcg cgtgggcctg    660

gacccctccc tgatctccac cttcgccggc tccaccgtgc cccgccgctc cggcgccacc    720

ggcgtggcca tcaagggcgg cggcaccctg gtggccgagg ccatccgctt catcggccgc    780

gccatggccg accgcggcct gctgcgcgac atcaaggcca agaccgccta cgagaagatc    840

ctgctgaacc tgaagaacaa gtgctccgcc ccccagcaga aggccctggt ggaccaggtg    900

atcggctccc gcaaccccgg catcgccgac atcgaggacc tgaccctgct ggcccgctcc    960

atggtggtgg tgcgcccctc cgtggcctcc aaggtggtgc tgcccatctc catctacgcc   1020

aagatccccc agctgggctt caacgtggag gagtactcca tggtgggcta cgaggccatg   1080

gccctgtaca acatggccac ccccgtgtcc atcctgcgca tgggcgacga cgccaaggac   1140

aagtcccagc tgttcttcat gtcctgcttc ggcgccgcct acgaggacct gcgcgtgctg   1200

tccgccctga ccggcaccga gttcaagccc cgctccgccc tgaagtgcaa gggcttccac   1260

gtgcccgcca aggagcaggt ggagggcatg ggcgccgccc tgatgtccat caagctgcag   1320

ttctgggccc ccatgacccg ctccggcggc aacgaggtgg gcggcgacgg cggctccggc   1380

cagatctcct gctcccccgt gttcgccgtg gagcgcccca tcgccctgtc caagcaggcc   1440

gtgcgccgca tgctgtccat gaacatcgag ggccgcgacg ccgacgtgaa gggcaacctg   1500

ctgaagatga tgaacgactc catggccaag aagacctccg gcaacgcctt catcggcaag   1560

aagatgttcc agatctccga caagaacaag accaacccca tcgagatccc catcaagcag   1620

accatcccca acttcttctt cggccgcgac accgccgagg actacgacga cctggactac   1680
```

<210> SEQ ID NO 73
<211> LENGTH: 560
<212> TYPE: PRT
<213> ORGANISM: Artificial Sequence
<220> FEATURE:
<223> OTHER INFORMATION: 2013 Influenza B (Yamagata lineage) - Sequence only on GISAID - NP antigen Amino Acid sequence

<400> SEQUENCE: 73

```
Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Asp Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala Tyr
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140
```

```
Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Val Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Ala Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
        515                 520                 525

Asn Lys Thr Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560
```

<210> SEQ ID NO 74
<211> LENGTH: 1680
<212> TYPE: DNA
<213> ORGANISM: Artificial Sequence
<220> FEATURE:
<223> OTHER INFORMATION: 2013 Influenza B (Yamagata lineage) - Sequence only on GISAID - Optimized DNA sequence encoding the nucleic acid sequence encoding NP antigen

<400> SEQUENCE: 74

```
atgtccaaca tggacatcga cggcatcaac accggcacca tcgacaagac ccccgaggag     60

atcacctccg gcacctccgg caccacccgc cccatcatcc gccccgccac cctggccccc    120

ccctccaaca agcgcacccg caacccctcc cccgagcgcg ccaccacctc ctccgaggac    180

gacgtgggcc gcaagaccca gaagaagcag acccccaccg agatcaagaa gtccgtgtac    240

aacatggtgg tgaagctggg cgagttctac aaccagatga tggtgaaggc cggcctgaac    300

gacgacatgg agcgcaacct gatccagaac gcctacgccg tggagcgcat cctgctggcc    360

gccaccgacg acaagaagac cgagttccag aagaagaaga acgcccgcga cgtgaaggag    420

ggcaaggagg agatcgacca caacaagacc ggcggcacct tctacaagat ggtgcgcgac    480

gacaagacca tctacttctc ccccatccgc atcaccttcc tgaaggagga ggtgaagacc    540

atgtacaaga ccaccatggg ctccgacggc ttctccggcc tgaaccacat catgatcggc    600

cactcccaga tgaacgacgt gtgcttccag cgctccaagg ccctgaagcg cgtgggcctg    660

gacccctccc tgatctccac cttcgccggc tccaccgtgc ccgccgctc  cggcgccacc    720

ggcgtggcca tcaagggcgg cggcaccctg gtggccgagg ccatccgctt catcggccgc    780

gccatggccg accgcggcct gctgcgcgac atcaaggcca agaccgccta cgagaagatc    840

ctgctgaacc tgaagaacaa gtgctccgcc ccccagcaga aggccctggt ggaccaggtg    900

atcggctccc gcaaccccgg catcgccgac atcgaggacc tgaccctgct ggcccgctcc    960

atggtggtgg tgcgcccctc cgtggcctcc aaggtggtgc tgcccatctc catctacgcc   1020

aagatccccc agctgggctt caacgtggag gagtactcca tggtgggcta cgaggccatg   1080

gccctgtaca acatggccac ccccgtgtcc atcctgcgca tgggcgacga cgccaaggac   1140

aagtcccagc tgttcttcat gtcctgcttc ggcgccgcct acgaggacct gcgcgtgctg   1200

tccgccctga ccggcaccga gttcaagccc cgctccgccc tgaagtgcaa gggcttccac   1260

gtgcccgcca aggagcaggt ggagggcatg ggcgccgccc tgatgtccat caagctgcag   1320

ttctgggccc ccatgacccg ctccggcggc aacgaggccg gcggcgacgg cggctccggc   1380

cagatctcct gctcccccgt gttcgccgtg gagcgcccca tcgccctgtc caagcaggcc   1440

gtgcgccgca tgctgtccat gaacatcgag ggccgcgacg ccgacgtgaa gggcaacctg   1500

ctgaagatga tgaacgactc catggccaag aagacctccg gcaacgcctt catcggcaag   1560

aagatgttcc agatctccga caagaacaag accaacccca tcgagatccc catcaagcag   1620

accatcccca acttcttctt cggccgcgac accgccgagg actacgacga cctggactac   1680
```

<210> SEQ ID NO 75
<211> LENGTH: 498
<212> TYPE: PRT
<213> ORGANISM: Artificial Sequence
<220> FEATURE:
<223> OTHER INFORMATION: 2015 H5N1 - NP antigen Amino Acid sequence

<400> SEQUENCE: 75

```
Met Ala Ser Gln Gly Thr Lys Arg Ser Tyr Glu Gln Met Glu Thr Gly
1               5                   10                  15
```

```
Gly Glu Arg Gln Asn Ala Thr Glu Ile Arg Ala Ser Val Gly Arg Met
            20                  25                  30

Val Ser Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Ile Pro Arg Gly Gln Leu Ser Thr Arg Gly Val Gln Ile Ala Ser Asn
        355                 360                 365

Glu Asn Met Glu Ala Met Asp Ser Asn Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Glu Arg Ala Thr Ile Met Ala Ala Phe Thr Gly Asn
            420                 425                 430
```

-continued

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu Tyr
                485                 490                 495

Asp Asn

<210> SEQ ID NO 76
<211> LENGTH: 1494
<212> TYPE: DNA
<213> ORGANISM: Artificial Sequence
<220> FEATURE:
<223> OTHER INFORMATION: 2015 H5N1 - Optimized DNA sequence encoding the nucleic acid sequence encoding NP antigen

<400> SEQUENCE: 76
atggcctccc agggcaccaa gcgctcctac gagcagatgg agaccggcgg cgagcgccag 60
aacgccaccg agatccgcgc ctccgtgggc cgcatggtgt ccggcatcgg ccgcttctac 120
atccagatgt gcaccgagct gaagctgtcc gactacgagg gccgcctgat ccagaactcc 180
atcaccatcg agcgcatggt gctgtccgcc ttcgacgagc gccgcaaccg ctacctggag 240
gagcacccct ccgccggcaa ggaccccaag aagaccggcg gccccatcta ccgccgccgc 300
gacggcaagt gggtgcgcga gctgatcctg tacgacaagg aggagatccg ccgcatctgg 360
cgccaggcca acaacggcga ggacgccacc gccggcctga cccacctgat gatctggcac 420
tccaacctga acgacgccac ctaccagcgc acccgcgccc tggtgcgcac cggcatggac 480
ccccgcatgt gctccctgat gcagggctcc accctgcccc gccgctccgg cgccgccggc 540
gccgccgtga agggcgtggg caccatggtg atggagctga tccgcatgat caagcgcggc 600
atcaacgacc gcaacttctg gcgcggcgag aacggccgcc gcacccgcat cgcctacgag 660
cgcatgtgca acatcctgaa gggcaagttc cagaccgccg cccagcgcgc catgatggac 720
caggtgcgcg agtcccgcaa ccccggcaac gccgagatcg aggacctgat cttcctggcc 780
cgctccgccc tgatcctgcg cggctccgtg gcccacaagt cctgcctgcc cgcctgcgtg 840
tacggcctgg ccgtggcctc cggctacgac ttcgagcgcg agggctactc cctggtgggc 900
atcgacccct tccgcctgct gcagaactcc caggtgttct ccctgatccg ccccaacgag 960
aaccccgccc acaagtccca gctggtgtgg atggcctgcc actccgccgc cttcgaggac 1020
ctgcgcgtgt cctccttcat ccgcggcacc cgcgtgatcc cccgcggcca gctgtccacc 1080
cgcggcgtgc agatcgcctc caacgagaac atggaggcca tggactccaa caccctggag 1140
ctgcgctccc gctactgggc catccgcacc cgctccggcg gcaacaccaa ccagcagcgc 1200
gcctccgccg gccagatctc catccagccc accttctccg tgcagcgcaa cctgcccttc 1260
gagcgcgcca ccatcatggc cgccttcacc ggcaacaccg agggccgcac ctccgacatg 1320
cgcaccgaga tcatccgcat gatggagtcc gcccgccccg aggacgtgtc cttccagggc 1380
cgcggcgtgt tcgagctgtc cgacgagaag gccaccaacc ccatcgtgcc ctccttcgac 1440
atgaacaacg agggctccta cttcttcggc gacaacgccg aggagtacga caac 1494

<210> SEQ ID NO 77
<211> LENGTH: 498
<212> TYPE: PRT

<213> ORGANISM: Artificial Sequence
<220> FEATURE:
<223> OTHER INFORMATION: 2017 H7N9 - NP antigen Amino Acid sequence
<220> FEATURE:
<221> NAME/KEY: misc_feature
<222> LOCATION: (272)..(272)
<223> OTHER INFORMATION: Xaa can be any naturally occurring amino acid

<400> SEQUENCE: 77

```
Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Ser Gly Ile Gly Arg Phe Tyr Ile Gln Met Cys Thr Glu Leu Lys
        35                  40                  45

Leu Ser Asp Asn Glu Gly Arg Leu Ile Gln Asn Ser Ile Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ser Gly Lys Asp Pro Lys Lys Thr Gly Gly Pro Ile
                85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala Xaa
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Lys Gly Thr Lys Met
            340                 345                 350

Val Pro Arg Gly Gln Leu Ser Thr Arg Gly Val Gln Ile Ala Ser Asn
        355                 360                 365
```

```
Glu Asn Met Glu Ala Met Asp Ser Asn Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Val Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu Tyr
                485                 490                 495

Asp Asn
```

<210> SEQ ID NO 78
<211> LENGTH: 1494
<212> TYPE: DNA
<213> ORGANISM: Artificial Sequence
<220> FEATURE:
<223> OTHER INFORMATION: 2017 H7N9 - Optimized DNA sequence encoding the nucleic acid sequence encoding NP antigen
<220> FEATURE:
<221> NAME/KEY: misc_feature
<222> LOCATION: (814)..(816)
<223> OTHER INFORMATION: any nucleotide

<400> SEQUENCE: 78

```
atggcctccc agggcaccaa gcgctcctac gagcagatgg agaccggcgg cgagcgccag     60

aacgccaccg agatccgcgc ctccgtgggc cgcatggtgt ccggcatcgg ccgcttctac    120

atccagatgt gcaccgagct gaagctgtcc gacaacgagg gccgcctgat ccagaactcc    180

atcaccatcg agcgcatggt gctgtccgcc ttcgacgagc gccgcaaccg ctacctggag    240

gagcacccct cctccggcaa ggaccccaag aagaccggcg gccccatcta ccgccgccgc    300

gacggcaagt gggtgcgcga gctgatcctg tacgacaagg aggagatccg ccgcatctgg    360

cgccaggcca acaacggcga ggacgccacc gccggcctga cccacctgat gatctggcac    420

tccaacctga acgacgccac ctaccagcgc acccgcgccc tggtgcgcac cggcatggac    480

ccccgcatgt gctccctgat gcagggctcc accctgcccc gccgctccgg cgccgccggc    540

gccgccgtga agggcatcgg caccatggtg atggagctgg tgcgcatgat caagcgcggc    600

atcaacgacc gcaacttctg gcgcggcgag aacggccgcc gcacccgcat cgcctacgag    660

cgcatgtgca acatcctgaa gggcaagttc cagaccgccg cccagcgcgc catgatggac    720

caggtgcgcg agtcccgcaa ccccggcaac gccgagatcg aggacctgat cttcctggcc    780

cgctccgccc tgatcctgcg cggctccgtg gccnnnaagt cctgcctgcc cgcctgcgtg    840

tacggcctgg ccgtggcctc cggctacgac ttcgagcgcg agggctactc cctggtgggc    900

atcgacccct tccgcctgct gcagaactcc caggtgttct ccctgatccg ccccaacgag    960

aaccccgccc acaagtccca gctggtgtgg atggcctgcc actccgccgc cttcgaggac   1020

ctgcgcgtgt cctccttcat caagggcacc aagatggtgc cccgcggcca gctgtccacc   1080

cgcggcgtgc agatcgcctc caacgagaac atggaggcca tggactccaa caccctggag   1140
```

```
ctgcgctccc gctactgggc catccgcacc cgctccggcg gcaacaccaa ccagcagcgc   1200

gcctccgccg gccaggtgtc cgtgcagccc accttctccg tgcagcgcaa cctgcccttc   1260

gagcgcgcca ccatcatggc cgccttcacc ggcaacaccg agggccgcac ctccgacatg   1320

cgcaccgaga tcatccgcat gatggagtcc gcccgccccg aggacgtgtc cttccagggc   1380

cgcggcgtgt tcgagctgtc cgacgagaag gccaccaacc ccatcgtgcc ctccttcgac   1440

atgaacaacg agggctccta cttcttcggc gacaacgccg aggagtacga caac         1494
```

<210> SEQ ID NO 79
<211> LENGTH: 498
<212> TYPE: PRT
<213> ORGANISM: Artificial Sequence
<220> FEATURE:
<223> OTHER INFORMATION: 2013 H10N8 - NP antigen Amino Acid sequence

<400> SEQUENCE: 79

```
Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Ser Gly Ile Gly Arg Phe Tyr Ile Gln Met Cys Thr Glu Leu Lys
        35                  40                  45

Leu Ser Asp Asn Glu Gly Arg Leu Ile Gln Asn Ser Ile Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Arg Thr Arg Val Ala Tyr Glu Arg Met Cys Asn
    210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300
```

Arg Leu Leu Gln Asn Ser Gln Val Phe Ser Leu Ile Arg Pro Asn Glu
305 310 315 320

Asn Pro Ala His Lys Ser Gln Leu Val Trp Met Ala Cys His Ser Ala
325 330 335

Ala Phe Glu Asp Leu Arg Val Ser Ser Phe Ile Arg Gly Thr Arg Met
340 345 350

Val Pro Arg Gly Gln Leu Ser Thr Arg Gly Val Gln Ile Ala Ser Asn
355 360 365

Glu Asn Met Glu Ala Met Asp Ser Asn Thr Leu Glu Leu Arg Ser Arg
370 375 380

Tyr Trp Ala Ile Arg Thr Arg Ser Gly Gly Asn Thr Asn Gln Gln Arg
385 390 395 400

Ala Ser Ala Gly Gln Ile Ser Val Gln Pro Thr Phe Ser Val Gln Arg
405 410 415

Asn Leu Pro Phe Glu Arg Ala Thr Ile Met Ala Ala Phe Thr Gly Asn
420 425 430

Thr Glu Gly Arg Thr Ser Asp Met Arg Thr Glu Ile Ile Arg Met Met
435 440 445

Glu Ser Ala Arg Pro Glu Asp Val Ser Phe Gln Gly Arg Gly Val Phe
450 455 460

Glu Leu Ser Asp Lys Lys Ala Thr Asn Pro Ile Val Pro Ser Phe Asp
465 470 475 480

Met Ser Asn Glu Gly Ser Tyr Phe Phe Gly Asp Asn Ala Glu Glu Tyr
485 490 495

Asp Asn

<210> SEQ ID NO 80
<211> LENGTH: 1494
<212> TYPE: DNA
<213> ORGANISM: Artificial Sequence
<220> FEATURE:
<223> OTHER INFORMATION: 2013 H10N8 - Optimized DNA sequence encoding the nucleic acid sequence encoding NP antigen

<400> SEQUENCE: 80
atggcctccc agggcaccaa gcgctcctac gagcagatgg agaccggcgg cgagcgccag 60
aacgccaccg agatccgcgc ctccgtgggc cgcatggtgt ccggcatcgg ccgcttctac 120
atccagatgt gcaccgagct gaagctgtcc gacaacgagg gccgcctgat ccagaactcc 180
atcaccatcg agcgcatggt gctgtccgcc ttcgacgagc gccgcaaccg ctacctggag 240
gagcacccct ccgccggcaa ggaccccaag aagaccggcg gccccatcta ccgccgccgc 300
gacggcaagt gggtgcgcga gctgatcctg tacgacaagg aggagatccg ccgcatctgg 360
cgccaggcca acaacggcga ggacgccacc gccggcctga cccacctgat gatctggcac 420
tccaacctga acgacgccac ctaccagcgc acccgcgccc tggtgcgcac cggcatggac 480
ccccgcatgt gctccctgat gcagggctcc accctgcccc gccgctccgg cgccgccggc 540
gccgccgtga agggcatcgg caccatggtg atggagctga tccgcatggt gaagcgcggc 600
atcaacgacc gcaacttctg gcgcggcgag aacggccgcc gcacccgcgt ggcctacgag 660
cgcatgtgca acatcctgaa gggcaagttc cagaccgccg cccagcgcgc catggtggac 720
caggtgcgcg agtcccgcaa ccccggcaac gccgagatcg aggacctgat cttcctggcc 780
cgctccgccc tgatcctgcg cggctccgtg gcccacaagt cctgcctgcc cgcctgcgtg 840
tacggcctgg ccgtggcctc cggctacgac ttcgagcgcg agggctactc cctggtgggc 900
atcgacccct tccgcctgct gcagaactcc caggtgttct ccctgatccg ccccaacgag 960
aaccccgccc acaagtccca gctggtgtgg atggcctgcc actccgccgc cttcgaggac 1020
ctgcgcgtgt cctccttcat ccgcggcacc cgcatggtgc cccgcggcca gctgtccacc 1080
cgcggcgtgc agatcgcctc caacgagaac atggaggcca tggactccaa caccctggag 1140
ctgcgctccc gctactgggc catccgcacc cgctccggcg gcaacaccaa ccagcagcgc 1200
gcctccgccg gccagatctc cgtgcagccc accttctccg tgcagcgcaa cctgcccttc 1260
gagcgcgcca ccatcatggc cgccttcacc ggcaacaccg agggccgcac ctccgacatg 1320
cgcaccgaga tcatccgcat gatggagtcc gcccgccccg aggacgtgtc cttccagggc 1380
cgcggcgtgt tcgagctgtc cgacaagaag gccaccaacc ccatcgtgcc ctccttcgac 1440
atgtccaacg agggctccta cttcttcggc gacaacgccg aggagtacga caac 1494

<210> SEQ ID NO 81
<211> LENGTH: 97
<212> TYPE: PRT
<213> ORGANISM: Artificial Sequence
<220> FEATURE:
<223> OTHER INFORMATION: 1918 H1N1 - M2 ion channel antigen Amino Acid sequence

<400> SEQUENCE: 81

Met Ser Leu Leu Thr Glu Val Glu Thr Pro Thr Arg Asn Glu Trp Gly
1 5 10 15

Cys Arg Cys Asn Asp Ser Ser Asp Pro Leu Val Ile Ala Ala Ser Ile
20 25 30

Ile Gly Ile Leu His Leu Ile Leu Trp Ile Leu Asp Arg Leu Phe Phe
35 40 45

Lys Cys Ile Tyr Arg Arg Leu Lys Tyr Gly Leu Lys Arg Gly Pro Ser
50 55 60

Thr Glu Gly Val Pro Glu Ser Met Arg Glu Glu Tyr Arg Lys Glu Gln
65 70 75 80

Gln Ser Ala Val Asp Val Asp Asp Gly His Phe Val Asn Ile Glu Leu
85 90 95

Glu

<210> SEQ ID NO 82
<211> LENGTH: 291
<212> TYPE: DNA
<213> ORGANISM: Artificial Sequence
<220> FEATURE:
<223> OTHER INFORMATION: 1918 H1N1 - Optimized DNA sequence encoding the nucleic acid sequence encoding M2 ion channel antigen

<400> SEQUENCE: 82
atgtccctgc tgaccgaggt ggagaccccc acccgcaacg agtggggctg ccgctgcaac 60
gactcctccg accccctggt gatcgccgcc tccatcatcg gcatcctgca cctgatcctg 120
tggatcctgg accgcctgtt cttcaagtgc atctaccgcc gcctgaagta cggcctgaag 180
cgcggcccct ccaccgaggg cgtgcccgag tccatgcgcg aggagtaccg caaggagcag 240
cagtccgccg tggacgtgga cgacggccac ttcgtgaaca tcgagctgga g 291

<210> SEQ ID NO 83
<211> LENGTH: 97
<212> TYPE: PRT
<213> ORGANISM: Artificial Sequence
<220> FEATURE:
<223> OTHER INFORMATION: 1957 H2N2 - M2 ion channel antigen Amino Acid sequence

<400> SEQUENCE: 83

Met Ser Leu Leu Thr Glu Val Glu Thr Pro Ile Arg Asn Glu Trp Gly
1 5 10 15

Cys Arg Cys Asn Asp Ser Ser Asp Pro Leu Val Val Ala Ala Ser Ile
20 25 30

Ile Gly Ile Leu His Leu Ile Leu Trp Ile Leu Asp Arg Leu Phe Phe
35 40 45

Lys Cys Ile Tyr Arg Phe Phe Lys His Gly Leu Lys Arg Gly Pro Ser
50 55 60

Thr Glu Gly Val Pro Glu Ser Met Arg Glu Glu Tyr Arg Lys Glu Gln
65 70 75 80

Gln Ser Ala Val Asp Ala Asp Asp Ser His Phe Val Ser Ile Glu Leu
85 90 95

Glu

<210> SEQ ID NO 84
<211> LENGTH: 291
<212> TYPE: DNA
<213> ORGANISM: Artificial Sequence
<220> FEATURE:
<223> OTHER INFORMATION: 1957 H2N2 - Optimized DNA sequence encoding the nucleic acid sequence encoding M2 ion channel antigen

<400> SEQUENCE: 84
atgtccctgc tgaccgaggt ggagacccc atccgcaacg agtggggctg ccgctgcaac 60
gactcctccg accccctggt ggtggccgcc tccatcatcg gcatcctgca cctgatcctg 120
tggatcctgg accgcctgtt cttcaagtgc atctaccgct tcttcaagca cggcctgaag 180
cgcggcccct ccaccgaggg cgtgcccgag tccatgcgcg aggagtaccg caaggagcag 240
cagtccgccg tggacgccga cgactcccac ttcgtgtcca tcgagctgga g 291

<210> SEQ ID NO 85
<211> LENGTH: 97
<212> TYPE: PRT
<213> ORGANISM: Artificial Sequence
<220> FEATURE:
<223> OTHER INFORMATION: 1968 H3N2 - M2 ion channel antigen Amino Acid sequence

<400> SEQUENCE: 85

Met Ser Leu Leu Thr Glu Val Glu Thr Pro Ile Arg Asn Glu Trp Gly
1 5 10 15

Cys Arg Cys Asn Asp Ser Ser Asp Pro Leu Val Val Ala Ala Ser Ile
20 25 30

Ile Gly Ile Leu His Leu Ile Leu Trp Ile Leu Asp Arg Leu Phe Phe
35 40 45

Lys Cys Ile Tyr Arg Phe Phe Glu His Gly Leu Lys Arg Gly Pro Ser
50 55 60

Thr Glu Gly Val Pro Glu Ser Met Arg Glu Glu Tyr Arg Lys Glu Gln
65 70 75 80

Gln Ser Ala Val Asp Ala Asp Asp Ser His Phe Val Ser Ile Glu Leu
85 90 95

Glu

<210> SEQ ID NO 86
<211> LENGTH: 291

<212> TYPE: DNA
<213> ORGANISM: Artificial Sequence
<220> FEATURE:
<223> OTHER INFORMATION: 1968 H3N2 - Optimized DNA sequence encoding the nucleic acid sequence encoding M2 ion channel antigen

<400> SEQUENCE: 86
atgtccctgc tgaccgaggt ggagaccccc atccgcaacg agtggggctg ccgctgcaac 60
gactcctccg accccctggt ggtggccgcc tccatcatcg gcatcctgca cctgatcctg 120
tggatcctgg accgcctgtt cttcaagtgc atctaccgct tcttcgagca cggcctgaag 180
cgcggcccct ccaccgaggg cgtgcccgag tccatgcgcg aggagtaccg caaggagcag 240
cagtccgccg tggacgccga cgactcccac ttcgtgtcca tcgagctgga g 291

<210> SEQ ID NO 87
<211> LENGTH: 97
<212> TYPE: PRT
<213> ORGANISM: Artificial Sequence
<220> FEATURE:
<223> OTHER INFORMATION: 1977 H1N1 - M2 ion channel antigen Amino Acid sequence

<400> SEQUENCE: 87

Met Ser Leu Leu Thr Glu Val Glu Thr Pro Ile Arg Asn Glu Trp Gly
1 5 10 15

Cys Arg Cys Asn Asp Ser Ser Asp Pro Leu Val Val Ala Ala Ser Ile
20 25 30

Ile Gly Ile Leu His Leu Ile Leu Trp Ile Leu Asp Arg Leu Phe Phe
35 40 45

Lys Cys Ile Tyr Arg Leu Phe Lys His Gly Leu Lys Arg Gly Pro Ser
50 55 60

Thr Glu Gly Val Pro Glu Ser Met Arg Glu Glu Tyr Arg Lys Glu Gln
65 70 75 80

Gln Asn Ala Val Asp Ala Asp Asp Ser His Phe Val Asn Ile Glu Leu
85 90 95

Glu

<210> SEQ ID NO 88
<211> LENGTH: 291
<212> TYPE: DNA
<213> ORGANISM: Artificial Sequence
<220> FEATURE:
<223> OTHER INFORMATION: 1977 H1N1 - Optimized DNA sequence encoding the nucleic acid sequence encoding M2 ion channel antigen

<400> SEQUENCE: 88
atgtccctgc tgaccgaggt ggagaccccc atccgcaacg agtggggctg ccgctgcaac 60
gactcctccg accccctggt ggtggccgcc tccatcatcg gcatcctgca cctgatcctg 120
tggatcctgg accgcctgtt cttcaagtgc atctaccgcc tgttcaagca cggcctgaag 180
cgcggcccct ccaccgaggg cgtgcccgag tccatgcgcg aggagtaccg caaggagcag 240
cagaacgccg tggacgccga cgactcccac ttcgtgaaca tcgagctgga g 291

<210> SEQ ID NO 89
<211> LENGTH: 97
<212> TYPE: PRT
<213> ORGANISM: Artificial Sequence
<220> FEATURE:
<223> OTHER INFORMATION: 2007 H1N1 - M2 ion channel antigen Amino Acid sequence

<400> SEQUENCE: 89

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Val His Leu Ile Leu Trp Ile Ile Asp Arg Leu Phe Ser
        35                  40                  45

Lys Ser Ile Tyr Arg Ile Phe Lys His Gly Leu Lys Arg Gly Pro Ser
    50                  55                  60

Thr Glu Gly Val Pro Glu Ser Met Arg Glu Glu Tyr Arg Glu Glu Gln
65                  70                  75                  80

Gln Asn Ala Val Asp Ala Asp Asp Asp His Phe Val Ser Ile Glu Leu
                85                  90                  95

Glu

<210> SEQ ID NO 90
<211> LENGTH: 291
<212> TYPE: DNA
<213> ORGANISM: Artificial Sequence
<220> FEATURE:
<223> OTHER INFORMATION: 2007 H1N1 - Optimized DNA sequence encoding the nucleic acid sequence encoding M2 ion channel antigen

<400> SEQUENCE: 90
atgtccctgc tgaccgaggt ggagaccccc atccgcaacg agtggggctg ccgctgcaac 60
gactcctccg accccctggt ggtggccgcc tccatcatcg gcatcgtgca cctgatcctg 120
tggatcatcg accgcctgtt ctccaagtcc atctaccgca tcttcaagca cggcctgaag 180
cgcggcccct ccaccgaggg cgtgcccgag tccatgcgcg aggagtaccg cgaggagcag 240
cagaacgccg tggacgccga cgacgaccac ttcgtgtcca tcgagctgga g 291

<210> SEQ ID NO 91
<211> LENGTH: 97
<212> TYPE: PRT
<213> ORGANISM: Artificial Sequence
<220> FEATURE:
<223> OTHER INFORMATION: 2009 H1N1 - M2 ion channel antigen Amino Acid sequence

<400> SEQUENCE: 91

Met Ser Leu Leu Thr Glu Val Glu Thr Pro Thr Arg Ser Glu Trp Glu
1               5                   10                  15

Cys Arg Cys Ser Asp Ser Ser Asp Pro Leu Val Ile Ala Ala Asn Ile
            20                  25                  30

Ile Gly Ile Leu His Leu Ile Leu Trp Ile Thr Asp Arg Leu Phe Phe
        35                  40                  45

Lys Cys Ile Tyr Arg Arg Phe Lys Tyr Gly Leu Lys Arg Gly Pro Ser
    50                  55                  60

Thr Glu Gly Val Pro Glu Ser Met Arg Glu Glu Tyr Gln Gln Glu Gln
65                  70                  75                  80

Gln Ser Ala Val Asp Val Asp Asp Gly His Phe Val Asn Ile Glu Leu
                85                  90                  95

Glu

<210> SEQ ID NO 92
<211> LENGTH: 291
<212> TYPE: DNA
<213> ORGANISM: Artificial Sequence
<220> FEATURE:
<223> OTHER INFORMATION: 2009 H1N1 - Optimized DNA sequence encoding the nucleic acid sequence encoding M2 ion channel antigen

<400> SEQUENCE: 92

```
atgtccctgc tgaccgaggt ggagaccccc acccgctccg agtgggagtg ccgctgctcc     60

gactcctccg accccctggt gatcgccgcc aacatcatcg gcatcctgca cctgatcctg    120

tggatcaccg accgcctgtt cttcaagtgc atctaccgcc gcttcaagta cggcctgaag    180

cgcggcccct ccaccgaggg cgtgcccgag tccatgcgcg aggagtacca gcaggagcag    240

cagtccgccg tggacgtgga cgacggccac ttcgtgaaca tcgagctgga g             291
```

<210> SEQ ID NO 93
<211> LENGTH: 97
<212> TYPE: PRT
<213> ORGANISM: Artificial Sequence
<220> FEATURE:
<223> OTHER INFORMATION: 2015 H1N1 - M2 ion channel antigen Amino Acid sequence

<400> SEQUENCE: 93

```
Met Ser Leu Leu Thr Glu Val Glu Thr Pro Thr Arg Ser Glu Trp Glu
1               5                   10                  15

Cys Arg Cys Ser Gly Ser Ser Asp Pro Leu Val Ile Ala Ala Asn Ile
            20                  25                  30

Ile Gly Ile Leu His Leu Ile Leu Trp Ile Thr Asp Arg Leu Phe Phe
        35                  40                  45

Lys Cys Ile Tyr Arg Arg Phe Lys Tyr Gly Leu Lys Arg Gly Pro Ser
    50                  55                  60

Thr Glu Gly Val Pro Glu Ser Met Arg Glu Glu Tyr Gln Gln Glu Gln
65                  70                  75                  80

Gln Ser Ala Val Asp Val Asp Asp Gly His Phe Val Asn Ile Glu Leu
                85                  90                  95

Glu
```

<210> SEQ ID NO 94
<211> LENGTH: 291
<212> TYPE: DNA
<213> ORGANISM: Artificial Sequence
<220> FEATURE:
<223> OTHER INFORMATION: 2015 H1N1 - Optimized DNA sequence encoding the nucleic acid sequence encoding M2 ion channel antigen

<400> SEQUENCE: 94

```
atgtccctgc tgaccgaggt ggagaccccc acccgctccg agtgggagtg ccgctgctcc     60

ggctcctccg accccctggt gatcgccgcc aacatcatcg gcatcctgca cctgatcctg    120

tggatcaccg accgcctgtt cttcaagtgc atctaccgcc gcttcaagta cggcctgaag    180

cgcggcccct ccaccgaggg cgtgcccgag tccatgcgcg aggagtacca gcaggagcag    240

cagtccgccg tggacgtgga cgacggccac ttcgtgaaca tcgagctgga g             291
```

<210> SEQ ID NO 95
<211> LENGTH: 97
<212> TYPE: PRT
<213> ORGANISM: Artificial Sequence
<220> FEATURE:
<223> OTHER INFORMATION: 2017 H3N2 - M2 ion channel antigen Amino Acid sequence

<400> SEQUENCE: 95

Met Ser Leu Leu Thr Glu Val Glu Thr Pro Ile Arg Asn Glu Trp Gly
1 5 10 15

Cys Arg Cys Asn Asp Ser Ser Asp Pro Leu Ile Val Ala Ala Asn Ile
20 25 30

Ile Gly Ile Leu His Leu Ile Leu Trp Ile Leu Asp Arg Leu Phe Phe
35 40 45

Lys Cys Val Cys Arg Leu Phe Lys His Gly Leu Lys Arg Gly Pro Ser
50 55 60

Thr Glu Gly Val Pro Glu Ser Met Arg Glu Glu Tyr Arg Lys Glu Gln
65 70 75 80

Gln Asn Ala Val Asp Ala Asp Asp Ser His Phe Val Ser Ile Glu Leu
85 90 95

Glu

<210> SEQ ID NO 96
<211> LENGTH: 291
<212> TYPE: DNA
<213> ORGANISM: Artificial Sequence
<220> FEATURE:
<223> OTHER INFORMATION: 2017 H3N2 - Optimized DNA sequence encoding the nucleic acid sequence encoding M2 ion channel antigen

<400> SEQUENCE: 96
atgtccctgc tgaccgaggt ggagaccccc atccgcaacg agtggggctg ccgctgcaac 60
gactcctccg accccctgat cgtggccgcc aacatcatcg gcatcctgca cctgatcctg 120
tggatcctgg accgcctgtt cttcaagtgc gtgtgccgcc tgttcaagca cggcctgaag 180
cgcggcccct ccaccgaggg cgtgcccgag tccatgcgcg aggagtaccg caaggagcag 240
cagaacgccg tggacgccga cgactcccac ttcgtgtcca tcgagctgga g 291

<210> SEQ ID NO 97
<211> LENGTH: 109
<212> TYPE: PRT
<213> ORGANISM: Artificial Sequence
<220> FEATURE:
<223> OTHER INFORMATION: 2017 Influenza B (Victoria lineage) - M2 ion channel antigen Amino Acid sequence

<400> SEQUENCE: 97

Met Leu Glu Pro Phe Gln Ile Leu Thr Ile Cys Ser Phe Ile Leu Ser
1 5 10 15

Ala Leu His Phe Met Ala Trp Thr Ile Gly His Leu Asn Gln Ile Lys
20 25 30

Arg Gly Ile Asn Met Lys Ile Arg Ile Lys Gly Pro Asn Lys Glu Thr
35 40 45

Ile Thr Arg Glu Val Ser Ile Leu Arg His Ser Tyr Gln Lys Glu Ile
50 55 60

Gln Ala Lys Glu Thr Met Lys Glu Val Leu Ser Asp Asn Met Glu Val
65 70 75 80

Leu Asn Asp His Ile Ile Ile Glu Gly Leu Ser Ala Glu Glu Ile Ile
85 90 95

Lys Met Gly Glu Thr Val Leu Glu Ile Glu Glu Leu His
100 105

<210> SEQ ID NO 98
<211> LENGTH: 327
<212> TYPE: DNA
<213> ORGANISM: Artificial Sequence
<220> FEATURE:

<223> OTHER INFORMATION: 2017 Influenza B (Victoria lineage) - Optimized DNA sequence encoding the nucleic acid sequence encoding M2 ion channel antigen

<400> SEQUENCE: 98

```
atgctggagc ccttccagat cctgaccatc tgctccttca tcctgtccgc cctgcacttc     60

atggcctgga ccatcggcca cctgaaccag atcaagcgcg gcatcaacat gaagatccgc    120

atcaagggcc ccaacaagga gaccatcacc cgcgaggtgt ccatcctgcg ccactcctac    180

cagaaggaga tccaggccaa ggagaccatg aaggaggtgc tgtccgacaa catggaggtg    240

ctgaacgacc acatcatcat cgagggcctg tccgccgagg agatcatcaa gatgggcgag    300

accgtgctgg agatcgagga gctgcac                                        327
```

<210> SEQ ID NO 99
<211> LENGTH: 109
<212> TYPE: PRT
<213> ORGANISM: Artificial Sequence
<220> FEATURE:
<223> OTHER INFORMATION: 2013 Influenza B (Yamagata lineage) - Sequence only on GISAID - M2 ion channel antigen Amino Acid sequence

<400> SEQUENCE: 99

```
Met Phe Glu Pro Phe Gln Ile Leu Ser Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Val Asn Met Lys Ile Arg Ile Lys Gly Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Ala Met Lys Glu Val Leu Ser Asp Asn Met Glu Val
65                  70                  75                  80

Leu Ser Asp His Ile Val Ile Glu Gly Leu Ser Ala Glu Glu Ile Ile
                85                  90                  95

Lys Met Gly Glu Thr Val Leu Glu Val Glu Glu Ser His
            100                 105
```

<210> SEQ ID NO 100
<211> LENGTH: 327
<212> TYPE: DNA
<213> ORGANISM: Artificial Sequence
<220> FEATURE:
<223> OTHER INFORMATION: 2013 Influenza B (Yamagata lineage) - Sequence only on GISAID - Optimized DNA sequence encoding the nucleic acid sequence encoding M2 ion channel antigen

<400> SEQUENCE: 100

```
atgttcgagc ccttccagat cctgtccatc tgctccttca tcctgtccgc cctgcacttc     60

atggcctgga ccatcggcca cctgaaccag atcaagcgcg gcgtgaacat gaagatccgc    120

atcaagggcc ccaacaagga gaccatcaac cgcgaggtgt ccatcctgcg ccactcctac    180

cagaaggaga tccaggccaa ggaggccatg aaggaggtgc tgtccgacaa catggaggtg    240

ctgtccgacc acatcgtgat cgagggcctg tccgccgagg agatcatcaa gatgggcgag    300

accgtgctgg aggtggagga gtcccac                                        327
```

<210> SEQ ID NO 101
<211> LENGTH: 97
<212> TYPE: PRT
<213> ORGANISM: Artificial Sequence
<220> FEATURE:
<223> OTHER INFORMATION: 2015 H5N1 - M2 ion channel antigen Amino Acid
sequence

<400> SEQUENCE: 101

Met Ser Leu Leu Thr Glu Val Glu Thr Leu Thr Lys Thr Gly Trp Glu
1 5 10 15

Cys Asn Cys Ser Gly Ser Ser Asp Pro Leu Gly Val Ala Ala Asn Ile
20 25 30

Ile Gly Ile Leu His Leu Ile Leu Trp Ile Leu Asp Arg Leu Phe Phe
35 40 45

Lys Cys Ile Tyr Arg Arg Phe Arg Tyr Gly Leu Lys Gly Gly Pro Ser
50 55 60

Thr Glu Gly Ile Pro Glu Ser Met Arg Glu Glu Tyr Arg Gln Glu Gln
65 70 75 80

Gln Asn Ala Val Asp Val Asp Asp Gly His Phe Val Asn Ile Glu Leu
85 90 95

Glu

<210> SEQ ID NO 102
<211> LENGTH: 291
<212> TYPE: DNA
<213> ORGANISM: Artificial Sequence
<220> FEATURE:
<223> OTHER INFORMATION: 2015 H5N1 - Optimized DNA sequence encoding the
nucleic acid sequence encoding M2 ion channel antigen

<400> SEQUENCE: 102
atgtccctgc tgaccgaggt ggagaccctg accaagaccg gctgggagtg caactgctcc 60
ggctcctccg accccctggg cgtggccgcc aacatcatcg gcatcctgca cctgatcctg 120
tggatcctgg accgcctgtt cttcaagtgc atctaccgcc gcttccgcta cggcctgaag 180
ggcggcccct ccaccgaggg catccccgag tccatgcgcg aggagtaccg ccaggagcag 240
cagaacgccg tggacgtgga cgacggccac ttcgtgaaca tcgagctgga g 291

<210> SEQ ID NO 103
<211> LENGTH: 97
<212> TYPE: PRT
<213> ORGANISM: Artificial Sequence
<220> FEATURE:
<223> OTHER INFORMATION: 2017 H7N9 - M2 ion channel antigen Amino Acid
sequence

<400> SEQUENCE: 103

Met Ser Leu Leu Thr Glu Val Glu Thr Pro Thr Arg Thr Gly Trp Glu
1 5 10 15

Cys Asn Cys Ser Gly Ser Ser Asp Pro Phe Val Val Ala Ala Asn Ile
20 25 30

Ile Gly Ile Leu His Leu Ile Leu Trp Ile Leu Asp Arg Leu Phe Phe
35 40 45

Lys Cys Ile Tyr Arg Arg Phe Lys Tyr Gly Leu Lys Arg Gly Pro Ser
50 55 60

Thr Glu Gly Met Pro Glu Ser Met Arg Glu Glu Tyr Arg Gln Glu Gln
65 70 75 80

Gln Asn Ala Val Asp Val Asp Asp Gly His Phe Val Asn Ile Glu Leu
85 90 95

Lys

<210> SEQ ID NO 104
<211> LENGTH: 291
<212> TYPE: DNA
<213> ORGANISM: Artificial Sequence
<220> FEATURE:
<223> OTHER INFORMATION: 2017 H7N9 - Optimized DNA sequence encoding the nucleic acid sequence encoding M2 ion channel antigen

<400> SEQUENCE: 104
atgtccctgc tgaccgaggt ggagaccccc acccgcaccg gctgggagtg caactgctcc 60
ggctcctccg accccttcgt ggtggccgcc aacatcatcg gcatcctgca cctgatcctg 120
tggatcctgg accgcctgtt cttcaagtgc atctaccgcc gcttcaagta cggcctgaag 180
cgcggcccct ccaccgaggg catgcccgag tccatgcgcg aggagtaccg ccaggagcag 240
cagaacgccg tggacgtgga cgacggccac ttcgtgaaca tcgagctgaa g 291

<210> SEQ ID NO 105
<211> LENGTH: 97
<212> TYPE: PRT
<213> ORGANISM: Artificial Sequence
<220> FEATURE:
<223> OTHER INFORMATION: 2013 H10N8 - M2 ion channel antigen Amino Acid sequence

<400> SEQUENCE: 105

Met Ser Leu Leu Thr Glu Val Glu Thr Leu Thr Lys Thr Gly Trp Glu
1 5 10 15

Cys Asn Cys Ser Gly Ser Ser Asp Pro Leu Val Val Ala Ala Asn Ile
20 25 30

Ile Gly Ile Leu His Leu Ile Leu Trp Ile Leu Asp Arg Leu Phe Phe
35 40 45

Lys Cys Ile Tyr Arg Arg Phe Lys Tyr Gly Leu Lys Arg Gly Pro Ser
50 55 60

Thr Glu Gly Met Pro Glu Ser Met Arg Glu Glu Tyr Arg Gln Glu Gln
65 70 75 80

Gln Asn Ala Val Asp Val Asp Asp Gly His Phe Val Asn Ile Glu Leu
85 90 95

Lys

<210> SEQ ID NO 106
<211> LENGTH: 291
<212> TYPE: DNA
<213> ORGANISM: Artificial Sequence
<220> FEATURE:
<223> OTHER INFORMATION: 2013 H10N8 - Optimized DNA sequence encoding the nucleic acid sequence encoding M2 ion channel antigen

<400> SEQUENCE: 106
atgtccctgc tgaccgaggt ggagaccctg accaagaccg gctgggagtg caactgctcc 60
ggctcctccg acccccctggt ggtggccgcc aacatcatcg gcatcctgca cctgatcctg 120
tggatcctgg accgcctgtt cttcaagtgc atctaccgcc gcttcaagta cggcctgaag 180
cgcggcccct ccaccgaggg catgcccgag tccatgcgcg aggagtaccg ccaggagcag 240
cagaacgccg tggacgtgga cgacggccac ttcgtgaaca tcgagctgaa g 291

<210> SEQ ID NO 107
<211> LENGTH: 252
<212> TYPE: PRT
<213> ORGANISM: Artificial Sequence
<220> FEATURE:
<223> OTHER INFORMATION: M1 antigen Amino Acid sequence

<400> SEQUENCE: 107

Met Ser Leu Leu Thr Glu Val Glu Thr Tyr Val Leu Ser Ile Ile Pro
1 5 10 15

Ser Gly Pro Leu Lys Ala Glu Ile Ala Gln Arg Leu Glu Ser Val Phe
20 25 30

Ala Gly Lys Asn Thr Asp Leu Glu Ala Leu Met Glu Trp Leu Lys Thr
35 40 45

Arg Pro Ile Leu Ser Pro Leu Thr Lys Gly Ile Leu Gly Phe Val Phe
50 55 60

Thr Leu Thr Val Pro Ser Glu Arg Gly Leu Gln Arg Arg Arg Phe Ile
65 70 75 80

Gln Asn Ala Leu Asn Gly Asn Gly Asp Pro Asn Asn Met Asp Arg Ala
85 90 95

Val Lys Leu Tyr Lys Lys Leu Lys Arg Glu Ile Thr Phe His Gly Ala
100 105 110

Lys Glu Val Ser Leu Ser Tyr Ser Thr Gly Ala Leu Ala Ser Cys Met
115 120 125

Gly Leu Ile Tyr Asn Arg Met Gly Thr Val Thr Thr Glu Ala Ala Phe
130 135 140

Gly Leu Val Cys Ala Thr Cys Glu Gln Ile Ala Asp Ser Gln His Arg
145 150 155 160

Ser His Arg Gln Met Ala Thr Thr Thr Asn Pro Leu Ile Arg His Glu
165 170 175

Asn Arg Met Val Leu Ala Ser Thr Thr Ala Lys Ala Met Glu Gln Val
180 185 190

Ala Gly Ser Ser Glu Gln Ala Ala Glu Ala Met Glu Val Ala Asn Lys
195 200 205

Thr Arg Gln Met Val His Ala Met Arg Thr Ile Gly Thr His Pro Ser
210 215 220

Ser Ser Ala Gly Leu Arg Asp Asp Leu Leu Glu Asn Leu Gln Ala Tyr
225 230 235 240

Gln Lys Arg Met Gly Val Gln Met Gln Arg Phe Lys
245 250

<210> SEQ ID NO 108
<211> LENGTH: 756
<212> TYPE: DNA
<213> ORGANISM: Artificial Sequence
<220> FEATURE:
<223> OTHER INFORMATION: Optimized DNA sequence encoding the nucleic acid sequence encoding M1 antigen

<400> SEQUENCE: 108
atgtccctgc tgaccgaggt ggagacctac gtgctgtcca tcatcccctc cggcccccctg 60 aaggccgaga tcgcccagcg cctggagtcc gtgttcgccg gcaagaacac cgacctggag 120
gccctgatgg agtggctgaa gacccgcccc atcctgtccc ccctgaccaa gggcatcctg 180
ggcttcgtgt tcaccctgac cgtgccctcc gagcgcggcc tgcagcgccg ccgcttcatc 240
cagaacgccc tgaacggcaa cggcgacccc aacaacatgg accgcgccgt gaagctgtac 300
aagaagctga agcgcgagat caccttccac ggcgccaagg aggtgtccct gtcctactcc 360
accggcgccc tggcctcctg catgggcctg atctacaacc gcatgggcac cgtgaccacc 420
gaggccgcct tcggcctggt gtgcgccacc tgcgagcaga tcgccgactc ccagcaccgc 480
tcccaccgcc agatggccac caccaccaac cccctgatcc gccacgagaa ccgcatggtg 540
ctggcctcca ccaccgccaa ggccatggag caggtggccg gctcctccga gcaggccgcc 600
gaggccatgg aggtggccaa caagacccgc cagatggtgc acgccatgcg caccatcggc 660
acccacccct cctcctccgc cggcctgcgc gacgacctgc tggagaacct gcaggcctac 720
cagaagcgca tgggcgtgca gatgcagcgg ttcaag 756

<210> SEQ ID NO 109
<211> LENGTH: 563
<212> TYPE: PRT
<213> ORGANISM: Artificial Sequence
<220> FEATURE:
<223> OTHER INFORMATION: HA amino acid sequence

<400> SEQUENCE: 109

Met Lys Ala Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Leu Leu Lys Gly Ile
50 55 60

Ala Pro Leu Gln Leu Gly Asn Cys Ser Val Ala Gly Trp Ile Leu Gly
65 70 75 80

Asn Pro Glu Cys Glu Leu Leu Ile Ser Lys Glu Ser Trp Ser Tyr Ile
85 90 95

Val Glu Thr Pro Asn Pro Glu Asn Gly Thr Cys Tyr Pro Gly Tyr Phe
100 105 110

Ala Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Thr
130 135 140

Val Thr Gly Val Ser Ala Ser Cys Ser His Asn Gly Lys Ser Ser Phe
145 150 155 160

Tyr Arg Asn Leu Leu Trp Leu Thr Gly Lys Asn Gly Leu Tyr Pro Asn
165 170 175

Leu Ser Lys Ser Tyr Val Asn Asn Lys Glu Lys Glu Val Leu Val Leu
180 185 190

Trp Gly Val His His Pro Pro Asn Ile Gly Asn Gln Arg Ala Leu Tyr
195 200 205

His Thr Glu Asn Ala Tyr Val Ser Val Val Ser Ser His Tyr Ser Arg
210 215 220

Arg Phe Thr Pro Glu Ile Ala Lys Arg Pro Lys Val Arg Asp Gln Glu
225 230 235 240

Gly Arg Ile Asn Tyr Tyr Trp Thr Leu Leu Glu Pro Gly Asp Thr Ile
245 250 255

Ile Phe Glu Ala Asn Gly Asn Leu Ile Ala Pro Trp Tyr Ala Phe Ala
260 265 270

Leu Ser Arg Gly Phe Gly Ser Gly Ile Ile Thr Ser Asn Ala Pro Met
275 280 285

Asp Glu Cys Asp Ala Lys Cys Gln Thr Pro Gln Gly Ala Ile Asn Ser
290 295 300

Ser Leu Pro Phe Gln Asn Val His Pro Val Thr Ile Gly Glu Cys Pro
305 310 315 320

```
Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Pro Gly Ser Gly Tyr Ile Pro Glu Ala Pro Arg
        515                 520                 525

Asp Gly Gln Ala Tyr Val Arg Lys Asp Gly Glu Trp Val Leu Leu Ser
    530                 535                 540

Thr Phe Leu Ser Gly Arg Leu Val Pro Arg Gly Ser Gly His His His
545                 550                 555                 560

His His His


<210> SEQ ID NO 110
<211> LENGTH: 332
<212> TYPE: PRT
<213> ORGANISM: Artificial Sequence
<220> FEATURE:
<223> OTHER INFORMATION: Gen1 HA SS amino acid sequence

<400> SEQUENCE: 110

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Gly Ser Gly Asp Ala Lys Cys
    50                  55                  60

Gln Thr Pro Gln Gly Ala Ile Asn Ser Ser Leu Pro Phe Gln Asn Val
65                  70                  75                  80

His Pro Val Thr Ile Gly Glu Cys Pro Lys Tyr Val Arg Ser Ala Lys
                85                  90                  95

Leu Arg Met Val Thr Gly Leu Arg Asn Ile Pro Gln Arg Glu Thr Arg
            100                 105                 110

Gly Leu Phe Gly Ala Ile Ala Gly Phe Ile Glu Gly Gly Trp Thr Gly
```

```
        115                 120                 125

Met Val Asp Gly Trp Tyr Gly Tyr His His Gln Asn Glu Gln Gly Ser
    130                 135                 140

Gly Tyr Ala Ala Asp Gln Lys Ser Thr Gln Asn Ala Ile Asn Gly Ile
145                 150                 155                 160

Thr Asn Lys Val Asn Ser Val Ile Glu Lys Met Asn Thr Gln Phe Thr
                165                 170                 175

Ala Val Gly Lys Glu Phe Asn Lys Leu Glu Arg Arg Met Glu Asn Leu
            180                 185                 190

Asn Lys Lys Val Asp Asp Gly Phe Leu Asp Ile Trp Thr Tyr Asn Ala
        195                 200                 205

Glu Leu Leu Val Leu Leu Glu Asn Glu Arg Thr Leu Asp Phe His Asp
    210                 215                 220

Ser Asn Val Lys Asn Leu Tyr Glu Lys Val Lys Ser Gln Leu Lys Asn
225                 230                 235                 240

Asn Ala Lys Glu Ile Gly Asn Gly Cys Phe Glu Phe Tyr His Lys Cys
                245                 250                 255

Asn Asn Glu Cys Met Glu Ser Val Lys Asn Gly Thr Tyr Asp Tyr Pro
            260                 265                 270

Lys Tyr Ser Glu Glu Ser Lys Leu Asn Arg Glu Lys Ile Asp Pro Gly
        275                 280                 285

Ser Gly Tyr Ile Pro Glu Ala Pro Arg Asp Gly Gln Ala Tyr Val Arg
    290                 295                 300

Lys Asp Gly Glu Trp Val Leu Leu Ser Thr Phe Leu Ser Gly Arg Leu
305                 310                 315                 320

Val Pro Arg Gly Ser Gly His His His His His His
                325                 330


<210> SEQ ID NO 111
<211> LENGTH: 379
<212> TYPE: PRT
<213> ORGANISM: Artificial Sequence
<220> FEATURE:
<223> OTHER INFORMATION: Gen2 HA SS amino acid sequence

<400> SEQUENCE: 111

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Gly Ser Gly Asp Ala Lys Cys
    50                  55                  60

Gln Thr Pro Gln Gly Ala Ile Asn Ser Ser Leu Pro Phe Gln Asn Val
65                  70                  75                  80

His Pro Val Thr Ile Gly Glu Cys Pro Lys Tyr Val Arg Ser Ala Lys
                85                  90                  95

Leu Arg Met Val Thr Gly Leu Arg Asn Ile Pro Gln Arg Glu Thr Arg
            100                 105                 110

Gly Leu Phe Gly Ala Ile Ala Gly Phe Ile Glu Gly Gly Trp Thr Gly
        115                 120                 125

Met Val Asp Gly Trp Tyr Gly Tyr His His Gln Asn Glu Gln Gly Ser
    130                 135                 140

Gly Tyr Ala Ala Asp Gln Lys Ser Thr Gln Asn Ala Ile Asn Gly Ile
```

```
145                 150                 155                 160

Thr Asn Lys Val Asn Ser Val Ile Glu Lys Met Asn Thr Gln Phe Thr
                165                 170                 175

Ala Thr Gly Trp Met Glu Trp Asp Arg Glu Ile Asn Asn Tyr Thr Ser
            180                 185                 190

Ile Ile Tyr Ser Leu Ile Glu Glu Ser Gln Asn Gln Gln Glu Asn Gly
        195                 200                 205

Thr Gly Gly Gly Ser Gly Ile Val Gln Gln Gln Asn Asn Leu Leu Arg
    210                 215                 220

Ala Ile Glu Ala Gln Gln His Leu Leu Gln Leu Thr Val Trp Gly Ile
225                 230                 235                 240

Lys Gln Leu Gln Asp Gly Phe Leu Asp Ile Trp Thr Tyr Asn Ala Glu
                245                 250                 255

Leu Leu Val Leu Leu Glu Asn Glu Arg Thr Leu Asp Phe His Asp Ser
            260                 265                 270

Asn Val Lys Asn Leu Tyr Glu Lys Val Lys Ser Gln Leu Lys Asn Asn
        275                 280                 285

Ala Lys Glu Ile Gly Asn Gly Cys Phe Glu Phe Tyr His Lys Cys Asn
    290                 295                 300

Asn Glu Cys Met Glu Ser Val Lys Asn Gly Thr Tyr Asp Tyr Pro Lys
305                 310                 315                 320

Tyr Ser Glu Glu Ser Lys Leu Asn Arg Glu Lys Ile Asp Pro Gly Ser
                325                 330                 335

Gly Tyr Ile Pro Glu Ala Pro Arg Asp Gly Gln Ala Tyr Val Arg Lys
            340                 345                 350

Asp Gly Glu Trp Val Leu Leu Ser Thr Phe Leu Ser Gly Arg Leu Val
        355                 360                 365

Pro Arg Gly Ser Gly His His His His His His
    370                 375


<210> SEQ ID NO 112
<211> LENGTH: 322
<212> TYPE: PRT
<213> ORGANISM: Artificial Sequence
<220> FEATURE:
<223> OTHER INFORMATION: Gen3 HA SS amino acid sequence

<400> SEQUENCE: 112

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Trp Gly Leu Arg Met Val Thr Gly Leu Arg Asn Ile Pro Gln
    50                  55                  60

Arg Glu Thr Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Gly Trp Met Glu Trp Asp Arg Glu Ile Asn Asn Tyr Thr Ser Ile Ile
```

130 135 140

Tyr Ser Leu Ile Glu Glu Ser Gln Asn Gln Gln Glu Asn Gly Thr Gly
145 150 155 160

Gly Gly Ser Gly Ile Val Gln Gln Gln Asn Asn Leu Leu Arg Ala Ile
165 170 175

Glu Ala Gln Gln His Leu Leu Gln Leu Thr Val Trp Gly Ile Lys Gln
180 185 190

Leu Gln Thr Tyr Asn Ala Glu Leu Leu Val Leu Leu Glu Asn Glu Arg
195 200 205

Thr Leu Asp Phe His Asp Ser Asn Val Lys Asn Leu Tyr Glu Lys Val
210 215 220

Lys Ser Gln Leu Lys Asn Asn Ala Lys Glu Ile Gly Asn Gly Cys Phe
225 230 235 240

Glu Phe Tyr His Lys Cys Asn Asn Glu Cys Met Glu Ser Val Lys Asn
245 250 255

Gly Thr Tyr Asp Tyr Pro Lys Tyr Ser Glu Glu Ser Lys Leu Asn Arg
260 265 270

Glu Lys Ile Asp Pro Gly Ser Gly Tyr Ile Pro Glu Ala Pro Arg Asp
275 280 285

Gly Gln Ala Tyr Val Arg Lys Asp Gly Glu Trp Val Leu Leu Ser Thr
290 295 300

Phe Leu Ser Gly Arg Leu Val Pro Arg Gly Ser Gly His His His His
305 310 315 320

His His

<210> SEQ ID NO 113
<211> LENGTH: 322
<212> TYPE: PRT
<213> ORGANISM: Artificial Sequence
<220> FEATURE:
<223> OTHER INFORMATION: Gen4 HA SS amino acid sequence

<400> SEQUENCE: 113

Met Lys Ala Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Gly Ser Gly Leu Arg Met Val Thr Gly Leu Arg Asn Ile Pro Gln
50 55 60

Arg Glu Thr Arg Gly Leu Phe Gly Ala Ile Ala Gly Phe Ile Glu Gly
65 70 75 80

Gly Trp Thr Gly Met Val Asp Gly Trp Tyr Gly Tyr His His Gln Asn
85 90 95

Glu Gln Gly Ser Gly Tyr Ala Ala Asp Gln Lys Ser Thr Gln Asn Ala
100 105 110

Ile Asn Gly Ile Thr Asn Lys Val Asn Ser Val Ile Glu Lys Met Gly
115 120 125

Gly Asp Pro Glu Trp Asp Arg Glu Ile Asn Asn Tyr Thr Ser Ile Ile
130 135 140

Tyr Ser Leu Ile Glu Glu Ser Gln Asn Gln Gln Glu Asn Gly Thr Gly
145 150 155 160

Gly Gly Ser Gly Ile Val Gln Gln Gln Asn Asn Leu Leu Arg Ala Ile
165 170 175

```
Glu Ala Gln Gln His Leu Leu Gln Leu Thr Val Trp Gly Ile Lys Gln
            180                 185                 190

Leu Gln Thr Tyr Asn Ala Glu Leu Leu Val Leu Leu Glu Asn Glu Arg
        195                 200                 205

Thr Leu Asp Phe His Asp Ser Asn Val Lys Asn Leu Tyr Glu Lys Val
    210                 215                 220

Lys Ser Gln Leu Lys Asn Asn Ala Lys Glu Ile Gly Asn Gly Cys Phe
225                 230                 235                 240

Glu Phe Tyr His Lys Cys Asn Asn Glu Cys Met Glu Ser Val Lys Asn
                245                 250                 255

Gly Thr Tyr Asp Tyr Pro Lys Tyr Ser Glu Glu Ser Lys Leu Asn Arg
            260                 265                 270

Glu Lys Ile Asp Pro Gly Ser Gly Tyr Ile Pro Glu Ala Pro Arg Asp
        275                 280                 285

Gly Gln Ala Tyr Val Arg Lys Asp Gly Glu Trp Val Leu Leu Ser Thr
    290                 295                 300

Phe Leu Ser Gly Arg Leu Val Pro Arg Gly Ser Gly His His His His
305                 310                 315                 320

His His


<210> SEQ ID NO 114
<211> LENGTH: 261
<212> TYPE: PRT
<213> ORGANISM: Artificial Sequence
<220> FEATURE:
<223> OTHER INFORMATION: Gen5 HA SS amino acid sequence

<400> SEQUENCE: 114

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Gln
    50                  55                  60

Arg Glu Thr Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Lys Val Asn Ser Val Ile Glu Lys Met Gly
        115                 120                 125

Ser Gly Gly Ser Gly Thr Asp Leu Ala Glu Leu Leu Val Leu Leu Glu
    130                 135                 140

Asn Glu Arg Thr Leu Asp Phe His Asp Ser Asn Val Lys Asn Leu Tyr
145                 150                 155                 160

Glu Lys Val Lys Ser Gln Leu Lys Asn Asn Ala Lys Glu Ile Gly Asn
                165                 170                 175

Gly Cys Phe Glu Phe Tyr His Lys Cys Asn Asn Glu Cys Met Glu Ser
            180                 185                 190

Val Lys Asn Gly Thr Tyr Asp Tyr Pro Lys Tyr Ser Glu Glu Ser Lys
        195                 200                 205
```

```
Leu Asn Arg Glu Lys Ile Asp Pro Gly Ser Gly Tyr Ile Pro Glu Ala
    210                 215                 220

Pro Arg Asp Gly Gln Ala Tyr Val Arg Lys Asp Gly Glu Trp Val Leu
225                 230                 235                 240

Leu Ser Thr Phe Leu Ser Gly Arg Leu Val Pro Arg Gly Ser Gly His
                245                 250                 255

His His His His His
            260


<210> SEQ ID NO 115
<211> LENGTH: 259
<212> TYPE: PRT
<213> ORGANISM: Artificial Sequence
<220> FEATURE:
<223> OTHER INFORMATION: Gen6 HA SS 1 amino acid sequence

<400> SEQUENCE: 115

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Gln
    50                  55                  60

Arg Glu Thr Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Met Val Asn Ser Val Ile Glu Gly Ser Gly
        115                 120                 125

Gly Ser Gly Thr Asp Leu Ala Glu Leu Leu Val Leu Leu Leu Asn Gln
    130                 135                 140

Trp Thr Leu Leu Phe His Asp Ser Asn Val Lys Asn Leu Tyr Glu Lys
145                 150                 155                 160

Val Lys Ser Gln Leu Lys Asn Asn Ala Lys Glu Ile Gly Asn Gly Cys
                165                 170                 175

Phe Glu Phe Tyr His Lys Cys Asn Asn Glu Cys Met Glu Ser Val Lys
            180                 185                 190

Asn Gly Thr Tyr Asp Tyr Pro Lys Tyr Ser Glu Glu Ser Lys Leu Asn
        195                 200                 205

Arg Glu Lys Ile Asp Pro Gly Ser Gly Tyr Ile Pro Glu Ala Pro Arg
    210                 215                 220

Asp Gly Gln Ala Tyr Val Arg Lys Asp Gly Glu Trp Val Leu Leu Ser
225                 230                 235                 240

Thr Phe Leu Ser Gly Arg Leu Val Pro Arg Gly Ser Gly His His His
                245                 250                 255

His His His


<210> SEQ ID NO 116
<211> LENGTH: 261
<212> TYPE: PRT
<213> ORGANISM: Artificial Sequence
<220> FEATURE:
<223> OTHER INFORMATION: Gen6 HA SS 2 amino acid sequence
```

<400> SEQUENCE: 116

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Gly Ser Gly Leu Arg Met Val Thr Gly Leu Arg Asn Ile Pro Gln
    50                  55                  60

Arg Glu Thr Arg Gly Leu Phe Gly Ala Ile Ala Gly Phe Ile Glu Gly
65                  70                  75                  80

Gly Trp Thr Gly Met Val Asp Gly Trp Tyr Gly Tyr His His Gln Asn
                85                  90                  95

Glu Gln Gly Ser Gly Tyr Ala Ala Asp Gln Lys Ser Thr Gln Asn Ala
            100                 105                 110

Ile Asn Gly Ile Thr Asn Met Val Asn Ser Val Ile Glu Lys Met Gly
        115                 120                 125

Ser Gly Gly Ser Gly Thr Asp Leu Ala Glu Leu Leu Val Leu Leu Leu
    130                 135                 140

Asn Glu Arg Thr Leu Asp Phe His Asp Ser Asn Val Lys Asn Leu Tyr
145                 150                 155                 160

Glu Lys Val Lys Ser Gln Leu Lys Asn Asn Ala Lys Glu Ile Gly Asn
                165                 170                 175

Gly Cys Phe Glu Phe Tyr His Lys Cys Asn Asn Glu Cys Met Glu Ser
            180                 185                 190

Val Lys Asn Gly Thr Tyr Asp Tyr Pro Lys Tyr Ser Glu Glu Ser Lys
        195                 200                 205

Leu Asn Arg Glu Lys Ile Asp Pro Gly Ser Gly Tyr Ile Pro Glu Ala
    210                 215                 220

Pro Arg Asp Gly Gln Ala Tyr Val Arg Lys Asp Gly Glu Trp Val Leu
225                 230                 235                 240

Leu Ser Thr Phe Leu Ser Gly Arg Leu Val Pro Arg Gly Ser Gly His
                245                 250                 255

His His His His His
            260
```

<210> SEQ ID NO 117
<211> LENGTH: 565
<212> TYPE: PRT
<213> ORGANISM: Artificial Sequence
<220> FEATURE:
<223> OTHER INFORMATION: FL HA amino acid sequence

<400> SEQUENCE: 117

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80
```

```
Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Lys Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Cys Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Glu Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Cys Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
```

```
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 118
<211> LENGTH: 275
<212> TYPE: PRT
<213> ORGANISM: Artificial Sequence
<220> FEATURE:
<223> OTHER INFORMATION: HA 2759 amino acid sequence

<400> SEQUENCE: 118

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Glu Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Glu Gly Arg His His His His
            260                 265                 270

His His His
        275
```

<210> SEQ ID NO 119
<211> LENGTH: 270
<212> TYPE: PRT
<213> ORGANISM: Artificial Sequence
<220> FEATURE:
<223> OTHER INFORMATION: HA 4157 amino acid sequence

<400> SEQUENCE: 119

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Glu Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Arg Ser
                245                 250                 255

Leu Val Pro Arg Gly Ser Pro Gly His His His His His His
            260                 265                 270
```

<210> SEQ ID NO 120
<211> LENGTH: 270
<212> TYPE: PRT
<213> ORGANISM: Artificial Sequence
<220> FEATURE:
<223> OTHER INFORMATION: HA 4454 amino acid sequence

<400> SEQUENCE: 120

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45
```

```
Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Ile Gly Lys Glu Tyr Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Arg Ser
                245                 250                 255

Leu Val Pro Arg Gly Ser Pro Gly His His His His His His
            260                 265                 270
```

<210> SEQ ID NO 121
<211> LENGTH: 270
<212> TYPE: PRT
<213> ORGANISM: Artificial Sequence
<220> FEATURE:
<223> OTHER INFORMATION: HA 4650 amino acid sequence

<400> SEQUENCE: 121

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140
```

```
Ile Gly Lys Glu Tyr Asn Lys Ser Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Arg Ser
                245                 250                 255

Leu Val Pro Arg Gly Ser Pro Gly His His His His His His
            260                 265                 270


<210> SEQ ID NO 122
<211> LENGTH: 275
<212> TYPE: PRT
<213> ORGANISM: Artificial Sequence
<220> FEATURE:
<223> OTHER INFORMATION: HA 4900 amino acid sequence

<400> SEQUENCE: 122

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Ile Gly Cys Glu Tyr Asn Lys Ser Glu Arg Cys Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240
```

Tyr Ser Glu Glu Ser Lys Leu Asn Arg Glu Lys Ile Asp Gly Val Lys
245 250 255

Leu Glu Ser Met Gly Val Tyr Gln Ile Glu Gly Arg His His His His
260 265 270

His His His
275

<210> SEQ ID NO 123
<211> LENGTH: 275
<212> TYPE: PRT
<213> ORGANISM: Artificial Sequence
<220> FEATURE:
<223> OTHER INFORMATION: mini HA 4900 amino acid sequence

<400> SEQUENCE: 123

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Lys Pro Ser Lys Gln Ser Gln Gly
65 70 75 80

Leu Phe Gly Ala Ile Ala Gly Phe Thr Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Tyr Thr Ala
130 135 140

Ile Gly Cys Glu Tyr Asn Lys Ser Glu Arg Cys Met Lys Gln Ile Glu
145 150 155 160

Asp Lys Ile Glu Glu Ile Glu Ser Lys Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Glu Gly Arg His His His His
260 265 270

His His His
275

<210> SEQ ID NO 124
<211> LENGTH: 275
<212> TYPE: PRT
<213> ORGANISM: Artificial Sequence
<220> FEATURE:

<223> OTHER INFORMATION: A California 04 2009 H1N1 amino acid sequence

<400> SEQUENCE: 124

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Tyr Val Lys Ser Thr Lys Leu
    50                  55                  60

Arg Leu Ala Thr Gly Leu Arg Asn Ile Pro Ser Ile Gln Ser Arg Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Leu Lys Ser Thr Gln Asn Ala Ile Asp Glu Ile Thr
        115                 120                 125

Asn Lys Val Asn Ser Val Ile Glu Lys Met Asn Thr Gln Phe Thr Ala
    130                 135                 140

Val Gly Lys Glu Phe Asn His Leu Glu Lys Arg Ile Glu Asn Leu Asn
145                 150                 155                 160

Lys Lys Val Asp Asp Gly Phe Leu Asp Ile Trp Thr Tyr Asn Ala Glu
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220

Asn Thr Cys Met Glu Ser Val Lys Asn Gly Thr Tyr Asp Tyr Pro Lys
225                 230                 235                 240

Tyr Ser Glu Glu Ala Lys Leu Asn Arg Glu Glu Ile Asp Gly Val Lys
                245                 250                 255

Leu Glu Ser Thr Arg Ile Tyr Gln Ile Leu Ala Ile Tyr Ser Thr Val
            260                 265                 270

Ala Ser Ser
        275

<210> SEQ ID NO 125
<211> LENGTH: 275
<212> TYPE: PRT
<213> ORGANISM: Artificial Sequence
<220> FEATURE:
<223> OTHER INFORMATION: A Brisbane 59 2007 H1N1 amino acid sequence

<400> SEQUENCE: 125

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Tyr Val Arg Ser Ala Lys Leu
    50                  55                  60

```
Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Val Gly Lys Glu Phe Asn Lys Leu Glu Arg Arg Met Glu Asn Leu Asn
145                 150                 155                 160

Lys Lys Val Asp Asp Gly Phe Ile Asp Ile Trp Thr Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser
        275


<210> SEQ ID NO 126
<211> LENGTH: 275
<212> TYPE: PRT
<213> ORGANISM: Artificial Sequence
<220> FEATURE:
<223> OTHER INFORMATION: A New Caledonia 20 1999 H1N1 amino acid
      sequence

<400> SEQUENCE: 126

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Tyr Val Arg Ser Ala Lys Leu
    50                  55                  60

Arg Met Val Thr Gly Leu Arg Asn Ile Pro Ser Ile Gln Ser Arg Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
```

```
    130                 135                 140

Val Gly Lys Glu Phe Asn Lys Leu Glu Arg Arg Met Glu Asn Leu Asn
145                 150                 155                 160

Lys Lys Val Asp Asp Gly Phe Leu Asp Ile Trp Thr Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asn Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser
        275


<210> SEQ ID NO 127
<211> LENGTH: 275
<212> TYPE: PRT
<213> ORGANISM: Artificial Sequence
<220> FEATURE:
<223> OTHER INFORMATION: A Puerto Rico 8 1934 H1N1 amino acid sequence

<400> SEQUENCE: 127

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Tyr Val Arg Ser Ala Lys Leu
    50                  55                  60

Arg Met Val Thr Gly Leu Arg Asn Ile Pro Ser Ile Gln Ser Arg Gly
65                  70                  75                  80

Leu Phe Gly Ala Ile Ala Gly Phe Ile Glu Gly Gly Trp Thr Gly Met
                85                  90                  95

Ile Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Thr Val Ile Glu Lys Met Asn Ile Gln Phe Thr Ala
    130                 135                 140

Val Gly Lys Glu Phe Asn Lys Leu Glu Lys Arg Met Glu Asn Leu Asn
145                 150                 155                 160

Lys Lys Val Asp Asp Gly Phe Leu Asp Ile Trp Thr Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asp
```

```
    210                 215                 220

Asn Glu Cys Met Glu Ser Val Arg Asn Gly Thr Tyr Asp Tyr Pro Lys
225                 230                 235                 240

Tyr Ser Glu Glu Ser Lys Leu Asn Arg Glu Lys Val Asp Gly Val Lys
                245                 250                 255

Leu Glu Ser Met Gly Ile Tyr Gln Ile Leu Ala Ile Tyr Ser Thr Val
            260                 265                 270

Ala Ser Ser
        275


<210> SEQ ID NO 128
<211> LENGTH: 278
<212> TYPE: PRT
<213> ORGANISM: Artificial Sequence
<220> FEATURE:
<223> OTHER INFORMATION: A Vietnam 1203 2004 H5N1

<400> SEQUENCE: 128

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Tyr Val Lys Ser Asn Arg Leu Val
    50                  55                  60

Leu Ala Thr Gly Leu Arg Asn Ser Pro Gln Arg Glu Arg Arg Arg Lys
65                  70                  75                  80

Lys Arg Gly Leu Phe Gly Ala Ile Ala Gly Phe Ile Glu Gly Gly Trp
                85                  90                  95

Gln Gly Met Val Asp Gly Trp Tyr Gly Tyr His His Ser Asn Glu Gln
            100                 105                 110

Gly Ser Gly Tyr Ala Ala Asp Lys Glu Ser Thr Gln Lys Ala Ile Asp
        115                 120                 125

Gly Val Thr Asn Lys Val Asn Ser Ile Ile Asp Lys Met Asn Thr Gln
    130                 135                 140

Phe Glu Ala Val Gly Arg Glu Phe Asn Asn Leu Glu Arg Arg Ile Glu
145                 150                 155                 160

Asn Leu Asn Lys Lys Met Glu Asp Gly Phe Leu Asp Val Trp Thr Tyr
                165                 170                 175

Asn Ala Glu Leu Leu Val Leu Met Glu Asn Glu Arg Thr Leu Asp Phe
            180                 185                 190

His Asp Ser Asn Val Lys Asn Leu Tyr Asp Lys Val Arg Leu Gln Leu
        195                 200                 205

Arg Asp Asn Ala Lys Glu Leu Gly Asn Gly Cys Phe Glu Phe Tyr His
    210                 215                 220

Lys Cys Asp Asn Glu Cys Met Glu Ser Val Arg Asn Gly Thr Tyr Asp
225                 230                 235                 240

Tyr Pro Gln Tyr Ser Glu Glu Ala Arg Leu Lys Arg Glu Glu Ile Ser
                245                 250                 255

Gly Val Lys Leu Glu Ser Ile Gly Ile Tyr Gln Ile Leu Ser Ile Tyr
            260                 265                 270

Ser Thr Val Ala Ser Ser
        275
```

```
<210> SEQ ID NO 129
<211> LENGTH: 276
<212> TYPE: PRT
<213> ORGANISM: Artificial Sequence
<220> FEATURE:
<223> OTHER INFORMATION: A Hong Kong 1073 1999 H9N2 amino acid sequence

<400> SEQUENCE: 129

Met Glu Thr Ile Ser Leu Ile Thr Ile Leu Leu Val Val Thr Ala Ser
1               5                   10                  15

Asn Ala Asp Lys Ile Cys Ile Gly His Gln Ser Thr Asn Ser Thr Glu
            20                  25                  30

Thr Val Asp Thr Leu Thr Glu Thr Asn Val Pro Val Thr His Ala Lys
        35                  40                  45

Glu Leu Leu His Thr Glu His Asn Gly Met Tyr Val Arg Val Asn Ser
    50                  55                  60

Leu Lys Leu Ala Val Gly Leu Arg Asn Val Pro Ala Arg Ser Ser Arg
65                  70                  75                  80

Gly Leu Phe Gly Ala Ile Ala Gly Phe Ile Glu Gly Gly Trp Pro Gly
                85                  90                  95

Leu Val Ala Gly Trp Tyr Gly Phe Gln His Ser Asn Asp Gln Gly Val
            100                 105                 110

Gly Met Ala Ala Asp Arg Asp Ser Thr Gln Lys Ala Ile Asp Lys Ile
        115                 120                 125

Thr Ser Lys Val Asn Asn Ile Val Asp Lys Met Asn Lys Gln Tyr Glu
    130                 135                 140

Ile Ile Asp His Glu Phe Ser Glu Val Glu Thr Arg Leu Asn Met Ile
145                 150                 155                 160

Asn Asn Lys Ile Asp Asp Gln Ile Gln Asp Val Trp Ala Tyr Asn Ala
                165                 170                 175

Glu Leu Leu Val Leu Leu Glu Asn Gln Lys Thr Leu Asp Glu His Asp
            180                 185                 190

Ala Asn Val Asn Asn Leu Tyr Asn Lys Val Lys Arg Ala Leu Gly Ser
        195                 200                 205

Asn Ala Met Glu Asp Gly Lys Gly Cys Phe Glu Leu Tyr His Lys Cys
    210                 215                 220

Asp Asp Gln Cys Met Glu Thr Ile Arg Asn Gly Thr Tyr Asn Arg Arg
225                 230                 235                 240

Lys Tyr Arg Glu Glu Ser Arg Leu Glu Arg Gln Lys Ile Glu Gly Val
                245                 250                 255

Lys Leu Glu Ser Glu Gly Thr Tyr Lys Ile Leu Thr Ile Tyr Ser Thr
            260                 265                 270

Val Ala Ser Ser
        275


<210> SEQ ID NO 130
<211> LENGTH: 283
<212> TYPE: PRT
<213> ORGANISM: Artificial Sequence
<220> FEATURE:
<223> OTHER INFORMATION: A Wisconsin 67 2005 H3N2 amino acid sequence

<400> SEQUENCE: 130

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30
```

```
His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Tyr Val Lys Gln Asn Thr Leu Lys Leu Ala Thr Gly Met Arg
65                  70                  75                  80

Asn Val Pro Glu Lys Gln Thr Gln Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110

Arg His Gln Asn Ser Glu Gly Ile Gly Gln Ala Ala Asp Leu Lys Ser
        115                 120                 125

Thr Gln Ala Ala Ile Asn Gln Ile Asn Gly Lys Leu Asn Arg Leu Ile
    130                 135                 140

Gly Lys Thr Asn Glu Lys Phe His Gln Ile Glu Lys Glu Phe Ser Glu
145                 150                 155                 160

Val Glu Gly Arg Ile Gln Asp Leu Glu Lys Tyr Val Glu Asp Thr Lys
                165                 170                 175

Ile Asp Leu Trp Ser Tyr Asn Ala Glu Leu Leu Val Ala Leu Glu Asn
            180                 185                 190

Gln His Thr Ile Asp Leu Thr Asp Ser Glu Met Asn Lys Leu Phe Glu
        195                 200                 205

Arg Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys
        275                 280


<210> SEQ ID NO 131
<211> LENGTH: 283
<212> TYPE: PRT
<213> ORGANISM: Artificial Sequence
<220> FEATURE:
<223> OTHER INFORMATION: A Brisbane 10 2007 H3N2 amino acid sequence

<400> SEQUENCE: 131

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Tyr Val Lys Gln Asn Thr Leu Lys Leu Ala Thr Gly Met Arg
65                  70                  75                  80

Asn Val Pro Glu Lys Gln Thr Arg Gly Ile Phe Gly Ala Ile Ala Gly
                85                  90                  95

Phe Ile Glu Asn Gly Trp Glu Gly Met Val Asp Gly Trp Tyr Gly Phe
            100                 105                 110
```

Arg His Gln Asn Ser Glu Gly Ile Gly Gln Ala Ala Asp Leu Lys Ser
115 120 125

Thr Gln Ala Ala Ile Asp Gln Ile Asn Gly Lys Leu Asn Arg Leu Ile
130 135 140

Gly Lys Thr Asn Glu Lys Phe His Gln Ile Glu Lys Glu Phe Ser Glu
145 150 155 160

Val Glu Gly Arg Ile Gln Asp Leu Glu Lys Tyr Val Glu Asp Thr Lys
165 170 175

Ile Asp Leu Trp Ser Tyr Asn Ala Glu Leu Leu Val Ala Leu Glu Asn
180 185 190

Gln His Thr Ile Asp Leu Thr Asp Ser Glu Met Asn Lys Leu Phe Glu
195 200 205

Lys Thr Lys Lys Gln Leu Arg Glu Asn Ala Glu Asp Met Gly Asn Gly
210 215 220

Cys Phe Lys Ile Tyr His Lys Cys Asp Asn Ala Cys Ile Gly Ser Ile
225 230 235 240

Arg Asn Gly Thr Tyr Asp His Asp Val Tyr Arg Asp Glu Ala Leu Asn
245 250 255

Asn Arg Phe Gln Ile Lys Gly Val Glu Leu Lys Ser Gly Tyr Lys Asp
260 265 270

Trp Ile Leu Trp Ile Ser Phe Ala Ile Ser Cys
275 280

<210> SEQ ID NO 132
<211> LENGTH: 283
<212> TYPE: PRT
<213> ORGANISM: Artificial Sequence
<220> FEATURE:
<223> OTHER INFORMATION: A Texas 50 2012 H3N2 amino acid sequence

<400> SEQUENCE: 132

Met Lys Thr Ile Ile Ala Leu Ser Tyr Ile Leu Cys Leu Val Phe Ala
1 5 10 15

Gln Lys Leu Pro Gly Asn Asp Asn Ser Thr Ala Thr Leu Cys Leu Gly
20 25 30

His His Ala Val Pro Asn Gly Thr Ile Val Lys Thr Ile Thr Asn Asp
35 40 45

Arg Ile Glu Val Thr Asn Ala Thr Glu Leu Val Gln Asn Ser Ser Ile
50 55 60

Gly Glu Tyr Val Lys Gln Ser Thr Leu Lys Leu Ala Thr Gly Met Arg
65 70 75 80

Asn Val Pro Glu Lys Gln Thr Arg Gly Ile Phe Gly Ala Ile Ala Gly
85 90 95

Phe Ile Glu Asn Gly Trp Glu Gly Met Val Asp Gly Trp Tyr Gly Phe
100 105 110

Arg His Gln Asn Ser Glu Gly Arg Gly Gln Ala Ala Asp Leu Lys Ser
115 120 125

Thr Gln Ala Ala Ile Asp Gln Ile Asn Gly Lys Leu Asn Arg Leu Ile
130 135 140

Gly Lys Thr Asn Glu Lys Phe His Gln Ile Glu Lys Glu Phe Ser Glu
145 150 155 160

Val Glu Gly Arg Ile Gln Asp Leu Glu Lys Tyr Val Glu Asp Thr Lys
165 170 175

Ile Asp Leu Trp Ser Tyr Asn Ala Glu Leu Leu Val Ala Leu Glu Asn
180 185 190

```
Gln His Thr Ile Asp Leu Thr Asp Ser Glu Met Asn Lys Leu Phe Glu
        195                 200                 205

Lys Thr Lys Lys Gln Leu Arg Glu Asn Ala Glu Asp Met Gly Asn Gly
    210                 215                 220

Cys Phe Lys Ile Tyr His Lys Cys Asp Asn Ala Cys Ile Gly Ser Ile
225                 230                 235                 240

Arg Asn Gly Thr Tyr Asp His Asp Val Tyr Arg Asp Glu Ala Leu Asn
                245                 250                 255

Asn Arg Phe Gln Ile Lys Gly Val Glu Leu Lys Ser Gly Tyr Lys Asp
            260                 265                 270

Trp Ile Leu Trp Ile Ser Phe Ala Ile Ser Cys
        275                 280


<210> SEQ ID NO 133
<211> LENGTH: 278
<212> TYPE: PRT
<213> ORGANISM: Artificial Sequence
<220> FEATURE:
<223> OTHER INFORMATION: A Netherlands 219 03 H7N7 amino acid sequence

<400> SEQUENCE: 133

Met Asn Thr Gln Ile Leu Val Phe Ala Leu Val Ala Ser Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Tyr Val Lys Gln Glu Ser
    50                  55                  60

Leu Leu Leu Ala Thr Gly Met Lys Asn Val Pro Glu Ile Pro Lys Arg
65                  70                  75                  80

Arg Arg Arg Gly Leu Phe Gly Ala Ile Ala Gly Phe Ile Glu Asn Gly
                85                  90                  95

Trp Glu Gly Leu Ile Asp Gly Trp Tyr Gly Phe Arg His Gln Asn Ala
            100                 105                 110

Gln Gly Glu Gly Thr Ala Ala Asp Tyr Lys Ser Thr Gln Ser Ala Ile
        115                 120                 125

Asp Gln Ile Thr Gly Lys Leu Asn Arg Leu Ile Glu Lys Thr Asn Gln
    130                 135                 140

Gln Phe Glu Leu Ile Asp Asn Glu Phe Thr Glu Val Glu Arg Gln Ile
145                 150                 155                 160

Gly Asn Val Ile Asn Trp Thr Arg Asp Ser Met Thr Glu Val Trp Ser
                165                 170                 175

Tyr Asn Ala Glu Leu Leu Val Ala Met Glu Asn Gln His Thr Ile Asp
            180                 185                 190

Leu Ala Asp Ser Glu Met Asn Lys Leu Tyr Glu Arg Val Lys Arg Gln
        195                 200                 205

Leu Arg Glu Asn Ala Glu Glu Asp Gly Thr Gly Cys Phe Glu Ile Phe
    210                 215                 220

His Lys Cys Asp Asp Asp Cys Met Ala Ser Ile Arg Asn Asn Thr Tyr
225                 230                 235                 240

Asp His Ser Lys Tyr Arg Glu Glu Ala Ile Gln Asn Arg Ile Gln Ile
                245                 250                 255
```

-continued

```
Asp Pro Val Lys Leu Ser Ser Gly Tyr Lys Asp Val Ile Leu Trp Phe
            260                 265                 270

Ser Phe Gly Ala Ser Cys
        275
```